United States Patent [19]
Chenchik et al.

[11] Patent Number: 5,994,076
[45] Date of Patent: Nov. 30, 1999

[54] METHODS OF ASSAYING DIFFERENTIAL EXPRESSION

[75] Inventors: Alex Chenchik, Palo Alto; George Jokhadze, Mountain View, both of Calif.; Robert Bibilashvilli, Moscow, Russian Federation

[73] Assignee: Clontech Laboratories, Inc., Palo Alto, Calif.

[21] Appl. No.: 08/859,998

[22] Filed: May 21, 1997

[51] Int. Cl.$^6$ .............................. C12Q 1/68; C12P 19/34; C07H 21/02; C07H 21/04

[52] U.S. Cl. ........................... 435/6; 435/91.1; 435/91.2; 536/23.1; 536/24.3; 536/24.31; 536/24.33

[58] Field of Search ............................ 435/6, 91.1, 91.2; 536/24.3, 24.31, 24.33, 23.1

[56] References Cited

U.S. PATENT DOCUMENTS

| | | |
|---|---|---|
| 4,888,274 | 12/1989 | Radding et al. . |
| 5,162,209 | 11/1992 | Scheele . |
| 5,223,414 | 6/1993 | Zarling et al. . |
| 5,387,510 | 2/1995 | Wu . |
| 5,434,047 | 7/1995 | Arnold, Jr. . |
| 5,436,327 | 7/1995 | Southern et al. . |
| 5,449,603 | 9/1995 | Nielson et al. . |
| 5,468,613 | 11/1995 | Erlich et al. . |
| 5,487,985 | 1/1996 | McClelland et al. . |
| 5,503,980 | 4/1996 | Cantor . |
| 5,512,462 | 4/1996 | Cheng . |
| 5,547,843 | 8/1996 | Studier . |
| 5,580,726 | 12/1996 | Villeponteau et al. . |
| 5,599,672 | 2/1997 | Liang et al. . |

FOREIGN PATENT DOCUMENTS

| | | |
|---|---|---|
| 0 229 442 | 7/1987 | WIPO . |
| 0 229 442 B1 | 7/1987 | WIPO . |
| WO 88/01302 | 2/1988 | WIPO . |
| 0 318 245 B1 | 5/1989 | WIPO . |
| WO 89/11548 | 11/1989 | WIPO . |
| 0 392 546 | 10/1990 | WIPO . |
| 0 481 065 B1 | 4/1992 | WIPO . |
| WO 95/21944 | 8/1995 | WIPO . |

OTHER PUBLICATIONS

Goodwin, Raymond G., et al., "Human Interleukin 7: Molecular Cloning and Growth Factor Activity on Human and Murine B–Lineage Cells," *Proc. Natl. Acad. Sci. USA* (Jan. 1989) vol. 86:302–306.

Leonard, Warren J., et al., "Molecular Cloning and Expression of cDNAs for the Human Interleukin–2 Receptor," *Nature* (Oct. 1984) vol. 311:626–631.

Nishi, Tatsunari et al., "Cloning and Expression of a Novel Variant of Human InterferonY cDNA," *J. Biochem* (1985) vol. 97:153–159.

Ehlers et al., "Differentiation of T cell lymphokine gene expression: the in vitro acquisition of T cell memory", J. Exp. Med. 173:25–36, Jan. 1991.

Goodwin et al, "Cloning of the human and murine interleukin 7 receptors: demonstration of a soluble form and homology to a new receptor superfamily", Cell 60:941–951, Mar. 1990.

Bauer, David et al., "Identification of Differentially expressed mRNA Species By An Improved Display Technique (DDRT–PCR)", *Nucleic Acids Research* (1993) vol. 21 No. 18; 4272–4280.

Chalifour, Lorraine et al., "A Method For Analysis of Gene Expression Patterns", *Analytical Biochemistry* (1994) vol. 216:299–304.

DeRisi, Joseph et al., "Use Of A cDNA Microarray To Analyse GeneExpression Patterns In Human Cancer", *Nature Genetics* vol. 14:457–460. (Dec. 1996).

Heller, Renu et al., "Discovery and Analysis of Inflammatory Disease–Related Genes Using cDNA Microarrays", *Proc. Nat.l Acad. Sci. USA* (1997) vol. 94:2150–2155.

Ikonomov, Ognian, et al., "Differential Display Protocol With Selected Primers That Preferentially Isolates mRNAs of Moderate–to–Low–Abundance in a Microscopic System", *BioTechniques* (1996) vol. 20 No.6; 1030–1042.

Liang, Peng et al., "Differential Display of Eukaryotic Messenger RNA by Means of the Polymerase Chain Reaction", *Science* (1992) vol. 257:967–971.

Liang, Peng et al., "Recent Advances in Differential Display", *Current Opinion in Immunology* (1995) vol. 7 : 274–280.

Lockhart, David et al., "Expression Monitoring By Hybridization to High–Density Oligonucleotide Arrays", *Nature Biotechnology* (1996) vol. 14: 1675–1680.

Nguyen, Catherine et al., "Differential Gene Expression in the Murine Thymus Assayed by Quantitative Hybridization of Arrayed cDNA Clones", *Genomics* (1995) vol.29:207–216.

Pietu, Genevieve et al., "Novel Gene Transcripts Preferentially Expressed in Human Muscles Revealed by Quantitative Hybridization of a High Density cDNA Array", *Genome Research* (1996) vol.6:492–503.

Prashar, Yatindra et al., "Analysis of Differential Gene Expression by Display of 3' End Restriction Fragments of cDNAs", *Proc. Nat.l Acad.Sci. USA* (1996) vol.93: 659–663.

(List continued on next page.)

*Primary Examiner*—Jeffrey Fredman
*Attorney, Agent, or Firm*—Bozicevic & Reed LLP; Bret E. Field

[57] ABSTRACT

Methods and compositions are provided for analyzing differences in the RNA profiles between a plurality of different physiological samples. In the subject methods, a set of a representational number of distinct gene specific primers is used to generate labeled nucleic acids from each of the different physiological samples. The labeled nucleic acids are then compared to each other and differences in the RNA profiles are determined. The subject methods find use in methods of identifying differential gene expression.

17 Claims, 1 Drawing Sheet

OTHER PUBLICATIONS

Schena, Mark et al., "Quantitative Monitoring of Gene Expression Patterns With a Complementary DNA Microarray", *Science* (1995) vol.270:467–470.

Schena, Mart et al., "Parallel Human Genome Analysis: Microarray–Based Expression Monitoring of 1000 Genes", *Proc. Nat.l Acad. Sci. USA* (1996) vol. 93:10614–10619.

Shalon, Dari et al., "A DNA Microarray System for Analyzing Complex DNA Samples Using Two–Color Fluorescent Probe Hybridization", *Genome Research* (1996) vol. 6: 639–645.

Sokolov, Boris et al., "A Rapid and Simple PCR–based Method For Isolation of cDNAs from Differentially Expressed Genes", *Nucleic Acids Research* (1994) vol. 22, No.19; 4009–4015.

Zhao, Nanding et al., "High–Density cDNA Filter Analysis: A Novel Approach for Large–Scale, Quantitative Analysis of Gene Expression", *Gene* (1995) vol. 156: 207–213.

"Atlas™ Human cDNA Expression Array I", *Clontechniques* Apr. 1997; 4–7.

METHODS OF ASSAYING DIFFERENTIAL EXPRESSION

TECHNICAL FIELD

The technical field of this invention is the analysis of differential gene expression.

BACKGROUND

In higher organisms, any given cell expresses only a fraction of the total number of genes present in its genome. The small fraction of the total number of genes that is expressed determine the life processes carried out by the cell, e.g. development and differentiation, homeostasis, response to insults, cell cycle regulation, aging, apoptosis, and the like. Alterations in gene expression decide the course of normal cell development and the appearance of diseased states, such as cancer. Because the choice of which genes are expressed has such a profound effect on the nature of any given cell, methods of analyzing gene expression are of critical import to basic molecular biological research. Identification of differentially-expressed genes can provide a key to diagnosis, prognosis and treatment of a variety of diseases or condition states in animals, including humans, and plants. Additionally, these methods can be used to identify differentially-expressed sequences due to changes in gene expression level associated with predisposition to disease, influence of external treatments, factors or infectious agents. Identification of such genes helps in development of new drugs and diagnostic methods for treating or preventing the occurrence of such diseases.

One way of analyzing gene expression in a particular cell is to perform differential gene expression assays, in which the expression of genes in different cells is compared and any discrepancies in expression are identified, where the presence of discrepancies indicates a difference in the classes of genes expressed in the cells being compared.

One method currently employed to identify differentially expressed genes begins with the generation of cDNA "targets" obtained from analogous cells, tissues or organs of a healthy and diseased organism. The cDNA targets are then hybridized to a set of target nucleic acid "probe" fragments immobilized on membrane. Differences between the resultant hybridization patterns are then detected and related to differences in gene expression in the two sources. In this procedure the number of analyzed gene-specific probes can reach several hundred thousand.

Modifications have been made to the above basic method in order to obtain improved results. These modifications include replacement of the traditional radioactive labeling procedure of the target nucleic acid sequences with nonisotopic labels, mainly fluorescent labels. Other modifications have focused on improved methods of immobilization of an array of the probe nucleic acids to surfaces of a variety of solid supports.

Despite the promise of analysis of differential expression using arrays of probes on solid supports, there is a continuing need for improvement of the methods currently employed by researchers. In current methods, hybridization of "target" to "probe" is slow. Furthermore, a number of additional events such as competitive hybridization events between distinct target sequences, nonspecific binding between "target" and "probe," and formation of secondary structures in target sequences can occur which adversely effect the results.

Accordingly, there is continued interest in the development of new methods of analyzing differential gene expression, where such methods provide for fast hybridization and high specificity of binding of "targets" to "probes."

Relevant Literature

Patents of interest include: EP 0 328 829 B1 and U.S. Pat. Nos. 5,468,613; 5,580,726; 5,599,672; 5,512,462; 5,162,209 and 5,162,209. Methods of analyzing differential gene expression are also described in Maniatis, et al., Molecular Cloning, A Laboratory Manual, (Cold Spring Harbor Press, Cold Spring Harbor, N.Y.)(1989); Nucleic Acid Hybridization, A Practical Approach (Hames, B. D., and Higgins, S. J. eds, IRL Press, Oxford)(1985); WO 95/21944; Chalifour, et al., Anal. Biochem. (1994) 216: 299–304; Nguyen et al., Genomics (1995) 29: 207–216; Pietu et al., Genome Res. (1996) 6: 492–503; and Zhao et al., Gene (1995) 166: 207–213.

Use of non-isotopic labels in methods of differential gene expression analysis are described in: Schena et al. Science (1995) 270: 467–470; Schena et al., Proc. Natl. Acad. Sci. USA (1996) 93: 10614–10619; DeRisi et al., Nature Genet. (1996) 14: 457–460; and Lockhart et al., Nature Biotechnol. (1996) 14: 1675–1680.

Methods of stably associating probes to the surface of substrates are described in: Hermanson, et al. Immobilized Affinity Ligand Techniques, Academic Press, (1992); WO 89/11548; European Patent No. 0 281 390 B1; WO 88/01302; European Patent Application No. 0392546; U.S. Pat. No. 5,436,327; U.S. Pat. No. 5,445,934.

Methods of improving hybridization of target to substrate surface associated probe are described in: EP 0 318 245 B1 (solution hybridization of probe to target followed by binding of hybridization complex to surface of substrate); Lockhart et al., Nature Biotechnol. (1996) 14: 1675–1680, EP 0 328 829 B1 (preamplification of target DNA/RNA); Maniatis et al., Molecular Cloning, A Laboratory Manual (Cold Spring Harbor Press, Cold Spring Harbor, N.Y., (1989), Nucleic Acid Hybridization, A Practical Approach (Hames, B. D., and Higgins, S. J. eds. IRL Press, Oxford) (1985), EP 0 229 442 (addition of an inert polymers such as dextran sulfate); U.S. Pat. No. 5,387,510, EP 0 318 245 B1 (use of "helper" oligonucleotides which reorder secondary and tertiary structure of target polynucleotide); WO 89/11548 (attaching probes to surface of substrate through long spacer arms).

Methods of improving specificity of hybridization are described in: U.S. Pat. Nos. 5,449,603 & 5,547,843 (use of single stranded nucleic acid binding protein); U.S. Pat. Nos. 4,888,274 & 5,223,414, EP 0 481 065 B1 (use of RecA protein-coated nucleoprotein target molecules); Khrapko et al., FEBS Lett. (1989) 256: 118–122 and U.S. Pat. No. 5,503,980 (continuous stacking interaction between short oligonucleotides of target and probe molecules, followed by enzymatic ligation step); and U.S. Pat. No. 5,434,047 (use of non-target probe which hybridized with non-target nucleic acid).

SUMMARY OF THE INVENTION

Methods and compositions for identifying differences between the nucleic acid profiles of a plurality of biological samples are provided. In the subject methods, a set of a representational number of different gene specific primers is used to generate labeled target nucleic acids from samples of nucleic acids, usually ribonucleic acids, derived from at least two different physiological sources. The labeled target nucleic acids derived from each physiological source are then compared, preferably by hybridization to arrays of probe nucleic acids stably associated with the surface of a substrate. The subject methods find use in differential gene expression analysis.

DESCRIPTION OF THE SPECIFIC EMBODIMENTS

Figure 1A:
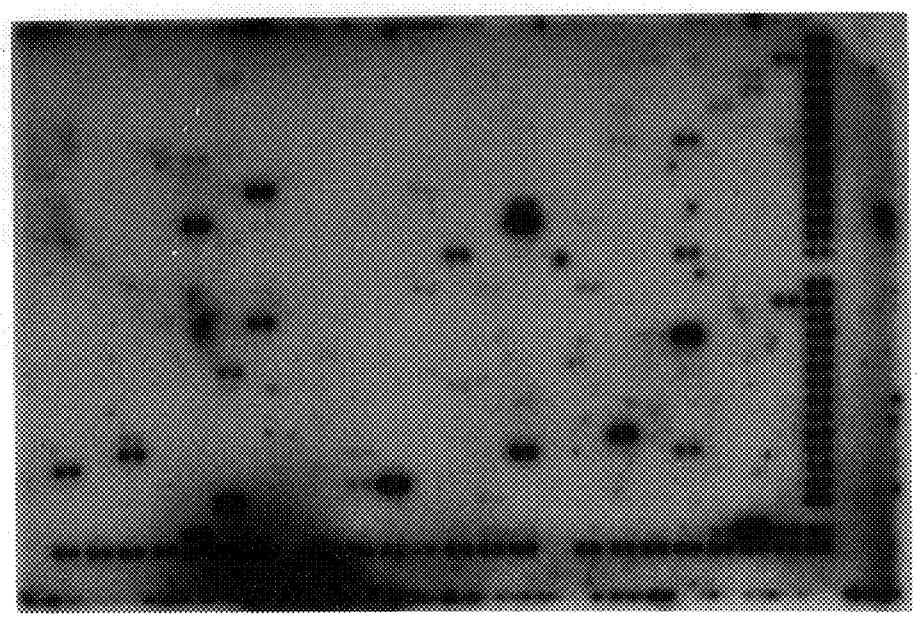
FIGS. 1A and B provides hybridization patterns obtained using target generated from: (B) a set of gene specific primers according to the subject invention and (A) oligo dT primers.

Methods and compositions are provided for analyzing differences in the ribonucleic acid profiles between two or more physiological sources. In the subject methods, a set of a representational number of gene specific primers is used to generate labeled target nucleic acids from the physiological sources. The labeled target nucleic acids from each of the samples are then compared, preferably by hybridizing the labeled target nucleic acids from each sample to an array of probe nucleic acids stably associated with the surface of a substrate. Also provided are sets of gene specific primers employed in the subject methods, as well as kits comprising the sets of gene specific primers. The subject methods find use in a variety of applications, including differential gene expression assays.

Before the subject invention is further described, it is to be understood that the invention is not limited to the particular embodiments of the invention described below, as variations of the particular embodiments may be made and still fall within the scope of the appended claims. It is also to be understood that the terminology employed is for the purpose of describing particular embodiments, and is not intended to be limiting. Instead, the scope of the present invention will be established by the appended claims.

It must be noted that as used in this specification and the appended claims, the singular forms "a," "an," and "the" include plural reference unless the context clearly dictates otherwise. Unless defined otherwise all technical and scientific terms used herein have the same meaning as commonly understood to one of ordinary skill in the art to which this invention belongs.

Critical to the subject invention is the use of a set of a representational number of gene specific primers to generate labeled nucleic acids from a sample of nucleic acids, usually ribonucleic acids (RNAs), where the labeled nucleic acids may act as "target" in subsequent hybridization assays, described in greater detail below. As used herein, the term nucleic acid is used in the broadest sense to refer to any sized multimer of nucleotide monomeric units, including short multimers such as dimers, trimers and the like, as well as longer multimers such as oligonucleotides and polynucleotides, where oligonucleotides generally denotes single stranded nucleotide multimers of from about 10 to 100 nucleotides and up to 200 nucleotides in length, and polynucleotides typically refers to single or double stranded nucleotide monomers of generally greater than 100 nucleotides in length.

As the subject sets comprise a representational number of primers, the total number of different primers in any given set will be only a fraction of the total number of different or distinct RNAs in the sample, where the total number of primers in the set will generally not exceed 80%, usually will not exceed 50% and more usually will not exceed 20% of the total number of distinct RNAs, usually the total number of distinct messenger RNAs (mRNAs), in the sample. Any two given RNAs in a sample will be considered distinct or different if they comprise a stretch of at least 100 nucleotides in length in which the sequence similarity is less then 98%. As the sets of gene specific primers comprise only a representational number of primers, with physiological sources comprising from 5,000 to 50,000 distinct RNAs, the number of different gene specific primers in the set of gene specific primers will typically range from about 20 to 10,000, usually from 50 to 2,000 and more usually from 75 to 1500.

Each of the gene specific primers of the sets described above will be of sufficient length to specifically hybridize to a distinct nucleic acid member of the sample, e.g. RNA or cDNA, where the length of the gene specific primers will usually be at least 8 nt, more usually at least 20 nt and may be as long as 25 nt or longer, but will usually not exceed 50 nt. The gene specific primers will be sufficiently specific to hybridize to complementary template sequence during the generation of labeled nucleic acids under conditions sufficient for first strand cDNA synthesis, which conditions are known by those of skill in the art. The number of mismatches between the gene specific primer sequences and their complementary template sequences to which they hybridize during the generation of labeled nucleic acids in the subject methods will generally not exceed 20%, usually will not exceed 10% and more usually will not exceed 5%.

Generally, the sets of gene specific primers will comprise primers that correspond to at least 20, usually at least 50 and more usually at least 75 distinct genes as represented by distinct mRNAs in the sample, where the term "distinct" when used to describe genes is as defined above, where any two genes are considered distinct if they comprise a stretch of at least 100 nt in their RNA coding regions in which the sequence similarity does not exceed 98%.

The gene specific oligonucleotide primers may be synthesized by conventional oligonucleotide chemistry methods, where the nucleotide units may be: (a) solely nucleotides comprising the heterocyclic nitrogenous bases found in naturally occurring DNA and RNA, e.g. adenine, cytosine, guanine, thymine and uracil; (b) solely nucleotide analogs which are capable of base pairing under hybridization conditions in the course of DNA synthesis such that they function as the above nucleotides found in naturally occurring DNA and RNA, where illustrative nucleotide analogs include inosine, xanthine, hypoxanthine, 1,2-diaminopurine and the like; or (c) from combinations of the nucleotides of (a) and nucleotide analogs of (b), where with primers comprising a combination of nucleotides and analogues thereof, the number of nucleotide analogues in the primers will typically be less than 25 and more typically less than 5. The gene specific primers may comprise reporter or hapten groups, usually 1 to 2, which serve to improve hybridization properties and simplify detection procedure.

Depending on the particular point at which the gene specific primers are employed in the generation of the labeled nucleic acids, e.g. during first strand cDNA synthesis or following one or more distinct amplification steps, each gene specific primer may correspond to a particular RNA by being complementary or similar, where similar usually means identical, to the particular RNA. For example, where the gene specific primers are employed in the synthesis of first strand cDNA, the gene specific primers will be complementary to regions of the RNAs to which they correspond.

Each gene specific primer can be complementary to a sequence of nucleotides which is unique in the population of nucleic acids, e.g. mRNAs, with which the primers are contacted, or one or more of the gene specific primers in the set may be complementary to several nucleic acids in a given population, e.g. multiple mRNAs, such that the gene specific primer generates labeled nucleic acid when one or more of set of related nucleic acid species, e.g. species having a conserved region to which the primer corresponds, are present in the sample. Examples of such related nucleic acid species include those comprising: repetitive sequences, such as Alu repeats, Al repeats and the like; homologous sequences in related members of a gene-family; polyadenylation signals; splicing signals; or arbitrary but conversed sequences.

The gene specific primers of the sets of primers according to the subject invention are typically chosen according to a number of different criteria. In some embodiments of the invention, primers of interest for inclusion in the set include primers corresponding to genes which are typically differentially expressed in different cell types, in disease states, in response to the influence of external agents, factors or infectious agents, and the like. In other embodiments, primers of interest are primers corresponding to genes which are expected to be, or already identified as being, differentially expressed in different cell, tissue or organism types. Preferably, at least 2 different gene functional classes will be represented in the sets of gene specific primers, where the number of different functional classes of genes represented in the primer sets will generally be at least 3, and will usually be at least 5. Gene functional classes of interest include oncogenes; genes encoding tumor suppressors; genes encoding cell cycle regulators; stress response genes; genes encoding ion channel proteins; genes encoding transport proteins; genes encoding intracellular signal transduction modulator and effector factors; apoptosis related genes; DNA synthesis/recombination/repair genes; genes encoding transcription factors; genes encoding DNA-binding proteins; genes encoding receptors, including receptors for growth factors, chemokines, interleukins, interferons, hormones, neurotransmitters, cell surface antigens, cell adhesion molecules etc.; genes encoding cell-cell communication proteins, such as growth factors, cytokines, chemokines, interleukins, interferons, hormones etc.; and the like. Less preferred are gene specific primers that are subject to formation of strong secondary structures with less than −10 kcal/mol; comprise stretches of homopolymeric regions, usually more than 5 identical nucleotides; comprise more than 3 repetitive sequences; have high, e.g. more than 80%, or low, e.g. less than 30%, GC content etc.

The particular genes represented in the set of gene specific primers will necessarily depend on the nature of physiological source from which the RNAs to be analyzed are derived. For analysis of RNA profiles of eukaryotic physiological sources, the genes to which the gene specific primers correspond will usually be Class II genes which are transcribed into RNAs having 5' caps, e.g. 7-methyl guanosine or 2,2,7-trimethylguanosine, where Class II genes of particular interest are those transcribed into cytoplasmic mRNA comprising a 7-methyl guanosine 5' cap and a polyA tail.

For analysis of RNA profiles of mammalian physiological sources, of particular interest are gene specific primers corresponding to the functional gene classes listed above. For analysis of RNA profiles of human physiological sources, the gene specific primers of particular interest are the gene specific primers identified in Table 1 as SEQ ID NO:01 to SEQ ID NO:1372, where sets of these primers will usually include at least 20 and more usually at least 50 of these specific sequences.

Depending on the particular nature of the labeled nucleic acid generation step of the subject methods, the gene specific primers may be modified in a variety of ways. One way the gene specific primers may be modified is to include an anchor sequence of nucleotides, where the anchor is usually located 5' of the gene specific portion of the primer and ranges in length from 10 to 50 nt in length, usually 15 to 40 nt in length. The anchor sequence may comprise a sequence of bases which serves a variety of functions, such as a sequence of bases which correspond to the sequence found in promoters for bacteriophage RNA polymerase, e.g. T7 polymerase, T 3 polymerase, SP6 polymerase, and the like; arbitrary sequences which can serve as subsequent primer binding sites; and the like.

Turning now to the methods employing the above sets of gene specific primers, the first step in the subject methods is to obtain a sample of nucleic acids, usually RNAs, from a physiological source, usually a plurality of physiological sources, where the term plurality is used to refer to 2 or more distinct physiological sources. The physiological source of RNAs will typically be eukaryotic, with physiological sources of interest including sources derived single celled organisms such as yeast and multicellular organisms, including plants and animals, particularly mammals, where the physiological sources from multicellular organisms may be derived from particular organs or tissues of the multicellular organism, or from isolated cells derived therefrom. Thus, the physiological sources may be different cells from different organisms of the same species, e.g. cells derived from different humans, or cells derived from the same human (or identical twins) such that the cells share a common genome, where such cells will usually be from different tissue types, including normal and diseased tissue types, e.g. neoplastic, cell types. In obtaining the sample of RNAs to be analyzed from the physiological source from which it is derived, the physiological source may be subjected to a number of different processing steps, where such processing steps might include tissue homogenation, nucleic acid extraction and the like, where such processing steps are known to the those of skill in the art. Methods of isolating RNA from cells, tissues, organs or whole organisms are known to those of skill in the art and are described in Maniatis et al., Molecular Cloning: A Laboratory Manual (Cold Spring Harbor Press)(1989).

The next step in the subject methods is the generation of labeled nucleic acids representative of the nucleic acid, usually RNA, profile of the physiological source. As mentioned above, a set of gene specific primers is used to generate the labeled nucleic acids from the sample of RNAs, where the labeled nucleic acids generated in this step may serve as "target" in subsequent assays in which the differences in the RNA profiles of at least two sources are analyzed. As used herein, the term "target" refers to single stranded RNA, single stranded DNA and double stranded DNA, where the target is generally greater than 50 nt in length.

The set of primers may be used either in first strand cDNA synthesis or following one or more amplification steps. Furthermore, the actual synthesis of the labeled nucleic acids may be at the same step during which the sets of gene specific primers are employed, or the synthesis of the labeled nucleic acids may be one more steps subsequent to the step in which the sets of gene specific primers are employed.

In a first embodiment of the invention, the set of gene specific primers is used to generate labeled first strand cDNA, where the labeled first strand cDNA is representative of the RNA profile of the physiological source being assayed. The labeled first strand cDNA is prepared by contacting the RNA sample with the primer set and requisite reagents under conditions sufficient for reverse transcription of the RNA template in the sample. Requisite reagents contacted with the primers and RNAs are known to those of skill in the art and will generally include at least an enzyme having reverse transcriptase activity and dNTPs in an appropriate buffer medium.

A variety of enzymes, usually DNA polymerases, possessing reverse transcriptase activity can be used for the first strand cDNA synthesis step. Examples of suitable DNA polymerases include the DNA polymerases derived from organisms selected from the group consisting of a thermophilic bacteria and archaebacteria, retroviruses, yeasts, Neurosporas, Drosophilas, primates and rodents. Preferably, the DNA polymerase will be selected from the group consisting of Moloney murine leukemia virus (M-MLV) as described in U.S. Pat. No. 4,943,531 and M-MLV reverse transciptase lacking RNaseH activity as described in U.S. Pat. No. 5,405,776 (the disclosures of which patents are herein incorporated by reference), human T-cell leukemia virus type I (HTLV-I), bovine leukemia virus (BLV), Rous sarcoma virus (RSV), human immunodeficiency virus (HIV) and Thermus aquaticus (Taq) or Thermus thermophilus (Tth) as described in U.S. Pat. No. 5,322,770, the disclosure of which is herein incorporated by reference. Suitable DNA polymerases possessing reverse transcriptase activity may be isolated from an organism, obtained commercially or obtained from cells which express high levels of cloned genes encoding the polymerases by methods known to those of skill in the art, where the particular manner of obtaining the polymerase will be chosen based primarily on factors such as convenience, cost, availability and the like.

The various dNTPs and buffer medium necessary for first strand cDNA synthesis through reverse transcription of the primed RNAs may be purchased commercially from various sources, where such sources include Clontech, Sigma, Life Technologies, Amersham, Boehringer-Mannheim. Buffer mediums suitable for first strand synthesis will usually comprise buffering agents, usually in a concentration ranging from 10 to 100 $\mu$M which typically support a pH in the range 6 to 9, such as Tris-HCl, HEPES-KOH, etc.; salts containing monovalent ions, such as KCl, NaCl, etc., at concentrations ranging from 0–200 mM; salts containing divalent cations like $MgCl_2$, Mg(OAc) etc, at concentrations usually ranging from 1 to 10 mM; and additional reagents such as reducing agents, e.g. DDT, detergents, albumin and the like. The conditions of the reagent mixture will be selected to promote efficient first strand synthesis. Typically the set of primers will first be combined with the RNA sample at an elevated temperature, usually ranging from 50 to 95° C., followed by a reduction in temperature to a range between about 0 to 60° C., to ensure specific annealing of the primers to their corresponding RNAs in the sample. Following this annealing step, the primed RNAs are then combined with dNTPs and reverse transcriptase under conditions sufficient to promote reverse transcription and first strand cDNA synthesis of the primed RNAs. By using appropriate types of reagents, all of the reagents can be combined at once if the activity of the polymerase can be postponed or timed to start after annealing of the primer to the RNA.

In this embodiment, one of either the gene specific primers or dNTPs, preferably the dNTPs, will be labeled such that the synthesized cDNAs are labeled. By labeled is meant that the entities comprise a member of a signal producing system and are thus detectable, either directly or through combined action with one or more additional members of a signal producing system. Examples of directly detectable labels include isotopic and fluorescent moieties incorporated into, usually covalently bonded to, a nucleotide monomeric unit, e.g. dNTP or monomeric unit of the primer. Isotopic moieties or labels of interest include $^{32}P$, $^{33}P$, $^{35}S$, $^{125}I$, and the like. Fluorescent moieties or labels of interest include coumarin and its derivatives, e.g. 7-amino-4-methylcoumarin, aminocoumarin, bodipy dyes, such as Bodipy FL, cascade blue, fluorescein and its derivatives, e.g. fluorescein isothiocyanate, Oregon green, rhodamine dyes, e.g. texas red, tetramethylrhodamine, eosins and erythrosins, cyanine dyes, e.g. Cy3 and Cy5, macrocyclic chelates of lanthanide ions, e.g. quantum dye™, fluorescent energy transfer dyes, such as thiazole orange-ethidium heterodimer, TOTAB, etc. Labels may also be members of a signal producing system that act in concert with one or more additional members of the same system to provide a detectable signal. Illustrative of such labels are members of a specific binding pair, such as ligands, e.g. biotin, fluorescein, digoxigenin, antigen, polyvalent cations, chelator groups and the like, where the members specifically bind to additional members of the signal producing system, where the additional members provide a detectable signal either directly or indirectly, e.g. antibody conjugated to a fluorescent moiety or an enzymatic moiety capable of converting a substrate to a chromogenic product, e.g. alkaline phosphatase conjugate antibody; and the like. For each sample of RNA, one can generate labeled oligos with the same labels. Alternatively, one can use different labels for each physiological source, which provides for additional assay configuration possibilities, as described in greater detail below.

In a variation of the above embodiment, where desired one can generate labeled RNA instead of labeled first strand cDNA. In this embodiment, first strand cDNA synthesis is carried out in the presence of unlabeled dNTPs and unlabeled gene specific primers. However, the primers are optionally modified to comprise a promotor for an RNA polymerase, such as T7 RNA polymerase, T3 RNA polymerase, SP6 RNA polymerase, and the like. In this embodiment, following first strand cDNA synthesis, the resultant single stranded cDNA is then converted to double stranded cDNA, where the resultant double stranded cDNA comprises the anchor sequence comprising the promoter region. Conversion of the mRNA:cDNA hybrid following first strand synthesis can be carried out as described in Okayama & Berg, Mol. Cell. Biol. (1982) 2:161–170, and Gubler & Hoffman, Gene (1983) 25: 253–269, where briefly the RNA is digested with a ribonuclease, such as *E.coli* RNase H, followed by repair synthesis using a DNA polymerase like DNA polymerase I, etc., and *E.coli* DNA ligase. One may also employ the modification of this basic method described in Wu, R, ed., Methods in Enzymology (1987), vol. 153 (Academic Press). Next, the double stranded cDNA is contacted with RNA polymerase and dNTPs, including labeled dNTPs, to produce linearly amplified labeled ribonucleic acids. For cDNA lacking the anchor sequence comprising a promoter region, a polymerase that does not need a promoter region but instead can initiate RNA strand synthesis randomly from cDNA, such as core fragment of *E.Coli* RNA polymerase, may be employed.

In another embodiment of the subject invention, the labeled nucleic acid generation step comprises one or more enzymatic amplification steps in which multiple DNA copies of the initial RNAs present in the sample are produced, from which multiple copies of the initial RNA or multiple copies of antisense RNA (aRNA) may be produced, using the polymerase chain reaction, as described in U.S. Pat. No. 4,683,195, the disclosure of which is herein incorporated by reference, in which repeated cycles of double stranded DNA denaturation, oligonucleotide primer annealing and DNA polymerase primer extension are performed, where the PCR conditions may be modified as described in U.S. Pat. No. 5,436,149, the disclosure of which is herein incorporated by reference.

In one embodiment involving enzymatic amplification, the set of gene-specific primers are employed in the generation of the first strand cDNA, followed by amplification of the first strand cDNA to produce amplified numbers of labeled cDNA. In this embodiment, as a set of gene-specific primers is employed in the first strand synthesis step, only a representative proportion of the total RNA in the sample is amplified during the subsequent amplification steps.

Amplification of the first strand cDNA can be conveniently achieved by using a CAPswitch™ oligonucleotide as described in U.S. patent application Ser. No. 08/582,562, the disclosure of which is herein incorporated by reference. Briefly, the CAPswitch™ technology uses a unique CAPswitch™ oligonucleotide in the first strand cDNA synthesis followed by PCR amplification in the second step to generate a high yield of ds cDNA. When included in the first-strand cDNA synthesis reaction mixture, the CAPswitch™0 oligonucleotide serves as a short extended template. When reverse transcriptase stops at the 5' end of the mRNA template in the course of first strand cDNA synthesis it switches templates and continues DNA synthesis to the end of the CAPswitch™ oligonucleotide. The resulting ss cDNA incorporates at the 3' end, sequence which is complimentary to complete 5' end of the mRNA and the CAPswitch™ oligonucleotide sequence.

Of particular interest as the CAPswitch™ oligonucleotide are oligonucleotides having the following formula:

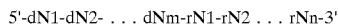

5'-dN1-dN2- . . . dNm-rN1-rN2 . . . rNn-3' wherein:
dN represents a deoxyribonucleotide selected from among dAMP, dCMP, dGMP and dTMP;

m represents an integer 0 and above, preferably from 10 to 50;

rN represents a ribonucleotide selected from the group consisting of AMP, CMP, GMP and UMP, preferably GMP; and n represents an integer 0 and above, preferably from 3 to 7.

The structure of the CAPswitch™ oligonucleotide may be modified in a number of ways, such as by replacement of 1 to 10 nucleotides with nucleotide analogs, incorporation of terminator nucleotides, such as 3'-amino NMP, 3'-phosphate NMP and the like, or non-natural nucleotides which can improve efficiency of the template switching reaction but still retain the main function of the CAPswitch™ oligonucleotide i.e. CAP-depended extension of full-length cDNA by reverse transcriptase using CAPswitch™ oligonucleotide as a template.

In using the CAPswitch™ oligonucleotide, first strand cDNA synthesis is carried out in the presence of a set of gene specific primers and a CAPswitch™ oligonucleotide, where the gene specific primers have been modified to comprise an arbitrary anchor sequence at their 5' ends. The first strand cDNA is then combined with primer sequences complementary to: (a) all or a portion of the CAPswitch™ oligonucleotide and (b) the arbitrary anchor sequence of the gene specific primers and additional PCR reagents, such as dNTPs, DNA polymerase, and the like, under conditions sufficient to amplify the first strand cDNA. Conveniently, PCR is carried out in the presence of labeled dNTPs such that the resultant, amplified cDNA is labeled and serves as the labeled or target nucleic acid. Labeled nucleic acid can also be produced by carrying out PCR in the presence of labeled primers, where either or both the CAPswitch™ oligonucleotide complementary primer and anchor sequence complementary primer may be labeled. In yet an alternative embodiment, instead of producing labeled amplified cDNA, one may generate labeled RNA from the amplified ds cDNA, e.g. by using an RNA polymerase such as E.coli RNA polymerase, or other RNA polymerases requiring promoter sequences, where such sequences may be incorporated into the arbitrary anchor sequence.

Instead of using the set of gene specific primers in the first strand cDNA synthesis step followed by subsequent amplification of only a representative fraction of the total number of distinct RNA species in the sample, one may also amplify all of the RNAs in the sample and use the set of gene specific primers to generate labeled nucleic acid following amplification. This embodiment may find use in situations where the RNA of interest to be amplified is known or postulated to be in small amounts in the sample.

In this embodiment, first strand synthesis is carried out using: (a) an oligo dT primer that usually comprises an arbitrary anchor sequence at its 5' end and (b) a CAPswitch™ oligonucleotide. During first strand synthesis the oligo(dT) anneals to the polyA tail of the mRNA in the sample and synthesis extends beyond the 3' end of the RNA to include the CAPswitch™ oligonucleotide, yielding a first strand cDNA comprising an arbitrary sequence at its 5' end and a region complementary to the CAPswitch™ oligonucleotide at its 3' end. The length of the dT primer will typically range from 15 to 30 nts, while the arbitrary anchor sequence or portion of the primer will typically range from 15 to 25 nt in length.

Following first strand synthesis, the cDNA is amplified by combining the first strand cDNA with primers that correspond at least partially to the anchor sequence and the CAPswitch™ oligonucleotide under conditions sufficient to produce an amplified amount of the cDNA. Labeled nucleic acid is then produced by contacting the resultant amplified cDNA with a set of gene specific primers, a polymerase and dNTPs, where at least one of the gene specific primers and dNTPs are labeled.

The labeled nucleic acids produced above provide a representation of the total RNA profile of the particular source from which the labeled nucleic acids are generated. Accordingly, the labeled nucleic acids find use in comparing the characteristic RNA profiles of different physiological sources and identifying differences in the RNA profiles between different physiological source. Comparison of the RNA profiles of two or more physiological sources finds particular use in methods of identifying differential gene expression in two physiological samples, such as cells or tissues derived from the same or different individual organisms, where the tissues may represent different diseased or normal states, different organ or tissue types, etc.

The labeled nucleic acids of the plurality of physiological sources may be compared in a number of different ways. Thus, one may compare the labeled nucleic acids from each source by separately resolving the labeled nucleic acids from each source under substantially identical electrophoretic conditions to yield an electrophoretic pattern of resolved bands for each of the different populations of labeled nucleic acids. The resultant electrophoretic patterns can then be resolved to identify differences between the labeled nucleic acid populations, which differences can then be attributed to differences in the RNA profiles of the each of the physiological sources, where such differences can, in turn, be attributed to difference in gene expression. See Liang & Pardee, Science (1992) 257: 967. Conveniently, electrophoretic separation under identical electrophoretic conditions can be achieved by running the labeled nucleic acids derived from each physiological source of interest in separate, side by side lanes on a slab gel. Automated electrophoretic machines as described in U.S. Pat. Nos. 5,410,412; 5,275,710; 5,217,591; and 5,104,512, the disclosures of which are herein incorporated by references, may be employed to resolve the labeled nucleic acids. In a modification of the above, where each set of labeled nucleic acids or targets of each physiological source has been labeled with a distinct and distinguishable label, the opportunity arises to resolve the nucleic acids in the same electrophoretic medium, e.g. the same column or in the same lane of a slab, thereby ensuring that the nucleic acids are resolved under identical electrophoretic conditions.

Alternatively, one may hybridize the labeled nucleic acids to predefined arrays of probe polymeric molecules stably associated with the surface of a substrate, where the probe polymeric molecules are capable of sequence specific base pair hybridization with complementary labeled target nucleic acids. A variety of different arrays which may be used are known in the art. The polymeric or probe molecules of the arrays may be oligonucleotides or hybridizing analogues or mimetics thereof, including: nucleic acids in which the phosphodiester linkage has been replaced with a substitute linkage, such as phophorothioate, methylimino, methylphosphonate, phosphoramidate, guanidine and the like; nucleic acids in which the ribose subunit has been substituted, e.g. hexose phosphodiester; peptide nucleic acids; and the like. The length of the probes will generally range from 10 to 1000 nts, where oligonucleotide probes usually range from 15 to 150 nts and more usually from 15 to 100 nts in length, and polynucleotide probes usually range in length from 150 to 1000 nts, where the polynucleotide probes may be single or double stranded, usually single stranded, and may be PCR fragments amplified from cDNA.

The probe molecules on the surface of the substrates will preferably correspond to known genes of the physiological source being analyzed so that positive hybridization events may be correlated to expression of a particular gene in the physiological source. Of particular interest are arrays of probes which correspond to a particular subset of the total genes expressed by a particular physiological source. For example, for analysis of human physiological sources, preferably the arrays of probes will correspond to a particular subset of all the expressed human genes, such as those genes associated with cell-cell communication, cancer related genes, etc. The arrays of probes may have sequences that are complementary to the template and/or non-template strands of the gene to which they correspond, depending on the nature of the labeled target nucleic acid to which they are to hybridize.

The substrates with which the probe molecules are stably associated may be fabricated from a variety of materials, including plastics, ceramics, metals, gels, membranes, glasses, and the like.

A variety of different methodologies have been developed for producing arrays of probes stably associated to the surface of a substrate. Representative methodologies include spotting methods, in which probes are immobilized or spotted on the surface of substrates as described in WO 95/35505 the disclosure of which is herein incorporated by reference, and methods in which the probes are synthesized or grown on the surface of the substrates, such as EP 0 373 203 B1 and U.S. Pat. No. 5,445,934, the disclosures of which are herein incorporated by reference. Arrays of probes spotted onto nylon membranes are described in Lennon & Lerach, Trends in Genetics (1991) 7:314–317; Gress et al., Mammalian Genome (1992) 3:609–619; Meier-Ewert et al., Nature (1993) 361:375–376; Nguyen et al., Genomics (1995) 29:207–216; Zhao et al., Gene (1995) 156:207–213; Takahashi et al., Gene (1995) 164:219–217; Milosavlijevic et al., Genome Research (1996) 6:132–141; Pietu et al., Genome Research (1996) 6:492–503; and Drmanac, Science (1993) 260:1649–1652. Arrays of probes spotted onto the surface of modified microscope glass slides are described in Shena et al., Science (1995) 270: 467–470 and Shalon et al., Genome Research (1996) 6: 639–645. Arrays in which the probes have been grown on the surface of a substrate are described in Lockhart et al., Nature Biotechnology (1996) 14:1675.

Of particular interest for use in the analysis of differential gene expression in human physiological sources are the arrays of subsets human cDNAs sold under the trademark Atlas™ by Clontech and described in CLONTECHniques (April, 1997) 12:4–7.

In analyzing the differences in the population of labeled nucleic acids generated from two or more physiological sources using the arrays described above, each population of labeled nucleic acids are separately contacted to identical probe arrays under conditions of hybridization, preferably under stringent hybridization conditions, such that labeled nucleic acids hybridize to their complementary probes on the substrate surface. Suitable hybridization conditions are well known to those of skill in the art and reviewed in Maniatis et al, supra and WO 95/21944.

As with the electrophoretic analysis, where all of the target sequences comprise the same label, different arrays will be employed for each physiological source (where different could include using the same array at different times). Alternatively, where the labels of the targets are different and distinguishable for each of the different physiological sources being assayed, the opportunity arises to use the same array at the same time for each of the different target populations.

In one preferred embodiment of assays using arrays, the number of gene specific primers used to generate the target will be chosen in view of the number of distinct probes present on the surface of the substrate of the array. In such instances, the number of gene specific primers in the set will not vary by more than 10 fold from the number of distinct probes, usually by not more than 5 fold and more usually by not more than 2 fold from the number of distinct probes in the array.

Following hybridization, non-hybridized labeled nucleic acid is removed from the support surface, conveniently by washing, generating a pattern of hybridized nucleic acid on the substrate surface. A variety of wash solutions are known to those of skill in the art and may be used.

The resultant hybridization patterns of labeled nucleic acids may be visualized or detected in a variety of ways, with the particular manner of detection being chosen based on the particular label of the nucleic acid, where representative detection means include scintillation counting, autoradiography, fluorescence measurement, calorimetric measurement, light emission measurement and the like.

Following detection or visualization, the hybridization patterns may be compared to identify differences between the patterns. Where arrays in which each of the different probes corresponds to a known gene are employed, any discrepancies can be related to a differential expression of a particular gene in the physiological sources being compared.

The subject methods find use in, among other applications, differential gene expression assays. Thus, one may use the subject methods in the differential expression analysis of: (a) diseased and normal tissue, e.g. neoplastic and normal tissue, (b) different tissue or subtissue types; and the like.

Also provided are kits for use in carrying out the subject methods, e.g. generating populations of labeled nucleic acids, performing differential gene expression analysis and the like. The kits according to the subject invention include at least the set of gene specific primers that are employed to generate the labeled oligonucleotides. Of particular interest are kits comprising a set of primers selected from the primers identified as SEQ ID NO: 01–1372, where in these kits of particular interest, at least twenty, usually at least 50 and more usually at least 100 of the gene specific primers in the kit will be selected from this group of primers identified as SEQ ID NO: 01–1372. The kits may further comprise one or more additional reagents employed the various methods, such as additional non-gene specific primers sequences, such as SEQ ID NO: 1373 to 1375, dNTPs and/or rNTPs, which may be either premixed or separate, one or more uniquely labeled dNTPs and/or rNTPs, such as biotinylated or Cy3 or Cy5 tagged dNTPs, enzymes, such as reverse transcriptases, DNA polymerases, and the like, various buffer mediums, e.g. hybridization and washing buffers, prefabricated probe arrays, labeled probe purification reagents and components, like spin columns, etc., signal generation and detection reagents, e.g. streptavidin-alkaline phosphatase conjugate, chemifluorescent or chemiluminescent substrate, and the like.

The following examples are offered by way of illustration and not by way of limitation. Except where noted otherwise, all percentages are by weight and all solvent mixture proportions are by volume.

EXPERIMENTAL

Example 1

Generation of $^{32}$P-labeled oligonucleotides during first strand cDNA synthesis Step A. cDNA synthesis/Labeling Procedure 1 μg of polyA+RNA was converted into $^{32}$P-labeled first-strand cDNA as follows. A sufficient volume of master mix for all labeling reactions and 1 extra reaction was prepared as follows to ensure sufficient volume. For each 10-μl labeling reaction, the following reagents were mixed:

| | |
|---|---|
| 2 μl | 5X First-strand buffer (250 μM Tris-HCl pH 8.3; 375 mM KCl; 15 mM MgCl$_2$) |
| 1 μl | 10XdNTP mix (500 μM dGTP, 500 μM dCTP, 500 μM dTTP, 5 μM dATP) |
| 4 μl | [α-$^{32}$P] dATP (Amersham, 3000 Ci/mmol, 10 mCi/ml) |
| 1 μl | MMLV reverse transcriptase (Amersham, 200 units/μl) |
| 8 μl | Final volume |

Next, the following reagents were combined in a 0.5-ml PCR test tube:

| | |
|---|---|
| 1 μg (1–2 μl) | polyA + RNA sample |
| 1 μl | 10x gene-specific primers mix (0.2 μM of each oligonucleotide ID No. 2, 4, 6, 8, 10, 12, . . . 1372) |

As a control, in separate test tube were mixed 1 μg of polyA+RNA sample with 1 ul of oligo dT primer (CDS1, ID No.1373).

For each tube ddH$_2$O was added to a final volume of 3 ul and the contents were mixed and spun briefly in a microcentrifuge. The tubes were then incubated in a preheated PCR thermocycler at 70° C. for 2 min. The temperature in thermocycle was reduced down to 50° C. and the tube contents were incubated for 2 min. 8 μl of master mix as prepared above were added to each reaction test tube. The contents of the test tubes were then mixed by gentle pipetting. The tubes were then incubated in a PCR thermocycler for 20 min at 50° C. The reaction was then stopped by adding 1 μl of 10× termination mix (0.1M EDTA, 1 mg/ml glycogen).

Step B. Column Chromatography

The $^{32}$P-labeled cDNAs were separated from unincorporated $^{32}$P-labeled nucleotides and small (<0.1-kb) cDNA fragments using the following procedure for each test tube. A CHROMA SPIN-200 column (CLONTECH, Palo Alto, Calif.) was placed into a 1.5-ml microcentrifuge tube, the water was allowed to drain through the column by gravity flow until the surface of the gel beads emerged in the column matrix. The sample was then applied to the center of the gel bed's flat surface and allowed to be fully absorbed into the resin bed. 25 μl of ddH$_2$O were then applied and allowed to completely drain out of the column. 200 μl of ddH$_2$O were then applied and allowed to completely drain out of the column until there was no liquid left above the resin bed. The column was then transferred to a clean 1.5-ml microcentrifuge tube.

To collect the first fraction, 100 μl of ddH$_2$O were added to the column and allowed to completely drain out of the column. The second, third and fourth fractions were collected in analogous fashion. The tubes with fractions 1–4 were then placed in scintillation counter empty vials, and Cerenkov counts for each fraction were obtained in the tritium channel. The fractions which showed the highest Cerenkov counts were pooled.

Example 2

Generation of Cy3-labeled hybridization polynucleotide target from total RNA using preamplification step CAPswitch™ technology can be effectively used for construction cDNA libraries using as a template 10–100 ng of total RNA. Any conventional procedure well known in art can be used to purify this small amount of total RNA from 10–50 mg of "difficult" cells or tissues, like human biopsy tissues, pathogenic microorganisms, tissues at different developmental stages etc.

Step A. First-Strand Synthesis—Template Switching 10 pmol of cDNA synthesis primer (oligo dT primer)

CDS1 (ID No. 1373): 5'-d(TCTAGAATTCAGCGGCCGC(T)30VN) -3'

(where V=G or A or C; N=G or A or T or C)

and 10 pmol of CAPswitch™ oligonucleotide (CSO1):

CSO1 (ID No. 1374): 5'-d(CTAATACGACTCACTATAGGGC)r(GGG)-3' were annealed to 100 ng of human skeletal muscle Total RNA (CLONTECH), in a volume of 5 ml of deionized water, by heating the mixture for 2 min at 70° C., followed by cooling on ice for 2 min. First-strand cDNA synthesis was then initiated by mixing the annealed primer-RNA with 200 units of M-MLVreverse transcriptase (Amersham) in a final volume of 10 μl, containing 50 mM Tris-HCl (pH 8.3 at 22° C.), 75 mM KCl, 6 mM MgCl2, 1 mM DTT, 1 mM of each dATP, dGTP, dCTP and dTTP. The first-strand cDNA synthesis-template switching reaction was incubated at 42° C. for 1.5 hr in an air incubator and then cooled on ice.

Step B. Generation of full-length cDNA by PCR

PCR amplification of full-length cDNA was performed using the Advantage KlenTaq Polymerase Mix (CLONTECH). Amplification was conducted in a 100-µl volume containing 2 µl of first-strand cDNA, 40 mM Tricine-KOH (pH 9.2 at 22° C.), 3.5 mM Mg(OAc)$_2$, 10 mM KOAc, 75 µg/ml BSA, 200 µM of each dATP, dGTP, dCTP and dTTP, 0.2 µM of each CAPswitch™ primer (CSP1, ID No. 1375) and CDS1 primer and 2 µl of KlenTaq Polymerase mix. Temperature parameters of the PCR reactions were as follows: 1 min at 95° C. followed by 20–22 cycles of 95° C. for 15 sec and 68° C. for 5 min; followed by a 10-min final extension at 68° C. PCR products were examined on 1.2% agarose/EtBr gels in 1× TBE buffer. As a DNA size marker, a 1 Kb DNA ladder was used. ds cDNA was then precipitated by addition of a half volume of 4M ammonium acetate (about 35 ml) and 3.7 volumes of 95% ethanol (about 260 ml). After vortexing, the tube was immediately centrifuged at 14,000 r.p.m. in a microcentrifuge for 20 min. The pellet was washed with 80% ethanol without vortexing, centrifuged as above for 10 min, air dried, and dissolved in 10 µl of deionized water. Yield of ds cDNA after amplification step is about 5 µg.

Step C. Labeling of cDNA by Cy3-dCTP.

5 µl of ds cDNA (2.5 µg) generated after amplification step were mixed with 4 µl of a mixture of 686 antisense gene-specific primers (0.1 µM each; ID No. 2,4,6,8,10, 12, ... 1372) in a 0.5-ml PCR test tube, boiled at 100° C. for 5 min and quickly cooled in the ice. To the denatured DNA/gene-specific primer mix was added 5 µl of 5× reaction buffer (250 mM Tris-HCl, pH 7.5, 50 mM MgCl$_2$, 5 mM DTT, 250 µg/ml BSA), 10 µl 2.5× dNTP mix (500 µM each of dATP, dGTP and dTTP, 350 µM dCTP and 150 µM Cy3-dCTP (Amersham)), 0.5 µl of [α-$^{32}$P]dCTP (Amersham, 3000 Ci/mmol, 10 mCi/ml) and 0.5 µl of Advantage KlenTaq mix (Clontech). The mixture was incubated at 68° C. for 10 min and the reaction stopped by adding 1 µl of 10× termination mix (0.1M EDTA, 1 mg/ml glycogen).

Step D. Column Chromatography

To purify the Cy3-labeled cDNAs from unincorporated Cy3-labeled nucleotides and small (<0.1-kb) cDNA fragments, a CHROMA SPIN-200 column (CLONTECH) was placed into a 1.5-ml microcentrifuge tube, water was drained from the column and the sample was applied to the center of the gel bed's flat surface and allowed to be fully absorbed into the resin bed. 25 µl of ddH$_2$O were applied and allowed to completely drain out of the column. 200 µl of ddH$_2$O were applied and the buffer was allowed to completely drain out of the column until there was no liquid left above the resin bed. The column was then transferred to a clean 1.5-ml microcentrifuge tube.

To collect the first fraction, 100 µl of ddH$_2$O was added to the column and allowed to completely drain out of the column. The second, third and fourth fractions were collected in analogous fashion. The tubes with fractions 1–4 were placed in scintillation counter empty vials, and Cerenkov counts were obtained for each fraction in the tritium channel. The fractions (usually fractions 2–3) which showed the highest Cerenkov counts were pooled, and other fractions were discarded.

Example 3

Generation of cDNA array probe immobilized on nylon membrane 686 cDNA fragments corresponding 686 different human genes were amplified from quick-clone cDNA (CLONTECH) in 686 separate test tubes using a combination of sense and antisense gene-specific primers: SEQ ID Nos. 1+2, 3+4, 5+6, 7+8, ... 1371+1372. Amplification was conducted in a 100-µl volume containing 2 µl of mixture of 10 Quick-clone cDNA from placenta, brain, liver, lung, leukocytes, spleen, skeletal muscle, testis, kidney and ovary (CLONTECH), 40 mM Tricine-KOH (pH 9.2 at 22° C.), 3.5 mM Mg(OAc)$_2$, 10 mM KOAc, 75 µg/ml BSA, 200 µM of each dTAP, dGTP, dCTP and dTTP, 0.2 µM of each sense and antisense gene-specific primers and 2 µl of KlenTaq Polymerase mix. Temperature parameters of the PCR reactions were as follows: 1 min at 95° C. followed by 20–35 cycles of 95° C. for 15 sec and 68° C. for 2 min; followed by a 10-min final extension at 68° C. PCR products were examined on 1.2% agarose/EtBr gels in 1× TBE buffer. As a DNA size marker we used a 1 Kb DNA Ladder. ds cDNA was then precipitated by addition of a half volume of 4M ammonium acetate (about 35 ul) and 3.7 volumes of 95% ethanol (about 260 ul). After vortexing, the tube was immediately centrifuged at 14,000 r.p.m. in a microcentrifuge for 20 min. The pellet was washed with 80% ethanol without vortexing, centrifuged as above for 10 min, air dried, and dissolved in 10 µl of deionized water. Yield of ds cDNA after amplification step was about 5 µg. The ds cDNA was denatured by adding 1 µl of 10× denaturing solution (1M NaOH, 10 mM EDTA) and incubating at 65° C. for 20 min. All cDNA probes were transferred in 384-well plate and loaded on positively charged nylon membrane (Schleher & Schull) using 384 pin tool and Biomek 2000 (Beckman) robot.

Example 4

Hybridization $^{32}$P-labeled cDNA Target with cDNA ARRAY

A solution of ExpressHyb™ (CLONTECH) and sheared salmon testes DNA (Sigma) was prepared by prewarming 15 ml of ExpressHyb™ at 50–60° C., heating 1.5 mg of sheared salmon testes DNA at 95–100° C. for 5 min followed by chilling quickly on ice, and combining the resultant heat-denatured sheared salmon testes DNA with the prewarmed ExpressHyb™.

A cDNA ARRAY (Atlas™Human cDNA Expression Array, Clontech, Palo Alto, Calif.) was then placed in a hybridization bottle and 10 ml of the solution prepared above was added to the bottle. Prehybridization was performed for 30 min with continuous agitation at 72° C. Labeled cDNA probe (Example 1, about 200 ul, total about 2–5×10$^6$ cpm) with 1/10th of the total volume (about 22 ul) of 10× denaturing solution (1M NaOH, 10 mM EDTA) was mixed and incubated at 65° C. for 20 min. 5 µl (1 µg/ul) of human Cot-1 DNA was then added, and an equal volume (about 225 µl) of 2× Neutralizing solution (1M NaHPO4, pH 7.0) was added and incubation continued at 65° C. for 10 min. The mixtures were then combined and thoroughly mixed.

The prehybridization solution was then replaced with the solution comprising the labeled oligonucleotide as prepared above and allowed to hybridize overnight with continuous agitation at 65° C. Following hybridization, the hybridization solution was carefully removed and discarded, replaced with 200 ml of Wash Solution 1 (2× SSC, 1% SDS). The ARRAY was washed for 20 min with continuous agitation at 65° C. Washing was repeated four times.

Two additional 20-min washes were then performed in 200 ml of prewarmed Wash Solution 2 (0.1× SSC, 0.5%

SDS) with continuous agitation at 65° C. Using forceps, cDNA ARRAY was removed from the container and excess wash solution was removed by shaking.

The damp membrane was immediately wrapped in plastic wrap, mounted on Whatman paper (3 mm Chr). Exposed to x-ray film at −70° C. with an intensifying screen.

Example 5

Comparison Between Using Sets of Gene Specific Primers and oligo dT

Figure 1B:
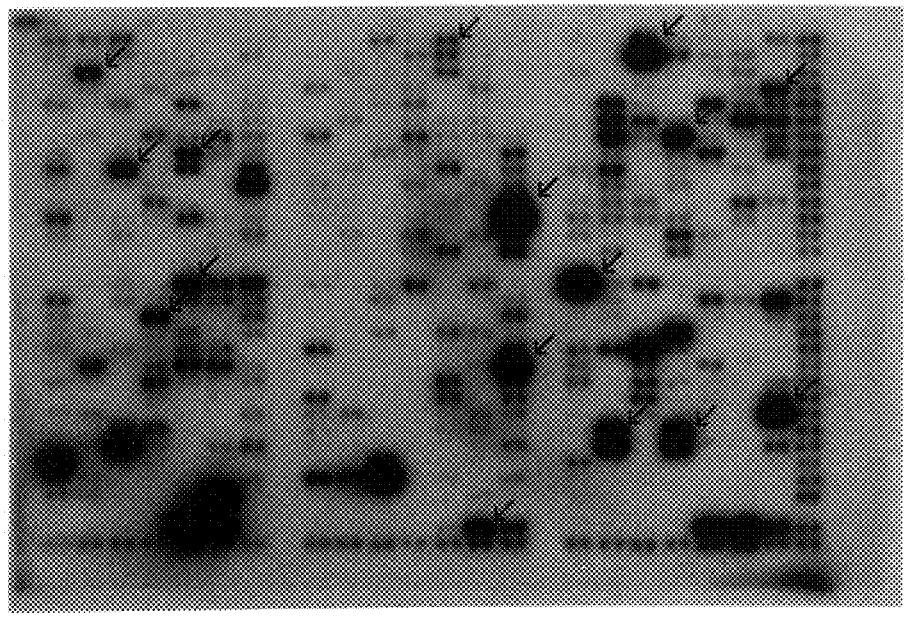

FIG. 1 illustrates the effectiveness of using $^{32}$P-labelled polynucleotide target generated using sets of gene specific primers according to the subject invention in hybridization with a cDNA array of 588 probes immobilized on a nylon membrane.

$^{32}$P-labeled cDNA target were synthesized by M-MLV reverse transcriptase from a mixture 588 antisense gene-specific primers (B) or oligo dT(A) using placenta polyA+ RNA as a template as described in Example 1. Primer extension products generated by reverse transcription were purified by gel filtration as described in Example 1 and hybridized separately with two cDNA arrays comprising 588 human genes under identical conditions as described in Example 4. The arrows in pattern B indicate the position of signals which can be detected by using cDNA target generated using the set of gene specific primers but can not be detected by using conventional target generated with oligo dT primers (pattern A). The level of non-specific background detected as signal generated by membrane alone outside of the regions with immobilized probes generated by target generated using oligo dT primers was significantly higher (filter A) in comparison with the background generated by the target generated by using the sets of gene specific primers (filter B).

SEQUENCES

The following Table 1 list provides the sequences referred to elsewhere in this application:

TABLE 1

| SEQUENCE DESCRIPTION | | Length |
|---|---|---|
| INTERLEUKIN-7 RECEPTOR | | |
| SEQ ID NO.1 | CAACTGCCCATCTGAGGATGTAGTCG | 26 |
| SEQ ID NO.2 | TTGTCGCTCACGGTAAGTTCAGTCTGG | 27 |
| HUIFN-GAMMA | | |
| SEQ ID NO.3 | ATCCAAAAGAGTGTGGAGACCATCAAGG | 28 |
| SEQ ID NO.4 | TTTTCGCTTCCCTGTTTTAGCTGCTGGC | 28 |
| INTERLEUKIN 7 | | |
| SEQ ID NO.5 | TAGGTATATCTTTGGACTTCCTCCCC | 26 |
| SEQ ID NO.6 | AAGAAATTGCCTCAACTTGCGAGCAGC | 27 |
| C-MYC | | |
| SEQ ID NO.7 | GCTCCTGGCAAAAGGTCAGAGTCTGG | 26 |
| SEQ ID NO.8 | GGGGCTGGTGCATTTTCGGTTGTTGC | 26 |
| INTERLEUKIN-2 RECEPTOR | | |
| SEQ ID NO.9 | GGTCACACTGGTAGAACGTAACCACG | 26 |
| SEQ ID NO.10 | CTCGAACTCCTGGGCTCAAGCAATCC | 26 |
| INTERLUEKIN 2 | | |
| SEQ ID NO.11 | CAGGATGCTCACATTTAAGTTTTACATGC | 29 |
| SEQ ID NO.12 | ATCCATCTGTTCAGAAATTCTACAATGG | 28 |
| EPIDERMAL GROWTH FACTOR RECEPTOR | | |
| SEQ ID NO.13 | ATGAATCGGCAACGAGATGGAGGTCC | 26 |
| SEQ ID NO.14 | GGAGCAGGAGTTACGTTCTCTGGGC | 25 |
| INSULIN-LIKE GROWTH FACTOR 1 RECEPTOR | | |
| SEQ ID NO.15 | GGCATACCTCAACGCCAATAAGTTCG | 26 |
| SEQ ID NO.16 | CTTGTTCTCCTCGCTGTAGTAGAAGG | 26 |
| INSULIN-LIKE GROWTH FACTOR II | | |
| SEQ ID NO.17 | CAGCCGTGGCATCGTTGAGGAGTGC | 25 |
| SEQ ID NO.18 | TGGACTGCTTCCAGGTGTCATATTGG | 26 |
| INDUCIBLE NITRIC OXIDE SYNTHASE | | |
| SEQ ID NO.19 | GGCTGCCAAGCTGAAATTGAATGAGG | 26 |
| SEQ ID NO.20 | AATCCAGGGTGCTACTTGTTAGGAGG | 26 |

TABLE 1-continued

| SEQUENCE DESCRIPTION | | Length |
|---|---|---|
| GLUTAMATE RECEPTOR SUBUNIT | | |
| SEQ ID NO.21 | GTCCACCATGAATGAGTACATTGAGC | 26 |
| SEQ ID NO.22 | TGTAGCAGAACTCGATTAAGGCAACC | 26 |
| C-FMS | | |
| SEQ ID NO.23 | TCACTTCTCCAGCCAAGTAGCCC | 23 |
| SEQ ID NO.24 | AGGATGCCAGGGTAGGGATTCAGC | 24 |
| TUMOR NECROSIS FACTOR RECEPTOR | | |
| SEQ ID NO.25 | GCCACTACACTCCAGCCTGAGC | 22 |
| SEQ ID NO.26 | CTGCCCTGTGATGCCAAGGAAGCC | 24 |
| P53-ASSOCIATED GENE | | |
| SEQ ID NO.27 | GGAGATATGTTGTGAAAGAAGCAGTAGC | 28 |
| SEQ ID NO.28 | GAAGTGCATTTCCAATAGTCAGCTAAGG | 28 |
| PLATELET-DERIVED GROWTH FACTOR B CHAIN | | |
| SEQ ID NO.29 | GCACACGCATGACAAGACGGC | 21 |
| SEQ ID NO.30 | AGGCAGGCTATGCTGAGAGGTCC | 23 |
| GLYCERALDEHYDE-3-PHOSPHATE DEHYDROGENASE | | |
| SEQ ID NO.31 | GGCTCTCCAGAACATCATCCCTGC | 24 |
| SEQ ID NO.32 | GGGTGTCGCTGTTGAAGTCAGAGG | 24 |
| TRANSFERRIN RECEPTOR | | |
| SEQ ID NO.33 | GGGACTTTGTATAGAAGGTTTTGGGG | 26 |
| SEQ ID NO.34 | TACGTGTGCGTAACACCCGAACCAGG | 26 |
| INTERLEUKIN 1 ALPHA | | |
| SEQ ID NO.35 | TCATAACAATTTTAGGAGGACCAGAGC | 27 |
| SEQ ID NO.36 | CATTTCGTGCTTTGCCTTCATCTTGAGG | 28 |
| INTERLEUKIN 1 BETA | | |
| SEQ ID NO.37 | CTTCTTCGACACATGGGATAACGAGG | 26 |
| SEQ ID NO.38 | GAGAGGTGCTGATGTACCAGTTGGGG | 26 |
| INTERLEUKIN 3 | | |
| SEQ ID NO.39 | GAGGAAACTGACGTTCTATCTGAAAACC | 28 |
| SEQ ID NO.40 | TCTGATGCCGCAGGAAAAGGTGAAATGC | 28 |
| INTERLEUKIN 4 | | |
| SEQ ID NO.41 | GACCGTAACAGACATCTTTGCTGC | 24 |
| SEQ ID NO.42 | GTACTCTGGTTGGCTTCCTTCACAGG | 26 |
| INTERLEUKIN BSF-2 | | |
| SEQ ID NO.43 | GGAGAAGATTCCAAAGATGTAGCCGC | 26 |
| SEQ ID NO.44 | CTGGCATTTGTGGTTGGGTCAGGGG | 25 |
| TUMOR NECROSIS FACTOR | | |
| SEQ ID NO.45 | TCACCCACACCATCAGCCGCATCG | 24 |
| SEQ ID NO.46 | GGGAAGGTTGGATGTTCGTCCTCC | 24 |
| LYMPHOTOXIN(TNF-BETA) | | |
| SEQ ID NO.47 | TCTTGCCCACAGCACCCTCAAACC | 24 |
| SEQ ID NO.48 | AGGCTTTCCCAGAGAAGACCACC | 23 |
| T-CELL SURFACE GLYCOPROTEIN T4 | | |
| SEQ ID NO.49 | ATGCTGGCTCTGGAAACCTCACC | 23 |
| SEQ ID NO.50 | TCCCGCTTCGAGACCTTTGCCTCC | 24 |
| T-CELL DIFFERENTIATION ANTIGEN | | |

TABLE 1-continued

| SEQUENCE DESCRIPTION | | Length |
|---|---|---|
| SEQ ID NO.51 | GCAAGTCAGGGTTGGAGCAGTACG | 24 |
| SEQ ID NO.52 | GCAAGGGCTGGGAGAGCAATTCCG | 24 |
| INTERLEUKIN 6 RECEPTOR | | |
| SEQ ID NO.53 | GGACGGCTTTTACTTAAAGCCCAAGG | 26 |
| SEQ ID NO.54 | ATCTTCCCTAGTTACCCAGGTTCAGC | 26 |
| INTERLEUKIN 5 | | |
| SEQ ID NO.55 | TTTCAGAGCCATGAGGATGCTTCTGC | 26 |
| SEQ ID NO.56 | AGTTTGACTCTCCAGTGTGCCTATTCCC | 28 |
| INTERFERON BETA-1 | | |
| SEQ ID NO.57 | TTTCAGACAAGATTCATCTAGCACTGG | 27 |
| SEQ ID NO.58 | ACATTAGCCATGAGTCACTTAAACAGC | 27 |
| GM-CSF | | |
| SEQ ID NO.59 | GGGAGCATGTGAATGCCATCCAGG | 24 |
| SEQ ID NO.60 | GTATCAGGGTCAGTGTGCCCAGGG | 24 |
| TRANSFORMING GROWTH FACTOR-ALPHA | | |
| SEQ ID NO.61 | GAAGAGCCCAGAGGAGGAGTTTGG | 24 |
| SEQ ID NO.62 | GTGGACTCAGACACCAACTGCTGC | 24 |
| INTERFERON ALPHA-C | | |
| SEQ ID NO.63 | AGCTACAAATCCATCTGTTCTCTGGGC | 27 |
| SEQ ID NO.64 | CCAACCTCCTGTATCACACATGCTTCC | 27 |
| TGF-BETA | | |
| SEQ ID NO.65 | GAGATGGCAGGGACTCTGATAACACC | 26 |
| SEQ ID NO.66 | AAAGTGCTAGGATTACAGGCGTGAGC | 26 |
| G-CSF | | |
| SEQ ID NO.67 | TGCAATGGGCACTGGGATGAGCCG | 24 |
| SEQ ID NO.68 | CGGTGATGTTCGGGAGTCAAACC | 23 |
| NF-KAPPA-B | | |
| SEQ ID NO.69 | CCTACGATGGAACCACACCCCTGC | 24 |
| SEQ ID NO.70 | TCCACCAGCTCTCTGACTGTACCC | 24 |
| C-MYB | | |
| SEQ ID NO.71 | CCAGTCAAGCTCGTAAATACGTGAATGC | 28 |
| SEQ ID NO.72 | ACTTGGTCGTGCTCTCAACTGTTGTACC | 28 |
| P53 CELLULAR TUMOR ANTIGEN | | |
| SEQ ID NO.73 | GCCCCTCCTCAGCATCTTATCCG | 23 |
| SEQ ID NO.74 | TCCCAGGACAGGCACAAACACGC | 23 |
| TRANSFORMING GROWTH FACTOR-BETA-2 | | |
| SEQ ID NO.75 | TCTAGGGTGGAAATGGATACACGAACC | 27 |
| SEQ ID NO.76 | TGTTACAAGCATCATCGTTGTCGTCG | 26 |
| C-KIT | | |
| SEQ ID NO.77 | CAGCTACCGCGATGAGAGGCGCTCGC | 26 |
| SEQ ID NO.78 | ACAGCGGACCAGCGTGTCGTTGTCTTCT | 28 |
| KIDNEY EPIDERMAL GROWTH FACTOR | | |
| SEQ ID NO.79 | CTCTCCTATCAGCTAACCCGTTATGG | 26 |
| SEQ ID NO.80 | ACTGACCAAACCAGTGTGACTGTCTGC | 27 |
| INTERFERON-ALPHA RECEPTOR | | |
| SEQ ID NO.81 | TCCTCGGGAGATATTTCAAACATTTGG | 27 |

TABLE 1-continued

| SEQUENCE DESCRIPTION | | Length |
|---|---|---|
| SEQ ID NO.82 | CTGGCTTTAATCCTAAACCATGTAAGGG | 28 |
| INTERLEUKIN 10 | | |
| SEQ ID NO.83 | GCCGTGGAGCAGGTGAAGAATGCC | 24 |
| SEQ ID NO.84 | AGCTATCCCAGAGCCCCAGATCCG | 24 |
| INTERLEUKIN 2 RECEPTOR BETA CHAIN | | |
| SEQ ID NO.85 | CCTTGGGAGCAGGTGCTTGTGG | 22 |
| SEQ ID NO.86 | AAGGAGACCGACTTGCAGAGAGG | 23 |
| INTERLEUKIN 3 RECEPTOR | | |
| SEQ ID NO.87 | GGTCCTCCTTTGGCTCACGCTGC | 23 |
| SEQ ID NO.88 | GGCTTCCCACTGTTCTCAGGG | 21 |
| INTERLEUKIN 4 RECEPTOR | | |
| SEQ ID NO.89 | GAGGGTCTCTTAGGTGCATGTCC | 23 |
| SEQ ID NO.90 | ACTCTCATGGGATGTGGCGAGCCC | 24 |
| INTERLEUKIN 5 RECEPTOR ALPHA | | |
| SEQ ID NO.91 | ATCCTCAGCAAAGGGCGTGACTGG | 24 |
| SEQ ID NO.92 | CCTGCCTCTCTGCACATGGAGC | 22 |
| BETA ACTIN | | |
| SEQ ID NO.93 | CTACGTCGCCCTGGACTTCGAGC | 23 |
| SEQ ID NO.94 | GATGGAGCCGCCGATCCACACGG | 23 |
| INTERFERON ALPHA/BETA RECEPTOR | | |
| SEQ ID NO.95 | CGCCTGATTACACAGATGAATCTTGC | 26 |
| SEQ ID NO.96 | TTCCCTCTGACTGTTCTTCAATGACG | 26 |
| CYTOKINE HUMIG | | |
| SEQ ID NO.97 | GCTCTTTCCTGGCTACTCCATGTTGG | 26 |
| SEQ ID NO.98 | TGAGTTTCGATAAGGATCTCGGTGGC | 26 |
| THYROID-STIMULATING HORMONE RECEPTOR | | |
| SEQ ID NO.99 | GATCTACATCACAGTCCGAAATCCGC | 26 |
| SEQ ID NO.100 | TGTTGTGGAGACCCTGCCTCATGTCG | 26 |
| CHOLINERGIC RECEPTOR, NICOTINIC, ALFA POLIPEPTIDE 3 | | |
| SEQ ID NO.101 | ACTGAGACCATCCCTTCCACCTCG | 24 |
| SEQ ID NO.102 | GGTAACCCTCCTTGCAGCCTTTGG | 24 |
| INTERLEUKIN 2 RECEPTOR, GAMMA POLIPEPTIDE | | |
| SEQ ID NO.103 | GTTTCGTGTTCGGAGCCGCTTTAACC | 26 |
| SEQ ID NO.104 | GGCAGAGTCGTTCACTGTAGTCTGGC | 26 |
| ANDROGEN RECEPTOR | | |
| SEQ ID NO.105 | GCATGGTGAGCAGAGTGCCCTATCC | 25 |
| SEQ ID NO.106 | ACAGGTACTTCTGTTTCCCTTCAGCG | 26 |
| CILIARY NEUROTROPIC FACTOR RECEPTOR | | |
| SEQ ID NO.107 | GCCGCTCCAACACTTACCCCAAGG | 24 |
| SEQ ID NO.108 | GGTGATAGCTGTGGCATTGTGGC | 23 |
| ADENOSINE RECEPTOR | | |
| SEQ ID NO.109 | CGCCCCTCTCTGGCTCATGTACC | 23 |
| SEQ ID NO.110 | CTGACCTGCTCTCCGTCACTGCC | 23 |
| INTERFERON, GAMMA RECEPTOR | | |
| SEQ ID NO.111 | CTCACGCAGAAGGAAGATGATTGTGACG | 28 |
| SEQ ID NO.112 | GAAAGAGTAGTAAAGCAGCAACAACTGG | 28 |

TABLE 1-continued

| SEQUENCE DESCRIPTION | | Length |
|---|---|---|
| ERYTHROPOIETIN RECEPTOR | | |
| SEQ ID NO.113 | ACACTGTGCCCTGAGCTGCCCCC | 23 |
| SEQ ID NO.114 | ATGCCCCTGCTCCTGAGAGAGGC | 23 |
| ADENOSINE RECEPTOR A1 | | |
| SEQ ID NO.115 | AATCTGAGTGCGGTGGAGCGGGCCTG | 26 |
| SEQ ID NO.116 | GGGTTCATGGCCGAGTTGCCGTGCG | 25 |
| ORPHAN HORMONE NUCLEAR RECEPTOR | | |
| SEQ ID NO.117 | TCCGTTCCCTGCCCATTGAAGACC | 24 |
| SEQ ID NO.118 | GAGTCAGTGCCATCTCCTGTTGC | 23 |
| ADENOSINE RECEPTOR A3 | | |
| SEQ ID NO.119 | TCTTGTTTGCTCTGTCATGGCTGC | 24 |
| SEQ ID NO.120 | GTGGAGTGGGGGAGATATAATTGG | 24 |
| CALCITONINE RECEPTOR | | |
| SEQ ID NO.121 | TTATCATCATCCACCTGGTTGAAGTAGTACCC | 32 |
| SEQ ID NO.122 | GTCACAAGCACCCGGACAATGTTGAGCAAA | 30 |
| COAGULATING FACTOR II RECEPTOR | | |
| SEQ ID NO.123 | AGGACTCCAGGCAGCAGACACATGC | 25 |
| SEQ ID NO.124 | TGATCTACTTTGCTCTTGAGGGCAGG | 26 |
| TRANSFORMING GROWTH FACTOR BETA RECEPTOR III | | |
| SEQ ID NO.125 | TAAACATGACCCTGGGCTTCTGTACC | 26 |
| SEQ ID NO.126 | TCTCCTCACTGGTTCTACTATCTGGC | 26 |
| INTERLEUKIN 9 RECEPTOR | | |
| SEQ ID NO.127 | GCACAGGGATCACATTGTCGGGG | 23 |
| SEQ ID NO.128 | GAGGGGCTGGAAGAACATCGC | 21 |
| INTERLEUKIN 10 RECEPTOR | | |
| SEQ ID NO.129 | GGCTTCCAGCTCAGAACCCATCC | 23 |
| SEQ ID NO.130 | AACACCAACAAGGCAGGGACCCC | 23 |
| NERVE GROWTH FACTOR RECEPTOR | | |
| SEQ ID NO.131 | GACTTCGACTGTGACCTGTGGGG | 23 |
| SEQ ID NO.132 | GGGTTCCATCTCAGCTCAAGGGG | 23 |
| VITRONECTIN RECEPTOR, ALPHA SUBUNIT | | |
| SEQ ID NO.133 | TCGACAGGCTCACATTCTACTTGACTGTGG | 30 |
| SEQ ID NO.134 | AGTTGAGTTCCAGCCTTCATTGGGTTTCCAA | 31 |
| GATA-BINDING PROTEIN 2 | | |
| SEQ ID NO.135 | GCGCAGCAAGGCTCGTTCCTGTTCAGAA | 28 |
| SEQ ID NO.136 | CGCCATAAGGTGGTGGTTGTCGTCTGACAA | 30 |
| GLUCOCORTICOID RECEPTOR REPRESSION FACTOR 1 | | |
| SEQ ID NO.137 | ACATTGAAGCCACAGGACTGAGCACGGAAG | 30 |
| SEQ ID NO.138 | CGTCCATAGTGCTGAAATCAGGTCTCATCAA | 31 |
| CCAAT-BOX DNA-BINDING PROTEIN, HAP2 HOMOLOG | | |
| SEQ ID NO.139 | AATTGCAGCGATGCCTGGCAAATTGAAGTTG | 31 |
| SEQ ID NO.140 | CAAAGCGTCCATTCAGTTAGTCAGTGTGAGA | 31 |
| RETINOIC ACID RECEPTOR, EPSILON | | |
| SEQ ID NO.141 | CATCTGCTTAATCTGTGGAGACCGCCAGG | 29 |
| SEQ ID NO.142 | CTAGGACTGTGCTCTGCTGTGTTCCCACT | 29 |
| B-MYB | | |
| SEQ ID NO.143 | CCGGAAGTCTCTGGCTGTTGACATTGTGG | 29 |

TABLE 1-continued

| SEQUENCE DESCRIPTION | | Length |
|---|---|---|
| SEQ ID NO.144 | CCCTGTAAACATGAGAATGGGCTCGTGACA | 30 |
| TYROSINE KINASE, RECEPTOR TIE | | |
| SEQ ID NO.145 | CTACAGTGTCTATACCACCAAGAGTGATGTC | 31 |
| SEQ ID NO.146 | GGCTGTAAGGGTCAGACTGGTCACAGGTTA | 30 |
| TYROSINE KINASE, RECEPTOR FLT4, CLASS III | | |
| SEQ ID NO.147 | CAGGTGCTTCCCAGACACTGGCGTTACT | 28 |
| SEQ ID NO.148 | ACTCATATTACCAAGGAATAACTGGCGGGCA | 31 |
| HELIX-LOOP-HELIX PROTEIN 1R21 | | |
| SEQ ID NO.149 | TGAAGTCAAGTGGGCAGGGCGAAGTTGG | 28 |
| SEQ ID NO.150 | AGCCAGGTGGAAATCCTACAGCGCGTCA | 28 |
| THROMBOMODULIN | | |
| SEQ ID NO.151 | CTACCAAAGCACCTTAGCTGGCATTACAGC | 30 |
| SEQ ID NO.152 | CTGTCACATGACAAGTGGGAGTTTGTAGAGA | 31 |
| BASIC TRANSCRIPTION ELEMENT-BINDING PROTEIN 2 | | |
| SEQ ID NO.153 | CAAATCAGACAGCAGCAATGGACACTCTTAA | 31 |
| SEQ ID NO.154 | GTAATCGCAGTAGTGGATGCGTCGTTTCTC | 30 |
| BASIC TRANSCRIPTION FACTOR, 62 KDA SUBUNIT | | |
| SEQ ID NO.155 | TGTAGCTGTTGGAGAACTTCTACGACATTTC | 31 |
| SEQ ID NO.156 | GTTGGCGTGGAGCAGATGTTTCTTATCACTG | 31 |
| HELIX-LOOP-HELIX PROTEIN ID-2 | | |
| SEQ ID NO.157 | GAAAGCCTTCAGTCCCGTGAGGTCCGTT | 28 |
| SEQ ID NO.158 | CTGGTGATGCAGGCTGACAATAGTGGGATG | 30 |
| ANGIOTENSIN II TYPE IA RECEPTOR | | |
| SEQ ID NO.159 | AAGATATGCTAAGCAGTAGTCGTCAAGTTGC | 31 |
| SEQ ID NO.160 | CTTGGGACCAGTGCAGCACCTTTACAAGTA | 30 |
| TYROSINE KINASE, RECEPTOR HEK | | |
| SEQ ID NO.161 | ATATCTCTACCTTCCGCACAACAGGTGACTG | 31 |
| SEQ ID NO.162 | CACCAGTATCTCCAGAATTATTGTCTGTCTG | 31 |
| DNA-BINDING PROTEIN SMBP2 | | |
| SEQ ID NO.163 | GCGAAGTCCGCCTCGTCAGTTTGCACAT | 28 |
| SEQ ID NO.164 | CATGGTTGTTGACAGTACGGGAGTCACAGA | 30 |
| GLOBAL TRANSCRIPTION ACTIVATOR | | |
| SEQ ID NO.165 | CTAAGTACCAGGGCTGGAGGTCTCGGAA | 28 |
| SEQ ID NO.166 | GCTTGTTAGACCGTTGGTCAATGAGTCTTCC | 31 |
| FMLP-RELATED RECEPTOR 1 | | |
| SEQ ID NO.167 | ACCATCATTGCTCTGGACCGCTGTATTTGTG | 31 |
| SEQ ID NO.168 | ACTGTGATGATGGACATAGGCACCGTGAAG | 30 |
| TRANSMEMBRANE RECEPTOR ROR1 | | |
| SEQ ID NO.169 | TTCCAAATCATCCTGGTGGAATGGGTATCAC | 31 |
| SEQ ID NO.170 | GTTGCGATGTCTGCTAAATGAGAACCTTACT | 31 |
| TYROSINE KINASE KDR, RECEPTOR | | |
| SEQ ID NO.171 | GTGGTCAACCTTCTAGGTGCCTGTACCAGG | 30 |
| SEQ ID NO.172 | CCAAGAACTCCATGCCCTTAGCCACTTGGA | 30 |
| DNA-BINDING PROTEIN ICS | | |
| SEQ ID NO.173 | CCGGATGTTTCCAGATATTTGTGCCTCACAC | 31 |
| SEQ ID NO.174 | CCTCCGAGAATGCCCTTATTAAAATTAAGTGC | 31 |

TABLE 1-continued

| SEQUENCE DESCRIPTION | | Length |
|---|---|---|
| THYROID HORMONE TRIIODOTHYRONINE RECEPTOR | | |
| SEQ ID NO.175 | GTCATAACGAGGCCCTAAATGGTCTGCGC | 29 |
| SEQ ID NO.176 | TTCACGTTGAACAACGAAGCAAAGCGCACC | 30 |
| CACCC-BOX DNA-BINDING PROTEIN | | |
| SEQ ID NO.177 | CAGGCTTTACTGGACTCAGAAGGCAATGCT | 30 |
| SEQ ID NO.178 | TATCTCATGCTGTCCATTAGCTTTGTGGGAA | 31 |
| TYROSINE KINASE RECEPTOR | | |
| SEQ ID NO.179 | ATGAGCAACCAGGATGTCATCAATGCCGTG | 30 |
| SEQ ID NO.180 | CCAACTGTCGTGAAGGTTGTGTAATCTGGG | 30 |
| DNA-BINDING PROTEIN TAX | | |
| SEQ ID NO.181 | CTAGATATTATCCTACTGAAGATGTGCCTCG | 31 |
| SEQ ID NO.182 | ATCTTGCGCTGCTCCGTAATCTCATATTTCT | 31 |
| ACTIVATING TRANSCRIPTION FACTOR 3 | | |
| SEQ ID NO.183 | AGCAGAAAGTTCAAGTTCCAAAGGGTTAGGA | 31 |
| SEQ ID NO.184 | GCTGCAAAGAGGGTGGGCCAGATTTCTTAAA | 31 |
| TYROSINE KINASE, RECEPTOR TRKC | | |
| SEQ ID NO.185 | TCTCCCAAATGCTCCACATTGCCAGTCAGA | 30 |
| SEQ ID NO.186 | TGACCTCCGTGTTTGAGAGTTGGAACCATG | 30 |
| TYROSINE KINASE, RECEPTOR TKT | | |
| SEQ ID NO.187 | GGAGAGTATCTTGCTGGGCAAGTTCACTAC | 30 |
| SEQ ID NO.188 | CATGGGTGAGTGGTAGGTCTTGTAGGGAG | 29 |
| DNA-BINDING PROTEIN HRFX2 | | |
| SEQ ID NO.189 | TAGATGTGGTGATGAACCTCCAGTTCCACTA | 31 |
| SEQ ID NO.190 | GGATGACCTGTTGTGGGAAGTCACTCATGG | 30 |
| PROSTAGLANDIN E2 RECEPTOR | | |
| SEQ ID NO.191 | CAGGAATTTGCTTCCAGGTGTGCCTG | 26 |
| SEQ ID NO.192 | CAGTGTTTCACTGGGAAATGTGACTTGCA | 29 |
| EPIDERMAL GROWTH FACTOR RECEPTOR | | |
| SEQ ID NO.193 | GCGCCTTGACTGAGGACAGCATAGACGA | 28 |
| SEQ ID NO.194 | GGAGCCCTTAAAGATGCCATTTGGCTTGGC | 30 |
| CCAAT ENHANCER-BINDING PROTEIN, ALPHA | | |
| SEQ ID NO.195 | CCCAGCCTCAGGATGTTGTATCTAAGTACAA | 31 |
| SEQ ID NO.196 | GAAAGTATCCAAGGCCATAAGGCACTGCTG | 30 |
| PLATELET-ACTIVATING FACTOR RECEPTOR | | |
| SEQ ID NO.197 | CCATTCAACCAGATCCCTGGCAATTCCCTC | 30 |
| SEQ ID NO.198 | TAAGGGACTCAGGATAAAGTCATCAGTCACA | 31 |
| THYROID HORMONE TRIIODOTHYRONINE RECEPTOR | | |
| SEQ ID NO.199 | AGCGTAAGCTGATTGAGCAGAACCGGGAG | 29 |
| SEQ ID NO.200 | GAGGATGATCTGGTCTTCGCAAGGCAGCT | 29 |
| TRYOSINE PHOSPHATASE RECEPTOR EPH | | |
| SEQ ID NO.201 | GAGCAATCAGGAGGTTATGAAGAGCATTGAG | 31 |
| SEQ ID NO.202 | GGGATCAGTCCTTGAATCCCTGAATACTGCA | 31 |
| HAES-1 | | |
| SEQ ID NO.203 | GACTCCTGCGACCGCATCAAAGACGAATTT | 30 |
| SEQ ID NO.204 | GCTGTCGGATGATAGAGTTCAGCTCGGGA | 29 |
| DNA-BINDING PROTEIN/PLASMINOGEN ACTIVATOR INHIBITOR-1 REGULATOR | | |

TABLE 1-continued

| SEQUENCE DESCRIPTION | | Length |
|---|---|---|
| SEQ ID NO.205 | CCTCTTGTCATCCCACTCAGCGCCATGT | 28 |
| SEQ ID NO.206 | CTCCCGTGTAATAGCGTAGTCCAACCACAT | 30 |
| INTERFERON, GAMMA RECEPTOR | | |
| SEQ ID NO.207 | ACGTTCCACAGGGCCAGGTGAGCTTTCT | 28 |
| SEQ ID NO.208 | AACTACATCCGGCAGCAGTCCGAGACCT | 28 |
| DNA-BINDING PROTEIN CN, STEROL REGULATING | | |
| SEQ ID NO.209 | TGCAGCCATGAGCAGCAATGAGTGCTTCAA | 30 |
| SEQ ID NO.210 | CTCTACCGCAGTTATAGCAGGCATCCTCC | 29 |
| V-ERBA RELATED EAR-2 PROTEIN | | |
| SEQ ID NO.211 | GGACAAGTCGAGCGGCAAGCATTACGGT | 28 |
| SEQ ID NO.212 | CCGGAAGCACTTCTTGAGACGGCAGTAC | 28 |
| V-ERBA RELATED EAR-3 PROTEIN | | |
| SEQ ID NO.213 | CATCGTGCTGTTCACGTCAGACGCCTGT | 28 |
| SEQ ID NO.214 | GTAACATATCGCGGATGAGAGTTTCGATGGG | 31 |
| CCAAT DISPLACEMENT PROTEIN | | |
| SEQ ID NO.215 | CTGCACAAGTTCCACGAGAATGACAACGGG | 30 |
| SEQ ID NO.216 | GAATCGGTGGTCACCCAATTAGCCTCGCA | 29 |
| GLUTAMATE RECEPTOR 2 | | |
| SEQ ID NO.217 | AGTGCGGAGCCCTCTGTGTTTGTGAGGA | 28 |
| SEQ ID NO.218 | GCTTGTCTAAGACGCCTTGCTCACTGACTT | 30 |
| BASIC TRNASCRIPTION FACTOR, 44 KDA SUBUNIT | | |
| SEQ ID NO.219 | TGCAGAAGTTCGCGTTTGCACTGTACTTGC | 30 |
| SEQ ID NO.220 | TCAGTATTGCCATCCAAATGCGCCATGCTG | 30 |
| ETS-RELATED PROTEIN | | |
| SEQ ID NO.221 | GATTCAGAAGTGCCTAACTGCCAGTCATCC | 30 |
| SEQ ID NO.222 | GGTTCTATCAGCTTGAACTCCATGCCTCGA | 30 |
| DNA-BINDING PROTEIN APRF | | |
| SEQ ID NO.223 | AGACCGAGGTGTATCACCAAGGTCTCAAGA | 30 |
| SEQ ID NO.224 | TGTGATCTGACACCCTGAGTAGTTCACACC | 30 |
| ESTROGEN RECEPTOR HSNF2B | | |
| SEQ ID NO.225 | CATCCAGACCATCGCGCTCATCACGTAC | 28 |
| SEQ ID NO.226 | CAACGGATCTTGGCGAGGATGTGCTTGTCT | 30 |
| TYROSINE KINASE HEK11, RECEPTOR | | |
| SEQ ID NO.227 | AAATTCCAGTAAGGTGGACAGCACCCGAAG | 30 |
| SEQ ID NO.228 | TGACCAACCAGTGTGATCCCTAAACTCATCA | 31 |
| UROKINASE-TYPE PLASMINOGEN ACTIVATOR RECEPTOR | | |
| SEQ ID NO.229 | CCTATTCCCGAAGCCGTTACCTCGAATGC | 29 |
| SEQ ID NO.230 | GAGTGCCGGTGGCTACCAGAGATTGATTCA | 30 |
| ETS-LIKE GENE | | |
| SEQ ID NO.231 | ACCAGGAGTCCTACCCTCTGTCAGTGTC | 28 |
| SEQ ID NO.232 | GATAGACGTAATCCCAAAGCAGTCTACAGTC | 31 |
| TYROSINE KINASE TRK-B, RECEPTOR | | |
| SEQ ID NO.233 | AGTGTGGCAGGTGATCCGGTTCCTAATATG | 30 |
| SEQ ID NO.234 | GCCGTGGTACTCCGTGTGATTGGTAAGATG | 30 |
| ELAV-LIKE NEURONAL PROTEIN 1 | | |
| SEQ ID NO.235 | GCTATCAACACCCTGAATGGATTGAGACTTC | 31 |

TABLE 1-continued

| SEQUENCE DESCRIPTION | | Length |
|---|---|---|
| SEQ ID NO.236 | TCGCTTGTCAAATCGAATAAACCCTACACCC | 31 |
| DNA-BINDING PROTEIN NFX1, CYSTEINE-RICH SPECIFIC | | |
| SEQ ID NO.237 | GTGACAAGCGGTGTAACAAGAAACGGTTGTG | 31 |
| SEQ ID NO.238 | ACCAGAATGATATACTGGATGGTCACACTCA | 31 |
| DP2, DIMERIZATION PARTNER OF E2F | | |
| SEQ ID NO.239 | CATAGATTGCAGGATCTCCAGTGACAAGTTT | 31 |
| SEQ ID NO.240 | CAGGAACTGCCCAGTTGCTAAGGCCACTT | 29 |
| GLIA MATURATION FACTOR, BETA | | |
| SEQ ID NO.241 | ATGAACTACCTGAACGACAACCTCGCTTC | 30 |
| SEQ ID NO.242 | CGTAACCATTCTTCAGTTAGGTCTTCGGTA | 31 |
| DNA-BINDING PROTEIN TAXREB67 | | |
| SEQ ID NO.243 | AATGGCTGGCTGTGGATGGGTTGGTCA | 28 |
| SEQ ID NO.244 | GATCATGGCAACGTAAGCAGTGTAGTCTG | 30 |
| CAMP-RESPONSIVE ELEMENT-BINDING PROTEIN | | |
| SEQ ID NO.245 | TCCAGCTCTGTCATCACTCAGGCACCT | 28 |
| SEQ ID NO.246 | TGGTGAGTCAATGCAGCCTTCAACCTCATT | 31 |
| TYROSINE KINASE EGF, RECEPTOR HER4 | | |
| SEQ ID NO.247 | CTTCAAGCATTGGATAATCCCGAATATCAC | 31 |
| SEQ ID NO.248 | AGCTTACACCACAGTATTCCGGTGTCTGTA | 31 |
| TYROSINE PHOSPHATASE, RECEPTOR, GAMMA POLYPEPTIDE | | |
| SEQ ID NO.249 | CTTCAGTTGTGCCATCTGAGCGTGCTCG | 29 |
| SEQ ID NO.250 | CACAGTCTGTCTTTGCTGATAAGGGTGAC | 30 |
| VASOACTIVE INTESTINAL PEPTIDE RECEPTOR RDC1 | | |
| SEQ ID NO.251 | CTCTCCAAGTCTCAGTGGCTTCATCTGTC | 30 |
| SEQ ID NO.252 | AGCAGTAAGAGTCCGTGCTTTCACATTCCT | 31 |
| DNA-BINDING PROTEIN PO-GA | | |
| SEQ ID NO.253 | CGCAGGCCATTTATCGGAGTGTTCTTCC | 29 |
| SEQ ID NO.254 | TACAAGTGCATCCCTTAGAAGCGACAGATA | 31 |
| CCAAT ENHANCER-BINDING PROTEIN, BETA | | |
| SEQ ID NO.255 | 28 GTGTTCGACCAGGGCCAGTTTGCCAA | |
| SEQ ID NO.256 | 30 CGCTGTCCTGGCGGATCTTTATGTCTTC | |
| C-JUN PROTO ONCOGENE(JUN) | | |
| SEQ ID NO.257 | TTAACAGTGGGTGCCAACTCATGCTAACGC | 30 |
| SEQ ID NO.258 | GAGATCGAATGTTAGGTCCATGCAGTTCTTG | 31 |
| INTERLEUKIN 1 RECEPTOR | | |
| SEQ ID NO.259 | ATATGCCACCGATTGCAGGACACAAGCACA | 30 |
| SEQ ID NO.260 | GTCACTAACCTAAGTTTCCAAATTGGCTTGC | 31 |
| TUMOR NECROSIS FACTOR RECEPTOR | | |
| SEQ ID NO.261 | TCTAAGGACCGTCCTGCGAGATCGCCTT | 28 |
| SEQ ID NO.262 | AAACGGGCATGAGGCATAGCGTCCCTCA | 28 |
| MACROPHAGE-SPECIFIC COLONY-STIMULATING FACTOR(CSF-1) | | |
| SEQ ID NO.263 | CAGCCTCGGCCTGATTTCCCGTAAAGGT | 28 |
| SEQ ID NO.264 | CTGGCAACCAGCACAGGGACTTAGGTGA | 28 |
| INSULIN-LIKE GROWTH FACTOR II RECEPTOR | | |
| SEQ ID NO.265 | TCCCAGAGGTGAAAGTTCACTCGGGCAG | 28 |
| SEQ ID NO.266 | GAGCCATGCCTTATTCCAATGACTGTAAACA | 31 |

TABLE 1-continued

| SEQUENCE DESCRIPTION | | Length |
|---|---|---|
| TYROSINE KINASE, RECEPTOR HER2 | | |
| SEQ ID NO.267 | TATGGCTGCCTCTTAGACCATGTCCGG | 28 |
| SEQ ID NO.268 | TTGGGACTCTTGACCAGCACGTTCCGA | 28 |
| FMLP-RELATED RECEPTOR | | |
| SEQ ID NO.269 | GCCGATGTCCATTGTTGCCATCTGCTATGG | 30 |
| SEQ ID NO.270 | GTAGATGAAGCTGGAACTGGCATTAGGGTAG | 31 |
| HM74 | | |
| SEQ ID NO.271 | AGCTTCTAGGCATCTGAAAGTTGCTTCATCTC | 32 |
| SEQ ID NO.272 | ATTAGTCGCTGGTTGAAAGCAGCAATGCCATT | 32 |
| HM89 | | |
| SEQ ID NO.273 | CCTTCTGGGCAGTTGATGCCGTGGCAAA | 28 |
| SEQ ID NO.274 | AGGATGACTGTGGTCTTGAGGGCCTTGC | 28 |
| HM145 | | |
| SEQ ID NO.275 | GAAGGGCTTGGACTCAAGCAAGATTTCAGATT | 32 |
| SEQ ID NO.276 | GTGCTTAGCCCACTCCCTGAATTGTTTGATTT | 32 |
| HEPATOCYTE GROWTH FACTOR ACTIVATOR PRECURSOR | | |
| SEQ ID NO.277 | ACCACGACCTCGTCCTGATCCGGCTG | 26 |
| SEQ ID NO.278 | CCGTAGAGGTAAGCCACGCCGTTCTTC | 27 |
| HEPATOMA-DERIVED GROWTH FACTOR | | |
| SEQ ID NO.279 | TGGTGTTCGCCAAGATGAAGGGCTACCC | 28 |
| SEQ ID NO.280 | GGAGGACTGATAGCCGGAAGCCTTGACA | 28 |
| BONE MORPHOGENETIC PROTEIN 4 | | |
| SEQ ID NO.281 | GCCGGAGGGCCAAGCGTAGCCCTAAG | 26 |
| SEQ ID NO.282 | CTGCCTGATCTCAGCGGCACCCACATC | 27 |
| FER TYROSINE KINASE | | |
| SEQ ID NO.283 | ACGCTGCTGCTGGTATGTTGTATCTCGAG | 29 |
| SEQ ID NO.284 | TGCTGATTTGTCATTCCAGGGTACGGACAA | 30 |
| ACTIVATION(ACT-2) | | |
| SEQ ID NO.285 | TTCCTCGCAACTTTGTGGTAGATTACTATGAG | 32 |
| SEQ ID NO.286 | CCCATAGGACACTTATCCTTTGGCTAAACTAA | 32 |
| ENDOTHELIN ET3 | | |
| SEQ ID NO.287 | GGCCTTGTTTGCAGGAAGCCGACTGTAAAG | 30 |
| SEQ ID NO.288 | GGGATAACATCTCCACACTCACAGTAAGCTC | 31 |
| NEUROLEUKIN | | |
| SEQ ID NO.289 | TGCGGGCAAGAGTCCAGAGGACCTTGAG | 28 |
| SEQ ID NO.290 | TTGATGAGCCCATTGGTAGAAGCGTCGTGA | 30 |
| TEK TYROSINE KINASE RECEPTOR | | |
| SEQ ID NO.291 | TTAGCTTAGGAGGCACACCCTACTGCGG | 28 |
| SEQ ID NO.292 | GCAGTTGTCAAGGGTCTCCCATGCCAGT | 28 |
| ENDOTHELIN RECEPTOR EDNRA | | |
| SEQ ID NO.293 | CAGCTTGAGAATTGCCCTCAGTGAACATCTTA | 32 |
| SEQ ID NO.294 | GCCAAGTTAATACCGATGTAATCCATGAGCAG | 32 |
| ENDOTHELIN RECEPTOR EDNRB | | |
| SEQ ID NO.295 | CCCGTGCCAAGGACCCATCGAGATCAAG | 28 |
| SEQ ID NO.296 | CACATAGACTCAGCACAGTGATTCCCACGG | 30 |
| INTERLEUKIN IL-13 | | |
| SEQ ID NO.297 | AAGACCCAGAGGATGCTGAGCGGATTCTG | 29 |

TABLE 1-continued

| SEQUENCE DESCRIPTION | | Length |
|---|---|---|
| SEQ ID NO.298 | GTAATGCTACAGTGTGCTCTAGGGCAGGG | 29 |
| CD40 LIGAND | | |
| SEQ ID NO.299 | GGGAGTCTTCATAATACAGCACAGCGGTTAAG | 32 |
| SEQ ID NO.300 | CATAGGAACCCAGAGTCAACCATAACTGAATG | 32 |
| CD27 LIGAND | | |
| SEQ ID NO.301 | CGGGCTTGGTGATCTGCCTCGTGGTG | 26 |
| SEQ ID NO.302 | GTCAGGCGCTGGGAGACAATGGTACAAC | 28 |
| CYTOKINE RECEPTOR(EB13) | | |
| SEQ ID NO.303 | CGGCTCAGGACCTCACAGACTACGGG | 26 |
| SEQ ID NO.304 | CCACTGCGCCCAGCCCAACAACAATTCT | 28 |
| GLIAL GROWTH FACTOR 2(RECOMBINANT) | | |
| SEQ ID NO.305 | CTTCGGTGTGAAACCAGTTCTGAATACTCCTC | 32 |
| SEQ ID NO.306 | AACTCATTTGGGCACTTGCACAAGTATCTCGA | 32 |
| GLIAL GROWTH FACTOR(RECOMBINANT) | | |
| SEQ ID NO.307 | CTCTGCCAATATCACCATCGTGGAATCAAACG | 32 |
| SEQ ID NO.308 | AACTCATTTGGGCACTTGCACAAGTATGTCGA | 32 |
| INTERLEUKIN IL-14 | | |
| SEQ ID NO.309 | CCTGCTTGAATGTGGTGAATACCTCGCTGC | 30 |
| SEQ ID NO.310 | AGATGGAACAGCACAATGAGCGCAACTCCA | 30 |
| THROMBOPROTEIN(MGDF/MPL LIGAND) | | |
| SEQ ID NO.311 | AGGAGACCAAGGCACAGGACATTCTGGG | 28 |
| SEQ ID NO.312 | CTCCAACAATCCAGAAGTCCTGTTTGGGAG | 30 |
| INSULIN RECEPTOR | | |
| SEQ ID NO.313 | ATCAAGGGTGAGGCAGAGACCCGCGTG | 27 |
| SEQ ID NO.314 | ACTCCGGTGCCATCCACCGTACAGGG | 26 |
| UROMODULIN | | |
| SEQ ID NO.315 | CCGGCATGTTCACCGTGCGGATGGCG | 26 |
| SEQ ID NO.316 | GACCCAAGTTCAGGACACGGGATTGATCTAT | 31 |
| RANTES PRO-INFLAMMATORY CYTOKINE | | |
| SEQ ID NO.317 | TACACCAGTGGCAAGTGCTCCAACCCAG | 28 |
| SEQ ID NO.318 | GTCTCGAACTCCTGACCTCAAGTGATCCAC | 30 |
| PDGF-ALPHA RECEPTOR | | |
| SEQ ID NO.319 | TCTCCCGTCTTCTGCCTCCCACTCCATA | 28 |
| SEQ ID NO.320 | GTCTAATTGGCTCTACAGAACCTAGTCAGGTT | 32 |
| PDGF-BETA RECEPTOR | | |
| SEQ ID NO.321 | ACGCAGTGCAGACTGTGGTCCGCCA | 25 |
| SEQ ID NO.322 | CGTAGCCGCTCTCAACCACGGTGATGT | 27 |
| BONE MORPHOGENETIC PROTEIN 1 | | |
| SEQ ID NO.323 | CACACTCGGCCAGACCGGGACCG | 23 |
| SEQ ID NO.324 | GGGTGTGACAGAGATGCGCCACACG | 25 |
| BONE MORPHOGENETIC PROTEIN 2A | | |
| SEQ ID NO.325 | CTGTATCGCAGGCACTCAGGTCAGCCG | 27 |
| SEQ ID NO.326 | CATGGTTGGCGTGTCCCTGTGCAGTCCA | 28 |
| BONE MORPHOGENETIC PROTEIN 3 | | |
| SEQ ID NO.327 | GCAGATATTGGCTGGAGTGAATGGATTATGTG | 32 |
| SEQ ID NO.328 | AGCGCAAGACTCTACTGTCATGTTAGGGTATA | 32 |

TABLE 1-continued

| SEQUENCE DESCRIPTION | | Length |
|---|---|---|
| MACROPHAGE INFLAMMATORY PROTEIN GOS19-1 | | |
| SEQ ID NO.329 | AGCAGCCAGTGCTCCAAGCCCGGTG | 25 |
| SEQ ID NO.330 | TTGTCAGTCTGGTGGCTTTGGTGCCATG | 28 |
| MONOCYTE CHEMOTACTIC AND ACTIVATING FACTOR MCAF | | |
| SEQ ID NO.331 | TTCTCAAACTGAAGCTCGCACTCTCGCC | 28 |
| SEQ ID NO.332 | TGTGGAGTGAGTGTTCAAGTCTTCGGAGTT | 30 |
| NEURONAL GROWTH PROTEIN GAP-43 | | |
| SEQ ID NO.333 | TCTTTACCCTCGTCCTGCCGGGCACTTT | 28 |
| SEQ ID NO.334 | GAAAGTGGACTCCCACAGGGCCACACG | 27 |
| ONCOSTATIN M | | |
| SEQ ID NO.335 | GGGCCACGCGGGACCGACTTTCCAT | 25 |
| SEQ ID NO.336 | TGGGACACCCTGCCGCTGTTACAGCT | 26 |
| AMPHIREGULIN AR | | |
| SEQ ID NO.337 | CAGTCAGAGTTGAACAGGTAGTTAAGCCCC | 30 |
| SEQ ID NO.338 | AGACATAAAGGCAGCTATGGCTGCTAATGCAA | 32 |
| INSULINE-LIKE GROWTH FACTOR BINDING PROTEIN 1 | | |
| SEQ ID NO.339 | CGTGCAGGAGTCTGACGCCTCCGCTC | 26 |
| SEQ ID NO.340 | GTAGACGCACCAGCAGAGTCCCGCCT | 26 |
| TNF-INDUCIBLE HYALURONATE-BINDING PROTEIN TSG-6 | | |
| SEQ ID NO.341 | TGGATGGATGGCTAAGGGCAGAGTTGGATA | 30 |
| SEQ ID NO.342 | CGCTGACCATACTTGAGTCTAATGTGCCAGTA | 32 |
| HEPARIN-BINDING VASCULAR ENDOTHELIAL GROWTH FACTOR VEGF | | |
| SEQ ID NO.343 | CAGCGCAGCTACTGCCATCCAATCGAGA | 28 |
| SEQ ID NO.344 | GCTTGTCACATCTGCAAGTACGTTCGTTTAAC | 32 |
| INSULINE-LIKE GROWTH FACTOR BINDING PROTEIN 2 | | |
| SEQ ID NO.345 | GCAAGGGTGGCAAGCATCACCTTGGC | 26 |
| SEQ ID NO.346 | AGGCACCGGCTGGCTGCGGTCTACT | 25 |
| RIBONUCLEASE/ANGIOGENUN INHIBITOR RAI | | |
| SEQ ID NO.347 | GCAAGGGTGGCAAGCATCACCTTGGC | 26 |
| SEQ ID NO.348 | CAATGCCGCACAGGTCCCGGCAGTTG | 26 |
| BFGF | | |
| SEQ ID NO.349 | CCCAGGGCTGGAATACTGCTACAACC | 26 |
| SEQ ID NO.350 | GGTGTAGATCCGGTCAAATAATGCCTCG | 28 |
| GLYCOPROTEIN GP130 | | |
| SEQ ID NO.351 | CTGATGGACCAGGAAGCCCTGAATCCATAA | 30 |
| SEQ ID NO.352 | TGTCAATAGGAATGCTAAGCAAACAGGCACGA | 32 |
| NERVE GROWTH FACTOR HBNF-1 | | |
| SEQ ID NO.353 | CACTCGGACTGGAGCTGAGTGCAAGC | 26 |
| SEQ ID NO.354 | CTTGAGGTTTGGGCTTGGTCAGTTTGCCA | 29 |
| SECRETED PROTEIN I-309 | | |
| SEQ ID NO.355 | ATACCAGCTCCATCTGCTCCAATGAGGGC | 29 |
| SEQ ID NO.356 | TCGGGGACAGGTGAAGCCATGTGGTTTCC | 29 |
| INTERLEUKIN 11 | | |
| SEQ ID NO.357 | GGGACCATGAACTGTGTTTGCCCCTGG | 27 |
| SEQ ID NO.358 | ACGTGCCGCAGGTAGGACAGTAGGTC | 26 |
| GRANULOCYTE COLONY-STIMULATING FACTOR RECEPTOR G-CSFRI | | |

TABLE 1-continued

| SEQUENCE DESCRIPTION | | Length |
|---|---|---|
| SEQ ID NO.359 | AGGCCCACGTCTGACCAGACTCCATG | 26 |
| SEQ ID NO.360 | AAGGACTGGTTCTGAGCGTTGGTCCAGA | 28 |
| STEM CELL FACTOR | | |
| SEQ ID NO.361 | AAGAGACAGCCAAGTCTTACAAGGGCAGTTG | 31 |
| SEQ ID NO.362 | CTAAATGAGACCCAAGTCCCGCAGTCCTTAAA | 32 |
| HEPARIN-BINDING PROTEIN HBP17 | | |
| SEQ ID NO.363 | TTCCTCAGCATAGTGCAGGACACGTCATGC | 30 |
| SEQ ID NO.364 | CACTGAAATTATCACTCTGGCTCATTCAGCTC | 32 |
| HEPARIN-BINDING EGF-LIKE GROWTH FACTOR | | |
| SEQ ID NO.365 | AAGAGGTTGGGCTTCCATGCCTGTAGCTTT | 30 |
| SEQ ID NO.366 | GGTAATCAGTTACCAAGAACAGTCAGCTCCAA | 32 |
| HGF(HEPATOCYTE GROWTH FACTOR) | | |
| SEQ ID NO.367 | TTGCGAGTTGTAAATGGGATTCCAACACGAAC | 32 |
| SEQ ID NO.368 | GTGCCACTCGTAATAGGCCATCATAGTTGATC | 32 |
| KERATINOCYTE GROWTH FACTOR | | |
| SEQ ID NO.369 | CATGAACACCCGGAGCACTACACTATAATG | 30 |
| SEQ ID NO.370 | ATTCCAACTGCCACTGTCCTGATTTCCATG | 30 |
| BRAIN-DERIVED NEUROTROPHIC FACTOR BDNF | | |
| SEQ ID NO.371 | GTGTGACAGTATTAGTGAGTGGGTAACGGC | 30 |
| SEQ ID NO.372 | GTCTATCCTTATGAATCGCCAGCCAATTCTCT | 32 |
| GROWTH/DIFFERENTIATION FACTOR GDF-1 | | |
| SEQ ID NO.373 | GTACCACAATGTGGGCATCCTTGTGCTC | 28 |
| SEQ ID NO.374 | GTCAACACCTTGGCTGCAAACGCCACGA | 28 |
| C5A ANAPHYLATOXIN RECEPTOR | | |
| SEQ ID NO.375 | CCACGCGGTCCACCAAGACACTCAAGG | 27 |
| SEQ ID NO.376 | GTGGCCCATGAGGCTGTCGCCTACAC | 26 |
| T CELL ACTIVATION ANTIGEN CD27 | | |
| SEQ ID NO.377 | CACACCCTCAGCCCACCCACTTACCTTA | 28 |
| SEQ ID NO.378 | GCAGTTGTGGCTGCCAGGTCTCACTCTC | 28 |
| ENDOTHELIN ET2 | | |
| SEQ ID NO.379 | CGCTCCCTGCCAAGGCGCTGTCAGT | 25 |
| SEQ ID NO.380 | CCCGCATGGCCTCCTGTTGTCGCTTG | 26 |
| INTERLEUKIN IL-12(NKSF P40) | | |
| SEQ ID NO.381 | GATGGATGGGAACGCAAGAGATACTTACATG | 31 |
| SEQ ID NO.382 | GTCTTGTTATGTTTCCCAGGCTGGTCAATCAT | 32 |
| INTERLEUKIN IL-12(NKSF P35) | | |
| SEQ ID NO.383 | ATGTACCAGGTGGAGTTCAAGACCATGAATGC | 32 |
| SEQ ID NO.384 | GGTATCATGTGGATGTAATAGTCCCATAATTC | 32 |
| FAS ANTIGEN | | |
| SEQ ID NO.385 | ATTCTAGCCTGGTTTGGAGATACTAACTGCTC | 32 |
| SEQ ID NO.386 | GAGGGTATGACAAGAGCAATTCCTAAATCCAG | 32 |
| INTERLEUKIN 8 RECEPTOR ALPHA(IL8RA) | | |
| SEQ ID NO.387 | TCTGGCTCTGGACAGGCACTATCTGGG | 27 |
| SEQ ID NO.388 | AGTGGGTTAAAGATGTGACGTTCAACGGGA | 30 |
| NMB-R(NEUROMEDIN B RECEPTOR) | | |
| SEQ ID NO.389 | TTTCAGAAGTGGCTCGCATCAGTAGCTTGG | 30 |

TABLE 1-continued

| SEQUENCE DESCRIPTION | | Length |
|---|---|---|
| SEQ ID NO.390 | GAGTAGGTAAAGAGCAAATGGGTTGACACAAG | 32 |
| HEPATOCYTE GROWTH FACTOR-LIKE PROTEIN | | |
| SEQ ID NO.391 | GAGAGCCAAGCCTACAGCGGGTCCCA | 26 |
| SEQ ID NO.392 | AGTTGTGGGTAAAGCAGGCAAGTGGGCC | 28 |
| AXL TYROSINE KINASE RECEPTOR | | |
| SEQ ID NO.393 | AGTGTACCTGCCCACTCAGATGCTAGTGAA | 30 |
| SEQ ID NO.394 | CACATCGCTCTTGCTGGTGTAGACACGGT | 29 |
| LYMPHOCYTE ACTIVATION ANTIGEN CD30 | | |
| SEQ ID NO.395 | AGTAGTGGCCCTGACTTCCGGTCGGA | 26 |
| SEQ ID NO.396 | GGTGTAACCACCTCTCGCAAGGCCAC | 26 |
| THYMOSIN BETA-10 | | |
| SEQ ID NO.397 | GGGAAATCGCCAGCTTCGATAAGGCCAA | 28 |
| SEQ ID NO.398 | GCAAACCGGAGAATTTGGCAGTCCGATTG | 29 |
| CONNECTIVE TISSUE GROWTH FACTOR | | |
| SEQ ID NO.399 | GTACCGGCCCGGTTAGTATCATCAGATCG | 29 |
| SEQ ID NO.400 | GGCTTGTTACAGGCAAATTCACTTGCCACAAG | 32 |
| TYROSINE PHOSPHATASE RECEPTOR ZETA-POLYPEPTIDE | | |
| SEQ ID NO.401 | TTATCTGTCTAGTGGTTCTTGTGGGTATTCTC | 32 |
| SEQ ID NO.402 | GGCATTGATATAATCAGTCAGTTTGCCATCCT | 32 |
| INTERLEUKIN 8 RECEPTOR BETA(IL8RB) | | |
| SEQ ID NO.403 | ATCTGGGCCGCCTCCAAGGTGAATGGC | 27 |
| SEQ ID NO.404 | GATCCGTAACAGCATCCGCCAGTTTGCTG | 29 |
| TDGF3 | | |
| SEQ ID NO.405 | GGACTCCAGAACTACCACCGTCTGCACG | 28 |
| SEQ ID NO.406 | GTGAACCGAGATCGCGTCATTGCAGTCC | 28 |
| RYK=RELATED TO RECEPTOR TYROSINE KINASE ISOLOG | | |
| SEQ ID NO.407 | AAAGTTGTAAGCTGCGAGGTCTTCATCACAGA | 32 |
| SEQ ID NO.408 | GATTATTGGCCTCTACTAACTTGCACTGTCGT | 32 |
| VEGF RECEPTOR | | |
| SEQ ID NO.409 | GTAGCTGGCAAGCGGTCTTACCGGCTC | 27 |
| SEQ ID NO.410 | GGATTTGTCTGCTGCCCAGTGGGTAGAGA | 29 |
| DUFFY BLOOD GROUP ANTIGEN(FYA-B+) | | |
| SEQ ID NO.411 | CCTCCCACCTGCCCCTCAGTTCC | 23 |
| SEQ ID NO.412 | GAGCTGCGAGTGCTACCTAGCCC | 23 |
| PRE-B CELL ENHANCING FACTOR(PBEF) | | |
| SEQ ID NO.413 | TTCCTGTTACTGAGAACTCAAAGGGTTACAAG | 32 |
| SEQ ID NO.414 | GTTAATCCCAAGGCCATTAGTTACAACATAGC | 32 |
| GROWTH FACTOR RECEPTOR TYROSINE KINASE STK-1 | | |
| SEQ ID NO.415 | CTGGCCGCCAGGAACGTGCTTGTCAC | 26 |
| SEQ ID NO.416 | GTAGGTGTGAGGACATTCCGAAACACGGC | 29 |
| INTERLEUKIN 12 RECEPTOR COMPONENT | | |
| SEQ ID NO.417 | AGACGTGGCACATTCCTGCCGACACCC | 27 |
| SEQ ID NO.418 | AAGTGGTAGGTGGACAGGACCGTAGACC | 28 |
| RECEPTOR 4-1BB PROTEIN | | |
| SEQ ID NO.419 | TCCTCCACCAGCAATGCAGAGTGTGACT | 28 |
| SEQ ID NO.420 | CGTCCCATTCACAAGCACAGACTTTCCATC | 30 |

TABLE 1-continued

| SEQUENCE DESCRIPTION | | Length |
|---|---|---|
| RECEPTOR 4-1BB LIGAND | | |
| SEQ ID NO.421 | CAGCCTCCCAAGCAACTGGGATTCATCC | 28 |
| SEQ ID NO.422 | TTGGCAACATAGCAATACCGTCTCCGCAAA | 30 |
| MCP-1RA | | |
| SEQ ID NO.423 | GGTATGTTTGGGAGACTGCTGAGTCAACCC | 30 |
| SEQ ID NO.424 | AACAATATGAGCATCAAGGACATCTGCGAAGC | 32 |
| MCP-1RB | | |
| SEQ ID NO.425 | AGAGACTTTGACTCTCCAGAAAGCTCATCTCA | 32 |
| SEQ ID NO.426 | TGACCTGGTGAACCCTTCAAGGTTAAATACAC | 32 |
| FLT3/FLK2 LIGAND | | |
| SEQ ID NO.427 | AAAGGGCTGTCACCCGGCTTGGCCC | 25 |
| SEQ ID NO.428 | GCGACAGTCTTGAGCCGCTCCATCCA | 26 |
| ENDOTHELIAL-MONOCYTE ACTIVATING POLYPEPTIDE II | | |
| SEQ ID NO.429 | GTGAAGCAAATAGCATTTCCATCTGGTACTCC | 32 |
| SEQ ID NO.430 | ACATGATTCACCAGGCCACTGACAACTGTC | 30 |
| KERATINOCYTE GROWTH FACTOR RECEPTOR | | |
| SEQ ID NO.431 | GCTCCATGCTGTGCCTGCGGCCAAC | 25 |
| SEQ ID NO.432 | CTTGAGGTAGGGCAGCCCGTCGGGC | 25 |
| CYSTEINE PROTEASE CPP32 ISOM ALPHA | | |
| SEQ ID NO.433 | GCAGAGACATGACTCAGCCTGTTCCATGAA | 30 |
| SEQ ID NO.434 | ATACTGACAGCCAGTGAGACTTGGTGCAGT | 30 |
| INTERLEUKIN IL-15 | | |
| SEQ ID NO.435 | TTGAGAAGTATTTCCATCCAGTGCTACTTGTG | 32 |
| SEQ ID NO.436 | CCCATTAGAAGACAAACTGTTGTTTGCTAGGA | 32 |
| ACTIVIN TYPE 1 RECEPTOR | | |
| SEQ ID NO.437 | TCACCTCAAGGAGCCTGAGCACCCGTC | 27 |
| SEQ ID NO.438 | CCCTGAACCAAGACCGTTCTTCACGAGAAG | 30 |
| CYTOKINE SDF-1-BETA | | |
| SEQ ID NO.439 | GAGGGTCAGACGCCTGAGGAACCCTTAC | 28 |
| SEQ ID NO.440 | TAGGCTTTGCCCAGGTTGACTGGTCCTG | 28 |
| VRP(VASCULAR ENDOTHELIAL GROWTH FACTOR RELATED PROTEIN) | | |
| SEQ ID NO.441 | CCTCGGATGCTGGAGATGACTCAACA | 26 |
| SEQ ID NO.442 | TCACAAGCCTTCTGGCGGTTCGTACA | 26 |
| IFN-GAMMA-INDUCIBLE CHEMOKINE IP-10 | | |
| SEQ ID NO.443 | AAGAGATGTCTGAATCCAGAATCGAAGGCC | 30 |
| SEQ ID NO.444 | CCTCAGTAGAGCTTACATTATAGTGCCAGG | 30 |
| MRP-14 | | |
| SEQ ID NO.445 | GCTCCTCGGCTTTGACAGAGTGCAAGAC | 28 |
| SEQ ID NO.446 | GCATTTGTGTCCAGGTCCTCCATGATGTGT | 30 |
| MRP-8 | | |
| SEQ ID NO.447 | GGGCAAGTTCCGTGGGCATCATGTTGAC | 28 |
| SEQ ID NO.448 | CCAGTAACTCAGCTACTCTTTGTGGCTTTCT | 31 |
| PLATELET-DERIVED GROWTH FACTOR A CHAIN | | |
| SEQ ID NO.449 | GCATCCGGGACCTCCAGCGACTCCT | 25 |
| SEQ ID NO.450 | AGGCTTGTGGTCGCGCAGGCGCACT | 25 |
| MELANOMA GROWTH FACTOR STIMULATORY ACTIVITY | | |
| SEQ ID NO.451 | CCCACTGCGCCCAAACCGAAGTCATAG | 27 |

TABLE 1-continued

| SEQUENCE DESCRIPTION | | Length |
|---|---|---|
| SEQ ID NO.452 | TTCTGTTCCTATAAGGGCAGGGCCTCCT | 28 |
| LEUKEMIA INHIBITORY FACTOR | | |
| SEQ ID NO.453 | GATGGCTCCCGACACAAGCGCCAGG | 25 |
| SEQ ID NO.454 | AGGGTTGTTCCAGGGCGCTATTTCAGAG | 28 |
| INTERLEUKIN IL-9(P40) | | |
| SEQ ID NO.455 | GCTAATGTGACCAGTTGTCTCTGTTTGGGC | 30 |
| SEQ ID NO.456 | CAGAAGACTCTTCAGAAATGTCAGCGCGTT | 30 |
| GM-CSFRA | | |
| SEQ ID NO.457 | CCAGGACCTATCAGAAGCTGTCGTACCTG | 29 |
| SEQ ID NO.458 | GACGATGCCACAGACAAGGGTTCCACG | 28 |
| FIBROBLAST GROWTH FACTOR FGF-1 | | |
| SEQ ID NO.459 | GAATAAATCCTTGGGAGTCATTACCACGCCTT | 32 |
| SEQ ID NO.460 | CTGAATCAGAATCTCCATTCAAACCAGGTCCC | 32 |
| CYTOKINE EFFECTOR | | |
| SEQ ID NO.461 | CAGTGCTCCAAGCCCAGTGTCATCTTCC | 28 |
| SEQ ID NO.462 | TTGTCAGTCTGGTGGCTTTGGTGCCATG | 28 |
| NERVE GROWTH FACTOR NGF-2 | | |
| SEQ ID NO.463 | AAGGAGTTTGCCAGAAGACTCGCTCAATTCC | 31 |
| SEQ ID NO.464 | CACGTAATCCTCCATGAGATACAAGGGCGG | 30 |
| MACROPHAGE INFLAMMATORY PROTEIN-2ALPHA | | |
| SEQ ID NO.465 | ACTGAACTGCGCTGCCAGTGCTTGCAG | 27 |
| SEQ ID NO.466 | CCTAAGTGATGCTCAAACACATTAGGCGCA | 30 |
| PLGF(PLACENTAL GROWTH FACTOR) | | |
| SEQ ID NO.467 | GGCCCTGCTACCTGTTCTTGGGCCTC | 26 |
| SEQ ID NO.468 | CCAGTACAAGCAAATGGCAAAGTGTGAGGG | 30 |
| INTERLEUKIN 1 RECEPTOR TYPE II | | |
| SEQ ID NO.469 | TTTCTGGGAACCGGCACACCCTTAACCAC | 29 |
| SEQ ID NO.470 | TTGAAAGTCTTGATGATGAGGCCATAGCACAG | 32 |
| CDW40 | | |
| SEQ ID NO.471 | TGCACAGAGTTCACTGAAACGGAATGCC | 28 |
| SEQ ID NO.472 | CAGACAACATCAGTCTTGTTTGTGCCTG | 28 |
| BETA-THROMBOGLOBULIN-LIKE PROTEIN | | |
| SEQ ID NO.473 | GGAGGGCACCCGCAGCTCCGTCTC | 24 |
| SEQ ID NO.474 | GCACTCGGAGTAATTCACGCGGGCGG | 26 |
| NEUTROPHIL-ACTIVATING PEPTIDE ENA-78 | | |
| SEQ ID NO.475 | GTTCAGGAACCCGCGACCGCTCGCA | 25 |
| SEQ ID NO.476 | CTGTGGGCCTATGGCGAACACTTGCAGA | 28 |
| OX40 LIGAND/GP34 | | |
| SEQ ID NO.477 | GTCTACTTGAATGTGACCACTGACAATACCTC | 32 |
| SEQ ID NO.478 | GTGCCTAGTAGGCTCAAGGCAATCTTGGG | 29 |
| MONOCYTE-DERIVED NEUTROPHIL CHEMOTACTIC FACTOR | | |
| SEQ ID NO.479 | AACATGACTTCCAAGCTGGCCGTGGCTC | 28 |
| SEQ ID NO.480 | GCGCAGTGTGGTCCACTCTCAATCACTC | 28 |
| sphingolipid activator proteins | | |
| SEQ ID NO.481 | GTACGGACCAACTCCACCTTTGTCCA | 26 |
| SEQ ID NO.482 | TCAGACTTTGCTGGGACCTCGTGCTT | 26 |

TABLE 1-continued

| SEQUENCE DESCRIPTION | | Length |
|---|---|---|
| protein kinase C delta-type | | |
| SEQ ID NO.483 | CCTTCTGTACGAGATGCTCATTGGCC | 26 |
| SEQ ID NO.484 | CGATGACCTTCTTGTCGCTGTAGGAGA | 27 |
| CRK-II | | |
| SEQ ID NO.485 | TCCAGGCAGGGTAGTGGAGTGATTCT | 26 |
| SEQ ID NO.486 | AAAGCCAAGGCTGTCTTGTCGTAGGC | 26 |
| transcription factor E4TF1-47 | | |
| SEQ ID NO.487 | TTCCAACCAGTGGAATTGGTCAGCCC | 26 |
| SEQ ID NO.488 | GACTGCGGCAAAGCACACCGGGTAAA | 26 |
| transcription factor E4TF1-53 | | |
| SEQ ID NO.489 | TTTCCAGATGTCCCTGGTAGATTTGGGA | 28 |
| SEQ ID NO.490 | GGCCCAATGGAGAGCTGTCATCTTTAAC | 28 |
| transcription factor E4TF1-60 | | |
| SEQ ID NO.491 | GCAGCCAAAGTACAAAGAGCGCCGAG | 26 |
| SEQ ID NO.492 | GCTGTGACTGGCTGGGCAATTCCATG | 26 |
| RecA-like protein HsRad51 | | |
| SEQ ID NO.493 | TTATTGTAGACAGTGCCACCGCCCTTTA | 28 |
| SEQ ID NO.494 | TCGTAGATTTGGCAGATTCTGGTTTCCC | 28 |
| alpha-catenin | | |
| SEQ ID NO.495 | GGCTCCTGAATATCAGTCACTGTTGC | 27 |
| SEQ ID NO.496 | ACCCTAACGCCGCCATCACTAAGAGA | 26 |
| Id-1H | | |
| SEQ ID NO.497 | CCGGCAAGACAGCGAGCGGTGCG | 23 |
| SEQ ID NO.498 | GGCGCTGATCTCGCCGTTGAGGG | 23 |
| Tax helper protein 1 | | |
| SEQ ID NO.499 | AGCTGGTGCATCACATCAACAACGAGC | 27 |
| SEQ ID NO.500 | CTGGGATCTTGCAGATGTAGGGTTTCTC | 28 |
| transcription factor AREB6 | | |
| SEQ ID NO.501 | CTACAGTCACTGCCCAGTTACCCACA | 26 |
| SEQ ID NO.502 | GGGCGGTGTAGAATCAGAGTCATTCTGA | 28 |
| DAD-1 | | |
| SEQ ID NO.503 | ACTCCGCAGCGTCTGAAGTTGCTGG | 25 |
| SEQ ID NO.504 | GGAGATGCCTTGGAAATCCGCTTTGTTC | 28 |
| Sky | | |
| SEQ ID NO.505 | GGTGGACATTGCCTGCGGCATGGA | 24 |
| SEQ ID NO.506 | CCCAAGATGTTCTCCAGTTCCATTCGCA | 28 |
| BST-1 | | |
| SEQ ID NO.507 | TTCAGAGCCAACAGGAGCCTATCCCA | 26 |
| SEQ ID NO.508 | CGACTTTAAGGCACAGTCAGGATGGGT | 27 |
| integrin alpha subunit | | |
| SEQ ID NO.509 | ACTGCTCAGAGTGGCAACACGGAGC | 25 |
| SEQ ID NO.510 | GGTGCTTGGGCCAGTGTTGTAGACCT | 26 |
| ZFM1 protein | | |
| SEQ ID NO.511 | ATCGGCTCAGAGTGGCAACACGGAGC | 26 |
| SEQ ID NO.512 | CCCTCGGTAACTTTACAAGACTCCCT | 26 |
| ZFM1 alternatively spliced product | | |

TABLE 1-continued

| SEQUENCE DESCRIPTION | | Length |
|---|---|---|
| SEQ ID NO.513 | AGCCGCTGGAACCAAGCACGAATGGA | 26 |
| SEQ ID NO.514 | GGTTTACAGTACCTGCGGTGTTCTCC | 26 |
| transcriptional activator hSNF2a | | |
| SEQ ID NO.515 | AGTCTTCAAGCCACGAGCGGAGGG | 24 |
| SEQ ID NO.516 | GAGGGCGTCACTGTAGTCCACGTCA | 25 |
| LIMK | | |
| SEQ ID NO.517 | AGGATAGGCACAGTGGACCGGGCA | 24 |
| SEQ ID NO.518 | GTCCCACGGGCCTGTTGGGATTGTTT | 26 |
| DB1 | | |
| SEQ ID NO.519 | AGCTGCTAACCTGTGCCAAACCTCCA | 26 |
| SEQ ID NO.520 | GGAGATGTGATGGTGACAGGGTGTGC | 26 |
| unknown product | | |
| SEQ ID NO.521 | 26 CCCTGTGGAATGTTGGGTCTGCGTCT | |
| SEQ ID NO.522 | 25 CAGGGACCTTAGCCCGATTCATGCC | |
| DNA-binding protein TAXREB302 | | |
| SEQ ID NO.523 | CCGGCGGTACAAGAACAACGAGGC | 24 |
| SEQ ID NO.524 | GATAGGGTCCTTGACGTGCCGGG | 23 |
| beta-14-galactosyltransferase | | |
| SEQ ID NO.525 | ACACTCCGTGGCCCACCCTTTGTTAC | 26 |
| SEQ ID NO.526 | GGTGGAACAGGAGGCTTTAGGACCGA | 26 |
| intercellular adhesion molecule-1(ICAM-1) | | |
| SEQ ID NO.527 | GGGAGCTTCGTGTCCTGTATGGCC | 24 |
| SEQ ID NO.528 | AGTGTGTATTTCTTGATCTTCCGCTGGC | 28 |
| transforming growth factor-beta 3(TGF-beta3) | | |
| SEQ ID NO.529 | CCCTGACCATCCTGTACTATGTTGGG | 26 |
| SEQ ID NO.530 | GGGTAGCCCAAATCCCATTGCCACAC | 26 |
| erythroid differentiation protein(EDF) | | |
| SEQ ID NO.531 | TCTGAAGACCACCCTCATCGCCGG | 24 |
| SEQ ID NO.532 | CAAGTGTATGAGCACCCACACTCCTC | 26 |
| sialophorin(CD43) | | |
| SEQ ID NO.533 | CTCCCATGTTTCCACCCGGCACCC | 24 |
| SEQ ID NO.534 | GGCGCGGAGGCTCATGTCTGTAATC | 25 |
| nucleotide binding protein | | |
| SEQ ID NO.535 | TGCCCATTTGATCGACAAGTAACAGACC | 28 |
| SEQ ID NO.536 | ACATGAGTGGGCTAGTTTGACAACCTTC | 28 |
| excision repair protein ERCC6 | | |
| SEQ ID NO.537 | GGGTTGGGTCCAACTGTAATTGTCTGTC | 28 |
| SEQ ID NO.538 | TCCATAAACACAGGCAACGTGCCTAACT | 28 |
| MAP kinase kinase | | |
| SEQ ID NO.539 | AGCTGGAGCTGATGTTTGGGTGCCAG | 26 |
| SEQ ID NO.540 | CTTAGACGCCAGCAGCATGGGTTGGT | 26 |
| transcription factor | | |
| SEQ ID NO.541 | CCGGAAACCTGCTAACGATAGAGACTC | 27 |
| SEQ ID NO.542 | TGGTGTTACTGATGCTCCGGTTCCTC | 26 |
| replication factor C 36-kDa subunit | | |
| SEQ ID NO.543 | GACTGTCTACACCTGCACCGGGCA | 24 |

TABLE 1-continued

| SEQUENCE DESCRIPTION | | Length |
|---|---|---|
| SEQ ID NO.544 | GAATGGCCCTCAGAGCATCTAGGCC | 25 |
| replication factor C 38-kDa subunit | | |
| SEQ ID NO.545 | ACCTATTCGTAGTAGGTGCTTGGCGG | 26 |
| SEQ ID NO.546 | AGCTCATACAGCCTTCCACGAACTTCAA | 28 |
| peroxisome proliferator activated receptor | | |
| SEQ ID NO.547 | TGCAGGTCCTGGTGGGTCAGCCC | 23 |
| SEQ ID NO.548 | ACCAGCGGTGTGGGACTGGTCCC | 23 |
| MXII | | |
| SEQ ID NO.549 | ACTAGGACCAGACTGCACCCGGCA | 24 |
| SEQ ID NO.550 | CCCTCGTCACTCCCAATACTCGGCA | 25 |
| achaete scute homologous protein(ASH1) | | |
| SEQ ID NO.551 | GGAGCAGGAGCTTCTCGACTTCACC | 25 |
| SEQ ID NO.552 | GCATTGACTCAGGTCCCAGTTGCTCTT | 27 |
| sex-determining region Y(SRY) | | |
| SEQ ID NO.553 | CTAGAGAATCCCAGAATGCGAAACTCAG | 28 |
| SEQ ID NO.554 | AGGTAGGTCTTTGTAGCCAATGTTACCC | 28 |
| moesin-ezrin-radixin-like protein | | |
| SEQ ID NO.555 | CTCTTTGATTTGGTGTGCCGGACTCTG | 27 |
| SEQ ID NO.556 | CACCATACTTGGCCTGGACGGCGTAA | 26 |
| Kruppel-related zinc finger protein(HTF10) | | |
| SEQ ID NO.557 | CCTGGAAGCCTAGAAATGGGACTGTTG | 27 |
| SEQ ID NO.558 | ATACTTTGCTCTGGGCAGTTGTGAGACA | 28 |
| focal adhesion kinase(FAK) | | |
| SEQ ID NO.559 | TACCCTCTACAGCCTTATGACGAAATGC | 28 |
| SEQ ID NO.560 | CAATCCCTCGCAGGTCCAATACTGTAGA | 28 |
| activated p21cdc42Hs kinase(ack) | | |
| SEQ ID NO.561 | AGAAGATCGGCATGGGTCGGCCTG | 24 |
| SEQ ID NO.562 | GGTTTCGGTGGTCGAGCGAGTGCAT | 25 |
| TR3 orphan receptor | | |
| SEQ ID NO.563 | TTCTCCACACCTTGAGGGCTCGGG | 24 |
| SEQ ID NO.564 | GCAGAACTGGCAGCGGTTTCGCCG | 24 |
| transcription factor RZR-alpha | | |
| SEQ ID NO.565 | CCTACTGTTCGTTCACCAACGGCGAG | 26 |
| SEQ ID NO.566 | CTGAGAGTCAAAGGCACGGCACACTC | 26 |
| aminopeptidase A | | |
| SEQ ID NO.567 | ATGGGATGCAGAACTCTGGCAATGAGAT | 28 |
| SEQ ID NO.568 | CAGTGTTGAATGGCTCTGCTATTGTGAC | 28 |
| tight junction(zonula occludens)protein ZO-1 | | |
| SEQ ID NO.569 | CTGCGCTTACCACACTGTGATCCTAAAA | 28 |
| SEQ ID NO.570 | GCCAATACCAACAGTCCCGTCAATCACA | 28 |
| c-myc transcription factor(puf) | | |
| SEQ ID NO.571 | CCTTCATCGCCATCAAGCCGGACG | 24 |
| SEQ ID NO.572 | GCTTTGAATCTGCTGGATTGGTCTCCC | 27 |
| NF-kappa-B transcription factor p65 subunit | | |
| SEQ ID NO.573 | CCCTGTCCTGATGGTCAGCTCCCT | 24 |
| SEQ ID NO.574 | CTCAAACGCTGGTGTTAGGCACAGGG | 26 |

TABLE 1-continued

| SEQUENCE DESCRIPTION | | Length |
|---|---|---|
| natural killer cell enhancing factor(NKEFB) | | |
| SEQ ID NO.575 | TCTCGGTGGACTCTCAGTTCAACCAC | 26 |
| SEQ ID NO.576 | ATCCGTTAGCCAGCCTAATTGTGTTTGG | 28 |
| paired box homeotic protein(PAX8) | | |
| SEQ ID NO.577 | GTAGACCTGGCCCACCAGGGTGTA | 24 |
| SEQ ID NO.578 | GTCTCGGATCTCCCAGGCAAACATGG | 26 |
| ERCC5 excision repair protein | | |
| SEQ ID NO.579 | TACTGCAACACTTGCGTCATCTAGTGTG | 28 |
| SEQ ID NO.580 | GTACAAGTTGGAGATGCCGGTGTCAGTT | 28 |
| protein serine/threonine kinase stk1 | | |
| SEQ ID NO.581 | ATGGCTCTGGACGTGAAGTCTCGGG | 25 |
| SEQ ID NO.582 | GATCATGGGCCTCAGGTGAAACTCCG | 26 |
| protein serine/threonine kinase stk2 | | |
| SEQ ID NO.583 | GTAATTCGTGGCCTGGGAGTTCAGCT | 26 |
| SEQ ID NO.584 | TGGTGAGTGGCTTCCAAATGACTGTTTG | 28 |
| 14-3-3n protein | | |
| SEQ ID NO.585 | GTGGTTGGTGCCAGGCGATCTTCC | 24 |
| SEQ ID NO.586 | GCGTGGAGTCCTTATAGGAATCCTCGTT | 28 |
| octamer binding transcription factor 1(OTF1) | | |
| SEQ ID NO.587 | CACAATTAGGTCTCACTCTGGTTAGGCA | 28 |
| SEQ ID NO.588 | GGTAGATCAATCCGTGAGACATTTCAGG | 28 |
| S protein | | |
| SEQ ID NO.589 | GTGCCCAGGCATAGGGTTAGCTCAG | 25 |
| SEQ ID NO.590 | GCATATTGGGTGGGTTGACTAGATGTCG | 28 |
| plasma membrane calcium ATPase isoform 2(ATP2B2) | | |
| SEQ ID NO.591 | GATCCGCGTCGTGAAGGCGTTCCG | 24 |
| SEQ ID NO.592 | GCCCGGAAAGCGGGTGACAGCGG | 23 |
| guanine nucleotide regulatory protein(G13) | | |
| SEQ ID NO.593 | CCACTTCACCACTGCTATCAACACGG | 26 |
| SEQ ID NO.594 | CAGCAAATCTTGGCGATGAGTCACTCAA | 28 |
| Bax beta | | |
| SEQ ID NO.595 | TGCAGAGGATGATTGCCGCCGTGG | 24 |
| SEQ ID NO.596 | CACCCAACCACCCTGGTCTTGGATC | 25 |
| Rad | | |
| SEQ ID NO.597 | AGCAGGGCACACCTATGATCGCTCC | 25 |
| SEQ ID NO.598 | CGGCCCTCATCCACCGAGACCTCA | 24 |
| calcium/calmodulin dependent protein kinase | | |
| SEQ ID NO.599 | TACATTTCAAGCTCTCCAGCATCCGTGG | 28 |
| SEQ ID NO.600 | CTGGAATAGCTTTCATGTCCTCGTTGCC | 28 |
| CTLA4 counter-receptor(B7-2) | | |
| SEQ ID NO.601 | GTCAGTGCTTGCTAACTTCAGTCAACCT | 28 |
| SEQ ID NO.602 | AACAGACAAGCTGATGGAAACGTCGTAC | 28 |
| GRB2 isoform | | |
| SEQ ID NO.603 | CTGCGGGACATAGAACAGGTGCCAC | 25 |
| SEQ ID NO.604 | GACTCTTAGACGTTCCGGTTCACGGG | 26 |
| nuclear factor I-X | | |
| SEQ ID NO.605 | TGGCGGCTGGACCTGGTCATGGTG | 24 |

TABLE 1-continued

| SEQUENCE DESCRIPTION | | Length |
|---|---|---|
| SEQ ID NO.606 | GATACTCTCACCAGCTCCGTCACATTC | 27 |
| protein kinase(MLK-3) | | |
| SEQ ID NO.607 | GGAGGCCCGGCTCTTCGCCATGC | 23 |
| SEQ ID NO.608 | GTCGGTGATCTTCAGGGTCTTGTGCT | 26 |
| CDC2-related protein kinase(PISSLRE) | | |
| SEQ ID NO.609 | CCTCCAGTATCTGCACAGGAACTTCATT | 28 |
| SEQ ID NO.610 | CAAGTCGATCTGGTGGATCTCGGAAGT | 27 |
| RNA polymerase II elongation factor SIII p15 subunit | | |
| SEQ ID NO.611 | GGCTGTGAAGGACCTGATGCCATGTA | 26 |
| SEQ ID NO.612 | TCGGTGGAGCTGTTAGTGTAGCGAAC | 26 |
| opioid-binding cell adhesion molecule | | |
| SEQ ID NO.613 | ACACCAATGCCAGCATCACATTGTATGG | 28 |
| SEQ ID NO.614 | GCTGGTTTGCTCTCCGCAGTGTAGAT | 26 |
| autocrine motility factor receptor(AMFR) | | |
| SEQ ID NO.615 | AATGCAGGTGTCCTGAGCACCACACC | 26 |
| SEQ ID NO.616 | GGAAAGTCAGTCCCAGATGTAGTGGGA | 27 |
| mas proto-oncogene | | |
| SEQ ID NO.617 | CTCCTCATGGATGGGTCAAACGTGAC | 26 |
| SEQ ID NO.618 | CAGACCAATGCCGACTGGTACTTGGG | 26 |
| guanine nucleotide-binding protein G-s aplha subunit | | |
| SEQ ID NO.619 | TCTCTGTGATCCTGTTCCTCAACAAGCA | 28 |
| SEQ ID NO.620 | AATGATGTCACGGCAGTCGTTAACACA | 28 |
| pro-urokinase | | |
| SEQ ID NO.621 | TAGCCAATGTGGGAGCAGCGGTTTGG | 26 |
| SEQ ID NO.622 | ATAAGTACATTCCCAGGCACTGTCACGT | 28 |
| tissue-type plasminogen activator(t-PA) | | |
| SEQ ID NO.623 | GCTCTCCGGCTACGGCAAGCATGA | 24 |
| SEQ ID NO.624 | GTCGGGTGTTCCTGGTCACGGTCG | 24 |
| MAL protein gene | | |
| SEQ ID NO.625 | CTCTGCTCTACGTGGTCCATGCGG | 24 |
| SEQ ID NO.626 | GAGAGTAAACACAGCACCCACGAGCA | 26 |
| homeo box c1 protein | | |
| SEQ ID NO.627 | GCGCCCTTTGAGCAGAACCTCTCC | 24 |
| SEQ ID NO.628 | GCGCCGGTTCTGAAACCAAATCTTGATC | 28 |
| plasminogen activator inhibitor 2(PAI-2) | | |
| SEQ ID NO.629 | CTTTCCGTGTAAACTCGGCTCAGCGC | 26 |
| SEQ ID NO.630 | GAAATTGGCCCGTCCCTTGTTGAAGG | 26 |
| fructose 16-biphosphatase | | |
| SEQ ID NO.631 | TGCTCTGCAACCAGGCCGGAACCT | 24 |
| SEQ ID NO.632 | CAGTGACGGCAGGGTCAAAGTCCTTG | 26 |
| differentiation antigen(CD19) | | |
| SEQ ID NO.633 | ATGGAGACGGGTCTGTTGTTGCCCC | 25 |
| SEQ ID NO.634 | GCACGTTCCCGTACTGGTTCTGGG | 24 |
| protein kinase C alpha-polypeptide(PKCA) | | |
| SEQ ID NO.635 | CCGGCCAGTGGATGGTACAAGTTGC | 25 |
| SEQ ID NO.636 | CTCCACGTCATCATCCTGAATCACCACA | 28 |

TABLE 1-continued

| SEQUENCE DESCRIPTION | | Length |
|---|---|---|
| differentiation antigen (CD33) | | |
| SEQ ID NO.637 | GACAGCAGTGGGCAGCAATGACACC | 25 |
| SEQ ID NO.638 | CTTCTAGCTGAGCCTGATGCTCTTGAG | 27 |
| prothymosin alpha(ProT-alpha) | | |
| SEQ ID NO.639 | TATTCACCCTCCACTTCCCGTCTCAG | 26 |
| SEQ ID NO.640 | CAGAAGTAGGACAGAGAACGCTCCGAA | 27 |
| GTP-binding protein(RAB3A) | | |
| SEQ ID NO.641 | GTACCGGACCATCACCACCGCATAC | 25 |
| SEQ ID NO.642 | CAGATGACATCCACCAGGCGCTCAAA | 26 |
| GTP-binding protein(RAB4) | | |
| SEQ ID NO.643 | GGGATACAGCAGGACAAGAACGATTCAG | 28 |
| SEQ ID NO.644 | CTTGAGCAAATCTGGAGGCTTCTAAGAAG | 29 |
| GTP-binding protein(RAB6) | | |
| SEQ ID NO.645 | TCTAGTTCCACAATGTCCACGGGCGG | 26 |
| SEQ ID NO.646 | GGAATCAAGCTCCTGAACCGCTCTTGA | 27 |
| GTP-binding protein(RAB2) | | |
| SEQ ID NO.647 | AAACTTCAGATATGGGATACGGCAGGGC | 28 |
| SEQ ID NO.648 | GCAGACGTTTCCATGAACATGAGTCCAT | 28 |
| GTP-binding protein(RAB3B) | | |
| SEQ ID NO.649 | CGGACCATCACAACAGCCTATTACCG | 26 |
| SEQ ID NO.650 | CAAATGGCATCCACCAGGCGCTCAAA | 26 |
| GTP-binding protein(RAB5) | | |
| SEQ ID NO.651 | TCGGGAAACAAGGCCGACCTAGCAAA | 26 |
| SEQ ID NO.652 | TGTGGGTTCGGTAAGGTCTACTCCTC | 26 |
| platelet endothelial cell adhesion molecule (PECAM-1) | | |
| SEQ ID NO.653 | GAAATGTCCAGGCCCAGCAGTACCACT | 26 |
| SEQ ID NO.654 | CTAGAGTATCTGCTTTCCACGGCATCAG | 28 |
| MUC18 glycoprotein | | |
| SEQ ID NO.655 | GAAGGGCAAGGCTGCCGTGCAGG | 23 |
| SEQ ID NO.656 | TGGGATGAGCTTCACTCAACGTGGAC | 26 |
| stem cell protein(SCL) | | |
| SEQ ID NO.657 | CTAGGGCTATGGTGTGGACTGAATGG | 26 |
| SEQ ID NO.658 | CTGAGTGACAGAACAAGACACCGTCTCT | 28 |
| myeloblastin | | |
| SEQ ID NO.659 | GCTGAGCAGCCCAGCCAACCTCAG | 24 |
| SEQ ID NO.660 | ACACGGCGCAGCGTAGAACGGATC | 24 |
| DNA-binding factor | | |
| SEQ ID NO.661 | GATCCTTTGTCAACCTCACAGACAACAAG | 29 |
| SEQ ID NO.662 | GTAGACATGCTGCTACCTGGTTGCACTT | 28 |
| vascular adhesion molecule 1 | | |
| SEQ ID NO.663 | TCGAGATGAGTGGTGGCCTCGTGAAT | 26 |
| SEQ ID NO.664 | GGAAAGCCCTGGCTCAAGCATGTCATAT | 28 |
| Endothelial leucocyte adhesion molecule I(ELAM1) | | |
| SEQ ID NO.665 | TGAAACCGCAACACCCATCACCACTTC | 27 |
| SEQ ID NO.666 | ACCCTCGCACAGAGCATTCAGTAGGA | 26 |
| Ku(p70/p80)subunit | | |

TABLE 1-continued

| SEQUENCE DESCRIPTION | | Length |
|---|---|---|
| SEQ ID NO.667 | AGCAGGTTACCTGGAGGCGGATCATC | 26 |
| SEQ ID NO.668 | GAGAAGTGAGTCCGTCCTTACCCATG | 26 |
| papillary thyroid carcinoma-encoded protein | | |
| SEQ ID NO.669 | AGAGGGCTCACAAGACACATTTGTGCC | 27 |
| SEQ ID NO.670 | AGGTGTAGCAGTCCTTGGTCATTGTGAT | 28 |
| transcription factor(E2A) | | |
| SEQ ID NO.671 | AAACTGCATCTTGGCCCTGTTGCCTG | 26 |
| SEQ ID NO.672 | TCTAGGAACAGCAGCAGAAATAGCGAGA | 28 |
| cyclic AMP response element-binding protein(HB16) | | |
| SEQ ID NO.673 | CAACAGCCAGCCACATCCACTACAGA | 26 |
| SEQ ID NO.674 | GCGGTTACAGGGCAATCTTTATGAGCCA | 28 |
| DNA repair helicase(ERCC3) | | |
| SEQ ID NO.675 | TACTCAACCAAGCGGCAGAGATTCTTGG | 28 |
| SEQ ID NO.676 | ACGAAGTACCCTGCCTAAGCATCATTTC | 28 |
| epithelial glucoprotein(EGP) | | |
| SEQ ID NO.677 | CGCAGGTCCTCGCGTTCGGGCTT | 23 |
| SEQ ID NO.678 | CCCGCTCTCATCGCAGTCAGGATCAT | 26 |
| Ku protein subunit | | |
| SEQ ID NO.679 | AGCAAGGGTACGCTGGGCAAGTTCAC | 26 |
| SEQ ID NO.680 | CCTCGACTTATGTCGGGTAGACTCTTC | 27 |
| cell adhesion protein(SQM1) | | |
| SEQ ID NO.681 | CCGGCGCTACCTGGGCGATGCTT | 23 |
| SEQ ID NO.682 | GCCCTCGTCCCGCTCAAACTCCTT | 24 |
| N-cadherin | | |
| SEQ ID NO.683 | AATTCAGCACCCGCCTCAGTCAACTG | 26 |
| SEQ ID NO.684 | TGCAGCGTTCCTGTTCCACTCATAGG | 26 |
| active transcription factor CREB | | |
| SEQ ID NO.685 | GCACCAGGAGTGCCAAGGATTGAAGA | 26 |
| SEQ ID NO.686 | CTAGTGGGTGCTGTCGCAATCTGGTAT | 27 |
| lymphocyte differentiation antigen CD38 | | |
| SEQ ID NO.687 | CATGTTCACCCTGGAGGACACGCTG | 25 |
| SEQ ID NO.688 | TCCATTGAGCATCACATGGACCACATCA | 28 |
| transcription factor IID | | |
| SEQ ID NO.689 | CCGAAACGCCGAATATAATCCCAAGCG | 27 |
| SEQ ID NO.690 | CTAAATTGTTGGTGGGTGAGCACAAGGC | 28 |
| cell 12-lipoxygenase | | |
| SEQ ID NO.691 | TTCCAACTGCACGAGATCCAGTATCACT | 28 |
| SEQ ID NO.692 | GCCGCCCGACGGAGCAAGTGTAC | 23 |
| ribosomal protein L7a(surf 3)large subunit | | |
| SEQ ID NO.693 | CCCAGGCCCTGGACCGCCAAACA | 23 |
| SEQ ID NO.694 | GCGATACGAGCCACAGACTTAGGACC | 26 |
| DNA-repair protein(XRCC1) | | |
| SEQ ID NO.695 | TCCAGTCTCCAGGGCCATAGGCAG | 24 |
| SEQ ID NO.696 | GAAGCCACTCAGCACCACTACCACAC | 26 |
| transducin beta-2-subunit | | |
| SEQ ID NO.697 | GCGAGGGCAACGTCAGGGTCAGC | 23 |

TABLE 1-continued

| SEQUENCE DESCRIPTION | | Length |
|---|---|---|
| SEQ ID NO.698 | CCGGTGGTGAAGGCGTAGCCGTTG | 24 |
| transducin beta-1-subunit | | |
| SEQ ID NO.699 | GCCTGCGGTGGCCTGGATAACATTTG | 26 |
| SEQ ID NO.700 | CATCACAAGCACCAGAGACGAACAGTCT | 28 |
| lymphoid-specific transcription factor | | |
| SEQ ID NO.701 | GCATCAAGCTGGGCTTCACGCAGG | 24 |
| SEQ ID NO.702 | AAGGCGAAGCGGACGTTTGTCTCGAT | 26 |
| sequence-specific DNA-binding protein(AP-2) | | |
| SEQ ID NO.703 | AGCTGTCCACCTAGCCAGGGACTTTG | 26 |
| SEQ ID NO.704 | GAGATGAGGTTGAAGTGGGTCAAGCAG | 27 |
| h-pim-1 protein | | |
| SEQ ID NO.705 | GCTCAAGCTCATCGACTTCGGGTCG | 25 |
| SEQ ID NO.706 | GGCCTATCTGATGGTCTCAGGGCCAA | 26 |
| B cell differentiation antigen | | |
| SEQ ID NO.707 | TTCACTGTTCGGAAATGGTGGTTCAGGG | 28 |
| SEQ ID NO.708 | TTGGCATGAGTGTCAACTCAGTGCAAAG | 28 |
| duronate-2-sulfatase | | |
| SEQ ID NO.709 | CGAGGGCACCTTGCCTGACAAACAG | 25 |
| SEQ ID NO.710 | GGCACACTGATGTTTAAGGCTTGGACGT | 28 |
| ribisomal protein S4(RPS4X)isoform | | |
| SEQ ID NO.711 | TGTATGGTGACTGGAGGTGCTAACCTAG | 28 |
| SEQ ID NO.712 | CATGTCACCCAGGGACCCATTTCACC | 26 |
| ribisomal protein (RPS4Y)isoform | | |
| SEQ ID NO.713 | TTGCACCTCGTCCATCGACAGGTCC | 25 |
| SEQ ID NO.714 | GGGTAGCGGATGGTTCGAGCATCATG | 26 |
| 75-kD autoantigen(PM-Sc1) | | |
| SEQ ID NO.715 | CTTGGACAGGTTTCCTGTGAACTTGTGT | 28 |
| SEQ ID NO.716 | GGAAATGACATAAGGCCACGATTGCAGC | 28 |
| ELAM-1 ligand fucosyltransferase(ELFT) | | |
| SEQ ID NO.717 | GACTGCCGCATCATGGGAGTAAGTTG | 26 |
| SEQ ID NO.718 | TGAGGAATCCAAACAACAAAGTCCCACC | 28 |
| cell adhesion molecule(CD44) | | |
| SEQ ID NO.719 | AACCATTACAGGGAGCTGGGACACTTAA | 28 |
| SEQ ID NO.720 | TTTGTTAGAAGCCATCCATAGCACACCC | 28 |
| neurofibromatosis protein type I(NF1) | | |
| SEQ ID NO.721 | TCAATCCTGCCATTGTCTCACCGTATGA | 28 |
| SEQ ID NO.722 | ACGATGTAAAGCAAGCACATTGCCGTCA | 28 |
| colorectal mutant cancer protein | | |
| SEQ ID NO.723 | TCTTCCACATGGGTGCATTTGTAGCTCT | 28 |
| SEQ ID NO.724 | TTGGTACTGCCTAGCCCTGTAAGCATTT | 28 |
| mitochondrial transcription factor 1 | | |
| SEQ ID NO.725 | TTCCAAGAAGCTAAGGGTGATTCACCGC | 28 |
| SEQ ID NO.726 | AGTATTATGCTGGCAGAAGTCCATGAGC | 28 |
| transcription factor ETR103 | | |
| SEQ ID NO.727 | TGGCTTCCAGGTTCCCATGATCCCC | 25 |
| SEQ ID NO.728 | GGCAAGCGTAAGGGCGTTCGTGGG | 24 |

TABLE 1-continued

| SEQUENCE DESCRIPTION | | Length |
|---|---|---|
| transcription factor ETR101 | | |
| SEQ ID NO.729 | TGCGCCCACAGGTGCTGTCTTAGTG | 25 |
| SEQ ID NO.730 | GGGTGAAGTAACTCAGGCCACTCTCC | 26 |
| replication protein A 70kDa subunit | | |
| SEQ ID NO.731 | ATGTACCAAGCCTGCCCGACTCAGG | 25 |
| SEQ ID NO.732 | TGGCCTTAATTCGAGACTCGTCGTTGTA | 28 |
| bullous pemphigoid antigen | | |
| SEQ ID NO.733 | TGTTGCAGGGTATTGGCTGACTGCTAG | 27 |
| SEQ ID NO.734 | GAGTGAACCTGTGGCTCTATCAACCCT | 27 |
| transcriptional enhancer factor(TEF1)DNA | | |
| SEQ ID NO.735 | CATCCTCACCAGCCTGTGGATACAATT | 27 |
| SEQ ID NO.736 | GATAGGTAGCTGGGCCTCTTAAACCTAA | 28 |
| aryl hydrocarbon receptor nuclear translocator(ARNT) | | |
| SEQ ID NO.737 | CCGGCAGAGAATTTCAGGAATAGTGGC | 27 |
| SEQ ID NO.738 | TCCACGATTGGTGAGACTAGGGTAGG | 26 |
| PML-1 protein(PML) | | |
| SEQ ID NO.739 | TCAGGATGCCTGGAGGCGTCGGG | 23 |
| SEQ ID NO.740 | TGGTCTTGCGGGTGCCGTCCAGG | 23 |
| cell adhesion molecule L1(L1CAM) | | |
| SEQ ID NO.741 | CCTTTCGCCACAGTATGTCAGCTACAAC | 28 |
| SEQ ID NO.742 | CTCCTTATCCTTCACTGAGTATTTGCCG | 28 |
| HHR6A(yeast RAD 6 homologue) | | |
| SEQ ID NO.743 | GATCCTCCAGCCGGAGTCAGCGG | 23 |
| SEQ ID NO.744 | GGAAGACACATCATAGGTTGGACTCCAA | 28 |
| dipeptidyl peptidase IV(CD26) | | |
| SEQ ID NO.745 | AAAGGCACCTGGGAAGTCATCGGGAT | 26 |
| SEQ ID NO.746 | GCTGAATTGTCTTCCAGGACTCTCAGC | 27 |
| sulfated glycoprotein-2 | | |
| SEQ ID NO.747 | TGCGGATGAAGGACCAGTGTGACAAG | 26 |
| SEQ ID NO.748 | CACCGTGGTGACCCGCAGATAGTAC | 25 |
| homeobox protein(HOX-11) | | |
| SEQ ID NO.749 | CTCCCAGAGGCGTCCCGCAGGTG | 23 |
| SEQ ID NO.750 | TGACCTGAGCCTGATCGTAAGGTCCA | 26 |
| 130-kD pemphigus vulgaris antigen | | |
| SEQ ID NO.751 | CTGTGGGCTCCGTGGGTTGTTGCA | 24 |
| SEQ ID NO.752 | AGGGAACCAGAAGCCGAGTAAGTCTC | 26 |
| DNA-binding protein(NF-E1) | | |
| SEQ ID NO.753 | AGATCAAGACCCTGGAGGGCGAGTTC | 26 |
| SEQ ID NO.754 | GACGTGGACTCTGGGACCGTGGGT | 24 |
| transcription factor(TFIIB) | | |
| SEQ ID NO.755 | CATGGCAGACAGAATCAATCTACCTCGA | 28 |
| SEQ ID NO.756 | AGTCCAATTCCACAGCTTTACGGGCTAT | 28 |
| HEB helix-loop-helix protein(HEB) | | |
| SEQ ID NO.757 | ATGAAACCTGCCTGCCACCACAACAAC | 27 |
| SEQ ID NO.758 | AAGAACAAGGCCACAGATAGAGTCCGAT | 28 |
| peroxisomal 70 kD membrane protein | | |
| SEQ ID NO.759 | TTTGGCTGGGCGTGAAATGACTAGATTG | 28 |

TABLE 1-continued

| SEQUENCE DESCRIPTION | | Length |
|---|---|---|
| SEQ ID NO.760 | GAAGTGTTCCAAGGGTCATGTAAGGTCT | 28 |
| transcription elongation factor(SII) | | |
| SEQ ID NO.761 | GAAGAACGCGGCTGGAGCATTGGATT | 26 |
| SEQ ID NO.762 | ACAGAATCAGAAGTGCTTGGTGCCCG | 26 |
| myeloid cell nuclear differentiation antigen | | |
| SEQ ID NO.763 | CCACCGCAAGAAACAAAGTGACATCGG | 27 |
| SEQ ID NO.764 | TAAATGGCGCTGTTGCTTTCAGTACCAC | 28 |
| S19 ribosomal protein | | |
| SEQ ID NO.765 | CCCGAATGGGTGGATACCGTCAAGC | 25 |
| SEQ ID NO.766 | TTTGTVVVTGAGGTGTCAGTTTGCGG | 26 |
| NRL gene product | | |
| SEQ ID NO.767 | GTCCTAGCCACGCCCTGTATGACC | 24 |
| SEQ ID NO.768 | CTCCCATTCACTGTGTCACCACACTTC | 27 |
| nuclease-sensitive element DNA-binding protein | | |
| SEQ ID NO.769 | GCAGGCGAAGTTCCCACCTTACTACA | 26 |
| SEQ ID NO.770 | TGGGCGTCTGCGTCGGTAATTGAAGT | 26 |
| retinoid X factor beta(RXR-beta) | | |
| SEQ ID NO.771 | CCTGAAGATGTGAAGCCACCAGTCTTAG | 28 |
| SEQ ID NO.772 | GATGTTAGTCACAGGGTCATTTGGGCTG | 28 |
| peroxisome assembly factor-1 | | |
| SEQ ID NO.773 | CACTTCCGGCTCCTGCGTCGCTC | 23 |
| SEQ ID NO.774 | CCAAACTAGCTGCTCCAGGGCCTTGT | 26 |
| replication factor C 40-kDa subunit(A1) | | |
| SEQ ID NO.775 | CGACGGAGCCCAGCAAGCCTTGAG | 24 |
| SEQ ID NO.776 | TTCAGCGCCTGCCTCATGTCTCCC | 24 |
| replication factor C 37-kDa subunit | | |
| SEQ ID NO.777 | AAAGGCGGGAACTGAGGCGACTGTG | 25 |
| SEQ ID NO.778 | GCAGCTACTCCTCGATCCTTGGTCAG | 26 |
| IFN-responsive transcription factor subunit | | |
| SEQ ID NO.779 | CCCACCGAAGTTCCAGGTAACAGTGA | 26 |
| SEQ ID NO.780 | GGCTTTAGAGTTGGGAGGTCAGGGAA | 26 |
| Lowe oculocerebrorenal syndrome(OCRL) | | |
| SEQ ID NO.781 | CATCCTTAGAGGCTCTGTGCCGTATG | 26 |
| SEQ ID NO.782 | AGAGTGGTTGCTGCCAGGGATTGTCT | 26 |
| c-myeloproliferative leukemia virus type P(c-mpl-P) | | |
| SEQ ID NO.783 | CTGTCAATGGCAGCAACAGGACCATG | 26 |
| SEQ ID NO.784 | CTGTAAACGGTAGCGAGATCGCGGG | 25 |
| homeobox 21 protein(HOX2A) | | |
| SEQ ID NO.785 | AGTTCCTGCTGCCTGGGTAGGCCC | 24 |
| SEQ ID NO.786 | CACGTAGCACAGCATCCAGTGGCTCA | 26 |
| zinc finger tanscriptional regulator | | |
| SEQ ID NO.787 | GATCCGACCCTGATGAATATGCCAGC | 26 |
| SEQ ID NO.788 | AAGAACCTCGGAAGACACTCCATCCC | 26 |
| FLI-1 | | |
| SEQ ID NO.789 | AGACGCCACAGTGGTGACACAGGAG | 25 |
| SEQ ID NO.790 | GGCCGTTGCTCTGTATTCTTACTGATCG | 28 |

TABLE 1-continued

| SEQUENCE DESCRIPTION | | Length |
|---|---|---|
| follicle stimulating hormone receptor | | |
| SEQ ID NO.791 | GACTGCAAGGTGCAGCTCCGCCAT | 24 |
| SEQ ID NO.792 | GGGTTCCGCACTGTGAGGTAGATGTG | 26 |
| nucleobindin precursor | | |
| SEQ ID NO.793 | CTGGCAGCCAAGCCCAGTTGAAGG | 24 |
| SEQ ID NO.794 | TCGGTGTAGGCAGGGTGCATCTCC | 24 |
| B-cell specific transcription factor(BSAP) | | |
| SEQ ID NO.795 | GGGCAGATGCCTAATTTCGCACAATGC | 27 |
| SEQ ID NO.796 | GGCTCTACCTGGCTGTTCTGACTTGA | 26 |
| MAR/SAR DNA binding protein(SATB1) | | |
| SEQ ID NO.797 | GGAGAGCAACGCGGTGCATCACCA | 24 |
| SEQ ID NO.798 | GAGGGTACAGGCCCACGTCTTGTATG | 26 |
| homeobox protein(HOX7) | | |
| SEQ ID NO.799 | TCTACACGGCCCATGTGGGCTACAG | 25 |
| SEQ ID NO.800 | GGCCTCTAGCTCTGTTCAACTGTCAATT | 28 |
| epidermal cytokeratin 2 | | |
| SEQ ID NO.801 | CCGAGGTCAAGGCCCAGTATGAGG | 24 |
| SEQ ID NO.802 | GTAGTCACGCAGCAGCCGCGCCAA | 24 |
| 5HT1a=5-hydroxytryptamine receptor | | |
| SEQ ID NO.803 | CATGGAGCAGCATCTCCCGCCCC | 23 |
| SEQ ID NO.804 | CATCTTGCGCTTCGCCTCGGCGTT | 24 |
| transmembrane 4 superfamily protein(SAS) | | |
| SEQ ID NO.805 | TTGTGGCTTATTCAACCTCACAACCCTG | 28 |
| SEQ ID NO.806 | GTTACAGACCCTAGATATTCCCTAAGGGA | 29 |
| guanine nucleotide regulatory protein(NET1) | | |
| SEQ ID NO.807 | CCTTCCAGTCGGCAGGCAGTCCAC | 24 |
| SEQ ID NO.808 | TCCCTCGCTCTTCGGATGCCGGG | 23 |
| guanine nucleotide regulatory protein(tim1) | | |
| SEQ ID NO.809 | TTTGCACTGGACTCTGGGAACCTTTCAT | 28 |
| SEQ ID NO.810 | CTCACATTGCCACCAACAGACATAGATC | 28 |
| neu differentiation factor | | |
| SEQ ID NO.811 | TGCAGATCCAGCTATCAGCAACTCATCT | 28 |
| SEQ ID NO.812 | GTGGTGTCACGAGAAGTAGAGGTCTCT | 27 |
| PAX3/forkhead transcription factor gene fusion | | |
| SEQ ID NO.813 | CCCACACCTCGGGTATGAACCGCC | 24 |
| SEQ ID NO.814 | CACTAACCCTCAGCCTGACACCCAG | 25 |
| TFIIIC Box B-binding subunit | | |
| SEQ ID NO.815 | GGCATCGTCAGCACCCGCAACCTC | 24 |
| SEQ ID NO.816 | CCAAGGCCGAGAACCGTCTGCGC | 23 |
| alpha palindromic binding protein | | |
| SEQ ID NO.817 | ACCCAGGCCCAGCTTCGGGCATTT | 24 |
| SEQ ID NO.818 | GGCAACGGTGACCGTGGTTGGCAATT | 26 |
| tumor suppressor(LUCA-1) | | |
| SEQ ID NO.819 | CAGCCACTGTCACAGGCATATTCCCT | 26 |
| SEQ ID NO.820 | CACAAACTCAGTAGGAGTGCAAGGGCT | 27 |
| transcription factor LSF | | |

TABLE 1-continued

| SEQUENCE DESCRIPTION | | Length |
|---|---|---|
| SEQ ID NO.821 | GAATATACTGAGCACTTACACTCGGCCA | 28 |
| SEQ ID NO.822 | GGTGTGGTTGTTGGTAAGAGGTTATCTG | 28 |
| transcription factor LSF-ID | | |
| SEQ ID NO.823 | TACAGTGGAGTTCCTGTGGGACCCTG | 26 |
| SEQ ID NO.824 | GGTGTGGTTGTTGGTAAGAGGTTATCTG | 28 |
| dioxin-inducible cytochrome P450(CTP1B1) | | |
| SEQ ID NO.825 | CCCGCGACATGATGGACGCCTTTATC | 26 |
| SEQ ID NO.826 | GGTGGCATGAGGAATAGTGACAGGCA | 26 |
| Ini1 | | |
| SEQ ID NO.827 | TGGAGGACGACGGCGAGTTCTACATG | 26 |
| SEQ ID NO.828 | CATGCGGTTCCTGTTGATGGTTGTGGA | 27 |
| FUSE binding protein | | |
| SEQ ID NO.829 | ACAGGACCTCCAGACCGATGTCAACA | 26 |
| SEQ ID NO.830 | AGTCTATCTGTTGTGGAGTGCCACGAAT | 28 |
| p55CDC | | |
| SEQ ID NO.831 | GGCACCAGTGATCGACACATTCGCAT | 26 |
| SEQ ID NO.832 | GCCATAGCCTCAGGGTCTCATCTGCT | 26 |
| interferon gamma recetor accessory factor-1(AF-1) clone pSK1 | | |
| SEQ ID NO.833 | ATCAAGCCATCGGAGCTGCTAGAGTTC | 27 |
| SEQ ID NO.834 | TCATTTGCCAAAGTCAAGACGACGACCA | 28 |
| voltage-gated calcium channel beta subunit | | |
| SEQ ID NO.835 | AGGGTGGCACACCCATCCGTTTGC | 24 |
| SEQ ID NO.836 | AACAAGCGGCAGCTATGAGTCAGGGA | 26 |
| mutant lymphocyte-specific protein tyrosine kinase | | |
| SEQ ID NO.837 | CGGCTGGTTCGGCTCTACGCTGTG | 24 |
| SEQ ID NO.838 | CCTCAATGAGGCGTGCTAGGCCAAAG | 26 |
| amphiphysin | | |
| SEQ ID NO.839 | GTCATAGAGCCTGCCTCCAACCATGA | 26 |
| SEQ ID NO.840 | CTCTGTACTGAAGCCAGTCTGATTCCTT | 28 |
| epidermal growth factor receptor substrate(eps15) | | |
| SEQ ID NO.841 | GTAGACTCAAGTTCGCTGACAGGTCC | 26 |
| SEQ ID NO.842 | TGAATCGCTTGCTGCAACAAGTGTTCCA | 28 |
| contractin 1 precursor(CNTN1) | | |
| SEQ ID NO.843 | TCAGTTCAGTAAGGTCTGGTTCACGCTA | 28 |
| SEQ ID NO.844 | CGAATTGTGGTCATCCCAGGGTTGAAG | 27 |
| NF-ATc | | |
| SEQ ID NO.845 | GCAGAGCACGGACAGCTATCCGGT | 24 |
| SEQ ID NO.846 | CGCGCTCATGTTCACGGCTTACGGT | 25 |
| R kappa B | | |
| SEQ ID NO.847 | AAAGCAGGCCAGACCATCACCGTTGC | 26 |
| SEQ ID NO.848 | GGAACTGTGATCCGTGTAGGCAACTTC | 27 |
| transcription factor LCR-F1 | | |
| SEQ ID NO.849 | ACGACCCTACTCGCCCAGTCAGTATG | 26 |
| SEQ ID NO.850 | CCCTGTCCGTCTAAATGGTCTGGCC | 25 |
| serine kinase | | |
| SEQ ID NO.851 | TTGCTGAAGTCAGTTCGCAATTCAGACC | 28 |

TABLE 1-continued

| SEQUENCE DESCRIPTION | | Length |
|---|---|---|
| SEQ ID NO.852 | CAGATCGCTGCCATTCTGTTGCTTCTG | 27 |
| melanoma differentiation associated(mda-6) | | |
| SEQ ID NO.853 | ATTAGCAGCGGAACAAGGACTCAGACAT | 28 |
| SEQ ID NO.854 | CTGTGAAAGACACAGAACAGTACAGGGT | 28 |
| JAK family protein tyrosine kinase JAK3 | | |
| SEQ ID NO.855 | GGCCTTATGAGGGTCCTCTACTTCAG | 26 |
| SEQ ID NO.856 | CACTGTGAGCCGAGATCGCTACCAC | 25 |
| nuclear factor NF45 | | |
| SEQ ID NO.857 | GTCTGCTATACAGCTCAGACTCTCGTC | 27 |
| SEQ ID NO.858 | GGGAGACTGGCAGCTAAGCCAATATCAA | 28 |
| nuclear factor NF90 | | |
| SEQ ID NO.859 | ACCAGTCCTCACAAGGCGGCTATGG | 25 |
| SEQ ID NO.860 | GGCTAAATATGGGTCACAGGACGGGC | 26 |
| HOX A1 homeodomain protein(HOXA1) | | |
| SEQ ID NO.861 | CAACAGTTGCGGCGGCGACGACC | 23 |
| SEQ ID NO.862 | TATGAGTGGTGAATGTATTGAGGCGAGC | 28 |
| epidermal growth factor receptor kinase substrate (Eps8) | | |
| SEQ ID NO.863 | TCCACAGACTGACCATTGGTCGGAGT | 26 |
| SEQ ID NO.864 | CCTGAATCACTAGCGGCAGCACTGATTT | 28 |
| positive regulator of programmed cell death ICH-1L | | |
| SEQ ID NO.865 | TTTCAGCTCTTTGACAACGCCAACTGCC | 28 |
| SEQ ID NO.866 | CTTCCCGATCCTTGATAAGTGCGTTCAC | 28 |
| negative regulator of programmed cell death ICH-1S | | |
| SEQ ID NO.867 | AGTCACGGACTCCTGCATCGTGGC | 24 |
| SEQ ID NO.868 | TGTTCCGCATGGCGGCAGTCCCTT | 24 |
| homolog of Drosphila discs large protein isoform 1(hdlg-1) | | |
| SEQ ID NO.869 | GCGATAGTGAAAGTAGTTACCGTGGTCA | 28 |
| SEQ ID NO.870 | CCAGACACATCAAGGATACAGTGTTTGC | 28 |
| ard-1 | | |
| SEQ ID NO.871 | GTAGGCGAGGATACCAGCGATGATCT | 26 |
| SEQ ID NO.872 | CACCATGTTCCTGAATCGACCAACTGAG | 28 |
| platelet-endothelial tetraspan antigen 3 | | |
| SEQ ID NO.873 | CATGTGGCACCGTTTGCCTCAAGTAC | 26 |
| SEQ ID NO.874 | GTAGGCGAGGATACCAGCGATGATCT | 26 |
| LIM domain transcription factor LIM-1(hLIM-1) | | |
| SEQ ID NO.875 | TCTTGAACGTGCTGGACAGGGCCTG | 25 |
| SEQ ID NO.876 | TCGTCGATGATGTAGAGTTCCTCGCC | 26 |
| dlk | | |
| SEQ ID NO.877 | GCTTCACCATCCTGGGCGTGCTCA | 24 |
| SEQ ID NO.878 | CACCACAAACATTAGGACAGACCGCGTA | 28 |
| Transcription factor IL-4 Stat | | |
| SEQ ID NO.879 | CTTCTCAATGAGCCCGACGGAACCTT | 26 |
| SEQ ID NO.880 | TCCACGGTCATCTTGATGGTAGCTGG | 26 |
| S-protein | | |
| SEQ ID NO.881 | CATGGCTGGCCGCATCTACATCTCAG | 26 |

TABLE 1-continued

| SEQUENCE DESCRIPTION | | Length |
|---|---|---|
| SEQ ID NO.882 | GAGCGATGGAGCGTGGGTAGGGAG | 24 |
| trk oncogene | | |
| SEQ ID NO.883 | CTGTGGGCCTGGCCGTCTTTGCC | 23 |
| SEQ ID NO.884 | CCGAGCACTCTCGGACGCCTCCT | 23 |
| DNA polymerase alpha-subunit | | |
| SEQ ID NO.885 | TGCAACGTGGTTGGGACTTGACCCC | 25 |
| SEQ ID NO.886 | TGACGAGTTCGATTGCGACAGGTTGG | 26 |
| X chromsome CCG1 protein inv in cell proliferation | | |
| SEQ ID NO.887 | CCCTCTATTATCAAACAAATGCGCCACC | 28 |
| SEQ ID NO.888 | GATGATAGACTCCAAGATGGACGACAGC | 28 |
| ski oncogene | | |
| SEQ ID NO.889 | ACACAGCACAACGTCTTACCGTGCCT | 26 |
| SEQ ID NO.890 | GTTGCGGGTCTTCAGATGGCGTCATG | 26 |
| sno oncogene(snoN protein ski-related) | | |
| SEQ ID NO.891 | AATTGGCCTTGTTGCTGCCGCTTCATC | 27 |
| SEQ ID NO.892 | GCCTATCGGCCTCAGCATGGTCCAAT | 26 |
| N-CAM(a nontransmembrane isoform) | | |
| SEQ ID NO.893 | CACAGCCATCCCAGCAACCTTGGG | 24 |
| SEQ ID NO.894 | GGGCAAACTCCTTATGAAGTGGCACAAA | 28 |
| Wilms tumor WT1 zinc finger protein Krueppel-like | | |
| SEQ ID NO.895 | CCGGTGCTTCTGGAAACTACCAGGTG | 26 |
| SEQ ID NO.896 | GGCTGACCTCGGGAATGTTAGACAAGAT | 28 |
| GATA-3-transcription factor | | |
| SEQ ID NO.897 | CCCTCATTAAGCCCAAGCGAAGGCTG | 26 |
| SEQ ID NO.898 | GCCGGGTTAAACGAGCTGTTCTTGGG | 26 |
| P120 antigen | | |
| SEQ ID NO.899 | CAGACTCAGAATTGTCCACTGTACCTTC | 28 |
| SEQ ID NO.900 | GGGCTGATGATGGTCCTTAGGTTTCAG | 27 |
| ZFX put transcription activator isoform 1 | | |
| SEQ ID NO.901 | CCCTGATGGACATCCTTTGACTGTCTAT | 28 |
| SEQ ID NO.902 | GTGGCGATTCAATAACCCTTGTTCAGCT | 28 |
| CD3-gamma start codon mutation associated with T-cell receptor immunodeficiency | | |
| SEQ ID NO.903 | CATCCTGTCCAGCAATGAAGTAGACCC | 27 |
| SEQ ID NO.904 | CAAGGTACTTTGGCCCAGTCAATCAAAG | 28 |
| proliferation-associated gene(pag) | | |
| SEQ ID NO.905 | GGCCTTCCAGTTCACTGACAAACATGG | 27 |
| SEQ ID NO.906 | ACGCCAACTCAGGCCATTCCTACCAA | 26 |
| MacMarcks | | |
| SEQ ID NO.907 | AAACTGTGCTGTCCTTGTGAGGTCACTG | 28 |
| SEQ ID NO.908 | CACTCAAGGTTTGGGAGTATAAGCACCC | 28 |
| TRK E | | |
| SEQ ID NO.909 | GGCCCACCATCAGCTACCCAATGC | 24 |
| SEQ ID NO.910 | CGTCACTCGCAGTCGTGAACTTCCC | 25 |
| NEFA protein | | |
| SEQ ID NO.911 | CCTGTGGAAAGTGCGAAGATAGAACCAC | 28 |
| SEQ ID NO.912 | CATAGTGTTCCAGATCACTTGTTGCCGC | 28 |

TABLE 1-continued

| SEQUENCE DESCRIPTION | | Length |
|---|---|---|
| desmoglein 2 | | |
| SEQ ID NO.913 | AACTTCCTATGTCACAGGGTCCACTATG | 28 |
| SEQ ID NO.914 | CTGTCCTACTGCTATATTAGGCATGGCC | 28 |
| ANGIOTENSIN-CONVERTING ENZYME(ACE) | | |
| SEQ ID NO.915 | GGCACCCAGGCCAGGAAGTTTGATG | 25 |
| SEQ ID NO.916 | ATCTACATAGCCATTGAGCCGGGCAG | 26 |
| RELAXIN H2 | | |
| SEQ ID NO.917 | CGCGCAGATTGCCATTTGCGGCATG | 25 |
| SEQ ID NO.918 | GTCTGCGGCTTCACTTTGTCTATTGCGA | 28 |
| RENIN-BINDING PROTEIN | | |
| SEQ ID NO.919 | GGTGGTGAGTTCTTGCTGCGGTATGC | 26 |
| SEQ ID NO.920 | CAGTAGCATCATGGGCACCGCCATG | 25 |
| GLUTAMATE RECEPTOR TYPE 1 SUBTYPE 5A | | |
| SEQ ID NO.921 | ACACAATGGCAAGCATAGTCGCCTGG | 26 |
| SEQ ID NO.922 | CACCCTCCGTTACGCTGTTTCACACG | 26 |
| GLUCAGON | | |
| SEQ ID NO.923 | AGGGCACATTCACCAGTGACTACAGC | 26 |
| SEQ ID NO.924 | TAAAGTCCCTGGCGGCAAGATTATCAAG | 28 |
| GLUTAMATE RECEPTOR 5 | | |
| SEQ ID NO.925 | GGGCGGTTAGAGATGGATCAACAATGAC | 28 |
| SEQ ID NO.926 | CCAATAGGTGTTCCCACTCCGTAACCTT | 28 |
| INHIBIN A-SUBUNIT | | |
| SEQ ID NO.927 | GAGAGCCCGACGCTCAACTCCCC | 23 |
| SEQ ID NO.928 | TCCATCCGAGGTGGTGCGGACATG | 24 |
| DIAZEPAM BINDING INHIBITOR | | |
| SEQ ID NO.929 | CACTGGGACAGAGGCTGAGTTTGAGA | 26 |
| SEQ ID NO.930 | CAGCTCATTCCAGGCATCCCACTTGG | 26 |
| BETA-2-ADRENERGIC RECEPTOR | | |
| SEQ ID NO.931 | AGGCATCATCATGGGCACTTTCACCC | 26 |
| SEQ ID NO.932 | TGTTATCGCTAGGCACAGTACCTTGATG | 28 |
| DOPAMINE D2 RECEPTOR | | |
| SEQ ID NO.933 | ACTGTGACTGCAACATCCCGCCTGTC | 26 |
| SEQ ID NO.934 | GGAGCATGGAGCCAAGCGAACACTG | 25 |
| INSULIN-LIKE GROWTH FACTOR-BINDING PROTEIN | | |
| SEQ ID NO.935 | CGTCAACGCTAGTGCCGTCAGCCG | 24 |
| SEQ ID NO.936 | GACCATATTCTGTCTCCCGCTTGGACT | 27 |
| DOPAMINE D5 RECEPTOR | | |
| SEQ ID NO.937 | GTGCGTCATCAGCGTGGACCGCTA | 24 |
| SEQ ID NO.938 | GGGATGTAGAAGCTGATGAGCGAGGAA | 27 |
| RETINOIC ACID-BINDING PROTEIN II | | |
| SEQ ID NO.939 | TGCACCAGGGTCTACGTCCGAGAG | 24 |
| SEQ ID NO.940 | GGTAGAAGCTAGAGGGCCAGTCTTTC | 26 |
| ALPHA A1 ADRENERGIC RECEPTOR | | |
| SEQ ID NO.941 | GGCCTACGAATTGGCCGACTACAGC | 25 |
| SEQ ID NO.942 | GGGCAGTGTTTCTCAAATAGGGATTGGG | 28 |
| PRO-GALANIN | | |

TABLE 1-continued

| SEQUENCE DESCRIPTION | | Length |
|---|---|---|
| SEQ ID NO.943 | ATGGCCTCACCAGCAAGCGGGAGC | 24 |
| SEQ ID NO.944 | GCTGACTCCGCATAAATTGGCCGAAGA | 27 |
| SERATONIN RECEPTOR TYPE 2 | | |
| SEQ ID NO.945 | CATGCAAGGTGCTGGGCATCGTCTTC | 26 |
| SEQ ID NO.946 | GACTTGTAGGCCAAAGCCGGTATTGTGT | 28 |
| SERATONIN RECEPTOR 5HT2C | | |
| SEQ ID NO.947 | ACATCTGGCTGTCCTCTGACATCAGG | 26 |
| SEQ ID NO.948 | CATAGAGTGAGGGTGGATTCAGGATGC | 27 |
| SERATONIN RECEPTOR 5HT1E | | |
| SEQ ID NO.949 | CCATTTACTCCACGCTGGGTGCGTTT | 26 |
| SEQ ID NO.950 | CCTTCCGTTCCCTGGTGCTAGAGATC | 26 |
| FOLLISTATIN-RELATED PROTEIN PRECURSOR | | |
| SEQ ID NO.951 | CTGCTACAGTCGCCAAATCACCAGTATT | 28 |
| SEQ ID NO.952 | CTCCGTGGAGCTTCCCAAACCTCTC | 25 |
| GLUTAMATE RECEPTOR FIP ISOM GLUR3-FLIP | | |
| SEQ ID NO.953 | GCAGACGGAGTGGCCCGAGTGCG | 23 |
| SEQ ID NO.954 | GTTTGGACTCTGCCCGTGATTTGTAACA | 28 |
| CORTICOTROPIN-RELEASING FACTOR-BINDING PROTEIN | | |
| SEQ ID NO.955 | CCCGGCCCAGATGAAAGTTGGCTG | 24 |
| SEQ ID NO.956 | GCGCTCAAGGCTGGGAAATACTGACT | 26 |
| CHOLINERGIC RECEPTOR | | |
| SEQ ID NO.957 | CTTACGGAGGCTGGTCCTTGGATCTG | 26 |
| SEQ ID NO.958 | CGGATGTTGCGGGCATGATCTCAGC | 25 |
| CYCLIN-DEPENDENT KINASE 2 | | |
| SEQ ID NO.959 | CATGGCCTTATGAGGCAGGTGAGAGA | 26 |
| SEQ ID NO.960 | AGCACTCAAGGACAAGGGTGACAGAG | 26 |
| CELL DIVISION CYCLE PROTEIN 25A | | |
| SEQ ID NO.961 | GGGAGGCCACATCAAGGGTGCAGT | 24 |
| SEQ ID NO.962 | GGTCCGGCTCTTGGTGCGGAACTT | 24 |
| CYCLIN D3 | | |
| SEQ ID NO.963 | GTGCATCTACACCGACCACGCTGTC | 25 |
| SEQ ID NO.964 | CAGGCCCGCAGGCAGTCCACTTCA | 24 |
| SINGLE-STRANDED DNA-BINDING PROTEIN PUR-ALPHA | | |
| SEQ ID NO.965 | GCGCATCCGCCAGACGGTCAACC | 23 |
| SEQ ID NO.966 | GGCCCACAGGTTGTAGGGCACGGT | 24 |
| CYCLIN A | | |
| SEQ ID NO.967 | GGCACTGCTGCTATGCTGTTAGCCTC | 26 |
| SEQ ID NO.968 | TTGTCCCGTGACTGTGTAGAGTGCTAAA | 28 |
| DNA TOPOISOMERASE I | | |
| SEQ ID NO.969 | CTAGGATCACAGTGGCTTGGTGCAAG | 26 |
| SEQ ID NO.970 | GCTGACAAATTCCCATCCACTTGCCC | 26 |
| DNA TOPOISOMERASE II, ALPHA | | |
| SEQ ID NO.971 | CAATGCTCAGCTCTTTGGCTCGATTGTT | 28 |
| SEQ ID NO.972 | TTCTCGGTGCCATTCAACATGGGTTCTA | 28 |
| 6-O-METHYLGUANINE-DNA-METHYLTRANSFERASE | | |
| SEQ ID NO.973 | CCCGCTGCGGTTCTCGGAGGTCC | 23 |

TABLE 1-continued

| SEQUENCE DESCRIPTION | | Length |
|---|---|---|
| SEQ ID NO.974 | CAGACCACTCTGTGGCACGGGATGA | 25 |
| DNA EXCISION REPAIR PROTEIN ERCC2 | | |
| SEQ ID NO.975 | TCACCATGACGCTGGCACGGGTCT | 24 |
| SEQ ID NO.976 | AGGGCGACACTGGTTTCGGCACCA | 24 |
| PROHIBITIN | | |
| SEQ ID NO.977 | GATTCCGTGGAGTGCAGGACATTGTG | 26 |
| SEQ ID NO.978 | TCAAAGCGAGCCACCACTGACTTGAG | 26 |
| PROTO-ONCOGENE RAF | | |
| SEQ ID NO.979 | CAGTTTCCAGTCGGATGTCTACTCCTAT | 28 |
| SEQ ID NO.980 | GCGCTCCGGTTGATCTTCGGTAGAGA | 26 |
| GLUTATHIONE REDUCTASE | | |
| SEQ ID NO.981 | GATCCTGTCAGCCCTGGGTTCTAAGA | 26 |
| SEQ ID NO.982 | CGTCTACGATGATATGACCCTTGTCATC | 28 |
| PROTO-ONCOGENE C-ABL | | |
| SEQ ID NO.983 | GGTCCTGGACAGCACCGAGGCGC | 23 |
| SEQ ID NO.984 | CATGGGTATGGGCGAGCCCGCATG | 24 |
| CYCLIN D1 | | |
| SEQ ID NO.985 | GCCTGTGATGCTGGGCACTTCATGTG | 26 |
| SEQ ID NO.986 | TTTGGTTCGGCAGCTTGCTAGGTGAC | 26 |
| GLUTATHIONE S-TRANSFERASE 12 | | |
| SEQ ID NO.987 | AAATGGTTGACCTCACCCAGGTAATGGA | 28 |
| SEQ ID NO.988 | AGATCCGTGCTCCGACAAATAGTCTGAA | 28 |
| DNA EXCISION REPAIR PROTEIN ERCC1 | | |
| SEQ ID NO.989 | GAAGAACTTCGCCTTGCGGGTCCTG | 25 |
| SEQ ID NO.990 | GGCGATGAGCTGTTCCAGAGCTGGAAAT | 28 |
| GLUTATHIONE S-TRANSFERASE M1 | | |
| SEQ ID NO.991 | CTATGATGTCCTTGACCTCCACCGTATA | 28 |
| SEQ ID NO.992 | ATGTTCACGAAGGATAGTGGGTAGCTGA | 28 |
| GLUTATHIONE S-TRANSFERASE P1 | | |
| SEQ ID NO.993 | CGGAGACCTCACCCTGTACCAGTC | 24 |
| SEQ ID NO.994 | GCAGCAAGTCCAGCAGGTTGTAGTCA | 26 |
| GLUTATHIONE S-TRANSFERASE A1 | | |
| SEQ ID NO.995 | AGCTGGTGCAGACCAGAGCCATTCTC | 26 |
| SEQ ID NO.996 | GGAGTCAAGCTCCTCGACGTAGTAGA | 26 |
| CYCLIN D2 | | |
| SEQ ID NO.997 | TCAGGACTTTGTGAGTTAGCATGACCCT | 28 |
| SEQ ID NO.998 | TACAGACTGTAAATAGAGTCGGGTAGGC | 28 |
| PROTO-ONCOGENE C-SRC1 | | |
| SEQ ID NO.999 | AAACCCTGAACGGTGGCACGATGTCT | 26 |
| SEQ ID NO.1000 | CAGGATGTTGGCTGCACGAAGGTCC | 25 |
| PROTO-ONCOGENE REL | | |
| SEQ ID NO.1001 | TCTCAAGTGGATTGTCACATCATGCCTC | 28 |
| SEQ ID NO.1002 | GGATGACGCTTCCATTCCGACTATGTCA | 28 |
| PROTO-ONCOGENE RHOA | | |
| SEQ ID NO.1003 | GAGGTGGATGGAAAGCAGGTAGAGTTC | 27 |
| SEQ ID NO.1004 | TTTCACCGGCTCCTGCTTCATCTTGG | 26 |

TABLE 1-continued

| SEQUENCE DESCRIPTION | | Length |
|---|---|---|
| GLUTATHIONE PEROXIDASE | | |
| SEQ ID NO.1005 | CCCTCTGCGGCACCACGGTCCGG | 23 |
| SEQ ID NO.1006 | TAAGCGCGGTGGCGTCGTCGCTG | 23 |
| PROTO-ONCOGENE SHB, SRC-2 HOMOLOG | | |
| SEQ ID NO.1007 | GTGCTGGCTACATGGAGCCCTATGAG | 26 |
| SEQ ID NO.1008 | GACTGCCGCTTCTCGTTGCCATTAAACT | 28 |
| APOPTOSIS REGULATOR BCL-X | | |
| SEQ ID NO.1009 | CAGGCGACGAGTTTGAACTGCGGTAC | 26 |
| SEQ ID NO.1010 | AAGGCTCTAGGTGGTCATTCAGGTAAGT | 28 |
| SUPEROXIDE DISMUTASE 1, CYTOSOLIC | | |
| SEQ ID NO.1011 | AGTGCAGGGCATCATCAATTTCGAGCAG | 28 |
| SEQ ID NO.1012 | GATGCAATGGTCTCCTGAGAGTGAGATC | 28 |
| DNA MISMATCH REPAIR PROTEIN HMLH1 | | |
| SEQ ID NO.1013 | GGTTATCGGAGCCAGCACCGCTCT | 24 |
| SEQ ID NO.1014 | GTCGAAGAATGAAGATAGGCAGTCCCTC | 28 |
| CELL DIVISION CYCLE PROTEIN 25 | | |
| SEQ ID NO.1015 | 26 CCTCCACAACTACAATGCCGTACTGG | |
| SEQ ID NO.1016 | 26 AAGTTGACCAGGCCGTCTTCCGTGTA | |
| TUMOR SUPPRESSOR DCC, COLORECTAL | | |
| SEQ ID NO.1017 | CCATCCCGGTGCCAACGCTAGAAAG | 25 |
| SEQ ID NO.1018 | ATTAGCAAAGCTGCGGAGTGGGTGAG | 26 |
| CYTOCHROME P450 REDUCTASE | | |
| SEQ ID NO.1019 | CCGGCTGAAGAGCTACGAGAACCAG | 25 |
| SEQ ID NO.1020 | GGAATGGGTGCTTCTTGTTGGACTCC | 26 |
| HHR23B | | |
| SEQ ID NO.1021 | AGTCAGCTCCTGCCAGCACTACAGC | 25 |
| SEQ ID NO.1022 | CGTAAGACTGACCCGTCACAAGTGCA | 26 |
| HHR23A | | |
| SEQ ID NO.1023 | CCCACCTCAGGCATGTCCCATCCC | 24 |
| SEQ ID NO.1024 | GCAGATACTCCACGGCTCGGTGGG | 24 |
| CYCLIN H | | |
| SEQ ID NO.1025 | TAGTGCCTCCAGGGCTGGAATTACTATG | 28 |
| SEQ ID NO.1026 | GATTCTACCAGGTCGTCATCAGTCCATT | 28 |
| GLUTATHIONE S-TRANSFERASE T1 | | |
| SEQ ID NO.1027 | TCTTCCAGGAGGCCCATGAGGTCATT | 26 |
| SEQ ID NO.1028 | TCTCATTGTGGCTTTCAGGCGGCTGT | 26 |
| IONIZING RADIATION RESISTANCE-CONFERRING PROTEIN | | |
| SEQ ID NO.1029 | CATAACACGGGTGAGGAACGCCACAG | 26 |
| SEQ ID NO.1030 | GACCCAGTCTGGCTCAAAGCCGACA | 25 |
| ENDOTHELIAL MEMBRANE GLYCOPROTEIN IIIA(GPIIIA) | | |
| SEQ ID NO.1031 | ACACTGGCAAGGATGCAGTGAATTGTAC | 28 |
| SEQ ID NO.1032 | CGTGATATTGGTGAAGGTAGACGTGGC | 27 |
| NEUTROPHIL ADHERENCE RECEPTOR APLHA-M SUBUNIT | | |
| SEQ ID NO.1033 | TGTTGTTGGTGCCCGTCCGGCTGA | 24 |
| SEQ ID NO.1034 | CTCACGATCAGGAGGTGGTTATGCGA | 26 |
| INTEGRIN BETA-5 SUBUNIT | | |
| SEQ ID NO.1035 | CTTGTCACCATCCACGACCGGAGG | 24 |

TABLE 1-continued

| SEQUENCE DESCRIPTION | | Length |
|---|---|---|
| SEQ ID NO.1036 | ATCAAGCCGAGCAGCCGTGCAAGG | 24 |
| INTEGRIN ALPHA 4 SUBUNIT | | |
| SEQ ID NO.1037 | CACAGCAGAGTGACTGTAGCAATACCTT | 28 |
| SEQ ID NO.1038 | CTGGACTATCGGTTTCAAGGTCTGCATT | 28 |
| INTEGRIN ALPHA E | | |
| SEQ ID NO.1039 | CTTTCCAAACAGGACAGCAGACATCACT | 28 |
| SEQ ID NO.1040 | GACCTCGTAATTTGGTTGGGACGCAAAT | 28 |
| INTEGRIN ALPHA 8 SUBUNIT | | |
| SEQ ID NO.1041 | CAAATCTCCTGTGCAGTGGGACGACT | 26 |
| SEQ ID NO.1042 | CTGTTCCCTGTCGGTCATGTCCTCC | 25 |
| LEUKOCYTE ADHESION PROTEIN | | |
| SEQ ID NO.1043 | GTTTGCTGAGAGTTAGGAGCACTTGGTG | 28 |
| SEQ ID NO.1044 | CAGACTGATGTCCTGACTTGCACAGGAA | 28 |
| VERY LATE ANTIGEN-2(VLA-2) | | |
| SEQ ID NO.1045 | GACCATTGTCCAGAAGACATCTCATGGC | 28 |
| SEQ ID NO.1046 | TACCAAGAGCACGTCTGTAATGGTGTCT | 28 |
| PLATELET GLYCOPROTEIN IIB(GPIIB) | | |
| SEQ ID NO.1047 | AGGAGACGGGCGGCGTGTTCCTG | 23 |
| SEQ ID NO.1048 | GAAGCCCGCTTCACAGTAACGCTTGT | 26 |
| INTEGRIN B-6 | | |
| SEQ ID NO.1049 | TCCAAATGTCACCACGGGAACGGCTC | 26 |
| SEQ ID NO.1050 | ACAGTCGCCGTTACCTCCGCAGAG | 24 |
| INTEGRIN ALPHA-3 CHAIN | | |
| SEQ ID NO.1051 | TGCTGTATCCCACGGAGATCACCGTC | 26 |
| SEQ ID NO.1052 | AATAGGGTAGCCCAGCCATTTACCCG | 26 |
| INTEGRIN BETA-7 SUBUNIT | | |
| SEQ ID NO.1053 | CTTCTTGGTGGAGGATGACGCCAGAG | 26 |
| SEQ ID NO.1054 | AGCGAGGATTGATGGTGGTCGTGATG | 26 |
| INTEGRIN BETA-8 SUBUNIT | | |
| SEQ ID NO.1055 | GTGCCCAATGACGGAAACTGTCATCTG | 27 |
| SEQ ID NO.1056 | CATTGCTCGTCACGTTTCTGCATCCTTC | 28 |
| LEUKOCYTE ADHESION GLYCOPROTEIN P150,95 | | |
| SEQ ID NO.1057 | CCTCCTGTTCACAGCCTTAGCAACTTC | 27 |
| SEQ ID NO.1058 | CACTGGTAGAGGCCACCCGTTTGGTT | 26 |
| FIBRONECTIN RECEPTOR APLHA SUBUNIT | | |
| SEQ ID NO.1059 | GCTGAGCTTCGGGTCACCGCCCC | 23 |
| SEQ ID NO.1060 | GGAAACCACGTCGCTTTGCGAGTTGT | 26 |
| FIBRONECTIN RECEPTOR BETA SUBUNIT | | |
| SEQ ID NO.1061 | CAAGGTAGAAAGTCGGGACAAATTACCC | 28 |
| SEQ ID NO.1062 | GGATTGACCACAGTTGTTACGGCACTCT | 28 |
| INTEGRIN ALPHA 6 | | |
| SEQ ID NO.1063 | CCTGAGGACTGATTTCAGAGTGACTACA | 28 |
| SEQ ID NO.1064 | TCTTGTGATGTGGGACAGCTAACGTGAT | 28 |
| INTEGRIN BETA 4 | | |
| SEQ ID NO.1065 | TTCGGGCCAGAGCGCGAGGGCAT | 23 |
| SEQ ID NO.1066 | GACGCCTAGTGGGACATGGCGGG | 23 |

TABLE 1-continued

| SEQUENCE DESCRIPTION | | Length |
|---|---|---|
| INTEGRIN, ALPHA-SUBUNIT | | |
| SEQ ID NO.1067 | ACAGCGAAGAACCTCCTGAAACCCTTTC | 28 |
| SEQ ID NO.1068 | GTTGGGTACAGCACAGGGTAACCATTTG | 28 |
| ALPHA 7B INTEGRIN | | |
| SEQ ID NO.1069 | GCTGTGGCTGCCCTCCATCCCTTC | 24 |
| SEQ ID NO.1070 | CCCTCTAGGTTAAGGCACTTCCGGG | 25 |
| LEUKOCYTE-ASSOCIATED MOLECULE-1 | | |
| SEQ ID NO.1071 | GTCAGGGCGTGGGACATCTAGTAGG | 25 |
| SEQ ID NO.1072 | TGGAGTGCAATGGCGCAATCTTGGCT | 26 |
| FAS LIGAND | | |
| SEQ ID NO.1073 | GAGCTGGCAGAACTCCGAGAGTCTAC | 26 |
| SEQ ID NO.1074 | CTTAGAGTTCCTCATGTAGACCTTGTGG | 28 |
| HEAT-SHOCK PROTEIN 40 | | |
| SEQ ID NO.1075 | TGTCTTTGGGCTTCTGGCTGGTAGATAA | 28 |
| SEQ ID NO.1076 | GTGTGACCCACAAAGTGAGGACATTCAG | 28 |
| TRANSCRIPTION FACTOR SP1 | | |
| SEQ ID NO.1077 | CCAGGTGTAGCTCTGAGTGTGGGC | 24 |
| SEQ ID NO.1078 | GATGATACAGATGGGTGCCGGGACC | 25 |
| ALPHA-TUBULIN | | |
| SEQ ID NO.1079 | CACCCTGGAGCACTCTGATTGTGCC | 25 |
| SEQ ID NO.1080 | GCATTGACATGTTTGGGAACCACGTCAC | 28 |
| RADIXIN | | |
| SEQ ID NO.1081 | ACGATGAGAATAATGCTGAAGCTAGTGCTA | 30 |
| SEQ ID NO.1082 | CTTTGTATTGCCTTGTCGAATCTGTCGC | 28 |
| PROTEIN KINASE C THETA(PKC) | | |
| SEQ ID NO.1083 | AGTCTACTTCACTAATGACGATGCCGTG | 28 |
| SEQ ID NO.1084 | GATTACTTGTCTGCGGCTGAGTGAGATC | 28 |
| PROTEIN KINASE(JNK1) | | |
| SEQ ID NO.1085 | GTAGATGAAGCTCTCCAACACCCGTAC | 27 |
| SEQ ID NO.1086 | GTCTGTATCAGAGGCCAAAGTCGGATCT | 28 |
| CDK4-INHIBITOR(P16-INK4) | | |
| SEQ ID NO.1087 | GCGGAAGGTCCCTCAGACATCCCC | 24 |
| SEQ ID NO.1088 | CTCGCAAGAAATGCCCACATGAATGTGC | 28 |
| P38 MITOGEN ACTIVATED PROTEIN(MAP) KINASE | | |
| SEQ ID NO.1089 | TGCATAATGGCCGAGCTGTTGACTGG | 26 |
| SEQ ID NO.1090 | AAGGGCTTGGGCCGCTGTAATTCTCT | 26 |
| MAP KINASE KINASE 3(MKK3) | | |
| SEQ ID NO.1091 | GCACACGAAGCTGTCGGTGATCCAC | 25 |
| SEQ ID NO.1092 | CAGGCACTGAGCAGTGAAGTCCACAAA | 27 |
| MAP KINASE KINASE 4(MKK4) | | |
| SEQ ID NO.1093 | AGCACTGTGAGTGGTTCAAGCACACTG | 27 |
| SEQ ID NO.1094 | CTGTGGTCGAAGGCAGACATAGAGCAAT | 28 |
| N-MYC ONCOGENE PROTEIN | | |
| SEQ ID NO.1095 | TTCCCATCCACCAGCAGCACAACTATG | 27 |
| SEQ ID NO.1096 | GTCTAGCAAGTCCGAGCGTGTTCAATTT | 28 |
| RETINOBLASTOMA SUSCEPTIBILITY | | |

TABLE 1-continued

| SEQUENCE DESCRIPTION | | Length |
|---|---|---|
| SEQ ID NO.1097 | CTGGCAGAAATGACTTCTACTCGAACAC | 28 |
| SEQ ID NO.1098 | TTTCAAGTGGCTTAGGACTCACCCAAAC | 28 |
| C-YES-1 | | |
| SEQ ID NO.1099 | TGGTTGATATGGCTGCTCAGATTGCTGA | 28 |
| SEQ ID NO.1100 | TGTATCCTCGCTCCACTTGTTCTAGTAC | 28 |
| LYN ENCODING A TYROSINE KINASE | | |
| SEQ ID NO.1101 | CGGGACCTGCGAGCAGCTAATGTTC | 25 |
| SEQ ID NO.1102 | CAGGGCGGTCATCACGTCGGCATTA | 25 |
| L-MYC PROTEIN GENE | | |
| SEQ ID NO.1103 | TCCTCATCTCAATCCTTGAGCGGCAAG | 27 |
| SEQ ID NO.1104 | CCATCATGGTTGGCTAAGCATATCTCCT | 28 |
| FGR PROTO-ONCOGENE | | |
| SEQ ID NO.1105 | CTGGCTGCATTCCCAGCAAGTACGTG | 26 |
| SEQ ID NO.1106 | CAGGTTGCACAGCCCGTCATTCACCT | 26 |
| CYCLIN B | | |
| SEQ ID NO.1107 | TGGGTCGGCCTCTACCTTTGCACTTC | 26 |
| SEQ ID NO.1108 | CGATGTGGCATACTTGTTCTTGACAGTCA | 29 |
| PROTEIN KINASE C(PKC) TYPE BETA I | | |
| SEQ ID NO.1109 | TTCTGAGGGACACATCAAGATTGCCGAT | 28 |
| SEQ ID NO.1110 | TGGGATAGGCTACGTTGTGTTCCATGAT | 28 |
| CAMP-DEPENDENT PROTEIN KINASE SUBUNIT RII-BETA | | |
| SEQ ID NO.1111 | CATTTGAAAGGCTTCTGGGACCTTGCAT | 28 |
| SEQ ID NO.1112 | GGCATCTACACAAACACATTCTCAGTGG | 28 |
| CHAPERONIN(HSP60) | | |
| SEQ ID NO.1113 | AGGTTGCTACGATTTCTGCAAACGGAGA | 28 |
| SEQ ID NO.1114 | CCAAAGGCTTACGGTGAGCATTGGCAAT | 28 |
| PROTEIN-TYROSINE KINASE(JAK1) | | |
| SEQ ID NO.1115 | TGAAGCCTGAGAGTGGAGGTAACCAC | 26 |
| SEQ ID NO.1116 | GCCAAGTCCCGGTGAACGTATTGCC | 25 |
| GADD45 | | |
| SEQ ID NO.1117 | TTGCTGCGAGAACGACATCAACATCCTG | 28 |
| SEQ ID NO.1118 | TCTGTAATCCTTGCATCAGTGTAGGGAG | 28 |
| CAMP-DEPENDENT PK REGULATORY SUBUNIT RI-BETA | | |
| SEQ ID NO.1119 | TATTCGATGCCATGTTCCCTGTCACTCA | 28 |
| SEQ ID NO.1120 | GAGGTCCGTCTTGGCTTTGACGGTC | 25 |
| CYCLIN E | | |
| SEQ ID NO.1121 | TCTTCTGTCTGTTGCAGCGGAGGCG | 25 |
| SEQ ID NO.1122 | CTGGCTATGGGCTCTGCACAACGCTT | 26 |
| APC GENE | | |
| SEQ ID NO.1123 | 28 GGTGAGAATTGAGGACTGTCCCATTAAC | |
| SEQ ID NO.1124 | 28 TTTGCTTGAGCTGCTAGAACTGAATGGG | |
| I-REL | | |
| SEQ ID NO.1125 | GCTGCCATTGAGCGGAAGATTCAACTG | 27 |
| SEQ ID NO.1126 | CACCTTGTCGCAGAGCAAGTAGAGCT | 26 |
| EXTRACELLULAR SIGNAL-REGULATED KINASE 2 | | |
| SEQ ID NO.1127 | AACAGGCTCTGGCCCACCCATATCTG | 26 |

TABLE 1-continued

| SEQUENCE DESCRIPTION | | Length |
|---|---|---|
| SEQ ID NO.1128 | CAAAGTGGATAAGCCAAGACGGGCTG | 26 |
| SP3 PROTEIN | | |
| SEQ ID NO.1129 | GGTAGCTTGCACCTGTCCCAACTGTA | 26 |
| SEQ ID NO.1130 | GCAGTAATCAAAGTATCATCTCGCGCAG | 28 |
| SP2 PROTEIN | | |
| SEQ ID NO.1131 | CAATATCCAGTACCAGGCGGTCCCTC | 26 |
| SEQ ID NO.1132 | ACTGGCGTTCACAAGGTTGTTGACGG | 26 |
| GADD153=GROWTH ARREST AND DNA-DAMAGE-INDUCIBLE | | |
| SEQ ID NO.1133 | GAAACGGAAACAGAGTGGTCATTCCCC | 27 |
| SEQ ID NO.1134 | GTGGGATTGAGGGTCACATGATTGGCA | 27 |
| CELL DEATH PROTEIN(RIP) | | |
| SEQ ID NO.1135 | GGGTTAGTTCTGGCTGACGTAAATCAAG | 28 |
| SEQ ID NO.1136 | GGGTTAGTTCTGGCTGACGTAAATCAAG | 28 |
| PUTATIVE SRC-LIKE ADAPTER PROTEIN(SLAP) | | |
| SEQ ID NO.1137 | ACTCACTGTCGGTGAGACACAGGCAG | 26 |
| SEQ ID NO.1138 | ACTCACTGTCGGTGAGACACAGGCAG | 26 |
| DNA-PK | | |
| SEQ ID NO.1139 | CGCTACACAGTTTCTGCCAGTCCCTG | 26 |
| SEQ ID NO.1140 | GGCACGAATGTTGTGATCTTTCGTTCCT | 28 |
| CDK INHIBITOR P19INK4D | | |
| SEQ ID NO.1141 | GAGGAGCACAGTTTGTGGCTTATAGGTG | 28 |
| SEQ ID NO.1142 | CTTAAATGCTCTGCCCTTGGGTCTCGT | 27 |
| CELL ADHESION KINASE BETA(CAKBETA) | | |
| SEQ ID NO.1143 | CTCTTCGGCCCTCAGATGTCCCTTG | 25 |
| SEQ ID NO.1144 | CCCAAGGTCCTATCTTGGCCGCATC | 25 |
| BREAST CANCER SUSCEPTIBILITY(BRCA2) | | |
| SEQ ID NO.1145 | ACTGCCTTTACCTCCACCTGTTAGTCC | 27 |
| SEQ ID NO.1146 | GAGCAGTCCTAGTGGATTCACTGACAGA | 28 |
| CYCLIN G1 | | |
| SEQ ID NO.1147 | GACTAGAAGCTCAACTGAAGGCATGTCA | 28 |
| SEQ ID NO.1148 | GCAGTACGCCCAGAAACAATCCATTTCAA | 29 |
| CYCLIN G2 | | |
| SEQ ID NO.1149 | ATAGTGTTCCTGAGCTGCCAACGATACC | 28 |
| SEQ ID NO.1150 | GGGCTAAACCAGGAAACTACCTATTCCC | 28 |
| BETA-TUBULIN CLASS III ISOTYPE(BETA-3) | | |
| SEQ ID NO.1151 | ACACGGTGGTGGAACCCTACAACGC | 25 |
| SEQ ID NO.1152 | CAGGCGGCCATCATGTTCTTGGCATC | 26 |
| CYCLIN A1 | | |
| SEQ ID NO.1153 | TCAGGACTGAGAACCTGGCTAAGTACG | 27 |
| SEQ ID NO.1154 | CCTAATTGCTTGCTGAGGTCGATGGG | 26 |
| N-RAS | | |
| SEQ ID NO.1155 | AGGTTCTTGCTGGTGTGAAATGACTGAG | 28 |
| SEQ ID NO.1156 | GCACCATAGGTACATCATCCGAGTCTTT | 28 |
| HEAT SHOCK PROTEIN HSP86 | | |
| SEQ ID NO.1157 | GCCAAGTCTGGGACCAAAGCGTTCAT | 26 |
| SEQ ID NO.1158 | GTGTCTGTCCTCACTGTCAATGATCCC | 27 |

TABLE 1-continued

| SEQUENCE DESCRIPTION | | Length |
|---|---|---|
| CAMP-DEPENDENT PK CATALYTIC SUBUNIT ALPHA | | |
| SEQ ID NO.1159 | GGGAGATGTTCTCACACCTACGGCG | 25 |
| SEQ ID NO.1160 | ATGTACCCTGGCATTGCCGACCGAAT | 26 |
| VASCULAR SMOOTH MUSCLE ALPHA-ACTIN | | |
| SEQ ID NO.1161 | ATGTACCCTGGCATTGCCGACCGAAT | 26 |
| SEQ ID NO.1162 | TAACGAGTCAGAGCTTTGCTGAGGAATG | 28 |
| FRA-2 | | |
| SEQ ID NO.1163 | GAGAAGCGTCGCATCCGGCGGGA | 23 |
| SEQ ID NO.1164 | ACTACAGCGCCCACCGAGCCACC | 23 |
| FRA-1 | | |
| SEQ ID NO.1165 | CCCTGCCGCCCTGTACCTTGTATC | 24 |
| SEQ ID NO.1166 | AGACATTGGCTAGGGTGGCATCTGCA | 26 |
| EZRIN | | |
| SEQ ID NO.1167 | CTACAGCGCGGAGCTGTCTAGTGAG | 25 |
| SEQ ID NO.1168 | GCTGTTACAGGGCCTCGAACTCGTC | 25 |
| HEAT SHOCK PROTEIN HSP27 | | |
| SEQ ID NO.1169 | ACGAGGAGCGGCAGGACGAGCATG | 24 |
| SEQ ID NO.1170 | CGGGCTAAGGCTTTACTTGGCGGCA | 25 |
| TYK2 | | |
| SEQ ID NO.1171 | ACCTTCGAGAACCTCATACCCATTCTGA | 28 |
| SEQ ID NO.1172 | GGGATTTAAGGGCTGGATTAGTGCCC | 26 |
| VIMENTIN | | |
| SEQ ID NO.1173 | AGGAAATGGCTCGTCACCTTCGTGAATA | 28 |
| SEQ ID NO.1174 | GGAGTGTCGGTTGTTAAGAACTAGAGCT | 28 |
| JUND | | |
| SEQ ID NO.1175 | GGGCTGGTCACCACCACGCCGAC | 23 |
| SEQ ID NO.1176 | CCCGCGTAGCTGCTCAGGTTCGC | 23 |
| C-SRC-KINASE | | |
| SEQ ID NO.1177 | TGCGTGAGCTGCGACGGCAAGGTG | 24 |
| SEQ ID NO.1178 | GGTTGCTATGCCGCAGTTGCGTCATG | 26 |
| ERK1(PROTEIN/SERINE/THREONINE KINASE) | | |
| SEQ ID NO.1179 | ATCTGGTCTGTGGGCTGCATTCTGGC | 26 |
| SEQ ID NO.1180 | CTGGCTCATCCGTCGGGTCATAGTAC | 26 |
| KINESIN(HEAVY CHAIN) | | |
| SEQ ID NO.1181 | TGCTGAGATTGATTCTGATGACACCGGA | 28 |
| SEQ ID NO.1182 | GCGATCTACTTCTTGCTGATAGCGTTTG | 28 |
| MITOTIC KINESIN-LIKE PROTEIN-I | | |
| SEQ ID NO.1183 | ACTCAGAACCAGAAACTTCAGCGACAGT | 28 |
| SEQ ID NO.1184 | CAGATACTGTGATGGCATGAGGGACATG | 28 |
| ERK3 | | |
| SEQ ID NO.1185 | TACATGGAGACAGACTTGGCTAATGTGC | 28 |
| SEQ ID NO.1186 | ATTACGCTGAGAAGCTCCTGACGATCTT | 28 |
| FAST KINASE | | |
| SEQ ID NO.1187 | CTGCCCTTTGGGCGACTGAACTACC | 25 |
| SEQ ID NO.1188 | GCTACTATGTCCTTGTGACTGTACTTGC | 28 |
| BETA-CATENIN | | |
| SEQ ID NO.1189 | GGGTCCTCTGTGAACTTGCTCAGGAC | 26 |

TABLE 1-continued

| SEQUENCE DESCRIPTION | | Length |
|---|---|---|
| SEQ ID NO.1190 | CTGGATAGTCAGCACCAGGGTGGTG | 25 |
| NBK APOPTOTIC INDUCER PROTEIN | | |
| SEQ ID NO.1191 | CCCGAGATAGTGCTGGAACACTGCTG | 26 |
| SEQ ID NO.1192 | GAGCACACCTGCTCCTCGGAATCTATT | 27 |
| P35, CYCLIN-LIKE CAK1-ASSOCIATED PROTEIN | | |
| SEQ ID NO.1193 | ACGATCAGGGTTGCCCTCGGTGTAAG | 26 |
| SEQ ID NO.1194 | CAGTGGGATCTTCAAAGAGTTGTACCCT | 28 |
| CENP-E | | |
| SEQ ID NO.1195 | AAGAAGTCAACAGGCCCAAGATACCTCA | 28 |
| SEQ ID NO.1196 | CTTGTAAATTCCGTTCCTTGCATTGAGAGG | 30 |
| PHOSPHATIDYLINOSITOL 3-KINASE | | |
| SEQ ID NO.1197 | AATGATGCTTGGCTCTGGAATGCCAGAA | 28 |
| SEQ ID NO.1198 | GCTGAGAGTTATTAACAGTGCAGTGTGG | 28 |
| LYMPHOTOXIN-BETA | | |
| SEQ ID NO.1199 | CTAGCTGTGGCAGGAGCCACTTCTC | 25 |
| SEQ ID NO.1200 | GCCGACGAGACAGTAGAGGTAATAGAG | 27 |
| PROTEIN KINASE(JNK2) | | |
| SEQ ID NO.1201 | CCCGAAGTCATCCTGGGTATGGGC | 24 |
| SEQ ID NO.1202 | TCGTCTACAGAGATCCGCTTGTCAGG | 26 |
| TYROSINE PHOSPHATASE | | |
| SEQ ID NO.1203 | GATATGGCTCCTGGGCAGAGTTATCAAC | 28 |
| SEQ ID NO.1204 | GTATCATTAACCTTTATGAGCCGGTCCC | 28 |
| TNF RECEPTOR-1 ASSOCIATED PROTEIN(TRADD) | | |
| SEQ ID NO.1205 | TGGAGAACCTGGATGGCCTTAGGGTT | 26 |
| SEQ ID NO.1206 | CAGGACACCAAAGATCAAGGTGCTTCAT | 28 |
| BCL-2 | | |
| SEQ ID NO.1207 | AATGACAACCTTCTGGTTGGTAGGGACA | 28 |
| SEQ ID NO.1208 | CCTTGTTGTTGATAGGATGTTTCGTTGAAGTT | 32 |
| INTERLEUKIN 1-BETA CONVERTING ENZYME | | |
| SEQ ID NO.1209 | CACAAGACCTCTGACAGCACGTTCCT | 26 |
| SEQ ID NO.1210 | CHCYCYAHHAYCTGGCTGCTCAAATGAA | 28 |
| NIP1 | | |
| SEQ ID NO.1211 | ATCCAGTACCATCACTGAGAGCCTCATG | 28 |
| SEQ ID NO.1212 | AGAAGTGGCACCTTTGGGATCTCACAAA | 28 |
| NIP3 | | |
| SEQ ID NO.1213 | ACCTCGCTCGCAGACACCACAAGATA | 26 |
| SEQ ID NO.1214 | TTGTCAGACGCCTTCCAATATAGATCCC | 28 |
| CYSTEINE PROTEASE MCH2 ISOM BETA(MCH2) | | |
| SEQ ID NO.1215 | TCACCGGGAAACTGTGAACGGCTCAT | 26 |
| SEQ ID NO.1216 | GGGATTACAGGTGTGAGTAACCACGC | 26 |
| BAK PROTEIN | | |
| SEQ ID NO.1217 | CAGACCAGAGCTGTCTGAACTCACGT | 26 |
| SEQ ID NO.1218 | GGATTCCTGATGGTGTTGATAGTCCTTC | 28 |
| CYSTEINE PROTEASE(ICEREL-II) | | |
| SEQ ID NO.1219 | CTGCCTCAGTCTGAAGGACAAACCCA | 26 |
| SEQ ID NO.1220 | CTTTGGCCCTTGGAGTTTCAAATGATTGC | 29 |

TABLE 1-continued

| SEQUENCE DESCRIPTION | | Length |
|---|---|---|
| A1 PROTEIN | | |
| SEQ ID NO.1221 | TCCACCAGGCAGAAGATGACAGACTG | 26 |
| SEQ ID NO.1222 | TGAATAGTGTTCTGGCAGTGTCTACGGA | 28 |
| JNK3 ALPHA2 PROTEIN KINASE(JNK3A2) | | |
| SEQ ID NO.1223 | CTTCCCAGCGGACTCCGAGCACAA | 24 |
| SEQ ID NO.1224 | TGTCAGATGCCAGGGTCTGGTCGG | 24 |
| MCH3 ISOM ALPHA | | |
| SEQ ID NO.1225 | TGTTACCACACCCAGGGCTATGAGGA | 26 |
| SEQ ID NO.1226 | GAAGATGTGAGGGCAGGATAGGTGAGA | 27 |
| INHIBITOR OF APOPTOSIS PROTEIN 1 | | |
| SEQ ID NO.1227 | TCAAGCCAGTTACCCTCATCTACTTGAAC | 29 |
| SEQ ID NO.1228 | GTAGACTATCCAGGATTGGAATTACACAAGT | 31 |
| INHIBITOR OF APOPTOSIS PROTEIN 2 | | |
| SEQ ID NO.1229 | ATCTGGTAGTATGCCAGGAATGTGCCC | 27 |
| SEQ ID NO.1230 | GCATAACAAGCAGGACGCTACTCCCT | 26 |
| X-LINKED INHIBITOR OF APOTOSIS PROTEIN XIAP | | |
| SEQ ID NO.1231 | GGCAATATGGAGACTCAGCAGTTGGAAG | 28 |
| SEQ ID NO.1232 | TAGTAGAGTCCAGCACTTGCTAACTCTC | 28 |
| CYSTEINE PROTEASE ICE-LAP6 | | |
| SEQ ID NO.1233 | AGCTGGACGCCATATCTAGTTTGCCC | 26 |
| SEQ ID NO.1234 | GGTGCAAGATAAGGCAGGGTGAGGG | 25 |
| APO-2 LIGAND | | |
| SEQ ID NO.1235 | GAGCTGAAGCAGATGCAGGACAAGTAC | 27 |
| SEQ ID NO.1236 | GACCAGTTCACCATTCCTCAAGTGCAAG | 28 |
| FADD-HOMOLOGOUS ICE/CED-3-LIKE PROTEASE | | |
| SEQ ID NO.1237 | TCTATGAGCTGACATCTCAGTTCACTGG | 28 |
| SEQ ID NO.1238 | CAAAGTGACTGGATGTACCAGGTTCCCT | 28 |
| APOPTOTIC CYSTEINE PROTEASE MCH4 | | |
| SEQ ID NO.1239 | AATTTGGTCTATGCCAGGCCCATTTCCT | 28 |
| SEQ ID NO.1240 | CAGTTGTGTCATCTTGGCTCAGGACAG | 27 |
| APOPTOTIC CYSTEINE PROTEASE MCH5 ISOM ALPHA | | |
| SEQ ID NO.1241 | TCTATGAGCTGACATCTCAGTTCACTGG | 28 |
| SEQ ID NO.1242 | CAAAGTGACTGGATGTACCAGGTTCCCT | 28 |
| INTERFERON REGULATORY FACTOR 1 | | |
| SEQ ID NO.1243 | TGAAAGACCAGAGCAGGAACAAGGGC | 26 |
| SEQ ID NO.1244 | ACTGTGTAGCTGCTGTGGTCATCAGG | 26 |
| FAN protein | | |
| SEQ ID NO.1245 | TTTAGCCCAGATAGTCGCCATGTCCTC | 27 |
| SEQ ID NO.1246 | CTCCTGTGATGATACTGCTACACTGTTC | 28 |
| WSL-LR, WSL-S1 AND WSL-S2 proteins | | |
| SEQ ID NO.1247 | TGCAGCGTGGCCCGTGACACGCA | 23 |
| SEQ ID NO.1248 | ACCGCGATCTCAGCCAAACTCCGG | 24 |
| HOMEOBOX HOX 4A GENE HOMEODOMAIN PROTEIN | | |
| SEQ ID NO.1249 | GCGCTACGCAGCGCCGGAGTTCG | 23 |
| SEQ ID NO.1250 | GGTGGGATGAGGGTCGCAAGGTCC | 24 |
| Tob | | |

TABLE 1-continued

| SEQUENCE DESCRIPTION | | Length |
|---|---|---|
| SEQ ID NO.1251 | AGTGGCCGTAGCAACAAGGTTGCACG | 26 |
| SEQ ID NO.1252 | GCTGTCACCTGGGAACATTCCATTGGT | 27 |
| PHOSPHOLIPASE C | | |
| SEQ ID NO.1253 | CAGAAGCAAATCCGACTCTGTAGGGAG | 27 |
| SEQ ID NO.1254 | GACGGCCTTAGAACATAACCACATCCC | 27 |
| Zinc-finger DNA-binding protein | | |
| SEQ ID NO.1255 | GAGAGGCATTTAGCTGATCTCTTACCCC | 28 |
| SEQ ID NO.1256 | CTAGCCGCTTTCCACCAACTCAGTCATT | 28 |
| SEROTONIN 5-HT3 RECEPTOR | | |
| SEQ ID NO.1257 | GGACAGAGGATTTGTGCTTAGGCCCC | 26 |
| SEQ ID NO.1258 | GTCCCTTATTCAGGTGAGGGTCAATGG | 27 |
| fetal brain:promyelogeneous leulocyte TPRD | | |
| SEQ ID NO.1259 | TTTCCTGCCTGTAACACGGTTCATCCC | 27 |
| SEQ ID NO.1260 | GGGAATACCACTGACAGGTGCTCAATAATA | 30 |
| ETS ONCOGENE(PEP1) | | |
| SEQ ID NO.1261 | AACAAGCTGGTGATGCCCAAGTACCC | 26 |
| SEQ ID NO.1262 | AATGGCATTCCTGGAGGACACGGGAT | 26 |
| CLK2 | | |
| SEQ ID NO.1263 | GTTGGGCTGGTCACAGCCTTGTGATG | 26 |
| SEQ ID NO.1264 | CAGCGGTTTGCAGTTCTCACGAAGATAG | 28 |
| CKL3 | | |
| SEQ ID NO.1265 | GCCCGGCTAGAAATCAACGTGCTCAA | 26 |
| SEQ ID NO.1266 | CAAGGATCACCTCAGGCGGGCGATA | 25 |
| CLK1 | | |
| SEQ ID NO.1267 | TTGTCCAGGACGATGAGACACTCAAAGA | 28 |
| SEQ ID NO.1268 | ACTATGGTTCTGATACCGGCTTTCATGG | 28 |
| fatty aldehyde dehydrogenase(FALDH) | | |
| SEQ ID NO.1269 | TTCCAGTGGGATGGGAGCTTATCACG | 26 |
| SEQ ID NO.1270 | AGGCACTAGGAGGTTGAACAGGATCATT | 28 |
| NMDA receptor | | |
| SEQ ID NO.1271 | GCACACCCACATGGTCAAGTTCAACC | 26 |
| SEQ ID NO.1272 | GCAGATCCCTGAGAGCCACACTGTCT | 26 |
| HEAT SHOCK PROTEIN(HSP 70) | | |
| SEQ ID NO.1273 | AAGAGCACCGGCAAGGCCAACAAGAT | 26 |
| SEQ ID NO.1274 | CACGAGATGACCTCTTGACAGTTGTCCA | 28 |
| INSULIN-LIKE GROWTH FACTOR | | |
| SEQ ID NO.1275 | GATCCTTTGCTCTGCACGAGTTACCTG | 27 |
| SEQ ID NO.1276 | TTTGTGGCTCTTGAGAGGCAGGGACT | 26 |
| PROTEIN C INHIBITOR | | |
| SEQ ID NO.1277 | GAGAGTCGAGGACCTCCATGTAGGTG | 26 |
| SEQ ID NO.1278 | GAAAGTGTCTGCCAGGTACAGCGTCTT | 27 |
| NEUROTROPHIN-4 | | |
| SEQ ID NO.1279 | AGCGAAACTGCACCAGCGAGTCGTC | 25 |
| SEQ ID NO.1280 | TGCAGACGCAGGCAGTGTCAATTCGA | 26 |
| SET GENE | | |
| SEQ ID NO.1281 | AGCTGGGAAACGTGGGTTCAATTTGCC | 27 |

TABLE 1-continued

| SEQUENCE DESCRIPTION | | Length |
|---|---|---|
| SEQ ID NO.1282 | TTATCCCACCCAGATTCACATGGTCACA | 28 |
| NT6-gamma=acidic neurotrophin 6 gamma | | |
| SEQ ID NO.1283 | CCCGGACCGCTGTGGACTTGGTTG | 24 |
| SEQ ID NO.1284 | GTATAAGTCTCAGGCCCGGCCAGTC | 25 |
| MAPKAP kinase(3pK) | | |
| SEQ ID NO.1285 | AGCGTGGCGACCAGGCTTTCACTG | 24 |
| SEQ ID NO.1286 | CCTGGCCCGTGTTGGAGTAGAAGG | 24 |
| ENTEROKINASE | | |
| SEQ ID NO.1287 | CCTGGCCCAGTAAAGGATGTGTTCTC | 26 |
| SEQ ID NO.1288 | GATGACCGTCACAGAGATTCACCAGTG | 27 |
| CDK TYROSINE 15-KINASE WEE1HU | | |
| SEQ ID NO.1289 | TTTCATATCTCGAACCTCAATCCCAAATGC | 30 |
| SEQ ID NO.1290 | GAAAGCACTTGTGGTATCCGAGGTAATCTA | 30 |
| DNA DAMAGE REPAIR AND RECOMBINATION PROTEIN RAD52 | | |
| SEQ ID NO.1291 | TTCGGCTTGTGAGGCTTCCCACTATTTA | 28 |
| SEQ ID NO.1292 | GGCAACATTAAAGGCATGGACCGTAAAG | 28 |
| RECEPTOR TYROSINE KINASE LIGAND LERK-3(EPLG3) | | |
| SEQ ID NO.1293 | TCCAACCAGCACCTGCGGCGAGAG | 24 |
| SEQ ID NO.1294 | TGGAGGCGCAGCAGACGAACACCT | 24 |
| RECEPTOR TYROSINE KINASE LERK-4(EPLG4) | | |
| SEQ ID NO.1295 | CTGGGCCTCAACGATTACCTAGACATTG | 28 |
| SEQ ID NO.1296 | GGGCACCGAGATGTAGTAGTAAGTCTCT | 28 |
| 3',5'-CYCLIC AMP PHOSPHODIESTERASE HPDE4A6 | | |
| SEQ ID NO.1297 | CCTCCTGCTAGATAACTACTCCGACC | 26 |
| SEQ ID NO.1298 | GCTGTAGTACCAGTCCCGGTTGTCCT | 26 |
| CD40 RECEPTOR ASSOCIATED FACTOR 1(CRAF1) | | |
| SEQ ID NO.1299 | TCCGCCGTGCAGCACGTCAACCTG | 24 |
| SEQ ID NO.1300 | GTCCACGCTCTCCAGCTCGGTCAC | 24 |
| CDK-INHIBITOR P57KIP2(KIP2) | | |
| SEQ ID NO.1301 | CGATCAAGAAGCTGTCCGGGCCTC | 24 |
| SEQ ID NO.1302 | CCGCCGGTTGCTGCTACATGAACG | 24 |
| EB1 | | |
| SEQ ID NO.1303 | GTTGCTCCAGCTCTGAATAAACCGAAGA | 28 |
| SEQ ID NO.1304 | TCTACAATCCTCTGCAATACAGGGTCGT | 28 |
| CBL-B | | |
| SEQ ID NO.1305 | CGAGGACTGCACCAGAAATTCACCAC | 26 |
| SEQ ID NO.1306 | ACATCCTGAGCAAGCATCGGTCTCCT | 26 |
| TRANSCRIPTION FACTOR TFIIIB 90 KDA SUBUNIT | | |
| SEQ ID NO.1307 | TGCACATGATGGGCAGCAAGCACTATG | 27 |
| SEQ ID NO.1308 | CATGCAGACGTTGGTCCGGTTTCCC | 25 |
| TRANSCRIPTION INITIATION FACTOR TFIID SUBUNIT TAFII31 | | |
| SEQ ID NO.1309 | CGATTGGCAATCCAGTGCCGCGCT | 24 |
| SEQ ID NO.1310 | TGGAGACTGAGAAGTAGGCATCTGTACT | 28 |
| IL-17 | | |
| SEQ ID NO.1311 | CCGATCCACCTCACCTTGGAATCTCC | 26 |
| SEQ ID NO.1312 | CTGGGTCGGCTCTCCATAGTCTAACT | 26 |

TABLE 1-continued

| SEQUENCE DESCRIPTION | | Length |
|---|---|---|
| cytoplasmic dynein light chain 1(hdlc1) | | |
| SEQ ID NO.1313 | CCCAGGAGACCGTTGCAGTCGGC | 23 |
| SEQ ID NO.1314 | GATGCAATGCCAGGTGGGATTGTACTTC | 28 |
| colon carcinoma kinase-4(CCK4) | | |
| SEQ ID NO.1315 | CCTGCCCTAGTGCAACAGGCATTGC | 25 |
| SEQ ID NO.1316 | AGCTCATCCCAAGCCTAGCCCTCC | 24 |
| ataxia telangiectasia(ATM) | | |
| SEQ ID NO.1317 | GGCATGGGCATTACGGGTGTTGAAGG | 26 |
| SEQ ID NO.1318 | GGGTGAAGCTCAGTTTCATCTTCCGG | 26 |
| RACH1 | | |
| SEQ ID NO.1319 | ATGGCGCTCACCTGGCAAACCCAC | 24 |
| SEQ ID NO.1320 | GAGCAGTCAGGCAGAAATGACTCGTGA | 27 |
| cysteine protease ICE-LAP3 | | |
| SEQ ID NO.1321 | TTCTTCATTCAGGCTTGCCGAGGGAC | 26 |
| SEQ ID NO.1322 | GTGTGGGTCATCAGACTGAGACTCAAAG | 28 |
| MAP kinase kinase 6(MKK6) | | |
| SEQ ID NO.1323 | TTGGAGTCTGGGCATCACGATGATTGAG | 28 |
| SEQ ID NO.1324 | CCACCAATCCACAGTAGGGTCAACCG | 26 |
| integrin-linked kinase(ILK) | | |
| SEQ ID NO.1325 | GAAGCCTGAAGACACAAACAGACGCTC | 27 |
| SEQ ID NO.1326 | GCAAGGACCTTCCAGTCCTACTTGTC | 26 |
| C-1 | | |
| SEQ ID NO.1327 | AAACCTAGAAGATGCTTGTGATGACATCATG | 31 |
| SEQ ID NO.1328 | AACTGAACTTTCAAATCTGCTAACACTCGC | 30 |
| Ets transcription factor(NERF-2) | | |
| SEQ ID NO.1329 | CATGGACTTCAGGCTGTTAGTGGCAG | 26 |
| SEQ ID NO.1330 | CAGTTAAGTGAGAACTGTGCGAACACAG | 28 |
| tryosine kinase(Tnk1) | | |
| SEQ ID NO.1331 | GGCTTGCCAGCCACCCGTCCAGT | 23 |
| SEQ ID NO.1332 | CTTTACGGGCTGGAGGCATTCCCATG | 26 |
| alpha-N-acetylglucosaminidase(NAGLU) | | |
| SEQ ID NO.1333 | CCCAGTGCTGCCTGCATTCGCGG | 23 |
| SEQ ID NO.1334 | CAGTCATGGCCTCATAGACGGCAGTG | 26 |
| ubiquitin-conjugating enzyme(UBE2I) | | |
| SEQ ID NO.1335 | GACTGGAGGCCAGCCATCACAATCAA | 26 |
| SEQ ID NO.1336 | CGGGCAATTCAGCGAATCGAGACCG | 25 |
| transming growth factor-beta signaling protein-1(bsp-1) | | |
| SEQ ID NO.1337 | CAGAATACCACCGCCAGGATGTTACTAG | 28 |
| SEQ ID NO.1338 | CAACAGTTGGTCACAGAGGTCAAGTATTAT | 30 |
| Bcl-w | | |
| SEQ ID NO.1339 | CCGCTGCACCAAGCCATGCGGGC | 23 |
| SEQ ID NO.1340 | CAGCCGCGTCTCCAGGTAGGCCA | 23 |
| TRAF-interacting protein I-TRAF | | |
| SEQ ID NO.1341 | AACTGAAACACAGTGCTCTGTGCCTATAC | 29 |
| SEQ ID NO.1342 | GAGCATTGTCCATAGGTGGAAACTTTGACA | 30 |
| semaphorin(CD100) | | |

TABLE 1-continued

| SEQUENCE DESCRIPTION | | Length |
|---|---|---|
| SEQ ID NO.1343 | CCTGGACACCGGCTATGAGACCGA | 24 |
| SEQ ID NO.1344 | CTCCGACTGACTTCGGAACACAAGAC | 26 |
| neogenin | | |
| SEQ ID NO.1345 | ATGACTGGGTTATTGAGCCTGTTGTGGG | 28 |
| SEQ ID NO.1346 | TCACTGATTTGCAGGCAGCTCGTTTCTT | 28 |
| Rad50 | | |
| SEQ ID NO.1347 | TGGCTTCACCATCAATCCTGATTCCTCT | 28 |
| SEQ ID NO.1348 | CCATGTGACTGAATCAAGACCCGGTATG | 28 |
| ubiquitin fusion-degradation protein(UFD1L) | | |
| SEQ ID NO.1349 | GTGGCTATGCTGGAGAGCTTGGCTTC | 26 |
| SEQ ID NO.1350 | GCCAACAGTCCTCACTTAGGGCTTTCT | 27 |
| thrombopoietin receptor(MPL) | | |
| SEQ ID NO.1351 | CCCATAGAGTTGTGACGAGGATTGAGAT | 28 |
| SEQ ID NO.1352 | TAAAGCATCACAGTGCTGTAGTAGATGTCT | 30 |
| serine proteinase inhibitor(P19) | | |
| SEQ ID NO.1353 | GGAAAGTGGAATGAACCGTTTGACGAAAC | 29 |
| SEQ ID NO.1354 | TCAACAATTCCCAAATGCCGAAGCACAG | 28 |
| DNA LIGASE IV | | |
| SEQ ID NO.1355 | AGCTATTAAAGCCTTGGAGCTTCGGTTTC | 29 |
| SEQ ID NO.1356 | ATCATTACCACCTGCTGCAATGAGTCTG | 28 |
| DNA LIGASE III | | |
| SEQ ID NO.1357 | AGCTGACGGGATCTCCATCCGATTCC | 26 |
| SEQ ID NO.1358 | TCATAGCGGAAGGCTTTGCAGTCTGC | 26 |
| DNASE X | | |
| SEQ ID NO.1359 | AAACCCAGATTGGTGAGATAGGACACTTG | 29 |
| SEQ ID NO.1360 | CTTTCCGGGACACCTGGGTTCACAC | 25 |
| glutaredoxin | | |
| SEQ ID NO.1361 | GGGAGACCGCAGCCCATCGGCAT | 23 |
| SEQ ID NO.1362 | GACTAGATCACTGCATCCGCCTATACAAT | 29 |
| ESTROGEN SULFOTRANSFERASE(STE) | | |
| SEQ ID NO.1363 | CTAATGGTGGCTGGTCATCCAAATCCTG | 28 |
| SEQ ID NO.1364 | GGTTCATAATTTCGTCTGGCAGTGTTGTG | 29 |
| BETA-PREPROTACHYKININ | | |
| SEQ ID NO.1365 | AGTGGCCCTGTTAAAGGCTCTTTATGGA | 28 |
| SEQ ID NO.1366 | GCTGACACAACTGCTTCAAAGCAATGATTT | 30 |
| PROTEIN TYROSINE PHOSPHATASE(CIP2) | | |
| SEQ ID NO.1367 | GAAGAGCCTATTGAAGATGAACAGACTCC | 29 |
| SEQ ID NO.1368 | CTCCCAAGTCCTCCATAGCAGTGTATTAA | 29 |
| CDC25B | | |
| SEQ ID NO.1369 | TTTCCTGTCCCACCATACGAGCACCT | 26 |
| SEQ ID NO.1370 | CGCAACAAGACAGCAGCAAGTTCTGAG | 27 |
| P14-CDK INHIBITOR | | |
| SEQ ID NO.1371 | AAAGCCCGGAGCTAACGACCGGCC | 24 |
| SEQ ID NO.1372 | CCGAAACGGTTGACTCCGTTGGGATC | 26 |
| Non-Gene Specific Sequences | | |
| ID NO.1373 CDS1 | TCTAGAATTCAGCGGCCGC(T)30VN (where V=G or C; N=G or A or T or C) | |

TABLE 1-continued

| SEQUENCE DESCRIPTION | | Length |
|---|---|---|
| ID NO.1374 CSO1 | d(CTAATACGACTCACTATAGGGC)r(GGG) | |
| ID NO.1375 CSP1 | CTAATACGACTCACTATAGGGC | |

It is evident from the above results and discussion that the subject invention provides for improved methods of assaying for differential expression. With the subject methods, specificity and efficiency are improved, as compared to previous methods of differential gene expression analysis in which sets of gene specific primers are not employed to generate labeled nucleic acids.

All publications and patent applications cited in this specification are herein incorporated by reference as if each individual publication or patent application were specifically and individually indicated to be incorporated by reference.

The citation of any publication is for its disclosure prior to the filing date and should not be construed as an admission that the present invention is not entitled to antedate such publication by virtue of prior invention.

Although the foregoing invention has been described in some detail by way of illustration and example for purposes of clarity of understanding, it is readily apparent to those of ordinary skill in the art in light of the teachings of this invention that certain changes and modifications may be made thereto without departing from the spirit or scope of the appended claims.

What is claimed is:

1. A method of producing a population of labeled nucleic acids, said method comprising;
   obtaining a sample of nucleic acids from a physiological source; and
   generating a population of labeled nucleic acids from the nucleic acids sample by using a set of primers comprising at least 20 primers selected from SEQ ID NOS:01–1372;
   whereby a population of labeled nucleic acids is produced.

2. The method according to claim 1, wherein the set of primers comprises at least 50 primers selected from SEQ ID NOS: 01–1372.

3. The method according to claim 1, wherein the labeled nucleic acids are first strand cDNA.

4. The method according to claim 1, wherein the generating step comprises at least one amplification step.

5. A method of analyzing the differences in the RNA profiles between a plurality of different physiological sources, said method comprising:

obtaining a sample of ribonucleic acids from each of the distinct physiological sources;

generating a population of labeled nucleic acids for each of the different physiological sources by using a set of primers comprising at least 20 primers selected from SEO ID NOS:01–1372; and comparing the populations of labeled nucleic acids for each physiological source to identify differences in the populations.

6. The method according to claim 5, wherein the comparing step comprises hybridizing the labeled nucleic acids for each of the distinct physiological sources to an array of probe nucleic acids stably associated with the surface of a substrate to produce a hybridization pattern for each of the different physiological sources; and comparing the hybridization patterns for each of the different physiological sources.

7. The method according to claim 5, wherein the labeled nucleic acids are first strand cDNA.

8. The method according to claim 5, wherein the generating step comprises an amplification step.

9. A method of analyzing the differential expression of genes in a plurality of distinct cell types, said method comprising:

obtaining a sample of distinct ribonucleic acids from each of the distinct cell types;

generating a population of labeled nucleic acids for each of the distinct cell types by using a set of primers comprising at least 20 primers selected from SEQ ID NOS:01–1372;

hybridizing the labeled nucleic acids for each of the distinct cell types to an array of probe nucleic acids stably associated with the surface of a substrate to produce a hybridization pattern for each of the distinct cell types; and comparing the hybridization patterns for each of the distinct cell types.

10. The method according to claim 9, wherein the labeled nucleic acids are first strand cDNA.

11. The method according to claim 9, wherein the generating step comprises an amplification step.

12. The method according to claim 9, wherein the number of primers in the set ranges from 20 to 1372.

13. The method according to claim 10, wherein the number of primers in the set does not vary by more than 50% from the number of probes bound to the substrate.

14. The method according to claim 9, wherein the distinct cell types share a common genome.

15. A method of analyzing the differential expression of genes in at least two different cell types sharing a common genome, said method comprising:

obtaining a population of distinct messenger ribonucleic acids from each of the different cell types;

generating a population of labeled nucleic acids for each of the different cell types by using a set of primers comprising at least 20 genes selected from SEQ ID NOS:01–1372, wherein the number of gene specific primers in the set ranges from 20 to 1372, hybridizing the labeled nucleic acids for each of the different cell types to an array of probe nucleic acids stably associated with the surface of a substrate to produce a hybridization pattern for each of the different cell types; and comparing the hybridization patterns for each of the different cell types.

16. The method according to claim 15, wherein the labeled nucleic acids are first strand cDNA.

17. The method according to claim 15, wherein the generating step comprises an amplification step.

* * * * *

SEQUENCE LISTING (1) GENERAL INFORMATION:

(iii) NUMBER OF SEQUENCES: 1375

(2) INFORMATION FOR SEQ ID NO:1:

(i) SEQUENCE CHARACTERISTICS:
      (A) LENGTH: 26 base pairs
      (B) TYPE: nucleic acid
      (C) STRANDEDNESS: single
      (D) TOPOLOGY: linear (ii) MOLECULE TYPE: DNA (ix) FEATURE:
      (D) OTHER INFORMATION: oligonucleotide primer (xi) SEQUENCE DESCRIPTION: SEQ ID NO:1:

CAACTGCCCA TCTGAGGATG TAGTCG      26

(2) INFORMATION FOR SEQ ID NO:2:

(i) SEQUENCE CHARACTERISTICS:
      (A) LENGTH: 27 base pairs
      (B) TYPE: nucleic acid
      (C) STRANDEDNESS: single
      (D) TOPOLOGY: linear (ii) MOLECULE TYPE: DNA (ix) FEATURE:
      (D) OTHER INFORMATION: oligonucleotide primer (xi) SEQUENCE DESCRIPTION: SEQ ID NO:2:

TTGTCGCTCA CGGTAAGTTC AGTCTGG      27

(2) INFORMATION FOR SEQ ID NO:3:

(i) SEQUENCE CHARACTERISTICS:
      (A) LENGTH: 28 base pairs
      (B) TYPE: nucleic acid
      (C) STRANDEDNESS: single
      (D) TOPOLOGY: linear (ii) MOLECULE TYPE: DNA (ix) FEATURE:
            (D) OTHER INFORMATION: oligonucleotide primer (xi) SEQUENCE DESCRIPTION: SEQ ID NO:3:

ATCCAAAAGA GTGTGGAGAC CATCAAGG                                              28

(2) INFORMATION FOR SEQ ID NO:4:

(i) SEQUENCE CHARACTERISTICS:
            (A) LENGTH: 28 base pairs
            (B) TYPE: nucleic acid
            (C) STRANDEDNESS: single
            (D) TOPOLOGY: linear (ii) MOLECULE TYPE: DNA (ix) FEATURE:
            (D) OTHER INFORMATION: oligonucleotide primer (xi) SEQUENCE DESCRIPTION: SEQ ID NO:4:

TTTTCGCTTC CCTGTTTTAG CTGCTGGC                                              28

(2) INFORMATION FOR SEQ ID NO:5:

(i) SEQUENCE CHARACTERISTICS:
            (A) LENGTH: 26 base pairs
            (B) TYPE: nucleic acid
            (C) STRANDEDNESS: single
            (D) TOPOLOGY: linear (ii) MOLECULE TYPE: DNA (ix) FEATURE:
            (D) OTHER INFORMATION: oligonucleotide primer (xi) SEQUENCE DESCRIPTION: SEQ ID NO:5:

TAGGTATATC TTTGGACTTC CTCCCC                                                26

(2) INFORMATION FOR SEQ ID NO:6:

(i) SEQUENCE CHARACTERISTICS:
            (A) LENGTH: 27 base pairs
            (B) TYPE: nucleic acid
            (C) STRANDEDNESS: single
            (D) TOPOLOGY: linear (ii) MOLECULE TYPE: DNA (ix) FEATURE:
            (D) OTHER INFORMATION: oligonucleotide primer (xi) SEQUENCE DESCRIPTION: SEQ ID NO:6:

AAGAAATTGC CTCAACTTGC GAGCAGC                                               27

(2) INFORMATION FOR SEQ ID NO:7:

(i) SEQUENCE CHARACTERISTICS:
            (A) LENGTH: 26 base pairs
            (B) TYPE: nucleic acid
            (C) STRANDEDNESS: single
            (D) TOPOLOGY: linear (ii) MOLECULE TYPE: DNA (ix) FEATURE:
            (D) OTHER INFORMATION: oligonucleotide primer (xi) SEQUENCE DESCRIPTION: SEQ ID NO:7:

GCTCCTGGCA AAAGGTCAGA GTCTGG                                                26

(2) INFORMATION FOR SEQ ID NO:8:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: DNA (ix) FEATURE:
        (D) OTHER INFORMATION: oligonucleotide primer (xi) SEQUENCE DESCRIPTION: SEQ ID NO:8:

GGGGCTGGTG CATTTTCGGT TGTTGC                                          26

(2) INFORMATION FOR SEQ ID NO:9:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: DNA (ix) FEATURE:
        (D) OTHER INFORMATION: oligonucleotide primer (xi) SEQUENCE DESCRIPTION: SEQ ID NO:9:

GGTCACACTG GTAGAACGTA ACCACG                                          26

(2) INFORMATION FOR SEQ ID NO:10:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: DNA (ix) FEATURE:
        (D) OTHER INFORMATION: oligonucleotide primer (xi) SEQUENCE DESCRIPTION: SEQ ID NO:10:

CTCGAACTCC TGGGCTCAAG CAATCC                                          26

(2) INFORMATION FOR SEQ ID NO:11:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (ii) MOLECULE TYPE: DNA (ix) FEATURE:
        (D) OTHER INFORMATION: oligonucleotide primer (xi) SEQUENCE DESCRIPTION: SEQ ID NO:11:

CAGGATGCTC ACATTTAAGT TTTACATGC                                      29

(2) INFORMATION FOR SEQ ID NO:12:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: DNA (ix) FEATURE:
     (D) OTHER INFORMATION: oligonucleotide primer (xi) SEQUENCE DESCRIPTION: SEQ ID NO:12:

ATCCATCTGT TCAGAAATTC TACAATGG                                28

(2) INFORMATION FOR SEQ ID NO:13:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: DNA (ix) FEATURE:
        (D) OTHER INFORMATION: oligonucleotide primer (xi) SEQUENCE DESCRIPTION: SEQ ID NO:13:

ATGAATCGGC AACGAGATGG AGGTGG                                  26

(2) INFORMATION FOR SEQ ID NO:14:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: DNA (ix) FEATURE:
        (D) OTHER INFORMATION: oligonucleotide primer (xi) SEQUENCE DESCRIPTION: SEQ ID NO:14:

GGAGCAGGAG TTACGTTCTC TGGGC                                   25

(2) INFORMATION FOR SEQ ID NO:15:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: DNA (ix) FEATURE:
        (D) OTHER INFORMATION: oligonucleotide primer (xi) SEQUENCE DESCRIPTION: SEQ ID NO:15:

GGCATACCTC AACGCCAATA AGTTCG                                  26

(2) INFORMATION FOR SEQ ID NO:16:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: DNA (ix) FEATURE:
        (D) OTHER INFORMATION: oligonucleotide primer (xi) SEQUENCE DESCRIPTION: SEQ ID NO:16:

```
CTTGTTCTCC TCGCTGTAGT AGAAGG                                    26

(2) INFORMATION FOR SEQ ID NO:17:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: DNA (ix) FEATURE:
        (D) OTHER INFORMATION: oligonucleotide primer (xi) SEQUENCE DESCRIPTION: SEQ ID NO:17:

CAGCCGTGGC ATCGTTGAGG AGTGC                                     25

(2) INFORMATION FOR SEQ ID NO:18:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: DNA (ix) FEATURE:
        (D) OTHER INFORMATION: oligonucleotide primer (xi) SEQUENCE DESCRIPTION: SEQ ID NO:18:

TGGACTGCTT CCAGGTGTCA TATTGG                                    26

(2) INFORMATION FOR SEQ ID NO:19:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: DNA (ix) FEATURE:
        (D) OTHER INFORMATION: oligonucleotide primer (xi) SEQUENCE DESCRIPTION: SEQ ID NO:19:

GGCTGCCAAG CTGAAATTGA ATGAGG                                    26

(2) INFORMATION FOR SEQ ID NO:20:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: DNA (ix) FEATURE:
        (D) OTHER INFORMATION: oligonucleotide primer (xi) SEQUENCE DESCRIPTION: SEQ ID NO:20:

AATCCAGGGT GCTACTTGTT AGGAGG                                    26

(2) INFORMATION FOR SEQ ID NO:21:

(i) SEQUENCE CHARACTERISTICS:
        (A) LENGTH: 26 base pairs
        (B) TYPE: nucleic acid
```

(C) STRANDEDNESS: single
            (D) TOPOLOGY: linear (ii) MOLECULE TYPE: DNA (ix) FEATURE:
            (D) OTHER INFORMATION: oligonucleotide primer (xi) SEQUENCE DESCRIPTION: SEQ ID NO:21:

GTCCACCATG AATGAGTACA TTGAGC                                              26

(2) INFORMATION FOR SEQ ID NO:22:

(i) SEQUENCE CHARACTERISTICS:
            (A) LENGTH: 26 base pairs
            (B) TYPE: nucleic acid
            (C) STRANDEDNESS: single
            (D) TOPOLOGY: linear (ii) MOLECULE TYPE: DNA (ix) FEATURE:
            (D) OTHER INFORMATION: oligonucleotide primer (xi) SEQUENCE DESCRIPTION: SEQ ID NO:22:

TGTAGCAGAA CTCGATTAAG GCAACC                                              26

(2) INFORMATION FOR SEQ ID NO:23:

(i) SEQUENCE CHARACTERISTICS:
            (A) LENGTH: 23 base pairs
            (B) TYPE: nucleic acid
            (C) STRANDEDNESS: single
            (D) TOPOLOGY: linear (ii) MOLECULE TYPE: DNA (ix) FEATURE:
            (D) OTHER INFORMATION: oligonucleotide primer (xi) SEQUENCE DESCRIPTION: SEQ ID NO:23:

TCACTTCTCC AGCCAAGTAG CCC                                                 23

(2) INFORMATION FOR SEQ ID NO:24:

(i) SEQUENCE CHARACTERISTICS:
            (A) LENGTH: 24 base pairs
            (B) TYPE: nucleic acid
            (C) STRANDEDNESS: single
            (D) TOPOLOGY: linear (ii) MOLECULE TYPE: DNA (ix) FEATURE:
            (D) OTHER INFORMATION: oligonucleotide primer (xi) SEQUENCE DESCRIPTION: SEQ ID NO:24:

AGGATGCCAG GGTAGGGATT CAGC                                                24

(2) INFORMATION FOR SEQ ID NO:25:

(i) SEQUENCE CHARACTERISTICS:
            (A) LENGTH: 22 base pairs
            (B) TYPE: nucleic acid
            (C) STRANDEDNESS: single
            (D) TOPOLOGY: linear (ii) MOLECULE TYPE: DNA (ix) FEATURE:
            (D) OTHER INFORMATION: oligonucleotide primer (xi) SEQUENCE DESCRIPTION: SEQ ID NO:25:

GCCACTACAC TCCAGCCTGA GC                                                    22

(2) INFORMATION FOR SEQ ID NO:26:

(i) SEQUENCE CHARACTERISTICS:
            (A) LENGTH: 24 base pairs
            (B) TYPE: nucleic acid
            (C) STRANDEDNESS: single
            (D) TOPOLOGY: linear (ii) MOLECULE TYPE: DNA (ix) FEATURE:
            (D) OTHER INFORMATION: oligonucleotide primer (xi) SEQUENCE DESCRIPTION: SEQ ID NO:26:

CTGCCCTGTG ATGCCAAGGA AGCC                                                  24

(2) INFORMATION FOR SEQ ID NO:27:

(i) SEQUENCE CHARACTERISTICS:
            (A) LENGTH: 28 base pairs
            (B) TYPE: nucleic acid
            (C) STRANDEDNESS: single
            (D) TOPOLOGY: linear (ii) MOLECULE TYPE: DNA (ix) FEATURE:
            (D) OTHER INFORMATION: oligonucleotide primer (xi) SEQUENCE DESCRIPTION: SEQ ID NO:27:

GGAGATATGT TGTGAAAGAA GCAGTAGC                                              28

(2) INFORMATION FOR SEQ ID NO:28:

(i) SEQUENCE CHARACTERISTICS:
            (A) LENGTH: 28 base pairs
            (B) TYPE: nucleic acid
            (C) STRANDEDNESS: single
            (D) TOPOLOGY: linear (ii) MOLECULE TYPE: DNA (ix) FEATURE:
            (D) OTHER INFORMATION: oligonucleotide primer (xi) SEQUENCE DESCRIPTION: SEQ ID NO:28:

GAAGTGCATT TCCAATAGTC AGCTAAGG                                              28

(2) INFORMATION FOR SEQ ID NO:29:

(i) SEQUENCE CHARACTERISTICS:
            (A) LENGTH: 21 base pairs
            (B) TYPE: nucleic acid
            (C) STRANDEDNESS: single
            (D) TOPOLOGY: linear (ii) MOLECULE TYPE: DNA (ix) FEATURE:
            (D) OTHER INFORMATION: oligonucleotide primer (xi) SEQUENCE DESCRIPTION: SEQ ID NO:29:

GCACACGCAT GACAAGACGG C                                                     21

(2) INFORMATION FOR SEQ ID NO:30:

(i) SEQUENCE CHARACTERISTICS:

(A) LENGTH: 23 base pairs
        (B) TYPE: nucleic acid
        (C) STRANDEDNESS: single
        (D) TOPOLOGY: linear (ii) MOLECULE TYPE: DNA (ix) FEATURE:
        (D) OTHER INFORMATION: oligonucleotide primer (xi) SEQUENCE DESCRIPTION: SEQ ID NO:30:

AGGCAGGCTA TGCTGAGAGG TCC                                              23

(2) INFORMATION FOR SEQ ID NO:31:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: DNA (ix) FEATURE:
        (D) OTHER INFORMATION: oligonucleotide primer (xi) SEQUENCE DESCRIPTION: SEQ ID NO:31:

GGCTCTCCAG AACATCATCC CTGC                                             24

(2) INFORMATION FOR SEQ ID NO:32:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: DNA (ix) FEATURE:
        (D) OTHER INFORMATION: oligonucleotide primer (xi) SEQUENCE DESCRIPTION: SEQ ID NO:32:

GGGTGTCGCT GTTGAAGTCA GAGG                                             24

(2) INFORMATION FOR SEQ ID NO:33:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: DNA (ix) FEATURE:
        (D) OTHER INFORMATION: oligonucleotide primer (xi) SEQUENCE DESCRIPTION: SEQ ID NO:33:

GGGACTTTGT ATAGAAGGTT TGGGGG                                           26

(2) INFORMATION FOR SEQ ID NO:34:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: DNA (ix) FEATURE:

(D) OTHER INFORMATION: oligonucleotide primer (xi) SEQUENCE DESCRIPTION: SEQ ID NO:34:

TACGTGTGCG TAACACCCGA ACCAGG                                    26

(2) INFORMATION FOR SEQ ID NO:35:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: DNA (ix) FEATURE:
        (D) OTHER INFORMATION: oligonucleotide primer (xi) SEQUENCE DESCRIPTION: SEQ ID NO:35:

TCATAACAAT TTTAGGAGGA CCAGAGC                                   27

(2) INFORMATION FOR SEQ ID NO:36:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: DNA (ix) FEATURE:
        (D) OTHER INFORMATION: oligonucleotide primer (xi) SEQUENCE DESCRIPTION: SEQ ID NO:36:

CATTTCGTGC TTTGCCTTCA TCTTGAGG                                  28

(2) INFORMATION FOR SEQ ID NO:37:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: DNA (ix) FEATURE:
        (D) OTHER INFORMATION: oligonucleotide primer (xi) SEQUENCE DESCRIPTION: SEQ ID NO:37:

CTTCTTCGAC ACATGGGATA ACGAGG                                    26

(2) INFORMATION FOR SEQ ID NO:38:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: DNA (ix) FEATURE:
        (D) OTHER INFORMATION: oligonucleotide primer (xi) SEQUENCE DESCRIPTION: SEQ ID NO:38:

GAGAGGTGCT GATGTACCAG TTGGGG                                    26

(2) INFORMATION FOR SEQ ID NO:39:

(i) SEQUENCE CHARACTERISTICS:
    (A) LENGTH: 28 base pairs
    (B) TYPE: nucleic acid
    (C) STRANDEDNESS: single
    (D) TOPOLOGY: linear (ii) MOLECULE TYPE: DNA (ix) FEATURE:
    (D) OTHER INFORMATION: oligonucleotide primer (xi) SEQUENCE DESCRIPTION: SEQ ID NO:39:

GAGGAAACTG ACGTTCTATC TGAAAACC                                              28

(2) INFORMATION FOR SEQ ID NO:40:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: DNA (ix) FEATURE:
        (D) OTHER INFORMATION: oligonucleotide primer (xi) SEQUENCE DESCRIPTION: SEQ ID NO:40:

TCTGATGCCG CAGGAAAAGG TGAAATGC                                              28

(2) INFORMATION FOR SEQ ID NO:41:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: DNA (ix) FEATURE:
        (D) OTHER INFORMATION: oligonucleotide primer (xi) SEQUENCE DESCRIPTION: SEQ ID NO:41:

GACCGTAACA GACATCTTTG CTGC                                                  24

(2) INFORMATION FOR SEQ ID NO:42:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: DNA (ix) FEATURE:
        (D) OTHER INFORMATION: oligonucleotide primer (xi) SEQUENCE DESCRIPTION: SEQ ID NO:42:

GTACTCTGGT TGGCTTCCTT CACAGG                                                26

(2) INFORMATION FOR SEQ ID NO:43:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: DNA (ix) FEATURE:
    (D) OTHER INFORMATION: oligonucleotide primer (xi) SEQUENCE DESCRIPTION: SEQ ID NO:43:

GGAGAAGATT CCAAAGATGT AGCCGC                    26

(2) INFORMATION FOR SEQ ID NO:44:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: DNA (ix) FEATURE:
        (D) OTHER INFORMATION: oligonucleotide primer (xi) SEQUENCE DESCRIPTION: SEQ ID NO:44:

CTGGCATTTG TGGTTGGGTC AGGGG                     25

(2) INFORMATION FOR SEQ ID NO:45:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: DNA (ix) FEATURE:
        (D) OTHER INFORMATION: oligonucleotide primer (xi) SEQUENCE DESCRIPTION: SEQ ID NO:45:

TCACCCACAC CATCAGCCGC ATCG                      24

(2) INFORMATION FOR SEQ ID NO:46:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: DNA (ix) FEATURE:
        (D) OTHER INFORMATION: oligonucleotide primer (xi) SEQUENCE DESCRIPTION: SEQ ID NO:46:

GGGAAGGTTG GATGTTCGTC CTCC                      24

(2) INFORMATION FOR SEQ ID NO:47:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: DNA (ix) FEATURE:
        (D) OTHER INFORMATION: oligonucleotide primer (xi) SEQUENCE DESCRIPTION: SEQ ID NO:47:

TCTTGCCCAC AGCACCCTCA AACC                      24

(2) INFORMATION FOR SEQ ID NO:48:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: DNA (ix) FEATURE:
        (D) OTHER INFORMATION: oligonucleotide primer (ii) MOLECULE TYPE: DNA (ix) FEATURE:
        (D) OTHER INFORMATION: oligonucleotide primer (xi) SEQUENCE DESCRIPTION: SEQ ID NO:48:

AGGCTTTCCC AGAGAAGACC ACC                                    23

(2) INFORMATION FOR SEQ ID NO:49:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: DNA (ix) FEATURE:
        (D) OTHER INFORMATION: oligonucleotide primer (xi) SEQUENCE DESCRIPTION: SEQ ID NO:49:

ATGCTGGCTC TGGAAACCTC ACC                                    23

(2) INFORMATION FOR SEQ ID NO:50:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: DNA (ix) FEATURE:
        (D) OTHER INFORMATION: oligonucleotide primer (xi) SEQUENCE DESCRIPTION: SEQ ID NO:50:

TCCCGCTTCG AGACCTTTGC CTCC                                   24

(2) INFORMATION FOR SEQ ID NO:51:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: DNA (ix) FEATURE:
        (D) OTHER INFORMATION: oligonucleotide primer (xi) SEQUENCE DESCRIPTION: SEQ ID NO:51:

GCAAGTCAGG GTTGGAGCAG TAGC                                   24

(2) INFORMATION FOR SEQ ID NO:52:

(i) SEQUENCE CHARACTERISTICS:
            (A) LENGTH: 24 base pairs
            (B) TYPE: nucleic acid
            (C) STRANDEDNESS: single
            (D) TOPOLOGY: linear (ii) MOLECULE TYPE: DNA (ix) FEATURE:
            (D) OTHER INFORMATION: oligonucleotide primer (xi) SEQUENCE DESCRIPTION: SEQ ID NO:52:

GCAAGGGCTG GGAGAGCAAT TCCG                                              24

(2) INFORMATION FOR SEQ ID NO:53:

(i) SEQUENCE CHARACTERISTICS:
            (A) LENGTH: 26 base pairs
            (B) TYPE: nucleic acid
            (C) STRANDEDNESS: single
            (D) TOPOLOGY: linear (ii) MOLECULE TYPE: DNA (ix) FEATURE:
            (D) OTHER INFORMATION: oligonucleotide primer (xi) SEQUENCE DESCRIPTION: SEQ ID NO:53:

GGACGGCTTT TACTTAAACG CCAAGG                                            26

(2) INFORMATION FOR SEQ ID NO:54:

(i) SEQUENCE CHARACTERISTICS:
            (A) LENGTH: 26 base pairs
            (B) TYPE: nucleic acid
            (C) STRANDEDNESS: single
            (D) TOPOLOGY: linear (ii) MOLECULE TYPE: DNA (ix) FEATURE:
            (D) OTHER INFORMATION: oligonucleotide primer (xi) SEQUENCE DESCRIPTION: SEQ ID NO:54:

ATCTTCCCTA GTTACCCAGG TTCAGC                                            26

(2) INFORMATION FOR SEQ ID NO:55:

(i) SEQUENCE CHARACTERISTICS:
            (A) LENGTH: 26 base pairs
            (B) TYPE: nucleic acid
            (C) STRANDEDNESS: single
            (D) TOPOLOGY: linear (ii) MOLECULE TYPE: DNA (ix) FEATURE:
            (D) OTHER INFORMATION: oligonucleotide primer (xi) SEQUENCE DESCRIPTION: SEQ ID NO:55:

TTTCAGAGCC ATGAGGATGC TTCTGC                                            26

(2) INFORMATION FOR SEQ ID NO:56:

(i) SEQUENCE CHARACTERISTICS:
            (A) LENGTH: 28 base pairs
            (B) TYPE: nucleic acid
            (C) STRANDEDNESS: single
            (D) TOPOLOGY: linear (ii) MOLECULE TYPE: DNA (ix) FEATURE:
         (D) OTHER INFORMATION: oligonucleotide primer (xi) SEQUENCE DESCRIPTION: SEQ ID NO:56:

AGTTTGACTC TCCAGTGTGC CTATTCCC                                              28

(2) INFORMATION FOR SEQ ID NO:57:

(i) SEQUENCE CHARACTERISTICS:
         (A) LENGTH: 27 base pairs
         (B) TYPE: nucleic acid
         (C) STRANDEDNESS: single
         (D) TOPOLOGY: linear (ii) MOLECULE TYPE: DNA (ix) FEATURE:
         (D) OTHER INFORMATION: oligonucleotide primer (xi) SEQUENCE DESCRIPTION: SEQ ID NO:57:

TTTCAGACAA GATTCATCTA GCACTGG                                               27

(2) INFORMATION FOR SEQ ID NO:58:

(i) SEQUENCE CHARACTERISTICS:
         (A) LENGTH: 27 base pairs
         (B) TYPE: nucleic acid
         (C) STRANDEDNESS: single
         (D) TOPOLOGY: linear (ii) MOLECULE TYPE: DNA (ix) FEATURE:
         (D) OTHER INFORMATION: oligonucleotide primer (xi) SEQUENCE DESCRIPTION: SEQ ID NO:58:

ACATTAGCCA TCAGTCACTT AAACAGC                                               27

(2) INFORMATION FOR SEQ ID NO:59:

(i) SEQUENCE CHARACTERISTICS:
         (A) LENGTH: 24 base pairs
         (B) TYPE: nucleic acid
         (C) STRANDEDNESS: single
         (D) TOPOLOGY: linear (ii) MOLECULE TYPE: DNA (ix) FEATURE:
         (D) OTHER INFORMATION: oligonucleotide primer (xi) SEQUENCE DESCRIPTION: SEQ ID NO:59:

GGGAGCATGT GAATGCCATC CAGG                                                  24

(2) INFORMATION FOR SEQ ID NO:60:

(i) SEQUENCE CHARACTERISTICS:
         (A) LENGTH: 24 base pairs
         (B) TYPE: nucleic acid
         (C) STRANDEDNESS: single
         (D) TOPOLOGY: linear (ii) MOLECULE TYPE: DNA (ix) FEATURE:
         (D) OTHER INFORMATION: oligonucleotide primer (xi) SEQUENCE DESCRIPTION: SEQ ID NO:60:

GTATCAGGGT CAGTGTGCCC AGGG                                                  24

(2) INFORMATION FOR SEQ ID NO:61:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: DNA (ix) FEATURE:
        (D) OTHER INFORMATION: oligonucleotide primer (xi) SEQUENCE DESCRIPTION: SEQ ID NO:61:

GAAGAGCCCA GAGGAGGAGT TTGG                                  24

(2) INFORMATION FOR SEQ ID NO:62:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: DNA (ix) FEATURE:
        (D) OTHER INFORMATION: oligonucleotide primer (xi) SEQUENCE DESCRIPTION: SEQ ID NO:62:

GTGGACTCAG ACACCAACTG CTGC                                  24

(2) INFORMATION FOR SEQ ID NO:63:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: DNA (ix) FEATURE:
        (D) OTHER INFORMATION: oligonucleotide primer (xi) SEQUENCE DESCRIPTION: SEQ ID NO:63:

AGCTACAAAT CCATCTGTTC TCTGGGC                              27

(2) INFORMATION FOR SEQ ID NO:64:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: DNA (ix) FEATURE:
        (D) OTHER INFORMATION: oligonucleotide primer (xi) SEQUENCE DESCRIPTION: SEQ ID NO:64:

CCAACCTCCT GTATCACACA TGCTTCC                              27

(2) INFORMATION FOR SEQ ID NO:65:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: DNA (ix) FEATURE:
            (D) OTHER INFORMATION: oligonucleotide primer (xi) SEQUENCE DESCRIPTION: SEQ ID NO:65:

GAGATGGCAG GGACTCTGAT AACACC                                              26

(2) INFORMATION FOR SEQ ID NO:66:

(i) SEQUENCE CHARACTERISTICS:
            (A) LENGTH: 26 base pairs
            (B) TYPE: nucleic acid
            (C) STRANDEDNESS: single
            (D) TOPOLOGY: linear (ii) MOLECULE TYPE: DNA (ix) FEATURE:
            (D) OTHER INFORMATION: oligonucleotide primer (xi) SEQUENCE DESCRIPTION: SEQ ID NO:66:

AAAGTGCTAG GATTACAGGC GTGAGC                                              26

(2) INFORMATION FOR SEQ ID NO:67:

(i) SEQUENCE CHARACTERISTICS:
            (A) LENGTH: 24 base pairs
            (B) TYPE: nucleic acid
            (C) STRANDEDNESS: single
            (D) TOPOLOGY: linear (ii) MOLECULE TYPE: DNA (ix) FEATURE:
            (D) OTHER INFORMATION: oligonucleotide primer (xi) SEQUENCE DESCRIPTION: SEQ ID NO:67:

TGCAATGGGC ACTGGGATGA GCCG                                                24

(2) INFORMATION FOR SEQ ID NO:68:

(i) SEQUENCE CHARACTERISTICS:
            (A) LENGTH: 23 base pairs
            (B) TYPE: nucleic acid
            (C) STRANDEDNESS: single
            (D) TOPOLOGY: linear (ii) MOLECULE TYPE: DNA (ix) FEATURE:
            (D) OTHER INFORMATION: oligonucleotide primer (xi) SEQUENCE DESCRIPTION: SEQ ID NO:68:

CGGTGATGTT CGGGAGTCAA ACC                                                 23

(2) INFORMATION FOR SEQ ID NO:69:

(i) SEQUENCE CHARACTERISTICS:
            (A) LENGTH: 24 base pairs
            (B) TYPE: nucleic acid
            (C) STRANDEDNESS: single
            (D) TOPOLOGY: linear (ii) MOLECULE TYPE: DNA (ix) FEATURE:
            (D) OTHER INFORMATION: oligonucleotide primer (xi) SEQUENCE DESCRIPTION: SEQ ID NO:69:

CCTACGATGG AACCACACCC CTGC                                                24

(2) INFORMATION FOR SEQ ID NO:70:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: DNA (ix) FEATURE:
        (D) OTHER INFORMATION: oligonucleotide primer (xi) SEQUENCE DESCRIPTION: SEQ ID NO:70:

TCCACCAGCT CTCTGACTGT ACCC                          24

(2) INFORMATION FOR SEQ ID NO:71:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: DNA (ix) FEATURE:
        (D) OTHER INFORMATION: oligonucleotide primer (xi) SEQUENCE DESCRIPTION: SEQ ID NO:71:

CCAGTCAAGC TCGTAAATAC GTGAATGC                    28

(2) INFORMATION FOR SEQ ID NO:72:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: DNA (ix) FEATURE:
        (D) OTHER INFORMATION: oligonucleotide primer (xi) SEQUENCE DESCRIPTION: SEQ ID NO:72:

ACTTGGTCGT GCTCTCAACT GTTGTACC                    28

(2) INFORMATION FOR SEQ ID NO:73:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: DNA (ix) FEATURE:
        (D) OTHER INFORMATION: oligonucleotide primer (xi) SEQUENCE DESCRIPTION: SEQ ID NO:73:

GCCCCTCCTC AGCATCTTAT CCG                           23

(2) INFORMATION FOR SEQ ID NO:74:

(i) SEQUENCE CHARACTERISTICS:
        (A) LENGTH: 23 base pairs
        (B) TYPE: nucleic acid
        (C) STRANDEDNESS: single (D) TOPOLOGY: linear (ii) MOLECULE TYPE: DNA (ix) FEATURE:
          (D) OTHER INFORMATION: oligonucleotide primer (xi) SEQUENCE DESCRIPTION: SEQ ID NO:74:

TCCCAGGACA GGCACAAACA CGC                                        23

(2) INFORMATION FOR SEQ ID NO:75:

(i) SEQUENCE CHARACTERISTICS:
          (A) LENGTH: 27 base pairs
          (B) TYPE: nucleic acid
          (C) STRANDEDNESS: single
          (D) TOPOLOGY: linear (ii) MOLECULE TYPE: DNA (ix) FEATURE:
          (D) OTHER INFORMATION: oligonucleotide primer (xi) SEQUENCE DESCRIPTION: SEQ ID NO:75:

TCTAGGGTGG AAATGGATAC ACGAACC                                    27

(2) INFORMATION FOR SEQ ID NO:76:

(i) SEQUENCE CHARACTERISTICS:
          (A) LENGTH: 26 base pairs
          (B) TYPE: nucleic acid
          (C) STRANDEDNESS: single
          (D) TOPOLOGY: linear (ii) MOLECULE TYPE: DNA (ix) FEATURE:
          (D) OTHER INFORMATION: oligonucleotide primer (xi) SEQUENCE DESCRIPTION: SEQ ID NO:76:

TGTTACAAGC ATCATCGTTG TCGTCG                                     26

(2) INFORMATION FOR SEQ ID NO:77:

(i) SEQUENCE CHARACTERISTICS:
          (A) LENGTH: 26 base pairs
          (B) TYPE: nucleic acid
          (C) STRANDEDNESS: single
          (D) TOPOLOGY: linear (ii) MOLECULE TYPE: DNA (ix) FEATURE:
          (D) OTHER INFORMATION: oligonucleotide primer (xi) SEQUENCE DESCRIPTION: SEQ ID NO:77:

CAGCTACCGC GATGAGAGGC GCTCGC                                     26

(2) INFORMATION FOR SEQ ID NO:78:

(i) SEQUENCE CHARACTERISTICS:
          (A) LENGTH: 28 base pairs
          (B) TYPE: nucleic acid
          (C) STRANDEDNESS: single
          (D) TOPOLOGY: linear (ii) MOLECULE TYPE: DNA (ix) FEATURE:
          (D) OTHER INFORMATION: oligonucleotide primer (xi) SEQUENCE DESCRIPTION: SEQ ID NO:78:

```
ACAGCGGACC AGCGTGTCGT TGTCTTCT                                              28

(2) INFORMATION FOR SEQ ID NO:79:

(i) SEQUENCE CHARACTERISTICS:
           (A) LENGTH: 26 base pairs
           (B) TYPE: nucleic acid
           (C) STRANDEDNESS: single
           (D) TOPOLOGY: linear (ii) MOLECULE TYPE: DNA (ix) FEATURE:
           (D) OTHER INFORMATION: oligonucleotide primer (xi) SEQUENCE DESCRIPTION: SEQ ID NO:79:

CTCTCCTATC AGCTAACCCA TTATGG                                                26

(2) INFORMATION FOR SEQ ID NO:80:

(i) SEQUENCE CHARACTERISTICS:
           (A) LENGTH: 27 base pairs
           (B) TYPE: nucleic acid
           (C) STRANDEDNESS: single
           (D) TOPOLOGY: linear (ii) MOLECULE TYPE: DNA (ix) FEATURE:
           (D) OTHER INFORMATION: oligonucleotide primer (xi) SEQUENCE DESCRIPTION: SEQ ID NO:80:

ACTGACCAAA CCAGTGTGAC TGTCTGC                                               27

(2) INFORMATION FOR SEQ ID NO:81:

(i) SEQUENCE CHARACTERISTICS:
           (A) LENGTH: 27 base pairs
           (B) TYPE: nucleic acid
           (C) STRANDEDNESS: single
           (D) TOPOLOGY: linear (ii) MOLECULE TYPE: DNA (ix) FEATURE:
           (D) OTHER INFORMATION: oligonucleotide primer (xi) SEQUENCE DESCRIPTION: SEQ ID NO:81:

TCCTCGGGAG ATATTTCAAA CATTTGG                                               27

(2) INFORMATION FOR SEQ ID NO:82:

(i) SEQUENCE CHARACTERISTICS:
           (A) LENGTH: 28 base pairs
           (B) TYPE: nucleic acid
           (C) STRANDEDNESS: single
           (D) TOPOLOGY: linear (ii) MOLECULE TYPE: DNA (ix) FEATURE:
           (D) OTHER INFORMATION: oligonucleotide primer (xi) SEQUENCE DESCRIPTION: SEQ ID NO:82:

CTGGCTTTAA TCCTAAACCA TGTAAGGG                                              28

(2) INFORMATION FOR SEQ ID NO:83:

(i) SEQUENCE CHARACTERISTICS:
           (A) LENGTH: 24 base pairs
```

(B) TYPE: nucleic acid
        (C) STRANDEDNESS: single
        (D) TOPOLOGY: linear (ii) MOLECULE TYPE: DNA (ix) FEATURE:
        (D) OTHER INFORMATION: oligonucleotide primer (xi) SEQUENCE DESCRIPTION: SEQ ID NO:83:

GCCGTGGAGC AGGTGAAGAA TGCC                                              24

(2) INFORMATION FOR SEQ ID NO:84:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: DNA (ix) FEATURE:
        (D) OTHER INFORMATION: oligonucleotide primer (xi) SEQUENCE DESCRIPTION: SEQ ID NO:84:

AGCTATCCCA GAGCCCCAGA TCCG                                              24

(2) INFORMATION FOR SEQ ID NO:85:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: DNA (ix) FEATURE:
        (D) OTHER INFORMATION: oligonucleotide primer (xi) SEQUENCE DESCRIPTION: SEQ ID NO:85:

CCTTGGGAGC AGGTGCTTGT GG                                                22

(2) INFORMATION FOR SEQ ID NO:86:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: DNA (ix) FEATURE:
        (D) OTHER INFORMATION: oligonucleotide primer (xi) SEQUENCE DESCRIPTION: SEQ ID NO:86:

AAGGAGACCG ACTTGCAGAG AGG                                               23

(2) INFORMATION FOR SEQ ID NO:87:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: DNA (ix) FEATURE:
        (D) OTHER INFORMATION: oligonucleotide primer (xi) SEQUENCE DESCRIPTION: SEQ ID NO:87:

GGTCCTCCTT TGGCTCACGC TGC                                               23

(2) INFORMATION FOR SEQ ID NO:88:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (ix) FEATURE:
        (D) OTHER INFORMATION: oligonucleotide primer (xi) SEQUENCE DESCRIPTION: SEQ ID NO:88:

GGCTTCCCAC TGTTCTCAGG G                                                 21

(2) INFORMATION FOR SEQ ID NO:89:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: DNA (ix) FEATURE:
        (D) OTHER INFORMATION: oligonucleotide primer (xi) SEQUENCE DESCRIPTION: SEQ ID NO:89:

GAGGGTCTCT TAGGTGCATG TCC                                               23

(2) INFORMATION FOR SEQ ID NO:90:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: DNA (ix) FEATURE:
        (D) OTHER INFORMATION: oligonucleotide primer (xi) SEQUENCE DESCRIPTION: SEQ ID NO:90:

ACTCTCATGG GATGTGGCGA GCCC                                              24

(2) INFORMATION FOR SEQ ID NO:91:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: DNA (ix) FEATURE:
        (D) OTHER INFORMATION: oligonucleotide primer (xi) SEQUENCE DESCRIPTION: SEQ ID NO:91:

ATCCTCAGCA AAGGGCGTGA CTGG                                              24

(2) INFORMATION FOR SEQ ID NO:92:

```
        (i) SEQUENCE CHARACTERISTICS:
            (A) LENGTH: 22 base pairs
            (B) TYPE: nucleic acid
            (C) STRANDEDNESS: single
            (D) TOPOLOGY: linear (ii) MOLECULE TYPE: DNA (ix) FEATURE:
            (D) OTHER INFORMATION: oligonucleotide primer (xi) SEQUENCE DESCRIPTION: SEQ ID NO:92:

CCTGCCTCTC TGCACATGGA GC                                              22

(2) INFORMATION FOR SEQ ID NO:93:

(i) SEQUENCE CHARACTERISTICS:
            (A) LENGTH: 23 base pairs
            (B) TYPE: nucleic acid
            (C) STRANDEDNESS: single
            (D) TOPOLOGY: linear (ii) MOLECULE TYPE: DNA (ix) FEATURE:
            (D) OTHER INFORMATION: oligonucleotide primer (xi) SEQUENCE DESCRIPTION: SEQ ID NO:93:

CTACGTCGCC CTGGACTTCG AGC                                             23

(2) INFORMATION FOR SEQ ID NO:94:

(i) SEQUENCE CHARACTERISTICS:
            (A) LENGTH: 23 base pairs
            (B) TYPE: nucleic acid
            (C) STRANDEDNESS: single
            (D) TOPOLOGY: linear (ii) MOLECULE TYPE: DNA (ix) FEATURE:
            (D) OTHER INFORMATION: oligonucleotide primer (xi) SEQUENCE DESCRIPTION: SEQ ID NO:94:

GATGGAGCCG CCGATCCACA CGG                                             23

(2) INFORMATION FOR SEQ ID NO:95:

(i) SEQUENCE CHARACTERISTICS:
            (A) LENGTH: 26 base pairs
            (B) TYPE: nucleic acid
            (C) STRANDEDNESS: single
            (D) TOPOLOGY: linear (ii) MOLECULE TYPE: DNA (ix) FEATURE:
            (D) OTHER INFORMATION: oligonucleotide primer (xi) SEQUENCE DESCRIPTION: SEQ ID NO:95:

CGCCTGATTA CACAGATGAA TCTTGC                                          26

(2) INFORMATION FOR SEQ ID NO:96:

(i) SEQUENCE CHARACTERISTICS:
            (A) LENGTH: 26 base pairs
            (B) TYPE: nucleic acid
            (C) STRANDEDNESS: single
            (D) TOPOLOGY: linear (ii) MOLECULE TYPE: DNA
```

(ix) FEATURE:
              (D) OTHER INFORMATION: oligonucleotide primer (xi) SEQUENCE DESCRIPTION: SEQ ID NO:96:

TTCCCTCTGA CTGTTCTTCA ATGACG                                       26

(2) INFORMATION FOR SEQ ID NO:97:

(i) SEQUENCE CHARACTERISTICS:
              (A) LENGTH: 26 base pairs
              (B) TYPE: nucleic acid
              (C) STRANDEDNESS: single
              (D) TOPOLOGY: linear (ii) MOLECULE TYPE: DNA (ix) FEATURE:
              (D) OTHER INFORMATION: oligonucleotide primer (xi) SEQUENCE DESCRIPTION: SEQ ID NO:97:

GCTCTTTCCT GGCTACTCCA TGTTGG                                       26

(2) INFORMATION FOR SEQ ID NO:98:

(i) SEQUENCE CHARACTERISTICS:
              (A) LENGTH: 26 base pairs
              (B) TYPE: nucleic acid
              (C) STRANDEDNESS: single
              (D) TOPOLOGY: linear (ii) MOLECULE TYPE: DNA (ix) FEATURE:
              (D) OTHER INFORMATION: oligonucleotide primer (xi) SEQUENCE DESCRIPTION: SEQ ID NO:98:

TGAGTTTCGA TAAGGATCTC GGTGGC                                       26

(2) INFORMATION FOR SEQ ID NO:99:

(i) SEQUENCE CHARACTERISTICS:
              (A) LENGTH: 26 base pairs
              (B) TYPE: nucleic acid
              (C) STRANDEDNESS: single
              (D) TOPOLOGY: linear (ii) MOLECULE TYPE: DNA (ix) FEATURE:
              (D) OTHER INFORMATION: oligonucleotide primer (xi) SEQUENCE DESCRIPTION: SEQ ID NO:99:

GATCTACATC ACAGTCCGAA ATCCGC                                       26

(2) INFORMATION FOR SEQ ID NO:100:

(i) SEQUENCE CHARACTERISTICS:
              (A) LENGTH: 26 base pairs
              (B) TYPE: nucleic acid
              (C) STRANDEDNESS: single
              (D) TOPOLOGY: linear (ii) MOLECULE TYPE: DNA (ix) FEATURE:
              (D) OTHER INFORMATION: oligonucleotide primer (xi) SEQUENCE DESCRIPTION: SEQ ID NO:100:

TGTTGTGGAG ACCCTGCCTC ATGTCG                                       26

(2) INFORMATION FOR SEQ ID NO:101:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: DNA (ix) FEATURE:
        (D) OTHER INFORMATION: oligonucleotide primer (xi) SEQUENCE DESCRIPTION: SEQ ID NO:101:

ACTGAGACCA TCCCTTCCAC CTCG                                  24

(2) INFORMATION FOR SEQ ID NO:102:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: DNA (ix) FEATURE:
        (D) OTHER INFORMATION: oligonucleotide primer (xi) SEQUENCE DESCRIPTION: SEQ ID NO:102:

GGTAACCCTC CTTGCAGCCT TTGG                                  24

(2) INFORMATION FOR SEQ ID NO:103:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: DNA (ix) FEATURE:
        (D) OTHER INFORMATION: oligonucleotide primer (xi) SEQUENCE DESCRIPTION: SEQ ID NO:103:

GTTTCGTGTT CGGAGCCGCT TTAACC                              26

(2) INFORMATION FOR SEQ ID NO:104:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: DNA (ix) FEATURE:
        (D) OTHER INFORMATION: oligonucleotide primer (xi) SEQUENCE DESCRIPTION: SEQ ID NO:104:

GGCAGAGTCG TTCACTGTAG TCTGGC                              26

(2) INFORMATION FOR SEQ ID NO:105:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: DNA (ix) FEATURE:
             (D) OTHER INFORMATION: oligonucleotide primer (xi) SEQUENCE DESCRIPTION: SEQ ID NO:105:

GCATGGTGAG CAGAGTGCCC TATCC                                             25

(2) INFORMATION FOR SEQ ID NO:106:

(i) SEQUENCE CHARACTERISTICS:
             (A) LENGTH: 26 base pairs
             (B) TYPE: nucleic acid
             (C) STRANDEDNESS: single
             (D) TOPOLOGY: linear (ii) MOLECULE TYPE: DNA (ix) FEATURE:
             (D) OTHER INFORMATION: oligonucleotide primer (xi) SEQUENCE DESCRIPTION: SEQ ID NO:106:

ACAGGTACTT CTGTTTCCCT TCAGCG                                            26

(2) INFORMATION FOR SEQ ID NO:107:

(i) SEQUENCE CHARACTERISTICS:
             (A) LENGTH: 24 base pairs
             (B) TYPE: nucleic acid
             (C) STRANDEDNESS: single
             (D) TOPOLOGY: linear (ii) MOLECULE TYPE: DNA (ix) FEATURE:
             (D) OTHER INFORMATION: oligonucleotide primer (xi) SEQUENCE DESCRIPTION: SEQ ID NO:107:

GCCGCTCCAA CACTTACCCC AAGG                                              24

(2) INFORMATION FOR SEQ ID NO:108:

(i) SEQUENCE CHARACTERISTICS:
             (A) LENGTH: 23 base pairs
             (B) TYPE: nucleic acid
             (C) STRANDEDNESS: single
             (D) TOPOLOGY: linear (ii) MOLECULE TYPE: DNA (ix) FEATURE:
             (D) OTHER INFORMATION: oligonucleotide primer (xi) SEQUENCE DESCRIPTION: SEQ ID NO:108:

GGTGATAGCT GTGGCATTGT GGC                                               23

(2) INFORMATION FOR SEQ ID NO:109:

(i) SEQUENCE CHARACTERISTICS:
             (A) LENGTH: 23 base pairs
             (B) TYPE: nucleic acid
             (C) STRANDEDNESS: single
             (D) TOPOLOGY: linear (ii) MOLECULE TYPE: DNA (ix) FEATURE:
             (D) OTHER INFORMATION: oligonucleotide primer (xi) SEQUENCE DESCRIPTION: SEQ ID NO:109:

CGCCCCTCTC TGGCTCATGT ACC                                               23

(2) INFORMATION FOR SEQ ID NO:110:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: DNA (ix) FEATURE:
        (D) OTHER INFORMATION: oligonucleotide primer (xi) SEQUENCE DESCRIPTION: SEQ ID NO:110:

CTGACCTGCT CTCCGTCACT GCC                                                  23

(2) INFORMATION FOR SEQ ID NO:111:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: DNA (ix) FEATURE:
        (D) OTHER INFORMATION: oligonucleotide primer (xi) SEQUENCE DESCRIPTION: SEQ ID NO:111:

CTCACGCAGA AGGAAGATGA TTGTGACG                                        28

(2) INFORMATION FOR SEQ ID NO:112:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: DNA (ix) FEATURE:
        (D) OTHER INFORMATION: oligonucleotide primer (xi) SEQUENCE DESCRIPTION: SEQ ID NO:112:

GAAAGAGTAG TAAAGCAGCA ACAACTGG                                        28

(2) INFORMATION FOR SEQ ID NO:113:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: DNA (ix) FEATURE:
        (D) OTHER INFORMATION: oligonucleotide primer (xi) SEQUENCE DESCRIPTION: SEQ ID NO:113:

ACACTGTGCC CTGAGCTGCC CCC                                                  23

(2) INFORMATION FOR SEQ ID NO:114:

(i) SEQUENCE CHARACTERISTICS:
        (A) LENGTH: 23 base pairs
        (B) TYPE: nucleic acid
        (C) STRANDEDNESS: single (D) TOPOLOGY: linear (ii) MOLECULE TYPE: DNA (ix) FEATURE:
            (D) OTHER INFORMATION: oligonucleotide primer (xi) SEQUENCE DESCRIPTION: SEQ ID NO:114:

ATGCCCCTGC TCCTGAGAGA GGC                                           23

(2) INFORMATION FOR SEQ ID NO:115:

(i) SEQUENCE CHARACTERISTICS:
            (A) LENGTH: 26 base pairs
            (B) TYPE: nucleic acid
            (C) STRANDEDNESS: single
            (D) TOPOLOGY: linear (ii) MOLECULE TYPE: DNA (ix) FEATURE:
            (D) OTHER INFORMATION: oligonucleotide primer (xi) SEQUENCE DESCRIPTION: SEQ ID NO:115:

AATCTGAGTG CGGTGGAGCG GGCCTG                                        26

(2) INFORMATION FOR SEQ ID NO:116:

(i) SEQUENCE CHARACTERISTICS:
            (A) LENGTH: 25 base pairs
            (B) TYPE: nucleic acid
            (C) STRANDEDNESS: single
            (D) TOPOLOGY: linear (ii) MOLECULE TYPE: DNA (ix) FEATURE:
            (D) OTHER INFORMATION: oligonucleotide primer (xi) SEQUENCE DESCRIPTION: SEQ ID NO:116:

GGGTTCATGG CCGAGTTGCC GTGCG                                         25

(2) INFORMATION FOR SEQ ID NO:117:

(i) SEQUENCE CHARACTERISTICS:
            (A) LENGTH: 24 base pairs
            (B) TYPE: nucleic acid
            (C) STRANDEDNESS: single
            (D) TOPOLOGY: linear (ii) MOLECULE TYPE: DNA (ix) FEATURE:
            (D) OTHER INFORMATION: oligonucleotide primer (xi) SEQUENCE DESCRIPTION: SEQ ID NO:117:

TCCGTTCCCT GCCCATTGAA GACC                                          24

(2) INFORMATION FOR SEQ ID NO:118:

(i) SEQUENCE CHARACTERISTICS:
            (A) LENGTH: 23 base pairs
            (B) TYPE: nucleic acid
            (C) STRANDEDNESS: single
            (D) TOPOLOGY: linear (ii) MOLECULE TYPE: DNA (ix) FEATURE:
            (D) OTHER INFORMATION: oligonucleotide primer (xi) SEQUENCE DESCRIPTION: SEQ ID NO:118:

```
GAGTCAGTGC CATCTCCTCT TGC                                    23
```

(2) INFORMATION FOR SEQ ID NO:119:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: DNA (ix) FEATURE:
        (D) OTHER INFORMATION: oligonucleotide primer (xi) SEQUENCE DESCRIPTION: SEQ ID NO:119:

```
TCTTGTTTGC TCTGTCATGG CTGC                                   24
```

(2) INFORMATION FOR SEQ ID NO:120:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: DNA (ix) FEATURE:
        (D) OTHER INFORMATION: oligonucleotide primer (xi) SEQUENCE DESCRIPTION: SEQ ID NO:120:

```
GTGGAGTGGG GGAGATATAA TTGG                                   24
```

(2) INFORMATION FOR SEQ ID NO:121:

(i) SEQUENCE CHARACTERISTICS:
        (A) LENGTH: 32 base pairs
        (B) TYPE: nucleic acid
        (C) STRANDEDNESS: single
        (D) TOPOLOGY: linear (ii) MOLECULE TYPE: DNA (ix) FEATURE:
        (D) OTHER INFORMATION: oligonucleotide primer (xi) SEQUENCE DESCRIPTION: SEQ ID NO:121:

```
TTATCATCAT CCACCTGGTT GAAGTAGTAC CC                          32
```

(2) INFORMATION FOR SEQ ID NO:122:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: DNA (ix) FEATURE:
        (D) OTHER INFORMATION: oligonucleotide primer (xi) SEQUENCE DESCRIPTION: SEQ ID NO:122:

```
GTCACAAGCA CCCGGACAAT GTTGAGCAAA                             30
```

(2) INFORMATION FOR SEQ ID NO:123:

(i) SEQUENCE CHARACTERISTICS:
        (A) LENGTH: 25 base pairs (B) TYPE: nucleic acid
        (C) STRANDEDNESS: single
        (D) TOPOLOGY: linear (ii) MOLECULE TYPE: DNA (ix) FEATURE:
        (D) OTHER INFORMATION: oligonucleotide primer (xi) SEQUENCE DESCRIPTION: SEQ ID NO:123:

AGGACTCCAG GCAGCAGACA CATGC                                                  25

(2) INFORMATION FOR SEQ ID NO:124:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: DNA (ix) FEATURE:
        (D) OTHER INFORMATION: oligonucleotide primer (xi) SEQUENCE DESCRIPTION: SEQ ID NO:124:

TGATCTACTT TGCTCTTGAG GGCAGG                                                 26

(2) INFORMATION FOR SEQ ID NO:125:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: DNA (ix) FEATURE:
        (D) OTHER INFORMATION: oligonucleotide primer (xi) SEQUENCE DESCRIPTION: SEQ ID NO:125:

TAAACATGAC CCTGGGCTTC TGTACC                                                 26

(2) INFORMATION FOR SEQ ID NO:126:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: DNA (ix) FEATURE:
        (D) OTHER INFORMATION: oligonucleotide primer (xi) SEQUENCE DESCRIPTION: SEQ ID NO:126:

TCTCCTCACT GGTTCTACTA TCTGGC                                                 26

(2) INFORMATION FOR SEQ ID NO:127:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: DNA (ix) FEATURE:
        (D) OTHER INFORMATION: oligonucleotide primer (xi) SEQUENCE DESCRIPTION: SEQ ID NO:127:

GCACAGGGAT CACATTGTCG GGG                                          23

(2) INFORMATION FOR SEQ ID NO:128:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (ix) FEATURE:
        (D) OTHER INFORMATION: oligonucleotide primer (xi) SEQUENCE DESCRIPTION: SEQ ID NO:128:

GAGGGGCTGG AAGAACATCG C                                            21

(2) INFORMATION FOR SEQ ID NO:129:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: DNA (ix) FEATURE:
        (D) OTHER INFORMATION: oligonucleotide primer (xi) SEQUENCE DESCRIPTION: SEQ ID NO:129:

GGCTTCCAGC TCAGAACCCA TCC                                          23

(2) INFORMATION FOR SEQ ID NO:130:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: DNA (ix) FEATURE:
        (D) OTHER INFORMATION: oligonucleotide primer (xi) SEQUENCE DESCRIPTION: SEQ ID NO:130:

AACACCAACA AGGCAGGGAC CCC                                          23

(2) INFORMATION FOR SEQ ID NO:131:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: DNA (ix) FEATURE:
        (D) OTHER INFORMATION: oligonucleotide primer (xi) SEQUENCE DESCRIPTION: SEQ ID NO:131:

GACTTCGACT GTGACCTGTG GGG                                          23

(2) INFORMATION FOR SEQ ID NO:132:

(i) SEQUENCE CHARACTERISTICS:
            (A) LENGTH: 23 base pairs
            (B) TYPE: nucleic acid
            (C) STRANDEDNESS: single
            (D) TOPOLOGY: linear (ii) MOLECULE TYPE: DNA (ix) FEATURE:
            (D) OTHER INFORMATION: oligonucleotide primer (xi) SEQUENCE DESCRIPTION: SEQ ID NO:132:

GGGTTCCATC TCAGCTCAAG GGG                                              23

(2) INFORMATION FOR SEQ ID NO:133:

(i) SEQUENCE CHARACTERISTICS:
            (A) LENGTH: 30 base pairs
            (B) TYPE: nucleic acid
            (C) STRANDEDNESS: single
            (D) TOPOLOGY: linear (ii) MOLECULE TYPE: DNA (ix) FEATURE:
            (D) OTHER INFORMATION: oligonucleotide primer (xi) SEQUENCE DESCRIPTION: SEQ ID NO:133:

TCGACAGGCT CACATTCTAC TTGACTGTGG                                       30

(2) INFORMATION FOR SEQ ID NO:134:

(i) SEQUENCE CHARACTERISTICS:
            (A) LENGTH: 31 base pairs
            (B) TYPE: nucleic acid
            (C) STRANDEDNESS: single
            (D) TOPOLOGY: linear (ii) MOLECULE TYPE: DNA (ix) FEATURE:
            (D) OTHER INFORMATION: oligonucleotide primer (xi) SEQUENCE DESCRIPTION: SEQ ID NO:134:

AGTTGAGTTC CAGCCTTCAT TGGGTTTCCA A                                     31

(2) INFORMATION FOR SEQ ID NO:135:

(i) SEQUENCE CHARACTERISTICS:
            (A) LENGTH: 28 base pairs
            (B) TYPE: nucleic acid
            (C) STRANDEDNESS: single
            (D) TOPOLOGY: linear (ii) MOLECULE TYPE: DNA (ix) FEATURE:
            (D) OTHER INFORMATION: oligonucleotide primer (xi) SEQUENCE DESCRIPTION: SEQ ID NO:135:

GCGCAGCAAG GCTCGTTCCT GTTCAGAA                                         28

(2) INFORMATION FOR SEQ ID NO:136:

(i) SEQUENCE CHARACTERISTICS:
            (A) LENGTH: 30 base pairs
            (B) TYPE: nucleic acid
            (C) STRANDEDNESS: single
            (D) TOPOLOGY: linear (ii) MOLECULE TYPE: DNA (ix) FEATURE:
            (D) OTHER INFORMATION: oligonucleotide primer (xi) SEQUENCE DESCRIPTION: SEQ ID NO:136:

CGCCATAAGG TGGTGGTTGT CGTCTGACAA                                              30

(2) INFORMATION FOR SEQ ID NO:137:

(i) SEQUENCE CHARACTERISTICS:
            (A) LENGTH: 30 base pairs
            (B) TYPE: nucleic acid
            (C) STRANDEDNESS: single
            (D) TOPOLOGY: linear (ii) MOLECULE TYPE: DNA (ix) FEATURE:
            (D) OTHER INFORMATION: oligonucleotide primer (xi) SEQUENCE DESCRIPTION: SEQ ID NO:137:

ACATTGAAGC CACAGGACTG AGCACGGAAG                                              30

(2) INFORMATION FOR SEQ ID NO:138:

(i) SEQUENCE CHARACTERISTICS:
            (A) LENGTH: 31 base pairs
            (B) TYPE: nucleic acid
            (C) STRANDEDNESS: single
            (D) TOPOLOGY: linear (ii) MOLECULE TYPE: DNA (ix) FEATURE:
            (D) OTHER INFORMATION: oligonucleotide primer (xi) SEQUENCE DESCRIPTION: SEQ ID NO:138:

CGTCCATAGT GCTGAAATCA GGTCTCATCA A                                           31

(2) INFORMATION FOR SEQ ID NO:139:

(i) SEQUENCE CHARACTERISTICS:
            (A) LENGTH: 31 base pairs
            (B) TYPE: nucleic acid
            (C) STRANDEDNESS: single
            (D) TOPOLOGY: linear (ii) MOLECULE TYPE: DNA (ix) FEATURE:
            (D) OTHER INFORMATION: oligonucleotide primer (xi) SEQUENCE DESCRIPTION: SEQ ID NO:139:

AATTGCAGCG ATGCCTGGCA AATTGAAGTT G                                           31

(2) INFORMATION FOR SEQ ID NO:140:

(i) SEQUENCE CHARACTERISTICS:
            (A) LENGTH: 31 base pairs
            (B) TYPE: nucleic acid
            (C) STRANDEDNESS: single
            (D) TOPOLOGY: linear (ii) MOLECULE TYPE: DNA (ix) FEATURE:
            (D) OTHER INFORMATION: oligonucleotide primer (xi) SEQUENCE DESCRIPTION: SEQ ID NO:140:

CAAAGCGTCC ATTCAGTTAG TCAGTGTGAG A                                           31

(2) INFORMATION FOR SEQ ID NO:141:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (ii) MOLECULE TYPE: DNA (ix) FEATURE:
        (D) OTHER INFORMATION: oligonucleotide primer (xi) SEQUENCE DESCRIPTION: SEQ ID NO:141:

CATCTGCTTA ATCTGTGGAG ACCGCCAGG                         29

(2) INFORMATION FOR SEQ ID NO:142:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (ii) MOLECULE TYPE: DNA (ix) FEATURE:
        (D) OTHER INFORMATION: oligonucleotide primer (xi) SEQUENCE DESCRIPTION: SEQ ID NO:142:

CTAGGACTGT GCTCTGCTGT GTTCCCACT                         29

(2) INFORMATION FOR SEQ ID NO:143:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (ii) MOLECULE TYPE: DNA (ix) FEATURE:
        (D) OTHER INFORMATION: oligonucleotide primer (xi) SEQUENCE DESCRIPTION: SEQ ID NO:143:

CCGGAAGTCT CTGGCTCTTG ACATTGTGG                         29

(2) INFORMATION FOR SEQ ID NO:144:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: DNA (ix) FEATURE:
        (D) OTHER INFORMATION: oligonucleotide primer (xi) SEQUENCE DESCRIPTION: SEQ ID NO:144:

CCCTGTAAAC ATGAGAATGG GCTCGTGACA                       30

(2) INFORMATION FOR SEQ ID NO:145:

(i) SEQUENCE CHARACTERISTICS:
        (A) LENGTH: 31 base pairs
        (B) TYPE: nucleic acid
        (C) STRANDEDNESS: single
        (D) TOPOLOGY: linear (ii) MOLECULE TYPE: DNA (ix) FEATURE:
             (D) OTHER INFORMATION: oligonucleotide primer (xi) SEQUENCE DESCRIPTION: SEQ ID NO:145:

CTACAGTGTC TATACCACCA AGAGTGATGT C                                31

(2) INFORMATION FOR SEQ ID NO:146:

(i) SEQUENCE CHARACTERISTICS:
             (A) LENGTH: 30 base pairs
             (B) TYPE: nucleic acid
             (C) STRANDEDNESS: single
             (D) TOPOLOGY: linear (ii) MOLECULE TYPE: DNA (ix) FEATURE:
             (D) OTHER INFORMATION: oligonucleotide primer (xi) SEQUENCE DESCRIPTION: SEQ ID NO:146:

GGCTGTAAGG GTCAGACTGG TCACAGGTTA                                  30

(2) INFORMATION FOR SEQ ID NO:147:

(i) SEQUENCE CHARACTERISTICS:
             (A) LENGTH: 28 base pairs
             (B) TYPE: nucleic acid
             (C) STRANDEDNESS: single
             (D) TOPOLOGY: linear (ii) MOLECULE TYPE: DNA (ix) FEATURE:
             (D) OTHER INFORMATION: oligonucleotide primer (xi) SEQUENCE DESCRIPTION: SEQ ID NO:147:

CAGGTGCTTC CCAGACACTG GCGTTACT                                    28

(2) INFORMATION FOR SEQ ID NO:148:

(i) SEQUENCE CHARACTERISTICS:
             (A) LENGTH: 31 base pairs
             (B) TYPE: nucleic acid
             (C) STRANDEDNESS: single
             (D) TOPOLOGY: linear (ii) MOLECULE TYPE: DNA (ix) FEATURE:
             (D) OTHER INFORMATION: oligonucleotide primer (xi) SEQUENCE DESCRIPTION: SEQ ID NO:148:

ACTCATATTA CCAAGGAATA ACTGGCGGGC A                                31

(2) INFORMATION FOR SEQ ID NO:149:

(i) SEQUENCE CHARACTERISTICS:
             (A) LENGTH: 28 base pairs
             (B) TYPE: nucleic acid
             (C) STRANDEDNESS: single
             (D) TOPOLOGY: linear (ii) MOLECULE TYPE: DNA (ix) FEATURE:
             (D) OTHER INFORMATION: oligonucleotide primer (xi) SEQUENCE DESCRIPTION: SEQ ID NO:149:

TGAAGTCAAG TGGGCAGGGC GAAGTTGG                                    28

(2) INFORMATION FOR SEQ ID NO:150:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: DNA (ix) FEATURE:
        (D) OTHER INFORMATION: oligonucleotide primer (xi) SEQUENCE DESCRIPTION: SEQ ID NO:150:

AGCCAGGTGG AAATCCTACA GCGCGTCA                          28

(2) INFORMATION FOR SEQ ID NO:151:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: DNA (ix) FEATURE:
        (D) OTHER INFORMATION: oligonucleotide primer (xi) SEQUENCE DESCRIPTION: SEQ ID NO:151:

CTACCAAAGC ACCTTAGCTG GCATTACAGC                       30

(2) INFORMATION FOR SEQ ID NO:152:

(i) SEQUENCE CHARACTERISTICS:
        (A) LENGTH: 31 base pairs
        (B) TYPE: nucleic acid
        (C) STRANDEDNESS: single
        (D) TOPOLOGY: linear (ii) MOLECULE TYPE: DNA (ix) FEATURE:
        (D) OTHER INFORMATION: oligonucleotide primer (xi) SEQUENCE DESCRIPTION: SEQ ID NO:152:

CTGTCACATG ACAAGTGGGA GTTTGTAGAG A                     31

(2) INFORMATION FOR SEQ ID NO:153:

(i) SEQUENCE CHARACTERISTICS:
        (A) LENGTH: 31 base pairs
        (B) TYPE: nucleic acid
        (C) STRANDEDNESS: single
        (D) TOPOLOGY: linear (ii) MOLECULE TYPE: DNA (ix) FEATURE:
        (D) OTHER INFORMATION: oligonucleotide primer (xi) SEQUENCE DESCRIPTION: SEQ ID NO:153:

CAAATCAGAC AGCAGCAATG GACACTCTTA A                     31

(2) INFORMATION FOR SEQ ID NO:154:

(i) SEQUENCE CHARACTERISTICS:
        (A) LENGTH: 30 base pairs
        (B) TYPE: nucleic acid
        (C) STRANDEDNESS: single (D) TOPOLOGY: linear (ii) MOLECULE TYPE: DNA (ix) FEATURE:
        (D) OTHER INFORMATION: oligonucleotide primer (xi) SEQUENCE DESCRIPTION: SEQ ID NO:154:

GTAATCGCAG TAGTGGATGC GTCGTTTCTC                                30

(2) INFORMATION FOR SEQ ID NO:155:

(i) SEQUENCE CHARACTERISTICS:
        (A) LENGTH: 31 base pairs
        (B) TYPE: nucleic acid
        (C) STRANDEDNESS: single
        (D) TOPOLOGY: linear (ii) MOLECULE TYPE: DNA (ix) FEATURE:
        (D) OTHER INFORMATION: oligonucleotide primer (xi) SEQUENCE DESCRIPTION: SEQ ID NO:155:

TGTAGCTGTT GGAGAACTTC TACGACATTT C                              31

(2) INFORMATION FOR SEQ ID NO:156:

(i) SEQUENCE CHARACTERISTICS:
        (A) LENGTH: 31 base pairs
        (B) TYPE: nucleic acid
        (C) STRANDEDNESS: single
        (D) TOPOLOGY: linear (ii) MOLECULE TYPE: DNA (ix) FEATURE:
        (D) OTHER INFORMATION: oligonucleotide primer (xi) SEQUENCE DESCRIPTION: SEQ ID NO:156:

GTTGGCGTGG AGCAGATGTT TCTTATCACT C                              31

(2) INFORMATION FOR SEQ ID NO:157:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: DNA (ix) FEATURE:
        (D) OTHER INFORMATION: oligonucleotide primer (xi) SEQUENCE DESCRIPTION: SEQ ID NO:157:

GAAAGCCTTC AGTCCCGTGA GGTCCGTT                                  28

(2) INFORMATION FOR SEQ ID NO:158:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: DNA (ix) FEATURE:
        (D) OTHER INFORMATION: oligonucleotide primer (xi) SEQUENCE DESCRIPTION: SEQ ID NO:158:

CTGGTGATGC AGGCTGACAA TAGTGGGATG                                      30

(2) INFORMATION FOR SEQ ID NO:159:

(i) SEQUENCE CHARACTERISTICS:
        (A) LENGTH: 31 base pairs
        (B) TYPE: nucleic acid
        (C) STRANDEDNESS: single
        (D) TOPOLOGY: linear (ii) MOLECULE TYPE: DNA (ix) FEATURE:
        (D) OTHER INFORMATION: oligonucleotide primer (xi) SEQUENCE DESCRIPTION: SEQ ID NO:159:

AAGATATGCT AAGCAGTAGT CGTCAAGTTG C                                    31

(2) INFORMATION FOR SEQ ID NO:160:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: DNA (ix) FEATURE:
        (D) OTHER INFORMATION: oligonucleotide primer (xi) SEQUENCE DESCRIPTION: SEQ ID NO:160:

CTTGGGACCA GTGCAGCACC TTTACAAGTA                                      30

(2) INFORMATION FOR SEQ ID NO:161:

(i) SEQUENCE CHARACTERISTICS:
        (A) LENGTH: 31 base pairs
        (B) TYPE: nucleic acid
        (C) STRANDEDNESS: single
        (D) TOPOLOGY: linear (ii) MOLECULE TYPE: DNA (ix) FEATURE:
        (D) OTHER INFORMATION: oligonucleotide primer (xi) SEQUENCE DESCRIPTION: SEQ ID NO:161:

ATATCTCTAC CTTCCGCACA ACAGGTGACT G                                    31

(2) INFORMATION FOR SEQ ID NO:162:

(i) SEQUENCE CHARACTERISTICS:
        (A) LENGTH: 31 base pairs
        (B) TYPE: nucleic acid
        (C) STRANDEDNESS: single
        (D) TOPOLOGY: linear (ii) MOLECULE TYPE: DNA (ix) FEATURE:
        (D) OTHER INFORMATION: oligonucleotide primer (xi) SEQUENCE DESCRIPTION: SEQ ID NO:162:

CACCAGTATC TCCAGAATTA TTGTCTGTCT G                                    31

(2) INFORMATION FOR SEQ ID NO:163:

(i) SEQUENCE CHARACTERISTICS:
        (A) LENGTH: 28 base pairs (B) TYPE: nucleic acid
          (C) STRANDEDNESS: single
          (D) TOPOLOGY: linear (ii) MOLECULE TYPE: DNA (ix) FEATURE:
          (D) OTHER INFORMATION: oligonucleotide primer (xi) SEQUENCE DESCRIPTION: SEQ ID NO:163:

GCGAAGTCCG CCTCGTCAGT TTGCACAT                                           28

(2) INFORMATION FOR SEQ ID NO:164:

(i) SEQUENCE CHARACTERISTICS:
          (A) LENGTH: 30 base pairs
          (B) TYPE: nucleic acid
          (C) STRANDEDNESS: single
          (D) TOPOLOGY: linear (ii) MOLECULE TYPE: DNA (ix) FEATURE:
          (D) OTHER INFORMATION: oligonucleotide primer (xi) SEQUENCE DESCRIPTION: SEQ ID NO:164:

CATGGTTGTT GACAGTACGG GAGTCACAGA                                         30

(2) INFORMATION FOR SEQ ID NO:165:

(i) SEQUENCE CHARACTERISTICS:
          (A) LENGTH: 28 base pairs
          (B) TYPE: nucleic acid
          (C) STRANDEDNESS: single
          (D) TOPOLOGY: linear (ii) MOLECULE TYPE: DNA (ix) FEATURE:
          (D) OTHER INFORMATION: oligonucleotide primer (xi) SEQUENCE DESCRIPTION: SEQ ID NO:165:

CTAAGTACCA GGGCTGGAGG TCTCGGAA                                           28

(2) INFORMATION FOR SEQ ID NO:166:

(i) SEQUENCE CHARACTERISTICS:
          (A) LENGTH: 31 base pairs
          (B) TYPE: nucleic acid
          (C) STRANDEDNESS: single
          (D) TOPOLOGY: linear (ii) MOLECULE TYPE: DNA (ix) FEATURE:
          (D) OTHER INFORMATION: oligonucleotide primer (xi) SEQUENCE DESCRIPTION: SEQ ID NO:166:

GCTTGTTAGA CCGTTGGTCA ATGAGTCTTC C                                       31

(2) INFORMATION FOR SEQ ID NO:167:

(i) SEQUENCE CHARACTERISTICS:
          (A) LENGTH: 31 base pairs
          (B) TYPE: nucleic acid
          (C) STRANDEDNESS: single
          (D) TOPOLOGY: linear (ii) MOLECULE TYPE: DNA (ix) FEATURE:
          (D) OTHER INFORMATION: oligonucleotide primer (xi) SEQUENCE DESCRIPTION: SEQ ID NO:167:

ACCATCATTG CTCTGGACCG CTGTATTTGT G                    31

(2) INFORMATION FOR SEQ ID NO:168:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: DNA (ix) FEATURE:
        (D) OTHER INFORMATION: oligonucleotide primer (xi) SEQUENCE DESCRIPTION: SEQ ID NO:168:

ACTGTGATGA TGGACATAGG CACCGTGAAG                      30

(2) INFORMATION FOR SEQ ID NO:169:

(i) SEQUENCE CHARACTERISTICS:
        (A) LENGTH: 31 base pairs
        (B) TYPE: nucleic acid
        (C) STRANDEDNESS: single
        (D) TOPOLOGY: linear (ii) MOLECULE TYPE: DNA (ix) FEATURE:
        (D) OTHER INFORMATION: oligonucleotide primer (xi) SEQUENCE DESCRIPTION: SEQ ID NO:169:

TTCCAAATCA TCCTGGTGGA ATGGGTATCA C                    31

(2) INFORMATION FOR SEQ ID NO:170:

(i) SEQUENCE CHARACTERISTICS:
        (A) LENGTH: 31 base pairs
        (B) TYPE: nucleic acid
        (C) STRANDEDNESS: single
        (D) TOPOLOGY: linear (ii) MOLECULE TYPE: DNA (ix) FEATURE:
        (D) OTHER INFORMATION: oligonucleotide primer (xi) SEQUENCE DESCRIPTION: SEQ ID NO:170:

GTTGCGATGT CTGCTAAATG AGAACCTTAC T                    31

(2) INFORMATION FOR SEQ ID NO:171:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: DNA (ix) FEATURE:
        (D) OTHER INFORMATION: oligonucleotide primer (xi) SEQUENCE DESCRIPTION: SEQ ID NO:171:

GTGGTCAACC TTCTAGGTGC CTGTACCAAG                      30

(2) INFORMATION FOR SEQ ID NO:172:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: DNA (ix) FEATURE:
        (D) OTHER INFORMATION: oligonucleotide primer (xi) SEQUENCE DESCRIPTION: SEQ ID NO:172:

CCAAGAACTC CATGCCCTTA GCCACTTGGA                                    30

(2) INFORMATION FOR SEQ ID NO:173:

(i) SEQUENCE CHARACTERISTICS:
        (A) LENGTH: 31 base pairs
        (B) TYPE: nucleic acid
        (C) STRANDEDNESS: single
        (D) TOPOLOGY: linear (ii) MOLECULE TYPE: DNA (ix) FEATURE:
        (D) OTHER INFORMATION: oligonucleotide primer (xi) SEQUENCE DESCRIPTION: SEQ ID NO:173:

CCGGATGTTT CCAGATATTT GTGCCTCACA C                                  31

(2) INFORMATION FOR SEQ ID NO:174:

(i) SEQUENCE CHARACTERISTICS:
        (A) LENGTH: 31 base pairs
        (B) TYPE: nucleic acid
        (C) STRANDEDNESS: single
        (D) TOPOLOGY: linear (ii) MOLECULE TYPE: DNA (ix) FEATURE:
        (D) OTHER INFORMATION: oligonucleotide primer (xi) SEQUENCE DESCRIPTION: SEQ ID NO:174:

CCTCCGAGAA TGCCCTTATT AAATTAAGTG C                                  31

(2) INFORMATION FOR SEQ ID NO:175:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (ii) MOLECULE TYPE: DNA (ix) FEATURE:
        (D) OTHER INFORMATION: oligonucleotide primer (xi) SEQUENCE DESCRIPTION: SEQ ID NO:175:

GTCATAACGA GGCCCTAAAT GGTCTGCGC                                     29

(2) INFORMATION FOR SEQ ID NO:176:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: DNA (ix) FEATURE:
    (D) OTHER INFORMATION: oligonucleotide primer (xi) SEQUENCE DESCRIPTION: SEQ ID NO:176:

TTCACGTTGA ACAACGAAGC AAAGCGCACC                          30

(2) INFORMATION FOR SEQ ID NO:177:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: DNA (ix) FEATURE:
        (D) OTHER INFORMATION: oligonucleotide primer (xi) SEQUENCE DESCRIPTION: SEQ ID NO:177:

CAGGCTTTAC TGGACTCAGA AGGCAATGCT                          30

(2) INFORMATION FOR SEQ ID NO:178:

(i) SEQUENCE CHARACTERISTICS:
        (A) LENGTH: 31 base pairs
        (B) TYPE: nucleic acid
        (C) STRANDEDNESS: single
        (D) TOPOLOGY: linear (ii) MOLECULE TYPE: DNA (ix) FEATURE:
        (D) OTHER INFORMATION: oligonucleotide primer (xi) SEQUENCE DESCRIPTION: SEQ ID NO:178:

TATCTCATGC TGTCCATTAG CTTTGTGGGA A                        31

(2) INFORMATION FOR SEQ ID NO:179:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: DNA (ix) FEATURE:
        (D) OTHER INFORMATION: oligonucleotide primer (xi) SEQUENCE DESCRIPTION: SEQ ID NO:179:

ATGAGCAACC AGGATGTCAT CAATGCCGTG                          30

(2) INFORMATION FOR SEQ ID NO:180:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: DNA (ix) FEATURE:
        (D) OTHER INFORMATION: oligonucleotide primer (xi) SEQUENCE DESCRIPTION: SEQ ID NO:180:

CCAACTGTCG TGAAGGTTGT GTAATCTGGG                          30

(2) INFORMATION FOR SEQ ID NO:181:

(i) SEQUENCE CHARACTERISTICS:
        (A) LENGTH: 31 base pairs
        (B) TYPE: nucleic acid
        (C) STRANDEDNESS: single
        (D) TOPOLOGY: linear (ii) MOLECULE TYPE: DNA (ix) FEATURE:
        (D) OTHER INFORMATION: oligonucleotide primer (xi) SEQUENCE DESCRIPTION: SEQ ID NO:181:

CTAGATATTA TCCTACTGAA GATGTGCCTC G                                31

(2) INFORMATION FOR SEQ ID NO:182:

(i) SEQUENCE CHARACTERISTICS:
        (A) LENGTH: 31 base pairs
        (B) TYPE: nucleic acid
        (C) STRANDEDNESS: single
        (D) TOPOLOGY: linear (ii) MOLECULE TYPE: DNA (ix) FEATURE:
        (D) OTHER INFORMATION: oligonucleotide primer (xi) SEQUENCE DESCRIPTION: SEQ ID NO:182:

ATCTTGCGCT GCTCCGTAAT CTCATATTTC T                                31

(2) INFORMATION FOR SEQ ID NO:183:

(i) SEQUENCE CHARACTERISTICS:
        (A) LENGTH: 31 base pairs
        (B) TYPE: nucleic acid
        (C) STRANDEDNESS: single
        (D) TOPOLOGY: linear (ii) MOLECULE TYPE: DNA (ix) FEATURE:
        (D) OTHER INFORMATION: oligonucleotide primer (xi) SEQUENCE DESCRIPTION: SEQ ID NO:183:

AGCAGAAAGT TCAACTTCCA AAGGGTTAGG A                                31

(2) INFORMATION FOR SEQ ID NO:184:

(i) SEQUENCE CHARACTERISTICS:
        (A) LENGTH: 31 base pairs
        (B) TYPE: nucleic acid
        (C) STRANDEDNESS: single
        (D) TOPOLOGY: linear (ii) MOLECULE TYPE: DNA (ix) FEATURE:
        (D) OTHER INFORMATION: oligonucleotide primer (xi) SEQUENCE DESCRIPTION: SEQ ID NO:184:

GCTGCAAACA CCCTGGGCCA GATTTCTTAA A                                31

(2) INFORMATION FOR SEQ ID NO:185:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: DNA (ix) FEATURE:
     (D) OTHER INFORMATION: oligonucleotide primer (xi) SEQUENCE DESCRIPTION: SEQ ID NO:185:

TCTCCCAAAT GCTCCACATT GCCAGTCAGA                              30

(2) INFORMATION FOR SEQ ID NO:186:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: DNA (ix) FEATURE:
         (D) OTHER INFORMATION: oligonucleotide primer (xi) SEQUENCE DESCRIPTION: SEQ ID NO:186:

TGACCTCCGT GTTTGAGAGT TGGAACCATG                              30

(2) INFORMATION FOR SEQ ID NO:187:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: DNA (ix) FEATURE:
         (D) OTHER INFORMATION: oligonucleotide primer (xi) SEQUENCE DESCRIPTION: SEQ ID NO:187:

GGAGAGTATC TTGCTGGGCA AGTTCACTAC                              30

(2) INFORMATION FOR SEQ ID NO:188:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (ii) MOLECULE TYPE: DNA (ix) FEATURE:
         (D) OTHER INFORMATION: oligonucleotide primer (xi) SEQUENCE DESCRIPTION: SEQ ID NO:188:

CATGGGTGAG TGGTAGGTCT TGTAGGGAG                               29

(2) INFORMATION FOR SEQ ID NO:189:

(i) SEQUENCE CHARACTERISTICS:
        (A) LENGTH: 31 base pairs
        (B) TYPE: nucleic acid
        (C) STRANDEDNESS: single
        (D) TOPOLOGY: linear (ii) MOLECULE TYPE: DNA (ix) FEATURE:
         (D) OTHER INFORMATION: oligonucleotide primer (xi) SEQUENCE DESCRIPTION: SEQ ID NO:189:

TAGATGTGGT GATGAACCTC CAGTTCCACT A                            31

(2) INFORMATION FOR SEQ ID NO:190:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: DNA (ix) FEATURE:
        (D) OTHER INFORMATION: oligonucleotide primer (xi) SEQUENCE DESCRIPTION: SEQ ID NO:190:

GGATGACCTG TTGTGGGAAG TCACTCATGG                              30

(2) INFORMATION FOR SEQ ID NO:191:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: DNA (ix) FEATURE:
        (D) OTHER INFORMATION: oligonucleotide primer (xi) SEQUENCE DESCRIPTION: SEQ ID NO:191:

CAGGAATTTG CTTCCAGGTG TGCCTG                                  26

(2) INFORMATION FOR SEQ ID NO:192:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (ii) MOLECULE TYPE: DNA (ix) FEATURE:
        (D) OTHER INFORMATION: oligonucleotide primer (xi) SEQUENCE DESCRIPTION: SEQ ID NO:192:

CAGTGTTTCA CTGGGAAATG TGACTTGCA                               29

(2) INFORMATION FOR SEQ ID NO:193:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: DNA (ix) FEATURE:
        (D) OTHER INFORMATION: oligonucleotide primer (xi) SEQUENCE DESCRIPTION: SEQ ID NO:193:

GCGCCTTGAC TGAGGACAGC ATAGACGA                                28

(2) INFORMATION FOR SEQ ID NO:194:

(i) SEQUENCE CHARACTERISTICS:
        (A) LENGTH: 30 base pairs
        (B) TYPE: nucleic acid
        (C) STRANDEDNESS: single

```
        (D) TOPOLOGY: linear (ii) MOLECULE TYPE: DNA (ix) FEATURE:
         (D) OTHER INFORMATION: oligonucleotide primer (xi) SEQUENCE DESCRIPTION: SEQ ID NO:194:

GGAGCCCTTA AAGATGCCAT TTGGCTTGGC                                         30

(2) INFORMATION FOR SEQ ID NO:195:

(i) SEQUENCE CHARACTERISTICS:
         (A) LENGTH: 31 base pairs
         (B) TYPE: nucleic acid
         (C) STRANDEDNESS: single
         (D) TOPOLOGY: linear (ii) MOLECULE TYPE: DNA (ix) FEATURE:
         (D) OTHER INFORMATION: oligonucleotide primer (xi) SEQUENCE DESCRIPTION: SEQ ID NO:195:

CCCAGCCTCA GGATGTTGTA TCTAAGTACA A                                       31

(2) INFORMATION FOR SEQ ID NO:196:

(i) SEQUENCE CHARACTERISTICS:
         (A) LENGTH: 30 base pairs
         (B) TYPE: nucleic acid
         (C) STRANDEDNESS: single
         (D) TOPOLOGY: linear (ii) MOLECULE TYPE: DNA (ix) FEATURE:
         (D) OTHER INFORMATION: oligonucleotide primer (xi) SEQUENCE DESCRIPTION: SEQ ID NO:196:

GAAAGTATCC AAGGCCATAA GGCACTGCTG                                         30

(2) INFORMATION FOR SEQ ID NO:197:

(i) SEQUENCE CHARACTERISTICS:
         (A) LENGTH: 30 base pairs
         (B) TYPE: nucleic acid
         (C) STRANDEDNESS: single
         (D) TOPOLOGY: linear (ii) MOLECULE TYPE: DNA (ix) FEATURE:
         (D) OTHER INFORMATION: oligonucleotide primer (xi) SEQUENCE DESCRIPTION: SEQ ID NO:197:

CCATTCAACC AGATCCCTGG CAATTCCCTC                                         30

(2) INFORMATION FOR SEQ ID NO:198:

(i) SEQUENCE CHARACTERISTICS:
         (A) LENGTH: 31 base pairs
         (B) TYPE: nucleic acid
         (C) STRANDEDNESS: single
         (D) TOPOLOGY: linear (ii) MOLECULE TYPE: DNA (ix) FEATURE:
         (D) OTHER INFORMATION: oligonucleotide primer (xi) SEQUENCE DESCRIPTION: SEQ ID NO:198:
```

```
TAAGGGACTC AGGATAAAGT CATCAGTCAC A                                          31

(2) INFORMATION FOR SEQ ID NO:199:

(i) SEQUENCE CHARACTERISTICS:
          (A) LENGTH: 29 base pairs
          (B) TYPE: nucleic acid
          (C) STRANDEDNESS: single
          (D) TOPOLOGY: linear (ii) MOLECULE TYPE: DNA (ix) FEATURE:
          (D) OTHER INFORMATION: oligonucleotide primer (xi) SEQUENCE DESCRIPTION: SEQ ID NO:199:

AGCGTAAGCT GATTGAGCAG AACCGGGAG                                             29

(2) INFORMATION FOR SEQ ID NO:200:

(i) SEQUENCE CHARACTERISTICS:
          (A) LENGTH: 29 base pairs
          (B) TYPE: nucleic acid
          (C) STRANDEDNESS: single
          (D) TOPOLOGY: linear (ii) MOLECULE TYPE: DNA (ix) FEATURE:
          (D) OTHER INFORMATION: oligonucleotide primer (xi) SEQUENCE DESCRIPTION: SEQ ID NO:200:

GAGGATGATC TGGTCTTCGC AAGGCAGCT                                             29

(2) INFORMATION FOR SEQ ID NO:201:

(i) SEQUENCE CHARACTERISTICS:
          (A) LENGTH: 31 base pairs
          (B) TYPE: nucleic acid
          (C) STRANDEDNESS: single
          (D) TOPOLOGY: linear (ii) MOLECULE TYPE: DNA (ix) FEATURE:
          (D) OTHER INFORMATION: oligonucleotide primer (xi) SEQUENCE DESCRIPTION: SEQ ID NO:201:

GAGCAATCAG GAGGTTATGA AGAGCATTGA G                                          31

(2) INFORMATION FOR SEQ ID NO:202:

(i) SEQUENCE CHARACTERISTICS:
          (A) LENGTH: 31 base pairs
          (B) TYPE: nucleic acid
          (C) STRANDEDNESS: single
          (D) TOPOLOGY: linear (ii) MOLECULE TYPE: DNA (ix) FEATURE:
          (D) OTHER INFORMATION: oligonucleotide primer (xi) SEQUENCE DESCRIPTION: SEQ ID NO:202:

GGGATCAGTC CTTGAATCCC TGAATACTGC A                                          31

(2) INFORMATION FOR SEQ ID NO:203:

(i) SEQUENCE CHARACTERISTICS:
          (A) LENGTH: 30 base pairs
```

```
            (B) TYPE: nucleic acid
            (C) STRANDEDNESS: single
            (D) TOPOLOGY: linear (ii) MOLECULE TYPE: DNA (ix) FEATURE:
            (D) OTHER INFORMATION: oligonucleotide primer (xi) SEQUENCE DESCRIPTION: SEQ ID NO:203:

GACTCCTGCG ACCGCATCAA AGACGAATTT                                         30

(2) INFORMATION FOR SEQ ID NO:204:

(i) SEQUENCE CHARACTERISTICS:
            (A) LENGTH: 29 base pairs
            (B) TYPE: nucleic acid
            (C) STRANDEDNESS: single
            (D) TOPOLOGY: linear (ii) MOLECULE TYPE: DNA (ix) FEATURE:
            (D) OTHER INFORMATION: oligonucleotide primer (xi) SEQUENCE DESCRIPTION: SEQ ID NO:204:

GCTGTCGGAT GATAGAGTTC AGCTCGGGA                                          29

(2) INFORMATION FOR SEQ ID NO:205:

(i) SEQUENCE CHARACTERISTICS:
            (A) LENGTH: 28 base pairs
            (B) TYPE: nucleic acid
            (C) STRANDEDNESS: single
            (D) TOPOLOGY: linear (ii) MOLECULE TYPE: DNA (ix) FEATURE:
            (D) OTHER INFORMATION: oligonucleotide primer (xi) SEQUENCE DESCRIPTION: SEQ ID NO:205:

CCTCTTGTCA TCCCACTCAG CGCCATGT                                           28

(2) INFORMATION FOR SEQ ID NO:206:

(i) SEQUENCE CHARACTERISTICS:
            (A) LENGTH: 30 base pairs
            (B) TYPE: nucleic acid
            (C) STRANDEDNESS: single
            (D) TOPOLOGY: linear (ii) MOLECULE TYPE: DNA (ix) FEATURE:
            (D) OTHER INFORMATION: oligonucleotide primer (xi) SEQUENCE DESCRIPTION: SEQ ID NO:206:

CTCCCGTGTA ATAGCGTAGT CCAACCACAT                                         30

(2) INFORMATION FOR SEQ ID NO:207:

(i) SEQUENCE CHARACTERISTICS:
            (A) LENGTH: 28 base pairs
            (B) TYPE: nucleic acid
            (C) STRANDEDNESS: single
            (D) TOPOLOGY: linear (ii) MOLECULE TYPE: DNA (ix) FEATURE:
            (D) OTHER INFORMATION: oligonucleotide primer
```

(xi) SEQUENCE DESCRIPTION: SEQ ID NO:207:

ACGTTCCACA GGGCCAGGTG AGCTTTCT                                28

(2) INFORMATION FOR SEQ ID NO:208:

(i) SEQUENCE CHARACTERISTICS:
      (A) LENGTH: 28 base pairs
      (B) TYPE: nucleic acid
      (C) STRANDEDNESS: single
      (D) TOPOLOGY: linear (ii) MOLECULE TYPE: DNA (ix) FEATURE:
      (D) OTHER INFORMATION: oligonucleotide primer (xi) SEQUENCE DESCRIPTION: SEQ ID NO:208:

AACTACATCC GGCAGCAGTC CGAGACCT                                28

(2) INFORMATION FOR SEQ ID NO:209:

(i) SEQUENCE CHARACTERISTICS:
      (A) LENGTH: 30 base pairs
      (B) TYPE: nucleic acid
      (C) STRANDEDNESS: single
      (D) TOPOLOGY: linear (ii) MOLECULE TYPE: DNA (ix) FEATURE:
      (D) OTHER INFORMATION: oligonucleotide primer (xi) SEQUENCE DESCRIPTION: SEQ ID NO:209:

TGCAGCCATG AGCAGCAATG AGTGCTTCAA                              30

(2) INFORMATION FOR SEQ ID NO:210:

(i) SEQUENCE CHARACTERISTICS:
      (A) LENGTH: 29 base pairs
      (B) TYPE: nucleic acid
      (C) STRANDEDNESS: single
      (D) TOPOLOGY: linear (ii) MOLECULE TYPE: DNA (ix) FEATURE:
      (D) OTHER INFORMATION: oligonucleotide primer (xi) SEQUENCE DESCRIPTION: SEQ ID NO:210:

CTCTACCGCA GTTATAGCAG GCATCCTCC                               29

(2) INFORMATION FOR SEQ ID NO:211:

(i) SEQUENCE CHARACTERISTICS:
      (A) LENGTH: 28 base pairs
      (B) TYPE: nucleic acid
      (C) STRANDEDNESS: single
      (D) TOPOLOGY: linear (ii) MOLECULE TYPE: DNA (ix) FEATURE:
      (D) OTHER INFORMATION: oligonucleotide primer (xi) SEQUENCE DESCRIPTION: SEQ ID NO:211:

GGACAAGTCG AGCGGCAAGC ATTACGGT                                28

(2) INFORMATION FOR SEQ ID NO:212:

(i) SEQUENCE CHARACTERISTICS:
    (A) LENGTH: 28 base pairs
    (B) TYPE: nucleic acid
    (C) STRANDEDNESS: single
    (D) TOPOLOGY: linear (ii) MOLECULE TYPE: DNA (ix) FEATURE:
    (D) OTHER INFORMATION: oligonucleotide primer (xi) SEQUENCE DESCRIPTION: SEQ ID NO:212:

CCGGAAGCAC TTCTTGAGAC GGCAGTAC                28

(2) INFORMATION FOR SEQ ID NO:213:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: DNA (ix) FEATURE:
        (D) OTHER INFORMATION: oligonucleotide primer (xi) SEQUENCE DESCRIPTION: SEQ ID NO:213:

CATCGTGCTG TTCACGTCAG ACGCCTGT                28

(2) INFORMATION FOR SEQ ID NO:214:

(i) SEQUENCE CHARACTERISTICS:
        (A) LENGTH: 31 base pairs
        (B) TYPE: nucleic acid
        (C) STRANDEDNESS: single
        (D) TOPOLOGY: linear (ii) MOLECULE TYPE: DNA (ix) FEATURE:
        (D) OTHER INFORMATION: oligonucleotide primer (xi) SEQUENCE DESCRIPTION: SEQ ID NO:214:

GTAACATATC GCGGATGAGA GTTTCGATGG G            31

(2) INFORMATION FOR SEQ ID NO:215:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: DNA (ix) FEATURE:
        (D) OTHER INFORMATION: oligonucleotide primer (xi) SEQUENCE DESCRIPTION: SEQ ID NO:215:

CTGCACAAGT TCCACGAGAA TGACAACGGG              30

(2) INFORMATION FOR SEQ ID NO:216:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (ii) MOLECULE TYPE: DNA (ix) FEATURE:
             (D) OTHER INFORMATION: oligonucleotide primer (xi) SEQUENCE DESCRIPTION: SEQ ID NO:216:

GAATCGGTGG TCACCCAATT AGCCTCGCA                              29

(2) INFORMATION FOR SEQ ID NO:217:

(i) SEQUENCE CHARACTERISTICS:
             (A) LENGTH: 28 base pairs
             (B) TYPE: nucleic acid
             (C) STRANDEDNESS: single
             (D) TOPOLOGY: linear (ii) MOLECULE TYPE: DNA (ix) FEATURE:
             (D) OTHER INFORMATION: oligonucleotide primer (xi) SEQUENCE DESCRIPTION: SEQ ID NO:217:

AGTGCGGAGC CCTCTGTGTT TGTGAGGA                               28

(2) INFORMATION FOR SEQ ID NO:218:

(i) SEQUENCE CHARACTERISTICS:
             (A) LENGTH: 30 base pairs
             (B) TYPE: nucleic acid
             (C) STRANDEDNESS: single
             (D) TOPOLOGY: linear (ii) MOLECULE TYPE: DNA (ix) FEATURE:
             (D) OTHER INFORMATION: oligonucleotide primer (xi) SEQUENCE DESCRIPTION: SEQ ID NO:218:

GCTTGTCTAA GACGCCTTGC TCACTGAGTT                             30

(2) INFORMATION FOR SEQ ID NO:219:

(i) SEQUENCE CHARACTERISTICS:
             (A) LENGTH: 30 base pairs
             (B) TYPE: nucleic acid
             (C) STRANDEDNESS: single
             (D) TOPOLOGY: linear (ii) MOLECULE TYPE: DNA (ix) FEATURE:
             (D) OTHER INFORMATION: oligonucleotide primer (xi) SEQUENCE DESCRIPTION: SEQ ID NO:219:

TGCAGAAGTT CGCGTTTGCA CTGTACTTGC                             30

(2) INFORMATION FOR SEQ ID NO:220:

(i) SEQUENCE CHARACTERISTICS:
             (A) LENGTH: 30 base pairs
             (B) TYPE: nucleic acid
             (C) STRANDEDNESS: single
             (D) TOPOLOGY: linear (ii) MOLECULE TYPE: DNA (ix) FEATURE:
             (D) OTHER INFORMATION: oligonucleotide primer (xi) SEQUENCE DESCRIPTION: SEQ ID NO:220:

TCAGTATTGC CATCCAAATG CGCCATGCTG                             30

(2) INFORMATION FOR SEQ ID NO:221:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: DNA (ix) FEATURE:
        (D) OTHER INFORMATION: oligonucleotide primer (xi) SEQUENCE DESCRIPTION: SEQ ID NO:221:

GATTCAGAAG TGCCTAACTG CCAGTCATCC                                    30

(2) INFORMATION FOR SEQ ID NO:222:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: DNA (ix) FEATURE:
        (D) OTHER INFORMATION: oligonucleotide primer (xi) SEQUENCE DESCRIPTION: SEQ ID NO:222:

GGTTCTATCA GCTTGAACTC CATGCCTCGA                                    30

(2) INFORMATION FOR SEQ ID NO:223:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: DNA (ix) FEATURE:
        (D) OTHER INFORMATION: oligonucleotide primer (xi) SEQUENCE DESCRIPTION: SEQ ID NO:223:

AGACCGAGGT GTATCACCAA GGTCTCAAGA                                    30

(2) INFORMATION FOR SEQ ID NO:224:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: DNA (ix) FEATURE:
        (D) OTHER INFORMATION: oligonucleotide primer (xi) SEQUENCE DESCRIPTION: SEQ ID NO:224:

TGTGATCTGA CACCCTGAGT AGTTCACACC                                    30

(2) INFORMATION FOR SEQ ID NO:225:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: DNA (ix) FEATURE:
                (D) OTHER INFORMATION: oligonucleotide primer (xi) SEQUENCE DESCRIPTION: SEQ ID NO:225:

CATCCAGACC ATCGCGCTCA TCACGTAC                                28

(2) INFORMATION FOR SEQ ID NO:226:

(i) SEQUENCE CHARACTERISTICS:
                (A) LENGTH: 30 base pairs
                (B) TYPE: nucleic acid
                (C) STRANDEDNESS: single
                (D) TOPOLOGY: linear (ii) MOLECULE TYPE: DNA (ix) FEATURE:
                (D) OTHER INFORMATION: oligonucleotide primer (xi) SEQUENCE DESCRIPTION: SEQ ID NO:226:

CAACGGATCT TGGCGAGGAT GTGCTTGTCT                              30

(2) INFORMATION FOR SEQ ID NO:227:

(i) SEQUENCE CHARACTERISTICS:
                (A) LENGTH: 30 base pairs
                (B) TYPE: nucleic acid
                (C) STRANDEDNESS: single
                (D) TOPOLOGY: linear (ii) MOLECULE TYPE: DNA (ix) FEATURE:
                (D) OTHER INFORMATION: oligonucleotide primer (xi) SEQUENCE DESCRIPTION: SEQ ID NO:227:

AAATTCCAGT AAGGTGGACA GCACCCGAAG                              30

(2) INFORMATION FOR SEQ ID NO:228:

(i) SEQUENCE CHARACTERISTICS:
                (A) LENGTH: 31 base pairs
                (B) TYPE: nucleic acid
                (C) STRANDEDNESS: single
                (D) TOPOLOGY: linear (ii) MOLECULE TYPE: DNA (ix) FEATURE:
                (D) OTHER INFORMATION: oligonucleotide primer (xi) SEQUENCE DESCRIPTION: SEQ ID NO:228:

TGACCAACCA GTGTGATCCC TAAACTCATC A                            31

(2) INFORMATION FOR SEQ ID NO:229:

(i) SEQUENCE CHARACTERISTICS:
                (A) LENGTH: 29 base pairs
                (B) TYPE: nucleic acid
                (C) STRANDEDNESS: single
                (D) TOPOLOGY: linear (ii) MOLECULE TYPE: DNA (ix) FEATURE:
                (D) OTHER INFORMATION: oligonucleotide primer (xi) SEQUENCE DESCRIPTION: SEQ ID NO:229:

CCTATTCCCG AAGCCGTTAC CTCGAATGC                               29

(2) INFORMATION FOR SEQ ID NO:230:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: DNA (ix) FEATURE:
        (D) OTHER INFORMATION: oligonucleotide primer (xi) SEQUENCE DESCRIPTION: SEQ ID NO:230:

GAGTGCCGGT GGCTACCAGA CATTGATTCA                          30

(2) INFORMATION FOR SEQ ID NO:231:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: DNA (ix) FEATURE:
        (D) OTHER INFORMATION: oligonucleotide primer (xi) SEQUENCE DESCRIPTION: SEQ ID NO:231:

ACCAGGAGTC CTACCCTCTG TCAGTGTC                            28

(2) INFORMATION FOR SEQ ID NO:232:

(i) SEQUENCE CHARACTERISTICS:
        (A) LENGTH: 31 base pairs
        (B) TYPE: nucleic acid
        (C) STRANDEDNESS: single
        (D) TOPOLOGY: linear (ii) MOLECULE TYPE: DNA (ix) FEATURE:
        (D) OTHER INFORMATION: oligonucleotide primer (xi) SEQUENCE DESCRIPTION: SEQ ID NO:232:

GATAGACGTA ATCCCAAAGC AGTCTACAGT C                       31

(2) INFORMATION FOR SEQ ID NO:233:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: DNA (ix) FEATURE:
        (D) OTHER INFORMATION: oligonucleotide primer (xi) SEQUENCE DESCRIPTION: SEQ ID NO:233:

AGTGTGGCAG GTGATCCGGT TCCTAATATG                          30

(2) INFORMATION FOR SEQ ID NO:234:

(i) SEQUENCE CHARACTERISTICS:
        (A) LENGTH: 30 base pairs
        (B) TYPE: nucleic acid
        (C) STRANDEDNESS: single (D) TOPOLOGY: linear (ii) MOLECULE TYPE: DNA (ix) FEATURE:
            (D) OTHER INFORMATION: oligonucleotide primer (xi) SEQUENCE DESCRIPTION: SEQ ID NO:234:

GCCGTGGTAC TCCGTGTGAT TGGTAACATG                                        30

(2) INFORMATION FOR SEQ ID NO:235:

(i) SEQUENCE CHARACTERISTICS:
            (A) LENGTH: 31 base pairs
            (B) TYPE: nucleic acid
            (C) STRANDEDNESS: single
            (D) TOPOLOGY: linear (ii) MOLECULE TYPE: DNA (ix) FEATURE:
            (D) OTHER INFORMATION: oligonucleotide primer (xi) SEQUENCE DESCRIPTION: SEQ ID NO:235:

GCTATCAACA CCCTGAATGG ATTGAGACTT C                                      31

(2) INFORMATION FOR SEQ ID NO:236:

(i) SEQUENCE CHARACTERISTICS:
            (A) LENGTH: 31 base pairs
            (B) TYPE: nucleic acid
            (C) STRANDEDNESS: single
            (D) TOPOLOGY: linear (ii) MOLECULE TYPE: DNA (ix) FEATURE:
            (D) OTHER INFORMATION: oligonucleotide primer (xi) SEQUENCE DESCRIPTION: SEQ ID NO:236:

TCGCTTGTCA AATCGAATAA ACCCTACACC C                                      31

(2) INFORMATION FOR SEQ ID NO:237:

(i) SEQUENCE CHARACTERISTICS:
            (A) LENGTH: 31 base pairs
            (B) TYPE: nucleic acid
            (C) STRANDEDNESS: single
            (D) TOPOLOGY: linear (ii) MOLECULE TYPE: DNA (ix) FEATURE:
            (D) OTHER INFORMATION: oligonucleotide primer (xi) SEQUENCE DESCRIPTION: SEQ ID NO:237:

GTGACAAGCG GTGTAACAAG AAACGGTTGT G                                      31

(2) INFORMATION FOR SEQ ID NO:238:

(i) SEQUENCE CHARACTERISTICS:
            (A) LENGTH: 31 base pairs
            (B) TYPE: nucleic acid
            (C) STRANDEDNESS: single
            (D) TOPOLOGY: linear (ii) MOLECULE TYPE: DNA (ix) FEATURE:
            (D) OTHER INFORMATION: oligonucleotide primer (xi) SEQUENCE DESCRIPTION: SEQ ID NO:238:

```
ACCAGAATGA TATACTGGAT GGTCACACTC A                                       31

(2) INFORMATION FOR SEQ ID NO:239:

(i) SEQUENCE CHARACTERISTICS:
          (A) LENGTH: 31 base pairs
          (B) TYPE: nucleic acid
          (C) STRANDEDNESS: single
          (D) TOPOLOGY: linear (ii) MOLECULE TYPE: DNA (ix) FEATURE:
          (D) OTHER INFORMATION: oligonucleotide primer (xi) SEQUENCE DESCRIPTION: SEQ ID NO:239:

CATAGATTGC AGCATCTCCA GTGACAAGTT T                                       31

(2) INFORMATION FOR SEQ ID NO:240:

(i) SEQUENCE CHARACTERISTICS:
          (A) LENGTH: 29 base pairs
          (B) TYPE: nucleic acid
          (C) STRANDEDNESS: single
          (D) TOPOLOGY: linear (ii) MOLECULE TYPE: DNA (ix) FEATURE:
          (D) OTHER INFORMATION: oligonucleotide primer (xi) SEQUENCE DESCRIPTION: SEQ ID NO:240:

CAGGAACTGC CCAGTTGCTA AGGCCACTT                                          29

(2) INFORMATION FOR SEQ ID NO:241:

(i) SEQUENCE CHARACTERISTICS:
          (A) LENGTH: 29 base pairs
          (B) TYPE: nucleic acid
          (C) STRANDEDNESS: single
          (D) TOPOLOGY: linear (ii) MOLECULE TYPE: DNA (ix) FEATURE:
          (D) OTHER INFORMATION: oligonucleotide primer (xi) SEQUENCE DESCRIPTION: SEQ ID NO:241:

ATGAACTACC TGAACGACAA CCTCGCTTC                                          29

(2) INFORMATION FOR SEQ ID NO:242:

(i) SEQUENCE CHARACTERISTICS:
          (A) LENGTH: 30 base pairs
          (B) TYPE: nucleic acid
          (C) STRANDEDNESS: single
          (D) TOPOLOGY: linear (ii) MOLECULE TYPE: DNA (ix) FEATURE:
          (D) OTHER INFORMATION: oligonucleotide primer (xi) SEQUENCE DESCRIPTION: SEQ ID NO:242:

CGTAACCATT CTTCAGTTAG GTCTTCGGTA                                         30

(2) INFORMATION FOR SEQ ID NO:243:

(i) SEQUENCE CHARACTERISTICS:
          (A) LENGTH: 27 base pairs
```

```
        (B) TYPE: nucleic acid
        (C) STRANDEDNESS: single
        (D) TOPOLOGY: linear (ii) MOLECULE TYPE: DNA (ix) FEATURE:
        (D) OTHER INFORMATION: oligonucleotide primer (xi) SEQUENCE DESCRIPTION: SEQ ID NO:243:

AATGGCTGGC TGTGGATGGG TTGGTCA                                          27

(2) INFORMATION FOR SEQ ID NO:244:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (ii) MOLECULE TYPE: DNA (ix) FEATURE:
        (D) OTHER INFORMATION: oligonucleotide primer (xi) SEQUENCE DESCRIPTION: SEQ ID NO:244:

GATCATGGCA ACGTAAGCAG TGTAGTCTG                                        29

(2) INFORMATION FOR SEQ ID NO:245:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: DNA (ix) FEATURE:
        (D) OTHER INFORMATION: oligonucleotide primer (xi) SEQUENCE DESCRIPTION: SEQ ID NO:245:

TCCAGCTCTG TCATCACTCA GGCACCT                                          27

(2) INFORMATION FOR SEQ ID NO:246:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: DNA (ix) FEATURE:
        (D) OTHER INFORMATION: oligonucleotide primer (xi) SEQUENCE DESCRIPTION: SEQ ID NO:246:

TGGTGAGTCA ATGCAGCCTT CAACCTCATT                                       30

(2) INFORMATION FOR SEQ ID NO:247:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: DNA (ix) FEATURE:
        (D) OTHER INFORMATION: oligonucleotide primer
```

(xi) SEQUENCE DESCRIPTION: SEQ ID NO:247:

CTTCAAGCAT TGGATAATCC CGAATATCAC                                            30

(2) INFORMATION FOR SEQ ID NO:248:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: DNA (ix) FEATURE:
        (D) OTHER INFORMATION: oligonucleotide primer (xi) SEQUENCE DESCRIPTION: SEQ ID NO:248:

AGCTTACACC ACAGTATTCC GGTGTCTGTA                                            30

(2) INFORMATION FOR SEQ ID NO:249:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: DNA (ix) FEATURE:
        (D) OTHER INFORMATION: oligonucleotide primer (xi) SEQUENCE DESCRIPTION: SEQ ID NO:249:

CTTCAGTTGT GCCATCTGAG CGTGCTCG                                              28

(2) INFORMATION FOR SEQ ID NO:250:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (ii) MOLECULE TYPE: DNA (ix) FEATURE:
        (D) OTHER INFORMATION: oligonucleotide primer (xi) SEQUENCE DESCRIPTION: SEQ ID NO:250:

CACAGTCTGT CTTTGCTGAT AAGGGTGAC                                             29

(2) INFORMATION FOR SEQ ID NO:251:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (ii) MOLECULE TYPE: DNA (ix) FEATURE:
        (D) OTHER INFORMATION: oligonucleotide primer (xi) SEQUENCE DESCRIPTION: SEQ ID NO:251:

CTCTCCAAGT CTCAGTGGCT TCATCTGTC                                             29

(2) INFORMATION FOR SEQ ID NO:252:

```
    (i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: DNA (ix) FEATURE:
        (D) OTHER INFORMATION: oligonucleotide primer (xi) SEQUENCE DESCRIPTION: SEQ ID NO:252:

AGCAGTAAGA GTCCGTGCTT TCACATTCCT                                      30

(2) INFORMATION FOR SEQ ID NO:253:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: DNA (ix) FEATURE:
        (D) OTHER INFORMATION: oligonucleotide primer (xi) SEQUENCE DESCRIPTION: SEQ ID NO:253:

CGCAGGCCAT TTATGCCAGT GTTCTTCC                                        28

(2) INFORMATION FOR SEQ ID NO:254:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: DNA (ix) FEATURE:
        (D) OTHER INFORMATION: oligonucleotide primer (xi) SEQUENCE DESCRIPTION: SEQ ID NO:254:

TACAAGTGCA TCCCTTAGAA GCGACAGATA                                      30

(2) INFORMATION FOR SEQ ID NO:255:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: DNA (ix) FEATURE:
        (D) OTHER INFORMATION: oligonucleotide primer (xi) SEQUENCE DESCRIPTION: SEQ ID NO:255:

GTGTTCGACC AGGGCCAGTT TGCCAA                                          26

(2) INFORMATION FOR SEQ ID NO:256:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: DNA
```

```
        (ix) FEATURE:
             (D) OTHER INFORMATION: oligonucleotide primer (xi) SEQUENCE DESCRIPTION: SEQ ID NO:256:

CGCTGTCCTG GCGGATCTTT ATGTCTTC                                          28

(2) INFORMATION FOR SEQ ID NO:257:

(i) SEQUENCE CHARACTERISTICS:
             (A) LENGTH: 30 base pairs
             (B) TYPE: nucleic acid
             (C) STRANDEDNESS: single
             (D) TOPOLOGY: linear (ii) MOLECULE TYPE: DNA (ix) FEATURE:
             (D) OTHER INFORMATION: oligonucleotide primer (xi) SEQUENCE DESCRIPTION: SEQ ID NO:257:

TTAACAGTGG GTGCCAACTC ATGCTAACGC                                        30

(2) INFORMATION FOR SEQ ID NO:258:

(i) SEQUENCE CHARACTERISTICS:
             (A) LENGTH: 31 base pairs
             (B) TYPE: nucleic acid
             (C) STRANDEDNESS: single
             (D) TOPOLOGY: linear (ii) MOLECULE TYPE: DNA (ix) FEATURE:
             (D) OTHER INFORMATION: oligonucleotide primer (xi) SEQUENCE DESCRIPTION: SEQ ID NO:258:

GAGATCGAAT GTTAGGTCCA TGCAGTTCTT G                                      31

(2) INFORMATION FOR SEQ ID NO:259:

(i) SEQUENCE CHARACTERISTICS:
             (A) LENGTH: 30 base pairs
             (B) TYPE: nucleic acid
             (C) STRANDEDNESS: single
             (D) TOPOLOGY: linear (ii) MOLECULE TYPE: DNA (ix) FEATURE:
             (D) OTHER INFORMATION: oligonucleotide primer (xi) SEQUENCE DESCRIPTION: SEQ ID NO:259:

ATATGCCACC GATTGCAGGA CACAAGCACA                                        30

(2) INFORMATION FOR SEQ ID NO:260:

(i) SEQUENCE CHARACTERISTICS:
             (A) LENGTH: 31 base pairs
             (B) TYPE: nucleic acid
             (C) STRANDEDNESS: single
             (D) TOPOLOGY: linear (ii) MOLECULE TYPE: DNA (ix) FEATURE:
             (D) OTHER INFORMATION: oligonucleotide primer (xi) SEQUENCE DESCRIPTION: SEQ ID NO:260:

GTCACTAACC TAAGTTTCCA AATTGGCTTG C                                      31
```

(2) INFORMATION FOR SEQ ID NO:261:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: DNA (ix) FEATURE:
        (D) OTHER INFORMATION: oligonucleotide primer (xi) SEQUENCE DESCRIPTION: SEQ ID NO:261:

TCTAAGGACC GTCCTGCGAG ATCGCCTT                          28

(2) INFORMATION FOR SEQ ID NO:262:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: DNA (ix) FEATURE:
        (D) OTHER INFORMATION: oligonucleotide primer (xi) SEQUENCE DESCRIPTION: SEQ ID NO:262:

AAACGGGCAT GAGGCATAGC GTCCCTCA                          28

(2) INFORMATION FOR SEQ ID NO:263:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: DNA (ix) FEATURE:
        (D) OTHER INFORMATION: oligonucleotide primer (xi) SEQUENCE DESCRIPTION: SEQ ID NO:263:

CAGCCTCGGC CTGATTTCCC GTAAAGGT                          28

(2) INFORMATION FOR SEQ ID NO:264:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: DNA (ix) FEATURE:
        (D) OTHER INFORMATION: oligonucleotide primer (xi) SEQUENCE DESCRIPTION: SEQ ID NO:264:

CTGGCAACCA GCACAGGGAC TTAGGTGA                          28

(2) INFORMATION FOR SEQ ID NO:265:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: DNA (ix) FEATURE:
             (D) OTHER INFORMATION: oligonucleotide primer (xi) SEQUENCE DESCRIPTION: SEQ ID NO:265:

TCCCAGAGGT GAAAGTTCAC TCGGGCAG                                28

(2) INFORMATION FOR SEQ ID NO:266:

(i) SEQUENCE CHARACTERISTICS:
            (A) LENGTH: 31 base pairs
            (B) TYPE: nucleic acid
            (C) STRANDEDNESS: single
            (D) TOPOLOGY: linear (ii) MOLECULE TYPE: DNA (ix) FEATURE:
             (D) OTHER INFORMATION: oligonucleotide primer (xi) SEQUENCE DESCRIPTION: SEQ ID NO:266:

GAGCCATGCC TTATTCCAAT GACTGTAAAC A                            31

(2) INFORMATION FOR SEQ ID NO:267:

(i) SEQUENCE CHARACTERISTICS:
            (A) LENGTH: 27 base pairs
            (B) TYPE: nucleic acid
            (C) STRANDEDNESS: single
            (D) TOPOLOGY: linear (ii) MOLECULE TYPE: DNA (ix) FEATURE:
             (D) OTHER INFORMATION: oligonucleotide primer (xi) SEQUENCE DESCRIPTION: SEQ ID NO:267:

TATGGCTGCC TCTTAGACCA TGTCCGG                                 27

(2) INFORMATION FOR SEQ ID NO:268:

(i) SEQUENCE CHARACTERISTICS:
            (A) LENGTH: 27 base pairs
            (B) TYPE: nucleic acid
            (C) STRANDEDNESS: single
            (D) TOPOLOGY: linear (ii) MOLECULE TYPE: DNA (ix) FEATURE:
             (D) OTHER INFORMATION: oligonucleotide primer (xi) SEQUENCE DESCRIPTION: SEQ ID NO:268:

TTGGGACTCT TGACCAGCAC GTTCCGA                                 27

(2) INFORMATION FOR SEQ ID NO:269:

(i) SEQUENCE CHARACTERISTICS:
            (A) LENGTH: 30 base pairs
            (B) TYPE: nucleic acid
            (C) STRANDEDNESS: single
            (D) TOPOLOGY: linear (ii) MOLECULE TYPE: DNA (ix) FEATURE:
             (D) OTHER INFORMATION: oligonucleotide primer (xi) SEQUENCE DESCRIPTION: SEQ ID NO:269:

GCCGATGTCC ATTGTTGCCA TCTGCTATGG                              30

(2) INFORMATION FOR SEQ ID NO:270:

(i) SEQUENCE CHARACTERISTICS:
        (A) LENGTH: 31 base pairs
        (B) TYPE: nucleic acid
        (C) STRANDEDNESS: single
        (D) TOPOLOGY: linear (ii) MOLECULE TYPE: DNA (ix) FEATURE:
        (D) OTHER INFORMATION: oligonucleotide primer (xi) SEQUENCE DESCRIPTION: SEQ ID NO:270:

GTAGATGAAG CTGGAACTGG CATTAGGGTA G                              31

(2) INFORMATION FOR SEQ ID NO:271:

(i) SEQUENCE CHARACTERISTICS:
        (A) LENGTH: 32 base pairs
        (B) TYPE: nucleic acid
        (C) STRANDEDNESS: single
        (D) TOPOLOGY: linear (ii) MOLECULE TYPE: DNA (ix) FEATURE:
        (D) OTHER INFORMATION: oligonucleotide primer (xi) SEQUENCE DESCRIPTION: SEQ ID NO:271:

AGCTTCTAGG CATCTGAAAC TTGCTTCATC TC                            32

(2) INFORMATION FOR SEQ ID NO:272:

(i) SEQUENCE CHARACTERISTICS:
        (A) LENGTH: 32 base pairs
        (B) TYPE: nucleic acid
        (C) STRANDEDNESS: single
        (D) TOPOLOGY: linear (ii) MOLECULE TYPE: DNA (ix) FEATURE:
        (D) OTHER INFORMATION: oligonucleotide primer (xi) SEQUENCE DESCRIPTION: SEQ ID NO:272:

ATTAGTCGCT GGTTGAAAGC AGCAATGCCA TT                            32

(2) INFORMATION FOR SEQ ID NO:273:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: DNA (ix) FEATURE:
        (D) OTHER INFORMATION: oligonucleotide primer (xi) SEQUENCE DESCRIPTION: SEQ ID NO:273:

CCTTCTGGGC AGTTGATGCC GTGGCAAA                                  28

(2) INFORMATION FOR SEQ ID NO:274:

(i) SEQUENCE CHARACTERISTICS:
        (A) LENGTH: 28 base pairs
        (B) TYPE: nucleic acid
        (C) STRANDEDNESS: single (D) TOPOLOGY: linear (ii) MOLECULE TYPE: DNA (ix) FEATURE:
         (D) OTHER INFORMATION: oligonucleotide primer (xi) SEQUENCE DESCRIPTION: SEQ ID NO:274:

AGGATGACTG TGGTCTTGAG GGCCTTGC                                         28

(2) INFORMATION FOR SEQ ID NO:275:

(i) SEQUENCE CHARACTERISTICS:
         (A) LENGTH: 32 base pairs
         (B) TYPE: nucleic acid
         (C) STRANDEDNESS: single
         (D) TOPOLOGY: linear (ii) MOLECULE TYPE: DNA (ix) FEATURE:
         (D) OTHER INFORMATION: oligonucleotide primer (xi) SEQUENCE DESCRIPTION: SEQ ID NO:275:

GAAGGGCTTG GACTCAAGCA AGATTTCAGA TT                                    32

(2) INFORMATION FOR SEQ ID NO:276:

(i) SEQUENCE CHARACTERISTICS:
         (A) LENGTH: 32 base pairs
         (B) TYPE: nucleic acid
         (C) STRANDEDNESS: single
         (D) TOPOLOGY: linear (ii) MOLECULE TYPE: DNA (ix) FEATURE:
         (D) OTHER INFORMATION: oligonucleotide primer (xi) SEQUENCE DESCRIPTION: SEQ ID NO:276:

GTGCTTAGCC CACTCCCTGA ATTGTTTGAT TT                                    32

(2) INFORMATION FOR SEQ ID NO:277:

(i) SEQUENCE CHARACTERISTICS:
         (A) LENGTH: 26 base pairs
         (B) TYPE: nucleic acid
         (C) STRANDEDNESS: single
         (D) TOPOLOGY: linear (ii) MOLECULE TYPE: DNA (ix) FEATURE:
         (D) OTHER INFORMATION: oligonucleotide primer (xi) SEQUENCE DESCRIPTION: SEQ ID NO:277:

ACCACGACCT CGTCCTGATC CGGCTG                                           26

(2) INFORMATION FOR SEQ ID NO:278:

(i) SEQUENCE CHARACTERISTICS:
         (A) LENGTH: 27 base pairs
         (B) TYPE: nucleic acid
         (C) STRANDEDNESS: single
         (D) TOPOLOGY: linear (ii) MOLECULE TYPE: DNA (ix) FEATURE:
         (D) OTHER INFORMATION: oligonucleotide primer (xi) SEQUENCE DESCRIPTION: SEQ ID NO:278:

```
CCGTAGAGGT AAGCCACGCC GTTCTTC                                            27
```

(2) INFORMATION FOR SEQ ID NO:279:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: DNA (ix) FEATURE:
        (D) OTHER INFORMATION: oligonucleotide primer (xi) SEQUENCE DESCRIPTION: SEQ ID NO:279:

```
TGGTGTTCGC CAAGATGAAG GGCTACCC                                           28
```

(2) INFORMATION FOR SEQ ID NO:280:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: DNA (ix) FEATURE:
        (D) OTHER INFORMATION: oligonucleotide primer (xi) SEQUENCE DESCRIPTION: SEQ ID NO:280:

```
GGAGGACTGA TAGCCGGAAG CCTTGACA                                           28
```

(2) INFORMATION FOR SEQ ID NO:281:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: DNA (ix) FEATURE:
        (D) OTHER INFORMATION: oligonucleotide primer (xi) SEQUENCE DESCRIPTION: SEQ ID NO:281:

```
GCCGGAGGGC CAAGCGTAGC CCTAAG                                             26
```

(2) INFORMATION FOR SEQ ID NO:282:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: DNA (ix) FEATURE:
        (D) OTHER INFORMATION: oligonucleotide primer (xi) SEQUENCE DESCRIPTION: SEQ ID NO:282:

```
CTGCCTGATC TCAGCGGCAC CCACATC                                            27
```

(2) INFORMATION FOR SEQ ID NO:283:

(i) SEQUENCE CHARACTERISTICS:
        (A) LENGTH: 29 base pairs (B) TYPE: nucleic acid
        (C) STRANDEDNESS: single
        (D) TOPOLOGY: linear (ii) MOLECULE TYPE: DNA (ix) FEATURE:
        (D) OTHER INFORMATION: oligonucleotide primer (xi) SEQUENCE DESCRIPTION: SEQ ID NO:283:

ACGCTGCTGC TGGTATGTTG TATCTCGAG                                            29

(2) INFORMATION FOR SEQ ID NO:284:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: DNA (ix) FEATURE:
        (D) OTHER INFORMATION: oligonucleotide primer (xi) SEQUENCE DESCRIPTION: SEQ ID NO:284:

TGCTGATTTG TCATTCCAGG GTACGGACAA                                           30

(2) INFORMATION FOR SEQ ID NO:285:

(i) SEQUENCE CHARACTERISTICS:
        (A) LENGTH: 32 base pairs
        (B) TYPE: nucleic acid
        (C) STRANDEDNESS: single
        (D) TOPOLOGY: linear (ii) MOLECULE TYPE: DNA (ix) FEATURE:
        (D) OTHER INFORMATION: oligonucleotide primer (xi) SEQUENCE DESCRIPTION: SEQ ID NO:285:

TTCCTCGCAA CTTTGTGGTA GATTACTATG AG                                        32

(2) INFORMATION FOR SEQ ID NO:286:

(i) SEQUENCE CHARACTERISTICS:
        (A) LENGTH: 32 base pairs
        (B) TYPE: nucleic acid
        (C) STRANDEDNESS: single
        (D) TOPOLOGY: linear (ii) MOLECULE TYPE: DNA (ix) FEATURE:
        (D) OTHER INFORMATION: oligonucleotide primer (xi) SEQUENCE DESCRIPTION: SEQ ID NO:286:

CCCATAGGAC ACTTATCCTT TGGCTAAACT AA                                        32

(2) INFORMATION FOR SEQ ID NO:287:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: DNA (ix) FEATURE:
        (D) OTHER INFORMATION: oligonucleotide primer (xi) SEQUENCE DESCRIPTION: SEQ ID NO:287:

GGCCTTGTTT GCAGGAAGCC GACTGTAAAG                30

(2) INFORMATION FOR SEQ ID NO:288:

(i) SEQUENCE CHARACTERISTICS:
        (A) LENGTH: 31 base pairs
        (B) TYPE: nucleic acid
        (C) STRANDEDNESS: single
        (D) TOPOLOGY: linear (ii) MOLECULE TYPE: DNA (ix) FEATURE:
        (D) OTHER INFORMATION: oligonucleotide primer (xi) SEQUENCE DESCRIPTION: SEQ ID NO:288:

GGGATAACAT CTCCACACTC ACAGTAAGCT C              31

(2) INFORMATION FOR SEQ ID NO:289:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: DNA (ix) FEATURE:
        (D) OTHER INFORMATION: oligonucleotide primer (xi) SEQUENCE DESCRIPTION: SEQ ID NO:289:

TGCGGGCAAG AGTCCAGAGG ACCTTGAG                  28

(2) INFORMATION FOR SEQ ID NO:290:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: DNA (ix) FEATURE:
        (D) OTHER INFORMATION: oligonucleotide primer (xi) SEQUENCE DESCRIPTION: SEQ ID NO:290:

TTGATGAGCC CATTGGTAGA AGCGTCGTGA                30

(2) INFORMATION FOR SEQ ID NO:291:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: DNA (ix) FEATURE:
        (D) OTHER INFORMATION: oligonucleotide primer (xi) SEQUENCE DESCRIPTION: SEQ ID NO:291:

TTAGCTTAGG AGGCACACCC TACTGCGG                  28

(2) INFORMATION FOR SEQ ID NO:292:

(i) SEQUENCE CHARACTERISTICS:
           (A) LENGTH: 28 base pairs
           (B) TYPE: nucleic acid
           (C) STRANDEDNESS: single
           (D) TOPOLOGY: linear (ii) MOLECULE TYPE: DNA (ix) FEATURE:
           (D) OTHER INFORMATION: oligonucleotide primer (xi) SEQUENCE DESCRIPTION: SEQ ID NO:292:

GCAGTTGTCA AGGGTCTCCC ATGCCAGT                                               28

(2) INFORMATION FOR SEQ ID NO:293:

(i) SEQUENCE CHARACTERISTICS:
           (A) LENGTH: 32 base pairs
           (B) TYPE: nucleic acid
           (C) STRANDEDNESS: single
           (D) TOPOLOGY: linear (ii) MOLECULE TYPE: DNA (ix) FEATURE:
           (D) OTHER INFORMATION: oligonucleotide primer (xi) SEQUENCE DESCRIPTION: SEQ ID NO:293:

CAGCTTGAGA ATTGCCCTCA GTGAACATCT TA                                          32

(2) INFORMATION FOR SEQ ID NO:294:

(i) SEQUENCE CHARACTERISTICS:
           (A) LENGTH: 32 base pairs
           (B) TYPE: nucleic acid
           (C) STRANDEDNESS: single
           (D) TOPOLOGY: linear (ii) MOLECULE TYPE: DNA (ix) FEATURE:
           (D) OTHER INFORMATION: oligonucleotide primer (xi) SEQUENCE DESCRIPTION: SEQ ID NO:294:

GCCAAGTTAA TACCGATGTA ATCCATGAGC AG                                          32

(2) INFORMATION FOR SEQ ID NO:295:

(i) SEQUENCE CHARACTERISTICS:
           (A) LENGTH: 28 base pairs
           (B) TYPE: nucleic acid
           (C) STRANDEDNESS: single
           (D) TOPOLOGY: linear (ii) MOLECULE TYPE: DNA (ix) FEATURE:
           (D) OTHER INFORMATION: oligonucleotide primer (xi) SEQUENCE DESCRIPTION: SEQ ID NO:295:

CCCGTGCCAA GGACCCATCG AGATCAAG                                               28

(2) INFORMATION FOR SEQ ID NO:296:

(i) SEQUENCE CHARACTERISTICS:
           (A) LENGTH: 30 base pairs
           (B) TYPE: nucleic acid
           (C) STRANDEDNESS: single
           (D) TOPOLOGY: linear (ii) MOLECULE TYPE: DNA

```
        (ix) FEATURE:
              (D) OTHER INFORMATION: oligonucleotide primer (xi) SEQUENCE DESCRIPTION: SEQ ID NO:296:

CACATAGACT CAGCACAGTG ATTCCCACGG                                    30

(2) INFORMATION FOR SEQ ID NO:297:

(i) SEQUENCE CHARACTERISTICS:
              (A) LENGTH: 29 base pairs
              (B) TYPE: nucleic acid
              (C) STRANDEDNESS: single
              (D) TOPOLOGY: linear (ii) MOLECULE TYPE: DNA (ix) FEATURE:
              (D) OTHER INFORMATION: oligonucleotide primer (xi) SEQUENCE DESCRIPTION: SEQ ID NO:297:

AAGACCCAGA GGATGCTGAG CGGATTCTG                                     29

(2) INFORMATION FOR SEQ ID NO:298:

(i) SEQUENCE CHARACTERISTICS:
              (A) LENGTH: 29 base pairs
              (B) TYPE: nucleic acid
              (C) STRANDEDNESS: single
              (D) TOPOLOGY: linear (ii) MOLECULE TYPE: DNA (ix) FEATURE:
              (D) OTHER INFORMATION: oligonucleotide primer (xi) SEQUENCE DESCRIPTION: SEQ ID NO:298:

GTAATGCTAC AGTGTGCTCT AGGGCAGGG                                     29

(2) INFORMATION FOR SEQ ID NO:299:

(i) SEQUENCE CHARACTERISTICS:
              (A) LENGTH: 32 base pairs
              (B) TYPE: nucleic acid
              (C) STRANDEDNESS: single
              (D) TOPOLOGY: linear (ii) MOLECULE TYPE: DNA (ix) FEATURE:
              (D) OTHER INFORMATION: oligonucleotide primer (xi) SEQUENCE DESCRIPTION: SEQ ID NO:299:

GGGAGTCTTC ATAATACAGC ACAGCGGTTA AG                                 32

(2) INFORMATION FOR SEQ ID NO:300:

(i) SEQUENCE CHARACTERISTICS:
              (A) LENGTH: 32 base pairs
              (B) TYPE: nucleic acid
              (C) STRANDEDNESS: single
              (D) TOPOLOGY: linear (ii) MOLECULE TYPE: DNA (ix) FEATURE:
              (D) OTHER INFORMATION: oligonucleotide primer (xi) SEQUENCE DESCRIPTION: SEQ ID NO:300:

CATAGGAACC CAGAGTCAAC CATAACTGAA TG                                 32
```

(2) INFORMATION FOR SEQ ID NO:301:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: DNA (ix) FEATURE:
        (D) OTHER INFORMATION: oligonucleotide primer (xi) SEQUENCE DESCRIPTION: SEQ ID NO:301:

CGGGCTTGGT GATCTGCCTC GTGGTG                                  26

(2) INFORMATION FOR SEQ ID NO:302:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: DNA (ix) FEATURE:
        (D) OTHER INFORMATION: oligonucleotide primer (xi) SEQUENCE DESCRIPTION: SEQ ID NO:302:

GTCAGGCGCT GGGAGACAAT GGTACAAC                              28

(2) INFORMATION FOR SEQ ID NO:303:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: DNA (ix) FEATURE:
        (D) OTHER INFORMATION: oligonucleotide primer (xi) SEQUENCE DESCRIPTION: SEQ ID NO:303:

CGGCTCAGGA CCTCACAGAC TACGGG                                  26

(2) INFORMATION FOR SEQ ID NO:304:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: DNA (ix) FEATURE:
        (D) OTHER INFORMATION: oligonucleotide primer (xi) SEQUENCE DESCRIPTION: SEQ ID NO:304:

CCACTGCGCC CAGCCCAACA ACAATTCT                              28

(2) INFORMATION FOR SEQ ID NO:305:

(i) SEQUENCE CHARACTERISTICS:
        (A) LENGTH: 32 base pairs
        (B) TYPE: nucleic acid
        (C) STRANDEDNESS: single
        (D) TOPOLOGY: linear

```
    (ii) MOLECULE TYPE: DNA (ix) FEATURE:
         (D) OTHER INFORMATION: oligonucleotide primer (xi) SEQUENCE DESCRIPTION: SEQ ID NO:305:

CTTCGGTGTG AAACCAGTTC TGAATACTCC TC                                  32

(2) INFORMATION FOR SEQ ID NO:306:

(i) SEQUENCE CHARACTERISTICS:
        (A) LENGTH: 32 base pairs
        (B) TYPE: nucleic acid
        (C) STRANDEDNESS: single
        (D) TOPOLOGY: linear (ii) MOLECULE TYPE: DNA (ix) FEATURE:
         (D) OTHER INFORMATION: oligonucleotide primer (xi) SEQUENCE DESCRIPTION: SEQ ID NO:306:

AACTCATTTG GGCACTTGCA CAAGTATCTC GA                                  32

(2) INFORMATION FOR SEQ ID NO:307:

(i) SEQUENCE CHARACTERISTICS:
        (A) LENGTH: 32 base pairs
        (B) TYPE: nucleic acid
        (C) STRANDEDNESS: single
        (D) TOPOLOGY: linear (ii) MOLECULE TYPE: DNA (ix) FEATURE:
         (D) OTHER INFORMATION: oligonucleotide primer (xi) SEQUENCE DESCRIPTION: SEQ ID NO:307:

CTCTGCCAAT ATCACCATCG TGGAATCAAA CG                                  32

(2) INFORMATION FOR SEQ ID NO:308:

(i) SEQUENCE CHARACTERISTICS:
        (A) LENGTH: 32 base pairs
        (B) TYPE: nucleic acid
        (C) STRANDEDNESS: single
        (D) TOPOLOGY: linear (ii) MOLECULE TYPE: DNA (ix) FEATURE:
         (D) OTHER INFORMATION: oligonucleotide primer (xi) SEQUENCE DESCRIPTION: SEQ ID NO:308:

AACTCATTTG GGCACTTGCA CAAGTATCTC GA                                  32

(2) INFORMATION FOR SEQ ID NO:309:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: DNA (ix) FEATURE:
         (D) OTHER INFORMATION: oligonucleotide primer (xi) SEQUENCE DESCRIPTION: SEQ ID NO:309:

CCTGCTTGAA TGTGGTGAAT ACCTCGCTGC                                     30
```

(2) INFORMATION FOR SEQ ID NO:310:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: DNA (ix) FEATURE:
        (D) OTHER INFORMATION: oligonucleotide primer (xi) SEQUENCE DESCRIPTION: SEQ ID NO:310:

AGATGGAACA GCACAATGAG CGCAACTCCA                          30

(2) INFORMATION FOR SEQ ID NO:311:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: DNA (ix) FEATURE:
        (D) OTHER INFORMATION: oligonucleotide primer (xi) SEQUENCE DESCRIPTION: SEQ ID NO:311:

AGGAGACCAA GGCACAGGAC ATTCTGGG                            28

(2) INFORMATION FOR SEQ ID NO:312:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: DNA (ix) FEATURE:
        (D) OTHER INFORMATION: oligonucleotide primer (xi) SEQUENCE DESCRIPTION: SEQ ID NO:312:

CTCCAACAAT CCAGAAGTCC TGTTTGGGAG                          30

(2) INFORMATION FOR SEQ ID NO:313:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: DNA (ix) FEATURE:
        (D) OTHER INFORMATION: oligonucleotide primer (xi) SEQUENCE DESCRIPTION: SEQ ID NO:313:

ATCAAGGGTG AGGCAGAGAC CCGCGTG                            27

(2) INFORMATION FOR SEQ ID NO:314:

(i) SEQUENCE CHARACTERISTICS:
        (A) LENGTH: 26 base pairs
        (B) TYPE: nucleic acid
        (C) STRANDEDNESS: single (D) TOPOLOGY: linear (ii) MOLECULE TYPE: DNA (ix) FEATURE:
        (D) OTHER INFORMATION: oligonucleotide primer (xi) SEQUENCE DESCRIPTION: SEQ ID NO:314:

ACTCCGGTGC CATCCACCGT ACAGGG                                            26

(2) INFORMATION FOR SEQ ID NO:315:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: DNA (ix) FEATURE:
        (D) OTHER INFORMATION: oligonucleotide primer (xi) SEQUENCE DESCRIPTION: SEQ ID NO:315:

CCGGCATGTT CACCGTGCGG ATGGCG                                            26

(2) INFORMATION FOR SEQ ID NO:316:

(i) SEQUENCE CHARACTERISTICS:
        (A) LENGTH: 31 base pairs
        (B) TYPE: nucleic acid
        (C) STRANDEDNESS: single
        (D) TOPOLOGY: linear (ii) MOLECULE TYPE: DNA (ix) FEATURE:
        (D) OTHER INFORMATION: oligonucleotide primer (xi) SEQUENCE DESCRIPTION: SEQ ID NO:316:

GACCCAAGTT CAGGACACGG GATTGATCTA T                                      31

(2) INFORMATION FOR SEQ ID NO:317:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: DNA (ix) FEATURE:
        (D) OTHER INFORMATION: oligonucleotide primer (xi) SEQUENCE DESCRIPTION: SEQ ID NO:317:

TACACCAGTG GCAAGTGCTC CAACCCAG                                          28

(2) INFORMATION FOR SEQ ID NO:318:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: DNA (ix) FEATURE:
        (D) OTHER INFORMATION: oligonucleotide primer (xi) SEQUENCE DESCRIPTION: SEQ ID NO:318:

```
GTCTCGAACT CCTGACCTCA AGTGATCCAC                                    30
```

(2) INFORMATION FOR SEQ ID NO:319:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: DNA (ix) FEATURE:
        (D) OTHER INFORMATION: oligonucleotide primer (xi) SEQUENCE DESCRIPTION: SEQ ID NO:319:

```
TCTCCCGTCT TCTGCCTCCC ACTCCATA                                      28
```

(2) INFORMATION FOR SEQ ID NO:320:

(i) SEQUENCE CHARACTERISTICS:
        (A) LENGTH: 32 base pairs
        (B) TYPE: nucleic acid
        (C) STRANDEDNESS: single
        (D) TOPOLOGY: linear (ii) MOLECULE TYPE: DNA (ix) FEATURE:
        (D) OTHER INFORMATION: oligonucleotide primer (xi) SEQUENCE DESCRIPTION: SEQ ID NO:320:

```
GTCTAATTGG CTCTACAGAA CCTAGTCAGG TT                                 32
```

(2) INFORMATION FOR SEQ ID NO:321:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: DNA (ix) FEATURE:
        (D) OTHER INFORMATION: oligonucleotide primer (xi) SEQUENCE DESCRIPTION: SEQ ID NO:321:

```
ACGCAGTGCA GACTGTGGTC CGCCA                                         25
```

(2) INFORMATION FOR SEQ ID NO:322:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: DNA (ix) FEATURE:
        (D) OTHER INFORMATION: oligonucleotide primer (xi) SEQUENCE DESCRIPTION: SEQ ID NO:322:

```
CGTAGCCGCT CTCAACCACG GTGATGT                                       27
```

(2) INFORMATION FOR SEQ ID NO:323:

(i) SEQUENCE CHARACTERISTICS:
        (A) LENGTH: 23 base pairs

```
            (B) TYPE: nucleic acid
            (C) STRANDEDNESS: single
            (D) TOPOLOGY: linear (ii) MOLECULE TYPE: DNA (ix) FEATURE:
            (D) OTHER INFORMATION: oligonucleotide primer (xi) SEQUENCE DESCRIPTION: SEQ ID NO:323:

CACACTCGGC CAGACCGGGA CCG                                              23

(2) INFORMATION FOR SEQ ID NO:324:

(i) SEQUENCE CHARACTERISTICS:
            (A) LENGTH: 25 base pairs
            (B) TYPE: nucleic acid
            (C) STRANDEDNESS: single
            (D) TOPOLOGY: linear (ii) MOLECULE TYPE: DNA (ix) FEATURE:
            (D) OTHER INFORMATION: oligonucleotide primer (xi) SEQUENCE DESCRIPTION: SEQ ID NO:324:

GGGTGTGACA GAGATGCGCC ACACG                                            25

(2) INFORMATION FOR SEQ ID NO:325:

(i) SEQUENCE CHARACTERISTICS:
            (A) LENGTH: 27 base pairs
            (B) TYPE: nucleic acid
            (C) STRANDEDNESS: single
            (D) TOPOLOGY: linear (ii) MOLECULE TYPE: DNA (ix) FEATURE:
            (D) OTHER INFORMATION: oligonucleotide primer (xi) SEQUENCE DESCRIPTION: SEQ ID NO:325:

CTGTATCGCA GGCACTCAGG TCAGCCG                                          27

(2) INFORMATION FOR SEQ ID NO:326:

(i) SEQUENCE CHARACTERISTICS:
            (A) LENGTH: 28 base pairs
            (B) TYPE: nucleic acid
            (C) STRANDEDNESS: single
            (D) TOPOLOGY: linear (ii) MOLECULE TYPE: DNA (ix) FEATURE:
            (D) OTHER INFORMATION: oligonucleotide primer (xi) SEQUENCE DESCRIPTION: SEQ ID NO:326:

CATGGTTGGC GTGTCCCTGT GCAGTCCA                                         28

(2) INFORMATION FOR SEQ ID NO:327:

(i) SEQUENCE CHARACTERISTICS:
            (A) LENGTH: 32 base pairs
            (B) TYPE: nucleic acid
            (C) STRANDEDNESS: single
            (D) TOPOLOGY: linear (ii) MOLECULE TYPE: DNA (ix) FEATURE:
            (D) OTHER INFORMATION: oligonucleotide primer
```

(xi) SEQUENCE DESCRIPTION: SEQ ID NO:327:

GCAGATATTG GCTGGAGTGA ATGGATTATC TC                                            32

(2) INFORMATION FOR SEQ ID NO:328:

(i) SEQUENCE CHARACTERISTICS:
            (A) LENGTH: 32 base pairs
            (B) TYPE: nucleic acid
            (C) STRANDEDNESS: single
            (D) TOPOLOGY: linear (ii) MOLECULE TYPE: DNA (ix) FEATURE:
            (D) OTHER INFORMATION: oligonucleotide primer (xi) SEQUENCE DESCRIPTION: SEQ ID NO:328:

AGCGCAAGAC TCTACTGTCA TGTTAGGGTA TA                                            32

(2) INFORMATION FOR SEQ ID NO:329:

(i) SEQUENCE CHARACTERISTICS:
            (A) LENGTH: 25 base pairs
            (B) TYPE: nucleic acid
            (C) STRANDEDNESS: single
            (D) TOPOLOGY: linear (ii) MOLECULE TYPE: DNA (ix) FEATURE:
            (D) OTHER INFORMATION: oligonucleotide primer (xi) SEQUENCE DESCRIPTION: SEQ ID NO:329:

AGCAGCCAGT GCTCCAAGCC CGGTG                                                    25

(2) INFORMATION FOR SEQ ID NO:330:

(i) SEQUENCE CHARACTERISTICS:
            (A) LENGTH: 28 base pairs
            (B) TYPE: nucleic acid
            (C) STRANDEDNESS: single
            (D) TOPOLOGY: linear (ii) MOLECULE TYPE: DNA (ix) FEATURE:
            (D) OTHER INFORMATION: oligonucleotide primer (xi) SEQUENCE DESCRIPTION: SEQ ID NO:330:

TTGTCAGTCT GGTGGCTTTG GTGCCATG                                                 28

(2) INFORMATION FOR SEQ ID NO:331:

(i) SEQUENCE CHARACTERISTICS:
            (A) LENGTH: 28 base pairs
            (B) TYPE: nucleic acid
            (C) STRANDEDNESS: single
            (D) TOPOLOGY: linear (ii) MOLECULE TYPE: DNA (ix) FEATURE:
            (D) OTHER INFORMATION: oligonucleotide primer (xi) SEQUENCE DESCRIPTION: SEQ ID NO:331:

TTCTCAAACT GAAGCTCGCA CTCTCGCC                                                 28

(2) INFORMATION FOR SEQ ID NO:332:

(i) SEQUENCE CHARACTERISTICS:
    (A) LENGTH: 30 base pairs
    (B) TYPE: nucleic acid
    (C) STRANDEDNESS: single
    (D) TOPOLOGY: linear (ii) MOLECULE TYPE: DNA (ix) FEATURE:
    (D) OTHER INFORMATION: oligonucleotide primer (xi) SEQUENCE DESCRIPTION: SEQ ID NO:332:

TGTGGAGTGA GTGTTCAAGT CTTCGGAGTT                                30

(2) INFORMATION FOR SEQ ID NO:333:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: DNA (ix) FEATURE:
        (D) OTHER INFORMATION: oligonucleotide primer (xi) SEQUENCE DESCRIPTION: SEQ ID NO:333:

TCTTTACCCT CGTCCTGCCG GGCACTTT                                  28

(2) INFORMATION FOR SEQ ID NO:334:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: DNA (ix) FEATURE:
        (D) OTHER INFORMATION: oligonucleotide primer (xi) SEQUENCE DESCRIPTION: SEQ ID NO:334:

GAAAGTGGAC TCCCACAGGG CCACACG                                   27

(2) INFORMATION FOR SEQ ID NO:335:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: DNA (ix) FEATURE:
        (D) OTHER INFORMATION: oligonucleotide primer (xi) SEQUENCE DESCRIPTION: SEQ ID NO:335:

GGGCCACGCG GGACCGACTT TCCAT                                     25

(2) INFORMATION FOR SEQ ID NO:336:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: DNA

```
    (ix) FEATURE:
          (D) OTHER INFORMATION: oligonucleotide primer (xi) SEQUENCE DESCRIPTION: SEQ ID NO:336:

TGGGACACCC TGCCGCTGTT ACAGCT                                           26

(2) INFORMATION FOR SEQ ID NO:337:

(i) SEQUENCE CHARACTERISTICS:
          (A) LENGTH: 30 base pairs
          (B) TYPE: nucleic acid
          (C) STRANDEDNESS: single
          (D) TOPOLOGY: linear (ii) MOLECULE TYPE: DNA (ix) FEATURE:
          (D) OTHER INFORMATION: oligonucleotide primer (xi) SEQUENCE DESCRIPTION: SEQ ID NO:337:

CAGTCAGAGT TGAACAGGTA GTTAAGCCCC                                       30

(2) INFORMATION FOR SEQ ID NO:338:

(i) SEQUENCE CHARACTERISTICS:
          (A) LENGTH: 32 base pairs
          (B) TYPE: nucleic acid
          (C) STRANDEDNESS: single
          (D) TOPOLOGY: linear (ii) MOLECULE TYPE: DNA (ix) FEATURE:
          (D) OTHER INFORMATION: oligonucleotide primer (xi) SEQUENCE DESCRIPTION: SEQ ID NO:338:

AGACATAAAG GCAGCTATGG CTGCTAATGC AA                                    32

(2) INFORMATION FOR SEQ ID NO:339:

(i) SEQUENCE CHARACTERISTICS:
          (A) LENGTH: 26 base pairs
          (B) TYPE: nucleic acid
          (C) STRANDEDNESS: single
          (D) TOPOLOGY: linear (ii) MOLECULE TYPE: DNA (ix) FEATURE:
          (D) OTHER INFORMATION: oligonucleotide primer (xi) SEQUENCE DESCRIPTION: SEQ ID NO:339:

CGTGCAGGAG TCTGACGCCT CCGCTC                                           26

(2) INFORMATION FOR SEQ ID NO:340:

(i) SEQUENCE CHARACTERISTICS:
          (A) LENGTH: 26 base pairs
          (B) TYPE: nucleic acid
          (C) STRANDEDNESS: single
          (D) TOPOLOGY: linear (ii) MOLECULE TYPE: DNA (ix) FEATURE:
          (D) OTHER INFORMATION: oligonucleotide primer (xi) SEQUENCE DESCRIPTION: SEQ ID NO:340:

GTAGACGCAC CAGCAGAGTC CCGCCT                                           26
```

(2) INFORMATION FOR SEQ ID NO:341:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: DNA (ix) FEATURE:
        (D) OTHER INFORMATION: oligonucleotide primer (xi) SEQUENCE DESCRIPTION: SEQ ID NO:341:

TGGATGGATG GCTAAGGGCA GAGTTGGATA                                30

(2) INFORMATION FOR SEQ ID NO:342:

(i) SEQUENCE CHARACTERISTICS:
        (A) LENGTH: 32 base pairs
        (B) TYPE: nucleic acid
        (C) STRANDEDNESS: single
        (D) TOPOLOGY: linear (ii) MOLECULE TYPE: DNA (ix) FEATURE:
        (D) OTHER INFORMATION: oligonucleotide primer (xi) SEQUENCE DESCRIPTION: SEQ ID NO:342:

CGCTGACCAT ACTTGAGTCT AATGTGCCAG TA                             32

(2) INFORMATION FOR SEQ ID NO:343:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: DNA (ix) FEATURE:
        (D) OTHER INFORMATION: oligonucleotide primer (xi) SEQUENCE DESCRIPTION: SEQ ID NO:343:

CAGCGCAGCT ACTGCCATCC AATCGAGA                                    28

(2) INFORMATION FOR SEQ ID NO:344:

(i) SEQUENCE CHARACTERISTICS:
        (A) LENGTH: 32 base pairs
        (B) TYPE: nucleic acid
        (C) STRANDEDNESS: single
        (D) TOPOLOGY: linear (ii) MOLECULE TYPE: DNA (ix) FEATURE:
        (D) OTHER INFORMATION: oligonucleotide primer (xi) SEQUENCE DESCRIPTION: SEQ ID NO:344:

GCTTGTCACA TCTGCAAGTA CGTTCGTTTA AC                             32

(2) INFORMATION FOR SEQ ID NO:345:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: DNA (ix) FEATURE:
             (D) OTHER INFORMATION: oligonucleotide primer (xi) SEQUENCE DESCRIPTION: SEQ ID NO:345:

GCAAGGGTGG CAAGCATCAC CTTGGC                                        26

(2) INFORMATION FOR SEQ ID NO:346:

(i) SEQUENCE CHARACTERISTICS:
            (A) LENGTH: 25 base pairs
            (B) TYPE: nucleic acid
            (C) STRANDEDNESS: single
            (D) TOPOLOGY: linear (ii) MOLECULE TYPE: DNA (ix) FEATURE:
             (D) OTHER INFORMATION: oligonucleotide primer (xi) SEQUENCE DESCRIPTION: SEQ ID NO:346:

AGGCACCGGC TGGCTGCGGT CTACT                                         25

(2) INFORMATION FOR SEQ ID NO:347:

(i) SEQUENCE CHARACTERISTICS:
            (A) LENGTH: 26 base pairs
            (B) TYPE: nucleic acid
            (C) STRANDEDNESS: single
            (D) TOPOLOGY: linear (ii) MOLECULE TYPE: DNA (ix) FEATURE:
             (D) OTHER INFORMATION: oligonucleotide primer (xi) SEQUENCE DESCRIPTION: SEQ ID NO:347:

TGCACCTCAG CGACAACCTC TTGGGG                                        26

(2) INFORMATION FOR SEQ ID NO:348:

(i) SEQUENCE CHARACTERISTICS:
            (A) LENGTH: 26 base pairs
            (B) TYPE: nucleic acid
            (C) STRANDEDNESS: single
            (D) TOPOLOGY: linear (ii) MOLECULE TYPE: DNA (ix) FEATURE:
             (D) OTHER INFORMATION: oligonucleotide primer (xi) SEQUENCE DESCRIPTION: SEQ ID NO:348:

CAATGCCGCA CAGGTCCCGG CAGTTG                                        26

(2) INFORMATION FOR SEQ ID NO:349:

(i) SEQUENCE CHARACTERISTICS:
            (A) LENGTH: 26 base pairs
            (B) TYPE: nucleic acid
            (C) STRANDEDNESS: single
            (D) TOPOLOGY: linear (ii) MOLECULE TYPE: DNA (ix) FEATURE:
             (D) OTHER INFORMATION: oligonucleotide primer (xi) SEQUENCE DESCRIPTION: SEQ ID NO:349:

CCCAGGGCTG GAATACTGCT ACAACC                                        26

(2) INFORMATION FOR SEQ ID NO:350:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: DNA (ix) FEATURE:
        (D) OTHER INFORMATION: oligonucleotide primer (xi) SEQUENCE DESCRIPTION: SEQ ID NO:350:

GGTGTAGATC CGGTCAAATA ATGCCTCG                      28

(2) INFORMATION FOR SEQ ID NO:351:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: DNA (ix) FEATURE:
        (D) OTHER INFORMATION: oligonucleotide primer (xi) SEQUENCE DESCRIPTION: SEQ ID NO:351:

CTGATGGACC AGGAAGCCCT GAATCCATAA                   30

(2) INFORMATION FOR SEQ ID NO:352:

(i) SEQUENCE CHARACTERISTICS:
        (A) LENGTH: 32 base pairs
        (B) TYPE: nucleic acid
        (C) STRANDEDNESS: single
        (D) TOPOLOGY: linear (ii) MOLECULE TYPE: DNA (ix) FEATURE:
        (D) OTHER INFORMATION: oligonucleotide primer (xi) SEQUENCE DESCRIPTION: SEQ ID NO:352:

TGTCAATAGG AATGCTAAGC AAACAGGCAC GA                32

(2) INFORMATION FOR SEQ ID NO:353:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: DNA (ix) FEATURE:
        (D) OTHER INFORMATION: oligonucleotide primer (xi) SEQUENCE DESCRIPTION: SEQ ID NO:353:

CACTCGGACT GGAGCTGAGT GCAAGC                        26

(2) INFORMATION FOR SEQ ID NO:354:

(i) SEQUENCE CHARACTERISTICS:
        (A) LENGTH: 29 base pairs
        (B) TYPE: nucleic acid
        (C) STRANDEDNESS: single (D) TOPOLOGY: linear (ii) MOLECULE TYPE: DNA (ix) FEATURE:
             (D) OTHER INFORMATION: oligonucleotide primer (xi) SEQUENCE DESCRIPTION: SEQ ID NO:354:

CTTGAGGTTT GGGCTTGGTC AGTTTGCCA                                              29

(2) INFORMATION FOR SEQ ID NO:355:

(i) SEQUENCE CHARACTERISTICS:
             (A) LENGTH: 29 base pairs
             (B) TYPE: nucleic acid
             (C) STRANDEDNESS: single
             (D) TOPOLOGY: linear (ii) MOLECULE TYPE: DNA (ix) FEATURE:
             (D) OTHER INFORMATION: oligonucleotide primer (xi) SEQUENCE DESCRIPTION: SEQ ID NO:355:

ATACCAGCTC CATCTGCTCC AATGAGGGC                                              29

(2) INFORMATION FOR SEQ ID NO:356:

(i) SEQUENCE CHARACTERISTICS:
             (A) LENGTH: 29 base pairs
             (B) TYPE: nucleic acid
             (C) STRANDEDNESS: single
             (D) TOPOLOGY: linear (ii) MOLECULE TYPE: DNA (ix) FEATURE:
             (D) OTHER INFORMATION: oligonucleotide primer (xi) SEQUENCE DESCRIPTION: SEQ ID NO:356:

TCGGGGACAG GTGAAGCCAT GTGGTTTCC                                              29

(2) INFORMATION FOR SEQ ID NO:357:

(i) SEQUENCE CHARACTERISTICS:
             (A) LENGTH: 27 base pairs
             (B) TYPE: nucleic acid
             (C) STRANDEDNESS: single
             (D) TOPOLOGY: linear (ii) MOLECULE TYPE: DNA (ix) FEATURE:
             (D) OTHER INFORMATION: oligonucleotide primer (xi) SEQUENCE DESCRIPTION: SEQ ID NO:357:

GGGACATGAA CTGTGTTTGC CGCCTGG                                                27

(2) INFORMATION FOR SEQ ID NO:358:

(i) SEQUENCE CHARACTERISTICS:
             (A) LENGTH: 26 base pairs
             (B) TYPE: nucleic acid
             (C) STRANDEDNESS: single
             (D) TOPOLOGY: linear (ii) MOLECULE TYPE: DNA (ix) FEATURE:
             (D) OTHER INFORMATION: oligonucleotide primer (xi) SEQUENCE DESCRIPTION: SEQ ID NO:358:

ACGTGCCGCA GGTAGGACAG TAGGTC                 26

(2) INFORMATION FOR SEQ ID NO:359:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: DNA (ix) FEATURE:
        (D) OTHER INFORMATION: oligonucleotide primer (xi) SEQUENCE DESCRIPTION: SEQ ID NO:359:

AGGCCCAGCT CTGACCAGAC TCCATG                 26

(2) INFORMATION FOR SEQ ID NO:360:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: DNA (ix) FEATURE:
        (D) OTHER INFORMATION: oligonucleotide primer (xi) SEQUENCE DESCRIPTION: SEQ ID NO:360:

AAGGACTGGT TCTGAGCGTT GGTCCAGA               28

(2) INFORMATION FOR SEQ ID NO:361:

(i) SEQUENCE CHARACTERISTICS:
        (A) LENGTH: 31 base pairs
        (B) TYPE: nucleic acid
        (C) STRANDEDNESS: single
        (D) TOPOLOGY: linear (ii) MOLECULE TYPE: DNA (ix) FEATURE:
        (D) OTHER INFORMATION: oligonucleotide primer (xi) SEQUENCE DESCRIPTION: SEQ ID NO:361:

AAGAGACAGC CAAGTCTTAC AAGGGCAGTT G           31

(2) INFORMATION FOR SEQ ID NO:362:

(i) SEQUENCE CHARACTERISTICS:
        (A) LENGTH: 32 base pairs
        (B) TYPE: nucleic acid
        (C) STRANDEDNESS: single
        (D) TOPOLOGY: linear (ii) MOLECULE TYPE: DNA (ix) FEATURE:
        (D) OTHER INFORMATION: oligonucleotide primer (xi) SEQUENCE DESCRIPTION: SEQ ID NO:362:

CTAAATGAGA CCCAAGTCCC GCAGTCCTTA AA          32

(2) INFORMATION FOR SEQ ID NO:363:

(i) SEQUENCE CHARACTERISTICS:
        (A) LENGTH: 30 base pairs (B) TYPE: nucleic acid
        (C) STRANDEDNESS: single
        (D) TOPOLOGY: linear (ii) MOLECULE TYPE: DNA (ix) FEATURE:
        (D) OTHER INFORMATION: oligonucleotide primer (xi) SEQUENCE DESCRIPTION: SEQ ID NO:363:

TTCCTCAGCA TAGTGCAGGA CACGTCATGC                                                30

(2) INFORMATION FOR SEQ ID NO:364:

(i) SEQUENCE CHARACTERISTICS:
        (A) LENGTH: 32 base pairs
        (B) TYPE: nucleic acid
        (C) STRANDEDNESS: single
        (D) TOPOLOGY: linear (ii) MOLECULE TYPE: DNA (ix) FEATURE:
        (D) OTHER INFORMATION: oligonucleotide primer (xi) SEQUENCE DESCRIPTION: SEQ ID NO:364:

CACTGAAATT ATCACTCTGG CTCATTCAGC TC                                             32

(2) INFORMATION FOR SEQ ID NO:365:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: DNA (ix) FEATURE:
        (D) OTHER INFORMATION: oligonucleotide primer (xi) SEQUENCE DESCRIPTION: SEQ ID NO:365:

AAGAGGTTGG GCTTCCATGC CTGTAGCTTT                                                30

(2) INFORMATION FOR SEQ ID NO:366:

(i) SEQUENCE CHARACTERISTICS:
        (A) LENGTH: 32 base pairs
        (B) TYPE: nucleic acid
        (C) STRANDEDNESS: single
        (D) TOPOLOGY: linear (ii) MOLECULE TYPE: DNA (ix) FEATURE:
        (D) OTHER INFORMATION: oligonucleotide primer (xi) SEQUENCE DESCRIPTION: SEQ ID NO:366:

GGTAATCAGT TACCAAGAAC AGTCAGCTCC AA                                             32

(2) INFORMATION FOR SEQ ID NO:367:

(i) SEQUENCE CHARACTERISTICS:
        (A) LENGTH: 32 base pairs
        (B) TYPE: nucleic acid
        (C) STRANDEDNESS: single
        (D) TOPOLOGY: linear (ii) MOLECULE TYPE: DNA (ix) FEATURE:
        (D) OTHER INFORMATION: oligonucleotide primer (xi) SEQUENCE DESCRIPTION: SEQ ID NO:367:

TTGCGAGTTG TAAATGGGAT TCCAACACGA AC                                           32

(2) INFORMATION FOR SEQ ID NO:368:

(i) SEQUENCE CHARACTERISTICS:
          (A) LENGTH: 32 base pairs
          (B) TYPE: nucleic acid
          (C) STRANDEDNESS: single
          (D) TOPOLOGY: linear (ii) MOLECULE TYPE: DNA (ix) FEATURE:
          (D) OTHER INFORMATION: oligonucleotide primer (xi) SEQUENCE DESCRIPTION: SEQ ID NO:368:

GTGCCACTCG TAATAGGCCA TCATAGTTGA TC                                           32

(2) INFORMATION FOR SEQ ID NO:369:

(i) SEQUENCE CHARACTERISTICS:
          (A) LENGTH: 30 base pairs
          (B) TYPE: nucleic acid
          (C) STRANDEDNESS: single
          (D) TOPOLOGY: linear (ii) MOLECULE TYPE: DNA (ix) FEATURE:
          (D) OTHER INFORMATION: oligonucleotide primer (xi) SEQUENCE DESCRIPTION: SEQ ID NO:369:

CATGAACACC CGGAGCACTA CACTATAATG                                              30

(2) INFORMATION FOR SEQ ID NO:370:

(i) SEQUENCE CHARACTERISTICS:
          (A) LENGTH: 30 base pairs
          (B) TYPE: nucleic acid
          (C) STRANDEDNESS: single
          (D) TOPOLOGY: linear (ii) MOLECULE TYPE: DNA (ix) FEATURE:
          (D) OTHER INFORMATION: oligonucleotide primer (xi) SEQUENCE DESCRIPTION: SEQ ID NO:370:

ATTCCAACTG CCACTGTCCT GATTTCCATG                                              30

(2) INFORMATION FOR SEQ ID NO:371:

(i) SEQUENCE CHARACTERISTICS:
          (A) LENGTH: 30 base pairs
          (B) TYPE: nucleic acid
          (C) STRANDEDNESS: single
          (D) TOPOLOGY: linear (ii) MOLECULE TYPE: DNA (ix) FEATURE:
          (D) OTHER INFORMATION: oligonucleotide primer (xi) SEQUENCE DESCRIPTION: SEQ ID NO:371:

GTGTGACAGT ATTAGTGAGT GGGTAACGGC                                              30

(2) INFORMATION FOR SEQ ID NO:372:

(i) SEQUENCE CHARACTERISTICS:
        (A) LENGTH: 32 base pairs
        (B) TYPE: nucleic acid
        (C) STRANDEDNESS: single
        (D) TOPOLOGY: linear (ii) MOLECULE TYPE: DNA (ix) FEATURE:
        (D) OTHER INFORMATION: oligonucleotide primer (xi) SEQUENCE DESCRIPTION: SEQ ID NO:372:

GTCTATCCTT ATGAATCGCC AGCCAATTCT CT                                         32

(2) INFORMATION FOR SEQ ID NO:373:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: DNA (ix) FEATURE:
        (D) OTHER INFORMATION: oligonucleotide primer (xi) SEQUENCE DESCRIPTION: SEQ ID NO:373:

GTACCACAAT GTGGGCATCC TTGTGCTC                                              28

(2) INFORMATION FOR SEQ ID NO:374:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: DNA (ix) FEATURE:
        (D) OTHER INFORMATION: oligonucleotide primer (xi) SEQUENCE DESCRIPTION: SEQ ID NO:374:

GTCAACACCT TGGCTGCAAA CGCCACGA                                              28

(2) INFORMATION FOR SEQ ID NO:375:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: DNA (ix) FEATURE:
        (D) OTHER INFORMATION: oligonucleotide primer (xi) SEQUENCE DESCRIPTION: SEQ ID NO:375:

CCACGCGGTC CACCAAGACA CTCAAGG                                               27

(2) INFORMATION FOR SEQ ID NO:376:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: DNA (ix) FEATURE:
    (D) OTHER INFORMATION: oligonucleotide primer (xi) SEQUENCE DESCRIPTION: SEQ ID NO:376:

GTGGCCCATG AGGCTGTCGC CTACAC                            26

(2) INFORMATION FOR SEQ ID NO:377:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: DNA (ix) FEATURE:
        (D) OTHER INFORMATION: oligonucleotide primer (xi) SEQUENCE DESCRIPTION: SEQ ID NO:377:

CACACCCTCA GCCCACCCAC TTACCTTA                          28

(2) INFORMATION FOR SEQ ID NO:378:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: DNA (ix) FEATURE:
        (D) OTHER INFORMATION: oligonucleotide primer (xi) SEQUENCE DESCRIPTION: SEQ ID NO:378:

GCAGTTGTGG CTGCCAGGTC TCACTCTC                          28

(2) INFORMATION FOR SEQ ID NO:379:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: DNA (ix) FEATURE:
        (D) OTHER INFORMATION: oligonucleotide primer (xi) SEQUENCE DESCRIPTION: SEQ ID NO:379:

CGCTCCCTGC CAAGGCGCTG TCAGT                             25

(2) INFORMATION FOR SEQ ID NO:380:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: DNA (ix) FEATURE:
        (D) OTHER INFORMATION: oligonucleotide primer (xi) SEQUENCE DESCRIPTION: SEQ ID NO:380:

CCCGCATGGC CTCCTGTTGT CGCTTG                            26

(2) INFORMATION FOR SEQ ID NO:381:

(i) SEQUENCE CHARACTERISTICS:
        (A) LENGTH: 31 base pairs
        (B) TYPE: nucleic acid
        (C) STRANDEDNESS: single
        (D) TOPOLOGY: linear (ii) MOLECULE TYPE: DNA (ix) FEATURE:
        (D) OTHER INFORMATION: oligonucleotide primer (xi) SEQUENCE DESCRIPTION: SEQ ID NO:381:

GATGGATGGG AACGCAAGAG ATACTTACAT G                                  31

(2) INFORMATION FOR SEQ ID NO:382:

(i) SEQUENCE CHARACTERISTICS:
        (A) LENGTH: 32 base pairs
        (B) TYPE: nucleic acid
        (C) STRANDEDNESS: single
        (D) TOPOLOGY: linear (ii) MOLECULE TYPE: DNA (ix) FEATURE:
        (D) OTHER INFORMATION: oligonucleotide primer (xi) SEQUENCE DESCRIPTION: SEQ ID NO:382:

GTCTTGTTAT GTTTCCCAGG CTGGTCAATC AT                               32

(2) INFORMATION FOR SEQ ID NO:383:

(i) SEQUENCE CHARACTERISTICS:
        (A) LENGTH: 32 base pairs
        (B) TYPE: nucleic acid
        (C) STRANDEDNESS: single
        (D) TOPOLOGY: linear (ii) MOLECULE TYPE: DNA (ix) FEATURE:
        (D) OTHER INFORMATION: oligonucleotide primer (xi) SEQUENCE DESCRIPTION: SEQ ID NO:383:

ATGTACCAGG TGGAGTTCAA GACCATGAAT GC                               32

(2) INFORMATION FOR SEQ ID NO:384:

(i) SEQUENCE CHARACTERISTICS:
        (A) LENGTH: 32 base pairs
        (B) TYPE: nucleic acid
        (C) STRANDEDNESS: single
        (D) TOPOLOGY: linear (ii) MOLECULE TYPE: DNA (ix) FEATURE:
        (D) OTHER INFORMATION: oligonucleotide primer (xi) SEQUENCE DESCRIPTION: SEQ ID NO:384:

GGTATCATGT GGATGTAATA GTCCCATCCT TC                               32

(2) INFORMATION FOR SEQ ID NO:385:

(i) SEQUENCE CHARACTERISTICS:
        (A) LENGTH: 32 base pairs
        (B) TYPE: nucleic acid
        (C) STRANDEDNESS: single
        (D) TOPOLOGY: linear (ii) MOLECULE TYPE: DNA (ix) FEATURE:
    (D) OTHER INFORMATION: oligonucleotide primer (xi) SEQUENCE DESCRIPTION: SEQ ID NO:385:

ATTCTAGCCT GGTTTGGAGA TACTAACTGC TC                32

(2) INFORMATION FOR SEQ ID NO:386:

(i) SEQUENCE CHARACTERISTICS:
        (A) LENGTH: 32 base pairs
        (B) TYPE: nucleic acid
        (C) STRANDEDNESS: single
        (D) TOPOLOGY: linear (ii) MOLECULE TYPE: DNA (ix) FEATURE:
        (D) OTHER INFORMATION: oligonucleotide primer (xi) SEQUENCE DESCRIPTION: SEQ ID NO:386:

GAGGGTATGA CAAGAGCAAT TCCTAAATCC AG                32

(2) INFORMATION FOR SEQ ID NO:387:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: DNA (ix) FEATURE:
        (D) OTHER INFORMATION: oligonucleotide primer (xi) SEQUENCE DESCRIPTION: SEQ ID NO:387:

TCTGGCTCTG GACAGGCACT ATCTGGG                      27

(2) INFORMATION FOR SEQ ID NO:388:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: DNA (ix) FEATURE:
        (D) OTHER INFORMATION: oligonucleotide primer (xi) SEQUENCE DESCRIPTION: SEQ ID NO:388:

AGTGGGTTAA AGATGTGACG TTCAACGGGA                   30

(2) INFORMATION FOR SEQ ID NO:389:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: DNA (ix) FEATURE:
        (D) OTHER INFORMATION: oligonucleotide primer (xi) SEQUENCE DESCRIPTION: SEQ ID NO:389:

TTTCAGAAGT GGCTCGCATC AGTAGCTTGG                   30

(2) INFORMATION FOR SEQ ID NO:390:

(i) SEQUENCE CHARACTERISTICS:
        (A) LENGTH: 32 base pairs
        (B) TYPE: nucleic acid
        (C) STRANDEDNESS: single
        (D) TOPOLOGY: linear (ii) MOLECULE TYPE: DNA (ix) FEATURE:
        (D) OTHER INFORMATION: oligonucleotide primer (xi) SEQUENCE DESCRIPTION: SEQ ID NO:390:

GAGTAGGTAA AGAGCAAATG GGTTGACACA AG                      32

(2) INFORMATION FOR SEQ ID NO:391:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: DNA (ix) FEATURE:
        (D) OTHER INFORMATION: oligonucleotide primer (xi) SEQUENCE DESCRIPTION: SEQ ID NO:391:

GAGAGCCAAG CCTACAGCGG GTCCCA                            26

(2) INFORMATION FOR SEQ ID NO:392:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: DNA (ix) FEATURE:
        (D) OTHER INFORMATION: oligonucleotide primer (xi) SEQUENCE DESCRIPTION: SEQ ID NO:392:

AGTTGTGGGT AAAGCAGGCA AGTGGGCC                          28

(2) INFORMATION FOR SEQ ID NO:393:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: DNA (ix) FEATURE:
        (D) OTHER INFORMATION: oligonucleotide primer (xi) SEQUENCE DESCRIPTION: SEQ ID NO:393:

AGTGTACCTG CCCACTCAGA TGCTAGTGAA                      30

(2) INFORMATION FOR SEQ ID NO:394:

(i) SEQUENCE CHARACTERISTICS:
        (A) LENGTH: 29 base pairs
        (B) TYPE: nucleic acid
        (C) STRANDEDNESS: single (D) TOPOLOGY: linear (ii) MOLECULE TYPE: DNA (ix) FEATURE:
        (D) OTHER INFORMATION: oligonucleotide primer (xi) SEQUENCE DESCRIPTION: SEQ ID NO:394:

CACATCGCTC TTGCTGGTGT AGACACGGT                                29

(2) INFORMATION FOR SEQ ID NO:395:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: DNA (ix) FEATURE:
        (D) OTHER INFORMATION: oligonucleotide primer (xi) SEQUENCE DESCRIPTION: SEQ ID NO:395:

AGTAGTGGCC CTGACTTCCG GTCGGC                                   26

(2) INFORMATION FOR SEQ ID NO:396:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: DNA (ix) FEATURE:
        (D) OTHER INFORMATION: oligonucleotide primer (xi) SEQUENCE DESCRIPTION: SEQ ID NO:396:

GGTGTAACCA CCTCTCGCAA GGCCAC                                   26

(2) INFORMATION FOR SEQ ID NO:397:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: DNA (ix) FEATURE:
        (D) OTHER INFORMATION: oligonucleotide primer (xi) SEQUENCE DESCRIPTION: SEQ ID NO:397:

GGGAAATCGC CAGCTTCGAT AAGGCCAA                                 28

(2) INFORMATION FOR SEQ ID NO:398:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (ii) MOLECULE TYPE: DNA (ix) FEATURE:
        (D) OTHER INFORMATION: oligonucleotide primer (xi) SEQUENCE DESCRIPTION: SEQ ID NO:398:

GCAAACCGGA GAATTTGGCA GTCCGATTG                                              29

(2) INFORMATION FOR SEQ ID NO:399:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (ii) MOLECULE TYPE: DNA (ix) FEATURE:
        (D) OTHER INFORMATION: oligonucleotide primer (xi) SEQUENCE DESCRIPTION: SEQ ID NO:399:

GTACCGGCCC GGTTAGTATC ATCAGATCG                                              29

(2) INFORMATION FOR SEQ ID NO:400:

(i) SEQUENCE CHARACTERISTICS:
        (A) LENGTH: 32 base pairs
        (B) TYPE: nucleic acid
        (C) STRANDEDNESS: single
        (D) TOPOLOGY: linear (ii) MOLECULE TYPE: DNA (ix) FEATURE:
        (D) OTHER INFORMATION: oligonucleotide primer (xi) SEQUENCE DESCRIPTION: SEQ ID NO:400:

GGCTTGTTAC AGGCAAATTC ACTTGCCACA AG                                          32

(2) INFORMATION FOR SEQ ID NO:401:

(i) SEQUENCE CHARACTERISTICS:
        (A) LENGTH: 32 base pairs
        (B) TYPE: nucleic acid
        (C) STRANDEDNESS: single
        (D) TOPOLOGY: linear (ii) MOLECULE TYPE: DNA (ix) FEATURE:
        (D) OTHER INFORMATION: oligonucleotide primer (xi) SEQUENCE DESCRIPTION: SEQ ID NO:401:

TTATCTGTCT AGTGGTTCTT GTGGGTATTC TC                                          32

(2) INFORMATION FOR SEQ ID NO:402:

(i) SEQUENCE CHARACTERISTICS:
        (A) LENGTH: 32 base pairs
        (B) TYPE: nucleic acid
        (C) STRANDEDNESS: single
        (D) TOPOLOGY: linear (ii) MOLECULE TYPE: DNA (ix) FEATURE:
        (D) OTHER INFORMATION: oligonucleotide primer (xi) SEQUENCE DESCRIPTION: SEQ ID NO:402:

GGCATTGATA TAATCAGTCA GTTTGCCATC CT                                          32

(2) INFORMATION FOR SEQ ID NO:403:

(i) SEQUENCE CHARACTERISTICS:
        (A) LENGTH: 27 base pairs

```
       (B) TYPE: nucleic acid
       (C) STRANDEDNESS: single
       (D) TOPOLOGY: linear (ii) MOLECULE TYPE: DNA (ix) FEATURE:
       (D) OTHER INFORMATION: oligonucleotide primer (xi) SEQUENCE DESCRIPTION: SEQ ID NO:403:

ATCTGGGCCG CCTCCAAGGT GAATGGC                                              27

(2) INFORMATION FOR SEQ ID NO:404:

(i) SEQUENCE CHARACTERISTICS:
       (A) LENGTH: 29 base pairs
       (B) TYPE: nucleic acid
       (C) STRANDEDNESS: single
       (D) TOPOLOGY: linear (ii) MOLECULE TYPE: DNA (ix) FEATURE:
       (D) OTHER INFORMATION: oligonucleotide primer (xi) SEQUENCE DESCRIPTION: SEQ ID NO:404:

GATCCGTAAC AGCATCCGCC AGTTTGCTG                                            29

(2) INFORMATION FOR SEQ ID NO:405:

(i) SEQUENCE CHARACTERISTICS:
       (A) LENGTH: 28 base pairs
       (B) TYPE: nucleic acid
       (C) STRANDEDNESS: single
       (D) TOPOLOGY: linear (ii) MOLECULE TYPE: DNA (ix) FEATURE:
       (D) OTHER INFORMATION: oligonucleotide primer (xi) SEQUENCE DESCRIPTION: SEQ ID NO:405:

GGACTCCAGA ACTACCACCG TCTGCACG                                             28

(2) INFORMATION FOR SEQ ID NO:406:

(i) SEQUENCE CHARACTERISTICS:
       (A) LENGTH: 28 base pairs
       (B) TYPE: nucleic acid
       (C) STRANDEDNESS: single
       (D) TOPOLOGY: linear (ii) MOLECULE TYPE: DNA (ix) FEATURE:
       (D) OTHER INFORMATION: oligonucleotide primer (xi) SEQUENCE DESCRIPTION: SEQ ID NO:406:

GTGAACCGAG ATCGCGTCAT TGCAGTCC                                             28

(2) INFORMATION FOR SEQ ID NO:407:

(i) SEQUENCE CHARACTERISTICS:
       (A) LENGTH: 32 base pairs
       (B) TYPE: nucleic acid
       (C) STRANDEDNESS: single
       (D) TOPOLOGY: linear (ii) MOLECULE TYPE: DNA (ix) FEATURE:
       (D) OTHER INFORMATION: oligonucleotide primer
```

(xi) SEQUENCE DESCRIPTION: SEQ ID NO:407:

AAAGTTGTAA GCTGCGAGGT CTTCATCACA GA                            32

(2) INFORMATION FOR SEQ ID NO:408:

(i) SEQUENCE CHARACTERISTICS:
            (A) LENGTH: 32 base pairs
            (B) TYPE: nucleic acid
            (C) STRANDEDNESS: single
            (D) TOPOLOGY: linear (ii) MOLECULE TYPE: DNA (ix) FEATURE:
            (D) OTHER INFORMATION: oligonucleotide primer (xi) SEQUENCE DESCRIPTION: SEQ ID NO:408:

GATTATTGGC CTCTACTAAC TTGCACTGTC GT                            32

(2) INFORMATION FOR SEQ ID NO:409:

(i) SEQUENCE CHARACTERISTICS:
            (A) LENGTH: 27 base pairs
            (B) TYPE: nucleic acid
            (C) STRANDEDNESS: single
            (D) TOPOLOGY: linear (ii) MOLECULE TYPE: DNA (ix) FEATURE:
            (D) OTHER INFORMATION: oligonucleotide primer (xi) SEQUENCE DESCRIPTION: SEQ ID NO:409:

GTAGCTGGCA AGCGGTCTTA CCGGCTC                                  27

(2) INFORMATION FOR SEQ ID NO:410:

(i) SEQUENCE CHARACTERISTICS:
            (A) LENGTH: 29 base pairs
            (B) TYPE: nucleic acid
            (C) STRANDEDNESS: single
            (D) TOPOLOGY: linear (ii) MOLECULE TYPE: DNA (ix) FEATURE:
            (D) OTHER INFORMATION: oligonucleotide primer (xi) SEQUENCE DESCRIPTION: SEQ ID NO:410:

GGATTTGTCT GCTGCCCAGT GGGTAGAGA                                29

(2) INFORMATION FOR SEQ ID NO:411:

(i) SEQUENCE CHARACTERISTICS:
            (A) LENGTH: 23 base pairs
            (B) TYPE: nucleic acid
            (C) STRANDEDNESS: single
            (D) TOPOLOGY: linear (ii) MOLECULE TYPE: DNA (ix) FEATURE:
            (D) OTHER INFORMATION: oligonucleotide primer (xi) SEQUENCE DESCRIPTION: SEQ ID NO:411:

CCTCCCACCT GCCCCTCAGT TCC                                      23

(2) INFORMATION FOR SEQ ID NO:412:

(i) SEQUENCE CHARACTERISTICS:
       (A) LENGTH: 23 base pairs
       (B) TYPE: nucleic acid
       (C) STRANDEDNESS: single
       (D) TOPOLOGY: linear (ii) MOLECULE TYPE: DNA (ix) FEATURE:
       (D) OTHER INFORMATION: oligonucleotide primer (xi) SEQUENCE DESCRIPTION: SEQ ID NO:412:

GAGCTGCGAG TGCTACCTAG CCC                                              23

(2) INFORMATION FOR SEQ ID NO:413:

(i) SEQUENCE CHARACTERISTICS:
       (A) LENGTH: 32 base pairs
       (B) TYPE: nucleic acid
       (C) STRANDEDNESS: single
       (D) TOPOLOGY: linear (ii) MOLECULE TYPE: DNA (ix) FEATURE:
       (D) OTHER INFORMATION: oligonucleotide primer (xi) SEQUENCE DESCRIPTION: SEQ ID NO:413:

TTCCTGTTAC TGAGAACTCA AAGGGTTACA AG                                    32

(2) INFORMATION FOR SEQ ID NO:414:

(i) SEQUENCE CHARACTERISTICS:
       (A) LENGTH: 32 base pairs
       (B) TYPE: nucleic acid
       (C) STRANDEDNESS: single
       (D) TOPOLOGY: linear (ii) MOLECULE TYPE: DNA (ix) FEATURE:
       (D) OTHER INFORMATION: oligonucleotide primer (xi) SEQUENCE DESCRIPTION: SEQ ID NO:414:

GTTAATCCCA AGGCCATTAG TTACAACATA GC                                    32

(2) INFORMATION FOR SEQ ID NO:415:

(i) SEQUENCE CHARACTERISTICS:
       (A) LENGTH: 26 base pairs
       (B) TYPE: nucleic acid
       (C) STRANDEDNESS: single
       (D) TOPOLOGY: linear (ii) MOLECULE TYPE: DNA (ix) FEATURE:
       (D) OTHER INFORMATION: oligonucleotide primer (xi) SEQUENCE DESCRIPTION: SEQ ID NO:415:

CTGGCCGCCA GGAACGTGCT TGTCAC                                           26

(2) INFORMATION FOR SEQ ID NO:416:

(i) SEQUENCE CHARACTERISTICS:
       (A) LENGTH: 29 base pairs
       (B) TYPE: nucleic acid
       (C) STRANDEDNESS: single
       (D) TOPOLOGY: linear (ii) MOLECULE TYPE: DNA

```
    (ix) FEATURE:
          (D) OTHER INFORMATION: oligonucleotide primer (xi) SEQUENCE DESCRIPTION: SEQ ID NO:416:

GTAGGTGTGA GGACATTCCG AAACACGGC                                      29

(2) INFORMATION FOR SEQ ID NO:417:

(i) SEQUENCE CHARACTERISTICS:
         (A) LENGTH: 27 base pairs
         (B) TYPE: nucleic acid
         (C) STRANDEDNESS: single
         (D) TOPOLOGY: linear (ii) MOLECULE TYPE: DNA (ix) FEATURE:
         (D) OTHER INFORMATION: oligonucleotide primer (xi) SEQUENCE DESCRIPTION: SEQ ID NO:417:

AGACGTGGCA CATTCCTGCC GACACCC                                        27

(2) INFORMATION FOR SEQ ID NO:418:

(i) SEQUENCE CHARACTERISTICS:
         (A) LENGTH: 28 base pairs
         (B) TYPE: nucleic acid
         (C) STRANDEDNESS: single
         (D) TOPOLOGY: linear (ii) MOLECULE TYPE: DNA (ix) FEATURE:
         (D) OTHER INFORMATION: oligonucleotide primer (xi) SEQUENCE DESCRIPTION: SEQ ID NO:418:

AAGTGGTAGG TGGACAGGAC CGTAGACC                                       28

(2) INFORMATION FOR SEQ ID NO:419:

(i) SEQUENCE CHARACTERISTICS:
         (A) LENGTH: 28 base pairs
         (B) TYPE: nucleic acid
         (C) STRANDEDNESS: single
         (D) TOPOLOGY: linear (ii) MOLECULE TYPE: DNA (ix) FEATURE:
         (D) OTHER INFORMATION: oligonucleotide primer (xi) SEQUENCE DESCRIPTION: SEQ ID NO:419:

TCCTCCACCA GCAATGCAGA GTGTGACT                                       28

(2) INFORMATION FOR SEQ ID NO:420:

(i) SEQUENCE CHARACTERISTICS:
         (A) LENGTH: 30 base pairs
         (B) TYPE: nucleic acid
         (C) STRANDEDNESS: single
         (D) TOPOLOGY: linear (ii) MOLECULE TYPE: DNA (ix) FEATURE:
         (D) OTHER INFORMATION: oligonucleotide primer (xi) SEQUENCE DESCRIPTION: SEQ ID NO:420:

CGTCCCATTC ACAAGCACAG ACTTTCCATC                                     30
```

(2) INFORMATION FOR SEQ ID NO:421:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: DNA (ix) FEATURE:
        (D) OTHER INFORMATION: oligonucleotide primer (xi) SEQUENCE DESCRIPTION: SEQ ID NO:421:

CAGCCTCCCA AGCAACTGGG ATTCATCC                      28

(2) INFORMATION FOR SEQ ID NO:422:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: DNA (ix) FEATURE:
        (D) OTHER INFORMATION: oligonucleotide primer (xi) SEQUENCE DESCRIPTION: SEQ ID NO:422:

TTGGCAACAT AGCAATACCG TCTCCGCAAA                    30

(2) INFORMATION FOR SEQ ID NO:423:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: DNA (ix) FEATURE:
        (D) OTHER INFORMATION: oligonucleotide primer (xi) SEQUENCE DESCRIPTION: SEQ ID NO:423:

GGTATGTTTG GGAGACTGCT GAGTCAACCC                    30

(2) INFORMATION FOR SEQ ID NO:424:

(i) SEQUENCE CHARACTERISTICS:
        (A) LENGTH: 32 base pairs
        (B) TYPE: nucleic acid
        (C) STRANDEDNESS: single
        (D) TOPOLOGY: linear (ii) MOLECULE TYPE: DNA (ix) FEATURE:
        (D) OTHER INFORMATION: oligonucleotide primer (xi) SEQUENCE DESCRIPTION: SEQ ID NO:424:

AACAATATGA GCATCAAGGA CATCTGCGAA GC                  32

(2) INFORMATION FOR SEQ ID NO:425:

(i) SEQUENCE CHARACTERISTICS:
        (A) LENGTH: 32 base pairs
        (B) TYPE: nucleic acid
        (C) STRANDEDNESS: single
        (D) TOPOLOGY: linear (ii) MOLECULE TYPE: DNA (ix) FEATURE:
             (D) OTHER INFORMATION: oligonucleotide primer (xi) SEQUENCE DESCRIPTION: SEQ ID NO:425:

AGAGACTTTG ACTCTCCAGA AAGCTCATCT CA                                 32

(2) INFORMATION FOR SEQ ID NO:426:

(i) SEQUENCE CHARACTERISTICS:
             (A) LENGTH: 32 base pairs
             (B) TYPE: nucleic acid
             (C) STRANDEDNESS: single
             (D) TOPOLOGY: linear (ii) MOLECULE TYPE: DNA (ix) FEATURE:
             (D) OTHER INFORMATION: oligonucleotide primer (xi) SEQUENCE DESCRIPTION: SEQ ID NO:426:

TGACCTGGTG AACCCTTCAA GGTTAAATAC AC                                 32

(2) INFORMATION FOR SEQ ID NO:427:

(i) SEQUENCE CHARACTERISTICS:
             (A) LENGTH: 25 base pairs
             (B) TYPE: nucleic acid
             (C) STRANDEDNESS: single
             (D) TOPOLOGY: linear (ii) MOLECULE TYPE: DNA (ix) FEATURE:
             (D) OTHER INFORMATION: oligonucleotide primer (xi) SEQUENCE DESCRIPTION: SEQ ID NO:427:

AAAGGGCTGT CACCCGGCTT GGCCC                                         25

(2) INFORMATION FOR SEQ ID NO:428:

(i) SEQUENCE CHARACTERISTICS:
             (A) LENGTH: 26 base pairs
             (B) TYPE: nucleic acid
             (C) STRANDEDNESS: single
             (D) TOPOLOGY: linear (ii) MOLECULE TYPE: DNA (ix) FEATURE:
             (D) OTHER INFORMATION: oligonucleotide primer (xi) SEQUENCE DESCRIPTION: SEQ ID NO:428:

GCGACAGTCT TGAGCCGCTC CATCCA                                        26

(2) INFORMATION FOR SEQ ID NO:429:

(i) SEQUENCE CHARACTERISTICS:
             (A) LENGTH: 32 base pairs
             (B) TYPE: nucleic acid
             (C) STRANDEDNESS: single
             (D) TOPOLOGY: linear (ii) MOLECULE TYPE: DNA (ix) FEATURE:
             (D) OTHER INFORMATION: oligonucleotide primer (xi) SEQUENCE DESCRIPTION: SEQ ID NO:429:

GTGAAGCAAA TAGCATTTCC ATCTGGTACT CC                                 32

(2) INFORMATION FOR SEQ ID NO:430:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: DNA (ix) FEATURE:
        (D) OTHER INFORMATION: oligonucleotide primer (xi) SEQUENCE DESCRIPTION: SEQ ID NO:430:

ACATGATTCA CCAGGCCACT GACAACTGTC                                        30

(2) INFORMATION FOR SEQ ID NO:431:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: DNA (ix) FEATURE:
        (D) OTHER INFORMATION: oligonucleotide primer (xi) SEQUENCE DESCRIPTION: SEQ ID NO:431:

GCTCCATGCT GTGCCTGCGG CCAAC                                             25

(2) INFORMATION FOR SEQ ID NO:432:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: DNA (ix) FEATURE:
        (D) OTHER INFORMATION: oligonucleotide primer (xi) SEQUENCE DESCRIPTION: SEQ ID NO:432:

CTTGAGGTAG GGCAGCCCGT CGGGC                                             25

(2) INFORMATION FOR SEQ ID NO:433:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: DNA (ix) FEATURE:
        (D) OTHER INFORMATION: oligonucleotide primer (xi) SEQUENCE DESCRIPTION: SEQ ID NO:433:

GCAGAGACAT GACTCAGCCT GTTCCATGAA                                        30

(2) INFORMATION FOR SEQ ID NO:434:

(i) SEQUENCE CHARACTERISTICS:
        (A) LENGTH: 30 base pairs
        (B) TYPE: nucleic acid
        (C) STRANDEDNESS: single (D) TOPOLOGY: linear (ii) MOLECULE TYPE: DNA (ix) FEATURE:
            (D) OTHER INFORMATION: oligonucleotide primer (xi) SEQUENCE DESCRIPTION: SEQ ID NO:434:

ATACTGACAG CCAGTGAGAC TTGGTGCAGT                                    30

(2) INFORMATION FOR SEQ ID NO:435:

(i) SEQUENCE CHARACTERISTICS:
            (A) LENGTH: 32 base pairs
            (B) TYPE: nucleic acid
            (C) STRANDEDNESS: single
            (D) TOPOLOGY: linear (ii) MOLECULE TYPE: DNA (ix) FEATURE:
            (D) OTHER INFORMATION: oligonucleotide primer (xi) SEQUENCE DESCRIPTION: SEQ ID NO:435:

TTGAGAAGTA TTTCCATCCA GTGCTACTTG TG                                 32

(2) INFORMATION FOR SEQ ID NO:436:

(i) SEQUENCE CHARACTERISTICS:
            (A) LENGTH: 32 base pairs
            (B) TYPE: nucleic acid
            (C) STRANDEDNESS: single
            (D) TOPOLOGY: linear (ii) MOLECULE TYPE: DNA (ix) FEATURE:
            (D) OTHER INFORMATION: oligonucleotide primer (xi) SEQUENCE DESCRIPTION: SEQ ID NO:436:

CCCATTAGAA GACAAACTGT TGTTTGCTAG GA                                 32

(2) INFORMATION FOR SEQ ID NO:437:

(i) SEQUENCE CHARACTERISTICS:
            (A) LENGTH: 27 base pairs
            (B) TYPE: nucleic acid
            (C) STRANDEDNESS: single
            (D) TOPOLOGY: linear (ii) MOLECULE TYPE: DNA (ix) FEATURE:
            (D) OTHER INFORMATION: oligonucleotide primer (xi) SEQUENCE DESCRIPTION: SEQ ID NO:437:

TCACCTCAAG GAGCCTGAGC ACCCGTC                                       27

(2) INFORMATION FOR SEQ ID NO:438:

(i) SEQUENCE CHARACTERISTICS:
            (A) LENGTH: 30 base pairs
            (B) TYPE: nucleic acid
            (C) STRANDEDNESS: single
            (D) TOPOLOGY: linear (ii) MOLECULE TYPE: DNA (ix) FEATURE:
            (D) OTHER INFORMATION: oligonucleotide primer (xi) SEQUENCE DESCRIPTION: SEQ ID NO:438:

```
CCCTGAACCA AGACCGTTCT TCACGAGAAG                                   30

(2) INFORMATION FOR SEQ ID NO:439:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: DNA (ix) FEATURE:
        (D) OTHER INFORMATION: oligonucleotide primer (xi) SEQUENCE DESCRIPTION: SEQ ID NO:439:

GAGGGTCAGA CGCCTGAGGA ACCCTTAC                                     28

(2) INFORMATION FOR SEQ ID NO:440:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: DNA (ix) FEATURE:
        (D) OTHER INFORMATION: oligonucleotide primer (xi) SEQUENCE DESCRIPTION: SEQ ID NO:440:

TAGGCTTTGC CCAGGTTGAC TGGTCCTG                                     28

(2) INFORMATION FOR SEQ ID NO:441:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: DNA (ix) FEATURE:
        (D) OTHER INFORMATION: oligonucleotide primer (xi) SEQUENCE DESCRIPTION: SEQ ID NO:441:

CCTCGGATGC TGGAGATGAC TCAACA                                       26

(2) INFORMATION FOR SEQ ID NO:442:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: DNA (ix) FEATURE:
        (D) OTHER INFORMATION: oligonucleotide primer (xi) SEQUENCE DESCRIPTION: SEQ ID NO:442:

TCACAAGCCT TCTGGCGGTT CGTACA                                       26

(2) INFORMATION FOR SEQ ID NO:443:

(i) SEQUENCE CHARACTERISTICS:
        (A) LENGTH: 30 base pairs
```

(B) TYPE: nucleic acid
          (C) STRANDEDNESS: single
          (D) TOPOLOGY: linear (ii) MOLECULE TYPE: DNA (ix) FEATURE:
          (D) OTHER INFORMATION: oligonucleotide primer (xi) SEQUENCE DESCRIPTION: SEQ ID NO:443:

AAGAGATGTC TGAATCCAGA ATCGAAGGCC                                             30

(2) INFORMATION FOR SEQ ID NO:444:

(i) SEQUENCE CHARACTERISTICS:
          (A) LENGTH: 30 base pairs
          (B) TYPE: nucleic acid
          (C) STRANDEDNESS: single
          (D) TOPOLOGY: linear (ii) MOLECULE TYPE: DNA (ix) FEATURE:
          (D) OTHER INFORMATION: oligonucleotide primer (xi) SEQUENCE DESCRIPTION: SEQ ID NO:444:

CCTCAGTAGA GCTTACATTA TAGTGCCAGG                                             30

(2) INFORMATION FOR SEQ ID NO:445:

(i) SEQUENCE CHARACTERISTICS:
          (A) LENGTH: 28 base pairs
          (B) TYPE: nucleic acid
          (C) STRANDEDNESS: single
          (D) TOPOLOGY: linear (ii) MOLECULE TYPE: DNA (ix) FEATURE:
          (D) OTHER INFORMATION: oligonucleotide primer (xi) SEQUENCE DESCRIPTION: SEQ ID NO:445:

GCTCCTCGGC TTTGACAGAG TGCAAGAC                                               28

(2) INFORMATION FOR SEQ ID NO:446:

(i) SEQUENCE CHARACTERISTICS:
          (A) LENGTH: 30 base pairs
          (B) TYPE: nucleic acid
          (C) STRANDEDNESS: single
          (D) TOPOLOGY: linear (ii) MOLECULE TYPE: DNA (ix) FEATURE:
          (D) OTHER INFORMATION: oligonucleotide primer (xi) SEQUENCE DESCRIPTION: SEQ ID NO:446:

GCATTTGTGT CCAGGTCCTC CATGATGTGT                                             30

(2) INFORMATION FOR SEQ ID NO:447:

(i) SEQUENCE CHARACTERISTICS:
          (A) LENGTH: 28 base pairs
          (B) TYPE: nucleic acid
          (C) STRANDEDNESS: single
          (D) TOPOLOGY: linear (ii) MOLECULE TYPE: DNA (ix) FEATURE:
          (D) OTHER INFORMATION: oligonucleotide primer (xi) SEQUENCE DESCRIPTION: SEQ ID NO:447:

GGGCAAGTTC CGTGGGCATC ATGTTGAC                                              28

(2) INFORMATION FOR SEQ ID NO:448:

(i) SEQUENCE CHARACTERISTICS:
        (A) LENGTH: 31 base pairs
        (B) TYPE: nucleic acid
        (C) STRANDEDNESS: single
        (D) TOPOLOGY: linear (ii) MOLECULE TYPE: DNA (ix) FEATURE:
        (D) OTHER INFORMATION: oligonucleotide primer (xi) SEQUENCE DESCRIPTION: SEQ ID NO:448:

CCAGTAACTC AGCTACTCTT TGTGGCTTTC T                                          31

(2) INFORMATION FOR SEQ ID NO:449:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: DNA (ix) FEATURE:
        (D) OTHER INFORMATION: oligonucleotide primer (xi) SEQUENCE DESCRIPTION: SEQ ID NO:449:

GCATCCGGGA CCTCCAGCGA CTCCT                                                 25

(2) INFORMATION FOR SEQ ID NO:450:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: DNA (ix) FEATURE:
        (D) OTHER INFORMATION: oligonucleotide primer (xi) SEQUENCE DESCRIPTION: SEQ ID NO:450:

AGGCTTGTGG TCGCGCAGGC GCACT                                                 25

(2) INFORMATION FOR SEQ ID NO:451:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: DNA (ix) FEATURE:
        (D) OTHER INFORMATION: oligonucleotide primer (xi) SEQUENCE DESCRIPTION: SEQ ID NO:451:

CCCACTGCGC CCAAACCGAA GTCATAG                                               27

(2) INFORMATION FOR SEQ ID NO:452:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: DNA (ix) FEATURE:
        (D) OTHER INFORMATION: oligonucleotide primer (xi) SEQUENCE DESCRIPTION: SEQ ID NO:452:

TTCTGTTCCT ATAAGGGCAG GGCCTCCT                                              28

(2) INFORMATION FOR SEQ ID NO:453:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: DNA (ix) FEATURE:
        (D) OTHER INFORMATION: oligonucleotide primer (xi) SEQUENCE DESCRIPTION: SEQ ID NO:453:

GATGGCTCCC GACACAAGCG CCAGG                                                 25

(2) INFORMATION FOR SEQ ID NO:454:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: DNA (ix) FEATURE:
        (D) OTHER INFORMATION: oligonucleotide primer (xi) SEQUENCE DESCRIPTION: SEQ ID NO:454:

AGGGTTGTTC CAGGGCGCTA TTTCAGAG                                              28

(2) INFORMATION FOR SEQ ID NO:455:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: DNA (ix) FEATURE:
        (D) OTHER INFORMATION: oligonucleotide primer (xi) SEQUENCE DESCRIPTION: SEQ ID NO:455:

GCTAATGTGA CCAGTTGTCT CTGTTTGGGC                                            30

(2) INFORMATION FOR SEQ ID NO:456:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: DNA

```
    (ix) FEATURE:
         (D) OTHER INFORMATION: oligonucleotide primer (xi) SEQUENCE DESCRIPTION: SEQ ID NO:456:

CAGAAGACTC TTCAGAAATG TCAGCGCGTT                                     30

(2) INFORMATION FOR SEQ ID NO:457:

(i) SEQUENCE CHARACTERISTICS:
         (A) LENGTH: 29 base pairs
         (B) TYPE: nucleic acid
         (C) STRANDEDNESS: single
         (D) TOPOLOGY: linear (ii) MOLECULE TYPE: DNA (ix) FEATURE:
         (D) OTHER INFORMATION: oligonucleotide primer (xi) SEQUENCE DESCRIPTION: SEQ ID NO:457:

CCAGGACCTA TCAGAAGCTG TCGTACCTG                                      29

(2) INFORMATION FOR SEQ ID NO:458:

(i) SEQUENCE CHARACTERISTICS:
         (A) LENGTH: 28 base pairs
         (B) TYPE: nucleic acid
         (C) STRANDEDNESS: single
         (D) TOPOLOGY: linear (ii) MOLECULE TYPE: DNA (ix) FEATURE:
         (D) OTHER INFORMATION: oligonucleotide primer (xi) SEQUENCE DESCRIPTION: SEQ ID NO:458:

GACGATGCCA CAGACAAGGG TTCCCACG                                       28

(2) INFORMATION FOR SEQ ID NO:459:

(i) SEQUENCE CHARACTERISTICS:
         (A) LENGTH: 32 base pairs
         (B) TYPE: nucleic acid
         (C) STRANDEDNESS: single
         (D) TOPOLOGY: linear (ii) MOLECULE TYPE: DNA (ix) FEATURE:
         (D) OTHER INFORMATION: oligonucleotide primer (xi) SEQUENCE DESCRIPTION: SEQ ID NO:459:

GAATAAATCC TTGGGAGTCA TTACCACGCC TT                                  32

(2) INFORMATION FOR SEQ ID NO:460:

(i) SEQUENCE CHARACTERISTICS:
         (A) LENGTH: 32 base pairs
         (B) TYPE: nucleic acid
         (C) STRANDEDNESS: single
         (D) TOPOLOGY: linear (ii) MOLECULE TYPE: DNA (ix) FEATURE:
         (D) OTHER INFORMATION: oligonucleotide primer (xi) SEQUENCE DESCRIPTION: SEQ ID NO:460:

CTGAATCAGA ATCTCCATTC AAACCAGGTC CC                                  32
```

(2) INFORMATION FOR SEQ ID NO:461:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: DNA (ix) FEATURE:
        (D) OTHER INFORMATION: oligonucleotide primer (xi) SEQUENCE DESCRIPTION: SEQ ID NO:461:

CAGTGCTCCA AGCCCAGTGT CATCTTCC                                      28

(2) INFORMATION FOR SEQ ID NO:462:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: DNA (ix) FEATURE:
        (D) OTHER INFORMATION: oligonucleotide primer (xi) SEQUENCE DESCRIPTION: SEQ ID NO:462:

TTGTCAGTCT GGTGGCTTTG GTGCCATC                                      28

(2) INFORMATION FOR SEQ ID NO:463:

(i) SEQUENCE CHARACTERISTICS:
        (A) LENGTH: 31 base pairs
        (B) TYPE: nucleic acid
        (C) STRANDEDNESS: single
        (D) TOPOLOGY: linear (ii) MOLECULE TYPE: DNA (ix) FEATURE:
        (D) OTHER INFORMATION: oligonucleotide primer (xi) SEQUENCE DESCRIPTION: SEQ ID NO:463:

AAGGAGTTTG CCAGAAGACT CGCTCAATTC C                                  31

(2) INFORMATION FOR SEQ ID NO:464:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: DNA (ix) FEATURE:
        (D) OTHER INFORMATION: oligonucleotide primer (xi) SEQUENCE DESCRIPTION: SEQ ID NO:464:

CACGTAATCC TCCATGAGAT ACAAGGGCGG                                    30

(2) INFORMATION FOR SEQ ID NO:465:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: DNA (ix) FEATURE:
    (D) OTHER INFORMATION: oligonucleotide primer (xi) SEQUENCE DESCRIPTION: SEQ ID NO:465:

ACTGAACTGC GCTGCCAGTG CTTGCAG                27

(2) INFORMATION FOR SEQ ID NO:466:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: DNA (ix) FEATURE:
        (D) OTHER INFORMATION: oligonucleotide primer (xi) SEQUENCE DESCRIPTION: SEQ ID NO:466:

CCTAAGTGAT GCTCAAACAC ATTAGGCGCA             30

(2) INFORMATION FOR SEQ ID NO:467:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: DNA (ix) FEATURE:
        (D) OTHER INFORMATION: oligonucleotide primer (xi) SEQUENCE DESCRIPTION: SEQ ID NO:467:

GGCCCTGCTA CCTGTTCTTG GGCCTC                 26

(2) INFORMATION FOR SEQ ID NO:468:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: DNA (ix) FEATURE:
        (D) OTHER INFORMATION: oligonucleotide primer (xi) SEQUENCE DESCRIPTION: SEQ ID NO:468:

CCAGTACAAG CAAATGGCAA AGTGTGAGGG             30

(2) INFORMATION FOR SEQ ID NO:469:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (ii) MOLECULE TYPE: DNA (ix) FEATURE:
        (D) OTHER INFORMATION: oligonucleotide primer (xi) SEQUENCE DESCRIPTION: SEQ ID NO:469:

TTTCTGGGAA CCGGCACACC CTTAACCAC              29

(2) INFORMATION FOR SEQ ID NO:470:

(i) SEQUENCE CHARACTERISTICS:
        (A) LENGTH: 32 base pairs
        (B) TYPE: nucleic acid
        (C) STRANDEDNESS: single
        (D) TOPOLOGY: linear (ii) MOLECULE TYPE: DNA (ix) FEATURE:
        (D) OTHER INFORMATION: oligonucleotide primer (xi) SEQUENCE DESCRIPTION: SEQ ID NO:470:

TTGAAAGTCT TGATGATGAG GCCATAGCAC AG                         32

(2) INFORMATION FOR SEQ ID NO:471:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: DNA (ix) FEATURE:
        (D) OTHER INFORMATION: oligonucleotide primer (xi) SEQUENCE DESCRIPTION: SEQ ID NO:471:

TGCACAGAGT TCACTGAAAC GGAATGCC                            28

(2) INFORMATION FOR SEQ ID NO:472:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: DNA (ix) FEATURE:
        (D) OTHER INFORMATION: oligonucleotide primer (xi) SEQUENCE DESCRIPTION: SEQ ID NO:472:

CAGACAACAT CAGTCTTGTT TGTGCCTG                            28

(2) INFORMATION FOR SEQ ID NO:473:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: DNA (ix) FEATURE:
        (D) OTHER INFORMATION: oligonucleotide primer (xi) SEQUENCE DESCRIPTION: SEQ ID NO:473:

GGAGGGCACC CGCAGCTCCG TCTC                                  24

(2) INFORMATION FOR SEQ ID NO:474:

(i) SEQUENCE CHARACTERISTICS:
        (A) LENGTH: 26 base pairs
        (B) TYPE: nucleic acid
        (C) STRANDEDNESS: single (D) TOPOLOGY: linear (ii) MOLECULE TYPE: DNA (ix) FEATURE:
          (D) OTHER INFORMATION: oligonucleotide primer (xi) SEQUENCE DESCRIPTION: SEQ ID NO:474:

GCACTCGGAG TAATTCACGC GGGCGG                                    26

(2) INFORMATION FOR SEQ ID NO:475:

(i) SEQUENCE CHARACTERISTICS:
          (A) LENGTH: 25 base pairs
          (B) TYPE: nucleic acid
          (C) STRANDEDNESS: single
          (D) TOPOLOGY: linear (ii) MOLECULE TYPE: DNA (ix) FEATURE:
          (D) OTHER INFORMATION: oligonucleotide primer (xi) SEQUENCE DESCRIPTION: SEQ ID NO:475:

GTTCAGGAAC CCGCGACCGC TCGCA                                     25

(2) INFORMATION FOR SEQ ID NO:476:

(i) SEQUENCE CHARACTERISTICS:
          (A) LENGTH: 28 base pairs
          (B) TYPE: nucleic acid
          (C) STRANDEDNESS: single
          (D) TOPOLOGY: linear (ii) MOLECULE TYPE: DNA (ix) FEATURE:
          (D) OTHER INFORMATION: oligonucleotide primer (xi) SEQUENCE DESCRIPTION: SEQ ID NO:476:

CTGTGGGCCT ATGGCGAACA CTTGCAGA                                  28

(2) INFORMATION FOR SEQ ID NO:477:

(i) SEQUENCE CHARACTERISTICS:
          (A) LENGTH: 32 base pairs
          (B) TYPE: nucleic acid
          (C) STRANDEDNESS: single
          (D) TOPOLOGY: linear (ii) MOLECULE TYPE: DNA (ix) FEATURE:
          (D) OTHER INFORMATION: oligonucleotide primer (xi) SEQUENCE DESCRIPTION: SEQ ID NO:477:

GTCTACTTGA ATGTGACCAC TGACAATACC TC                             32

(2) INFORMATION FOR SEQ ID NO:478:

(i) SEQUENCE CHARACTERISTICS:
          (A) LENGTH: 29 base pairs
          (B) TYPE: nucleic acid
          (C) STRANDEDNESS: single
          (D) TOPOLOGY: linear (ii) MOLECULE TYPE: DNA (ix) FEATURE:
          (D) OTHER INFORMATION: oligonucleotide primer (xi) SEQUENCE DESCRIPTION: SEQ ID NO:478:

GTGCCTAGTA GGCTCAAGGC AATCTTGGG                                              29

(2) INFORMATION FOR SEQ ID NO:479:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: DNA (ix) FEATURE:
        (D) OTHER INFORMATION: oligonucleotide primer (xi) SEQUENCE DESCRIPTION: SEQ ID NO:479:

AACATGACTT CCAAGCTGGC CGTGGCTC                                               28

(2) INFORMATION FOR SEQ ID NO:480:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: DNA (ix) FEATURE:
        (D) OTHER INFORMATION: oligonucleotide primer (xi) SEQUENCE DESCRIPTION: SEQ ID NO:480:

GCGCAGTGTG GTCCACTCTC AATCACTC                                               28

(2) INFORMATION FOR SEQ ID NO:481:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: DNA (ix) FEATURE:
        (D) OTHER INFORMATION: oligonucleotide primer (xi) SEQUENCE DESCRIPTION: SEQ ID NO:481:

GTACGGACCA ACTCCACCTT TGTCCA                                                 26

(2) INFORMATION FOR SEQ ID NO:482:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: DNA (ix) FEATURE:
        (D) OTHER INFORMATION: oligonucleotide primer (xi) SEQUENCE DESCRIPTION: SEQ ID NO:482:

TCAGACTTTG CTGGGACCTC GTGCTT                                                 26

(2) INFORMATION FOR SEQ ID NO:483:

(i) SEQUENCE CHARACTERISTICS:
        (A) LENGTH: 26 base pairs (B) TYPE: nucleic acid
            (C) STRANDEDNESS: single
            (D) TOPOLOGY: linear (ii) MOLECULE TYPE: DNA (ix) FEATURE:
            (D) OTHER INFORMATION: oligonucleotide primer (xi) SEQUENCE DESCRIPTION: SEQ ID NO:483:

CCTTCTGTAC GAGATGCTCA TTGGCC                                              26

(2) INFORMATION FOR SEQ ID NO:484:

(i) SEQUENCE CHARACTERISTICS:
            (A) LENGTH: 27 base pairs
            (B) TYPE: nucleic acid
            (C) STRANDEDNESS: single
            (D) TOPOLOGY: linear (ii) MOLECULE TYPE: DNA (ix) FEATURE:
            (D) OTHER INFORMATION: oligonucleotide primer (xi) SEQUENCE DESCRIPTION: SEQ ID NO:484:

CGATGAGGTT CTTGTCGCTG TAGGAGA                                             27

(2) INFORMATION FOR SEQ ID NO:485:

(i) SEQUENCE CHARACTERISTICS:
            (A) LENGTH: 26 base pairs
            (B) TYPE: nucleic acid
            (C) STRANDEDNESS: single
            (D) TOPOLOGY: linear (ii) MOLECULE TYPE: DNA (ix) FEATURE:
            (D) OTHER INFORMATION: oligonucleotide primer (xi) SEQUENCE DESCRIPTION: SEQ ID NO:485:

TCCAGGCAGG GTAGTGGAGT GATTCT                                              26

(2) INFORMATION FOR SEQ ID NO:486:

(i) SEQUENCE CHARACTERISTICS:
            (A) LENGTH: 26 base pairs
            (B) TYPE: nucleic acid
            (C) STRANDEDNESS: single
            (D) TOPOLOGY: linear (ii) MOLECULE TYPE: DNA (ix) FEATURE:
            (D) OTHER INFORMATION: oligonucleotide primer (xi) SEQUENCE DESCRIPTION: SEQ ID NO:486:

AAAGCCAAGG CTGTCTTGTC GTAGGC                                              26

(2) INFORMATION FOR SEQ ID NO:487:

(i) SEQUENCE CHARACTERISTICS:
            (A) LENGTH: 26 base pairs
            (B) TYPE: nucleic acid
            (C) STRANDEDNESS: single
            (D) TOPOLOGY: linear (ii) MOLECULE TYPE: DNA (ix) FEATURE:
            (D) OTHER INFORMATION: oligonucleotide primer (xi) SEQUENCE DESCRIPTION: SEQ ID NO:487:

TTCCAACCAG TGGAATTGGT CAGCCC                                          26

(2) INFORMATION FOR SEQ ID NO:488:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: DNA (ix) FEATURE:
        (D) OTHER INFORMATION: oligonucleotide primer (xi) SEQUENCE DESCRIPTION: SEQ ID NO:488:

GACTGCGGCA AAGCACACCG GGTAAA                                          26

(2) INFORMATION FOR SEQ ID NO:489:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: DNA (ix) FEATURE:
        (D) OTHER INFORMATION: oligonucleotide primer (xi) SEQUENCE DESCRIPTION: SEQ ID NO:489:

TTTCCAGATG TCCCTGGTAG ATTTGGGA                                        28

(2) INFORMATION FOR SEQ ID NO:490:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: DNA (ix) FEATURE:
        (D) OTHER INFORMATION: oligonucleotide primer (xi) SEQUENCE DESCRIPTION: SEQ ID NO:490:

GGCCCAATGG AGAGCTGTCA TCTTTAAC                                        28

(2) INFORMATION FOR SEQ ID NO:491:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: DNA (ix) FEATURE:
        (D) OTHER INFORMATION: oligonucleotide primer (xi) SEQUENCE DESCRIPTION: SEQ ID NO:491:

GCAGCCAAAG TACAAAGAGC GCCGAG                                          26

(2) INFORMATION FOR SEQ ID NO:492:

```
        (i) SEQUENCE CHARACTERISTICS:
            (A) LENGTH: 26 base pairs
            (B) TYPE: nucleic acid
            (C) STRANDEDNESS: single
            (D) TOPOLOGY: linear (ii) MOLECULE TYPE: DNA (ix) FEATURE:
            (D) OTHER INFORMATION: oligonucleotide primer (xi) SEQUENCE DESCRIPTION: SEQ ID NO:492:

GCTGTGACTG GCTGGGCAAT TCCATG                                          26

(2) INFORMATION FOR SEQ ID NO:493:

(i) SEQUENCE CHARACTERISTICS:
            (A) LENGTH: 28 base pairs
            (B) TYPE: nucleic acid
            (C) STRANDEDNESS: single
            (D) TOPOLOGY: linear (ii) MOLECULE TYPE: DNA (ix) FEATURE:
            (D) OTHER INFORMATION: oligonucleotide primer (xi) SEQUENCE DESCRIPTION: SEQ ID NO:493:

TTATTGTAGA CAGTGCCACC GCCCTTTA                                        28

(2) INFORMATION FOR SEQ ID NO:494:

(i) SEQUENCE CHARACTERISTICS:
            (A) LENGTH: 28 base pairs
            (B) TYPE: nucleic acid
            (C) STRANDEDNESS: single
            (D) TOPOLOGY: linear (ii) MOLECULE TYPE: DNA (ix) FEATURE:
            (D) OTHER INFORMATION: oligonucleotide primer (xi) SEQUENCE DESCRIPTION: SEQ ID NO:494:

TCGTAGATTT GGCAGATTCT GGTTTCCC                                        28

(2) INFORMATION FOR SEQ ID NO:495:

(i) SEQUENCE CHARACTERISTICS:
            (A) LENGTH: 26 base pairs
            (B) TYPE: nucleic acid
            (C) STRANDEDNESS: single
            (D) TOPOLOGY: linear (ii) MOLECULE TYPE: DNA (ix) FEATURE:
            (D) OTHER INFORMATION: oligonucleotide primer (xi) SEQUENCE DESCRIPTION: SEQ ID NO:495:

GGCTCCTGAA TATCAGTCAC TGTTCG                                          26

(2) INFORMATION FOR SEQ ID NO:496:

(i) SEQUENCE CHARACTERISTICS:
            (A) LENGTH: 26 base pairs
            (B) TYPE: nucleic acid
            (C) STRANDEDNESS: single
            (D) TOPOLOGY: linear (ii) MOLECULE TYPE: DNA
```

```
        (ix) FEATURE:
              (D) OTHER INFORMATION: oligonucleotide primer (xi) SEQUENCE DESCRIPTION: SEQ ID NO:496:

ACCCTAACGC CGCCATCACT AAGAGA                                              26

(2) INFORMATION FOR SEQ ID NO:497:

(i) SEQUENCE CHARACTERISTICS:
              (A) LENGTH: 23 base pairs
              (B) TYPE: nucleic acid
              (C) STRANDEDNESS: single
              (D) TOPOLOGY: linear (ii) MOLECULE TYPE: DNA (ix) FEATURE:
              (D) OTHER INFORMATION: oligonucleotide primer (xi) SEQUENCE DESCRIPTION: SEQ ID NO:497:

CCGGCAAGAC AGCGAGCGGT GCG                                                 23

(2) INFORMATION FOR SEQ ID NO:498:

(i) SEQUENCE CHARACTERISTICS:
              (A) LENGTH: 23 base pairs
              (B) TYPE: nucleic acid
              (C) STRANDEDNESS: single
              (D) TOPOLOGY: linear (ii) MOLECULE TYPE: DNA (ix) FEATURE:
              (D) OTHER INFORMATION: oligonucleotide primer (xi) SEQUENCE DESCRIPTION: SEQ ID NO:498:

GGCGCTGATC TCGCCGTTGA GGG                                                 23

(2) INFORMATION FOR SEQ ID NO:499:

(i) SEQUENCE CHARACTERISTICS:
              (A) LENGTH: 27 base pairs
              (B) TYPE: nucleic acid
              (C) STRANDEDNESS: single
              (D) TOPOLOGY: linear (ii) MOLECULE TYPE: DNA (ix) FEATURE:
              (D) OTHER INFORMATION: oligonucleotide primer (xi) SEQUENCE DESCRIPTION: SEQ ID NO:499:

AGCTGGTGCA TCACATCAAC AACGAGC                                             27

(2) INFORMATION FOR SEQ ID NO:500:

(i) SEQUENCE CHARACTERISTICS:
              (A) LENGTH: 28 base pairs
              (B) TYPE: nucleic acid
              (C) STRANDEDNESS: single
              (D) TOPOLOGY: linear (ii) MOLECULE TYPE: DNA (ix) FEATURE:
              (D) OTHER INFORMATION: oligonucleotide primer (xi) SEQUENCE DESCRIPTION: SEQ ID NO:500:

CTGGGATCTT GCAGATGTAG GGTTTCTC                                            28
```

(2) INFORMATION FOR SEQ ID NO:501:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: DNA (ix) FEATURE:
        (D) OTHER INFORMATION: oligonucleotide primer (xi) SEQUENCE DESCRIPTION: SEQ ID NO:501:

CTACAGTCAC TGCCCAGTTA CCCACA                                                  26

(2) INFORMATION FOR SEQ ID NO:502:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: DNA (ix) FEATURE:
        (D) OTHER INFORMATION: oligonucleotide primer (xi) SEQUENCE DESCRIPTION: SEQ ID NO:502:

GGGCGGTGTA GAATCAGAGT CATTCTGA                                            28

(2) INFORMATION FOR SEQ ID NO:503:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: DNA (ix) FEATURE:
        (D) OTHER INFORMATION: oligonucleotide primer (xi) SEQUENCE DESCRIPTION: SEQ ID NO:503:

ACTCCGCAGC GTCTGAAGTT GCTGG                                                25

(2) INFORMATION FOR SEQ ID NO:504:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: DNA (ix) FEATURE:
        (D) OTHER INFORMATION: oligonucleotide primer (xi) SEQUENCE DESCRIPTION: SEQ ID NO:504:

GGAGATGCCT TGGAAATCCG CTTTGTTC                                            28

(2) INFORMATION FOR SEQ ID NO:505:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: DNA (ix) FEATURE:
             (D) OTHER INFORMATION: oligonucleotide primer (xi) SEQUENCE DESCRIPTION: SEQ ID NO:505:

GGTGGACATT GCCTGCGGCA TGGA                                                  24

(2) INFORMATION FOR SEQ ID NO:506:

(i) SEQUENCE CHARACTERISTICS:
             (A) LENGTH: 28 base pairs
             (B) TYPE: nucleic acid
             (C) STRANDEDNESS: single
             (D) TOPOLOGY: linear (ii) MOLECULE TYPE: DNA (ix) FEATURE:
             (D) OTHER INFORMATION: oligonucleotide primer (xi) SEQUENCE DESCRIPTION: SEQ ID NO:506:

CCCAAGATGT TCTCCAGTTC CATTCGCA                                              28

(2) INFORMATION FOR SEQ ID NO:507:

(i) SEQUENCE CHARACTERISTICS:
             (A) LENGTH: 26 base pairs
             (B) TYPE: nucleic acid
             (C) STRANDEDNESS: single
             (D) TOPOLOGY: linear (ii) MOLECULE TYPE: DNA (ix) FEATURE:
             (D) OTHER INFORMATION: oligonucleotide primer (xi) SEQUENCE DESCRIPTION: SEQ ID NO:507:

TTCAGAGCCA ACAGGAGCCT ATCCCA                                                26

(2) INFORMATION FOR SEQ ID NO:508:

(i) SEQUENCE CHARACTERISTICS:
             (A) LENGTH: 27 base pairs
             (B) TYPE: nucleic acid
             (C) STRANDEDNESS: single
             (D) TOPOLOGY: linear (ii) MOLECULE TYPE: DNA (ix) FEATURE:
             (D) OTHER INFORMATION: oligonucleotide primer (xi) SEQUENCE DESCRIPTION: SEQ ID NO:508:

CGACTTTAAG GCACAGTCAG GATGGGT                                               27

(2) INFORMATION FOR SEQ ID NO:509:

(i) SEQUENCE CHARACTERISTICS:
             (A) LENGTH: 25 base pairs
             (B) TYPE: nucleic acid
             (C) STRANDEDNESS: single
             (D) TOPOLOGY: linear (ii) MOLECULE TYPE: DNA (ix) FEATURE:
             (D) OTHER INFORMATION: oligonucleotide primer (xi) SEQUENCE DESCRIPTION: SEQ ID NO:509:

ACTGCTCAGA GTGGCAACAC GGAGC                                                 25

(2) INFORMATION FOR SEQ ID NO:510:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: DNA (ix) FEATURE:
        (D) OTHER INFORMATION: oligonucleotide primer (xi) SEQUENCE DESCRIPTION: SEQ ID NO:510:

GGTGCTTGGG CCAGTGTTGT AGACCT                       26

(2) INFORMATION FOR SEQ ID NO:511:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: DNA (ix) FEATURE:
        (D) OTHER INFORMATION: oligonucleotide primer (xi) SEQUENCE DESCRIPTION: SEQ ID NO:511:

ATCGGAACAC GCTGGCTCCA TATCGT                       26

(2) INFORMATION FOR SEQ ID NO:512:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: DNA (ix) FEATURE:
        (D) OTHER INFORMATION: oligonucleotide primer (xi) SEQUENCE DESCRIPTION: SEQ ID NO:512:

CCCTCGGCAA CTTTACAAGA CTCCCT                       26

(2) INFORMATION FOR SEQ ID NO:513:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: DNA (ix) FEATURE:
        (D) OTHER INFORMATION: oligonucleotide primer (xi) SEQUENCE DESCRIPTION: SEQ ID NO:513:

AGCCGCTGGA ACCAAGACAC AATGGA                       26

(2) INFORMATION FOR SEQ ID NO:514:

(i) SEQUENCE CHARACTERISTICS:
        (A) LENGTH: 26 base pairs
        (B) TYPE: nucleic acid
        (C) STRANDEDNESS: single (D) TOPOLOGY: linear (ii) MOLECULE TYPE: DNA (ix) FEATURE:
        (D) OTHER INFORMATION: oligonucleotide primer (xi) SEQUENCE DESCRIPTION: SEQ ID NO:514:

GGTTTACAGT ACCTGCGGTG TTCTCC                                              26

(2) INFORMATION FOR SEQ ID NO:515:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: DNA (ix) FEATURE:
        (D) OTHER INFORMATION: oligonucleotide primer (xi) SEQUENCE DESCRIPTION: SEQ ID NO:515:

AGTCTTCAAG CCACGAGCGG AGGG                                                24

(2) INFORMATION FOR SEQ ID NO:516:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: DNA (ix) FEATURE:
        (D) OTHER INFORMATION: oligonucleotide primer (xi) SEQUENCE DESCRIPTION: SEQ ID NO:516:

GAGGGCGTCA CTGTAGTCCA CGTCA                                               25

(2) INFORMATION FOR SEQ ID NO:517:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: DNA (ix) FEATURE:
        (D) OTHER INFORMATION: oligonucleotide primer (xi) SEQUENCE DESCRIPTION: SEQ ID NO:517:

AGGATAGGCA CAGTGGACCG GGCA                                                24

(2) INFORMATION FOR SEQ ID NO:518:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: DNA (ix) FEATURE:
        (D) OTHER INFORMATION: oligonucleotide primer (xi) SEQUENCE DESCRIPTION: SEQ ID NO:518:

GTCCCACGGG CCTGTTGGGA TTGTTT                                       26

(2) INFORMATION FOR SEQ ID NO:519:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: DNA (ix) FEATURE:
        (D) OTHER INFORMATION: oligonucleotide primer (xi) SEQUENCE DESCRIPTION: SEQ ID NO:519:

AGCTGCTAAC CTGTGCCAAA CCTCCA                                       26

(2) INFORMATION FOR SEQ ID NO:520:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: DNA (ix) FEATURE:
        (D) OTHER INFORMATION: oligonucleotide primer (xi) SEQUENCE DESCRIPTION: SEQ ID NO:520:

GGAGATGTGA TGGTGACAGG GTGTGC                                       26

(2) INFORMATION FOR SEQ ID NO:521:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: DNA (ix) FEATURE:
        (D) OTHER INFORMATION: oligonucleotide primer (xi) SEQUENCE DESCRIPTION: SEQ ID NO:521:

CCCTGTGGAA TGTTGGGTCT CACTCT                                       26

(2) INFORMATION FOR SEQ ID NO:522:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: DNA (ix) FEATURE:
        (D) OTHER INFORMATION: oligonucleotide primer (xi) SEQUENCE DESCRIPTION: SEQ ID NO:522:

CAGGGACCTT AGCCCGATTC ATGCC                                        25

(2) INFORMATION FOR SEQ ID NO:523:

(i) SEQUENCE CHARACTERISTICS:
        (A) LENGTH: 24 base pairs

```
          (B) TYPE: nucleic acid
          (C) STRANDEDNESS: single
          (D) TOPOLOGY: linear (ii) MOLECULE TYPE: DNA (ix) FEATURE:
          (D) OTHER INFORMATION: oligonucleotide primer (xi) SEQUENCE DESCRIPTION: SEQ ID NO:523:

CCGGCGGTAC AAGAACAACG AGGC                                              24

(2) INFORMATION FOR SEQ ID NO:524:

(i) SEQUENCE CHARACTERISTICS:
          (A) LENGTH: 23 base pairs
          (B) TYPE: nucleic acid
          (C) STRANDEDNESS: single
          (D) TOPOLOGY: linear (ii) MOLECULE TYPE: DNA (ix) FEATURE:
          (D) OTHER INFORMATION: oligonucleotide primer (xi) SEQUENCE DESCRIPTION: SEQ ID NO:524:

GATAGGGTCC CTGACGTGCC GGG                                               23

(2) INFORMATION FOR SEQ ID NO:525:

(i) SEQUENCE CHARACTERISTICS:
          (A) LENGTH: 26 base pairs
          (B) TYPE: nucleic acid
          (C) STRANDEDNESS: single
          (D) TOPOLOGY: linear (ii) MOLECULE TYPE: DNA (ix) FEATURE:
          (D) OTHER INFORMATION: oligonucleotide primer (xi) SEQUENCE DESCRIPTION: SEQ ID NO:525:

ACACTCCGTG GCCCACCCTT TGTTAC                                            26

(2) INFORMATION FOR SEQ ID NO:526:

(i) SEQUENCE CHARACTERISTICS:
          (A) LENGTH: 26 base pairs
          (B) TYPE: nucleic acid
          (C) STRANDEDNESS: single
          (D) TOPOLOGY: linear (ii) MOLECULE TYPE: DNA (ix) FEATURE:
          (D) OTHER INFORMATION: oligonucleotide primer (xi) SEQUENCE DESCRIPTION: SEQ ID NO:526:

GGTGGAACAG GAGGCTTTAG GACCGA                                            26

(2) INFORMATION FOR SEQ ID NO:527:

(i) SEQUENCE CHARACTERISTICS:
          (A) LENGTH: 24 base pairs
          (B) TYPE: nucleic acid
          (C) STRANDEDNESS: single
          (D) TOPOLOGY: linear (ii) MOLECULE TYPE: DNA (ix) FEATURE:
          (D) OTHER INFORMATION: oligonucleotide primer
```

(xi) SEQUENCE DESCRIPTION: SEQ ID NO:527:

GGGAGCTTCG TGTCCTGTAT GGCC                                                24

(2) INFORMATION FOR SEQ ID NO:528:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: DNA (ix) FEATURE:
        (D) OTHER INFORMATION: oligonucleotide primer (xi) SEQUENCE DESCRIPTION: SEQ ID NO:528:

AGTCTGTATT TCTTGATCTT CCGCTGGC                                            28

(2) INFORMATION FOR SEQ ID NO:529:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: DNA (ix) FEATURE:
        (D) OTHER INFORMATION: oligonucleotide primer (xi) SEQUENCE DESCRIPTION: SEQ ID NO:529:

CCCTGACCAT CCTGTACTAT GTTGGG                                              26

(2) INFORMATION FOR SEQ ID NO:530:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: DNA (ix) FEATURE:
        (D) OTHER INFORMATION: oligonucleotide primer (xi) SEQUENCE DESCRIPTION: SEQ ID NO:530:

GGGTAGCCCA AATCCCATTG CCACAC                                              26

(2) INFORMATION FOR SEQ ID NO:531:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: DNA (ix) FEATURE:
        (D) OTHER INFORMATION: oligonucleotide primer (xi) SEQUENCE DESCRIPTION: SEQ ID NO:531:

TCTGAAGACC ACCCTCATCG CCGG                                                24

(2) INFORMATION FOR SEQ ID NO:532:

```
    (i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: DNA (ix) FEATURE:
        (D) OTHER INFORMATION: oligonucleotide primer (xi) SEQUENCE DESCRIPTION: SEQ ID NO:532:

CAACTCTATG AGCACCCACA CTCCTC                                             26

(2) INFORMATION FOR SEQ ID NO:533:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: DNA (ix) FEATURE:
        (D) OTHER INFORMATION: oligonucleotide primer (xi) SEQUENCE DESCRIPTION: SEQ ID NO:533:

CTCCCATGTT TCCACCCGGC ACCC                                               24

(2) INFORMATION FOR SEQ ID NO:534:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: DNA (ix) FEATURE:
        (D) OTHER INFORMATION: oligonucleotide primer (xi) SEQUENCE DESCRIPTION: SEQ ID NO:534:

GGCGCGGAGG CTCATGTCTG TAATC                                              25

(2) INFORMATION FOR SEQ ID NO:535:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: DNA (ix) FEATURE:
        (D) OTHER INFORMATION: oligonucleotide primer (xi) SEQUENCE DESCRIPTION: SEQ ID NO:535:

TGCCCATTTG ATCGACAAGT AACAGACC                                           28

(2) INFORMATION FOR SEQ ID NO:536:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: DNA
```

(ix) FEATURE:
              (D) OTHER INFORMATION: oligonucleotide primer (xi) SEQUENCE DESCRIPTION: SEQ ID NO:536:

ACATGAGTGG GCTAGTTTGA CAACCTTC                                            28

(2) INFORMATION FOR SEQ ID NO:537:

(i) SEQUENCE CHARACTERISTICS:
              (A) LENGTH: 28 base pairs
              (B) TYPE: nucleic acid
              (C) STRANDEDNESS: single
              (D) TOPOLOGY: linear (ii) MOLECULE TYPE: DNA (ix) FEATURE:
              (D) OTHER INFORMATION: oligonucleotide primer (xi) SEQUENCE DESCRIPTION: SEQ ID NO:537:

GGGTTGGGTC CAACTGTAAT TGTCTGTC                                            28

(2) INFORMATION FOR SEQ ID NO:538:

(i) SEQUENCE CHARACTERISTICS:
              (A) LENGTH: 28 base pairs
              (B) TYPE: nucleic acid
              (C) STRANDEDNESS: single
              (D) TOPOLOGY: linear (ii) MOLECULE TYPE: DNA (ix) FEATURE:
              (D) OTHER INFORMATION: oligonucleotide primer (xi) SEQUENCE DESCRIPTION: SEQ ID NO:538:

TCCATAAACA CAGGCAACGT GCCTAACT                                            28

(2) INFORMATION FOR SEQ ID NO:539:

(i) SEQUENCE CHARACTERISTICS:
              (A) LENGTH: 26 base pairs
              (B) TYPE: nucleic acid
              (C) STRANDEDNESS: single
              (D) TOPOLOGY: linear (ii) MOLECULE TYPE: DNA (ix) FEATURE:
              (D) OTHER INFORMATION: oligonucleotide primer (xi) SEQUENCE DESCRIPTION: SEQ ID NO:539:

AGCTGGAGCT GATGTTTGGG TGCCAG                                              26

(2) INFORMATION FOR SEQ ID NO:540:

(i) SEQUENCE CHARACTERISTICS:
              (A) LENGTH: 26 base pairs
              (B) TYPE: nucleic acid
              (C) STRANDEDNESS: single
              (D) TOPOLOGY: linear (ii) MOLECULE TYPE: DNA (ix) FEATURE:
              (D) OTHER INFORMATION: oligonucleotide primer (xi) SEQUENCE DESCRIPTION: SEQ ID NO:540:

CTTAGACGCC AGCAGCATGG GTTGGT                                              26

(2) INFORMATION FOR SEQ ID NO:541:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: DNA (ix) FEATURE:
        (D) OTHER INFORMATION: oligonucleotide primer (xi) SEQUENCE DESCRIPTION: SEQ ID NO:541:

CCGGAAACCT GCTAACGATA GAGACTC                                   27

(2) INFORMATION FOR SEQ ID NO:542:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: DNA (ix) FEATURE:
        (D) OTHER INFORMATION: oligonucleotide primer (xi) SEQUENCE DESCRIPTION: SEQ ID NO:542:

TGGTGTTACT GATGCTCCGG TTCCTC                                    26

(2) INFORMATION FOR SEQ ID NO:543:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: DNA (ix) FEATURE:
        (D) OTHER INFORMATION: oligonucleotide primer (xi) SEQUENCE DESCRIPTION: SEQ ID NO:543:

GACTGTCTAC ACCTGCACCG GGCA                                      24

(2) INFORMATION FOR SEQ ID NO:544:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: DNA (ix) FEATURE:
        (D) OTHER INFORMATION: oligonucleotide primer (xi) SEQUENCE DESCRIPTION: SEQ ID NO:544:

GAATGGCCCT CAGAGCATCT AGGCC                                     25

(2) INFORMATION FOR SEQ ID NO:545:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: DNA (ix) FEATURE:
                     (D) OTHER INFORMATION: oligonucleotide primer (xi) SEQUENCE DESCRIPTION: SEQ ID NO:545:

ACCTATTCGT AGTAGGTGCT TGGCGG                                              26

(2) INFORMATION FOR SEQ ID NO:546:

(i) SEQUENCE CHARACTERISTICS:
                     (A) LENGTH: 28 base pairs
                     (B) TYPE: nucleic acid
                     (C) STRANDEDNESS: single
                     (D) TOPOLOGY: linear (ii) MOLECULE TYPE: DNA (ix) FEATURE:
                     (D) OTHER INFORMATION: oligonucleotide primer (xi) SEQUENCE DESCRIPTION: SEQ ID NO:546:

AGCTCATACA GCCTTCCACG AACTTCAA                                            28

(2) INFORMATION FOR SEQ ID NO:547:

(i) SEQUENCE CHARACTERISTICS:
                     (A) LENGTH: 23 base pairs
                     (B) TYPE: nucleic acid
                     (C) STRANDEDNESS: single
                     (D) TOPOLOGY: linear (ii) MOLECULE TYPE: DNA (ix) FEATURE:
                     (D) OTHER INFORMATION: oligonucleotide primer (xi) SEQUENCE DESCRIPTION: SEQ ID NO:547:

TGCAGGTCCT GGTGGGTCAG CCC                                                 23

(2) INFORMATION FOR SEQ ID NO:548:

(i) SEQUENCE CHARACTERISTICS:
                     (A) LENGTH: 23 base pairs
                     (B) TYPE: nucleic acid
                     (C) STRANDEDNESS: single
                     (D) TOPOLOGY: linear (ii) MOLECULE TYPE: DNA (ix) FEATURE:
                     (D) OTHER INFORMATION: oligonucleotide primer (xi) SEQUENCE DESCRIPTION: SEQ ID NO:548:

ACCAGCGGTG TGGGACTGGT CCC                                                 23

(2) INFORMATION FOR SEQ ID NO:549:

(i) SEQUENCE CHARACTERISTICS:
                     (A) LENGTH: 24 base pairs
                     (B) TYPE: nucleic acid
                     (C) STRANDEDNESS: single
                     (D) TOPOLOGY: linear (ii) MOLECULE TYPE: DNA (ix) FEATURE:
                     (D) OTHER INFORMATION: oligonucleotide primer (xi) SEQUENCE DESCRIPTION: SEQ ID NO:549:

ACTAGGACCA GACTGCACCC GGCA                                                24

(2) INFORMATION FOR SEQ ID NO:550:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: DNA (ix) FEATURE:
        (D) OTHER INFORMATION: oligonucleotide primer (xi) SEQUENCE DESCRIPTION: SEQ ID NO:550:

CCCTCGTCAC TCCCAATACT CGGCA                                          25

(2) INFORMATION FOR SEQ ID NO:551:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: DNA (ix) FEATURE:
        (D) OTHER INFORMATION: oligonucleotide primer (xi) SEQUENCE DESCRIPTION: SEQ ID NO:551:

GGAGCAGGAG CTTCTCGACT TCACC                                          25

(2) INFORMATION FOR SEQ ID NO:552:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: DNA (ix) FEATURE:
        (D) OTHER INFORMATION: oligonucleotide primer (xi) SEQUENCE DESCRIPTION: SEQ ID NO:552:

GCATTGACTC AGGTCCCAGT TGCTCTT                                     27

(2) INFORMATION FOR SEQ ID NO:553:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: DNA (ix) FEATURE:
        (D) OTHER INFORMATION: oligonucleotide primer (xi) SEQUENCE DESCRIPTION: SEQ ID NO:553:

CTAGAGAATC CCAGAATGCG AAACTCAG                                   28

(2) INFORMATION FOR SEQ ID NO:554:

(i) SEQUENCE CHARACTERISTICS:
        (A) LENGTH: 27 base pairs
        (B) TYPE: nucleic acid
        (C) STRANDEDNESS: single (D) TOPOLOGY: linear (ii) MOLECULE TYPE: DNA (ix) FEATURE:
           (D) OTHER INFORMATION: oligonucleotide primer (xi) SEQUENCE DESCRIPTION: SEQ ID NO:554:

AGGTAGGTCT TTGTAGCCAA TGTTACC                                              27

(2) INFORMATION FOR SEQ ID NO:555:

(i) SEQUENCE CHARACTERISTICS:
           (A) LENGTH: 27 base pairs
           (B) TYPE: nucleic acid
           (C) STRANDEDNESS: single
           (D) TOPOLOGY: linear (ii) MOLECULE TYPE: DNA (ix) FEATURE:
           (D) OTHER INFORMATION: oligonucleotide primer (xi) SEQUENCE DESCRIPTION: SEQ ID NO:555:

CTCTTTGATT TGGTGTGCCG GACTCTG                                              27

(2) INFORMATION FOR SEQ ID NO:556:

(i) SEQUENCE CHARACTERISTICS:
           (A) LENGTH: 26 base pairs
           (B) TYPE: nucleic acid
           (C) STRANDEDNESS: single
           (D) TOPOLOGY: linear (ii) MOLECULE TYPE: DNA (ix) FEATURE:
           (D) OTHER INFORMATION: oligonucleotide primer (xi) SEQUENCE DESCRIPTION: SEQ ID NO:556:

CACCATACTT GGCCTGGACG GCGTAA                                               26

(2) INFORMATION FOR SEQ ID NO:557:

(i) SEQUENCE CHARACTERISTICS:
           (A) LENGTH: 27 base pairs
           (B) TYPE: nucleic acid
           (C) STRANDEDNESS: single
           (D) TOPOLOGY: linear (ii) MOLECULE TYPE: DNA (ix) FEATURE:
           (D) OTHER INFORMATION: oligonucleotide primer (xi) SEQUENCE DESCRIPTION: SEQ ID NO:557:

CCTGGAAGCC TAGAAATGGG ACTGTTG                                              27

(2) INFORMATION FOR SEQ ID NO:558:

(i) SEQUENCE CHARACTERISTICS:
           (A) LENGTH: 28 base pairs
           (B) TYPE: nucleic acid
           (C) STRANDEDNESS: single
           (D) TOPOLOGY: linear (ii) MOLECULE TYPE: DNA (ix) FEATURE:
           (D) OTHER INFORMATION: oligonucleotide primer (xi) SEQUENCE DESCRIPTION: SEQ ID NO:558:

```
ATACTTTGCT CTGGGCAGTT GTGAGACA                                              28

(2) INFORMATION FOR SEQ ID NO:559:

(i) SEQUENCE CHARACTERISTICS:
         (A) LENGTH: 28 base pairs
         (B) TYPE: nucleic acid
         (C) STRANDEDNESS: single
         (D) TOPOLOGY: linear (ii) MOLECULE TYPE: DNA (ix) FEATURE:
         (D) OTHER INFORMATION: oligonucleotide primer (xi) SEQUENCE DESCRIPTION: SEQ ID NO:559:

TACCCTCTAC AGCCTTATGA CGAAATGC                                              28

(2) INFORMATION FOR SEQ ID NO:560:

(i) SEQUENCE CHARACTERISTICS:
         (A) LENGTH: 28 base pairs
         (B) TYPE: nucleic acid
         (C) STRANDEDNESS: single
         (D) TOPOLOGY: linear (ii) MOLECULE TYPE: DNA (ix) FEATURE:
         (D) OTHER INFORMATION: oligonucleotide primer (xi) SEQUENCE DESCRIPTION: SEQ ID NO:560:

CAATCCCTCG CAGGTCCAAT ACTGTAGA                                              28

(2) INFORMATION FOR SEQ ID NO:561:

(i) SEQUENCE CHARACTERISTICS:
         (A) LENGTH: 24 base pairs
         (B) TYPE: nucleic acid
         (C) STRANDEDNESS: single
         (D) TOPOLOGY: linear (ii) MOLECULE TYPE: DNA (ix) FEATURE:
         (D) OTHER INFORMATION: oligonucleotide primer (xi) SEQUENCE DESCRIPTION: SEQ ID NO:561:

AGAAGATCGG CATGGGTCGG CCTG                                                  24

(2) INFORMATION FOR SEQ ID NO:562:

(i) SEQUENCE CHARACTERISTICS:
         (A) LENGTH: 25 base pairs
         (B) TYPE: nucleic acid
         (C) STRANDEDNESS: single
         (D) TOPOLOGY: linear (ii) MOLECULE TYPE: DNA (ix) FEATURE:
         (D) OTHER INFORMATION: oligonucleotide primer (xi) SEQUENCE DESCRIPTION: SEQ ID NO:562:

GGTTTCGGTG GTCGAGCGAG TGCAT                                                 25

(2) INFORMATION FOR SEQ ID NO:563:

(i) SEQUENCE CHARACTERISTICS:
         (A) LENGTH: 24 base pairs
```

(B) TYPE: nucleic acid
           (C) STRANDEDNESS: single
           (D) TOPOLOGY: linear (ii) MOLECULE TYPE: DNA (ix) FEATURE:
           (D) OTHER INFORMATION: oligonucleotide primer (xi) SEQUENCE DESCRIPTION: SEQ ID NO:563:

TTCTCCACAC CTTGAGGGCT CGGG                                              24

(2) INFORMATION FOR SEQ ID NO:564:

(i) SEQUENCE CHARACTERISTICS:
           (A) LENGTH: 24 base pairs
           (B) TYPE: nucleic acid
           (C) STRANDEDNESS: single
           (D) TOPOLOGY: linear (ii) MOLECULE TYPE: DNA (ix) FEATURE:
           (D) OTHER INFORMATION: oligonucleotide primer (xi) SEQUENCE DESCRIPTION: SEQ ID NO:564:

GCAGAACTGG CAGCGGTTTC GCCG                                              24

(2) INFORMATION FOR SEQ ID NO:565:

(i) SEQUENCE CHARACTERISTICS:
           (A) LENGTH: 26 base pairs
           (B) TYPE: nucleic acid
           (C) STRANDEDNESS: single
           (D) TOPOLOGY: linear (ii) MOLECULE TYPE: DNA (ix) FEATURE:
           (D) OTHER INFORMATION: oligonucleotide primer (xi) SEQUENCE DESCRIPTION: SEQ ID NO:565:

CCTACTGTTC GTTCACCAAC GGCGAG                                            26

(2) INFORMATION FOR SEQ ID NO:566:

(i) SEQUENCE CHARACTERISTICS:
           (A) LENGTH: 26 base pairs
           (B) TYPE: nucleic acid
           (C) STRANDEDNESS: single
           (D) TOPOLOGY: linear (ii) MOLECULE TYPE: DNA (ix) FEATURE:
           (D) OTHER INFORMATION: oligonucleotide primer (xi) SEQUENCE DESCRIPTION: SEQ ID NO:566:

CTGAGAGTCA AAGGCACGGC ACACTC                                            26

(2) INFORMATION FOR SEQ ID NO:567:

(i) SEQUENCE CHARACTERISTICS:
           (A) LENGTH: 28 base pairs
           (B) TYPE: nucleic acid
           (C) STRANDEDNESS: single
           (D) TOPOLOGY: linear (ii) MOLECULE TYPE: DNA (ix) FEATURE:
           (D) OTHER INFORMATION: oligonucleotide primer (xi) SEQUENCE DESCRIPTION: SEQ ID NO:567:

ATGGGATGCA GAACTCTGGC AATGAGAT                              28

(2) INFORMATION FOR SEQ ID NO:568:

(i) SEQUENCE CHARACTERISTICS:
      (A) LENGTH: 28 base pairs
      (B) TYPE: nucleic acid
      (C) STRANDEDNESS: single
      (D) TOPOLOGY: linear (ii) MOLECULE TYPE: DNA (ix) FEATURE:
      (D) OTHER INFORMATION: oligonucleotide primer (xi) SEQUENCE DESCRIPTION: SEQ ID NO:568:

CAGTGTTGAA TGGCTCTGCT ATTGTGAC                              28

(2) INFORMATION FOR SEQ ID NO:569:

(i) SEQUENCE CHARACTERISTICS:
      (A) LENGTH: 28 base pairs
      (B) TYPE: nucleic acid
      (C) STRANDEDNESS: single
      (D) TOPOLOGY: linear (ii) MOLECULE TYPE: DNA (ix) FEATURE:
      (D) OTHER INFORMATION: oligonucleotide primer (xi) SEQUENCE DESCRIPTION: SEQ ID NO:569:

CTGCGCTTAC CACACTGTGA TCCTAAAA                              28

(2) INFORMATION FOR SEQ ID NO:570:

(i) SEQUENCE CHARACTERISTICS:
      (A) LENGTH: 28 base pairs
      (B) TYPE: nucleic acid
      (C) STRANDEDNESS: single
      (D) TOPOLOGY: linear (ii) MOLECULE TYPE: DNA (ix) FEATURE:
      (D) OTHER INFORMATION: oligonucleotide primer (xi) SEQUENCE DESCRIPTION: SEQ ID NO:570:

GCCAATACCA ACAGTCCCGT CAATCACA                              28

(2) INFORMATION FOR SEQ ID NO:571:

(i) SEQUENCE CHARACTERISTICS:
      (A) LENGTH: 24 base pairs
      (B) TYPE: nucleic acid
      (C) STRANDEDNESS: single
      (D) TOPOLOGY: linear (ii) MOLECULE TYPE: DNA (ix) FEATURE:
      (D) OTHER INFORMATION: oligonucleotide primer (xi) SEQUENCE DESCRIPTION: SEQ ID NO:571:

CCTTCATCGC CATCAAGCCG GACG                                  24

(2) INFORMATION FOR SEQ ID NO:572:

```
    (i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: DNA (ix) FEATURE:
        (D) OTHER INFORMATION: oligonucleotide primer (xi) SEQUENCE DESCRIPTION: SEQ ID NO:572:

GCTTTGAATC TGCTGGATTG GTCTCCC                                   27

(2) INFORMATION FOR SEQ ID NO:573:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: DNA (ix) FEATURE:
        (D) OTHER INFORMATION: oligonucleotide primer (xi) SEQUENCE DESCRIPTION: SEQ ID NO:573:

CCCTGTCCTG ATGGTCAGCT CCCT                                      24

(2) INFORMATION FOR SEQ ID NO:574:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: DNA (ix) FEATURE:
        (D) OTHER INFORMATION: oligonucleotide primer (xi) SEQUENCE DESCRIPTION: SEQ ID NO:574:

CTCAAACGCT GGTGTTAGGC ACAGGG                                    26

(2) INFORMATION FOR SEQ ID NO:575:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: DNA (ix) FEATURE:
        (D) OTHER INFORMATION: oligonucleotide primer (xi) SEQUENCE DESCRIPTION: SEQ ID NO:575:

TCTCGGTGGA CTCTCAGTTC AACCAC                                    26

(2) INFORMATION FOR SEQ ID NO:576:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: DNA
```

(ix) FEATURE:
          (D) OTHER INFORMATION: oligonucleotide primer (xi) SEQUENCE DESCRIPTION: SEQ ID NO:576:

ATCCGTTAGC CAGCCTAATT GTGTTTGG                                              28

(2) INFORMATION FOR SEQ ID NO:577:

(i) SEQUENCE CHARACTERISTICS:
          (A) LENGTH: 24 base pairs
          (B) TYPE: nucleic acid
          (C) STRANDEDNESS: single
          (D) TOPOLOGY: linear (ii) MOLECULE TYPE: DNA (ix) FEATURE:
          (D) OTHER INFORMATION: oligonucleotide primer (xi) SEQUENCE DESCRIPTION: SEQ ID NO:577:

GTAGACCTGG CCCACCAGGG TGTA                                                  24

(2) INFORMATION FOR SEQ ID NO:578:

(i) SEQUENCE CHARACTERISTICS:
          (A) LENGTH: 26 base pairs
          (B) TYPE: nucleic acid
          (C) STRANDEDNESS: single
          (D) TOPOLOGY: linear (ii) MOLECULE TYPE: DNA (ix) FEATURE:
          (D) OTHER INFORMATION: oligonucleotide primer (xi) SEQUENCE DESCRIPTION: SEQ ID NO:578:

GTCTCGGATC TCCCAGGCAA ACATGG                                                26

(2) INFORMATION FOR SEQ ID NO:579:

(i) SEQUENCE CHARACTERISTICS:
          (A) LENGTH: 28 base pairs
          (B) TYPE: nucleic acid
          (C) STRANDEDNESS: single
          (D) TOPOLOGY: linear (ii) MOLECULE TYPE: DNA (ix) FEATURE:
          (D) OTHER INFORMATION: oligonucleotide primer (xi) SEQUENCE DESCRIPTION: SEQ ID NO:579:

TACTGCAACA CTTGCGTCAT CTAGTGTG                                              28

(2) INFORMATION FOR SEQ ID NO:580:

(i) SEQUENCE CHARACTERISTICS:
          (A) LENGTH: 28 base pairs
          (B) TYPE: nucleic acid
          (C) STRANDEDNESS: single
          (D) TOPOLOGY: linear (ii) MOLECULE TYPE: DNA (ix) FEATURE:
          (D) OTHER INFORMATION: oligonucleotide primer (xi) SEQUENCE DESCRIPTION: SEQ ID NO:580:

GTACAAGTTG GAGATGCCGG TGTCAGTT                                              28

(2) INFORMATION FOR SEQ ID NO:581:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: DNA (ix) FEATURE:
        (D) OTHER INFORMATION: oligonucleotide primer (xi) SEQUENCE DESCRIPTION: SEQ ID NO:581:

ATGGCTCTGG ACGTGAAGTC TCGGG                                    25

(2) INFORMATION FOR SEQ ID NO:582:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: DNA (ix) FEATURE:
        (D) OTHER INFORMATION: oligonucleotide primer (xi) SEQUENCE DESCRIPTION: SEQ ID NO:582:

GATCATGGGC CTCAGGTGAA ACTCCG                                  26

(2) INFORMATION FOR SEQ ID NO:583:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: DNA (ix) FEATURE:
        (D) OTHER INFORMATION: oligonucleotide primer (xi) SEQUENCE DESCRIPTION: SEQ ID NO:583:

GTAATTCGTG GCCTGGGAGT TCAGCT                                  26

(2) INFORMATION FOR SEQ ID NO:584:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: DNA (ix) FEATURE:
        (D) OTHER INFORMATION: oligonucleotide primer (xi) SEQUENCE DESCRIPTION: SEQ ID NO:584:

TGGTGAGTGG CTTCCAAATG ACTGTTTG                                28

(2) INFORMATION FOR SEQ ID NO:585:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: DNA (ix) FEATURE:
            (D) OTHER INFORMATION: oligonucleotide primer (xi) SEQUENCE DESCRIPTION: SEQ ID NO:585:

GTGGTTGGTG CCAGGCGATC TTCC                                          24

(2) INFORMATION FOR SEQ ID NO:586:

(i) SEQUENCE CHARACTERISTICS:
            (A) LENGTH: 28 base pairs
            (B) TYPE: nucleic acid
            (C) STRANDEDNESS: single
            (D) TOPOLOGY: linear (ii) MOLECULE TYPE: DNA (ix) FEATURE:
            (D) OTHER INFORMATION: oligonucleotide primer (xi) SEQUENCE DESCRIPTION: SEQ ID NO:586:

GCGTGGAGTC CTTATAGGAA TCCTCGTT                                      28

(2) INFORMATION FOR SEQ ID NO:587:

(i) SEQUENCE CHARACTERISTICS:
            (A) LENGTH: 28 base pairs
            (B) TYPE: nucleic acid
            (C) STRANDEDNESS: single
            (D) TOPOLOGY: linear (ii) MOLECULE TYPE: DNA (ix) FEATURE:
            (D) OTHER INFORMATION: oligonucleotide primer (xi) SEQUENCE DESCRIPTION: SEQ ID NO:587:

CACAATTAGG TCTCACTCTG GTTAGGCA                                      28

(2) INFORMATION FOR SEQ ID NO:588:

(i) SEQUENCE CHARACTERISTICS:
            (A) LENGTH: 28 base pairs
            (B) TYPE: nucleic acid
            (C) STRANDEDNESS: single
            (D) TOPOLOGY: linear (ii) MOLECULE TYPE: DNA (ix) FEATURE:
            (D) OTHER INFORMATION: oligonucleotide primer (xi) SEQUENCE DESCRIPTION: SEQ ID NO:588:

GGTAGATCAA TCCGTGAGAC ATTTCAGG                                      28

(2) INFORMATION FOR SEQ ID NO:589:

(i) SEQUENCE CHARACTERISTICS:
            (A) LENGTH: 25 base pairs
            (B) TYPE: nucleic acid
            (C) STRANDEDNESS: single
            (D) TOPOLOGY: linear (ii) MOLECULE TYPE: DNA (ix) FEATURE:
            (D) OTHER INFORMATION: oligonucleotide primer (xi) SEQUENCE DESCRIPTION: SEQ ID NO:589:

GTGCCCAGGC ATAGGGTTAG CTCAG                                         25

-continued (2) INFORMATION FOR SEQ ID NO:590:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: DNA (ix) FEATURE:
        (D) OTHER INFORMATION: oligonucleotide primer (xi) SEQUENCE DESCRIPTION: SEQ ID NO:590:

GCATATTGGG TGGGTTGACT AGATGTCG                          28

(2) INFORMATION FOR SEQ ID NO:591:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: DNA (ix) FEATURE:
        (D) OTHER INFORMATION: oligonucleotide primer (xi) SEQUENCE DESCRIPTION: SEQ ID NO:591:

GATCCGCGTC GTGAAGGCGT TCCG                             24

(2) INFORMATION FOR SEQ ID NO:592:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: DNA (ix) FEATURE:
        (D) OTHER INFORMATION: oligonucleotide primer (xi) SEQUENCE DESCRIPTION: SEQ ID NO:592:

GCCCGGAAAG CGGGTGACAG CGG                              23

(2) INFORMATION FOR SEQ ID NO:593:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: DNA (ix) FEATURE:
        (D) OTHER INFORMATION: oligonucleotide primer (xi) SEQUENCE DESCRIPTION: SEQ ID NO:593:

CCACTTCACC ACTGCTATCA ACACGG                          26

(2) INFORMATION FOR SEQ ID NO:594:

(i) SEQUENCE CHARACTERISTICS:
        (A) LENGTH: 28 base pairs
        (B) TYPE: nucleic acid
        (C) STRANDEDNESS: single (D) TOPOLOGY: linear (ii) MOLECULE TYPE: DNA (ix) FEATURE:
          (D) OTHER INFORMATION: oligonucleotide primer (xi) SEQUENCE DESCRIPTION: SEQ ID NO:594:

CAGCAAATCT TGGCGATGAG TCACTCAA                                            28

(2) INFORMATION FOR SEQ ID NO:595:

(i) SEQUENCE CHARACTERISTICS:
          (A) LENGTH: 24 base pairs
          (B) TYPE: nucleic acid
          (C) STRANDEDNESS: single
          (D) TOPOLOGY: linear (ii) MOLECULE TYPE: DNA (ix) FEATURE:
          (D) OTHER INFORMATION: oligonucleotide primer (xi) SEQUENCE DESCRIPTION: SEQ ID NO:595:

TGCAGAGGAT GATTGCCGCC GTGG                                                24

(2) INFORMATION FOR SEQ ID NO:596:

(i) SEQUENCE CHARACTERISTICS:
          (A) LENGTH: 25 base pairs
          (B) TYPE: nucleic acid
          (C) STRANDEDNESS: single
          (D) TOPOLOGY: linear (ii) MOLECULE TYPE: DNA (ix) FEATURE:
          (D) OTHER INFORMATION: oligonucleotide primer (xi) SEQUENCE DESCRIPTION: SEQ ID NO:596:

CACCCAACCA CCCTGGTCTT GGATC                                               25

(2) INFORMATION FOR SEQ ID NO:597:

(i) SEQUENCE CHARACTERISTICS:
          (A) LENGTH: 25 base pairs
          (B) TYPE: nucleic acid
          (C) STRANDEDNESS: single
          (D) TOPOLOGY: linear (ii) MOLECULE TYPE: DNA (ix) FEATURE:
          (D) OTHER INFORMATION: oligonucleotide primer (xi) SEQUENCE DESCRIPTION: SEQ ID NO:597:

AGCAGGGCAC ACCTATGATC GCTCC                                               25

(2) INFORMATION FOR SEQ ID NO:598:

(i) SEQUENCE CHARACTERISTICS:
          (A) LENGTH: 24 base pairs
          (B) TYPE: nucleic acid
          (C) STRANDEDNESS: single
          (D) TOPOLOGY: linear (ii) MOLECULE TYPE: DNA (ix) FEATURE:
          (D) OTHER INFORMATION: oligonucleotide primer (xi) SEQUENCE DESCRIPTION: SEQ ID NO:598:

CGGCCCTCAT CCACCGAGAC CTCA                                      24

(2) INFORMATION FOR SEQ ID NO:599:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: DNA (ix) FEATURE:
        (D) OTHER INFORMATION: oligonucleotide primer (xi) SEQUENCE DESCRIPTION: SEQ ID NO:599:

TACATTTCAA GCTCTCCAGC ATCCGTGG                                  28

(2) INFORMATION FOR SEQ ID NO:600:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: DNA (ix) FEATURE:
        (D) OTHER INFORMATION: oligonucleotide primer (xi) SEQUENCE DESCRIPTION: SEQ ID NO:600:

CTGGAATAGC TTTCATGTCC TCGTTGCC                                  28

(2) INFORMATION FOR SEQ ID NO:601:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: DNA (ix) FEATURE:
        (D) OTHER INFORMATION: oligonucleotide primer (xi) SEQUENCE DESCRIPTION: SEQ ID NO:601:

GTCAGTGCTT GCTAACTTCA GTCAACCT                                  28

(2) INFORMATION FOR SEQ ID NO:602:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: DNA (ix) FEATURE:
        (D) OTHER INFORMATION: oligonucleotide primer (xi) SEQUENCE DESCRIPTION: SEQ ID NO:602:

AACAGACAAG CTGATGGAAA CGTCGTAC                                  28

(2) INFORMATION FOR SEQ ID NO:603:

(i) SEQUENCE CHARACTERISTICS:
        (A) LENGTH: 25 base pairs

```
        (B) TYPE: nucleic acid
        (C) STRANDEDNESS: single
        (D) TOPOLOGY: linear (ii) MOLECULE TYPE: DNA (ix) FEATURE:
        (D) OTHER INFORMATION: oligonucleotide primer (xi) SEQUENCE DESCRIPTION: SEQ ID NO:603:

CTGCGGGACA TAGAACAGGT GCCAC                                              25

(2) INFORMATION FOR SEQ ID NO:604:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: DNA (ix) FEATURE:
        (D) OTHER INFORMATION: oligonucleotide primer (xi) SEQUENCE DESCRIPTION: SEQ ID NO:604:

GACTCTTAGA CGTTCCGGTT CACGGG                                             26

(2) INFORMATION FOR SEQ ID NO:605:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: DNA (ix) FEATURE:
        (D) OTHER INFORMATION: oligonucleotide primer (xi) SEQUENCE DESCRIPTION: SEQ ID NO:605:

TGGCGGCTGG ACCTGGTCAT GGTG                                               24

(2) INFORMATION FOR SEQ ID NO:606:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: DNA (ix) FEATURE:
        (D) OTHER INFORMATION: oligonucleotide primer (xi) SEQUENCE DESCRIPTION: SEQ ID NO:606:

GATACTCTCA CCAGCTCCGT CACATTC                                            27

(2) INFORMATION FOR SEQ ID NO:607:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: DNA (ix) FEATURE:
        (D) OTHER INFORMATION: oligonucleotide primer
```

(xi) SEQUENCE DESCRIPTION: SEQ ID NO:607:

GGAGGCCCGG CTCTTCGCCA TGC                                              23

(2) INFORMATION FOR SEQ ID NO:608:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: DNA (ix) FEATURE:
        (D) OTHER INFORMATION: oligonucleotide primer (xi) SEQUENCE DESCRIPTION: SEQ ID NO:608:

GTCGGTGATC TTCAGGGTCT TGTGCT                                           26

(2) INFORMATION FOR SEQ ID NO:609:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: DNA (ix) FEATURE:
        (D) OTHER INFORMATION: oligonucleotide primer (xi) SEQUENCE DESCRIPTION: SEQ ID NO:609:

CCTCCAGTAT CTGCACAGGA ACTTCATT                                         28

(2) INFORMATION FOR SEQ ID NO:610:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: DNA (ix) FEATURE:
        (D) OTHER INFORMATION: oligonucleotide primer (xi) SEQUENCE DESCRIPTION: SEQ ID NO:610:

CAAGTCGATC TGGTGGATCT CGGAAGT                                          27

(2) INFORMATION FOR SEQ ID NO:611:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: DNA (ix) FEATURE:
        (D) OTHER INFORMATION: oligonucleotide primer (xi) SEQUENCE DESCRIPTION: SEQ ID NO:611:

GGCTGTGAAG GACCTGATGC CATGTA                                           26

(2) INFORMATION FOR SEQ ID NO:612:

(i) SEQUENCE CHARACTERISTICS:
    (A) LENGTH: 26 base pairs
    (B) TYPE: nucleic acid
    (C) STRANDEDNESS: single
    (D) TOPOLOGY: linear (ii) MOLECULE TYPE: DNA (ix) FEATURE:
    (D) OTHER INFORMATION: oligonucleotide primer (xi) SEQUENCE DESCRIPTION: SEQ ID NO:612:

TCGGTGGAGC TGTTAGTGTA GCGAAC                                              26

(2) INFORMATION FOR SEQ ID NO:613:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: DNA (ix) FEATURE:
        (D) OTHER INFORMATION: oligonucleotide primer (xi) SEQUENCE DESCRIPTION: SEQ ID NO:613:

ACACCAATGC CAGCATCACA TTGTATGG                                            28

(2) INFORMATION FOR SEQ ID NO:614:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: DNA (ix) FEATURE:
        (D) OTHER INFORMATION: oligonucleotide primer (xi) SEQUENCE DESCRIPTION: SEQ ID NO:614:

GCTGGTTTGC TCTCCGCAGT GTAGAT                                              26

(2) INFORMATION FOR SEQ ID NO:615:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: DNA (ix) FEATURE:
        (D) OTHER INFORMATION: oligonucleotide primer (xi) SEQUENCE DESCRIPTION: SEQ ID NO:615:

AATGCAGGTG TCCTGAGCAC CACACC                                              26

(2) INFORMATION FOR SEQ ID NO:616:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: DNA (ix) FEATURE:
        (D) OTHER INFORMATION: oligonucleotide primer (xi) SEQUENCE DESCRIPTION: SEQ ID NO:616:

GGAAAGTCAG TCCCAGATGT AGTGGGA                                    27

(2) INFORMATION FOR SEQ ID NO:617:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: DNA (ix) FEATURE:
        (D) OTHER INFORMATION: oligonucleotide primer (xi) SEQUENCE DESCRIPTION: SEQ ID NO:617:

CTCCTCATGG ATGGGTCAAA CGTGAC                                     26

(2) INFORMATION FOR SEQ ID NO:618:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: DNA (ix) FEATURE:
        (D) OTHER INFORMATION: oligonucleotide primer (xi) SEQUENCE DESCRIPTION: SEQ ID NO:618:

CAGACCAATG CCGACTGGTA CTTGGG                                     26

(2) INFORMATION FOR SEQ ID NO:619:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: DNA (ix) FEATURE:
        (D) OTHER INFORMATION: oligonucleotide primer (xi) SEQUENCE DESCRIPTION: SEQ ID NO:619:

TCTCTGTGAT CCTGTTCCTC AACAAGCA                                   28

(2) INFORMATION FOR SEQ ID NO:620:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: DNA (ix) FEATURE:
        (D) OTHER INFORMATION: oligonucleotide primer (xi) SEQUENCE DESCRIPTION: SEQ ID NO:620:

AATGATGTCA CGGCAGTCGT TGAACACA                                   28

(2) INFORMATION FOR SEQ ID NO:621:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: DNA (ix) FEATURE:
        (D) OTHER INFORMATION: oligonucleotide primer (xi) SEQUENCE DESCRIPTION: SEQ ID NO:621:

TAGCCAATGT GGGAGCAGCG GTTTGG                         26

(2) INFORMATION FOR SEQ ID NO:622:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: DNA (ix) FEATURE:
        (D) OTHER INFORMATION: oligonucleotide primer (xi) SEQUENCE DESCRIPTION: SEQ ID NO:622:

ATAAGTACAT TCCCAGGCAC TGTCACGT                     28

(2) INFORMATION FOR SEQ ID NO:623:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: DNA (ix) FEATURE:
        (D) OTHER INFORMATION: oligonucleotide primer (xi) SEQUENCE DESCRIPTION: SEQ ID NO:623:

GCTCTCCGGC TACGGCAAGC ATGA                           24

(2) INFORMATION FOR SEQ ID NO:624:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: DNA (ix) FEATURE:
        (D) OTHER INFORMATION: oligonucleotide primer (xi) SEQUENCE DESCRIPTION: SEQ ID NO:624:

GTCGGGTGTT CCTGGTCACG GTCG                           24

(2) INFORMATION FOR SEQ ID NO:625:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: DNA (ix) FEATURE:
    (D) OTHER INFORMATION: oligonucleotide primer (xi) SEQUENCE DESCRIPTION: SEQ ID NO:625:

CTCTGCTCTA CGTGGTCCAT GCGG                                              24

(2) INFORMATION FOR SEQ ID NO:626:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: DNA (ix) FEATURE:
        (D) OTHER INFORMATION: oligonucleotide primer (xi) SEQUENCE DESCRIPTION: SEQ ID NO:626:

GAGAGTAAAC ACAGCACCCA CGAGCA                                            26

(2) INFORMATION FOR SEQ ID NO:627:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: DNA (ix) FEATURE:
        (D) OTHER INFORMATION: oligonucleotide primer (xi) SEQUENCE DESCRIPTION: SEQ ID NO:627:

GCGCCCTTTG AGCAGAACCT CTCC                                              24

(2) INFORMATION FOR SEQ ID NO:628:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: DNA (ix) FEATURE:
        (D) OTHER INFORMATION: oligonucleotide primer (xi) SEQUENCE DESCRIPTION: SEQ ID NO:628:

GCGCCGGTTC TGAAACCAAA TCTTGATC                                          28

(2) INFORMATION FOR SEQ ID NO:629:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: DNA (ix) FEATURE:
        (D) OTHER INFORMATION: oligonucleotide primer (xi) SEQUENCE DESCRIPTION: SEQ ID NO:629:

CTTTCCGTGT AAACTCGGCT CAGCGC                                            26

(2) INFORMATION FOR SEQ ID NO:630:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: DNA (ix) FEATURE:
        (D) OTHER INFORMATION: oligonucleotide primer (xi) SEQUENCE DESCRIPTION: SEQ ID NO:630:

GAAATTGGCC CGTCCCTTGT TGAAGG                             26

(2) INFORMATION FOR SEQ ID NO:631:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: DNA (ix) FEATURE:
        (D) OTHER INFORMATION: oligonucleotide primer (xi) SEQUENCE DESCRIPTION: SEQ ID NO:631:

TGCTCTGCAA CCAGGCCGGA ACCT                               24

(2) INFORMATION FOR SEQ ID NO:632:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: DNA (ix) FEATURE:
        (D) OTHER INFORMATION: oligonucleotide primer (xi) SEQUENCE DESCRIPTION: SEQ ID NO:632:

CAGTGACGGC AGGGTCAAAG TCCTTG                             26

(2) INFORMATION FOR SEQ ID NO:633:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: DNA (ix) FEATURE:
        (D) OTHER INFORMATION: oligonucleotide primer (xi) SEQUENCE DESCRIPTION: SEQ ID NO:633:

ATGGAGACGG GTCTGTTGTT GCCCC                              25

(2) INFORMATION FOR SEQ ID NO:634:

(i) SEQUENCE CHARACTERISTICS:
        (A) LENGTH: 24 base pairs
        (B) TYPE: nucleic acid
        (C) STRANDEDNESS: single (D) TOPOLOGY: linear (ii) MOLECULE TYPE: DNA (ix) FEATURE:
            (D) OTHER INFORMATION: oligonucleotide primer (xi) SEQUENCE DESCRIPTION: SEQ ID NO:634:

GCACGTTCCC GTACTGGTTC TGGG                                          24

(2) INFORMATION FOR SEQ ID NO:635:

(i) SEQUENCE CHARACTERISTICS:
            (A) LENGTH: 25 base pairs
            (B) TYPE: nucleic acid
            (C) STRANDEDNESS: single
            (D) TOPOLOGY: linear (ii) MOLECULE TYPE: DNA (ix) FEATURE:
            (D) OTHER INFORMATION: oligonucleotide primer (xi) SEQUENCE DESCRIPTION: SEQ ID NO:635:

CCGGCCAGTG GATGGTACAA GTTGC                                         25

(2) INFORMATION FOR SEQ ID NO:636:

(i) SEQUENCE CHARACTERISTICS:
            (A) LENGTH: 28 base pairs
            (B) TYPE: nucleic acid
            (C) STRANDEDNESS: single
            (D) TOPOLOGY: linear (ii) MOLECULE TYPE: DNA (ix) FEATURE:
            (D) OTHER INFORMATION: oligonucleotide primer (xi) SEQUENCE DESCRIPTION: SEQ ID NO:636:

CTCCACGTCA TCATCCTGAA TCACCACA                                      28

(2) INFORMATION FOR SEQ ID NO:637:

(i) SEQUENCE CHARACTERISTICS:
            (A) LENGTH: 25 base pairs
            (B) TYPE: nucleic acid
            (C) STRANDEDNESS: single
            (D) TOPOLOGY: linear (ii) MOLECULE TYPE: DNA (ix) FEATURE:
            (D) OTHER INFORMATION: oligonucleotide primer (xi) SEQUENCE DESCRIPTION: SEQ ID NO:637:

GACAGCAGTG GGCAGCAATG ACACC                                         25

(2) INFORMATION FOR SEQ ID NO:638:

(i) SEQUENCE CHARACTERISTICS:
            (A) LENGTH: 27 base pairs
            (B) TYPE: nucleic acid
            (C) STRANDEDNESS: single
            (D) TOPOLOGY: linear (ii) MOLECULE TYPE: DNA (ix) FEATURE:
            (D) OTHER INFORMATION: oligonucleotide primer (xi) SEQUENCE DESCRIPTION: SEQ ID NO:638:

```
CTTCTAGCTG AGCCTGATGC TCTTGAG                                                      27
```

(2) INFORMATION FOR SEQ ID NO:639:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: DNA (ix) FEATURE:
        (D) OTHER INFORMATION: oligonucleotide primer (xi) SEQUENCE DESCRIPTION: SEQ ID NO:639:

```
TATTCACCCT CCACTTCCCG TCTCAG                                                       26
```

(2) INFORMATION FOR SEQ ID NO:640:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: DNA (ix) FEATURE:
        (D) OTHER INFORMATION: oligonucleotide primer (xi) SEQUENCE DESCRIPTION: SEQ ID NO:640:

```
CAGAAGTAGG ACAGAGAACG CTCCGAA                                                      27
```

(2) INFORMATION FOR SEQ ID NO:641:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: DNA (ix) FEATURE:
        (D) OTHER INFORMATION: oligonucleotide primer (xi) SEQUENCE DESCRIPTION: SEQ ID NO:641:

```
GTACCGGACC ATCACCACCG CATAC                                                        25
```

(2) INFORMATION FOR SEQ ID NO:642:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: DNA (ix) FEATURE:
        (D) OTHER INFORMATION: oligonucleotide primer (xi) SEQUENCE DESCRIPTION: SEQ ID NO:642:

```
CAGATGACAT CCACCAGGCG CTCAAA                                                       26
```

(2) INFORMATION FOR SEQ ID NO:643:

(i) SEQUENCE CHARACTERISTICS:
        (A) LENGTH: 28 base pairs (B) TYPE: nucleic acid
        (C) STRANDEDNESS: single
        (D) TOPOLOGY: linear (ii) MOLECULE TYPE: DNA (ix) FEATURE:
        (D) OTHER INFORMATION: oligonucleotide primer (xi) SEQUENCE DESCRIPTION: SEQ ID NO:643:

GGGATACAGC AGGACAAGAA CGATTCAG                                      28

(2) INFORMATION FOR SEQ ID NO:644:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (ii) MOLECULE TYPE: DNA (ix) FEATURE:
        (D) OTHER INFORMATION: oligonucleotide primer (xi) SEQUENCE DESCRIPTION: SEQ ID NO:644:

CTTGAGCAAA TCTGGAGGCT TCTAAGAAG                                     29

(2) INFORMATION FOR SEQ ID NO:645:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: DNA (ix) FEATURE:
        (D) OTHER INFORMATION: oligonucleotide primer (xi) SEQUENCE DESCRIPTION: SEQ ID NO:645:

TCTAGTTCCA CAATGTCCAC GGGCGG                                        26

(2) INFORMATION FOR SEQ ID NO:646:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: DNA (ix) FEATURE:
        (D) OTHER INFORMATION: oligonucleotide primer (xi) SEQUENCE DESCRIPTION: SEQ ID NO:646:

GGAATCAAGC TCCTGAACCG CTCTTGA                                       27

(2) INFORMATION FOR SEQ ID NO:647:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: DNA (ix) FEATURE:
        (D) OTHER INFORMATION: oligonucleotide primer (xi) SEQUENCE DESCRIPTION: SEQ ID NO:647:

AAACTTCAGA TATGGGATAC GGCAGGGC                                    28

(2) INFORMATION FOR SEQ ID NO:648:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: DNA (ix) FEATURE:
        (D) OTHER INFORMATION: oligonucleotide primer (xi) SEQUENCE DESCRIPTION: SEQ ID NO:648:

GCAGACGTTT CCATGAACAT GAGTCCAT                                    28

(2) INFORMATION FOR SEQ ID NO:649:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: DNA (ix) FEATURE:
        (D) OTHER INFORMATION: oligonucleotide primer (xi) SEQUENCE DESCRIPTION: SEQ ID NO:649:

CGGACCATCA CAACAGCCTA TTACCG                                      26

(2) INFORMATION FOR SEQ ID NO:650:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: DNA (ix) FEATURE:
        (D) OTHER INFORMATION: oligonucleotide primer (xi) SEQUENCE DESCRIPTION: SEQ ID NO:650:

CAAATGGCAT CCACCAGGCG CTCAAA                                      26

(2) INFORMATION FOR SEQ ID NO:651:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: DNA (ix) FEATURE:
        (D) OTHER INFORMATION: oligonucleotide primer (xi) SEQUENCE DESCRIPTION: SEQ ID NO:651:

TCGGGAAACA AGGCCGACCT AGCAAA                                      26

(2) INFORMATION FOR SEQ ID NO:652:

```
        (i) SEQUENCE CHARACTERISTICS:
            (A) LENGTH: 26 base pairs
            (B) TYPE: nucleic acid
            (C) STRANDEDNESS: single
            (D) TOPOLOGY: linear (ii) MOLECULE TYPE: DNA (ix) FEATURE:
            (D) OTHER INFORMATION: oligonucleotide primer (xi) SEQUENCE DESCRIPTION: SEQ ID NO:652:

TGTGGGTTCG GTAAGGTCTA CTCCTC                                              26

(2) INFORMATION FOR SEQ ID NO:653:

(i) SEQUENCE CHARACTERISTICS:
            (A) LENGTH: 26 base pairs
            (B) TYPE: nucleic acid
            (C) STRANDEDNESS: single
            (D) TOPOLOGY: linear (ii) MOLECULE TYPE: DNA (ix) FEATURE:
            (D) OTHER INFORMATION: oligonucleotide primer (xi) SEQUENCE DESCRIPTION: SEQ ID NO:653:

GAAATGTCCA GGCCAGCAGT ACCACT                                              26

(2) INFORMATION FOR SEQ ID NO:654:

(i) SEQUENCE CHARACTERISTICS:
            (A) LENGTH: 28 base pairs
            (B) TYPE: nucleic acid
            (C) STRANDEDNESS: single
            (D) TOPOLOGY: linear (ii) MOLECULE TYPE: DNA (ix) FEATURE:
            (D) OTHER INFORMATION: oligonucleotide primer (xi) SEQUENCE DESCRIPTION: SEQ ID NO:654:

CTAGAGTATC TGCTTTCCAC GGCATCAG                                            28

(2) INFORMATION FOR SEQ ID NO:655:

(i) SEQUENCE CHARACTERISTICS:
            (A) LENGTH: 23 base pairs
            (B) TYPE: nucleic acid
            (C) STRANDEDNESS: single
            (D) TOPOLOGY: linear (ii) MOLECULE TYPE: DNA (ix) FEATURE:
            (D) OTHER INFORMATION: oligonucleotide primer (xi) SEQUENCE DESCRIPTION: SEQ ID NO:655:

GAAGGGCAAG GCTGCCGTGC AGG                                                 23

(2) INFORMATION FOR SEQ ID NO:656:

(i) SEQUENCE CHARACTERISTICS:
            (A) LENGTH: 26 base pairs
            (B) TYPE: nucleic acid
            (C) STRANDEDNESS: single
            (D) TOPOLOGY: linear (ii) MOLECULE TYPE: DNA
```

```
    (ix) FEATURE:
          (D) OTHER INFORMATION: oligonucleotide primer (xi) SEQUENCE DESCRIPTION: SEQ ID NO:656:

TGGGATGAGC TTCACTCAAC GTGGAG                                        26

(2) INFORMATION FOR SEQ ID NO:657:

(i) SEQUENCE CHARACTERISTICS:
         (A) LENGTH: 26 base pairs
         (B) TYPE: nucleic acid
         (C) STRANDEDNESS: single
         (D) TOPOLOGY: linear (ii) MOLECULE TYPE: DNA (ix) FEATURE:
          (D) OTHER INFORMATION: oligonucleotide primer (xi) SEQUENCE DESCRIPTION: SEQ ID NO:657:

CTAGGGCTAT GGTGTGGACT GAATGG                                        26

(2) INFORMATION FOR SEQ ID NO:658:

(i) SEQUENCE CHARACTERISTICS:
         (A) LENGTH: 28 base pairs
         (B) TYPE: nucleic acid
         (C) STRANDEDNESS: single
         (D) TOPOLOGY: linear (ii) MOLECULE TYPE: DNA (ix) FEATURE:
          (D) OTHER INFORMATION: oligonucleotide primer (xi) SEQUENCE DESCRIPTION: SEQ ID NO:658:

CTGAGTGACA GAACAAGACA CCGTCTCT                                      28

(2) INFORMATION FOR SEQ ID NO:659:

(i) SEQUENCE CHARACTERISTICS:
         (A) LENGTH: 24 base pairs
         (B) TYPE: nucleic acid
         (C) STRANDEDNESS: single
         (D) TOPOLOGY: linear (ii) MOLECULE TYPE: DNA (ix) FEATURE:
          (D) OTHER INFORMATION: oligonucleotide primer (xi) SEQUENCE DESCRIPTION: SEQ ID NO:659:

GCTGAGCAGC CCAGCCAACC TCAG                                          24

(2) INFORMATION FOR SEQ ID NO:660:

(i) SEQUENCE CHARACTERISTICS:
         (A) LENGTH: 24 base pairs
         (B) TYPE: nucleic acid
         (C) STRANDEDNESS: single
         (D) TOPOLOGY: linear (ii) MOLECULE TYPE: DNA (ix) FEATURE:
          (D) OTHER INFORMATION: oligonucleotide primer (xi) SEQUENCE DESCRIPTION: SEQ ID NO:660:

ACACGGCGCA GCGTAGAACG GATC                                          24
```

(2) INFORMATION FOR SEQ ID NO:661:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (ii) MOLECULE TYPE: DNA (ix) FEATURE:
        (D) OTHER INFORMATION: oligonucleotide primer (xi) SEQUENCE DESCRIPTION: SEQ ID NO:661:

GATCCTTTGT CAACCTCACA GACAACAAG                                             29

(2) INFORMATION FOR SEQ ID NO:662:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: DNA (ix) FEATURE:
        (D) OTHER INFORMATION: oligonucleotide primer (xi) SEQUENCE DESCRIPTION: SEQ ID NO:662:

GTAGACATGC TGCTACCTGG TTGCACTT                                              28

(2) INFORMATION FOR SEQ ID NO:663:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: DNA (ix) FEATURE:
        (D) OTHER INFORMATION: oligonucleotide primer (xi) SEQUENCE DESCRIPTION: SEQ ID NO:663:

TCGAGATGAG TGGTGGCCTC GTGAAT                                                26

(2) INFORMATION FOR SEQ ID NO:664:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: DNA (ix) FEATURE:
        (D) OTHER INFORMATION: oligonucleotide primer (xi) SEQUENCE DESCRIPTION: SEQ ID NO:664:

GGAAAGCCCT GGCTCAAGCA TGTCATAT                                              28

(2) INFORMATION FOR SEQ ID NO:665:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: DNA (ix) FEATURE:
             (D) OTHER INFORMATION: oligonucleotide primer (xi) SEQUENCE DESCRIPTION: SEQ ID NO:665:

TGAAACCGCA ACACCCATCA CCACTTC                                          27

(2) INFORMATION FOR SEQ ID NO:666:

(i) SEQUENCE CHARACTERISTICS:
             (A) LENGTH: 26 base pairs
             (B) TYPE: nucleic acid
             (C) STRANDEDNESS: single
             (D) TOPOLOGY: linear (ii) MOLECULE TYPE: DNA (ix) FEATURE:
             (D) OTHER INFORMATION: oligonucleotide primer (xi) SEQUENCE DESCRIPTION: SEQ ID NO:666:

ACCCTCGCAC AGAGCATTCA GTAGGA                                           26

(2) INFORMATION FOR SEQ ID NO:667:

(i) SEQUENCE CHARACTERISTICS:
             (A) LENGTH: 26 base pairs
             (B) TYPE: nucleic acid
             (C) STRANDEDNESS: single
             (D) TOPOLOGY: linear (ii) MOLECULE TYPE: DNA (ix) FEATURE:
             (D) OTHER INFORMATION: oligonucleotide primer (xi) SEQUENCE DESCRIPTION: SEQ ID NO:667:

AGCAGGTTAC CTGGAGGCGG ATCATC                                           26

(2) INFORMATION FOR SEQ ID NO:668:

(i) SEQUENCE CHARACTERISTICS:
             (A) LENGTH: 26 base pairs
             (B) TYPE: nucleic acid
             (C) STRANDEDNESS: single
             (D) TOPOLOGY: linear (ii) MOLECULE TYPE: DNA (ix) FEATURE:
             (D) OTHER INFORMATION: oligonucleotide primer (xi) SEQUENCE DESCRIPTION: SEQ ID NO:668:

GAGAAGTGAG TCCGTCCTTA CCCATG                                           26

(2) INFORMATION FOR SEQ ID NO:669:

(i) SEQUENCE CHARACTERISTICS:
             (A) LENGTH: 27 base pairs
             (B) TYPE: nucleic acid
             (C) STRANDEDNESS: single
             (D) TOPOLOGY: linear (ii) MOLECULE TYPE: DNA (ix) FEATURE:
             (D) OTHER INFORMATION: oligonucleotide primer (xi) SEQUENCE DESCRIPTION: SEQ ID NO:669:

AGAGGGCTCA CAAGACACAT TTGTGCC                                          27

(2) INFORMATION FOR SEQ ID NO:670:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: DNA (ix) FEATURE:
        (D) OTHER INFORMATION: oligonucleotide primer (xi) SEQUENCE DESCRIPTION: SEQ ID NO:670:

AGGTGTAGCA GTCCTTGGTC ATTGTCAT                                            28

(2) INFORMATION FOR SEQ ID NO:671:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: DNA (ix) FEATURE:
        (D) OTHER INFORMATION: oligonucleotide primer (xi) SEQUENCE DESCRIPTION: SEQ ID NO:671:

AAACTGCATC TTGGCCCTGT TGCCTG                                              26

(2) INFORMATION FOR SEQ ID NO:672:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: DNA (ix) FEATURE:
        (D) OTHER INFORMATION: oligonucleotide primer (xi) SEQUENCE DESCRIPTION: SEQ ID NO:672:

TCTAGGAACA GCAGCAGAAA TAGCGAGA                                            28

(2) INFORMATION FOR SEQ ID NO:673:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: DNA (ix) FEATURE:
        (D) OTHER INFORMATION: oligonucleotide primer (xi) SEQUENCE DESCRIPTION: SEQ ID NO:673:

CAACAGCCAG CCACATCCAC TACAGA                                              26

(2) INFORMATION FOR SEQ ID NO:674:

(i) SEQUENCE CHARACTERISTICS:
        (A) LENGTH: 28 base pairs
        (B) TYPE: nucleic acid
        (C) STRANDEDNESS: single -continued (D) TOPOLOGY: linear (ii) MOLECULE TYPE: DNA (ix) FEATURE:
        (D) OTHER INFORMATION: oligonucleotide primer (xi) SEQUENCE DESCRIPTION: SEQ ID NO:674:

GCGGTTACAG GGCAATCTTT ATGAGCCA                                          28

(2) INFORMATION FOR SEQ ID NO:675:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: DNA (ix) FEATURE:
        (D) OTHER INFORMATION: oligonucleotide primer (xi) SEQUENCE DESCRIPTION: SEQ ID NO:675:

TACTCAACCA AGCGGCAGAG ATTCTTGG                                          28

(2) INFORMATION FOR SEQ ID NO:676:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: DNA (ix) FEATURE:
        (D) OTHER INFORMATION: oligonucleotide primer (xi) SEQUENCE DESCRIPTION: SEQ ID NO:676:

ACGAAGTACC CTGCCTAAGC ATCATTTC                                          28

(2) INFORMATION FOR SEQ ID NO:677:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: DNA (ix) FEATURE:
        (D) OTHER INFORMATION: oligonucleotide primer (xi) SEQUENCE DESCRIPTION: SEQ ID NO:677:

CGCAGGTCCT CGCGTTCGGG CTT                                               23

(2) INFORMATION FOR SEQ ID NO:678:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: DNA (ix) FEATURE:
        (D) OTHER INFORMATION: oligonucleotide primer (xi) SEQUENCE DESCRIPTION: SEQ ID NO:678:

```
CCCGCTCTCA TCGCAGTCAG GATCAT                                    26

(2) INFORMATION FOR SEQ ID NO:679:

(i) SEQUENCE CHARACTERISTICS:
          (A) LENGTH: 26 base pairs
          (B) TYPE: nucleic acid
          (C) STRANDEDNESS: single
          (D) TOPOLOGY: linear (ii) MOLECULE TYPE: DNA (ix) FEATURE:
          (D) OTHER INFORMATION: oligonucleotide primer (xi) SEQUENCE DESCRIPTION: SEQ ID NO:679:

AGCAAGGGTA CGCTGGGCAA GTTCAC                                    26

(2) INFORMATION FOR SEQ ID NO:680:

(i) SEQUENCE CHARACTERISTICS:
          (A) LENGTH: 27 base pairs
          (B) TYPE: nucleic acid
          (C) STRANDEDNESS: single
          (D) TOPOLOGY: linear (ii) MOLECULE TYPE: DNA (ix) FEATURE:
          (D) OTHER INFORMATION: oligonucleotide primer (xi) SEQUENCE DESCRIPTION: SEQ ID NO:680:

CCTCGACTTA TGTCGGGTAG ACTCTTC                                   27

(2) INFORMATION FOR SEQ ID NO:681:

(i) SEQUENCE CHARACTERISTICS:
          (A) LENGTH: 23 base pairs
          (B) TYPE: nucleic acid
          (C) STRANDEDNESS: single
          (D) TOPOLOGY: linear (ii) MOLECULE TYPE: DNA (ix) FEATURE:
          (D) OTHER INFORMATION: oligonucleotide primer (xi) SEQUENCE DESCRIPTION: SEQ ID NO:681:

CCGGCGCTAC CTGGGCGATG CTT                                       23

(2) INFORMATION FOR SEQ ID NO:682:

(i) SEQUENCE CHARACTERISTICS:
          (A) LENGTH: 24 base pairs
          (B) TYPE: nucleic acid
          (C) STRANDEDNESS: single
          (D) TOPOLOGY: linear (ii) MOLECULE TYPE: DNA (ix) FEATURE:
          (D) OTHER INFORMATION: oligonucleotide primer (xi) SEQUENCE DESCRIPTION: SEQ ID NO:682:

GCCCTCGTCC CGCTCAAACT CCTT                                      24

(2) INFORMATION FOR SEQ ID NO:683:

(i) SEQUENCE CHARACTERISTICS:
          (A) LENGTH: 26 base pairs
```

(B) TYPE: nucleic acid
        (C) STRANDEDNESS: single
        (D) TOPOLOGY: linear (ii) MOLECULE TYPE: DNA (ix) FEATURE:
        (D) OTHER INFORMATION: oligonucleotide primer (xi) SEQUENCE DESCRIPTION: SEQ ID NO:683:

AATTCAGCAC CCGCCTCAGT CAACTG                                              26

(2) INFORMATION FOR SEQ ID NO:684:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: DNA (ix) FEATURE:
        (D) OTHER INFORMATION: oligonucleotide primer (xi) SEQUENCE DESCRIPTION: SEQ ID NO:684:

TGCAGCGTTC CTGTTCCACT CATAGG                                              26

(2) INFORMATION FOR SEQ ID NO:685:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: DNA (ix) FEATURE:
        (D) OTHER INFORMATION: oligonucleotide primer (xi) SEQUENCE DESCRIPTION: SEQ ID NO:685:

GCACCAGGAG TGCCAAGGAT TGAAGA                                              26

(2) INFORMATION FOR SEQ ID NO:686:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: DNA (ix) FEATURE:
        (D) OTHER INFORMATION: oligonucleotide primer (xi) SEQUENCE DESCRIPTION: SEQ ID NO:686:

CTAGTGGGTG CTGTGCGAAT CTGGTAT                                             27

(2) INFORMATION FOR SEQ ID NO:687:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: DNA (ix) FEATURE:
        (D) OTHER INFORMATION: oligonucleotide primer (xi) SEQUENCE DESCRIPTION: SEQ ID NO:687:

CATGTTCACC CTGGAGGACA CGCTG                                              25

(2) INFORMATION FOR SEQ ID NO:688:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: DNA (ix) FEATURE:
        (D) OTHER INFORMATION: oligonucleotide primer (xi) SEQUENCE DESCRIPTION: SEQ ID NO:688:

TCCATTGAGC ATCACATGGA CCACATCA                                           28

(2) INFORMATION FOR SEQ ID NO:689:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: DNA (ix) FEATURE:
        (D) OTHER INFORMATION: oligonucleotide primer (xi) SEQUENCE DESCRIPTION: SEQ ID NO:689:

CCGAAACGCC GAATATAATC CCAAGCG                                            27

(2) INFORMATION FOR SEQ ID NO:690:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: DNA (ix) FEATURE:
        (D) OTHER INFORMATION: oligonucleotide primer (xi) SEQUENCE DESCRIPTION: SEQ ID NO:690:

CTAAATTGTT GGTGGGTGAG CACAAGGC                                           28

(2) INFORMATION FOR SEQ ID NO:691:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: DNA (ix) FEATURE:
        (D) OTHER INFORMATION: oligonucleotide primer (xi) SEQUENCE DESCRIPTION: SEQ ID NO:691:

TTCCAACTGC ACGAGATCCA GTATCACT                                           28

(2) INFORMATION FOR SEQ ID NO:692:

```
        (i) SEQUENCE CHARACTERISTICS:
            (A) LENGTH: 23 base pairs
            (B) TYPE: nucleic acid
            (C) STRANDEDNESS: single
            (D) TOPOLOGY: linear (ii) MOLECULE TYPE: DNA (ix) FEATURE:
            (D) OTHER INFORMATION: oligonucleotide primer (xi) SEQUENCE DESCRIPTION: SEQ ID NO:692:

GCCGCCCGAC GGAGCAACTG TAC                                              23

(2) INFORMATION FOR SEQ ID NO:693:

(i) SEQUENCE CHARACTERISTICS:
            (A) LENGTH: 23 base pairs
            (B) TYPE: nucleic acid
            (C) STRANDEDNESS: single
            (D) TOPOLOGY: linear (ii) MOLECULE TYPE: DNA (ix) FEATURE:
            (D) OTHER INFORMATION: oligonucleotide primer (xi) SEQUENCE DESCRIPTION: SEQ ID NO:693:

CCCAGGCCCT GGACCGCCAA ACA                                              23

(2) INFORMATION FOR SEQ ID NO:694:

(i) SEQUENCE CHARACTERISTICS:
            (A) LENGTH: 26 base pairs
            (B) TYPE: nucleic acid
            (C) STRANDEDNESS: single
            (D) TOPOLOGY: linear (ii) MOLECULE TYPE: DNA (ix) FEATURE:
            (D) OTHER INFORMATION: oligonucleotide primer (xi) SEQUENCE DESCRIPTION: SEQ ID NO:694:

GCGATACGAG CCACAGACTT AGGACC                                           26

(2) INFORMATION FOR SEQ ID NO:695:

(i) SEQUENCE CHARACTERISTICS:
            (A) LENGTH: 24 base pairs
            (B) TYPE: nucleic acid
            (C) STRANDEDNESS: single
            (D) TOPOLOGY: linear (ii) MOLECULE TYPE: DNA (ix) FEATURE:
            (D) OTHER INFORMATION: oligonucleotide primer (xi) SEQUENCE DESCRIPTION: SEQ ID NO:695:

TCCAGTCTCC AGGGCCATAG GCAG                                             24

(2) INFORMATION FOR SEQ ID NO:696:

(i) SEQUENCE CHARACTERISTICS:
            (A) LENGTH: 26 base pairs
            (B) TYPE: nucleic acid
            (C) STRANDEDNESS: single
            (D) TOPOLOGY: linear (ii) MOLECULE TYPE: DNA
```

```
       (ix) FEATURE:
             (D) OTHER INFORMATION: oligonucleotide primer (xi) SEQUENCE DESCRIPTION: SEQ ID NO:696:

GAAGCCACTC AGCACCACTA CCACAC                                              26

(2) INFORMATION FOR SEQ ID NO:697:

(i) SEQUENCE CHARACTERISTICS:
             (A) LENGTH: 23 base pairs
             (B) TYPE: nucleic acid
             (C) STRANDEDNESS: single
             (D) TOPOLOGY: linear (ii) MOLECULE TYPE: DNA (ix) FEATURE:
             (D) OTHER INFORMATION: oligonucleotide primer (xi) SEQUENCE DESCRIPTION: SEQ ID NO:697:

GCGAGGGCAA CGTCAGGGTC AGC                                                 23

(2) INFORMATION FOR SEQ ID NO:698:

(i) SEQUENCE CHARACTERISTICS:
             (A) LENGTH: 24 base pairs
             (B) TYPE: nucleic acid
             (C) STRANDEDNESS: single
             (D) TOPOLOGY: linear (ii) MOLECULE TYPE: DNA (ix) FEATURE:
             (D) OTHER INFORMATION: oligonucleotide primer (xi) SEQUENCE DESCRIPTION: SEQ ID NO:698:

CCGGTGGTGA AGGCGTAGCC GTTG                                                24

(2) INFORMATION FOR SEQ ID NO:699:

(i) SEQUENCE CHARACTERISTICS:
             (A) LENGTH: 26 base pairs
             (B) TYPE: nucleic acid
             (C) STRANDEDNESS: single
             (D) TOPOLOGY: linear (ii) MOLECULE TYPE: DNA (ix) FEATURE:
             (D) OTHER INFORMATION: oligonucleotide primer (xi) SEQUENCE DESCRIPTION: SEQ ID NO:699:

GCCTGCGGTG GCCTGGATAA CATTTG                                              26

(2) INFORMATION FOR SEQ ID NO:700:

(i) SEQUENCE CHARACTERISTICS:
             (A) LENGTH: 28 base pairs
             (B) TYPE: nucleic acid
             (C) STRANDEDNESS: single
             (D) TOPOLOGY: linear (ii) MOLECULE TYPE: DNA (ix) FEATURE:
             (D) OTHER INFORMATION: oligonucleotide primer (xi) SEQUENCE DESCRIPTION: SEQ ID NO:700:

CATCACAAGC ACCAGAGACG AACAGTCT                                            28
```

(2) INFORMATION FOR SEQ ID NO:701:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: DNA (ix) FEATURE:
        (D) OTHER INFORMATION: oligonucleotide primer (xi) SEQUENCE DESCRIPTION: SEQ ID NO:701:

GCATCAAGCT GGGCTTCACG CAGG                          24

(2) INFORMATION FOR SEQ ID NO:702:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: DNA (ix) FEATURE:
        (D) OTHER INFORMATION: oligonucleotide primer (xi) SEQUENCE DESCRIPTION: SEQ ID NO:702:

AAGGCGAAGC GGACGTTTGT CTCGAT                      26

(2) INFORMATION FOR SEQ ID NO:703:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: DNA (ix) FEATURE:
        (D) OTHER INFORMATION: oligonucleotide primer (xi) SEQUENCE DESCRIPTION: SEQ ID NO:703:

AGCTGTCCAC CTAGCCAGGG ACTTTG                      26

(2) INFORMATION FOR SEQ ID NO:704:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: DNA (ix) FEATURE:
        (D) OTHER INFORMATION: oligonucleotide primer (xi) SEQUENCE DESCRIPTION: SEQ ID NO:704:

GAGATGAGGT TGAAGTGGGT CAAGCAG                    27

(2) INFORMATION FOR SEQ ID NO:705:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: DNA (ix) FEATURE:
            (D) OTHER INFORMATION: oligonucleotide primer (xi) SEQUENCE DESCRIPTION: SEQ ID NO:705:

GCTCAAGCTC ATCGACTTCG GGTCG                                              25

(2) INFORMATION FOR SEQ ID NO:706:

(i) SEQUENCE CHARACTERISTICS:
            (A) LENGTH: 26 base pairs
            (B) TYPE: nucleic acid
            (C) STRANDEDNESS: single
            (D) TOPOLOGY: linear (ii) MOLECULE TYPE: DNA (ix) FEATURE:
            (D) OTHER INFORMATION: oligonucleotide primer (xi) SEQUENCE DESCRIPTION: SEQ ID NO:706:

GGCCTATCTG ATGGTCTCAG GGCCAA                                             26

(2) INFORMATION FOR SEQ ID NO:707:

(i) SEQUENCE CHARACTERISTICS:
            (A) LENGTH: 28 base pairs
            (B) TYPE: nucleic acid
            (C) STRANDEDNESS: single
            (D) TOPOLOGY: linear (ii) MOLECULE TYPE: DNA (ix) FEATURE:
            (D) OTHER INFORMATION: oligonucleotide primer (xi) SEQUENCE DESCRIPTION: SEQ ID NO:707:

TTCACTGTTG CCAAATGGTG GTTCAGGG                                           28

(2) INFORMATION FOR SEQ ID NO:708:

(i) SEQUENCE CHARACTERISTICS:
            (A) LENGTH: 28 base pairs
            (B) TYPE: nucleic acid
            (C) STRANDEDNESS: single
            (D) TOPOLOGY: linear (ii) MOLECULE TYPE: DNA (ix) FEATURE:
            (D) OTHER INFORMATION: oligonucleotide primer (xi) SEQUENCE DESCRIPTION: SEQ ID NO:708:

TTGGCATGAG TGTCAACTCA GTGCAAAG                                           28

(2) INFORMATION FOR SEQ ID NO:709:

(i) SEQUENCE CHARACTERISTICS:
            (A) LENGTH: 25 base pairs
            (B) TYPE: nucleic acid
            (C) STRANDEDNESS: single
            (D) TOPOLOGY: linear (ii) MOLECULE TYPE: DNA (ix) FEATURE:
            (D) OTHER INFORMATION: oligonucleotide primer (xi) SEQUENCE DESCRIPTION: SEQ ID NO:709:

CGAGGGCACC TTGCCTGACA AACAG                                              25

(2) INFORMATION FOR SEQ ID NO:710:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: DNA (ix) FEATURE:
        (D) OTHER INFORMATION: oligonucleotide primer (xi) SEQUENCE DESCRIPTION: SEQ ID NO:710:

GGCACACTGA TGTTTAAGGC TTGGACGT                          28

(2) INFORMATION FOR SEQ ID NO:711:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: DNA (ix) FEATURE:
        (D) OTHER INFORMATION: oligonucleotide primer (xi) SEQUENCE DESCRIPTION: SEQ ID NO:711:

TGTATGGTGA CTGGAGGTGC TAACCTAG                          28

(2) INFORMATION FOR SEQ ID NO:712:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: DNA (ix) FEATURE:
        (D) OTHER INFORMATION: oligonucleotide primer (xi) SEQUENCE DESCRIPTION: SEQ ID NO:712:

CATGTCACCC AGGGACCCAT TTCACC                            26

(2) INFORMATION FOR SEQ ID NO:713:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: DNA (ix) FEATURE:
        (D) OTHER INFORMATION: oligonucleotide primer (xi) SEQUENCE DESCRIPTION: SEQ ID NO:713:

TTGCACCTCG TCCATCGACA GGTCC                              25

(2) INFORMATION FOR SEQ ID NO:714:

(i) SEQUENCE CHARACTERISTICS:
        (A) LENGTH: 26 base pairs
        (B) TYPE: nucleic acid
        (C) STRANDEDNESS: single (D) TOPOLOGY: linear (ii) MOLECULE TYPE: DNA (ix) FEATURE:
         (D) OTHER INFORMATION: oligonucleotide primer (xi) SEQUENCE DESCRIPTION: SEQ ID NO:714:

GGGTAGCGGA TGGTTCGAGC ATCATG                                              26

(2) INFORMATION FOR SEQ ID NO:715:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: DNA (ix) FEATURE:
         (D) OTHER INFORMATION: oligonucleotide primer (xi) SEQUENCE DESCRIPTION: SEQ ID NO:715:

CTTGGACAGG TTTCCTGTGA ACTTGTGT                                            28

(2) INFORMATION FOR SEQ ID NO:716:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: DNA (ix) FEATURE:
         (D) OTHER INFORMATION: oligonucleotide primer (xi) SEQUENCE DESCRIPTION: SEQ ID NO:716:

GGAAATGACA TAAGGCCACG ATTGCAGC                                            28

(2) INFORMATION FOR SEQ ID NO:717:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: DNA (ix) FEATURE:
         (D) OTHER INFORMATION: oligonucleotide primer (xi) SEQUENCE DESCRIPTION: SEQ ID NO:717:

GACTGCCGCA TCATGGGAGT AAGTTC                                              26

(2) INFORMATION FOR SEQ ID NO:718:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: DNA (ix) FEATURE:
         (D) OTHER INFORMATION: oligonucleotide primer (xi) SEQUENCE DESCRIPTION: SEQ ID NO:718:

TGAGGAATCC AAACAACAAA GTCCCACC                                       28

(2) INFORMATION FOR SEQ ID NO:719:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: DNA (ix) FEATURE:
        (D) OTHER INFORMATION: oligonucleotide primer (xi) SEQUENCE DESCRIPTION: SEQ ID NO:719:

AACCATTACA GGGAGCTGGG ACACTTAA                                       28

(2) INFORMATION FOR SEQ ID NO:720:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: DNA (ix) FEATURE:
        (D) OTHER INFORMATION: oligonucleotide primer (xi) SEQUENCE DESCRIPTION: SEQ ID NO:720:

TTTGTTAGAA GCCATCCATA GCACACCC                                       28

(2) INFORMATION FOR SEQ ID NO:721:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: DNA (ix) FEATURE:
        (D) OTHER INFORMATION: oligonucleotide primer (xi) SEQUENCE DESCRIPTION: SEQ ID NO:721:

TCAATCCTGC CATTGTCTCA CCGTATGA                                       28

(2) INFORMATION FOR SEQ ID NO:722:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: DNA (ix) FEATURE:
        (D) OTHER INFORMATION: oligonucleotide primer (xi) SEQUENCE DESCRIPTION: SEQ ID NO:722:

ACGATGTAAA GCAAGCACAT TGCCGTCA                                       28

(2) INFORMATION FOR SEQ ID NO:723:

(i) SEQUENCE CHARACTERISTICS:
        (A) LENGTH: 28 base pairs

```
            (B) TYPE: nucleic acid
            (C) STRANDEDNESS: single
            (D) TOPOLOGY: linear (ii) MOLECULE TYPE: DNA (ix) FEATURE:
            (D) OTHER INFORMATION: oligonucleotide primer (xi) SEQUENCE DESCRIPTION: SEQ ID NO:723:

TCTTCCACAT GGGTGCATTT GTAGCTCT                                    28

(2) INFORMATION FOR SEQ ID NO:724:

(i) SEQUENCE CHARACTERISTICS:
            (A) LENGTH: 28 base pairs
            (B) TYPE: nucleic acid
            (C) STRANDEDNESS: single
            (D) TOPOLOGY: linear (ii) MOLECULE TYPE: DNA (ix) FEATURE:
            (D) OTHER INFORMATION: oligonucleotide primer (xi) SEQUENCE DESCRIPTION: SEQ ID NO:724:

TTGGTACTGC CTAGCCCTGT AAGCATTT                                    28

(2) INFORMATION FOR SEQ ID NO:725:

(i) SEQUENCE CHARACTERISTICS:
            (A) LENGTH: 28 base pairs
            (B) TYPE: nucleic acid
            (C) STRANDEDNESS: single
            (D) TOPOLOGY: linear (ii) MOLECULE TYPE: DNA (ix) FEATURE:
            (D) OTHER INFORMATION: oligonucleotide primer (xi) SEQUENCE DESCRIPTION: SEQ ID NO:725:

TTCCAAGAAG CTAAGGGTGA TTCACCGC                                    28

(2) INFORMATION FOR SEQ ID NO:726:

(i) SEQUENCE CHARACTERISTICS:
            (A) LENGTH: 28 base pairs
            (B) TYPE: nucleic acid
            (C) STRANDEDNESS: single
            (D) TOPOLOGY: linear (ii) MOLECULE TYPE: DNA (ix) FEATURE:
            (D) OTHER INFORMATION: oligonucleotide primer (xi) SEQUENCE DESCRIPTION: SEQ ID NO:726:

AGTATTATGC TGGCAGAAGT CCATGAGC                                    28

(2) INFORMATION FOR SEQ ID NO:727:

(i) SEQUENCE CHARACTERISTICS:
            (A) LENGTH: 25 base pairs
            (B) TYPE: nucleic acid
            (C) STRANDEDNESS: single
            (D) TOPOLOGY: linear (ii) MOLECULE TYPE: DNA (ix) FEATURE:
            (D) OTHER INFORMATION: oligonucleotide primer
```

(xi) SEQUENCE DESCRIPTION: SEQ ID NO:727:

TGGCTTCCAG GTTCCCATGA TCCCC                                          25

(2) INFORMATION FOR SEQ ID NO:728:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: DNA (ix) FEATURE:
        (D) OTHER INFORMATION: oligonucleotide primer (xi) SEQUENCE DESCRIPTION: SEQ ID NO:728:

GGCAAGCGTA AGGGCGTTCG TGGG                                           24

(2) INFORMATION FOR SEQ ID NO:729:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: DNA (ix) FEATURE:
        (D) OTHER INFORMATION: oligonucleotide primer (xi) SEQUENCE DESCRIPTION: SEQ ID NO:729:

TGCGCCCACA GGTGCTGTCT TAGTG                                          25

(2) INFORMATION FOR SEQ ID NO:730:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: DNA (ix) FEATURE:
        (D) OTHER INFORMATION: oligonucleotide primer (xi) SEQUENCE DESCRIPTION: SEQ ID NO:730:

GGGTGAAGTA ACTCAGGCCA CTCTCC                                         26

(2) INFORMATION FOR SEQ ID NO:731:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: DNA (ix) FEATURE:
        (D) OTHER INFORMATION: oligonucleotide primer (xi) SEQUENCE DESCRIPTION: SEQ ID NO:731:

ATGTACCAAG CCTGCCCGAC TCAGG                                          25

(2) INFORMATION FOR SEQ ID NO:732:

```
      (i) SEQUENCE CHARACTERISTICS:
          (A) LENGTH: 28 base pairs
          (B) TYPE: nucleic acid
          (C) STRANDEDNESS: single
          (D) TOPOLOGY: linear (ii) MOLECULE TYPE: DNA (ix) FEATURE:
          (D) OTHER INFORMATION: oligonucleotide primer (xi) SEQUENCE DESCRIPTION: SEQ ID NO:732:

TGGCCTTAAT TCGAGACTCG TCGTTGTA                                              28

(2) INFORMATION FOR SEQ ID NO:733:

(i) SEQUENCE CHARACTERISTICS:
          (A) LENGTH: 27 base pairs
          (B) TYPE: nucleic acid
          (C) STRANDEDNESS: single
          (D) TOPOLOGY: linear (ii) MOLECULE TYPE: DNA (ix) FEATURE:
          (D) OTHER INFORMATION: oligonucleotide primer (xi) SEQUENCE DESCRIPTION: SEQ ID NO:733:

TGTTGCAGGG TATTGGCTGA CTGCTAG                                               27

(2) INFORMATION FOR SEQ ID NO:734:

(i) SEQUENCE CHARACTERISTICS:
          (A) LENGTH: 27 base pairs
          (B) TYPE: nucleic acid
          (C) STRANDEDNESS: single
          (D) TOPOLOGY: linear (ii) MOLECULE TYPE: DNA (ix) FEATURE:
          (D) OTHER INFORMATION: oligonucleotide primer (xi) SEQUENCE DESCRIPTION: SEQ ID NO:734:

GAGTGAACCT GTGGCTCTAT CAACCCT                                               27

(2) INFORMATION FOR SEQ ID NO:735:

(i) SEQUENCE CHARACTERISTICS:
          (A) LENGTH: 27 base pairs
          (B) TYPE: nucleic acid
          (C) STRANDEDNESS: single
          (D) TOPOLOGY: linear (ii) MOLECULE TYPE: DNA (ix) FEATURE:
          (D) OTHER INFORMATION: oligonucleotide primer (xi) SEQUENCE DESCRIPTION: SEQ ID NO:735:

CATCCTCACC AGCCTGTGGA TACATTC                                               27

(2) INFORMATION FOR SEQ ID NO:736:

(i) SEQUENCE CHARACTERISTICS:
          (A) LENGTH: 28 base pairs
          (B) TYPE: nucleic acid
          (C) STRANDEDNESS: single
          (D) TOPOLOGY: linear (ii) MOLECULE TYPE: DNA
```

```
        (ix) FEATURE:
              (D) OTHER INFORMATION: oligonucleotide primer (xi) SEQUENCE DESCRIPTION: SEQ ID NO:736:

GATAGGTAGC TGGGCCTCTT AAACCTAA                                            28

(2) INFORMATION FOR SEQ ID NO:737:

(i) SEQUENCE CHARACTERISTICS:
              (A) LENGTH: 27 base pairs
              (B) TYPE: nucleic acid
              (C) STRANDEDNESS: single
              (D) TOPOLOGY: linear (ii) MOLECULE TYPE: DNA (ix) FEATURE:
              (D) OTHER INFORMATION: oligonucleotide primer (xi) SEQUENCE DESCRIPTION: SEQ ID NO:737:

CCGGCAGAGA ATTTCAGGAA TAGTGGC                                             27

(2) INFORMATION FOR SEQ ID NO:738:

(i) SEQUENCE CHARACTERISTICS:
              (A) LENGTH: 26 base pairs
              (B) TYPE: nucleic acid
              (C) STRANDEDNESS: single
              (D) TOPOLOGY: linear (ii) MOLECULE TYPE: DNA (ix) FEATURE:
              (D) OTHER INFORMATION: oligonucleotide primer (xi) SEQUENCE DESCRIPTION: SEQ ID NO:738:

TCCACGATTG GTGAGACTAG GGTAGG                                              26

(2) INFORMATION FOR SEQ ID NO:739:

(i) SEQUENCE CHARACTERISTICS:
              (A) LENGTH: 23 base pairs
              (B) TYPE: nucleic acid
              (C) STRANDEDNESS: single
              (D) TOPOLOGY: linear (ii) MOLECULE TYPE: DNA (ix) FEATURE:
              (D) OTHER INFORMATION: oligonucleotide primer (xi) SEQUENCE DESCRIPTION: SEQ ID NO:739:

TCAGGATGCC TGGAGGCGTC GGG                                                 23

(2) INFORMATION FOR SEQ ID NO:740:

(i) SEQUENCE CHARACTERISTICS:
              (A) LENGTH: 23 base pairs
              (B) TYPE: nucleic acid
              (C) STRANDEDNESS: single
              (D) TOPOLOGY: linear (ii) MOLECULE TYPE: DNA (ix) FEATURE:
              (D) OTHER INFORMATION: oligonucleotide primer (xi) SEQUENCE DESCRIPTION: SEQ ID NO:740:

TGGTCTTGCG GGTGCCGTCC AGG                                                 23
```

(2) INFORMATION FOR SEQ ID NO:741:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: DNA (ix) FEATURE:
        (D) OTHER INFORMATION: oligonucleotide primer (xi) SEQUENCE DESCRIPTION: SEQ ID NO:741:

CCTTTCGCCA CAGTATGTCA GCTACAAC                                             28

(2) INFORMATION FOR SEQ ID NO:742:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: DNA (ix) FEATURE:
        (D) OTHER INFORMATION: oligonucleotide primer (xi) SEQUENCE DESCRIPTION: SEQ ID NO:742:

CTCCTTATCC TTCACTGAGT ATTTGCCG                                             28

(2) INFORMATION FOR SEQ ID NO:743:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: DNA (ix) FEATURE:
        (D) OTHER INFORMATION: oligonucleotide primer (xi) SEQUENCE DESCRIPTION: SEQ ID NO:743:

GATCCTCCAG CCGGAGTCAG CGG                                                  23

(2) INFORMATION FOR SEQ ID NO:744:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: DNA (ix) FEATURE:
        (D) OTHER INFORMATION: oligonucleotide primer (xi) SEQUENCE DESCRIPTION: SEQ ID NO:744:

GGAAGACACA TCATAGGTTG GACTCCAA                                             28

(2) INFORMATION FOR SEQ ID NO:745:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: DNA (ix) FEATURE:
            (D) OTHER INFORMATION: oligonucleotide primer (xi) SEQUENCE DESCRIPTION: SEQ ID NO:745:

AAAGGCACCT GGGAAGTCAT CGGGAT                                              26

(2) INFORMATION FOR SEQ ID NO:746:

(i) SEQUENCE CHARACTERISTICS:
            (A) LENGTH: 27 base pairs
            (B) TYPE: nucleic acid
            (C) STRANDEDNESS: single
            (D) TOPOLOGY: linear (ii) MOLECULE TYPE: DNA (ix) FEATURE:
            (D) OTHER INFORMATION: oligonucleotide primer (xi) SEQUENCE DESCRIPTION: SEQ ID NO:746:

GCTGAATTGT CTTCCAGGAC TCTCAGC                                             27

(2) INFORMATION FOR SEQ ID NO:747:

(i) SEQUENCE CHARACTERISTICS:
            (A) LENGTH: 26 base pairs
            (B) TYPE: nucleic acid
            (C) STRANDEDNESS: single
            (D) TOPOLOGY: linear (ii) MOLECULE TYPE: DNA (ix) FEATURE:
            (D) OTHER INFORMATION: oligonucleotide primer (xi) SEQUENCE DESCRIPTION: SEQ ID NO:747:

TGCGGATGAA GGACCAGTGT GACAAG                                              26

(2) INFORMATION FOR SEQ ID NO:748:

(i) SEQUENCE CHARACTERISTICS:
            (A) LENGTH: 25 base pairs
            (B) TYPE: nucleic acid
            (C) STRANDEDNESS: single
            (D) TOPOLOGY: linear (ii) MOLECULE TYPE: DNA (ix) FEATURE:
            (D) OTHER INFORMATION: oligonucleotide primer (xi) SEQUENCE DESCRIPTION: SEQ ID NO:748:

CACCGTGGTG ACCCGCAGAT AGTAC                                               25

(2) INFORMATION FOR SEQ ID NO:749:

(i) SEQUENCE CHARACTERISTICS:
            (A) LENGTH: 23 base pairs
            (B) TYPE: nucleic acid
            (C) STRANDEDNESS: single
            (D) TOPOLOGY: linear (ii) MOLECULE TYPE: DNA (ix) FEATURE:
            (D) OTHER INFORMATION: oligonucleotide primer (xi) SEQUENCE DESCRIPTION: SEQ ID NO:749:

CTCCCAGAGG CGTCCCGCAC CTG                                                 23

(2) INFORMATION FOR SEQ ID NO:750:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: DNA (ix) FEATURE:
        (D) OTHER INFORMATION: oligonucleotide primer (xi) SEQUENCE DESCRIPTION: SEQ ID NO:750:

TGACCTGAGC CTGATCGTAA GGTCCA                                  26

(2) INFORMATION FOR SEQ ID NO:751:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: DNA (ix) FEATURE:
        (D) OTHER INFORMATION: oligonucleotide primer (xi) SEQUENCE DESCRIPTION: SEQ ID NO:751:

CTGTGGGCTC CGTGGGTTGT TGCA                                    24

(2) INFORMATION FOR SEQ ID NO:752:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: DNA (ix) FEATURE:
        (D) OTHER INFORMATION: oligonucleotide primer (xi) SEQUENCE DESCRIPTION: SEQ ID NO:752:

AGGGAACCAG AAGCCGAGTA AGTCTC                                  26

(2) INFORMATION FOR SEQ ID NO:753:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: DNA (ix) FEATURE:
        (D) OTHER INFORMATION: oligonucleotide primer (xi) SEQUENCE DESCRIPTION: SEQ ID NO:753:

AGATCAAGAC CCTGGAGGGC GAGTTC                                  26

(2) INFORMATION FOR SEQ ID NO:754:

(i) SEQUENCE CHARACTERISTICS:
        (A) LENGTH: 24 base pairs
        (B) TYPE: nucleic acid
        (C) STRANDEDNESS: single (D) TOPOLOGY: linear (ii) MOLECULE TYPE: DNA (ix) FEATURE:
            (D) OTHER INFORMATION: oligonucleotide primer (xi) SEQUENCE DESCRIPTION: SEQ ID NO:754:

GACGTGGACT CTGGGACCGT GGGT                                          24

(2) INFORMATION FOR SEQ ID NO:755:

(i) SEQUENCE CHARACTERISTICS:
            (A) LENGTH: 28 base pairs
            (B) TYPE: nucleic acid
            (C) STRANDEDNESS: single
            (D) TOPOLOGY: linear (ii) MOLECULE TYPE: DNA (ix) FEATURE:
            (D) OTHER INFORMATION: oligonucleotide primer (xi) SEQUENCE DESCRIPTION: SEQ ID NO:755:

CATGGCAGAC AGAATCAATC TACCTCGA                                      28

(2) INFORMATION FOR SEQ ID NO:756:

(i) SEQUENCE CHARACTERISTICS:
            (A) LENGTH: 28 base pairs
            (B) TYPE: nucleic acid
            (C) STRANDEDNESS: single
            (D) TOPOLOGY: linear (ii) MOLECULE TYPE: DNA (ix) FEATURE:
            (D) OTHER INFORMATION: oligonucleotide primer (xi) SEQUENCE DESCRIPTION: SEQ ID NO:756:

AGTCCAATTC CACAGCTTTA CGGGCTAT                                      28

(2) INFORMATION FOR SEQ ID NO:757:

(i) SEQUENCE CHARACTERISTICS:
            (A) LENGTH: 27 base pairs
            (B) TYPE: nucleic acid
            (C) STRANDEDNESS: single
            (D) TOPOLOGY: linear (ii) MOLECULE TYPE: DNA (ix) FEATURE:
            (D) OTHER INFORMATION: oligonucleotide primer (xi) SEQUENCE DESCRIPTION: SEQ ID NO:757:

ATGAAACCTG CCTGCCACCA CAACAAC                                       27

(2) INFORMATION FOR SEQ ID NO:758:

(i) SEQUENCE CHARACTERISTICS:
            (A) LENGTH: 28 base pairs
            (B) TYPE: nucleic acid
            (C) STRANDEDNESS: single
            (D) TOPOLOGY: linear (ii) MOLECULE TYPE: DNA (ix) FEATURE:
            (D) OTHER INFORMATION: oligonucleotide primer (xi) SEQUENCE DESCRIPTION: SEQ ID NO:758:

```
AAGAACAAGG CCACAGATAG AGTCCGAT                                              28

(2) INFORMATION FOR SEQ ID NO:759:

(i) SEQUENCE CHARACTERISTICS:
          (A) LENGTH: 28 base pairs
          (B) TYPE: nucleic acid
          (C) STRANDEDNESS: single
          (D) TOPOLOGY: linear (ii) MOLECULE TYPE: DNA (ix) FEATURE:
          (D) OTHER INFORMATION: oligonucleotide primer (xi) SEQUENCE DESCRIPTION: SEQ ID NO:759:

TTTGGCTGGG CGTGAAATGA CTAGATTG                                              28

(2) INFORMATION FOR SEQ ID NO:760:

(i) SEQUENCE CHARACTERISTICS:
          (A) LENGTH: 28 base pairs
          (B) TYPE: nucleic acid
          (C) STRANDEDNESS: single
          (D) TOPOLOGY: linear (ii) MOLECULE TYPE: DNA (ix) FEATURE:
          (D) OTHER INFORMATION: oligonucleotide primer (xi) SEQUENCE DESCRIPTION: SEQ ID NO:760:

GAAGTGTTCC AAGGGTCATG TAAGGTCT                                              28

(2) INFORMATION FOR SEQ ID NO:761:

(i) SEQUENCE CHARACTERISTICS:
          (A) LENGTH: 26 base pairs
          (B) TYPE: nucleic acid
          (C) STRANDEDNESS: single
          (D) TOPOLOGY: linear (ii) MOLECULE TYPE: DNA (ix) FEATURE:
          (D) OTHER INFORMATION: oligonucleotide primer (xi) SEQUENCE DESCRIPTION: SEQ ID NO:761:

GAAGAACGCG GCTGGAGCAT TGGATT                                                26

(2) INFORMATION FOR SEQ ID NO:762:

(i) SEQUENCE CHARACTERISTICS:
          (A) LENGTH: 26 base pairs
          (B) TYPE: nucleic acid
          (C) STRANDEDNESS: single
          (D) TOPOLOGY: linear (ii) MOLECULE TYPE: DNA (ix) FEATURE:
          (D) OTHER INFORMATION: oligonucleotide primer (xi) SEQUENCE DESCRIPTION: SEQ ID NO:762:

ACAGAATCAG AAGTGCTTGG TGCCCG                                                26

(2) INFORMATION FOR SEQ ID NO:763:

(i) SEQUENCE CHARACTERISTICS:
          (A) LENGTH: 27 base pairs
```

(B) TYPE: nucleic acid
        (C) STRANDEDNESS: single
        (D) TOPOLOGY: linear (ii) MOLECULE TYPE: DNA (ix) FEATURE:
        (D) OTHER INFORMATION: oligonucleotide primer (xi) SEQUENCE DESCRIPTION: SEQ ID NO:763:

CCACCGCAAG AAACAAACTG ACATCGG                                            27

(2) INFORMATION FOR SEQ ID NO:764:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: DNA (ix) FEATURE:
        (D) OTHER INFORMATION: oligonucleotide primer (xi) SEQUENCE DESCRIPTION: SEQ ID NO:764:

TAAATGGCGC TGTTGCTTTC AGTACCAC                                           28

(2) INFORMATION FOR SEQ ID NO:765:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: DNA (ix) FEATURE:
        (D) OTHER INFORMATION: oligonucleotide primer (xi) SEQUENCE DESCRIPTION: SEQ ID NO:765:

CCCGAATGGG TGGATACCGT CAAGC                                              25

(2) INFORMATION FOR SEQ ID NO:766:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: DNA (ix) FEATURE:
        (D) OTHER INFORMATION: oligonucleotide primer (xi) SEQUENCE DESCRIPTION: SEQ ID NO:766:

TTTGTCCCTG AGGTGTCAGT TTGCGG                                             26

(2) INFORMATION FOR SEQ ID NO:767:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: DNA (ix) FEATURE:
        (D) OTHER INFORMATION: oligonucleotide primer (xi) SEQUENCE DESCRIPTION: SEQ ID NO:767:

GTCCTAGCCA CGCCCTGTAT GACC                                                    24

(2) INFORMATION FOR SEQ ID NO:768:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: DNA (ix) FEATURE:
        (D) OTHER INFORMATION: oligonucleotide primer (xi) SEQUENCE DESCRIPTION: SEQ ID NO:768:

CTCCCATTCA CTGTGTCACC ACACTTC                                                 27

(2) INFORMATION FOR SEQ ID NO:769:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: DNA (ix) FEATURE:
        (D) OTHER INFORMATION: oligonucleotide primer (xi) SEQUENCE DESCRIPTION: SEQ ID NO:769:

GCAGGCGAAG TTCCCACCTT ACTACA                                                  26

(2) INFORMATION FOR SEQ ID NO:770:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: DNA (ix) FEATURE:
        (D) OTHER INFORMATION: oligonucleotide primer (xi) SEQUENCE DESCRIPTION: SEQ ID NO:770:

TGGGCGTCTG CGTCGGTAAT TGAAGT                                                  26

(2) INFORMATION FOR SEQ ID NO:771:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: DNA (ix) FEATURE:
        (D) OTHER INFORMATION: oligonucleotide primer (xi) SEQUENCE DESCRIPTION: SEQ ID NO:771:

CCTGAAGATG TGAAGCCACC AGTCTTAG                                                28

(2) INFORMATION FOR SEQ ID NO:772:

(i) SEQUENCE CHARACTERISTICS:
           (A) LENGTH: 28 base pairs
           (B) TYPE: nucleic acid
           (C) STRANDEDNESS: single
           (D) TOPOLOGY: linear (ii) MOLECULE TYPE: DNA (ix) FEATURE:
           (D) OTHER INFORMATION: oligonucleotide primer (xi) SEQUENCE DESCRIPTION: SEQ ID NO:772:

GATGTTAGTC ACAGGGTCAT TTGGGCTG                                                28

(2) INFORMATION FOR SEQ ID NO:773:

(i) SEQUENCE CHARACTERISTICS:
           (A) LENGTH: 23 base pairs
           (B) TYPE: nucleic acid
           (C) STRANDEDNESS: single
           (D) TOPOLOGY: linear (ii) MOLECULE TYPE: DNA (ix) FEATURE:
           (D) OTHER INFORMATION: oligonucleotide primer (xi) SEQUENCE DESCRIPTION: SEQ ID NO:773:

CACTTCCGGC TCCTGCGTCG CTC                                                     23

(2) INFORMATION FOR SEQ ID NO:774:

(i) SEQUENCE CHARACTERISTICS:
           (A) LENGTH: 26 base pairs
           (B) TYPE: nucleic acid
           (C) STRANDEDNESS: single
           (D) TOPOLOGY: linear (ii) MOLECULE TYPE: DNA (ix) FEATURE:
           (D) OTHER INFORMATION: oligonucleotide primer (xi) SEQUENCE DESCRIPTION: SEQ ID NO:774:

CCAAACTAGC TGCTCCAGGG CCTTGT                                                  26

(2) INFORMATION FOR SEQ ID NO:775:

(i) SEQUENCE CHARACTERISTICS:
           (A) LENGTH: 24 base pairs
           (B) TYPE: nucleic acid
           (C) STRANDEDNESS: single
           (D) TOPOLOGY: linear (ii) MOLECULE TYPE: DNA (ix) FEATURE:
           (D) OTHER INFORMATION: oligonucleotide primer (xi) SEQUENCE DESCRIPTION: SEQ ID NO:775:

CGACGGAGCC CAGCAAGCCT TGAG                                                    24

(2) INFORMATION FOR SEQ ID NO:776:

(i) SEQUENCE CHARACTERISTICS:
           (A) LENGTH: 24 base pairs
           (B) TYPE: nucleic acid
           (C) STRANDEDNESS: single
           (D) TOPOLOGY: linear (ii) MOLECULE TYPE: DNA

```
        (ix) FEATURE:
             (D) OTHER INFORMATION: oligonucleotide primer (xi) SEQUENCE DESCRIPTION: SEQ ID NO:776:

TTCAGCGCCT GCCTCATGTC TCCC                                              24

(2) INFORMATION FOR SEQ ID NO:777:

(i) SEQUENCE CHARACTERISTICS:
             (A) LENGTH: 25 base pairs
             (B) TYPE: nucleic acid
             (C) STRANDEDNESS: single
             (D) TOPOLOGY: linear (ii) MOLECULE TYPE: DNA (ix) FEATURE:
             (D) OTHER INFORMATION: oligonucleotide primer (xi) SEQUENCE DESCRIPTION: SEQ ID NO:777:

AAAGGCGGGA ACTGAGGCGA CTGTG                                             25

(2) INFORMATION FOR SEQ ID NO:778:

(i) SEQUENCE CHARACTERISTICS:
             (A) LENGTH: 26 base pairs
             (B) TYPE: nucleic acid
             (C) STRANDEDNESS: single
             (D) TOPOLOGY: linear (ii) MOLECULE TYPE: DNA (ix) FEATURE:
             (D) OTHER INFORMATION: oligonucleotide primer (xi) SEQUENCE DESCRIPTION: SEQ ID NO:778:

GCAGCTACTC CTCGATCCTT GGTCAG                                            26

(2) INFORMATION FOR SEQ ID NO:779:

(i) SEQUENCE CHARACTERISTICS:
             (A) LENGTH: 26 base pairs
             (B) TYPE: nucleic acid
             (C) STRANDEDNESS: single
             (D) TOPOLOGY: linear (ii) MOLECULE TYPE: DNA (ix) FEATURE:
             (D) OTHER INFORMATION: oligonucleotide primer (xi) SEQUENCE DESCRIPTION: SEQ ID NO:779:

CCCACCGAAG TTCCAGGTAA CACTGA                                            26

(2) INFORMATION FOR SEQ ID NO:780:

(i) SEQUENCE CHARACTERISTICS:
             (A) LENGTH: 26 base pairs
             (B) TYPE: nucleic acid
             (C) STRANDEDNESS: single
             (D) TOPOLOGY: linear (ii) MOLECULE TYPE: DNA (ix) FEATURE:
             (D) OTHER INFORMATION: oligonucleotide primer (xi) SEQUENCE DESCRIPTION: SEQ ID NO:780:

GGCTTTAGAG TTGGGAGGTC AGGGAA                                            26
```

(2) INFORMATION FOR SEQ ID NO:781:

(i) SEQUENCE CHARACTERISTICS:
    (A) LENGTH: 26 base pairs
    (B) TYPE: nucleic acid
    (C) STRANDEDNESS: single
    (D) TOPOLOGY: linear (ii) MOLECULE TYPE: DNA (ix) FEATURE:
    (D) OTHER INFORMATION: oligonucleotide primer (xi) SEQUENCE DESCRIPTION: SEQ ID NO:781:

CATCCTTAGA GGCTCTGTGC CGTATG                            26

(2) INFORMATION FOR SEQ ID NO:782:

(i) SEQUENCE CHARACTERISTICS:
    (A) LENGTH: 26 base pairs
    (B) TYPE: nucleic acid
    (C) STRANDEDNESS: single
    (D) TOPOLOGY: linear (ii) MOLECULE TYPE: DNA (ix) FEATURE:
    (D) OTHER INFORMATION: oligonucleotide primer (xi) SEQUENCE DESCRIPTION: SEQ ID NO:782:

AGAGTGGTTG CTGCCAGGGA TTGTCT                            26

(2) INFORMATION FOR SEQ ID NO:783:

(i) SEQUENCE CHARACTERISTICS:
    (A) LENGTH: 26 base pairs
    (B) TYPE: nucleic acid
    (C) STRANDEDNESS: single
    (D) TOPOLOGY: linear (ii) MOLECULE TYPE: DNA (ix) FEATURE:
    (D) OTHER INFORMATION: oligonucleotide primer (xi) SEQUENCE DESCRIPTION: SEQ ID NO:783:

CTGTCAATGG CAGCAACAGG ACCATG                            26

(2) INFORMATION FOR SEQ ID NO:784:

(i) SEQUENCE CHARACTERISTICS:
    (A) LENGTH: 25 base pairs
    (B) TYPE: nucleic acid
    (C) STRANDEDNESS: single
    (D) TOPOLOGY: linear (ii) MOLECULE TYPE: DNA (ix) FEATURE:
    (D) OTHER INFORMATION: oligonucleotide primer (xi) SEQUENCE DESCRIPTION: SEQ ID NO:784:

CTGTAAACGG TAGCGAGATC GCGGG                             25

(2) INFORMATION FOR SEQ ID NO:785:

(i) SEQUENCE CHARACTERISTICS:
    (A) LENGTH: 24 base pairs
    (B) TYPE: nucleic acid
    (C) STRANDEDNESS: single
    (D) TOPOLOGY: linear (ii) MOLECULE TYPE: DNA (ix) FEATURE:
             (D) OTHER INFORMATION: oligonucleotide primer (xi) SEQUENCE DESCRIPTION: SEQ ID NO:785:

AGTTCCTGCT GCCTGGGTAG GCCC                                            24

(2) INFORMATION FOR SEQ ID NO:786:

(i) SEQUENCE CHARACTERISTICS:
             (A) LENGTH: 26 base pairs
             (B) TYPE: nucleic acid
             (C) STRANDEDNESS: single
             (D) TOPOLOGY: linear (ii) MOLECULE TYPE: DNA (ix) FEATURE:
             (D) OTHER INFORMATION: oligonucleotide primer (xi) SEQUENCE DESCRIPTION: SEQ ID NO:786:

CACGTAGCAC AGCATCCACT CGCTCA                                          26

(2) INFORMATION FOR SEQ ID NO:787:

(i) SEQUENCE CHARACTERISTICS:
             (A) LENGTH: 26 base pairs
             (B) TYPE: nucleic acid
             (C) STRANDEDNESS: single
             (D) TOPOLOGY: linear (ii) MOLECULE TYPE: DNA (ix) FEATURE:
             (D) OTHER INFORMATION: oligonucleotide primer (xi) SEQUENCE DESCRIPTION: SEQ ID NO:787:

GATCCGACCC TGATGAATAT GCCAGC                                          26

(2) INFORMATION FOR SEQ ID NO:788:

(i) SEQUENCE CHARACTERISTICS:
             (A) LENGTH: 26 base pairs
             (B) TYPE: nucleic acid
             (C) STRANDEDNESS: single
             (D) TOPOLOGY: linear (ii) MOLECULE TYPE: DNA (ix) FEATURE:
             (D) OTHER INFORMATION: oligonucleotide primer (xi) SEQUENCE DESCRIPTION: SEQ ID NO:788:

AAGAACCTCG GAAGACACTC CATCCC                                          26

(2) INFORMATION FOR SEQ ID NO:789:

(i) SEQUENCE CHARACTERISTICS:
             (A) LENGTH: 25 base pairs
             (B) TYPE: nucleic acid
             (C) STRANDEDNESS: single
             (D) TOPOLOGY: linear (ii) MOLECULE TYPE: DNA (ix) FEATURE:
             (D) OTHER INFORMATION: oligonucleotide primer (xi) SEQUENCE DESCRIPTION: SEQ ID NO:789:

AGACGCCACA CTGGTGACAC AGGAG                                           25

(2) INFORMATION FOR SEQ ID NO:790:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: DNA (ix) FEATURE:
        (D) OTHER INFORMATION: oligonucleotide primer (xi) SEQUENCE DESCRIPTION: SEQ ID NO:790:

GGCCGTTGCT CTGTATTCTT ACTGATCG                  28

(2) INFORMATION FOR SEQ ID NO:791:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: DNA (ix) FEATURE:
        (D) OTHER INFORMATION: oligonucleotide primer (xi) SEQUENCE DESCRIPTION: SEQ ID NO:791:

GACTGCAAGG TGCAGCTCCG CCAT                      24

(2) INFORMATION FOR SEQ ID NO:792:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: DNA (ix) FEATURE:
        (D) OTHER INFORMATION: oligonucleotide primer (xi) SEQUENCE DESCRIPTION: SEQ ID NO:792:

GGGTTCCGCA CTGTGAGGTA GATGTG                    26

(2) INFORMATION FOR SEQ ID NO:793:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: DNA (ix) FEATURE:
        (D) OTHER INFORMATION: oligonucleotide primer (xi) SEQUENCE DESCRIPTION: SEQ ID NO:793:

CTGGCAGCCA AGCCCAGTTG AAGG                      24

(2) INFORMATION FOR SEQ ID NO:794:

(i) SEQUENCE CHARACTERISTICS:
        (A) LENGTH: 24 base pairs
        (B) TYPE: nucleic acid
        (C) STRANDEDNESS: single (D) TOPOLOGY: linear (ii) MOLECULE TYPE: DNA (ix) FEATURE:
            (D) OTHER INFORMATION: oligonucleotide primer (xi) SEQUENCE DESCRIPTION: SEQ ID NO:794:

TCGGTGTAGG CAGGGTGCAT CTCC                                              24

(2) INFORMATION FOR SEQ ID NO:795:

(i) SEQUENCE CHARACTERISTICS:
            (A) LENGTH: 27 base pairs
            (B) TYPE: nucleic acid
            (C) STRANDEDNESS: single
            (D) TOPOLOGY: linear (ii) MOLECULE TYPE: DNA (ix) FEATURE:
            (D) OTHER INFORMATION: oligonucleotide primer (xi) SEQUENCE DESCRIPTION: SEQ ID NO:795:

GGGCAGATGC CTAATTTCGC ACAATGC                                           27

(2) INFORMATION FOR SEQ ID NO:796:

(i) SEQUENCE CHARACTERISTICS:
            (A) LENGTH: 26 base pairs
            (B) TYPE: nucleic acid
            (C) STRANDEDNESS: single
            (D) TOPOLOGY: linear (ii) MOLECULE TYPE: DNA (ix) FEATURE:
            (D) OTHER INFORMATION: oligonucleotide primer (xi) SEQUENCE DESCRIPTION: SEQ ID NO:796:

GGCTCTACCT GGCTGTTCTG ACTTGA                                            26

(2) INFORMATION FOR SEQ ID NO:797:

(i) SEQUENCE CHARACTERISTICS:
            (A) LENGTH: 24 base pairs
            (B) TYPE: nucleic acid
            (C) STRANDEDNESS: single
            (D) TOPOLOGY: linear (ii) MOLECULE TYPE: DNA (ix) FEATURE:
            (D) OTHER INFORMATION: oligonucleotide primer (xi) SEQUENCE DESCRIPTION: SEQ ID NO:797:

GGAGAGCAAC GCGGTGCATC ACCA                                              24

(2) INFORMATION FOR SEQ ID NO:798:

(i) SEQUENCE CHARACTERISTICS:
            (A) LENGTH: 26 base pairs
            (B) TYPE: nucleic acid
            (C) STRANDEDNESS: single
            (D) TOPOLOGY: linear (ii) MOLECULE TYPE: DNA (ix) FEATURE:
            (D) OTHER INFORMATION: oligonucleotide primer (xi) SEQUENCE DESCRIPTION: SEQ ID NO:798:

CAGGGTACAG GCCCACGTCT TGTATG         26

(2) INFORMATION FOR SEQ ID NO:799:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: DNA (ix) FEATURE:
        (D) OTHER INFORMATION: oligonucleotide primer (xi) SEQUENCE DESCRIPTION: SEQ ID NO:799:

TCTACACGGC CCATGTGGGC TACAG         25

(2) INFORMATION FOR SEQ ID NO:800:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: DNA (ix) FEATURE:
        (D) OTHER INFORMATION: oligonucleotide primer (xi) SEQUENCE DESCRIPTION: SEQ ID NO:800:

GGCCTCTAGC TCTGTTCAAC TGTCAATT         28

(2) INFORMATION FOR SEQ ID NO:801:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: DNA (ix) FEATURE:
        (D) OTHER INFORMATION: oligonucleotide primer (xi) SEQUENCE DESCRIPTION: SEQ ID NO:801:

CCGAGGTCAA GGCCCAGTAT GAGG         24

(2) INFORMATION FOR SEQ ID NO:802:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: DNA (ix) FEATURE:
        (D) OTHER INFORMATION: oligonucleotide primer (xi) SEQUENCE DESCRIPTION: SEQ ID NO:802:

GTAGTCACGC AGCAGCCGCG CCAA         24

(2) INFORMATION FOR SEQ ID NO:803:

(i) SEQUENCE CHARACTERISTICS:
        (A) LENGTH: 23 base pairs

```
        (B) TYPE: nucleic acid
        (C) STRANDEDNESS: single
        (D) TOPOLOGY: linear (ii) MOLECULE TYPE: DNA (ix) FEATURE:
        (D) OTHER INFORMATION: oligonucleotide primer (xi) SEQUENCE DESCRIPTION: SEQ ID NO:803:

CATGGAGCAG CATCTCCCGC CCC                                            23

(2) INFORMATION FOR SEQ ID NO:804:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: DNA (ix) FEATURE:
        (D) OTHER INFORMATION: oligonucleotide primer (xi) SEQUENCE DESCRIPTION: SEQ ID NO:804:

CATCTTGCGC TTCGCCTCGG CGTT                                           24

(2) INFORMATION FOR SEQ ID NO:805:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: DNA (ix) FEATURE:
        (D) OTHER INFORMATION: oligonucleotide primer (xi) SEQUENCE DESCRIPTION: SEQ ID NO:805:

TTGTGGCTTA TTCAACCTCA CAACCCTG                                       28

(2) INFORMATION FOR SEQ ID NO:806:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (ii) MOLECULE TYPE: DNA (ix) FEATURE:
        (D) OTHER INFORMATION: oligonucleotide primer (xi) SEQUENCE DESCRIPTION: SEQ ID NO:806:

GTTACAGACC CTAGATATTC CCTAAGGGA                                      29

(2) INFORMATION FOR SEQ ID NO:807:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: DNA (ix) FEATURE:
        (D) OTHER INFORMATION: oligonucleotide primer
```

(xi) SEQUENCE DESCRIPTION: SEQ ID NO:807:

CCTTCCAGTC GGCAGGCAGT CCAC                24

(2) INFORMATION FOR SEQ ID NO:808:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: DNA (ix) FEATURE:
        (D) OTHER INFORMATION: oligonucleotide primer (xi) SEQUENCE DESCRIPTION: SEQ ID NO:808:

TCCCTCGCTC TTCGGATGCC GGG                 23

(2) INFORMATION FOR SEQ ID NO:809:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: DNA (ix) FEATURE:
        (D) OTHER INFORMATION: oligonucleotide primer (xi) SEQUENCE DESCRIPTION: SEQ ID NO:809:

TTTGCACTGG ACTCTGGGAA CCTTTCAT            28

(2) INFORMATION FOR SEQ ID NO:810:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: DNA (ix) FEATURE:
        (D) OTHER INFORMATION: oligonucleotide primer (xi) SEQUENCE DESCRIPTION: SEQ ID NO:810:

CTCACATTGC CACCAACAGA CATAGATC            28

(2) INFORMATION FOR SEQ ID NO:811:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: DNA (ix) FEATURE:
        (D) OTHER INFORMATION: oligonucleotide primer (xi) SEQUENCE DESCRIPTION: SEQ ID NO:811:

TGCAGATCCA GCTATCAGCA ACTCATCT            28

(2) INFORMATION FOR SEQ ID NO:812:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: DNA (ix) FEATURE:
        (D) OTHER INFORMATION: oligonucleotide primer (xi) SEQUENCE DESCRIPTION: SEQ ID NO:812:

GTGGTGTCAC GAGAAGTAGA GGTCTCT                                    27

(2) INFORMATION FOR SEQ ID NO:813:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: DNA (ix) FEATURE:
        (D) OTHER INFORMATION: oligonucleotide primer (xi) SEQUENCE DESCRIPTION: SEQ ID NO:813:

CCCACACCTC GGGTATGAAC CGCC                                       24

(2) INFORMATION FOR SEQ ID NO:814:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: DNA (ix) FEATURE:
        (D) OTHER INFORMATION: oligonucleotide primer (xi) SEQUENCE DESCRIPTION: SEQ ID NO:814:

CACTAACCCT CAGCCTGACA CCCAG                                      25

(2) INFORMATION FOR SEQ ID NO:815:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: DNA (ix) FEATURE:
        (D) OTHER INFORMATION: oligonucleotide primer (xi) SEQUENCE DESCRIPTION: SEQ ID NO:815:

GGCATCGTCA GCACCCGCAA CCTC                                       24

(2) INFORMATION FOR SEQ ID NO:816:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: DNA (ix) FEATURE:
          (D) OTHER INFORMATION: oligonucleotide primer (xi) SEQUENCE DESCRIPTION: SEQ ID NO:816:

CCAAGGCCGA GAACCGTCTG CGC                                               23

(2) INFORMATION FOR SEQ ID NO:817:

(i) SEQUENCE CHARACTERISTICS:
         (A) LENGTH: 24 base pairs
         (B) TYPE: nucleic acid
         (C) STRANDEDNESS: single
         (D) TOPOLOGY: linear (ii) MOLECULE TYPE: DNA (ix) FEATURE:
          (D) OTHER INFORMATION: oligonucleotide primer (xi) SEQUENCE DESCRIPTION: SEQ ID NO:817:

ACCCAGGCCC AGCTTCGGGC ATTT                                              24

(2) INFORMATION FOR SEQ ID NO:818:

(i) SEQUENCE CHARACTERISTICS:
         (A) LENGTH: 26 base pairs
         (B) TYPE: nucleic acid
         (C) STRANDEDNESS: single
         (D) TOPOLOGY: linear (ii) MOLECULE TYPE: DNA (ix) FEATURE:
          (D) OTHER INFORMATION: oligonucleotide primer (xi) SEQUENCE DESCRIPTION: SEQ ID NO:818:

GGCAACGGTG ACCGTGGTTG GCAATT                                            26

(2) INFORMATION FOR SEQ ID NO:819:

(i) SEQUENCE CHARACTERISTICS:
         (A) LENGTH: 26 base pairs
         (B) TYPE: nucleic acid
         (C) STRANDEDNESS: single
         (D) TOPOLOGY: linear (ii) MOLECULE TYPE: DNA (ix) FEATURE:
          (D) OTHER INFORMATION: oligonucleotide primer (xi) SEQUENCE DESCRIPTION: SEQ ID NO:819:

CAGCCACTGT CACAGGCATA TTCCCT                                            26

(2) INFORMATION FOR SEQ ID NO:820:

(i) SEQUENCE CHARACTERISTICS:
         (A) LENGTH: 27 base pairs
         (B) TYPE: nucleic acid
         (C) STRANDEDNESS: single
         (D) TOPOLOGY: linear (ii) MOLECULE TYPE: DNA (ix) FEATURE:
          (D) OTHER INFORMATION: oligonucleotide primer (xi) SEQUENCE DESCRIPTION: SEQ ID NO:820:

CACAAACTCA GTAGGAGTGC AAGGGCT                                           27

(2) INFORMATION FOR SEQ ID NO:821:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: DNA (ix) FEATURE:
        (D) OTHER INFORMATION: oligonucleotide primer (xi) SEQUENCE DESCRIPTION: SEQ ID NO:821:

GAATATACTG AGCACTTACA CTCGGCCA                                28

(2) INFORMATION FOR SEQ ID NO:822:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: DNA (ix) FEATURE:
        (D) OTHER INFORMATION: oligonucleotide primer (xi) SEQUENCE DESCRIPTION: SEQ ID NO:822:

GGTGTGGTTG TTGGTAAGAG GTTATCTG                                28

(2) INFORMATION FOR SEQ ID NO:823:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: DNA (ix) FEATURE:
        (D) OTHER INFORMATION: oligonucleotide primer (xi) SEQUENCE DESCRIPTION: SEQ ID NO:823:

TACAGTGGAG TTCCTGTGGG ACCCTG                                  26

(2) INFORMATION FOR SEQ ID NO:824:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: DNA (ix) FEATURE:
        (D) OTHER INFORMATION: oligonucleotide primer (xi) SEQUENCE DESCRIPTION: SEQ ID NO:824:

GGTGTGGTTG TTGGTAAGAG GTTATCTG                                28

(2) INFORMATION FOR SEQ ID NO:825:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: DNA (ix) FEATURE:
            (D) OTHER INFORMATION: oligonucleotide primer (xi) SEQUENCE DESCRIPTION: SEQ ID NO:825:

CCCGCGACAT GATGGACGCC TTTATC                                                26

(2) INFORMATION FOR SEQ ID NO:826:

(i) SEQUENCE CHARACTERISTICS:
            (A) LENGTH: 26 base pairs
            (B) TYPE: nucleic acid
            (C) STRANDEDNESS: single
            (D) TOPOLOGY: linear (ii) MOLECULE TYPE: DNA (ix) FEATURE:
            (D) OTHER INFORMATION: oligonucleotide primer (xi) SEQUENCE DESCRIPTION: SEQ ID NO:826:

GGTGGCATGA GGAATAGTGA CAGGCA                                                26

(2) INFORMATION FOR SEQ ID NO:827:

(i) SEQUENCE CHARACTERISTICS:
            (A) LENGTH: 26 base pairs
            (B) TYPE: nucleic acid
            (C) STRANDEDNESS: single
            (D) TOPOLOGY: linear (ii) MOLECULE TYPE: DNA (ix) FEATURE:
            (D) OTHER INFORMATION: oligonucleotide primer (xi) SEQUENCE DESCRIPTION: SEQ ID NO:827:

TGGAGGACGA CGGCGAGTTC TACATG                                                26

(2) INFORMATION FOR SEQ ID NO:828:

(i) SEQUENCE CHARACTERISTICS:
            (A) LENGTH: 27 base pairs
            (B) TYPE: nucleic acid
            (C) STRANDEDNESS: single
            (D) TOPOLOGY: linear (ii) MOLECULE TYPE: DNA (ix) FEATURE:
            (D) OTHER INFORMATION: oligonucleotide primer (xi) SEQUENCE DESCRIPTION: SEQ ID NO:828:

CATGCGGTTC CTGTTGATGG TTGTGGA                                               27

(2) INFORMATION FOR SEQ ID NO:829:

(i) SEQUENCE CHARACTERISTICS:
            (A) LENGTH: 26 base pairs
            (B) TYPE: nucleic acid
            (C) STRANDEDNESS: single
            (D) TOPOLOGY: linear (ii) MOLECULE TYPE: DNA (ix) FEATURE:
            (D) OTHER INFORMATION: oligonucleotide primer (xi) SEQUENCE DESCRIPTION: SEQ ID NO:829:

ACAGGACCTC CAGACCGATG TCAACA                                                26

(2) INFORMATION FOR SEQ ID NO:830:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: DNA (ix) FEATURE:
        (D) OTHER INFORMATION: oligonucleotide primer (xi) SEQUENCE DESCRIPTION: SEQ ID NO:830:

AGTCTATCTG TTGTGGAGTG CCACGAAT                            28

(2) INFORMATION FOR SEQ ID NO:831:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: DNA (ix) FEATURE:
        (D) OTHER INFORMATION: oligonucleotide primer (xi) SEQUENCE DESCRIPTION: SEQ ID NO:831:

GGCACCAGTG ATCGACACAT TCGCAT                              26

(2) INFORMATION FOR SEQ ID NO:832:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: DNA (ix) FEATURE:
        (D) OTHER INFORMATION: oligonucleotide primer (xi) SEQUENCE DESCRIPTION: SEQ ID NO:832:

GCCATAGCCT CAGGGTCTCA TCTGCT                              26

(2) INFORMATION FOR SEQ ID NO:833:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: DNA (ix) FEATURE:
        (D) OTHER INFORMATION: oligonucleotide primer (xi) SEQUENCE DESCRIPTION: SEQ ID NO:833:

ATCAAGCCAT CGGAGCTGCT AGAGTTC                            27

(2) INFORMATION FOR SEQ ID NO:834:

(i) SEQUENCE CHARACTERISTICS:
        (A) LENGTH: 28 base pairs
        (B) TYPE: nucleic acid
        (C) STRANDEDNESS: single (D) TOPOLOGY: linear (ii) MOLECULE TYPE: DNA (ix) FEATURE:
        (D) OTHER INFORMATION: oligonucleotide primer (xi) SEQUENCE DESCRIPTION: SEQ ID NO:834:

TCATTTGCCA AAGTCAAGAC GACGACCA                                      28

(2) INFORMATION FOR SEQ ID NO:835:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: DNA (ix) FEATURE:
        (D) OTHER INFORMATION: oligonucleotide primer (xi) SEQUENCE DESCRIPTION: SEQ ID NO:835:

AGGGTGGCAC ACCCATCCGT TTGC                                          24

(2) INFORMATION FOR SEQ ID NO:836:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: DNA (ix) FEATURE:
        (D) OTHER INFORMATION: oligonucleotide primer (xi) SEQUENCE DESCRIPTION: SEQ ID NO:836:

AACAAGCGGC AGCTATGAGT CAGGGA                                        26

(2) INFORMATION FOR SEQ ID NO:837:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: DNA (ix) FEATURE:
        (D) OTHER INFORMATION: oligonucleotide primer (xi) SEQUENCE DESCRIPTION: SEQ ID NO:837:

CGGCTGGTTC GGCTCTACGC TGTG                                          24

(2) INFORMATION FOR SEQ ID NO:838:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: DNA (ix) FEATURE:
        (D) OTHER INFORMATION: oligonucleotide primer (xi) SEQUENCE DESCRIPTION: SEQ ID NO:838:

```
CCTCAATGAG GCGTGCTAGG CCAAAG                                          26
```

(2) INFORMATION FOR SEQ ID NO:839:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: DNA (ix) FEATURE:
        (D) OTHER INFORMATION: oligonucleotide primer (xi) SEQUENCE DESCRIPTION: SEQ ID NO:839:

```
GTCATAGAGC CTGCCTCCAA CCATGA                                          26
```

(2) INFORMATION FOR SEQ ID NO:840:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: DNA (ix) FEATURE:
        (D) OTHER INFORMATION: oligonucleotide primer (xi) SEQUENCE DESCRIPTION: SEQ ID NO:840:

```
CTCTGTACTG AAGCCAGTCT GATTCCTT                                        28
```

(2) INFORMATION FOR SEQ ID NO:841:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: DNA (ix) FEATURE:
        (D) OTHER INFORMATION: oligonucleotide primer (xi) SEQUENCE DESCRIPTION: SEQ ID NO:841:

```
GTAGACTCAA GTTCGCTGAC AGGTCC                                          26
```

(2) INFORMATION FOR SEQ ID NO:842:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: DNA (ix) FEATURE:
        (D) OTHER INFORMATION: oligonucleotide primer (xi) SEQUENCE DESCRIPTION: SEQ ID NO:842:

```
TGAATCGCTT GCTGCAACAA CTGTTCCA                                        28
```

(2) INFORMATION FOR SEQ ID NO:843:

(i) SEQUENCE CHARACTERISTICS:
        (A) LENGTH: 28 base pairs (B) TYPE: nucleic acid
        (C) STRANDEDNESS: single
        (D) TOPOLOGY: linear (ii) MOLECULE TYPE: DNA (ix) FEATURE:
        (D) OTHER INFORMATION: oligonucleotide primer (xi) SEQUENCE DESCRIPTION: SEQ ID NO:843:

TCAGTTCAGT AAGGTCTGGT TCACGCTA                                28

(2) INFORMATION FOR SEQ ID NO:844:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: DNA (ix) FEATURE:
        (D) OTHER INFORMATION: oligonucleotide primer (xi) SEQUENCE DESCRIPTION: SEQ ID NO:844:

GGAATTGTGG TCATCCCAGG GTTGAAG                                 27

(2) INFORMATION FOR SEQ ID NO:845:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: DNA (ix) FEATURE:
        (D) OTHER INFORMATION: oligonucleotide primer (xi) SEQUENCE DESCRIPTION: SEQ ID NO:845:

GCAGAGCACG GACAGCTATC CGGT                                    24

(2) INFORMATION FOR SEQ ID NO:846:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: DNA (ix) FEATURE:
        (D) OTHER INFORMATION: oligonucleotide primer (xi) SEQUENCE DESCRIPTION: SEQ ID NO:846:

CGCGCTCATG TTCACGGCTT ACGGT                                   25

(2) INFORMATION FOR SEQ ID NO:847:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: DNA (ix) FEATURE:
        (D) OTHER INFORMATION: oligonucleotide primer

```
        (xi) SEQUENCE DESCRIPTION: SEQ ID NO:847:

AAAGCAGGCC AGACCATCAC CGTTGC                                              26

(2) INFORMATION FOR SEQ ID NO:848:

(i) SEQUENCE CHARACTERISTICS:
         (A) LENGTH: 27 base pairs
         (B) TYPE: nucleic acid
         (C) STRANDEDNESS: single
         (D) TOPOLOGY: linear (ii) MOLECULE TYPE: DNA (ix) FEATURE:
         (D) OTHER INFORMATION: oligonucleotide primer (xi) SEQUENCE DESCRIPTION: SEQ ID NO:848:

GGAACTGTGA TCCGTGTAGG CAACTTC                                             27

(2) INFORMATION FOR SEQ ID NO:849:

(i) SEQUENCE CHARACTERISTICS:
         (A) LENGTH: 26 base pairs
         (B) TYPE: nucleic acid
         (C) STRANDEDNESS: single
         (D) TOPOLOGY: linear (ii) MOLECULE TYPE: DNA (ix) FEATURE:
         (D) OTHER INFORMATION: oligonucleotide primer (xi) SEQUENCE DESCRIPTION: SEQ ID NO:849:

ACGACCCTAC TCGCCCAGTC AGTATG                                              26

(2) INFORMATION FOR SEQ ID NO:850:

(i) SEQUENCE CHARACTERISTICS:
         (A) LENGTH: 25 base pairs
         (B) TYPE: nucleic acid
         (C) STRANDEDNESS: single
         (D) TOPOLOGY: linear (ii) MOLECULE TYPE: DNA (ix) FEATURE:
         (D) OTHER INFORMATION: oligonucleotide primer (xi) SEQUENCE DESCRIPTION: SEQ ID NO:850:

CCCTGTCCGT CTAAATGGTC TGGCC                                               25

(2) INFORMATION FOR SEQ ID NO:851:

(i) SEQUENCE CHARACTERISTICS:
         (A) LENGTH: 28 base pairs
         (B) TYPE: nucleic acid
         (C) STRANDEDNESS: single
         (D) TOPOLOGY: linear (ii) MOLECULE TYPE: DNA (ix) FEATURE:
         (D) OTHER INFORMATION: oligonucleotide primer (xi) SEQUENCE DESCRIPTION: SEQ ID NO:851:

TTGCTGAAGT CAGTTCGCAA TTCAGACC                                            28

(2) INFORMATION FOR SEQ ID NO:852:
```

```
         (i) SEQUENCE CHARACTERISTICS:
             (A) LENGTH: 27 base pairs
             (B) TYPE: nucleic acid
             (C) STRANDEDNESS: single
             (D) TOPOLOGY: linear (ii) MOLECULE TYPE: DNA (ix) FEATURE:
             (D) OTHER INFORMATION: oligonucleotide primer (xi) SEQUENCE DESCRIPTION: SEQ ID NO:852:

CAGATCGCTG CCATTCTGTT GCTTCTG                                              27

(2) INFORMATION FOR SEQ ID NO:853:

(i) SEQUENCE CHARACTERISTICS:
             (A) LENGTH: 28 base pairs
             (B) TYPE: nucleic acid
             (C) STRANDEDNESS: single
             (D) TOPOLOGY: linear (ii) MOLECULE TYPE: DNA (ix) FEATURE:
             (D) OTHER INFORMATION: oligonucleotide primer (xi) SEQUENCE DESCRIPTION: SEQ ID NO:853:

ATTAGCAGCG GAACAAGGAG TCAGACAT                                             28

(2) INFORMATION FOR SEQ ID NO:854:

(i) SEQUENCE CHARACTERISTICS:
             (A) LENGTH: 28 base pairs
             (B) TYPE: nucleic acid
             (C) STRANDEDNESS: single
             (D) TOPOLOGY: linear (ii) MOLECULE TYPE: DNA (ix) FEATURE:
             (D) OTHER INFORMATION: oligonucleotide primer (xi) SEQUENCE DESCRIPTION: SEQ ID NO:854:

CTGTGAAAGA CACAGAACAG TACAGGGT                                            28

(2) INFORMATION FOR SEQ ID NO:855:

(i) SEQUENCE CHARACTERISTICS:
             (A) LENGTH: 26 base pairs
             (B) TYPE: nucleic acid
             (C) STRANDEDNESS: single
             (D) TOPOLOGY: linear (ii) MOLECULE TYPE: DNA (ix) FEATURE:
             (D) OTHER INFORMATION: oligonucleotide primer (xi) SEQUENCE DESCRIPTION: SEQ ID NO:855:

GGCCTTATGA GGGTCCTCTA CTTCAG                                              26

(2) INFORMATION FOR SEQ ID NO:856:

(i) SEQUENCE CHARACTERISTICS:
             (A) LENGTH: 25 base pairs
             (B) TYPE: nucleic acid
             (C) STRANDEDNESS: single
             (D) TOPOLOGY: linear (ii) MOLECULE TYPE: DNA
```

```
    (ix) FEATURE:
          (D) OTHER INFORMATION: oligonucleotide primer (xi) SEQUENCE DESCRIPTION: SEQ ID NO:856:

CACTGTGAGC CGAGATCGCT ACCAC                                          25

(2) INFORMATION FOR SEQ ID NO:857:

(i) SEQUENCE CHARACTERISTICS:
          (A) LENGTH: 27 base pairs
          (B) TYPE: nucleic acid
          (C) STRANDEDNESS: single
          (D) TOPOLOGY: linear (ii) MOLECULE TYPE: DNA (ix) FEATURE:
          (D) OTHER INFORMATION: oligonucleotide primer (xi) SEQUENCE DESCRIPTION: SEQ ID NO:857:

GTCTGCTATA CAGCTCAGAC TCTCGTC                                        27

(2) INFORMATION FOR SEQ ID NO:858:

(i) SEQUENCE CHARACTERISTICS:
          (A) LENGTH: 28 base pairs
          (B) TYPE: nucleic acid
          (C) STRANDEDNESS: single
          (D) TOPOLOGY: linear (ii) MOLECULE TYPE: DNA (ix) FEATURE:
          (D) OTHER INFORMATION: oligonucleotide primer (xi) SEQUENCE DESCRIPTION: SEQ ID NO:858:

GGGAGACTGG CAGCTAAGCC AATATCAA                                       28

(2) INFORMATION FOR SEQ ID NO:859:

(i) SEQUENCE CHARACTERISTICS:
          (A) LENGTH: 25 base pairs
          (B) TYPE: nucleic acid
          (C) STRANDEDNESS: single
          (D) TOPOLOGY: linear (ii) MOLECULE TYPE: DNA (ix) FEATURE:
          (D) OTHER INFORMATION: oligonucleotide primer (xi) SEQUENCE DESCRIPTION: SEQ ID NO:859:

ACCAGTCCTC ACAAGGCGGC TATGG                                          25

(2) INFORMATION FOR SEQ ID NO:860:

(i) SEQUENCE CHARACTERISTICS:
          (A) LENGTH: 26 base pairs
          (B) TYPE: nucleic acid
          (C) STRANDEDNESS: single
          (D) TOPOLOGY: linear (ii) MOLECULE TYPE: DNA (ix) FEATURE:
          (D) OTHER INFORMATION: oligonucleotide primer (xi) SEQUENCE DESCRIPTION: SEQ ID NO:860:

GGCTAAATAT GGGTCACAGG ACGGGC                                         26
```

(2) INFORMATION FOR SEQ ID NO:861:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: DNA (ix) FEATURE:
        (D) OTHER INFORMATION: oligonucleotide primer (xi) SEQUENCE DESCRIPTION: SEQ ID NO:861:

CAACAGTTGC GGCGGCGACG ACC                                               23

(2) INFORMATION FOR SEQ ID NO:862:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: DNA (ix) FEATURE:
        (D) OTHER INFORMATION: oligonucleotide primer (xi) SEQUENCE DESCRIPTION: SEQ ID NO:862:

TATGAGTGGT GAATGTATTG AGGCGAGC                                          28

(2) INFORMATION FOR SEQ ID NO:863:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: DNA (ix) FEATURE:
        (D) OTHER INFORMATION: oligonucleotide primer (xi) SEQUENCE DESCRIPTION: SEQ ID NO:863:

TCCACAGACT GACCATTGGT CGGAGT                                            26

(2) INFORMATION FOR SEQ ID NO:864:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: DNA (ix) FEATURE:
        (D) OTHER INFORMATION: oligonucleotide primer (xi) SEQUENCE DESCRIPTION: SEQ ID NO:864:

CCTGAATCAC TAGCGGCAGC ACTGATTT                                          28

(2) INFORMATION FOR SEQ ID NO:865:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: DNA (ix) FEATURE:
             (D) OTHER INFORMATION: oligonucleotide primer (xi) SEQUENCE DESCRIPTION: SEQ ID NO:865:

TTTCAGCTCT TGACAACGC CAACTGCC                                               28

(2) INFORMATION FOR SEQ ID NO:866:

(i) SEQUENCE CHARACTERISTICS:
             (A) LENGTH: 28 base pairs
             (B) TYPE: nucleic acid
             (C) STRANDEDNESS: single
             (D) TOPOLOGY: linear (ii) MOLECULE TYPE: DNA (ix) FEATURE:
             (D) OTHER INFORMATION: oligonucleotide primer (xi) SEQUENCE DESCRIPTION: SEQ ID NO:866:

CTTCCCGATC CTTGATAAGT GCGTTCAC                                              28

(2) INFORMATION FOR SEQ ID NO:867:

(i) SEQUENCE CHARACTERISTICS:
             (A) LENGTH: 24 base pairs
             (B) TYPE: nucleic acid
             (C) STRANDEDNESS: single
             (D) TOPOLOGY: linear (ii) MOLECULE TYPE: DNA (ix) FEATURE:
             (D) OTHER INFORMATION: oligonucleotide primer (xi) SEQUENCE DESCRIPTION: SEQ ID NO:867:

AGTCACGGAC TCCTGCATCG TGGC                                                  24

(2) INFORMATION FOR SEQ ID NO:868:

(i) SEQUENCE CHARACTERISTICS:
             (A) LENGTH: 24 base pairs
             (B) TYPE: nucleic acid
             (C) STRANDEDNESS: single
             (D) TOPOLOGY: linear (ii) MOLECULE TYPE: DNA (ix) FEATURE:
             (D) OTHER INFORMATION: oligonucleotide primer (xi) SEQUENCE DESCRIPTION: SEQ ID NO:868:

TGTTCCGCAT GGCGGCAGTC CCTT                                                  24

(2) INFORMATION FOR SEQ ID NO:869:

(i) SEQUENCE CHARACTERISTICS:
             (A) LENGTH: 28 base pairs
             (B) TYPE: nucleic acid
             (C) STRANDEDNESS: single
             (D) TOPOLOGY: linear (ii) MOLECULE TYPE: DNA (ix) FEATURE:
             (D) OTHER INFORMATION: oligonucleotide primer (xi) SEQUENCE DESCRIPTION: SEQ ID NO:869:

GCGATAGTGA AAGTAGTTAC CGTGGTCA                                              28

(2) INFORMATION FOR SEQ ID NO:870:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: DNA (ix) FEATURE:
        (D) OTHER INFORMATION: oligonucleotide primer (xi) SEQUENCE DESCRIPTION: SEQ ID NO:870:

CCAGACACAT CAAGGATACA GTGTTTGC                        28

(2) INFORMATION FOR SEQ ID NO:871:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: DNA (ix) FEATURE:
        (D) OTHER INFORMATION: oligonucleotide primer (xi) SEQUENCE DESCRIPTION: SEQ ID NO:871:

ACCATTGACC ACCAGTCTTG CTCTCG                          26

(2) INFORMATION FOR SEQ ID NO:872:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: DNA (ix) FEATURE:
        (D) OTHER INFORMATION: oligonucleotide primer (xi) SEQUENCE DESCRIPTION: SEQ ID NO:872:

CACCATGTTC CTGAATCGAC CAACTGAG                        28

(2) INFORMATION FOR SEQ ID NO:873:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: DNA (ix) FEATURE:
        (D) OTHER INFORMATION: oligonucleotide primer (xi) SEQUENCE DESCRIPTION: SEQ ID NO:873:

CATGTGGCAC CGTTTGCCTC AAGTAC                          26

(2) INFORMATION FOR SEQ ID NO:874:

(i) SEQUENCE CHARACTERISTICS:
        (A) LENGTH: 26 base pairs
        (B) TYPE: nucleic acid
        (C) STRANDEDNESS: single (D) TOPOLOGY: linear (ii) MOLECULE TYPE: DNA (ix) FEATURE:
            (D) OTHER INFORMATION: oligonucleotide primer (xi) SEQUENCE DESCRIPTION: SEQ ID NO:874:

GTAGGCGAGG ATACCAGCGA TGATCT                                              26

(2) INFORMATION FOR SEQ ID NO:875:

(i) SEQUENCE CHARACTERISTICS:
            (A) LENGTH: 25 base pairs
            (B) TYPE: nucleic acid
            (C) STRANDEDNESS: single
            (D) TOPOLOGY: linear (ii) MOLECULE TYPE: DNA (ix) FEATURE:
            (D) OTHER INFORMATION: oligonucleotide primer (xi) SEQUENCE DESCRIPTION: SEQ ID NO:875:

TCTTGAACGT GCTGGACAGG GCCTG                                               25

(2) INFORMATION FOR SEQ ID NO:876:

(i) SEQUENCE CHARACTERISTICS:
            (A) LENGTH: 26 base pairs
            (B) TYPE: nucleic acid
            (C) STRANDEDNESS: single
            (D) TOPOLOGY: linear (ii) MOLECULE TYPE: DNA (ix) FEATURE:
            (D) OTHER INFORMATION: oligonucleotide primer (xi) SEQUENCE DESCRIPTION: SEQ ID NO:876:

TCGTCGATGA TGTAGAGTTC CTCGCC                                              26

(2) INFORMATION FOR SEQ ID NO:877:

(i) SEQUENCE CHARACTERISTICS:
            (A) LENGTH: 24 base pairs
            (B) TYPE: nucleic acid
            (C) STRANDEDNESS: single
            (D) TOPOLOGY: linear (ii) MOLECULE TYPE: DNA (ix) FEATURE:
            (D) OTHER INFORMATION: oligonucleotide primer (xi) SEQUENCE DESCRIPTION: SEQ ID NO:877:

GCTTCACCAT CCTGGGCGTG CTCA                                                24

(2) INFORMATION FOR SEQ ID NO:878:

(i) SEQUENCE CHARACTERISTICS:
            (A) LENGTH: 28 base pairs
            (B) TYPE: nucleic acid
            (C) STRANDEDNESS: single
            (D) TOPOLOGY: linear (ii) MOLECULE TYPE: DNA (ix) FEATURE:
            (D) OTHER INFORMATION: oligonucleotide primer (xi) SEQUENCE DESCRIPTION: SEQ ID NO:878:

-continued

```
CACCACAAAG ATTAGGACAG ACCGCGTA                                    28

(2) INFORMATION FOR SEQ ID NO:879:

(i) SEQUENCE CHARACTERISTICS:
          (A) LENGTH: 26 base pairs
          (B) TYPE: nucleic acid
          (C) STRANDEDNESS: single
          (D) TOPOLOGY: linear (ii) MOLECULE TYPE: DNA (ix) FEATURE:
          (D) OTHER INFORMATION: oligonucleotide primer (xi) SEQUENCE DESCRIPTION: SEQ ID NO:879:

CTTCTCAATG AGCCCGACGG AACCTT                                      26

(2) INFORMATION FOR SEQ ID NO:880:

(i) SEQUENCE CHARACTERISTICS:
          (A) LENGTH: 26 base pairs
          (B) TYPE: nucleic acid
          (C) STRANDEDNESS: single
          (D) TOPOLOGY: linear (ii) MOLECULE TYPE: DNA (ix) FEATURE:
          (D) OTHER INFORMATION: oligonucleotide primer (xi) SEQUENCE DESCRIPTION: SEQ ID NO:880:

TCCACGGTCA TCTTGATGGT AGCTGG                                      26

(2) INFORMATION FOR SEQ ID NO:881:

(i) SEQUENCE CHARACTERISTICS:
          (A) LENGTH: 26 base pairs
          (B) TYPE: nucleic acid
          (C) STRANDEDNESS: single
          (D) TOPOLOGY: linear (ii) MOLECULE TYPE: DNA (ix) FEATURE:
          (D) OTHER INFORMATION: oligonucleotide primer (xi) SEQUENCE DESCRIPTION: SEQ ID NO:881:

CATGGCTGGC CGCATCTACA TCTCAG                                      26

(2) INFORMATION FOR SEQ ID NO:882:

(i) SEQUENCE CHARACTERISTICS:
          (A) LENGTH: 24 base pairs
          (B) TYPE: nucleic acid
          (C) STRANDEDNESS: single
          (D) TOPOLOGY: linear (ii) MOLECULE TYPE: DNA (ix) FEATURE:
          (D) OTHER INFORMATION: oligonucleotide primer (xi) SEQUENCE DESCRIPTION: SEQ ID NO:882:

GAGCGATGGA GCGTGGGTAG GGAG                                        24

(2) INFORMATION FOR SEQ ID NO:883:

(i) SEQUENCE CHARACTERISTICS:
          (A) LENGTH: 23 base pairs
```

(B) TYPE: nucleic acid
            (C) STRANDEDNESS: single
            (D) TOPOLOGY: linear (ii) MOLECULE TYPE: DNA (ix) FEATURE:
            (D) OTHER INFORMATION: oligonucleotide primer (xi) SEQUENCE DESCRIPTION: SEQ ID NO:883:

CTGTGGGCCT GGCCGTCTTT GCC                                                        23

(2) INFORMATION FOR SEQ ID NO:884:

(i) SEQUENCE CHARACTERISTICS:
            (A) LENGTH: 23 base pairs
            (B) TYPE: nucleic acid
            (C) STRANDEDNESS: single
            (D) TOPOLOGY: linear (ii) MOLECULE TYPE: DNA (ix) FEATURE:
            (D) OTHER INFORMATION: oligonucleotide primer (xi) SEQUENCE DESCRIPTION: SEQ ID NO:884:

CCGAGCACTC TCGGACGCCT CCT                                                        23

(2) INFORMATION FOR SEQ ID NO:885:

(i) SEQUENCE CHARACTERISTICS:
            (A) LENGTH: 25 base pairs
            (B) TYPE: nucleic acid
            (C) STRANDEDNESS: single
            (D) TOPOLOGY: linear (ii) MOLECULE TYPE: DNA (ix) FEATURE:
            (D) OTHER INFORMATION: oligonucleotide primer (xi) SEQUENCE DESCRIPTION: SEQ ID NO:885:

TGCAACGTGG TTGGGACTTG ACCCC                                                      25

(2) INFORMATION FOR SEQ ID NO:886:

(i) SEQUENCE CHARACTERISTICS:
            (A) LENGTH: 26 base pairs
            (B) TYPE: nucleic acid
            (C) STRANDEDNESS: single
            (D) TOPOLOGY: linear (ii) MOLECULE TYPE: DNA (ix) FEATURE:
            (D) OTHER INFORMATION: oligonucleotide primer (xi) SEQUENCE DESCRIPTION: SEQ ID NO:886:

TGACGAGTTC GATTGCGACA GGTTGG                                                     26

(2) INFORMATION FOR SEQ ID NO:887:

(i) SEQUENCE CHARACTERISTICS:
            (A) LENGTH: 28 base pairs
            (B) TYPE: nucleic acid
            (C) STRANDEDNESS: single
            (D) TOPOLOGY: linear (ii) MOLECULE TYPE: DNA (ix) FEATURE:
            (D) OTHER INFORMATION: oligonucleotide primer (xi) SEQUENCE DESCRIPTION: SEQ ID NO:887:

CCCTCTATTA TCAAACAAAT GCGCCACC                                28

(2) INFORMATION FOR SEQ ID NO:888:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: DNA (ix) FEATURE:
        (D) OTHER INFORMATION: oligonucleotide primer (xi) SEQUENCE DESCRIPTION: SEQ ID NO:888:

GATGATAGAC TCCAAGATGG ACGACAGC                                28

(2) INFORMATION FOR SEQ ID NO:889:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: DNA (ix) FEATURE:
        (D) OTHER INFORMATION: oligonucleotide primer (xi) SEQUENCE DESCRIPTION: SEQ ID NO:889:

ACACAGCACA ACGTCTTACC GTGCCT                                  26

(2) INFORMATION FOR SEQ ID NO:890:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: DNA (ix) FEATURE:
        (D) OTHER INFORMATION: oligonucleotide primer (xi) SEQUENCE DESCRIPTION: SEQ ID NO:890:

GTTGCGGGTC TTCAGATGGC GTCATG                                  26

(2) INFORMATION FOR SEQ ID NO:891:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: DNA (ix) FEATURE:
        (D) OTHER INFORMATION: oligonucleotide primer (xi) SEQUENCE DESCRIPTION: SEQ ID NO:891:

AATTGGCCTT GTTGCTGCCG CTTCATC                                 27

(2) INFORMATION FOR SEQ ID NO:892:

```
    (i) SEQUENCE CHARACTERISTICS:
         (A) LENGTH: 26 base pairs
         (B) TYPE: nucleic acid
         (C) STRANDEDNESS: single
         (D) TOPOLOGY: linear (ii) MOLECULE TYPE: DNA (ix) FEATURE:
         (D) OTHER INFORMATION: oligonucleotide primer (xi) SEQUENCE DESCRIPTION: SEQ ID NO:892:

GCCTATCGGC CTCAGCATGG TCCAAT                                              26

(2) INFORMATION FOR SEQ ID NO:893:

(i) SEQUENCE CHARACTERISTICS:
         (A) LENGTH: 24 base pairs
         (B) TYPE: nucleic acid
         (C) STRANDEDNESS: single
         (D) TOPOLOGY: linear (ii) MOLECULE TYPE: DNA (ix) FEATURE:
         (D) OTHER INFORMATION: oligonucleotide primer (xi) SEQUENCE DESCRIPTION: SEQ ID NO:893:

CACAGCCATC CCAGCAACCT TGGG                                                24

(2) INFORMATION FOR SEQ ID NO:894:

(i) SEQUENCE CHARACTERISTICS:
         (A) LENGTH: 28 base pairs
         (B) TYPE: nucleic acid
         (C) STRANDEDNESS: single
         (D) TOPOLOGY: linear (ii) MOLECULE TYPE: DNA (ix) FEATURE:
         (D) OTHER INFORMATION: oligonucleotide primer (xi) SEQUENCE DESCRIPTION: SEQ ID NO:894:

GGGCAAACTC CTTATGAAGT GGCACAAA                                            28

(2) INFORMATION FOR SEQ ID NO:895:

(i) SEQUENCE CHARACTERISTICS:
         (A) LENGTH: 26 base pairs
         (B) TYPE: nucleic acid
         (C) STRANDEDNESS: single
         (D) TOPOLOGY: linear (ii) MOLECULE TYPE: DNA (ix) FEATURE:
         (D) OTHER INFORMATION: oligonucleotide primer (xi) SEQUENCE DESCRIPTION: SEQ ID NO:895:

CCGGTGCTTC TGGAAACTAC CAGGTG                                              26

(2) INFORMATION FOR SEQ ID NO:896:

(i) SEQUENCE CHARACTERISTICS:
         (A) LENGTH: 28 base pairs
         (B) TYPE: nucleic acid
         (C) STRANDEDNESS: single
         (D) TOPOLOGY: linear (ii) MOLECULE TYPE: DNA
```

(ix) FEATURE:
          (D) OTHER INFORMATION: oligonucleotide primer (xi) SEQUENCE DESCRIPTION: SEQ ID NO:896:

GGCTGACCTC GGGAATGTTA GACAAGAT                                              28

(2) INFORMATION FOR SEQ ID NO:897:

(i) SEQUENCE CHARACTERISTICS:
         (A) LENGTH: 26 base pairs
         (B) TYPE: nucleic acid
         (C) STRANDEDNESS: single
         (D) TOPOLOGY: linear (ii) MOLECULE TYPE: DNA (ix) FEATURE:
          (D) OTHER INFORMATION: oligonucleotide primer (xi) SEQUENCE DESCRIPTION: SEQ ID NO:897:

CCCTCATTAA GCCCAAGCGA AGGCTG                                                26

(2) INFORMATION FOR SEQ ID NO:898:

(i) SEQUENCE CHARACTERISTICS:
         (A) LENGTH: 26 base pairs
         (B) TYPE: nucleic acid
         (C) STRANDEDNESS: single
         (D) TOPOLOGY: linear (ii) MOLECULE TYPE: DNA (ix) FEATURE:
          (D) OTHER INFORMATION: oligonucleotide primer (xi) SEQUENCE DESCRIPTION: SEQ ID NO:898:

GCCGGGTTAA ACGAGCTGTT CTTGGG                                                26

(2) INFORMATION FOR SEQ ID NO:899:

(i) SEQUENCE CHARACTERISTICS:
         (A) LENGTH: 28 base pairs
         (B) TYPE: nucleic acid
         (C) STRANDEDNESS: single
         (D) TOPOLOGY: linear (ii) MOLECULE TYPE: DNA (ix) FEATURE:
          (D) OTHER INFORMATION: oligonucleotide primer (xi) SEQUENCE DESCRIPTION: SEQ ID NO:899:

CAGACTCAGA ATTGTCCACT GTACCTTC                                              28

(2) INFORMATION FOR SEQ ID NO:900:

(i) SEQUENCE CHARACTERISTICS:
         (A) LENGTH: 27 base pairs
         (B) TYPE: nucleic acid
         (C) STRANDEDNESS: single
         (D) TOPOLOGY: linear (ii) MOLECULE TYPE: DNA (ix) FEATURE:
          (D) OTHER INFORMATION: oligonucleotide primer (xi) SEQUENCE DESCRIPTION: SEQ ID NO:900:

GGGCTGATGA TGGTCCTTAG GTTTCAG                                               27

-continued (2) INFORMATION FOR SEQ ID NO:901:

(i) SEQUENCE CHARACTERISTICS:
      (A) LENGTH: 28 base pairs
      (B) TYPE: nucleic acid
      (C) STRANDEDNESS: single
      (D) TOPOLOGY: linear (ii) MOLECULE TYPE: DNA (ix) FEATURE:
      (D) OTHER INFORMATION: oligonucleotide primer (xi) SEQUENCE DESCRIPTION: SEQ ID NO:901:

CCCTGATGGA CATCCTTTGA CTGTCTAT                                28

(2) INFORMATION FOR SEQ ID NO:902:

(i) SEQUENCE CHARACTERISTICS:
      (A) LENGTH: 28 base pairs
      (B) TYPE: nucleic acid
      (C) STRANDEDNESS: single
      (D) TOPOLOGY: linear (ii) MOLECULE TYPE: DNA (ix) FEATURE:
      (D) OTHER INFORMATION: oligonucleotide primer (xi) SEQUENCE DESCRIPTION: SEQ ID NO:902:

GTGGCGATTC AATAACCCTT GTTCAGCT                                28

(2) INFORMATION FOR SEQ ID NO:903:

(i) SEQUENCE CHARACTERISTICS:
      (A) LENGTH: 27 base pairs
      (B) TYPE: nucleic acid
      (C) STRANDEDNESS: single
      (D) TOPOLOGY: linear (ii) MOLECULE TYPE: DNA (ix) FEATURE:
      (D) OTHER INFORMATION: oligonucleotide primer (xi) SEQUENCE DESCRIPTION: SEQ ID NO:903:

CATCCTGTCC AGCAATGAAG TAGACCC                                 27

(2) INFORMATION FOR SEQ ID NO:904:

(i) SEQUENCE CHARACTERISTICS:
      (A) LENGTH: 28 base pairs
      (B) TYPE: nucleic acid
      (C) STRANDEDNESS: single
      (D) TOPOLOGY: linear (ii) MOLECULE TYPE: DNA (ix) FEATURE:
      (D) OTHER INFORMATION: oligonucleotide primer (xi) SEQUENCE DESCRIPTION: SEQ ID NO:904:

CAAGGTACTT TGGCCCAGTC AATCAAAG                                28

(2) INFORMATION FOR SEQ ID NO:905:

(i) SEQUENCE CHARACTERISTICS:
      (A) LENGTH: 27 base pairs
      (B) TYPE: nucleic acid
      (C) STRANDEDNESS: single
      (D) TOPOLOGY: linear (ii) MOLECULE TYPE: DNA (ix) FEATURE:
             (D) OTHER INFORMATION: oligonucleotide primer (xi) SEQUENCE DESCRIPTION: SEQ ID NO:905:

GGCCTTCCAG TTCACTGACA AACATGG                                    27

(2) INFORMATION FOR SEQ ID NO:906:

(i) SEQUENCE CHARACTERISTICS:
            (A) LENGTH: 26 base pairs
            (B) TYPE: nucleic acid
            (C) STRANDEDNESS: single
            (D) TOPOLOGY: linear (ii) MOLECULE TYPE: DNA (ix) FEATURE:
             (D) OTHER INFORMATION: oligonucleotide primer (xi) SEQUENCE DESCRIPTION: SEQ ID NO:906:

ACGCCAACTC AGGCCATTCC TACCAA                                     26

(2) INFORMATION FOR SEQ ID NO:907:

(i) SEQUENCE CHARACTERISTICS:
            (A) LENGTH: 28 base pairs
            (B) TYPE: nucleic acid
            (C) STRANDEDNESS: single
            (D) TOPOLOGY: linear (ii) MOLECULE TYPE: DNA (ix) FEATURE:
             (D) OTHER INFORMATION: oligonucleotide primer (xi) SEQUENCE DESCRIPTION: SEQ ID NO:907:

AAACTGTGCT GTCCTTGTGA GGTCACTG                                   28

(2) INFORMATION FOR SEQ ID NO:908:

(i) SEQUENCE CHARACTERISTICS:
            (A) LENGTH: 28 base pairs
            (B) TYPE: nucleic acid
            (C) STRANDEDNESS: single
            (D) TOPOLOGY: linear (ii) MOLECULE TYPE: DNA (ix) FEATURE:
             (D) OTHER INFORMATION: oligonucleotide primer (xi) SEQUENCE DESCRIPTION: SEQ ID NO:908:

CACTCAAGGT TTGGGAGTAT AAGCACCC                                   28

(2) INFORMATION FOR SEQ ID NO:909:

(i) SEQUENCE CHARACTERISTICS:
            (A) LENGTH: 24 base pairs
            (B) TYPE: nucleic acid
            (C) STRANDEDNESS: single
            (D) TOPOLOGY: linear (ii) MOLECULE TYPE: DNA (ix) FEATURE:
             (D) OTHER INFORMATION: oligonucleotide primer (xi) SEQUENCE DESCRIPTION: SEQ ID NO:909:

GGCCCACCAT CAGCTACCCA ATGC                                       24

(2) INFORMATION FOR SEQ ID NO:910:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: DNA (ix) FEATURE:
        (D) OTHER INFORMATION: oligonucleotide primer (xi) SEQUENCE DESCRIPTION: SEQ ID NO:910:

CGTCACTCGC AGTCGTGAAC TTCCC                          25

(2) INFORMATION FOR SEQ ID NO:911:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: DNA (ix) FEATURE:
        (D) OTHER INFORMATION: oligonucleotide primer (xi) SEQUENCE DESCRIPTION: SEQ ID NO:911:

CCTGTGGAAA GTGCGAAGAT AGAACCAC                      28

(2) INFORMATION FOR SEQ ID NO:912:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: DNA (ix) FEATURE:
        (D) OTHER INFORMATION: oligonucleotide primer (xi) SEQUENCE DESCRIPTION: SEQ ID NO:912:

CATAGTGTTC CAGATCACTT GTTGCCGC                      28

(2) INFORMATION FOR SEQ ID NO:913:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: DNA (ix) FEATURE:
        (D) OTHER INFORMATION: oligonucleotide primer (xi) SEQUENCE DESCRIPTION: SEQ ID NO:913:

AACTTCCTAT GTCACAGGGT CCACTATG                      28

(2) INFORMATION FOR SEQ ID NO:914:

(i) SEQUENCE CHARACTERISTICS:
        (A) LENGTH: 28 base pairs
        (B) TYPE: nucleic acid
        (C) STRANDEDNESS: single (D) TOPOLOGY: linear (ii) MOLECULE TYPE: DNA (ix) FEATURE:
         (D) OTHER INFORMATION: oligonucleotide primer (xi) SEQUENCE DESCRIPTION: SEQ ID NO:914:

CTGTCCTACT GCTATATTAG GCATGGCC                                                28

(2) INFORMATION FOR SEQ ID NO:915:

(i) SEQUENCE CHARACTERISTICS:
         (A) LENGTH: 25 base pairs
         (B) TYPE: nucleic acid
         (C) STRANDEDNESS: single
         (D) TOPOLOGY: linear (ii) MOLECULE TYPE: DNA (ix) FEATURE:
         (D) OTHER INFORMATION: oligonucleotide primer (xi) SEQUENCE DESCRIPTION: SEQ ID NO:915:

GGCACCCAGG CCAGGAAGTT TGATG                                                   25

(2) INFORMATION FOR SEQ ID NO:916:

(i) SEQUENCE CHARACTERISTICS:
         (A) LENGTH: 26 base pairs
         (B) TYPE: nucleic acid
         (C) STRANDEDNESS: single
         (D) TOPOLOGY: linear (ii) MOLECULE TYPE: DNA (ix) FEATURE:
         (D) OTHER INFORMATION: oligonucleotide primer (xi) SEQUENCE DESCRIPTION: SEQ ID NO:916:

ATCTACATAG CCATTGAGCC GGGCAG                                                  26

(2) INFORMATION FOR SEQ ID NO:917:

(i) SEQUENCE CHARACTERISTICS:
         (A) LENGTH: 25 base pairs
         (B) TYPE: nucleic acid
         (C) STRANDEDNESS: single
         (D) TOPOLOGY: linear (ii) MOLECULE TYPE: DNA (ix) FEATURE:
         (D) OTHER INFORMATION: oligonucleotide primer (xi) SEQUENCE DESCRIPTION: SEQ ID NO:917:

CGCGCAGATT GCCATTTGCG GCATG                                                   25

(2) INFORMATION FOR SEQ ID NO:918:

(i) SEQUENCE CHARACTERISTICS:
         (A) LENGTH: 28 base pairs
         (B) TYPE: nucleic acid
         (C) STRANDEDNESS: single
         (D) TOPOLOGY: linear (ii) MOLECULE TYPE: DNA (ix) FEATURE:
         (D) OTHER INFORMATION: oligonucleotide primer (xi) SEQUENCE DESCRIPTION: SEQ ID NO:918:

GTCTGCGGCT TCACTTTGTC TATTGCGA                                28

(2) INFORMATION FOR SEQ ID NO:919:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: DNA (ix) FEATURE:
        (D) OTHER INFORMATION: oligonucleotide primer (xi) SEQUENCE DESCRIPTION: SEQ ID NO:919:

GGTGGTGAGT TCTTGCTGCG GTATGC                                  26

(2) INFORMATION FOR SEQ ID NO:920:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: DNA (ix) FEATURE:
        (D) OTHER INFORMATION: oligonucleotide primer (xi) SEQUENCE DESCRIPTION: SEQ ID NO:920:

CAGTAGCATC ATGGGCACCG CCATG                                   25

(2) INFORMATION FOR SEQ ID NO:921:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: DNA (ix) FEATURE:
        (D) OTHER INFORMATION: oligonucleotide primer (xi) SEQUENCE DESCRIPTION: SEQ ID NO:921:

ACACAATGGC AAGCATAGTC GCCTGG                                  26

(2) INFORMATION FOR SEQ ID NO:922:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: DNA (ix) FEATURE:
        (D) OTHER INFORMATION: oligonucleotide primer (xi) SEQUENCE DESCRIPTION: SEQ ID NO:922:

CACCCTCCGT TACGCTGTTT CACACG                                  26

(2) INFORMATION FOR SEQ ID NO:923:

(i) SEQUENCE CHARACTERISTICS:
        (A) LENGTH: 26 base pairs (B) TYPE: nucleic acid
            (C) STRANDEDNESS: single
            (D) TOPOLOGY: linear (ii) MOLECULE TYPE: DNA (ix) FEATURE:
            (D) OTHER INFORMATION: oligonucleotide primer (xi) SEQUENCE DESCRIPTION: SEQ ID NO:923:

AGGGCACATT CACCAGTGAC TACAGC                                                26

(2) INFORMATION FOR SEQ ID NO:924:

(i) SEQUENCE CHARACTERISTICS:
            (A) LENGTH: 28 base pairs
            (B) TYPE: nucleic acid
            (C) STRANDEDNESS: single
            (D) TOPOLOGY: linear (ii) MOLECULE TYPE: DNA (ix) FEATURE:
            (D) OTHER INFORMATION: oligonucleotide primer (xi) SEQUENCE DESCRIPTION: SEQ ID NO:924:

TAAAGTCCCT GGCGGCAAGA TTATCAAG                                              28

(2) INFORMATION FOR SEQ ID NO:925:

(i) SEQUENCE CHARACTERISTICS:
            (A) LENGTH: 28 base pairs
            (B) TYPE: nucleic acid
            (C) STRANDEDNESS: single
            (D) TOPOLOGY: linear (ii) MOLECULE TYPE: DNA (ix) FEATURE:
            (D) OTHER INFORMATION: oligonucleotide primer (xi) SEQUENCE DESCRIPTION: SEQ ID NO:925:

GGGCGGTTAG AGATGGATCA ACAATGAC                                              28

(2) INFORMATION FOR SEQ ID NO:926:

(i) SEQUENCE CHARACTERISTICS:
            (A) LENGTH: 28 base pairs
            (B) TYPE: nucleic acid
            (C) STRANDEDNESS: single
            (D) TOPOLOGY: linear (ii) MOLECULE TYPE: DNA (ix) FEATURE:
            (D) OTHER INFORMATION: oligonucleotide primer (xi) SEQUENCE DESCRIPTION: SEQ ID NO:926:

CCAATAGGTG TTCCCACTCC GTAACCTT                                              28

(2) INFORMATION FOR SEQ ID NO:927:

(i) SEQUENCE CHARACTERISTICS:
            (A) LENGTH: 23 base pairs
            (B) TYPE: nucleic acid
            (C) STRANDEDNESS: single
            (D) TOPOLOGY: linear (ii) MOLECULE TYPE: DNA (ix) FEATURE:
            (D) OTHER INFORMATION: oligonucleotide primer (xi) SEQUENCE DESCRIPTION: SEQ ID NO:927:

GAGAGCCCGA CGCTCAACTC CCC                                             23

(2) INFORMATION FOR SEQ ID NO:928:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: DNA (ix) FEATURE:
        (D) OTHER INFORMATION: oligonucleotide primer (xi) SEQUENCE DESCRIPTION: SEQ ID NO:928:

TCCATCCGAG GTGGTGCGGA CATG                                            24

(2) INFORMATION FOR SEQ ID NO:929:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: DNA (ix) FEATURE:
        (D) OTHER INFORMATION: oligonucleotide primer (xi) SEQUENCE DESCRIPTION: SEQ ID NO:929:

CACTGGGACA GAGGCTGAGT TTGAGA                                          26

(2) INFORMATION FOR SEQ ID NO:930:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: DNA (ix) FEATURE:
        (D) OTHER INFORMATION: oligonucleotide primer (xi) SEQUENCE DESCRIPTION: SEQ ID NO:930:

CAGCTCATTC CAGGCATCCC ACTTGG                                          26

(2) INFORMATION FOR SEQ ID NO:931:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: DNA (ix) FEATURE:
        (D) OTHER INFORMATION: oligonucleotide primer (xi) SEQUENCE DESCRIPTION: SEQ ID NO:931:

AGGCATCATC ATGGGCACTT TCACCC                                          26

(2) INFORMATION FOR SEQ ID NO:932:

```
    (i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: DNA (ix) FEATURE:
        (D) OTHER INFORMATION: oligonucleotide primer (xi) SEQUENCE DESCRIPTION: SEQ ID NO:932:

TGTTATCGCT AGGCACAGTA CCTTGATG                                     28

(2) INFORMATION FOR SEQ ID NO:933:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: DNA (ix) FEATURE:
        (D) OTHER INFORMATION: oligonucleotide primer (xi) SEQUENCE DESCRIPTION: SEQ ID NO:933:

ACTGTGACTG CAACATCCCG CCTGTC                                       26

(2) INFORMATION FOR SEQ ID NO:934:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: DNA (ix) FEATURE:
        (D) OTHER INFORMATION: oligonucleotide primer (xi) SEQUENCE DESCRIPTION: SEQ ID NO:934:

GGAGCATGGA GCCAAGCGAA CACTG                                        25

(2) INFORMATION FOR SEQ ID NO:935:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: DNA (ix) FEATURE:
        (D) OTHER INFORMATION: oligonucleotide primer (xi) SEQUENCE DESCRIPTION: SEQ ID NO:935:

CGTCAACGCT AGTGCCGTCA GCCG                                         24

(2) INFORMATION FOR SEQ ID NO:936:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: DNA
```

(ix) FEATURE:
        (D) OTHER INFORMATION: oligonucleotide primer (xi) SEQUENCE DESCRIPTION: SEQ ID NO:936:

GACCATATTC TGTCTCCCGC TTGGACT                                              27

(2) INFORMATION FOR SEQ ID NO:937:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: DNA (ix) FEATURE:
        (D) OTHER INFORMATION: oligonucleotide primer (xi) SEQUENCE DESCRIPTION: SEQ ID NO:937:

GTGCGTCATC AGCGTGGACC GCTA                                                 24

(2) INFORMATION FOR SEQ ID NO:938:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: DNA (ix) FEATURE:
        (D) OTHER INFORMATION: oligonucleotide primer (xi) SEQUENCE DESCRIPTION: SEQ ID NO:938:

GGGATGTAGA AGCTGATGAG CGAGGAA                                              27

(2) INFORMATION FOR SEQ ID NO:939:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: DNA (ix) FEATURE:
        (D) OTHER INFORMATION: oligonucleotide primer (xi) SEQUENCE DESCRIPTION: SEQ ID NO:939:

TGCACCAGGG TCTACGTCCG AGAG                                                 24

(2) INFORMATION FOR SEQ ID NO:940:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: DNA (ix) FEATURE:
        (D) OTHER INFORMATION: oligonucleotide primer (xi) SEQUENCE DESCRIPTION: SEQ ID NO:940:

GGTAGAAGCT AGAGGGCCAG TCTTTC                                               26

(2) INFORMATION FOR SEQ ID NO:941:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: DNA (ix) FEATURE:
        (D) OTHER INFORMATION: oligonucleotide primer (xi) SEQUENCE DESCRIPTION: SEQ ID NO:941:

GGCCTACGAA TTGGCCGACT ACAGC                                      25

(2) INFORMATION FOR SEQ ID NO:942:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: DNA (ix) FEATURE:
        (D) OTHER INFORMATION: oligonucleotide primer (xi) SEQUENCE DESCRIPTION: SEQ ID NO:942:

GGGCAGTGTT TCTCAAATAG GGATTGGG                                 28

(2) INFORMATION FOR SEQ ID NO:943:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: DNA (ix) FEATURE:
        (D) OTHER INFORMATION: oligonucleotide primer (xi) SEQUENCE DESCRIPTION: SEQ ID NO:943:

ATGGCCTCAC CAGCAAGCGG GAGC                                        24

(2) INFORMATION FOR SEQ ID NO:944:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: DNA (ix) FEATURE:
        (D) OTHER INFORMATION: oligonucleotide primer (xi) SEQUENCE DESCRIPTION: SEQ ID NO:944:

GCTGACTCCG CATAAATTGG CCGAAGA                                 27

(2) INFORMATION FOR SEQ ID NO:945:

(i) SEQUENCE CHARACTERISTICS:
        (A) LENGTH: 26 base pairs
        (B) TYPE: nucleic acid
        (C) STRANDEDNESS: single
        (D) TOPOLOGY: linear

```
        (ii) MOLECULE TYPE: DNA (ix) FEATURE:
             (D) OTHER INFORMATION: oligonucleotide primer (xi) SEQUENCE DESCRIPTION: SEQ ID NO:945:

CATGCAAGGT GCTGGGCATC GTCTTC                                          26

(2) INFORMATION FOR SEQ ID NO:946:

(i) SEQUENCE CHARACTERISTICS:
            (A) LENGTH: 28 base pairs
            (B) TYPE: nucleic acid
            (C) STRANDEDNESS: single
            (D) TOPOLOGY: linear (ii) MOLECULE TYPE: DNA (ix) FEATURE:
             (D) OTHER INFORMATION: oligonucleotide primer (xi) SEQUENCE DESCRIPTION: SEQ ID NO:946:

GACTTGTAGG CCAAAGCCGG TATTGTGT                                        28

(2) INFORMATION FOR SEQ ID NO:947:

(i) SEQUENCE CHARACTERISTICS:
            (A) LENGTH: 26 base pairs
            (B) TYPE: nucleic acid
            (C) STRANDEDNESS: single
            (D) TOPOLOGY: linear (ii) MOLECULE TYPE: DNA (ix) FEATURE:
             (D) OTHER INFORMATION: oligonucleotide primer (xi) SEQUENCE DESCRIPTION: SEQ ID NO:947:

ACATCTGGCT GTCCTCTGAC ATCACG                                          26

(2) INFORMATION FOR SEQ ID NO:948:

(i) SEQUENCE CHARACTERISTICS:
            (A) LENGTH: 27 base pairs
            (B) TYPE: nucleic acid
            (C) STRANDEDNESS: single
            (D) TOPOLOGY: linear (ii) MOLECULE TYPE: DNA (ix) FEATURE:
             (D) OTHER INFORMATION: oligonucleotide primer (xi) SEQUENCE DESCRIPTION: SEQ ID NO:948:

CATAGAGTGA GGGTGGATTC AGGATGC                                         27

(2) INFORMATION FOR SEQ ID NO:949:

(i) SEQUENCE CHARACTERISTICS:
            (A) LENGTH: 26 base pairs
            (B) TYPE: nucleic acid
            (C) STRANDEDNESS: single
            (D) TOPOLOGY: linear (ii) MOLECULE TYPE: DNA (ix) FEATURE:
             (D) OTHER INFORMATION: oligonucleotide primer (xi) SEQUENCE DESCRIPTION: SEQ ID NO:949:

CCATTTACTC CACGCTGGGT GCGTTT                                          26
```

(2) INFORMATION FOR SEQ ID NO:950:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: DNA (ix) FEATURE:
        (D) OTHER INFORMATION: oligonucleotide primer (xi) SEQUENCE DESCRIPTION: SEQ ID NO:950:

CCTTCCGTTC CCTGGTGCTA GAGATC                                  26

(2) INFORMATION FOR SEQ ID NO:951:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: DNA (ix) FEATURE:
        (D) OTHER INFORMATION: oligonucleotide primer (xi) SEQUENCE DESCRIPTION: SEQ ID NO:951:

CTGCTACAGT CGCCAAATCA CCAGTATT                                28

(2) INFORMATION FOR SEQ ID NO:952:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: DNA (ix) FEATURE:
        (D) OTHER INFORMATION: oligonucleotide primer (xi) SEQUENCE DESCRIPTION: SEQ ID NO:952:

CTCCGTGGAG CTTCCCAAAC CTCTC                                   25

(2) INFORMATION FOR SEQ ID NO:953:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: DNA (ix) FEATURE:
        (D) OTHER INFORMATION: oligonucleotide primer (xi) SEQUENCE DESCRIPTION: SEQ ID NO:953:

GCAGACGGAG TGGCCCGAGT GCG                                      23

(2) INFORMATION FOR SEQ ID NO:954:

(i) SEQUENCE CHARACTERISTICS:
        (A) LENGTH: 28 base pairs
        (B) TYPE: nucleic acid
        (C) STRANDEDNESS: single (D) TOPOLOGY: linear (ii) MOLECULE TYPE: DNA (ix) FEATURE:
                (D) OTHER INFORMATION: oligonucleotide primer (xi) SEQUENCE DESCRIPTION: SEQ ID NO:954:

GTTTGGACTC TGCCCGTGAT TTGTAACA                                        28

(2) INFORMATION FOR SEQ ID NO:955:

(i) SEQUENCE CHARACTERISTICS:
                (A) LENGTH: 24 base pairs
                (B) TYPE: nucleic acid
                (C) STRANDEDNESS: single
                (D) TOPOLOGY: linear (ii) MOLECULE TYPE: DNA (ix) FEATURE:
                (D) OTHER INFORMATION: oligonucleotide primer (xi) SEQUENCE DESCRIPTION: SEQ ID NO:955:

CCCGGCCCAG ATGAAAGTTG GCTG                                            24

(2) INFORMATION FOR SEQ ID NO:956:

(i) SEQUENCE CHARACTERISTICS:
                (A) LENGTH: 26 base pairs
                (B) TYPE: nucleic acid
                (C) STRANDEDNESS: single
                (D) TOPOLOGY: linear (ii) MOLECULE TYPE: DNA (ix) FEATURE:
                (D) OTHER INFORMATION: oligonucleotide primer (xi) SEQUENCE DESCRIPTION: SEQ ID NO:956:

GCGCTCAAGG CTGGGAAATA CTGACT                                          26

(2) INFORMATION FOR SEQ ID NO:957:

(i) SEQUENCE CHARACTERISTICS:
                (A) LENGTH: 26 base pairs
                (B) TYPE: nucleic acid
                (C) STRANDEDNESS: single
                (D) TOPOLOGY: linear (ii) MOLECULE TYPE: DNA (ix) FEATURE:
                (D) OTHER INFORMATION: oligonucleotide primer (xi) SEQUENCE DESCRIPTION: SEQ ID NO:957:

CTTACGGAGG CTGGTCCTTG GATCTG                                          26

(2) INFORMATION FOR SEQ ID NO:958:

(i) SEQUENCE CHARACTERISTICS:
                (A) LENGTH: 25 base pairs
                (B) TYPE: nucleic acid
                (C) STRANDEDNESS: single
                (D) TOPOLOGY: linear (ii) MOLECULE TYPE: DNA (ix) FEATURE:
                (D) OTHER INFORMATION: oligonucleotide primer (xi) SEQUENCE DESCRIPTION: SEQ ID NO:958:

CGGATGTTGC GGGCATGATC TCAGC        25

(2) INFORMATION FOR SEQ ID NO:959:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: DNA (ix) FEATURE:
        (D) OTHER INFORMATION: oligonucleotide primer (xi) SEQUENCE DESCRIPTION: SEQ ID NO:959:

CATGGCCTTA TGAGGCAGGT GAGAGA        26

(2) INFORMATION FOR SEQ ID NO:960:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: DNA (ix) FEATURE:
        (D) OTHER INFORMATION: oligonucleotide primer (xi) SEQUENCE DESCRIPTION: SEQ ID NO:960:

AGCACTCAAG GACAAGGGTG ACAGAG        26

(2) INFORMATION FOR SEQ ID NO:961:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: DNA (ix) FEATURE:
        (D) OTHER INFORMATION: oligonucleotide primer (xi) SEQUENCE DESCRIPTION: SEQ ID NO:961:

GGGAGGCCAC ATCAAGGGTG CAGT          24

(2) INFORMATION FOR SEQ ID NO:962:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: DNA (ix) FEATURE:
        (D) OTHER INFORMATION: oligonucleotide primer (xi) SEQUENCE DESCRIPTION: SEQ ID NO:962:

GGTCCGGCTC TTGGTGCGGA ACTT          24

(2) INFORMATION FOR SEQ ID NO:963:

(i) SEQUENCE CHARACTERISTICS:
        (A) LENGTH: 25 base pairs (B) TYPE: nucleic acid
          (C) STRANDEDNESS: single
          (D) TOPOLOGY: linear (ii) MOLECULE TYPE: DNA (ix) FEATURE:
          (D) OTHER INFORMATION: oligonucleotide primer (xi) SEQUENCE DESCRIPTION: SEQ ID NO:963:

GTGCATCTAC ACCGACCACG CTGTC                                                  25

(2) INFORMATION FOR SEQ ID NO:964:

(i) SEQUENCE CHARACTERISTICS:
          (A) LENGTH: 24 base pairs
          (B) TYPE: nucleic acid
          (C) STRANDEDNESS: single
          (D) TOPOLOGY: linear (ii) MOLECULE TYPE: DNA (ix) FEATURE:
          (D) OTHER INFORMATION: oligonucleotide primer (xi) SEQUENCE DESCRIPTION: SEQ ID NO:964:

CAGGCCCGCA GGCAGTCCAC TTCA                                                   24

(2) INFORMATION FOR SEQ ID NO:965:

(i) SEQUENCE CHARACTERISTICS:
          (A) LENGTH: 23 base pairs
          (B) TYPE: nucleic acid
          (C) STRANDEDNESS: single
          (D) TOPOLOGY: linear (ii) MOLECULE TYPE: DNA (ix) FEATURE:
          (D) OTHER INFORMATION: oligonucleotide primer (xi) SEQUENCE DESCRIPTION: SEQ ID NO:965:

GCGCATCCGC CAGACGGTCA ACC                                                    23

(2) INFORMATION FOR SEQ ID NO:966:

(i) SEQUENCE CHARACTERISTICS:
          (A) LENGTH: 24 base pairs
          (B) TYPE: nucleic acid
          (C) STRANDEDNESS: single
          (D) TOPOLOGY: linear (ii) MOLECULE TYPE: DNA (ix) FEATURE:
          (D) OTHER INFORMATION: oligonucleotide primer (xi) SEQUENCE DESCRIPTION: SEQ ID NO:966:

GGCCCACACC TTGTAGGGCA CGGT                                                   24

(2) INFORMATION FOR SEQ ID NO:967:

(i) SEQUENCE CHARACTERISTICS:
          (A) LENGTH: 26 base pairs
          (B) TYPE: nucleic acid
          (C) STRANDEDNESS: single
          (D) TOPOLOGY: linear (ii) MOLECULE TYPE: DNA (ix) FEATURE:
          (D) OTHER INFORMATION: oligonucleotide primer (xi) SEQUENCE DESCRIPTION: SEQ ID NO:967:

GGCACTGCTG CTATGCTGTT AGCCTC                                    26

(2) INFORMATION FOR SEQ ID NO:968:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: DNA (ix) FEATURE:
        (D) OTHER INFORMATION: oligonucleotide primer (xi) SEQUENCE DESCRIPTION: SEQ ID NO:968:

TTGTCCCGTG ACTGTGTAGA GTGCTAAA                                  28

(2) INFORMATION FOR SEQ ID NO:969:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: DNA (ix) FEATURE:
        (D) OTHER INFORMATION: oligonucleotide primer (xi) SEQUENCE DESCRIPTION: SEQ ID NO:969:

CTAGGATCAC AGTGGCTTGG TGCAAG                                    26

(2) INFORMATION FOR SEQ ID NO:970:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: DNA (ix) FEATURE:
        (D) OTHER INFORMATION: oligonucleotide primer (xi) SEQUENCE DESCRIPTION: SEQ ID NO:970:

GCTGACAAAT TCCCATCCAC TTGCCC                                    26

(2) INFORMATION FOR SEQ ID NO:971:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: DNA (ix) FEATURE:
        (D) OTHER INFORMATION: oligonucleotide primer (xi) SEQUENCE DESCRIPTION: SEQ ID NO:971:

CAATGCTCAG CTCTTTGGCT CGATTGTT                                  28

(2) INFORMATION FOR SEQ ID NO:972:

(i) SEQUENCE CHARACTERISTICS:
    (A) LENGTH: 28 base pairs
    (B) TYPE: nucleic acid
    (C) STRANDEDNESS: single
    (D) TOPOLOGY: linear (ii) MOLECULE TYPE: DNA (ix) FEATURE:
    (D) OTHER INFORMATION: oligonucleotide primer (xi) SEQUENCE DESCRIPTION: SEQ ID NO:972:

TTCTCGGTGC CATTCAACAT GGGTTCTA                                28

(2) INFORMATION FOR SEQ ID NO:973:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: DNA (ix) FEATURE:
        (D) OTHER INFORMATION: oligonucleotide primer (xi) SEQUENCE DESCRIPTION: SEQ ID NO:973:

CCCGCTGCGG TTCTCGGAGG TCC                                     23

(2) INFORMATION FOR SEQ ID NO:974:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: DNA (ix) FEATURE:
        (D) OTHER INFORMATION: oligonucleotide primer (xi) SEQUENCE DESCRIPTION: SEQ ID NO:974:

CAGACCACTC TGTGGCACGG GATGA                                   25

(2) INFORMATION FOR SEQ ID NO:975:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: DNA (ix) FEATURE:
        (D) OTHER INFORMATION: oligonucleotide primer (xi) SEQUENCE DESCRIPTION: SEQ ID NO:975:

TCACCATGAC GCTGGCACGG GTCT                                    24

(2) INFORMATION FOR SEQ ID NO:976:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: DNA (ix) FEATURE:
              (D) OTHER INFORMATION: oligonucleotide primer (xi) SEQUENCE DESCRIPTION: SEQ ID NO:976:

AGGGCGACAC TGGTTTCGGC ACCA                                                       24

(2) INFORMATION FOR SEQ ID NO:977:

(i) SEQUENCE CHARACTERISTICS:
              (A) LENGTH: 26 base pairs
              (B) TYPE: nucleic acid
              (C) STRANDEDNESS: single
              (D) TOPOLOGY: linear (ii) MOLECULE TYPE: DNA (ix) FEATURE:
              (D) OTHER INFORMATION: oligonucleotide primer (xi) SEQUENCE DESCRIPTION: SEQ ID NO:977:

GATTCCGTGG AGTGCAGGAC ATTGTG                                                     26

(2) INFORMATION FOR SEQ ID NO:978:

(i) SEQUENCE CHARACTERISTICS:
              (A) LENGTH: 26 base pairs
              (B) TYPE: nucleic acid
              (C) STRANDEDNESS: single
              (D) TOPOLOGY: linear (ii) MOLECULE TYPE: DNA (ix) FEATURE:
              (D) OTHER INFORMATION: oligonucleotide primer (xi) SEQUENCE DESCRIPTION: SEQ ID NO:978:

TCAAAGCGAG CCACCACTGA CTTGAG                                                     26

(2) INFORMATION FOR SEQ ID NO:979:

(i) SEQUENCE CHARACTERISTICS:
              (A) LENGTH: 28 base pairs
              (B) TYPE: nucleic acid
              (C) STRANDEDNESS: single
              (D) TOPOLOGY: linear (ii) MOLECULE TYPE: DNA (ix) FEATURE:
              (D) OTHER INFORMATION: oligonucleotide primer (xi) SEQUENCE DESCRIPTION: SEQ ID NO:979:

CAGTTTCCAG TCGGATGTCT ACTCCTAT                                                   28

(2) INFORMATION FOR SEQ ID NO:980:

(i) SEQUENCE CHARACTERISTICS:
              (A) LENGTH: 26 base pairs
              (B) TYPE: nucleic acid
              (C) STRANDEDNESS: single
              (D) TOPOLOGY: linear (ii) MOLECULE TYPE: DNA (ix) FEATURE:
              (D) OTHER INFORMATION: oligonucleotide primer (xi) SEQUENCE DESCRIPTION: SEQ ID NO:980:

GCGCTCCGGT TGATCTTCGG TAGAGA                                                     26

(2) INFORMATION FOR SEQ ID NO:981:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: DNA (ix) FEATURE:
        (D) OTHER INFORMATION: oligonucleotide primer (xi) SEQUENCE DESCRIPTION: SEQ ID NO:981:

GATCCTGTCA GCCCTGGGTT CTAAGA                        26

(2) INFORMATION FOR SEQ ID NO:982:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: DNA (ix) FEATURE:
        (D) OTHER INFORMATION: oligonucleotide primer (xi) SEQUENCE DESCRIPTION: SEQ ID NO:982:

CGTCTACGAT GATATGACCC TTGTCATC                    28

(2) INFORMATION FOR SEQ ID NO:983:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: DNA (ix) FEATURE:
        (D) OTHER INFORMATION: oligonucleotide primer (xi) SEQUENCE DESCRIPTION: SEQ ID NO:983:

GGTCCTGGAC AGCACCGAGG CGC                           23

(2) INFORMATION FOR SEQ ID NO:984:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: DNA (ix) FEATURE:
        (D) OTHER INFORMATION: oligonucleotide primer (xi) SEQUENCE DESCRIPTION: SEQ ID NO:984:

CATGGGTATG GGCGAGCCCG CATG                        24

(2) INFORMATION FOR SEQ ID NO:985:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: DNA (ix) FEATURE:
            (D) OTHER INFORMATION: oligonucleotide primer (xi) SEQUENCE DESCRIPTION: SEQ ID NO:985:

GCCTGTGATG CTGGGCACTT CATCTG                                             26

(2) INFORMATION FOR SEQ ID NO:986:

(i) SEQUENCE CHARACTERISTICS:
            (A) LENGTH: 26 base pairs
            (B) TYPE: nucleic acid
            (C) STRANDEDNESS: single
            (D) TOPOLOGY: linear (ii) MOLECULE TYPE: DNA (ix) FEATURE:
            (D) OTHER INFORMATION: oligonucleotide primer (xi) SEQUENCE DESCRIPTION: SEQ ID NO:986:

TTTGGTTCGG CAGCTTGCTA GGTGAC                                             26

(2) INFORMATION FOR SEQ ID NO:987:

(i) SEQUENCE CHARACTERISTICS:
            (A) LENGTH: 28 base pairs
            (B) TYPE: nucleic acid
            (C) STRANDEDNESS: single
            (D) TOPOLOGY: linear (ii) MOLECULE TYPE: DNA (ix) FEATURE:
            (D) OTHER INFORMATION: oligonucleotide primer (xi) SEQUENCE DESCRIPTION: SEQ ID NO:987:

AAATGGTTGA CCTCACCCAG GTAATGGA                                           28

(2) INFORMATION FOR SEQ ID NO:988:

(i) SEQUENCE CHARACTERISTICS:
            (A) LENGTH: 28 base pairs
            (B) TYPE: nucleic acid
            (C) STRANDEDNESS: single
            (D) TOPOLOGY: linear (ii) MOLECULE TYPE: DNA (ix) FEATURE:
            (D) OTHER INFORMATION: oligonucleotide primer (xi) SEQUENCE DESCRIPTION: SEQ ID NO:988:

AGATCCGTGC TCCGACAAAT AGTCTGAA                                           28

(2) INFORMATION FOR SEQ ID NO:989:

(i) SEQUENCE CHARACTERISTICS:
            (A) LENGTH: 25 base pairs
            (B) TYPE: nucleic acid
            (C) STRANDEDNESS: single
            (D) TOPOLOGY: linear (ii) MOLECULE TYPE: DNA (ix) FEATURE:
            (D) OTHER INFORMATION: oligonucleotide primer (xi) SEQUENCE DESCRIPTION: SEQ ID NO:989:

GAAGAACTTC GCCTTGCGGG TCCTG                                              25

(2) INFORMATION FOR SEQ ID NO:990:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: DNA (ix) FEATURE:
        (D) OTHER INFORMATION: oligonucleotide primer (xi) SEQUENCE DESCRIPTION: SEQ ID NO:990:

GGCGATGAGC TGTTCCAGAG ATCCAAAT                    28

(2) INFORMATION FOR SEQ ID NO:991:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: DNA (ix) FEATURE:
        (D) OTHER INFORMATION: oligonucleotide primer (xi) SEQUENCE DESCRIPTION: SEQ ID NO:991:

CTATGATGTC CTTGACCTCC ACCGTATA                    28

(2) INFORMATION FOR SEQ ID NO:992:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: DNA (ix) FEATURE:
        (D) OTHER INFORMATION: oligonucleotide primer (xi) SEQUENCE DESCRIPTION: SEQ ID NO:992:

ATGTTCACGA AGGATAGTGG GTAGCTGA                    28

(2) INFORMATION FOR SEQ ID NO:993:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: DNA (ix) FEATURE:
        (D) OTHER INFORMATION: oligonucleotide primer (xi) SEQUENCE DESCRIPTION: SEQ ID NO:993:

CGGAGACCTC ACCCTGTACC AGTC                        24

(2) INFORMATION FOR SEQ ID NO:994:

(i) SEQUENCE CHARACTERISTICS:
        (A) LENGTH: 26 base pairs
        (B) TYPE: nucleic acid
        (C) STRANDEDNESS: single (D) TOPOLOGY: linear (ii) MOLECULE TYPE: DNA (ix) FEATURE:
        (D) OTHER INFORMATION: oligonucleotide primer (xi) SEQUENCE DESCRIPTION: SEQ ID NO:994:

GCAGCAAGTC CAGCAGGTTG TAGTCA                                              26

(2) INFORMATION FOR SEQ ID NO:995:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: DNA (ix) FEATURE:
        (D) OTHER INFORMATION: oligonucleotide primer (xi) SEQUENCE DESCRIPTION: SEQ ID NO:995:

AGCTGGTGCA GACCAGAGCC ATTCTC                                              26

(2) INFORMATION FOR SEQ ID NO:996:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: DNA (ix) FEATURE:
        (D) OTHER INFORMATION: oligonucleotide primer (xi) SEQUENCE DESCRIPTION: SEQ ID NO:996:

GGAGTCAAGC TCCTCGACGT AGTAGA                                              26

(2) INFORMATION FOR SEQ ID NO:997:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: DNA (ix) FEATURE:
        (D) OTHER INFORMATION: oligonucleotide primer (xi) SEQUENCE DESCRIPTION: SEQ ID NO:997:

TCAGGACTTT GTGAGTTAGC ATGACCCT                                            28

(2) INFORMATION FOR SEQ ID NO:998:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: DNA (ix) FEATURE:
        (D) OTHER INFORMATION: oligonucleotide primer (xi) SEQUENCE DESCRIPTION: SEQ ID NO:998:

TACAGACTGT AAATAGAGTC GGGTAGGC        28

(2) INFORMATION FOR SEQ ID NO:999:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: DNA (ix) FEATURE:
        (D) OTHER INFORMATION: oligonucleotide primer (xi) SEQUENCE DESCRIPTION: SEQ ID NO:999:

AAACCCTGAA GCCTGGCACG ATGTCT        26

(2) INFORMATION FOR SEQ ID NO:1000:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: DNA (ix) FEATURE:
        (D) OTHER INFORMATION: oligonucleotide primer (xi) SEQUENCE DESCRIPTION: SEQ ID NO:1000:

CAGGATGTTG GCTGCACGAA GGTCC        25

(2) INFORMATION FOR SEQ ID NO:1001:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: DNA (ix) FEATURE:
        (D) OTHER INFORMATION: oligonucleotide primer (xi) SEQUENCE DESCRIPTION: SEQ ID NO:1001:

TCTCAAGTGG ATTGTCACAT CATGCCTC        28

(2) INFORMATION FOR SEQ ID NO:1002:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: DNA (ix) FEATURE:
        (D) OTHER INFORMATION: oligonucleotide primer (xi) SEQUENCE DESCRIPTION: SEQ ID NO:1002:

GGATGACGCT TCCATTCCGA CTATGTCA        28

(2) INFORMATION FOR SEQ ID NO:1003:

(i) SEQUENCE CHARACTERISTICS:
        (A) LENGTH: 27 base pairs (B) TYPE: nucleic acid
        (C) STRANDEDNESS: single
        (D) TOPOLOGY: linear (ii) MOLECULE TYPE: DNA (ix) FEATURE:
        (D) OTHER INFORMATION: oligonucleotide primer (xi) SEQUENCE DESCRIPTION: SEQ ID NO:1003:

GAGGTGGATG GAAAGCAGGT AGAGTTG                                              27

(2) INFORMATION FOR SEQ ID NO:1004:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: DNA (ix) FEATURE:
        (D) OTHER INFORMATION: oligonucleotide primer (xi) SEQUENCE DESCRIPTION: SEQ ID NO:1004:

TTTCACCGGC TCCTGCTTCA TCTTGG                                               26

(2) INFORMATION FOR SEQ ID NO:1005:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: DNA (ix) FEATURE:
        (D) OTHER INFORMATION: oligonucleotide primer (xi) SEQUENCE DESCRIPTION: SEQ ID NO:1005:

CCCTCTGAGG CACCACGGTC CGG                                                  23

(2) INFORMATION FOR SEQ ID NO:1006:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: DNA (ix) FEATURE:
        (D) OTHER INFORMATION: oligonucleotide primer (xi) SEQUENCE DESCRIPTION: SEQ ID NO:1006:

TAAGCGCGGT GGCGTCGTCG CTG                                                  23

(2) INFORMATION FOR SEQ ID NO:1007:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: DNA (ix) FEATURE:
        (D) OTHER INFORMATION: oligonucleotide primer (xi) SEQUENCE DESCRIPTION: SEQ ID NO:1007:

GTGCTGGCTA CATGGAGCCC TATGAG                        26

(2) INFORMATION FOR SEQ ID NO:1008:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: DNA (ix) FEATURE:
        (D) OTHER INFORMATION: oligonucleotide primer (xi) SEQUENCE DESCRIPTION: SEQ ID NO:1008:

GACTGCCGCT TCTCGTTGCC ATTAAACT                      28

(2) INFORMATION FOR SEQ ID NO:1009:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: DNA (ix) FEATURE:
        (D) OTHER INFORMATION: oligonucleotide primer (xi) SEQUENCE DESCRIPTION: SEQ ID NO:1009:

CAGGCGACGA GTTTGAACTG CGGTAC                        26

(2) INFORMATION FOR SEQ ID NO:1010:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: DNA (ix) FEATURE:
        (D) OTHER INFORMATION: oligonucleotide primer (xi) SEQUENCE DESCRIPTION: SEQ ID NO:1010:

AAGGCTCTAG GTGGTCATTC AGGTAAGT                      28

(2) INFORMATION FOR SEQ ID NO:1011:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: DNA (ix) FEATURE:
        (D) OTHER INFORMATION: oligonucleotide primer (xi) SEQUENCE DESCRIPTION: SEQ ID NO:1011:

AGTGCAGGGC ATCATCAATT TCGAGCAG                      28

(2) INFORMATION FOR SEQ ID NO:1012:

```
      (i) SEQUENCE CHARACTERISTICS:
          (A) LENGTH: 28 base pairs
          (B) TYPE: nucleic acid
          (C) STRANDEDNESS: single
          (D) TOPOLOGY: linear (ii) MOLECULE TYPE: DNA (ix) FEATURE:
          (D) OTHER INFORMATION: oligonucleotide primer (xi) SEQUENCE DESCRIPTION: SEQ ID NO:1012:

GATGCAATGG TCTCCTGAGA GTGAGATC                                      28

(2) INFORMATION FOR SEQ ID NO:1013:

(i) SEQUENCE CHARACTERISTICS:
          (A) LENGTH: 24 base pairs
          (B) TYPE: nucleic acid
          (C) STRANDEDNESS: single
          (D) TOPOLOGY: linear (ii) MOLECULE TYPE: DNA (ix) FEATURE:
          (D) OTHER INFORMATION: oligonucleotide primer (xi) SEQUENCE DESCRIPTION: SEQ ID NO:1013:

GGTTATCGGA GCCAGCACCG CTCT                                          24

(2) INFORMATION FOR SEQ ID NO:1014:

(i) SEQUENCE CHARACTERISTICS:
          (A) LENGTH: 28 base pairs
          (B) TYPE: nucleic acid
          (C) STRANDEDNESS: single
          (D) TOPOLOGY: linear (ii) MOLECULE TYPE: DNA (ix) FEATURE:
          (D) OTHER INFORMATION: oligonucleotide primer (xi) SEQUENCE DESCRIPTION: SEQ ID NO:1014:

GTCGAAGAAT GAAGATAGGC AGTCCCTC                                      28

(2) INFORMATION FOR SEQ ID NO:1015:

(i) SEQUENCE CHARACTERISTICS:
          (A) LENGTH: 26 base pairs
          (B) TYPE: nucleic acid
          (C) STRANDEDNESS: single
          (D) TOPOLOGY: linear (ii) MOLECULE TYPE: DNA (ix) FEATURE:
          (D) OTHER INFORMATION: oligonucleotide primer (xi) SEQUENCE DESCRIPTION: SEQ ID NO:1015:

CCTCCACAAC TACAATGCCG TACTGG                                        26

(2) INFORMATION FOR SEQ ID NO:1016:

(i) SEQUENCE CHARACTERISTICS:
          (A) LENGTH: 26 base pairs
          (B) TYPE: nucleic acid
          (C) STRANDEDNESS: single
          (D) TOPOLOGY: linear (ii) MOLECULE TYPE: DNA
```

(ix) FEATURE:
            (D) OTHER INFORMATION: oligonucleotide primer (xi) SEQUENCE DESCRIPTION: SEQ ID NO:1016:

AAGTTGACCA GGCCGTCTTC CGTGTA                                    26

(2) INFORMATION FOR SEQ ID NO:1017:

(i) SEQUENCE CHARACTERISTICS:
            (A) LENGTH: 25 base pairs
            (B) TYPE: nucleic acid
            (C) STRANDEDNESS: single
            (D) TOPOLOGY: linear (ii) MOLECULE TYPE: DNA (ix) FEATURE:
            (D) OTHER INFORMATION: oligonucleotide primer (xi) SEQUENCE DESCRIPTION: SEQ ID NO:1017:

CCATCCCGGT GCCAACGCTA GAAAG                                     25

(2) INFORMATION FOR SEQ ID NO:1018:

(i) SEQUENCE CHARACTERISTICS:
            (A) LENGTH: 26 base pairs
            (B) TYPE: nucleic acid
            (C) STRANDEDNESS: single
            (D) TOPOLOGY: linear (ii) MOLECULE TYPE: DNA (ix) FEATURE:
            (D) OTHER INFORMATION: oligonucleotide primer (xi) SEQUENCE DESCRIPTION: SEQ ID NO:1018:

ATTAGCAAAG CTGCGGAGTG GGTGAG                                    26

(2) INFORMATION FOR SEQ ID NO:1019:

(i) SEQUENCE CHARACTERISTICS:
            (A) LENGTH: 25 base pairs
            (B) TYPE: nucleic acid
            (C) STRANDEDNESS: single
            (D) TOPOLOGY: linear (ii) MOLECULE TYPE: DNA (ix) FEATURE:
            (D) OTHER INFORMATION: oligonucleotide primer (xi) SEQUENCE DESCRIPTION: SEQ ID NO:1019:

CCGGCTGAAG AGCTACGAGA ACCAG                                     25

(2) INFORMATION FOR SEQ ID NO:1020:

(i) SEQUENCE CHARACTERISTICS:
            (A) LENGTH: 26 base pairs
            (B) TYPE: nucleic acid
            (C) STRANDEDNESS: single
            (D) TOPOLOGY: linear (ii) MOLECULE TYPE: DNA (ix) FEATURE:
            (D) OTHER INFORMATION: oligonucleotide primer (xi) SEQUENCE DESCRIPTION: SEQ ID NO:1020:

GGAATGGGTG CTTCTTGTTG GACTCC                                    26

(2) INFORMATION FOR SEQ ID NO:1021:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: DNA (ix) FEATURE:
        (D) OTHER INFORMATION: oligonucleotide primer (xi) SEQUENCE DESCRIPTION: SEQ ID NO:1021:

AGTCAGCTCC TGCCAGCACT ACAGC                        25

(2) INFORMATION FOR SEQ ID NO:1022:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: DNA (ix) FEATURE:
        (D) OTHER INFORMATION: oligonucleotide primer (xi) SEQUENCE DESCRIPTION: SEQ ID NO:1022:

CGTAAGACTG ACCCGTCACA AGTGCA                     26

(2) INFORMATION FOR SEQ ID NO:1023:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: DNA (ix) FEATURE:
        (D) OTHER INFORMATION: oligonucleotide primer (xi) SEQUENCE DESCRIPTION: SEQ ID NO:1023:

CCCACCTCAG GCATGTCCCA TCCC                         24

(2) INFORMATION FOR SEQ ID NO:1024:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: DNA (ix) FEATURE:
        (D) OTHER INFORMATION: oligonucleotide primer (xi) SEQUENCE DESCRIPTION: SEQ ID NO:1024:

GCAGATACTC CACGGCTCGG TGGG                         24

(2) INFORMATION FOR SEQ ID NO:1025:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: DNA (ix) FEATURE:
             (D) OTHER INFORMATION: oligonucleotide primer (xi) SEQUENCE DESCRIPTION: SEQ ID NO:1025:

TAGTGCCTCC AGGGCTGGAA TTACTATG                                           28

(2) INFORMATION FOR SEQ ID NO:1026:

(i) SEQUENCE CHARACTERISTICS:
             (A) LENGTH: 28 base pairs
             (B) TYPE: nucleic acid
             (C) STRANDEDNESS: single
             (D) TOPOLOGY: linear (ii) MOLECULE TYPE: DNA (ix) FEATURE:
             (D) OTHER INFORMATION: oligonucleotide primer (xi) SEQUENCE DESCRIPTION: SEQ ID NO:1026:

GATTCTACCA GGTCGTCATC AGTCCATT                                           28

(2) INFORMATION FOR SEQ ID NO:1027:

(i) SEQUENCE CHARACTERISTICS:
             (A) LENGTH: 26 base pairs
             (B) TYPE: nucleic acid
             (C) STRANDEDNESS: single
             (D) TOPOLOGY: linear (ii) MOLECULE TYPE: DNA (ix) FEATURE:
             (D) OTHER INFORMATION: oligonucleotide primer (xi) SEQUENCE DESCRIPTION: SEQ ID NO:1027:

TCTTCCAGGA GGCCCATGAG GTCATT                                             26

(2) INFORMATION FOR SEQ ID NO:1028:

(i) SEQUENCE CHARACTERISTICS:
             (A) LENGTH: 26 base pairs
             (B) TYPE: nucleic acid
             (C) STRANDEDNESS: single
             (D) TOPOLOGY: linear (ii) MOLECULE TYPE: DNA (ix) FEATURE:
             (D) OTHER INFORMATION: oligonucleotide primer (xi) SEQUENCE DESCRIPTION: SEQ ID NO:1028:

TCTCATTGTG GCTTTCAGGC GGCTGT                                             26

(2) INFORMATION FOR SEQ ID NO:1029:

(i) SEQUENCE CHARACTERISTICS:
             (A) LENGTH: 26 base pairs
             (B) TYPE: nucleic acid
             (C) STRANDEDNESS: single
             (D) TOPOLOGY: linear (ii) MOLECULE TYPE: DNA (ix) FEATURE:
             (D) OTHER INFORMATION: oligonucleotide primer (xi) SEQUENCE DESCRIPTION: SEQ ID NO:1029:

CATAACACGG GTGAGGAACG CCACAG                                             26

(2) INFORMATION FOR SEQ ID NO:1030:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: DNA (ix) FEATURE:
        (D) OTHER INFORMATION: oligonucleotide primer (xi) SEQUENCE DESCRIPTION: SEQ ID NO:1030:

GACCCAGTCT GGCTCAAAGC CGACA                                   25

(2) INFORMATION FOR SEQ ID NO:1031:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: DNA (ix) FEATURE:
        (D) OTHER INFORMATION: oligonucleotide primer (xi) SEQUENCE DESCRIPTION: SEQ ID NO:1031:

ACACTGGCAA GGATGCAGTG AATTGTAC                               28

(2) INFORMATION FOR SEQ ID NO:1032:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: DNA (ix) FEATURE:
        (D) OTHER INFORMATION: oligonucleotide primer (xi) SEQUENCE DESCRIPTION: SEQ ID NO:1032:

CGTGATATTG GTGAAGGTAG ACGTGGC                               27

(2) INFORMATION FOR SEQ ID NO:1033:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: DNA (ix) FEATURE:
        (D) OTHER INFORMATION: oligonucleotide primer (xi) SEQUENCE DESCRIPTION: SEQ ID NO:1033:

TGTTCTTGGT GCCCGTCCGG CTGA                                   24

(2) INFORMATION FOR SEQ ID NO:1034:

(i) SEQUENCE CHARACTERISTICS:
        (A) LENGTH: 26 base pairs
        (B) TYPE: nucleic acid
        (C) STRANDEDNESS: single (D) TOPOLOGY: linear (ii) MOLECULE TYPE: DNA (ix) FEATURE:
        (D) OTHER INFORMATION: oligonucleotide primer (xi) SEQUENCE DESCRIPTION: SEQ ID NO:1034:

CTCACGATCA GGAGGTGGTT ATGCGA                                        26

(2) INFORMATION FOR SEQ ID NO:1035:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: DNA (ix) FEATURE:
        (D) OTHER INFORMATION: oligonucleotide primer (xi) SEQUENCE DESCRIPTION: SEQ ID NO:1035:

CTTGTCACCA TCCACGACCG GAGG                                          24

(2) INFORMATION FOR SEQ ID NO:1036:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: DNA (ix) FEATURE:
        (D) OTHER INFORMATION: oligonucleotide primer (xi) SEQUENCE DESCRIPTION: SEQ ID NO:1036:

ATCAAGCCGA GCAGCCGTGC AAGG                                          24

(2) INFORMATION FOR SEQ ID NO:1037:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: DNA (ix) FEATURE:
        (D) OTHER INFORMATION: oligonucleotide primer (xi) SEQUENCE DESCRIPTION: SEQ ID NO:1037:

CACAGCAGAG TGACTGTAGC AATACCTT                                      28

(2) INFORMATION FOR SEQ ID NO:1038:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: DNA (ix) FEATURE:
        (D) OTHER INFORMATION: oligonucleotide primer (xi) SEQUENCE DESCRIPTION: SEQ ID NO:1038:

```
CTGGACTATG CCTTTCAAGG TCTGCATT                                              28

(2) INFORMATION FOR SEQ ID NO:1039:

(i) SEQUENCE CHARACTERISTICS:
          (A) LENGTH: 28 base pairs
          (B) TYPE: nucleic acid
          (C) STRANDEDNESS: single
          (D) TOPOLOGY: linear (ii) MOLECULE TYPE: DNA (ix) FEATURE:
          (D) OTHER INFORMATION: oligonucleotide primer (xi) SEQUENCE DESCRIPTION: SEQ ID NO:1039:

CTTTCCAAAC AGGACAGCAG ACATCACT                                              28

(2) INFORMATION FOR SEQ ID NO:1040:

(i) SEQUENCE CHARACTERISTICS:
          (A) LENGTH: 28 base pairs
          (B) TYPE: nucleic acid
          (C) STRANDEDNESS: single
          (D) TOPOLOGY: linear (ii) MOLECULE TYPE: DNA (ix) FEATURE:
          (D) OTHER INFORMATION: oligonucleotide primer (xi) SEQUENCE DESCRIPTION: SEQ ID NO:1040:

GACCTCGTAA TTTGGTTGGG ACGCAAAT                                              28

(2) INFORMATION FOR SEQ ID NO:1041:

(i) SEQUENCE CHARACTERISTICS:
          (A) LENGTH: 26 base pairs
          (B) TYPE: nucleic acid
          (C) STRANDEDNESS: single
          (D) TOPOLOGY: linear (ii) MOLECULE TYPE: DNA (ix) FEATURE:
          (D) OTHER INFORMATION: oligonucleotide primer (xi) SEQUENCE DESCRIPTION: SEQ ID NO:1041:

CAAATCTCCT GTGCAGTGGG ACGACT                                                26

(2) INFORMATION FOR SEQ ID NO:1042:

(i) SEQUENCE CHARACTERISTICS:
          (A) LENGTH: 25 base pairs
          (B) TYPE: nucleic acid
          (C) STRANDEDNESS: single
          (D) TOPOLOGY: linear (ii) MOLECULE TYPE: DNA (ix) FEATURE:
          (D) OTHER INFORMATION: oligonucleotide primer (xi) SEQUENCE DESCRIPTION: SEQ ID NO:1042:

CTGTTCCCTG TCGGTCATGT CCTCC                                                 25

(2) INFORMATION FOR SEQ ID NO:1043:

(i) SEQUENCE CHARACTERISTICS:
          (A) LENGTH: 28 base pairs
```

```
        (B) TYPE: nucleic acid
        (C) STRANDEDNESS: single
        (D) TOPOLOGY: linear (ii) MOLECULE TYPE: DNA (ix) FEATURE:
        (D) OTHER INFORMATION: oligonucleotide primer (xi) SEQUENCE DESCRIPTION: SEQ ID NO:1043:

GTTTGCTGAG AGTTAGGAGC ACTTGGTG                                          28

(2) INFORMATION FOR SEQ ID NO:1044:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: DNA (ix) FEATURE:
        (D) OTHER INFORMATION: oligonucleotide primer (xi) SEQUENCE DESCRIPTION: SEQ ID NO:1044:

CAGACTGATG TCCTGACTTG CACAGGAA                                          28

(2) INFORMATION FOR SEQ ID NO:1045:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: DNA (ix) FEATURE:
        (D) OTHER INFORMATION: oligonucleotide primer (xi) SEQUENCE DESCRIPTION: SEQ ID NO:1045:

GACCATTGTC CAGAAGACAT CTCATGGC                                          28

(2) INFORMATION FOR SEQ ID NO:1046:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: DNA (ix) FEATURE:
        (D) OTHER INFORMATION: oligonucleotide primer (xi) SEQUENCE DESCRIPTION: SEQ ID NO:1046:

TACCAAGAGC ACGTCTGTAA TGGTGTCT                                          28

(2) INFORMATION FOR SEQ ID NO:1047:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: DNA (ix) FEATURE:
        (D) OTHER INFORMATION: oligonucleotide primer
```

(xi) SEQUENCE DESCRIPTION: SEQ ID NO:1047:

AGGAGACGGG CGGCGTGTTC CTG                                           23

(2) INFORMATION FOR SEQ ID NO:1048:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: DNA (ix) FEATURE:
        (D) OTHER INFORMATION: oligonucleotide primer (xi) SEQUENCE DESCRIPTION: SEQ ID NO:1048:

GAAGCCCGCT TCACAGTAAC GCTTGT                                        26

(2) INFORMATION FOR SEQ ID NO:1049:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: DNA (ix) FEATURE:
        (D) OTHER INFORMATION: oligonucleotide primer (xi) SEQUENCE DESCRIPTION: SEQ ID NO:1049:

TCCAAATGTC ACCACGGGAA CGGCTC                                        26

(2) INFORMATION FOR SEQ ID NO:1050:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: DNA (ix) FEATURE:
        (D) OTHER INFORMATION: oligonucleotide primer (xi) SEQUENCE DESCRIPTION: SEQ ID NO:1050:

ACAGTCGCCG TTACCTCCGC AGAG                                          24

(2) INFORMATION FOR SEQ ID NO:1051:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: DNA (ix) FEATURE:
        (D) OTHER INFORMATION: oligonucleotide primer (xi) SEQUENCE DESCRIPTION: SEQ ID NO:1051:

TGCTGTATCC CACGGAGATC ACCGTC                                        26

(2) INFORMATION FOR SEQ ID NO:1052:

(i) SEQUENCE CHARACTERISTICS:
    (A) LENGTH: 26 base pairs
    (B) TYPE: nucleic acid
    (C) STRANDEDNESS: single
    (D) TOPOLOGY: linear (ii) MOLECULE TYPE: DNA (ix) FEATURE:
    (D) OTHER INFORMATION: oligonucleotide primer (xi) SEQUENCE DESCRIPTION: SEQ ID NO:1052:

AATAGGGTAG CCCAGCCATT TACCCG                    26

(2) INFORMATION FOR SEQ ID NO:1053:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: DNA (ix) FEATURE:
        (D) OTHER INFORMATION: oligonucleotide primer (xi) SEQUENCE DESCRIPTION: SEQ ID NO:1053:

CTTCTTGGTG GAGGATGACG CCAGAG                    26

(2) INFORMATION FOR SEQ ID NO:1054:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: DNA (ix) FEATURE:
        (D) OTHER INFORMATION: oligonucleotide primer (xi) SEQUENCE DESCRIPTION: SEQ ID NO:1054:

AGCGAGGATT GATGGTGGTC GTGATG                    26

(2) INFORMATION FOR SEQ ID NO:1055:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: DNA (ix) FEATURE:
        (D) OTHER INFORMATION: oligonucleotide primer (xi) SEQUENCE DESCRIPTION: SEQ ID NO:1055:

GTGCCCAATG ACGGAAACTG TCATCTG                   27

(2) INFORMATION FOR SEQ ID NO:1056:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: DNA (ix) FEATURE:
         (D) OTHER INFORMATION: oligonucleotide primer (xi) SEQUENCE DESCRIPTION: SEQ ID NO:1056:

CATTGCTCGT CACGTTTCTG CATCCTTC                                          28

(2) INFORMATION FOR SEQ ID NO:1057:

(i) SEQUENCE CHARACTERISTICS:
         (A) LENGTH: 27 base pairs
         (B) TYPE: nucleic acid
         (C) STRANDEDNESS: single
         (D) TOPOLOGY: linear (ii) MOLECULE TYPE: DNA (ix) FEATURE:
         (D) OTHER INFORMATION: oligonucleotide primer (xi) SEQUENCE DESCRIPTION: SEQ ID NO:1057:

CCTCCTGTTC ACAGCCTTAG CAACTTC                                           27

(2) INFORMATION FOR SEQ ID NO:1058:

(i) SEQUENCE CHARACTERISTICS:
         (A) LENGTH: 26 base pairs
         (B) TYPE: nucleic acid
         (C) STRANDEDNESS: single
         (D) TOPOLOGY: linear (ii) MOLECULE TYPE: DNA (ix) FEATURE:
         (D) OTHER INFORMATION: oligonucleotide primer (xi) SEQUENCE DESCRIPTION: SEQ ID NO:1058:

CACTGGTAGA GGCCACCCGT TTGGTT                                            26

(2) INFORMATION FOR SEQ ID NO:1059:

(i) SEQUENCE CHARACTERISTICS:
         (A) LENGTH: 23 base pairs
         (B) TYPE: nucleic acid
         (C) STRANDEDNESS: single
         (D) TOPOLOGY: linear (ii) MOLECULE TYPE: DNA (ix) FEATURE:
         (D) OTHER INFORMATION: oligonucleotide primer (xi) SEQUENCE DESCRIPTION: SEQ ID NO:1059:

GCTGAGCTTC GGGTCACCGC CCC                                               23

(2) INFORMATION FOR SEQ ID NO:1060:

(i) SEQUENCE CHARACTERISTICS:
         (A) LENGTH: 26 base pairs
         (B) TYPE: nucleic acid
         (C) STRANDEDNESS: single
         (D) TOPOLOGY: linear (ii) MOLECULE TYPE: DNA (ix) FEATURE:
         (D) OTHER INFORMATION: oligonucleotide primer (xi) SEQUENCE DESCRIPTION: SEQ ID NO:1060:

GGAAACCACG TCGCTTTGCG AGTTGT                                            26

(2) INFORMATION FOR SEQ ID NO:1061:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: DNA (ix) FEATURE:
        (D) OTHER INFORMATION: oligonucleotide primer (xi) SEQUENCE DESCRIPTION: SEQ ID NO:1061:

CAAGGTAGAA AGTCGGGACA AATTACCC                                    28

(2) INFORMATION FOR SEQ ID NO:1062:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: DNA (ix) FEATURE:
        (D) OTHER INFORMATION: oligonucleotide primer (xi) SEQUENCE DESCRIPTION: SEQ ID NO:1062:

GGATTGACCA CAGTTGTTAC GGCACTCT                                    28

(2) INFORMATION FOR SEQ ID NO:1063:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: DNA (ix) FEATURE:
        (D) OTHER INFORMATION: oligonucleotide primer (xi) SEQUENCE DESCRIPTION: SEQ ID NO:1063:

CCTGAGGACT GATTTCAGAG TGACTACA                                    28

(2) INFORMATION FOR SEQ ID NO:1064:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: DNA (ix) FEATURE:
        (D) OTHER INFORMATION: oligonucleotide primer (xi) SEQUENCE DESCRIPTION: SEQ ID NO:1064:

TCTTGTGATG TGGGACAGCT AACGTGAT                                    28

(2) INFORMATION FOR SEQ ID NO:1065:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: DNA (ix) FEATURE:
             (D) OTHER INFORMATION: oligonucleotide primer (xi) SEQUENCE DESCRIPTION: SEQ ID NO:1065:

TTCGGGCCAG AGCGCGAGGG CAT                                              23

(2) INFORMATION FOR SEQ ID NO:1066:

(i) SEQUENCE CHARACTERISTICS:
            (A) LENGTH: 23 base pairs
            (B) TYPE: nucleic acid
            (C) STRANDEDNESS: single
            (D) TOPOLOGY: linear (ii) MOLECULE TYPE: DNA (ix) FEATURE:
             (D) OTHER INFORMATION: oligonucleotide primer (xi) SEQUENCE DESCRIPTION: SEQ ID NO:1066:

GACGCCTAGT GGGACATGGC GGG                                              23

(2) INFORMATION FOR SEQ ID NO:1067:

(i) SEQUENCE CHARACTERISTICS:
            (A) LENGTH: 28 base pairs
            (B) TYPE: nucleic acid
            (C) STRANDEDNESS: single
            (D) TOPOLOGY: linear (ii) MOLECULE TYPE: DNA (ix) FEATURE:
             (D) OTHER INFORMATION: oligonucleotide primer (xi) SEQUENCE DESCRIPTION: SEQ ID NO:1067:

ACAGCGAAGA ACCTCCTGAA ACCCTTTC                                         28

(2) INFORMATION FOR SEQ ID NO:1068:

(i) SEQUENCE CHARACTERISTICS:
            (A) LENGTH: 28 base pairs
            (B) TYPE: nucleic acid
            (C) STRANDEDNESS: single
            (D) TOPOLOGY: linear (ii) MOLECULE TYPE: DNA (ix) FEATURE:
             (D) OTHER INFORMATION: oligonucleotide primer (xi) SEQUENCE DESCRIPTION: SEQ ID NO:1068:

GTTGGGTACA GCACAGGGTA ACCATTTG                                         28

(2) INFORMATION FOR SEQ ID NO:1069:

(i) SEQUENCE CHARACTERISTICS:
            (A) LENGTH: 24 base pairs
            (B) TYPE: nucleic acid
            (C) STRANDEDNESS: single
            (D) TOPOLOGY: linear (ii) MOLECULE TYPE: DNA (ix) FEATURE:
             (D) OTHER INFORMATION: oligonucleotide primer (xi) SEQUENCE DESCRIPTION: SEQ ID NO:1069:

GCTGTGGCTG CCCTCCATCC CTTC                                             24

(2) INFORMATION FOR SEQ ID NO:1070:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: DNA (ix) FEATURE:
        (D) OTHER INFORMATION: oligonucleotide primer (xi) SEQUENCE DESCRIPTION: SEQ ID NO:1070:

CCCTCTAGGT TAAGGCACTT CCGGG                                          25

(2) INFORMATION FOR SEQ ID NO:1071:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: DNA (ix) FEATURE:
        (D) OTHER INFORMATION: oligonucleotide primer (xi) SEQUENCE DESCRIPTION: SEQ ID NO:1071:

GTCAGGGCGT GGGACATCTA GTAGG                                          25

(2) INFORMATION FOR SEQ ID NO:1072:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: DNA (ix) FEATURE:
        (D) OTHER INFORMATION: oligonucleotide primer (xi) SEQUENCE DESCRIPTION: SEQ ID NO:1072:

TGGAGTGCAA TGGCGCAATC TTGGCT                                         26

(2) INFORMATION FOR SEQ ID NO:1073:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: DNA (ix) FEATURE:
        (D) OTHER INFORMATION: oligonucleotide primer (xi) SEQUENCE DESCRIPTION: SEQ ID NO:1073:

GAGCTGGCAG AACTCCGAGA GTCTAC                                         26

(2) INFORMATION FOR SEQ ID NO:1074:

(i) SEQUENCE CHARACTERISTICS:
        (A) LENGTH: 28 base pairs
        (B) TYPE: nucleic acid
        (C) STRANDEDNESS: single (D) TOPOLOGY: linear (ii) MOLECULE TYPE: DNA (ix) FEATURE:
           (D) OTHER INFORMATION: oligonucleotide primer (xi) SEQUENCE DESCRIPTION: SEQ ID NO:1074:

CTTAGAGTTC CTCATGTAGA CCTTGTGG                                              28

(2) INFORMATION FOR SEQ ID NO:1075:

(i) SEQUENCE CHARACTERISTICS:
           (A) LENGTH: 28 base pairs
           (B) TYPE: nucleic acid
           (C) STRANDEDNESS: single
           (D) TOPOLOGY: linear (ii) MOLECULE TYPE: DNA (ix) FEATURE:
           (D) OTHER INFORMATION: oligonucleotide primer (xi) SEQUENCE DESCRIPTION: SEQ ID NO:1075:

TGTCTTTGGG CTTCTGGCTG GTAGATAA                                              28

(2) INFORMATION FOR SEQ ID NO:1076:

(i) SEQUENCE CHARACTERISTICS:
           (A) LENGTH: 28 base pairs
           (B) TYPE: nucleic acid
           (C) STRANDEDNESS: single
           (D) TOPOLOGY: linear (ii) MOLECULE TYPE: DNA (ix) FEATURE:
           (D) OTHER INFORMATION: oligonucleotide primer (xi) SEQUENCE DESCRIPTION: SEQ ID NO:1076:

GTGTGACCCA CAAAGTGAGG ACATTCAG                                              28

(2) INFORMATION FOR SEQ ID NO:1077:

(i) SEQUENCE CHARACTERISTICS:
           (A) LENGTH: 24 base pairs
           (B) TYPE: nucleic acid
           (C) STRANDEDNESS: single
           (D) TOPOLOGY: linear (ii) MOLECULE TYPE: DNA (ix) FEATURE:
           (D) OTHER INFORMATION: oligonucleotide primer (xi) SEQUENCE DESCRIPTION: SEQ ID NO:1077:

CCAGGTGTAG CTCTGAGTGT GGGC                                                  24

(2) INFORMATION FOR SEQ ID NO:1078:

(i) SEQUENCE CHARACTERISTICS:
           (A) LENGTH: 25 base pairs
           (B) TYPE: nucleic acid
           (C) STRANDEDNESS: single
           (D) TOPOLOGY: linear (ii) MOLECULE TYPE: DNA (ix) FEATURE:
           (D) OTHER INFORMATION: oligonucleotide primer (xi) SEQUENCE DESCRIPTION: SEQ ID NO:1078:

```
GATGATACAG ATGGGTGCCG GGACC                                                  25

(2) INFORMATION FOR SEQ ID NO:1079:

(i) SEQUENCE CHARACTERISTICS:
         (A) LENGTH: 25 base pairs
         (B) TYPE: nucleic acid
         (C) STRANDEDNESS: single
         (D) TOPOLOGY: linear (ii) MOLECULE TYPE: DNA (ix) FEATURE:
         (D) OTHER INFORMATION: oligonucleotide primer (xi) SEQUENCE DESCRIPTION: SEQ ID NO:1079:

CACCCTGGAG CACTCTGATT GTGCC                                                  25

(2) INFORMATION FOR SEQ ID NO:1080:

(i) SEQUENCE CHARACTERISTICS:
         (A) LENGTH: 28 base pairs
         (B) TYPE: nucleic acid
         (C) STRANDEDNESS: single
         (D) TOPOLOGY: linear (ii) MOLECULE TYPE: DNA (ix) FEATURE:
         (D) OTHER INFORMATION: oligonucleotide primer (xi) SEQUENCE DESCRIPTION: SEQ ID NO:1080:

GCATTGACAT CTTTGGGAAC CACGTCAC                                               28

(2) INFORMATION FOR SEQ ID NO:1081:

(i) SEQUENCE CHARACTERISTICS:
         (A) LENGTH: 30 base pairs
         (B) TYPE: nucleic acid
         (C) STRANDEDNESS: single
         (D) TOPOLOGY: linear (ii) MOLECULE TYPE: DNA (ix) FEATURE:
         (D) OTHER INFORMATION: oligonucleotide primer (xi) SEQUENCE DESCRIPTION: SEQ ID NO:1081:

ACGATGAGAA TAATGCTGAA GCTAGTGCTG                                             30

(2) INFORMATION FOR SEQ ID NO:1082:

(i) SEQUENCE CHARACTERISTICS:
         (A) LENGTH: 28 base pairs
         (B) TYPE: nucleic acid
         (C) STRANDEDNESS: single
         (D) TOPOLOGY: linear (ii) MOLECULE TYPE: DNA (ix) FEATURE:
         (D) OTHER INFORMATION: oligonucleotide primer (xi) SEQUENCE DESCRIPTION: SEQ ID NO:1082:

CTTTGTATTG CCTTGTCGAA TCTGTCGC                                               28

(2) INFORMATION FOR SEQ ID NO:1083:

(i) SEQUENCE CHARACTERISTICS:
         (A) LENGTH: 28 base pairs
```

(B) TYPE: nucleic acid
            (C) STRANDEDNESS: single
            (D) TOPOLOGY: linear (ii) MOLECULE TYPE: DNA (ix) FEATURE:
            (D) OTHER INFORMATION: oligonucleotide primer (xi) SEQUENCE DESCRIPTION: SEQ ID NO:1083:

AGTCTACTTC ACTAATGACG ATGCCGTG                                              28

(2) INFORMATION FOR SEQ ID NO:1084:

(i) SEQUENCE CHARACTERISTICS:
            (A) LENGTH: 28 base pairs
            (B) TYPE: nucleic acid
            (C) STRANDEDNESS: single
            (D) TOPOLOGY: linear (ii) MOLECULE TYPE: DNA (ix) FEATURE:
            (D) OTHER INFORMATION: oligonucleotide primer (xi) SEQUENCE DESCRIPTION: SEQ ID NO:1084:

GATTACTTGT CTGCGGCTGA GTGAGATC                                              28

(2) INFORMATION FOR SEQ ID NO:1085:

(i) SEQUENCE CHARACTERISTICS:
            (A) LENGTH: 27 base pairs
            (B) TYPE: nucleic acid
            (C) STRANDEDNESS: single
            (D) TOPOLOGY: linear (ii) MOLECULE TYPE: DNA (ix) FEATURE:
            (D) OTHER INFORMATION: oligonucleotide primer (xi) SEQUENCE DESCRIPTION: SEQ ID NO:1085:

GTAGATGAAG CTCTCCAACA CCCGTAC                                               27

(2) INFORMATION FOR SEQ ID NO:1086:

(i) SEQUENCE CHARACTERISTICS:
            (A) LENGTH: 28 base pairs
            (B) TYPE: nucleic acid
            (C) STRANDEDNESS: single
            (D) TOPOLOGY: linear (ii) MOLECULE TYPE: DNA (ix) FEATURE:
            (D) OTHER INFORMATION: oligonucleotide primer (xi) SEQUENCE DESCRIPTION: SEQ ID NO:1086:

GTCTGTATCA GAGGCCAAAG TCGGATCT                                              28

(2) INFORMATION FOR SEQ ID NO:1087:

(i) SEQUENCE CHARACTERISTICS:
            (A) LENGTH: 24 base pairs
            (B) TYPE: nucleic acid
            (C) STRANDEDNESS: single
            (D) TOPOLOGY: linear (ii) MOLECULE TYPE: DNA (ix) FEATURE:
            (D) OTHER INFORMATION: oligonucleotide primer (xi) SEQUENCE DESCRIPTION: SEQ ID NO:1087:

GCGGAAGGTC CCTCAGACAT CCCC                                          24

(2) INFORMATION FOR SEQ ID NO:1088:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: DNA (ix) FEATURE:
         (D) OTHER INFORMATION: oligonucleotide primer (xi) SEQUENCE DESCRIPTION: SEQ ID NO:1088:

CTCGCAAGAA ATGCCCACAT GAATGTGC                                      28

(2) INFORMATION FOR SEQ ID NO:1089:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: DNA (ix) FEATURE:
         (D) OTHER INFORMATION: oligonucleotide primer (xi) SEQUENCE DESCRIPTION: SEQ ID NO:1089:

TGCATAATGG CCGAGCTGTT GACTGG                                        26

(2) INFORMATION FOR SEQ ID NO:1090:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: DNA (ix) FEATURE:
         (D) OTHER INFORMATION: oligonucleotide primer (xi) SEQUENCE DESCRIPTION: SEQ ID NO:1090:

AAGGGCTTGG GCCGCTGTAA TTCTCT                                        26

(2) INFORMATION FOR SEQ ID NO:1091:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: DNA (ix) FEATURE:
         (D) OTHER INFORMATION: oligonucleotide primer (xi) SEQUENCE DESCRIPTION: SEQ ID NO:1091:

GCACAGCAAG CTGTCGGTGA TCCAC                                         25

(2) INFORMATION FOR SEQ ID NO:1092:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: DNA (ix) FEATURE:
        (D) OTHER INFORMATION: oligonucleotide primer (xi) SEQUENCE DESCRIPTION: SEQ ID NO:1092:

CAGGCACTGA GCAGTGAAGT CCACAAA                                              27

(2) INFORMATION FOR SEQ ID NO:1093:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: DNA (ix) FEATURE:
        (D) OTHER INFORMATION: oligonucleotide primer (xi) SEQUENCE DESCRIPTION: SEQ ID NO:1093:

AGCACTGTGA GTGGTTCAAG CACACTG                                              27

(2) INFORMATION FOR SEQ ID NO:1094:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: DNA (ix) FEATURE:
        (D) OTHER INFORMATION: oligonucleotide primer (xi) SEQUENCE DESCRIPTION: SEQ ID NO:1094:

CTGTGGTCGA AGGCAGACAT AGAGCAAT                                             28

(2) INFORMATION FOR SEQ ID NO:1095:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: DNA (ix) FEATURE:
        (D) OTHER INFORMATION: oligonucleotide primer (xi) SEQUENCE DESCRIPTION: SEQ ID NO:1095:

TTCCCATCCA CCAGCAGCAC AACTATG                                              27

(2) INFORMATION FOR SEQ ID NO:1096:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: DNA (ix) FEATURE:
              (D) OTHER INFORMATION: oligonucleotide primer (xi) SEQUENCE DESCRIPTION: SEQ ID NO:1096:

GTCTAGCAAG TCCGAGCGTG TTCAATTT                                              28

(2) INFORMATION FOR SEQ ID NO:1097:

(i) SEQUENCE CHARACTERISTICS:
              (A) LENGTH: 28 base pairs
              (B) TYPE: nucleic acid
              (C) STRANDEDNESS: single
              (D) TOPOLOGY: linear (ii) MOLECULE TYPE: DNA (ix) FEATURE:
              (D) OTHER INFORMATION: oligonucleotide primer (xi) SEQUENCE DESCRIPTION: SEQ ID NO:1097:

CTGGCAGAAA TGACTTCTAC TCGAACAC                                              28

(2) INFORMATION FOR SEQ ID NO:1098:

(i) SEQUENCE CHARACTERISTICS:
              (A) LENGTH: 28 base pairs
              (B) TYPE: nucleic acid
              (C) STRANDEDNESS: single
              (D) TOPOLOGY: linear (ii) MOLECULE TYPE: DNA (ix) FEATURE:
              (D) OTHER INFORMATION: oligonucleotide primer (xi) SEQUENCE DESCRIPTION: SEQ ID NO:1098:

TTTCAAGTGG CTTAGGACTC ACCCAAAC                                              28

(2) INFORMATION FOR SEQ ID NO:1099:

(i) SEQUENCE CHARACTERISTICS:
              (A) LENGTH: 28 base pairs
              (B) TYPE: nucleic acid
              (C) STRANDEDNESS: single
              (D) TOPOLOGY: linear (ii) MOLECULE TYPE: DNA (ix) FEATURE:
              (D) OTHER INFORMATION: oligonucleotide primer (xi) SEQUENCE DESCRIPTION: SEQ ID NO:1099:

TGGTTGATAT GGCTGCTCAG ATTGCTGA                                              28

(2) INFORMATION FOR SEQ ID NO:1100:

(i) SEQUENCE CHARACTERISTICS:
              (A) LENGTH: 28 base pairs
              (B) TYPE: nucleic acid
              (C) STRANDEDNESS: single
              (D) TOPOLOGY: linear (ii) MOLECULE TYPE: DNA (ix) FEATURE:
              (D) OTHER INFORMATION: oligonucleotide primer (xi) SEQUENCE DESCRIPTION: SEQ ID NO:1100:

TGTATCCTCG CTCCACTTGT TCTAGTAC                                              28

(2) INFORMATION FOR SEQ ID NO:1101:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: DNA (ix) FEATURE:
        (D) OTHER INFORMATION: oligonucleotide primer (xi) SEQUENCE DESCRIPTION: SEQ ID NO:1101:

CGGGACCTGC GAGCAGCTAA TGTTC                         25

(2) INFORMATION FOR SEQ ID NO:1102:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: DNA (ix) FEATURE:
        (D) OTHER INFORMATION: oligonucleotide primer (xi) SEQUENCE DESCRIPTION: SEQ ID NO:1102:

CAGGGCGGTC ATCACGTCGG CATTA                         25

(2) INFORMATION FOR SEQ ID NO:1103:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: DNA (ix) FEATURE:
        (D) OTHER INFORMATION: oligonucleotide primer (xi) SEQUENCE DESCRIPTION: SEQ ID NO:1103:

TCCTCATCTC AATCCTTGAG CGGCAAG                       27

(2) INFORMATION FOR SEQ ID NO:1104:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: DNA (ix) FEATURE:
        (D) OTHER INFORMATION: oligonucleotide primer (xi) SEQUENCE DESCRIPTION: SEQ ID NO:1104:

CCATCATGGT TGGCTAAGCA TATCTCCT                     28

(2) INFORMATION FOR SEQ ID NO:1105:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: DNA (ix) FEATURE:
             (D) OTHER INFORMATION: oligonucleotide primer (xi) SEQUENCE DESCRIPTION: SEQ ID NO:1105:

CTGGCTGCAT TCCCAGCAAC TACGTG                                              26

(2) INFORMATION FOR SEQ ID NO:1106:

(i) SEQUENCE CHARACTERISTICS:
             (A) LENGTH: 26 base pairs
             (B) TYPE: nucleic acid
             (C) STRANDEDNESS: single
             (D) TOPOLOGY: linear (ii) MOLECULE TYPE: DNA (ix) FEATURE:
             (D) OTHER INFORMATION: oligonucleotide primer (xi) SEQUENCE DESCRIPTION: SEQ ID NO:1106:

CAGGTTGCAC AGCCCGTCAT TCACCT                                              26

(2) INFORMATION FOR SEQ ID NO:1107:

(i) SEQUENCE CHARACTERISTICS:
             (A) LENGTH: 26 base pairs
             (B) TYPE: nucleic acid
             (C) STRANDEDNESS: single
             (D) TOPOLOGY: linear (ii) MOLECULE TYPE: DNA (ix) FEATURE:
             (D) OTHER INFORMATION: oligonucleotide primer (xi) SEQUENCE DESCRIPTION: SEQ ID NO:1107:

TGGGTCGGCC TCTACCTTTG CACTTC                                              26

(2) INFORMATION FOR SEQ ID NO:1108:

(i) SEQUENCE CHARACTERISTICS:
             (A) LENGTH: 29 base pairs
             (B) TYPE: nucleic acid
             (C) STRANDEDNESS: single
             (D) TOPOLOGY: linear (ii) MOLECULE TYPE: DNA (ix) FEATURE:
             (D) OTHER INFORMATION: oligonucleotide primer (xi) SEQUENCE DESCRIPTION: SEQ ID NO:1108:

CGATGTGGCA TACTTGTTCT TGACAGTCA                                           29

(2) INFORMATION FOR SEQ ID NO:1109:

(i) SEQUENCE CHARACTERISTICS:
             (A) LENGTH: 28 base pairs
             (B) TYPE: nucleic acid
             (C) STRANDEDNESS: single
             (D) TOPOLOGY: linear (ii) MOLECULE TYPE: DNA (ix) FEATURE:
             (D) OTHER INFORMATION: oligonucleotide primer (xi) SEQUENCE DESCRIPTION: SEQ ID NO:1109:

TTCTGAGGGA CACATCAAGA TTGCCGAT                                            28

(2) INFORMATION FOR SEQ ID NO:1110:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: DNA (ix) FEATURE:
        (D) OTHER INFORMATION: oligonucleotide primer (xi) SEQUENCE DESCRIPTION: SEQ ID NO:1110:

TGGGATAGGC TACGTTGTGT TCCATGAT                      28

(2) INFORMATION FOR SEQ ID NO:1111:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: DNA (ix) FEATURE:
        (D) OTHER INFORMATION: oligonucleotide primer (xi) SEQUENCE DESCRIPTION: SEQ ID NO:1111:

CATTTGAAAG GCTTCTGGGA CCTTGCAT                      28

(2) INFORMATION FOR SEQ ID NO:1112:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: DNA (ix) FEATURE:
        (D) OTHER INFORMATION: oligonucleotide primer (xi) SEQUENCE DESCRIPTION: SEQ ID NO:1112:

GGCATCTACA CAAACACATT CTCAGTGG                      28

(2) INFORMATION FOR SEQ ID NO:1113:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: DNA (ix) FEATURE:
        (D) OTHER INFORMATION: oligonucleotide primer (xi) SEQUENCE DESCRIPTION: SEQ ID NO:1113:

AGGTTGCTAC GATTTCTGCA AACGGAGA                      28

(2) INFORMATION FOR SEQ ID NO:1114:

(i) SEQUENCE CHARACTERISTICS:
        (A) LENGTH: 28 base pairs
        (B) TYPE: nucleic acid
        (C) STRANDEDNESS: single (D) TOPOLOGY: linear (ii) MOLECULE TYPE: DNA (ix) FEATURE:
            (D) OTHER INFORMATION: oligonucleotide primer (xi) SEQUENCE DESCRIPTION: SEQ ID NO:1114:

CCAAAGGCTT ACGGTGAGCA TTGGCAAT                                               28

(2) INFORMATION FOR SEQ ID NO:1115:

(i) SEQUENCE CHARACTERISTICS:
            (A) LENGTH: 26 base pairs
            (B) TYPE: nucleic acid
            (C) STRANDEDNESS: single
            (D) TOPOLOGY: linear (ii) MOLECULE TYPE: DNA (ix) FEATURE:
            (D) OTHER INFORMATION: oligonucleotide primer (xi) SEQUENCE DESCRIPTION: SEQ ID NO:1115:

TGAAGCCTGA GAGTGGAGGT AACCAC                                                 26

(2) INFORMATION FOR SEQ ID NO:1116:

(i) SEQUENCE CHARACTERISTICS:
            (A) LENGTH: 25 base pairs
            (B) TYPE: nucleic acid
            (C) STRANDEDNESS: single
            (D) TOPOLOGY: linear (ii) MOLECULE TYPE: DNA (ix) FEATURE:
            (D) OTHER INFORMATION: oligonucleotide primer (xi) SEQUENCE DESCRIPTION: SEQ ID NO:1116:

GCCAAGTCCC GGTGAACGTA TTGCC                                                  25

(2) INFORMATION FOR SEQ ID NO:1117:

(i) SEQUENCE CHARACTERISTICS:
            (A) LENGTH: 28 base pairs
            (B) TYPE: nucleic acid
            (C) STRANDEDNESS: single
            (D) TOPOLOGY: linear (ii) MOLECULE TYPE: DNA (ix) FEATURE:
            (D) OTHER INFORMATION: oligonucleotide primer (xi) SEQUENCE DESCRIPTION: SEQ ID NO:1117:

TTGCTGCGAG AACGACATCA ACATCCTG                                               28

(2) INFORMATION FOR SEQ ID NO:1118:

(i) SEQUENCE CHARACTERISTICS:
            (A) LENGTH: 28 base pairs
            (B) TYPE: nucleic acid
            (C) STRANDEDNESS: single
            (D) TOPOLOGY: linear (ii) MOLECULE TYPE: DNA (ix) FEATURE:
            (D) OTHER INFORMATION: oligonucleotide primer (xi) SEQUENCE DESCRIPTION: SEQ ID NO:1118:

```
TCTGTAATCC TTGCATCAGT GTAGGGAG                                              28

(2) INFORMATION FOR SEQ ID NO:1119:

(i) SEQUENCE CHARACTERISTICS:
         (A) LENGTH: 28 base pairs
         (B) TYPE: nucleic acid
         (C) STRANDEDNESS: single
         (D) TOPOLOGY: linear (ii) MOLECULE TYPE: DNA (ix) FEATURE:
         (D) OTHER INFORMATION: oligonucleotide primer (xi) SEQUENCE DESCRIPTION: SEQ ID NO:1119:

TATTCGATGC CATGTTCCCT GTCACTCA                                              28

(2) INFORMATION FOR SEQ ID NO:1120:

(i) SEQUENCE CHARACTERISTICS:
         (A) LENGTH: 25 base pairs
         (B) TYPE: nucleic acid
         (C) STRANDEDNESS: single
         (D) TOPOLOGY: linear (ii) MOLECULE TYPE: DNA (ix) FEATURE:
         (D) OTHER INFORMATION: oligonucleotide primer (xi) SEQUENCE DESCRIPTION: SEQ ID NO:1120:

GAGGTCCGTC TTGGCTTTCA CGGTC                                                 25

(2) INFORMATION FOR SEQ ID NO:1121:

(i) SEQUENCE CHARACTERISTICS:
         (A) LENGTH: 25 base pairs
         (B) TYPE: nucleic acid
         (C) STRANDEDNESS: single
         (D) TOPOLOGY: linear (ii) MOLECULE TYPE: DNA (ix) FEATURE:
         (D) OTHER INFORMATION: oligonucleotide primer (xi) SEQUENCE DESCRIPTION: SEQ ID NO:1121:

TCTTCTGTCT GTTGCAGCGG AGGCG                                                 25

(2) INFORMATION FOR SEQ ID NO:1122:

(i) SEQUENCE CHARACTERISTICS:
         (A) LENGTH: 26 base pairs
         (B) TYPE: nucleic acid
         (C) STRANDEDNESS: single
         (D) TOPOLOGY: linear (ii) MOLECULE TYPE: DNA (ix) FEATURE:
         (D) OTHER INFORMATION: oligonucleotide primer (xi) SEQUENCE DESCRIPTION: SEQ ID NO:1122:

CTGGCTATGG GCTCTGCACA ACGCTT                                                26

(2) INFORMATION FOR SEQ ID NO:1123:

(i) SEQUENCE CHARACTERISTICS:
         (A) LENGTH: 28 base pairs
```

(B) TYPE: nucleic acid
        (C) STRANDEDNESS: single
        (D) TOPOLOGY: linear (ii) MOLECULE TYPE: DNA (ix) FEATURE:
        (D) OTHER INFORMATION: oligonucleotide primer (xi) SEQUENCE DESCRIPTION: SEQ ID NO:1123:

GGTGAGAATT GAGGACTGTC CCATTAAC                                              28

(2) INFORMATION FOR SEQ ID NO:1124:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: DNA (ix) FEATURE:
        (D) OTHER INFORMATION: oligonucleotide primer (xi) SEQUENCE DESCRIPTION: SEQ ID NO:1124:

TTTGCTTGAG CTGCTAGAAC TGAATGGG                                              28

(2) INFORMATION FOR SEQ ID NO:1125:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: DNA (ix) FEATURE:
        (D) OTHER INFORMATION: oligonucleotide primer (xi) SEQUENCE DESCRIPTION: SEQ ID NO:1125:

GCTGCCATTG AGCGGAAGAT TCAACTG                                               27

(2) INFORMATION FOR SEQ ID NO:1126:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: DNA (ix) FEATURE:
        (D) OTHER INFORMATION: oligonucleotide primer (xi) SEQUENCE DESCRIPTION: SEQ ID NO:1126:

CACCTTGTCG CAGAGCAAGT AGAGCT                                                26

(2) INFORMATION FOR SEQ ID NO:1127:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: DNA (ix) FEATURE:
        (D) OTHER INFORMATION: oligonucleotide primer (xi) SEQUENCE DESCRIPTION: SEQ ID NO:1127:

AACAGGCTCT GGCCCACCCA TATCTG                                      26

(2) INFORMATION FOR SEQ ID NO:1128:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: DNA (ix) FEATURE:
        (D) OTHER INFORMATION: oligonucleotide primer (xi) SEQUENCE DESCRIPTION: SEQ ID NO:1128:

CAAAGTGGAT AAGCCAAGAC GGGCTG                                      26

(2) INFORMATION FOR SEQ ID NO:1129:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: DNA (ix) FEATURE:
        (D) OTHER INFORMATION: oligonucleotide primer (xi) SEQUENCE DESCRIPTION: SEQ ID NO:1129:

GGTAGCTTGC ACCTGTCCCA ACTGTA                                      26

(2) INFORMATION FOR SEQ ID NO:1130:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: DNA (ix) FEATURE:
        (D) OTHER INFORMATION: oligonucleotide primer (xi) SEQUENCE DESCRIPTION: SEQ ID NO:1130:

GCAGTAATCA AAGTATCATC TCGCGCAG                                    28

(2) INFORMATION FOR SEQ ID NO:1131:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: DNA (ix) FEATURE:
        (D) OTHER INFORMATION: oligonucleotide primer (xi) SEQUENCE DESCRIPTION: SEQ ID NO:1131:

CAATATCCAG TACCAGGCGG TCCCTC                                      26

(2) INFORMATION FOR SEQ ID NO:1132:

(i) SEQUENCE CHARACTERISTICS:
    (A) LENGTH: 26 base pairs
    (B) TYPE: nucleic acid
    (C) STRANDEDNESS: single
    (D) TOPOLOGY: linear (ii) MOLECULE TYPE: DNA (ix) FEATURE:
    (D) OTHER INFORMATION: oligonucleotide primer (xi) SEQUENCE DESCRIPTION: SEQ ID NO:1132:

ACTGGCGTTC ACAAGGTTGT TGACGG                                    26

(2) INFORMATION FOR SEQ ID NO:1133:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: DNA (ix) FEATURE:
        (D) OTHER INFORMATION: oligonucleotide primer (xi) SEQUENCE DESCRIPTION: SEQ ID NO:1133:

GAAACGGAAA CAGAGTGGTC ATTCCCC                                   27

(2) INFORMATION FOR SEQ ID NO:1134:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: DNA (ix) FEATURE:
        (D) OTHER INFORMATION: oligonucleotide primer (xi) SEQUENCE DESCRIPTION: SEQ ID NO:1134:

GTGGGATTGA GGGTCACATC ATTGGCA                                   27

(2) INFORMATION FOR SEQ ID NO:1135:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: DNA (ix) FEATURE:
        (D) OTHER INFORMATION: oligonucleotide primer (xi) SEQUENCE DESCRIPTION: SEQ ID NO:1135:

TGACGGATAA ACACCTGGAC CCAATCAG                                  28

(2) INFORMATION FOR SEQ ID NO:1136:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: DNA

```
      (ix) FEATURE:
           (D) OTHER INFORMATION: oligonucleotide primer (xi) SEQUENCE DESCRIPTION: SEQ ID NO:1136:

GGGTTAGTTC TGGCTGACGT AAATCAAG                                           28

(2) INFORMATION FOR SEQ ID NO:1137:

(i) SEQUENCE CHARACTERISTICS:
           (A) LENGTH: 26 base pairs
           (B) TYPE: nucleic acid
           (C) STRANDEDNESS: single
           (D) TOPOLOGY: linear (ii) MOLECULE TYPE: DNA (ix) FEATURE:
           (D) OTHER INFORMATION: oligonucleotide primer (xi) SEQUENCE DESCRIPTION: SEQ ID NO:1137:

ACTCACTGTC GGTGAGACAC AGGCAG                                             26

(2) INFORMATION FOR SEQ ID NO:1138:

(i) SEQUENCE CHARACTERISTICS:
           (A) LENGTH: 26 base pairs
           (B) TYPE: nucleic acid
           (C) STRANDEDNESS: single
           (D) TOPOLOGY: linear (ii) MOLECULE TYPE: DNA (ix) FEATURE:
           (D) OTHER INFORMATION: oligonucleotide primer (xi) SEQUENCE DESCRIPTION: SEQ ID NO:1138:

GGTGTTGTCC TCACTGGTCA GGGACA                                             26

(2) INFORMATION FOR SEQ ID NO:1139:

(i) SEQUENCE CHARACTERISTICS:
           (A) LENGTH: 26 base pairs
           (B) TYPE: nucleic acid
           (C) STRANDEDNESS: single
           (D) TOPOLOGY: linear (ii) MOLECULE TYPE: DNA (ix) FEATURE:
           (D) OTHER INFORMATION: oligonucleotide primer (xi) SEQUENCE DESCRIPTION: SEQ ID NO:1139:

CGCTACACAG TTTCTGCCAG TCCCTG                                             26

(2) INFORMATION FOR SEQ ID NO:1140:

(i) SEQUENCE CHARACTERISTICS:
           (A) LENGTH: 28 base pairs
           (B) TYPE: nucleic acid
           (C) STRANDEDNESS: single
           (D) TOPOLOGY: linear (ii) MOLECULE TYPE: DNA (ix) FEATURE:
           (D) OTHER INFORMATION: oligonucleotide primer (xi) SEQUENCE DESCRIPTION: SEQ ID NO:1140:

GGCACGAATG TTGTGATCTT TGCTTCCT                                           28
```

(2) INFORMATION FOR SEQ ID NO:1141:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: DNA (ix) FEATURE:
        (D) OTHER INFORMATION: oligonucleotide primer (xi) SEQUENCE DESCRIPTION: SEQ ID NO:1141:

GAGGAGCACA GTTTGTGGCT TATAGGTG                    28

(2) INFORMATION FOR SEQ ID NO:1142:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: DNA (ix) FEATURE:
        (D) OTHER INFORMATION: oligonucleotide primer (xi) SEQUENCE DESCRIPTION: SEQ ID NO:1142:

CTTAAATGCT CTGCCCTTGG GTCTCGT                     27

(2) INFORMATION FOR SEQ ID NO:1143:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: DNA (ix) FEATURE:
        (D) OTHER INFORMATION: oligonucleotide primer (xi) SEQUENCE DESCRIPTION: SEQ ID NO:1143:

CTCTTCGGCC CTCAGATGTC CCTTG                       25

(2) INFORMATION FOR SEQ ID NO:1144:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: DNA (ix) FEATURE:
        (D) OTHER INFORMATION: oligonucleotide primer (xi) SEQUENCE DESCRIPTION: SEQ ID NO:1144:

CCCAAGGTCC TATCTTGGCC GCATC                       25

(2) INFORMATION FOR SEQ ID NO:1145:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: DNA (ix) FEATURE:
             (D) OTHER INFORMATION: oligonucleotide primer (xi) SEQUENCE DESCRIPTION: SEQ ID NO:1145:

ACTGCCTTTA CCTCCACCTG TTAGTCC                                         27

(2) INFORMATION FOR SEQ ID NO:1146:

(i) SEQUENCE CHARACTERISTICS:
             (A) LENGTH: 28 base pairs
             (B) TYPE: nucleic acid
             (C) STRANDEDNESS: single
             (D) TOPOLOGY: linear (ii) MOLECULE TYPE: DNA (ix) FEATURE:
             (D) OTHER INFORMATION: oligonucleotide primer (xi) SEQUENCE DESCRIPTION: SEQ ID NO:1146:

GAGCAGTCCT AGTGGATTCA CTGACAGA                                        28

(2) INFORMATION FOR SEQ ID NO:1147:

(i) SEQUENCE CHARACTERISTICS:
             (A) LENGTH: 28 base pairs
             (B) TYPE: nucleic acid
             (C) STRANDEDNESS: single
             (D) TOPOLOGY: linear (ii) MOLECULE TYPE: DNA (ix) FEATURE:
             (D) OTHER INFORMATION: oligonucleotide primer (xi) SEQUENCE DESCRIPTION: SEQ ID NO:1147:

GACTAGAAGC TCAACTGAAG GCATGTCA                                        28

(2) INFORMATION FOR SEQ ID NO:1148:

(i) SEQUENCE CHARACTERISTICS:
             (A) LENGTH: 29 base pairs
             (B) TYPE: nucleic acid
             (C) STRANDEDNESS: single
             (D) TOPOLOGY: linear (ii) MOLECULE TYPE: DNA (ix) FEATURE:
             (D) OTHER INFORMATION: oligonucleotide primer (xi) SEQUENCE DESCRIPTION: SEQ ID NO:1148:

GCAGTACGCC CAGAAACAAT CCATTTCAA                                       29

(2) INFORMATION FOR SEQ ID NO:1149:

(i) SEQUENCE CHARACTERISTICS:
             (A) LENGTH: 28 base pairs
             (B) TYPE: nucleic acid
             (C) STRANDEDNESS: single
             (D) TOPOLOGY: linear (ii) MOLECULE TYPE: DNA (ix) FEATURE:
             (D) OTHER INFORMATION: oligonucleotide primer (xi) SEQUENCE DESCRIPTION: SEQ ID NO:1149:

ATAGTGTTCC TGAGCTGCCA ACGATACC                                        28

(2) INFORMATION FOR SEQ ID NO:1150:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: DNA (ix) FEATURE:
        (D) OTHER INFORMATION: oligonucleotide primer (xi) SEQUENCE DESCRIPTION: SEQ ID NO:1150:

GGGCTAAACC AGGAAACTAC CTATTCCC                        28

(2) INFORMATION FOR SEQ ID NO:1151:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: DNA (ix) FEATURE:
        (D) OTHER INFORMATION: oligonucleotide primer (xi) SEQUENCE DESCRIPTION: SEQ ID NO:1151:

ACACGGTGGT GGAACCCTAC AACGC                           25

(2) INFORMATION FOR SEQ ID NO:1152:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: DNA (ix) FEATURE:
        (D) OTHER INFORMATION: oligonucleotide primer (xi) SEQUENCE DESCRIPTION: SEQ ID NO:1152:

CAGGCGGCCA TCATGTTCTT GGCATC                        26

(2) INFORMATION FOR SEQ ID NO:1153:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: DNA (ix) FEATURE:
        (D) OTHER INFORMATION: oligonucleotide primer (xi) SEQUENCE DESCRIPTION: SEQ ID NO:1153:

TCAGGACTGA GAACCTGGCT AAGTACG                     27

(2) INFORMATION FOR SEQ ID NO:1154:

(i) SEQUENCE CHARACTERISTICS:
        (A) LENGTH: 26 base pairs
        (B) TYPE: nucleic acid
        (C) STRANDEDNESS: single (D) TOPOLOGY: linear (ii) MOLECULE TYPE: DNA (ix) FEATURE:
              (D) OTHER INFORMATION: oligonucleotide primer (xi) SEQUENCE DESCRIPTION: SEQ ID NO:1154:

CCTAATTGCT TGCTGAGGTC GATGGG                                              26

(2) INFORMATION FOR SEQ ID NO:1155:

(i) SEQUENCE CHARACTERISTICS:
              (A) LENGTH: 28 base pairs
              (B) TYPE: nucleic acid
              (C) STRANDEDNESS: single
              (D) TOPOLOGY: linear (ii) MOLECULE TYPE: DNA (ix) FEATURE:
              (D) OTHER INFORMATION: oligonucleotide primer (xi) SEQUENCE DESCRIPTION: SEQ ID NO:1155:

AGGTTCTTGC TGGTGTGAAA TGACTGAG                                            28

(2) INFORMATION FOR SEQ ID NO:1156:

(i) SEQUENCE CHARACTERISTICS:
              (A) LENGTH: 28 base pairs
              (B) TYPE: nucleic acid
              (C) STRANDEDNESS: single
              (D) TOPOLOGY: linear (ii) MOLECULE TYPE: DNA (ix) FEATURE:
              (D) OTHER INFORMATION: oligonucleotide primer (xi) SEQUENCE DESCRIPTION: SEQ ID NO:1156:

GCACCATAGG TACATCATCC GAGTCTTT                                            28

(2) INFORMATION FOR SEQ ID NO:1157:

(i) SEQUENCE CHARACTERISTICS:
              (A) LENGTH: 26 base pairs
              (B) TYPE: nucleic acid
              (C) STRANDEDNESS: single
              (D) TOPOLOGY: linear (ii) MOLECULE TYPE: DNA (ix) FEATURE:
              (D) OTHER INFORMATION: oligonucleotide primer (xi) SEQUENCE DESCRIPTION: SEQ ID NO:1157:

GCCAAGTCTG GGACCAAAGC GTTCAT                                              26

(2) INFORMATION FOR SEQ ID NO:1158:

(i) SEQUENCE CHARACTERISTICS:
              (A) LENGTH: 27 base pairs
              (B) TYPE: nucleic acid
              (C) STRANDEDNESS: single
              (D) TOPOLOGY: linear (ii) MOLECULE TYPE: DNA (ix) FEATURE:
              (D) OTHER INFORMATION: oligonucleotide primer (xi) SEQUENCE DESCRIPTION: SEQ ID NO:1158:

```
GTGTCTGTCC TCACTGTGAA TGATCCC                                                  27

(2) INFORMATION FOR SEQ ID NO:1159:

(i) SEQUENCE CHARACTERISTICS:
           (A) LENGTH: 25 base pairs
           (B) TYPE: nucleic acid
           (C) STRANDEDNESS: single
           (D) TOPOLOGY: linear (ii) MOLECULE TYPE: DNA (ix) FEATURE:
           (D) OTHER INFORMATION: oligonucleotide primer (xi) SEQUENCE DESCRIPTION: SEQ ID NO:1159:

GGGAGATGTT CTCACACCTA CGGCG                                                    25

(2) INFORMATION FOR SEQ ID NO:1160:

(i) SEQUENCE CHARACTERISTICS:
           (A) LENGTH: 26 base pairs
           (B) TYPE: nucleic acid
           (C) STRANDEDNESS: single
           (D) TOPOLOGY: linear (ii) MOLECULE TYPE: DNA (ix) FEATURE:
           (D) OTHER INFORMATION: oligonucleotide primer (xi) SEQUENCE DESCRIPTION: SEQ ID NO:1160:

ACGGCCTTGT TGTAGCCTTT GCTCAG                                                   26

(2) INFORMATION FOR SEQ ID NO:1161:

(i) SEQUENCE CHARACTERISTICS:
           (A) LENGTH: 26 base pairs
           (B) TYPE: nucleic acid
           (C) STRANDEDNESS: single
           (D) TOPOLOGY: linear (ii) MOLECULE TYPE: DNA (ix) FEATURE:
           (D) OTHER INFORMATION: oligonucleotide primer (xi) SEQUENCE DESCRIPTION: SEQ ID NO:1161:

ATGTACCCTG GCATTGCCGA CCGAAT                                                   26

(2) INFORMATION FOR SEQ ID NO:1162:

(i) SEQUENCE CHARACTERISTICS:
           (A) LENGTH: 28 base pairs
           (B) TYPE: nucleic acid
           (C) STRANDEDNESS: single
           (D) TOPOLOGY: linear (ii) MOLECULE TYPE: DNA (ix) FEATURE:
           (D) OTHER INFORMATION: oligonucleotide primer (xi) SEQUENCE DESCRIPTION: SEQ ID NO:1162:

TAACGAGTCA GAGCTTTGGC TAGGAATG                                                 28

(2) INFORMATION FOR SEQ ID NO:1163:

(i) SEQUENCE CHARACTERISTICS:
           (A) LENGTH: 23 base pairs
```

(B) TYPE: nucleic acid
            (C) STRANDEDNESS: single
            (D) TOPOLOGY: linear (ii) MOLECULE TYPE: DNA (ix) FEATURE:
            (D) OTHER INFORMATION: oligonucleotide primer (xi) SEQUENCE DESCRIPTION: SEQ ID NO:1163:

GAGAAGCGTC GCATCCGGCG GGA                                               23

(2) INFORMATION FOR SEQ ID NO:1164:

(i) SEQUENCE CHARACTERISTICS:
            (A) LENGTH: 23 base pairs
            (B) TYPE: nucleic acid
            (C) STRANDEDNESS: single
            (D) TOPOLOGY: linear (ii) MOLECULE TYPE: DNA (ix) FEATURE:
            (D) OTHER INFORMATION: oligonucleotide primer (xi) SEQUENCE DESCRIPTION: SEQ ID NO:1164:

ACTACAGCGC CCACCGAGCC ACC                                               23

(2) INFORMATION FOR SEQ ID NO:1165:

(i) SEQUENCE CHARACTERISTICS:
            (A) LENGTH: 24 base pairs
            (B) TYPE: nucleic acid
            (C) STRANDEDNESS: single
            (D) TOPOLOGY: linear (ii) MOLECULE TYPE: DNA (ix) FEATURE:
            (D) OTHER INFORMATION: oligonucleotide primer (xi) SEQUENCE DESCRIPTION: SEQ ID NO:1165:

CCCTGCCGCC CTGTACCTTG TATC                                              24

(2) INFORMATION FOR SEQ ID NO:1166:

(i) SEQUENCE CHARACTERISTICS:
            (A) LENGTH: 26 base pairs
            (B) TYPE: nucleic acid
            (C) STRANDEDNESS: single
            (D) TOPOLOGY: linear (ii) MOLECULE TYPE: DNA (ix) FEATURE:
            (D) OTHER INFORMATION: oligonucleotide primer (xi) SEQUENCE DESCRIPTION: SEQ ID NO:1166:

AGACATTGGC TAGGGTGGCA TCTGCA                                            26

(2) INFORMATION FOR SEQ ID NO:1167:

(i) SEQUENCE CHARACTERISTICS:
            (A) LENGTH: 25 base pairs
            (B) TYPE: nucleic acid
            (C) STRANDEDNESS: single
            (D) TOPOLOGY: linear (ii) MOLECULE TYPE: DNA (ix) FEATURE:
            (D) OTHER INFORMATION: oligonucleotide primer (xi) SEQUENCE DESCRIPTION: SEQ ID NO:1167:

CTACAGCGCG GAGCTGTCTA GTGAG                                         25

(2) INFORMATION FOR SEQ ID NO:1168:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: DNA (ix) FEATURE:
        (D) OTHER INFORMATION: oligonucleotide primer (xi) SEQUENCE DESCRIPTION: SEQ ID NO:1168:

GCTGTTACAG GGCCTCGAAC TCGTC                                         25

(2) INFORMATION FOR SEQ ID NO:1169:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: DNA (ix) FEATURE:
        (D) OTHER INFORMATION: oligonucleotide primer (xi) SEQUENCE DESCRIPTION: SEQ ID NO:1169:

ACGAGGAGCG GCAGGACGAG CATG                                          24

(2) INFORMATION FOR SEQ ID NO:1170:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: DNA (ix) FEATURE:
        (D) OTHER INFORMATION: oligonucleotide primer (xi) SEQUENCE DESCRIPTION: SEQ ID NO:1170:

CGGGCTAAGG CTTTACTTGG CGGCA                                         25

(2) INFORMATION FOR SEQ ID NO:1171:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: DNA (ix) FEATURE:
        (D) OTHER INFORMATION: oligonucleotide primer (xi) SEQUENCE DESCRIPTION: SEQ ID NO:1171:

ACCTTCGAGA ACCTCATACC CATTCTGA                                      28

(2) INFORMATION FOR SEQ ID NO:1172:

(i) SEQUENCE CHARACTERISTICS:
    (A) LENGTH: 26 base pairs
    (B) TYPE: nucleic acid
    (C) STRANDEDNESS: single
    (D) TOPOLOGY: linear (ii) MOLECULE TYPE: DNA (ix) FEATURE:
    (D) OTHER INFORMATION: oligonucleotide primer (xi) SEQUENCE DESCRIPTION: SEQ ID NO:1172:

GGGATTTAAG GGCTGGATTA GTGCCC                                          26

(2) INFORMATION FOR SEQ ID NO:1173:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: DNA (ix) FEATURE:
        (D) OTHER INFORMATION: oligonucleotide primer (xi) SEQUENCE DESCRIPTION: SEQ ID NO:1173:

AGGAAATGGC TCGTCACCTT CGTGAATA                                        28

(2) INFORMATION FOR SEQ ID NO:1174:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: DNA (ix) FEATURE:
        (D) OTHER INFORMATION: oligonucleotide primer (xi) SEQUENCE DESCRIPTION: SEQ ID NO:1174:

GGAGTGTCGG TTGTTAAGAA CTAGAGCT                                        28

(2) INFORMATION FOR SEQ ID NO:1175:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: DNA (ix) FEATURE:
        (D) OTHER INFORMATION: oligonucleotide primer (xi) SEQUENCE DESCRIPTION: SEQ ID NO:1175:

GGGCTGGTCA CCACCACGCC GAC                                             23

(2) INFORMATION FOR SEQ ID NO:1176:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: DNA (ix) FEATURE:
          (D) OTHER INFORMATION: oligonucleotide primer (xi) SEQUENCE DESCRIPTION: SEQ ID NO:1176:

CCCGCGTAGC TGCTCAGGTT CGC                                                   23

(2) INFORMATION FOR SEQ ID NO:1177:

(i) SEQUENCE CHARACTERISTICS:
          (A) LENGTH: 24 base pairs
          (B) TYPE: nucleic acid
          (C) STRANDEDNESS: single
          (D) TOPOLOGY: linear (ii) MOLECULE TYPE: DNA (ix) FEATURE:
          (D) OTHER INFORMATION: oligonucleotide primer (xi) SEQUENCE DESCRIPTION: SEQ ID NO:1177:

TGCGTGAGCT GCGACGGCAA GGTG                                                  24

(2) INFORMATION FOR SEQ ID NO:1178:

(i) SEQUENCE CHARACTERISTICS:
          (A) LENGTH: 26 base pairs
          (B) TYPE: nucleic acid
          (C) STRANDEDNESS: single
          (D) TOPOLOGY: linear (ii) MOLECULE TYPE: DNA (ix) FEATURE:
          (D) OTHER INFORMATION: oligonucleotide primer (xi) SEQUENCE DESCRIPTION: SEQ ID NO:1178:

GGTTGCTATG CCGCAGTTGC GTCATG                                                26

(2) INFORMATION FOR SEQ ID NO:1179:

(i) SEQUENCE CHARACTERISTICS:
          (A) LENGTH: 26 base pairs
          (B) TYPE: nucleic acid
          (C) STRANDEDNESS: single
          (D) TOPOLOGY: linear (ii) MOLECULE TYPE: DNA (ix) FEATURE:
          (D) OTHER INFORMATION: oligonucleotide primer (xi) SEQUENCE DESCRIPTION: SEQ ID NO:1179:

ATCTGGTCTG TGGGCTGCAT TCTGGC                                                26

(2) INFORMATION FOR SEQ ID NO:1180:

(i) SEQUENCE CHARACTERISTICS:
          (A) LENGTH: 26 base pairs
          (B) TYPE: nucleic acid
          (C) STRANDEDNESS: single
          (D) TOPOLOGY: linear (ii) MOLECULE TYPE: DNA (ix) FEATURE:
          (D) OTHER INFORMATION: oligonucleotide primer (xi) SEQUENCE DESCRIPTION: SEQ ID NO:1180:

CTGGCTCATC CGTCGGGTCA TAGTAC                                                26

(2) INFORMATION FOR SEQ ID NO:1181:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: DNA (ix) FEATURE:
        (D) OTHER INFORMATION: oligonucleotide primer (xi) SEQUENCE DESCRIPTION: SEQ ID NO:1181:

TGCTGAGATT GATTCTGATG ACACCGGA                          28

(2) INFORMATION FOR SEQ ID NO:1182:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: DNA (ix) FEATURE:
        (D) OTHER INFORMATION: oligonucleotide primer (xi) SEQUENCE DESCRIPTION: SEQ ID NO:1182:

GCGATCTACT TCTTGCTGAT AGCGTTTG                          28

(2) INFORMATION FOR SEQ ID NO:1183:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: DNA (ix) FEATURE:
        (D) OTHER INFORMATION: oligonucleotide primer (xi) SEQUENCE DESCRIPTION: SEQ ID NO:1183:

ACTCAGAACC AGAAACTTCA GCGACAGT                          28

(2) INFORMATION FOR SEQ ID NO:1184:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: DNA (ix) FEATURE:
        (D) OTHER INFORMATION: oligonucleotide primer (xi) SEQUENCE DESCRIPTION: SEQ ID NO:1184:

CAGATACTGT GATGGCATGA GGGACATG                          28

(2) INFORMATION FOR SEQ ID NO:1185:

(i) SEQUENCE CHARACTERISTICS:
        (A) LENGTH: 28 base pairs
        (B) TYPE: nucleic acid
        (C) STRANDEDNESS: single
        (D) TOPOLOGY: linear -continued (ii) MOLECULE TYPE: DNA (ix) FEATURE:
             (D) OTHER INFORMATION: oligonucleotide primer (xi) SEQUENCE DESCRIPTION: SEQ ID NO:1185:

TACATGGAGA CAGACTTGGC TAATGTGC                                              28

(2) INFORMATION FOR SEQ ID NO:1186:

(i) SEQUENCE CHARACTERISTICS:
             (A) LENGTH: 28 base pairs
             (B) TYPE: nucleic acid
             (C) STRANDEDNESS: single
             (D) TOPOLOGY: linear (ii) MOLECULE TYPE: DNA (ix) FEATURE:
             (D) OTHER INFORMATION: oligonucleotide primer (xi) SEQUENCE DESCRIPTION: SEQ ID NO:1186:

ATTACGCTGA GAAGCTCCTG ACGATCTT                                              28

(2) INFORMATION FOR SEQ ID NO:1187:

(i) SEQUENCE CHARACTERISTICS:
             (A) LENGTH: 25 base pairs
             (B) TYPE: nucleic acid
             (C) STRANDEDNESS: single
             (D) TOPOLOGY: linear (ii) MOLECULE TYPE: DNA (ix) FEATURE:
             (D) OTHER INFORMATION: oligonucleotide primer (xi) SEQUENCE DESCRIPTION: SEQ ID NO:1187:

CTGCCCTTTG GGCGACTGAA CTACC                                                 25

(2) INFORMATION FOR SEQ ID NO:1188:

(i) SEQUENCE CHARACTERISTICS:
             (A) LENGTH: 28 base pairs
             (B) TYPE: nucleic acid
             (C) STRANDEDNESS: single
             (D) TOPOLOGY: linear (ii) MOLECULE TYPE: DNA (ix) FEATURE:
             (D) OTHER INFORMATION: oligonucleotide primer (xi) SEQUENCE DESCRIPTION: SEQ ID NO:1188:

GCTACTATGT CCTTGTGACT GTACTTGC                                              28

(2) INFORMATION FOR SEQ ID NO:1189:

(i) SEQUENCE CHARACTERISTICS:
             (A) LENGTH: 26 base pairs
             (B) TYPE: nucleic acid
             (C) STRANDEDNESS: single
             (D) TOPOLOGY: linear (ii) MOLECULE TYPE: DNA (ix) FEATURE:
             (D) OTHER INFORMATION: oligonucleotide primer (xi) SEQUENCE DESCRIPTION: SEQ ID NO:1189:

GGGTCCTCTG TGAACTTGCT CAGGAC                                                26

(2) INFORMATION FOR SEQ ID NO:1190:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: DNA (ix) FEATURE:
        (D) OTHER INFORMATION: oligonucleotide primer (xi) SEQUENCE DESCRIPTION: SEQ ID NO:1190:

CTGGATAGTC AGCACCAGGG TGGTG                                      25

(2) INFORMATION FOR SEQ ID NO:1191:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: DNA (ix) FEATURE:
        (D) OTHER INFORMATION: oligonucleotide primer (xi) SEQUENCE DESCRIPTION: SEQ ID NO:1191:

CCCGAGATAG TGCTGGAACA CTGCTG                                   26

(2) INFORMATION FOR SEQ ID NO:1192:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: DNA (ix) FEATURE:
        (D) OTHER INFORMATION: oligonucleotide primer (xi) SEQUENCE DESCRIPTION: SEQ ID NO:1192:

GAGCACACCT GCTCCTCGGA ATCTATT                                27

(2) INFORMATION FOR SEQ ID NO:1193:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: DNA (ix) FEATURE:
        (D) OTHER INFORMATION: oligonucleotide primer (xi) SEQUENCE DESCRIPTION: SEQ ID NO:1193:

ACGATCAGGG TTGCCCTCGG TGTAAG                                   26

(2) INFORMATION FOR SEQ ID NO:1194:

(i) SEQUENCE CHARACTERISTICS:
        (A) LENGTH: 28 base pairs
        (B) TYPE: nucleic acid
        (C) STRANDEDNESS: single (D) TOPOLOGY: linear (ii) MOLECULE TYPE: DNA (ix) FEATURE:
        (D) OTHER INFORMATION: oligonucleotide primer (xi) SEQUENCE DESCRIPTION: SEQ ID NO:1194:

CAGTGGGATC TTCAAAGAGT TGTACCCT                                                28

(2) INFORMATION FOR SEQ ID NO:1195:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: DNA (ix) FEATURE:
        (D) OTHER INFORMATION: oligonucleotide primer (xi) SEQUENCE DESCRIPTION: SEQ ID NO:1195:

AAGAAGTCAA CAGGCCCAAG ATACCTCA                                                28

(2) INFORMATION FOR SEQ ID NO:1196:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: DNA (ix) FEATURE:
        (D) OTHER INFORMATION: oligonucleotide primer (xi) SEQUENCE DESCRIPTION: SEQ ID NO:1196:

CTTGTAAATT CCGTTCCTTG CATTGAGAGG                                              30

(2) INFORMATION FOR SEQ ID NO:1197:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: DNA (ix) FEATURE:
        (D) OTHER INFORMATION: oligonucleotide primer (xi) SEQUENCE DESCRIPTION: SEQ ID NO:1197:

AATGATGCTT GGCTCTGGAA TGCCAGAA                                                28

(2) INFORMATION FOR SEQ ID NO:1198:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: DNA (ix) FEATURE:
        (D) OTHER INFORMATION: oligonucleotide primer (xi) SEQUENCE DESCRIPTION: SEQ ID NO:1198:

```
GCTGAGAGTT ATTAACAGTG CAGTGTGG                                              28

(2) INFORMATION FOR SEQ ID NO:1199:

(i) SEQUENCE CHARACTERISTICS:
         (A) LENGTH: 25 base pairs
         (B) TYPE: nucleic acid
         (C) STRANDEDNESS: single
         (D) TOPOLOGY: linear (ii) MOLECULE TYPE: DNA (ix) FEATURE:
         (D) OTHER INFORMATION: oligonucleotide primer (xi) SEQUENCE DESCRIPTION: SEQ ID NO:1199:

CTAGCTGTGG CAGGAGCCAC TTCTC                                                 25

(2) INFORMATION FOR SEQ ID NO:1200:

(i) SEQUENCE CHARACTERISTICS:
         (A) LENGTH: 27 base pairs
         (B) TYPE: nucleic acid
         (C) STRANDEDNESS: single
         (D) TOPOLOGY: linear (ii) MOLECULE TYPE: DNA (ix) FEATURE:
         (D) OTHER INFORMATION: oligonucleotide primer (xi) SEQUENCE DESCRIPTION: SEQ ID NO:1200:

GCCGACGAGA CAGTAGAGGT AATAGAG                                               27

(2) INFORMATION FOR SEQ ID NO:1201:

(i) SEQUENCE CHARACTERISTICS:
         (A) LENGTH: 24 base pairs
         (B) TYPE: nucleic acid
         (C) STRANDEDNESS: single
         (D) TOPOLOGY: linear (ii) MOLECULE TYPE: DNA (ix) FEATURE:
         (D) OTHER INFORMATION: oligonucleotide primer (xi) SEQUENCE DESCRIPTION: SEQ ID NO:1201:

CCCGAAGTCA TCCTGGGTAT GGGC                                                  24

(2) INFORMATION FOR SEQ ID NO:1202:

(i) SEQUENCE CHARACTERISTICS:
         (A) LENGTH: 26 base pairs
         (B) TYPE: nucleic acid
         (C) STRANDEDNESS: single
         (D) TOPOLOGY: linear (ii) MOLECULE TYPE: DNA (ix) FEATURE:
         (D) OTHER INFORMATION: oligonucleotide primer (xi) SEQUENCE DESCRIPTION: SEQ ID NO:1202:

TCGTCTACAG AGATCCGCTT GTCAGG                                                26

(2) INFORMATION FOR SEQ ID NO:1203:

(i) SEQUENCE CHARACTERISTICS:
         (A) LENGTH: 28 base pairs
```

(B) TYPE: nucleic acid
        (C) STRANDEDNESS: single
        (D) TOPOLOGY: linear (ii) MOLECULE TYPE: DNA (ix) FEATURE:
        (D) OTHER INFORMATION: oligonucleotide primer (xi) SEQUENCE DESCRIPTION: SEQ ID NO:1203:

GATATGGCTC CTGGGCAGAG TTATCAAC                                          28

(2) INFORMATION FOR SEQ ID NO:1204:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: DNA (ix) FEATURE:
        (D) OTHER INFORMATION: oligonucleotide primer (xi) SEQUENCE DESCRIPTION: SEQ ID NO:1204:

GTATCATTAA CCTTTATGAG CCGGTCCC                                          28

(2) INFORMATION FOR SEQ ID NO:1205:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: DNA (ix) FEATURE:
        (D) OTHER INFORMATION: oligonucleotide primer (xi) SEQUENCE DESCRIPTION: SEQ ID NO:1205:

TGGAGAACCT GGATGGCCTT AGGGTT                                            26

(2) INFORMATION FOR SEQ ID NO:1206:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: DNA (ix) FEATURE:
        (D) OTHER INFORMATION: oligonucleotide primer (xi) SEQUENCE DESCRIPTION: SEQ ID NO:1206:

CAGGACACCA AAGATCAAGG TGCTTCAT                                          28

(2) INFORMATION FOR SEQ ID NO:1207:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: DNA (ix) FEATURE:
        (D) OTHER INFORMATION: oligonucleotide primer (xi) SEQUENCE DESCRIPTION: SEQ ID NO:1207:

AATGACAACC TTCTGGTTGG TAGGGACA                                              28

(2) INFORMATION FOR SEQ ID NO:1208:

(i) SEQUENCE CHARACTERISTICS:
            (A) LENGTH: 32 base pairs
            (B) TYPE: nucleic acid
            (C) STRANDEDNESS: single
            (D) TOPOLOGY: linear (ii) MOLECULE TYPE: DNA (ix) FEATURE:
            (D) OTHER INFORMATION: oligonucleotide primer (xi) SEQUENCE DESCRIPTION: SEQ ID NO:1208:

CCTTGTTGTT GATAGGATGT TTGCTTGAAG TT                                         32

(2) INFORMATION FOR SEQ ID NO:1209:

(i) SEQUENCE CHARACTERISTICS:
            (A) LENGTH: 26 base pairs
            (B) TYPE: nucleic acid
            (C) STRANDEDNESS: single
            (D) TOPOLOGY: linear (ii) MOLECULE TYPE: DNA (ix) FEATURE:
            (D) OTHER INFORMATION: oligonucleotide primer (xi) SEQUENCE DESCRIPTION: SEQ ID NO:1209:

CACAAGACCT CTGACAGCAC GTTCCT                                                26

(2) INFORMATION FOR SEQ ID NO:1210:

(i) SEQUENCE CHARACTERISTICS:
            (A) LENGTH: 28 base pairs
            (B) TYPE: nucleic acid
            (C) STRANDEDNESS: single
            (D) TOPOLOGY: linear (ii) MOLECULE TYPE: DNA (ix) FEATURE:
            (D) OTHER INFORMATION: oligonucleotide primer (xi) SEQUENCE DESCRIPTION: SEQ ID NO:1210:

CGCTCTACCA TCTGGCTGCT CAAATGAA                                              28

(2) INFORMATION FOR SEQ ID NO:1211:

(i) SEQUENCE CHARACTERISTICS:
            (A) LENGTH: 28 base pairs
            (B) TYPE: nucleic acid
            (C) STRANDEDNESS: single
            (D) TOPOLOGY: linear (ii) MOLECULE TYPE: DNA (ix) FEATURE:
            (D) OTHER INFORMATION: oligonucleotide primer (xi) SEQUENCE DESCRIPTION: SEQ ID NO:1211:

ATCCAGTACC ATCACTGAGA GCCTCATG                                              28

(2) INFORMATION FOR SEQ ID NO:1212:

```
        (i) SEQUENCE CHARACTERISTICS:
            (A) LENGTH: 28 base pairs
            (B) TYPE: nucleic acid
            (C) STRANDEDNESS: single
            (D) TOPOLOGY: linear (ii) MOLECULE TYPE: DNA (ix) FEATURE:
            (D) OTHER INFORMATION: oligonucleotide primer (xi) SEQUENCE DESCRIPTION: SEQ ID NO:1212:

AGAACTGGCA CCTTTGGGAT CTCACAAA                                          28

(2) INFORMATION FOR SEQ ID NO:1213:

(i) SEQUENCE CHARACTERISTICS:
            (A) LENGTH: 26 base pairs
            (B) TYPE: nucleic acid
            (C) STRANDEDNESS: single
            (D) TOPOLOGY: linear (ii) MOLECULE TYPE: DNA (ix) FEATURE:
            (D) OTHER INFORMATION: oligonucleotide primer (xi) SEQUENCE DESCRIPTION: SEQ ID NO:1213:

ACCTCGCTCG CAGACACCAC AAGATA                                            26

(2) INFORMATION FOR SEQ ID NO:1214:

(i) SEQUENCE CHARACTERISTICS:
            (A) LENGTH: 28 base pairs
            (B) TYPE: nucleic acid
            (C) STRANDEDNESS: single
            (D) TOPOLOGY: linear (ii) MOLECULE TYPE: DNA (ix) FEATURE:
            (D) OTHER INFORMATION: oligonucleotide primer (xi) SEQUENCE DESCRIPTION: SEQ ID NO:1214:

TTGTCAGACG CCTTCCAATA TAGATCCC                                          28

(2) INFORMATION FOR SEQ ID NO:1215:

(i) SEQUENCE CHARACTERISTICS:
            (A) LENGTH: 26 base pairs
            (B) TYPE: nucleic acid
            (C) STRANDEDNESS: single
            (D) TOPOLOGY: linear (ii) MOLECULE TYPE: DNA (ix) FEATURE:
            (D) OTHER INFORMATION: oligonucleotide primer (xi) SEQUENCE DESCRIPTION: SEQ ID NO:1215:

TCACCGGGAA ACTGTGAACG GCTCAT                                            26

(2) INFORMATION FOR SEQ ID NO:1216:

(i) SEQUENCE CHARACTERISTICS:
            (A) LENGTH: 26 base pairs
            (B) TYPE: nucleic acid
            (C) STRANDEDNESS: single
            (D) TOPOLOGY: linear (ii) MOLECULE TYPE: DNA
```

(ix) FEATURE:
            (D) OTHER INFORMATION: oligonucleotide primer (xi) SEQUENCE DESCRIPTION: SEQ ID NO:1216:

GGGATTACAG GTGTGAGTAA CCACGC                                           26

(2) INFORMATION FOR SEQ ID NO:1217:

(i) SEQUENCE CHARACTERISTICS:
            (A) LENGTH: 26 base pairs
            (B) TYPE: nucleic acid
            (C) STRANDEDNESS: single
            (D) TOPOLOGY: linear (ii) MOLECULE TYPE: DNA (ix) FEATURE:
            (D) OTHER INFORMATION: oligonucleotide primer (xi) SEQUENCE DESCRIPTION: SEQ ID NO:1217:

CAGACCAGAG CTGTCTGAAC TCACGT                                           26

(2) INFORMATION FOR SEQ ID NO:1218:

(i) SEQUENCE CHARACTERISTICS:
            (A) LENGTH: 28 base pairs
            (B) TYPE: nucleic acid
            (C) STRANDEDNESS: single
            (D) TOPOLOGY: linear (ii) MOLECULE TYPE: DNA (ix) FEATURE:
            (D) OTHER INFORMATION: oligonucleotide primer (xi) SEQUENCE DESCRIPTION: SEQ ID NO:1218:

GGATTCCTAG TGGTGTTGAT AGTCCTTC                                         28

(2) INFORMATION FOR SEQ ID NO:1219:

(i) SEQUENCE CHARACTERISTICS:
            (A) LENGTH: 26 base pairs
            (B) TYPE: nucleic acid
            (C) STRANDEDNESS: single
            (D) TOPOLOGY: linear (ii) MOLECULE TYPE: DNA (ix) FEATURE:
            (D) OTHER INFORMATION: oligonucleotide primer (xi) SEQUENCE DESCRIPTION: SEQ ID NO:1219:

CTGCCTCAGT CTGAAGGACA AACCCA                                           26

(2) INFORMATION FOR SEQ ID NO:1220:

(i) SEQUENCE CHARACTERISTICS:
            (A) LENGTH: 29 base pairs
            (B) TYPE: nucleic acid
            (C) STRANDEDNESS: single
            (D) TOPOLOGY: linear (ii) MOLECULE TYPE: DNA (ix) FEATURE:
            (D) OTHER INFORMATION: oligonucleotide primer (xi) SEQUENCE DESCRIPTION: SEQ ID NO:1220:

CTTTGGCCCT TGGAGTTTCA AATGATTGC                                        29

(2) INFORMATION FOR SEQ ID NO:1221:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: DNA (ix) FEATURE:
        (D) OTHER INFORMATION: oligonucleotide primer (xi) SEQUENCE DESCRIPTION: SEQ ID NO:1221:

TCCACCAGGC AGAAGATGAC AGACTG                                    26

(2) INFORMATION FOR SEQ ID NO:1222:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: DNA (ix) FEATURE:
        (D) OTHER INFORMATION: oligonucleotide primer (xi) SEQUENCE DESCRIPTION: SEQ ID NO:1222:

TGAATAGTGT TCTGGCAGTG TCTACGGA                                28

(2) INFORMATION FOR SEQ ID NO:1223:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: DNA (ix) FEATURE:
        (D) OTHER INFORMATION: oligonucleotide primer (xi) SEQUENCE DESCRIPTION: SEQ ID NO:1223:

CTTCCCAGCG GACTCCGAGC ACAA                                      24

(2) INFORMATION FOR SEQ ID NO:1224:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: DNA (ix) FEATURE:
        (D) OTHER INFORMATION: oligonucleotide primer (xi) SEQUENCE DESCRIPTION: SEQ ID NO:1224:

TGTCAGATGC CAGGGTCTGG TCGG                                      24

(2) INFORMATION FOR SEQ ID NO:1225:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: DNA (ix) FEATURE:
             (D) OTHER INFORMATION: oligonucleotide primer (xi) SEQUENCE DESCRIPTION: SEQ ID NO:1225:

TGTTACCACA CCCAGGGCTA TGAGGA                                              26

(2) INFORMATION FOR SEQ ID NO:1226:

(i) SEQUENCE CHARACTERISTICS:
             (A) LENGTH: 27 base pairs
             (B) TYPE: nucleic acid
             (C) STRANDEDNESS: single
             (D) TOPOLOGY: linear (ii) MOLECULE TYPE: DNA (ix) FEATURE:
             (D) OTHER INFORMATION: oligonucleotide primer (xi) SEQUENCE DESCRIPTION: SEQ ID NO:1226:

GAAGATGTGA GGGCAGGATA GGTGAGA                                             27

(2) INFORMATION FOR SEQ ID NO:1227:

(i) SEQUENCE CHARACTERISTICS:
             (A) LENGTH: 29 base pairs
             (B) TYPE: nucleic acid
             (C) STRANDEDNESS: single
             (D) TOPOLOGY: linear (ii) MOLECULE TYPE: DNA (ix) FEATURE:
             (D) OTHER INFORMATION: oligonucleotide primer (xi) SEQUENCE DESCRIPTION: SEQ ID NO:1227:

TCAAGCCAGT TACCCTCATC TACTTGAAC                                           29

(2) INFORMATION FOR SEQ ID NO:1228:

(i) SEQUENCE CHARACTERISTICS:
             (A) LENGTH: 31 base pairs
             (B) TYPE: nucleic acid
             (C) STRANDEDNESS: single
             (D) TOPOLOGY: linear (ii) MOLECULE TYPE: DNA (ix) FEATURE:
             (D) OTHER INFORMATION: oligonucleotide primer (xi) SEQUENCE DESCRIPTION: SEQ ID NO:1228:

GTAGACTATC CAGGATTGGA ATTACACAAG T                                        31

(2) INFORMATION FOR SEQ ID NO:1229:

(i) SEQUENCE CHARACTERISTICS:
             (A) LENGTH: 27 base pairs
             (B) TYPE: nucleic acid
             (C) STRANDEDNESS: single
             (D) TOPOLOGY: linear (ii) MOLECULE TYPE: DNA (ix) FEATURE:
             (D) OTHER INFORMATION: oligonucleotide primer (xi) SEQUENCE DESCRIPTION: SEQ ID NO:1229:

ATCTGGTAGT ATGCCAGGAA TGTGCCC                                             27

(2) INFORMATION FOR SEQ ID NO:1230:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: DNA (ix) FEATURE:
        (D) OTHER INFORMATION: oligonucleotide primer (xi) SEQUENCE DESCRIPTION: SEQ ID NO:1230:

GCATAACAAG CAGGACGCTA CTCCCT                                  26

(2) INFORMATION FOR SEQ ID NO:1231:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: DNA (ix) FEATURE:
        (D) OTHER INFORMATION: oligonucleotide primer (xi) SEQUENCE DESCRIPTION: SEQ ID NO:1231:

GGCAATATGG AGACTCAGCA GTTGGAAG                                28

(2) INFORMATION FOR SEQ ID NO:1232:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: DNA (ix) FEATURE:
        (D) OTHER INFORMATION: oligonucleotide primer (xi) SEQUENCE DESCRIPTION: SEQ ID NO:1232:

TAGTAGAGTC CAGCACTTGC TAACTCTC                                28

(2) INFORMATION FOR SEQ ID NO:1233:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: DNA (ix) FEATURE:
        (D) OTHER INFORMATION: oligonucleotide primer (xi) SEQUENCE DESCRIPTION: SEQ ID NO:1233:

AGCTGGACGC CATATCTAGT TTGCCC                                  26

(2) INFORMATION FOR SEQ ID NO:1234:

(i) SEQUENCE CHARACTERISTICS:
        (A) LENGTH: 25 base pairs
        (B) TYPE: nucleic acid
        (C) STRANDEDNESS: single (D) TOPOLOGY: linear (ii) MOLECULE TYPE: DNA (ix) FEATURE:
        (D) OTHER INFORMATION: oligonucleotide primer (xi) SEQUENCE DESCRIPTION: SEQ ID NO:1234:

GGTGCAAGAT AAGGCAGGGT GAGGG                                      25

(2) INFORMATION FOR SEQ ID NO:1235:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: DNA (ix) FEATURE:
        (D) OTHER INFORMATION: oligonucleotide primer (xi) SEQUENCE DESCRIPTION: SEQ ID NO:1235:

GAGCTGAAGC AGATGCAGGA CAAGTAC                                    27

(2) INFORMATION FOR SEQ ID NO:1236:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: DNA (ix) FEATURE:
        (D) OTHER INFORMATION: oligonucleotide primer (xi) SEQUENCE DESCRIPTION: SEQ ID NO:1236:

GACCAGTTCA CCATTCCTCA AGTGCAAG                                   28

(2) INFORMATION FOR SEQ ID NO:1237:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: DNA (ix) FEATURE:
        (D) OTHER INFORMATION: oligonucleotide primer (xi) SEQUENCE DESCRIPTION: SEQ ID NO:1237:

TCTATGAGCT GACATCTCAG TTCACTGG                                   28

(2) INFORMATION FOR SEQ ID NO:1238:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: DNA (ix) FEATURE:
        (D) OTHER INFORMATION: oligonucleotide primer (xi) SEQUENCE DESCRIPTION: SEQ ID NO:1238:

CAAAGTGACT GGATGTACCA GGTTCCCT                                                    28

(2) INFORMATION FOR SEQ ID NO:1239:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: DNA (ix) FEATURE:
        (D) OTHER INFORMATION: oligonucleotide primer (xi) SEQUENCE DESCRIPTION: SEQ ID NO:1239:

AATTTGGTCT ATGCCAGGCC CATTTCCT                                                    28

(2) INFORMATION FOR SEQ ID NO:1240:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: DNA (ix) FEATURE:
        (D) OTHER INFORMATION: oligonucleotide primer (xi) SEQUENCE DESCRIPTION: SEQ ID NO:1240:

CAGTTGTGTC ATCTTGGCTC ACCACAG                                                     27

(2) INFORMATION FOR SEQ ID NO:1241:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: DNA (ix) FEATURE:
        (D) OTHER INFORMATION: oligonucleotide primer (xi) SEQUENCE DESCRIPTION: SEQ ID NO:1241:

TCTATGAGCT GACATCTCAG TTCACTGG                                                    28

(2) INFORMATION FOR SEQ ID NO:1242:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: DNA (ix) FEATURE:
        (D) OTHER INFORMATION: oligonucleotide primer (xi) SEQUENCE DESCRIPTION: SEQ ID NO:1242:

CAAAGTGACT GGATGTACCA GGTTCCCT                                                    28

(2) INFORMATION FOR SEQ ID NO:1243:

(i) SEQUENCE CHARACTERISTICS:
        (A) LENGTH: 26 base pairs

```
        (B) TYPE: nucleic acid
        (C) STRANDEDNESS: single
        (D) TOPOLOGY: linear (ii) MOLECULE TYPE: DNA (ix) FEATURE:
        (D) OTHER INFORMATION: oligonucleotide primer (xi) SEQUENCE DESCRIPTION: SEQ ID NO:1243:

TGAAAGACCA GAGCAGGAAC AAGGGC                                              26

(2) INFORMATION FOR SEQ ID NO:1244:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: DNA (ix) FEATURE:
        (D) OTHER INFORMATION: oligonucleotide primer (xi) SEQUENCE DESCRIPTION: SEQ ID NO:1244:

ACTGTGTAGC TGCTGTGGTC ATCAGG                                              26

(2) INFORMATION FOR SEQ ID NO:1245:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: DNA (ix) FEATURE:
        (D) OTHER INFORMATION: oligonucleotide primer (xi) SEQUENCE DESCRIPTION: SEQ ID NO:1245:

TTTAGCCCAG ATAGTCGCCA TGTCCTC                                             27

(2) INFORMATION FOR SEQ ID NO:1246:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: DNA (ix) FEATURE:
        (D) OTHER INFORMATION: oligonucleotide primer (xi) SEQUENCE DESCRIPTION: SEQ ID NO:1246:

CTCCTGTGAT GATACTGCTA CACTGTTC                                            28

(2) INFORMATION FOR SEQ ID NO:1247:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: DNA (ix) FEATURE:
        (D) OTHER INFORMATION: oligonucleotide primer
```

(xi) SEQUENCE DESCRIPTION: SEQ ID NO:1247:

TGCAGCGTGG CCCGTGACAC GCA                                                    23

(2) INFORMATION FOR SEQ ID NO:1248:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: DNA (ix) FEATURE:
        (D) OTHER INFORMATION: oligonucleotide primer (xi) SEQUENCE DESCRIPTION: SEQ ID NO:1248:

ACCGCGATCT CAGCCAAACT CCGG                                                   24

(2) INFORMATION FOR SEQ ID NO:1249:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: DNA (ix) FEATURE:
        (D) OTHER INFORMATION: oligonucleotide primer (xi) SEQUENCE DESCRIPTION: SEQ ID NO:1249:

GCGCTACGCA GCGCCGGAGT TCG                                                    23

(2) INFORMATION FOR SEQ ID NO:1250:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: DNA (ix) FEATURE:
        (D) OTHER INFORMATION: oligonucleotide primer (xi) SEQUENCE DESCRIPTION: SEQ ID NO:1250:

GGTGGGATGA GGGTCGCAAG GTCC                                                   24

(2) INFORMATION FOR SEQ ID NO:1251:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: DNA (ix) FEATURE:
        (D) OTHER INFORMATION: oligonucleotide primer (xi) SEQUENCE DESCRIPTION: SEQ ID NO:1251:

AGTGGCCGTA GCAACAAGGT TGCACG                                                 26

(2) INFORMATION FOR SEQ ID NO:1252:

(i) SEQUENCE CHARACTERISTICS:
            (A) LENGTH: 27 base pairs
            (B) TYPE: nucleic acid
            (C) STRANDEDNESS: single
            (D) TOPOLOGY: linear (ii) MOLECULE TYPE: DNA (ix) FEATURE:
            (D) OTHER INFORMATION: oligonucleotide primer (xi) SEQUENCE DESCRIPTION: SEQ ID NO:1252:

GCTGTCACCT GGGAACATTC CATTGGT                                                27

(2) INFORMATION FOR SEQ ID NO:1253:

(i) SEQUENCE CHARACTERISTICS:
            (A) LENGTH: 27 base pairs
            (B) TYPE: nucleic acid
            (C) STRANDEDNESS: single
            (D) TOPOLOGY: linear (ii) MOLECULE TYPE: DNA (ix) FEATURE:
            (D) OTHER INFORMATION: oligonucleotide primer (xi) SEQUENCE DESCRIPTION: SEQ ID NO:1253:

CAGAAGCAAA TCCGACTCTG TAGGGAG                                                27

(2) INFORMATION FOR SEQ ID NO:1254:

(i) SEQUENCE CHARACTERISTICS:
            (A) LENGTH: 27 base pairs
            (B) TYPE: nucleic acid
            (C) STRANDEDNESS: single
            (D) TOPOLOGY: linear (ii) MOLECULE TYPE: DNA (ix) FEATURE:
            (D) OTHER INFORMATION: oligonucleotide primer (xi) SEQUENCE DESCRIPTION: SEQ ID NO:1254:

GACGGCCTTA GAACATAACC ACATCCC                                                27

(2) INFORMATION FOR SEQ ID NO:1255:

(i) SEQUENCE CHARACTERISTICS:
            (A) LENGTH: 28 base pairs
            (B) TYPE: nucleic acid
            (C) STRANDEDNESS: single
            (D) TOPOLOGY: linear (ii) MOLECULE TYPE: DNA (ix) FEATURE:
            (D) OTHER INFORMATION: oligonucleotide primer (xi) SEQUENCE DESCRIPTION: SEQ ID NO:1255:

GAGAGGCATT TAGCTGATCT CTTACCCC                                               28

(2) INFORMATION FOR SEQ ID NO:1256:

(i) SEQUENCE CHARACTERISTICS:
            (A) LENGTH: 28 base pairs
            (B) TYPE: nucleic acid
            (C) STRANDEDNESS: single
            (D) TOPOLOGY: linear (ii) MOLECULE TYPE: DNA

```
        (ix) FEATURE:
              (D) OTHER INFORMATION: oligonucleotide primer (xi) SEQUENCE DESCRIPTION: SEQ ID NO:1256:

CTAGCCGCTT TCCACCAACT CAGTCATT                                              28

(2) INFORMATION FOR SEQ ID NO:1257:

(i) SEQUENCE CHARACTERISTICS:
              (A) LENGTH: 26 base pairs
              (B) TYPE: nucleic acid
              (C) STRANDEDNESS: single
              (D) TOPOLOGY: linear (ii) MOLECULE TYPE: DNA (ix) FEATURE:
              (D) OTHER INFORMATION: oligonucleotide primer (xi) SEQUENCE DESCRIPTION: SEQ ID NO:1257:

GGACAGAGGA TTTCTGCTTA GGCCCC                                                26

(2) INFORMATION FOR SEQ ID NO:1258:

(i) SEQUENCE CHARACTERISTICS:
              (A) LENGTH: 27 base pairs
              (B) TYPE: nucleic acid
              (C) STRANDEDNESS: single
              (D) TOPOLOGY: linear (ii) MOLECULE TYPE: DNA (ix) FEATURE:
              (D) OTHER INFORMATION: oligonucleotide primer (xi) SEQUENCE DESCRIPTION: SEQ ID NO:1258:

GTCCCTTATT CAGGTGAGGG TCAATGG                                               27

(2) INFORMATION FOR SEQ ID NO:1259:

(i) SEQUENCE CHARACTERISTICS:
              (A) LENGTH: 27 base pairs
              (B) TYPE: nucleic acid
              (C) STRANDEDNESS: single
              (D) TOPOLOGY: linear (ii) MOLECULE TYPE: DNA (ix) FEATURE:
              (D) OTHER INFORMATION: oligonucleotide primer (xi) SEQUENCE DESCRIPTION: SEQ ID NO:1259:

TTTCCTGCCT GTAACACGGT TCATCCC                                               27

(2) INFORMATION FOR SEQ ID NO:1260:

(i) SEQUENCE CHARACTERISTICS:
              (A) LENGTH: 30 base pairs
              (B) TYPE: nucleic acid
              (C) STRANDEDNESS: single
              (D) TOPOLOGY: linear (ii) MOLECULE TYPE: DNA (ix) FEATURE:
              (D) OTHER INFORMATION: oligonucleotide primer (xi) SEQUENCE DESCRIPTION: SEQ ID NO:1260:

GGGAATACCA CTGACAGGTG CTCAATAATA                                            30
```

(2) INFORMATION FOR SEQ ID NO:1261:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: DNA (ix) FEATURE:
        (D) OTHER INFORMATION: oligonucleotide primer (xi) SEQUENCE DESCRIPTION: SEQ ID NO:1261:

AACAAGCTGG TGATGCCCAA CTACCC                     26

(2) INFORMATION FOR SEQ ID NO:1262:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: DNA (ix) FEATURE:
        (D) OTHER INFORMATION: oligonucleotide primer (xi) SEQUENCE DESCRIPTION: SEQ ID NO:1262:

AATGGCATTC CTGGAGGACA CGGGAT                     26

(2) INFORMATION FOR SEQ ID NO:1263:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: DNA (ix) FEATURE:
        (D) OTHER INFORMATION: oligonucleotide primer (xi) SEQUENCE DESCRIPTION: SEQ ID NO:1263:

GTTGGGCTGG TCACAGCCTT GTGATG                     26

(2) INFORMATION FOR SEQ ID NO:1264:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: DNA (ix) FEATURE:
        (D) OTHER INFORMATION: oligonucleotide primer (xi) SEQUENCE DESCRIPTION: SEQ ID NO:1264:

CAGCGGTTTG CAGTTCTCAC GAACATAG                   28

(2) INFORMATION FOR SEQ ID NO:1265:

(i) SEQUENCE CHARACTERISTICS:
        (A) LENGTH: 26 base pairs
        (B) TYPE: nucleic acid
        (C) STRANDEDNESS: single
        (D) TOPOLOGY: linear

```
         (ii) MOLECULE TYPE: DNA (ix) FEATURE:
              (D) OTHER INFORMATION: oligonucleotide primer (xi) SEQUENCE DESCRIPTION: SEQ ID NO:1265:

GCCCGGCTAG AAATCAACGT GCTCAA                                              26

(2) INFORMATION FOR SEQ ID NO:1266:

(i) SEQUENCE CHARACTERISTICS:
              (A) LENGTH: 25 base pairs
              (B) TYPE: nucleic acid
              (C) STRANDEDNESS: single
              (D) TOPOLOGY: linear (ii) MOLECULE TYPE: DNA (ix) FEATURE:
              (D) OTHER INFORMATION: oligonucleotide primer (xi) SEQUENCE DESCRIPTION: SEQ ID NO:1266:

CAAGGATCAC CTCAGGCGGG CGATA                                               25

(2) INFORMATION FOR SEQ ID NO:1267:

(i) SEQUENCE CHARACTERISTICS:
              (A) LENGTH: 28 base pairs
              (B) TYPE: nucleic acid
              (C) STRANDEDNESS: single
              (D) TOPOLOGY: linear (ii) MOLECULE TYPE: DNA (ix) FEATURE:
              (D) OTHER INFORMATION: oligonucleotide primer (xi) SEQUENCE DESCRIPTION: SEQ ID NO:1267:

TTGTCCAGGA CGATGAGACA CTCAAAGA                                            28

(2) INFORMATION FOR SEQ ID NO:1268:

(i) SEQUENCE CHARACTERISTICS:
              (A) LENGTH: 28 base pairs
              (B) TYPE: nucleic acid
              (C) STRANDEDNESS: single
              (D) TOPOLOGY: linear (ii) MOLECULE TYPE: DNA (ix) FEATURE:
              (D) OTHER INFORMATION: oligonucleotide primer (xi) SEQUENCE DESCRIPTION: SEQ ID NO:1268:

ACTATGGTTC TGATACCGGC TTTCATGG                                            28

(2) INFORMATION FOR SEQ ID NO:1269:

(i) SEQUENCE CHARACTERISTICS:
              (A) LENGTH: 26 base pairs
              (B) TYPE: nucleic acid
              (C) STRANDEDNESS: single
              (D) TOPOLOGY: linear (ii) MOLECULE TYPE: DNA (ix) FEATURE:
              (D) OTHER INFORMATION: oligonucleotide primer (xi) SEQUENCE DESCRIPTION: SEQ ID NO:1269:

TTCCAGTGGG ATGGGAGCTT ATCACG                                              26
```

(2) INFORMATION FOR SEQ ID NO:1270:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: DNA (ix) FEATURE:
        (D) OTHER INFORMATION: oligonucleotide primer (xi) SEQUENCE DESCRIPTION: SEQ ID NO:1270:

AGGCACTAGG AGGTTGAACA GGATCATT                                  28

(2) INFORMATION FOR SEQ ID NO:1271:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: DNA (ix) FEATURE:
        (D) OTHER INFORMATION: oligonucleotide primer (xi) SEQUENCE DESCRIPTION: SEQ ID NO:1271:

GCACACCCAC ATGGTCAAGT TCAACC                                    26

(2) INFORMATION FOR SEQ ID NO:1272:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: DNA (ix) FEATURE:
        (D) OTHER INFORMATION: oligonucleotide primer (xi) SEQUENCE DESCRIPTION: SEQ ID NO:1272:

GCAGATCCCT GAGAGCCACA CTGTCT                                    26

(2) INFORMATION FOR SEQ ID NO:1273:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: DNA (ix) FEATURE:
        (D) OTHER INFORMATION: oligonucleotide primer (xi) SEQUENCE DESCRIPTION: SEQ ID NO:1273:

AAGAGCACCG GCAAGGCCAA CAAGAT                                    26

(2) INFORMATION FOR SEQ ID NO:1274:

(i) SEQUENCE CHARACTERISTICS:
        (A) LENGTH: 28 base pairs
        (B) TYPE: nucleic acid
        (C) STRANDEDNESS: single (D) TOPOLOGY: linear (ii) MOLECULE TYPE: DNA (ix) FEATURE:
            (D) OTHER INFORMATION: oligonucleotide primer (xi) SEQUENCE DESCRIPTION: SEQ ID NO:1274:

CACGAGATGA CCTCTTGACA CTTGTCCA                                    28

(2) INFORMATION FOR SEQ ID NO:1275:

(i) SEQUENCE CHARACTERISTICS:
            (A) LENGTH: 27 base pairs
            (B) TYPE: nucleic acid
            (C) STRANDEDNESS: single
            (D) TOPOLOGY: linear (ii) MOLECULE TYPE: DNA (ix) FEATURE:
            (D) OTHER INFORMATION: oligonucleotide primer (xi) SEQUENCE DESCRIPTION: SEQ ID NO:1275:

GATCCTTTGC TCTGCACGAG TTACCTG                                     27

(2) INFORMATION FOR SEQ ID NO:1276:

(i) SEQUENCE CHARACTERISTICS:
            (A) LENGTH: 26 base pairs
            (B) TYPE: nucleic acid
            (C) STRANDEDNESS: single
            (D) TOPOLOGY: linear (ii) MOLECULE TYPE: DNA (ix) FEATURE:
            (D) OTHER INFORMATION: oligonucleotide primer (xi) SEQUENCE DESCRIPTION: SEQ ID NO:1276:

TTTGTGGCTC TTGAGAGGCA GGGACT                                      26

(2) INFORMATION FOR SEQ ID NO:1277:

(i) SEQUENCE CHARACTERISTICS:
            (A) LENGTH: 26 base pairs
            (B) TYPE: nucleic acid
            (C) STRANDEDNESS: single
            (D) TOPOLOGY: linear (ii) MOLECULE TYPE: DNA (ix) FEATURE:
            (D) OTHER INFORMATION: oligonucleotide primer (xi) SEQUENCE DESCRIPTION: SEQ ID NO:1277:

GAGAGTCGAG GACCTCCATG TAGGTG                                      26

(2) INFORMATION FOR SEQ ID NO:1278:

(i) SEQUENCE CHARACTERISTICS:
            (A) LENGTH: 27 base pairs
            (B) TYPE: nucleic acid
            (C) STRANDEDNESS: single
            (D) TOPOLOGY: linear (ii) MOLECULE TYPE: DNA (ix) FEATURE:
            (D) OTHER INFORMATION: oligonucleotide primer (xi) SEQUENCE DESCRIPTION: SEQ ID NO:1278:

```
GAAAGTGTCT GCCAGGTACA GCGTCTT                                          27

(2) INFORMATION FOR SEQ ID NO:1279:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: DNA (ix) FEATURE:
        (D) OTHER INFORMATION: oligonucleotide primer (xi) SEQUENCE DESCRIPTION: SEQ ID NO:1279:

AGCGAAACTG CACCAGCGAG TCGTC                                            25

(2) INFORMATION FOR SEQ ID NO:1280:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: DNA (ix) FEATURE:
        (D) OTHER INFORMATION: oligonucleotide primer (xi) SEQUENCE DESCRIPTION: SEQ ID NO:1280:

TGCAGACGCA GGCAGTGTCA ATTCGA                                           26

(2) INFORMATION FOR SEQ ID NO:1281:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: DNA (ix) FEATURE:
        (D) OTHER INFORMATION: oligonucleotide primer (xi) SEQUENCE DESCRIPTION: SEQ ID NO:1281:

AGCTGGGAAA CGTGGGTTCA ATTTGCC                                          27

(2) INFORMATION FOR SEQ ID NO:1282:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: DNA (ix) FEATURE:
        (D) OTHER INFORMATION: oligonucleotide primer (xi) SEQUENCE DESCRIPTION: SEQ ID NO:1282:

TTATCCCACC CAGATTCACA TGGTCACA                                         28

(2) INFORMATION FOR SEQ ID NO:1283:

(i) SEQUENCE CHARACTERISTICS:
        (A) LENGTH: 24 base pairs
```

(B) TYPE: nucleic acid
        (C) STRANDEDNESS: single
        (D) TOPOLOGY: linear (ii) MOLECULE TYPE: DNA (ix) FEATURE:
        (D) OTHER INFORMATION: oligonucleotide primer (xi) SEQUENCE DESCRIPTION: SEQ ID NO:1283:

CCCGGACCGC TGTGGACTTG GTTG                                                  24

(2) INFORMATION FOR SEQ ID NO:1284:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: DNA (ix) FEATURE:
        (D) OTHER INFORMATION: oligonucleotide primer (xi) SEQUENCE DESCRIPTION: SEQ ID NO:1284:

GTATAAGTCT CAGGCCCGGC CAGTC                                                 25

(2) INFORMATION FOR SEQ ID NO:1285:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: DNA (ix) FEATURE:
        (D) OTHER INFORMATION: oligonucleotide primer (xi) SEQUENCE DESCRIPTION: SEQ ID NO:1285:

AGCGTGGCGA CCAGGCTTTC ACTG                                                  24

(2) INFORMATION FOR SEQ ID NO:1286:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: DNA (ix) FEATURE:
        (D) OTHER INFORMATION: oligonucleotide primer (xi) SEQUENCE DESCRIPTION: SEQ ID NO:1286:

CCTGGCCCGT GTTGGAGTAG AAGG                                                  24

(2) INFORMATION FOR SEQ ID NO:1287:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: DNA (ix) FEATURE:
        (D) OTHER INFORMATION: oligonucleotide primer (xi) SEQUENCE DESCRIPTION: SEQ ID NO:1287:

CCTGGCCCAG TAAAGGATGT GTTCTC                                                                26

(2) INFORMATION FOR SEQ ID NO:1288:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: DNA (ix) FEATURE:
        (D) OTHER INFORMATION: oligonucleotide primer (xi) SEQUENCE DESCRIPTION: SEQ ID NO:1288:

GATGACCGTC ACAGAGATTC ACCAGTG                                                               27

(2) INFORMATION FOR SEQ ID NO:1289:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: DNA (ix) FEATURE:
        (D) OTHER INFORMATION: oligonucleotide primer (xi) SEQUENCE DESCRIPTION: SEQ ID NO:1289:

TTTCATATCT CGAACCTCAA TCCCAAATGC                                                            30

(2) INFORMATION FOR SEQ ID NO:1290:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: DNA (ix) FEATURE:
        (D) OTHER INFORMATION: oligonucleotide primer (xi) SEQUENCE DESCRIPTION: SEQ ID NO:1290:

GAAAGCACTT GTGGTATCCG AGGTAATCTA                                                            30

(2) INFORMATION FOR SEQ ID NO:1291:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: DNA (ix) FEATURE:
        (D) OTHER INFORMATION: oligonucleotide primer (xi) SEQUENCE DESCRIPTION: SEQ ID NO:1291:

TTCGGCTTGT GAGGCTTCCC ACTATTTA                                                              28

(2) INFORMATION FOR SEQ ID NO:1292:

(i) SEQUENCE CHARACTERISTICS:
         (A) LENGTH: 28 base pairs
         (B) TYPE: nucleic acid
         (C) STRANDEDNESS: single
         (D) TOPOLOGY: linear (ii) MOLECULE TYPE: DNA (ix) FEATURE:
         (D) OTHER INFORMATION: oligonucleotide primer (xi) SEQUENCE DESCRIPTION: SEQ ID NO:1292:

GGCAACATTA AAGGCATGGA CCGTAAAG                                          28

(2) INFORMATION FOR SEQ ID NO:1293:

(i) SEQUENCE CHARACTERISTICS:
         (A) LENGTH: 24 base pairs
         (B) TYPE: nucleic acid
         (C) STRANDEDNESS: single
         (D) TOPOLOGY: linear (ii) MOLECULE TYPE: DNA (ix) FEATURE:
         (D) OTHER INFORMATION: oligonucleotide primer (xi) SEQUENCE DESCRIPTION: SEQ ID NO:1293:

TCCAACCAGC ACCTGCGGCG AGAG                                              24

(2) INFORMATION FOR SEQ ID NO:1294:

(i) SEQUENCE CHARACTERISTICS:
         (A) LENGTH: 24 base pairs
         (B) TYPE: nucleic acid
         (C) STRANDEDNESS: single
         (D) TOPOLOGY: linear (ii) MOLECULE TYPE: DNA (ix) FEATURE:
         (D) OTHER INFORMATION: oligonucleotide primer (xi) SEQUENCE DESCRIPTION: SEQ ID NO:1294:

TGGAGGCGCA GCAGACGAAC ACCT                                              24

(2) INFORMATION FOR SEQ ID NO:1295:

(i) SEQUENCE CHARACTERISTICS:
         (A) LENGTH: 28 base pairs
         (B) TYPE: nucleic acid
         (C) STRANDEDNESS: single
         (D) TOPOLOGY: linear (ii) MOLECULE TYPE: DNA (ix) FEATURE:
         (D) OTHER INFORMATION: oligonucleotide primer (xi) SEQUENCE DESCRIPTION: SEQ ID NO:1295:

CTGGGCCTCA ACGATTACCT AGACATTG                                          28

(2) INFORMATION FOR SEQ ID NO:1296:

(i) SEQUENCE CHARACTERISTICS:
         (A) LENGTH: 28 base pairs
         (B) TYPE: nucleic acid
         (C) STRANDEDNESS: single
         (D) TOPOLOGY: linear (ii) MOLECULE TYPE: DNA

```
    (ix) FEATURE:
         (D) OTHER INFORMATION: oligonucleotide primer (xi) SEQUENCE DESCRIPTION: SEQ ID NO:1296:

GGGCACCGAG ATGTAGTAGT AAGTCTCT                                      28

(2) INFORMATION FOR SEQ ID NO:1297:

(i) SEQUENCE CHARACTERISTICS:
         (A) LENGTH: 26 base pairs
         (B) TYPE: nucleic acid
         (C) STRANDEDNESS: single
         (D) TOPOLOGY: linear (ii) MOLECULE TYPE: DNA (ix) FEATURE:
         (D) OTHER INFORMATION: oligonucleotide primer (xi) SEQUENCE DESCRIPTION: SEQ ID NO:1297:

CCTCCTGCTA GATAACTACT CCGACC                                        26

(2) INFORMATION FOR SEQ ID NO:1298:

(i) SEQUENCE CHARACTERISTICS:
         (A) LENGTH: 26 base pairs
         (B) TYPE: nucleic acid
         (C) STRANDEDNESS: single
         (D) TOPOLOGY: linear (ii) MOLECULE TYPE: DNA (ix) FEATURE:
         (D) OTHER INFORMATION: oligonucleotide primer (xi) SEQUENCE DESCRIPTION: SEQ ID NO:1298:

GCTGTAGTAC CAGTCCCGGT TGTCCT                                        26

(2) INFORMATION FOR SEQ ID NO:1299:

(i) SEQUENCE CHARACTERISTICS:
         (A) LENGTH: 24 base pairs
         (B) TYPE: nucleic acid
         (C) STRANDEDNESS: single
         (D) TOPOLOGY: linear (ii) MOLECULE TYPE: DNA (ix) FEATURE:
         (D) OTHER INFORMATION: oligonucleotide primer (xi) SEQUENCE DESCRIPTION: SEQ ID NO:1299:

TCCGCCGTGC AGCACGTCAA CCTG                                          24

(2) INFORMATION FOR SEQ ID NO:1300:

(i) SEQUENCE CHARACTERISTICS:
         (A) LENGTH: 24 base pairs
         (B) TYPE: nucleic acid
         (C) STRANDEDNESS: single
         (D) TOPOLOGY: linear (ii) MOLECULE TYPE: DNA (ix) FEATURE:
         (D) OTHER INFORMATION: oligonucleotide primer (xi) SEQUENCE DESCRIPTION: SEQ ID NO:1300:

GTCCACGCTC TCCAGCTCGG TCAC                                          24
```

(2) INFORMATION FOR SEQ ID NO:1301:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: DNA (ix) FEATURE:
        (D) OTHER INFORMATION: oligonucleotide primer (xi) SEQUENCE DESCRIPTION: SEQ ID NO:1301:

CGATCAAGAA GCTGTCCGGG CCTC                                   24

(2) INFORMATION FOR SEQ ID NO:1302:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: DNA (ix) FEATURE:
        (D) OTHER INFORMATION: oligonucleotide primer (xi) SEQUENCE DESCRIPTION: SEQ ID NO:1302:

CCGCCGGTTG CTGCTACATG AACG                                   24

(2) INFORMATION FOR SEQ ID NO:1303:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: DNA (ix) FEATURE:
        (D) OTHER INFORMATION: oligonucleotide primer (xi) SEQUENCE DESCRIPTION: SEQ ID NO:1303:

GTTGCTCCAG CTCTGAATAA ACCGAAGA                               28

(2) INFORMATION FOR SEQ ID NO:1304:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: DNA (ix) FEATURE:
        (D) OTHER INFORMATION: oligonucleotide primer (xi) SEQUENCE DESCRIPTION: SEQ ID NO:1304:

TCTACAATCC TCTGCAATAC AGGGTCGT                               28

(2) INFORMATION FOR SEQ ID NO:1305:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: DNA (ix) FEATURE:
             (D) OTHER INFORMATION: oligonucleotide primer (xi) SEQUENCE DESCRIPTION: SEQ ID NO:1305:

GCAGGACTGC ACCAGAAATT CACCAC                                              26

(2) INFORMATION FOR SEQ ID NO:1306:

(i) SEQUENCE CHARACTERISTICS:
             (A) LENGTH: 26 base pairs
             (B) TYPE: nucleic acid
             (C) STRANDEDNESS: single
             (D) TOPOLOGY: linear (ii) MOLECULE TYPE: DNA (ix) FEATURE:
             (D) OTHER INFORMATION: oligonucleotide primer (xi) SEQUENCE DESCRIPTION: SEQ ID NO:1306:

ACATCCTGAG CAAGCATCGG TCTCCT                                              26

(2) INFORMATION FOR SEQ ID NO:1307:

(i) SEQUENCE CHARACTERISTICS:
             (A) LENGTH: 27 base pairs
             (B) TYPE: nucleic acid
             (C) STRANDEDNESS: single
             (D) TOPOLOGY: linear (ii) MOLECULE TYPE: DNA (ix) FEATURE:
             (D) OTHER INFORMATION: oligonucleotide primer (xi) SEQUENCE DESCRIPTION: SEQ ID NO:1307:

TGCAGATGAT GGGCAGCAAC GACTATG                                             27

(2) INFORMATION FOR SEQ ID NO:1308:

(i) SEQUENCE CHARACTERISTICS:
             (A) LENGTH: 25 base pairs
             (B) TYPE: nucleic acid
             (C) STRANDEDNESS: single
             (D) TOPOLOGY: linear (ii) MOLECULE TYPE: DNA (ix) FEATURE:
             (D) OTHER INFORMATION: oligonucleotide primer (xi) SEQUENCE DESCRIPTION: SEQ ID NO:1308:

CATGCAGACG TTGGTCCGGT TTCCC                                               25

(2) INFORMATION FOR SEQ ID NO:1309:

(i) SEQUENCE CHARACTERISTICS:
             (A) LENGTH: 24 base pairs
             (B) TYPE: nucleic acid
             (C) STRANDEDNESS: single
             (D) TOPOLOGY: linear (ii) MOLECULE TYPE: DNA (ix) FEATURE:
             (D) OTHER INFORMATION: oligonucleotide primer (xi) SEQUENCE DESCRIPTION: SEQ ID NO:1309:

CGATTGGCAA TCCAGTGCCG CGCT                                                24

(2) INFORMATION FOR SEQ ID NO:1310:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: DNA (ix) FEATURE:
        (D) OTHER INFORMATION: oligonucleotide primer (xi) SEQUENCE DESCRIPTION: SEQ ID NO:1310:

TGGAGACTGA GAAGTAGGCA TCTGTACT                           28

(2) INFORMATION FOR SEQ ID NO:1311:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: DNA (ix) FEATURE:
        (D) OTHER INFORMATION: oligonucleotide primer (xi) SEQUENCE DESCRIPTION: SEQ ID NO:1311:

CCGATCCACC TCACCTTGGA ATCTCC                             26

(2) INFORMATION FOR SEQ ID NO:1312:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: DNA (ix) FEATURE:
        (D) OTHER INFORMATION: oligonucleotide primer (xi) SEQUENCE DESCRIPTION: SEQ ID NO:1312:

CTGGGTCGGC TCTCCATAGT CTAACT                             26

(2) INFORMATION FOR SEQ ID NO:1313:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: DNA (ix) FEATURE:
        (D) OTHER INFORMATION: oligonucleotide primer (xi) SEQUENCE DESCRIPTION: SEQ ID NO:1313:

CCCAGGAGAC CGTTGCAGTC GGC                                23

(2) INFORMATION FOR SEQ ID NO:1314:

(i) SEQUENCE CHARACTERISTICS:
        (A) LENGTH: 28 base pairs
        (B) TYPE: nucleic acid
        (C) STRANDEDNESS: single (D) TOPOLOGY: linear (ii) MOLECULE TYPE: DNA (ix) FEATURE:
        (D) OTHER INFORMATION: oligonucleotide primer (xi) SEQUENCE DESCRIPTION: SEQ ID NO:1314:

GATGCAATGC CAGGTGGGAT TGTACTTC                                        28

(2) INFORMATION FOR SEQ ID NO:1315:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: DNA (ix) FEATURE:
        (D) OTHER INFORMATION: oligonucleotide primer (xi) SEQUENCE DESCRIPTION: SEQ ID NO:1315:

CCTGCCCTAG TGCAACAGGC ATTGC                                           25

(2) INFORMATION FOR SEQ ID NO:1316:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: DNA (ix) FEATURE:
        (D) OTHER INFORMATION: oligonucleotide primer (xi) SEQUENCE DESCRIPTION: SEQ ID NO:1316:

AGCTCATCCC AAGCCTAGCC CTCC                                            24

(2) INFORMATION FOR SEQ ID NO:1317:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: DNA (ix) FEATURE:
        (D) OTHER INFORMATION: oligonucleotide primer (xi) SEQUENCE DESCRIPTION: SEQ ID NO:1317:

GGCATGGGCA TTACGGGTGT TGAAGG                                          26

(2) INFORMATION FOR SEQ ID NO:1318:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: DNA (ix) FEATURE:
        (D) OTHER INFORMATION: oligonucleotide primer (xi) SEQUENCE DESCRIPTION: SEQ ID NO:1318:

```
GGGTGAAGCT CAGTTTCATC TTCCGG                                                  26

(2) INFORMATION FOR SEQ ID NO:1319:

(i) SEQUENCE CHARACTERISTICS:
         (A) LENGTH: 24 base pairs
         (B) TYPE: nucleic acid
         (C) STRANDEDNESS: single
         (D) TOPOLOGY: linear (ii) MOLECULE TYPE: DNA (ix) FEATURE:
         (D) OTHER INFORMATION: oligonucleotide primer (xi) SEQUENCE DESCRIPTION: SEQ ID NO:1319:

ATGGCGCTCA CCTGGCAAAC CCAC                                                    24

(2) INFORMATION FOR SEQ ID NO:1320:

(i) SEQUENCE CHARACTERISTICS:
         (A) LENGTH: 27 base pairs
         (B) TYPE: nucleic acid
         (C) STRANDEDNESS: single
         (D) TOPOLOGY: linear (ii) MOLECULE TYPE: DNA (ix) FEATURE:
         (D) OTHER INFORMATION: oligonucleotide primer (xi) SEQUENCE DESCRIPTION: SEQ ID NO:1320:

GAGCAGTCAG GCAGAAATGA CTCGTGA                                                 27

(2) INFORMATION FOR SEQ ID NO:1321:

(i) SEQUENCE CHARACTERISTICS:
         (A) LENGTH: 26 base pairs
         (B) TYPE: nucleic acid
         (C) STRANDEDNESS: single
         (D) TOPOLOGY: linear (ii) MOLECULE TYPE: DNA (ix) FEATURE:
         (D) OTHER INFORMATION: oligonucleotide primer (xi) SEQUENCE DESCRIPTION: SEQ ID NO:1321:

TTCTTCATTC AGGCTTGCCG AGGGAC                                                  26

(2) INFORMATION FOR SEQ ID NO:1322:

(i) SEQUENCE CHARACTERISTICS:
         (A) LENGTH: 28 base pairs
         (B) TYPE: nucleic acid
         (C) STRANDEDNESS: single
         (D) TOPOLOGY: linear (ii) MOLECULE TYPE: DNA (ix) FEATURE:
         (D) OTHER INFORMATION: oligonucleotide primer (xi) SEQUENCE DESCRIPTION: SEQ ID NO:1322:

GTGTGGGTCA TCAGACTGAG ACTCAAAG                                                28

(2) INFORMATION FOR SEQ ID NO:1323:

(i) SEQUENCE CHARACTERISTICS:
         (A) LENGTH: 28 base pairs
```

(B) TYPE: nucleic acid
        (C) STRANDEDNESS: single
        (D) TOPOLOGY: linear (ii) MOLECULE TYPE: DNA (ix) FEATURE:
        (D) OTHER INFORMATION: oligonucleotide primer (xi) SEQUENCE DESCRIPTION: SEQ ID NO:1323:

TTGGAGTCTG GGCATCACGA TGATTGAG                                           28

(2) INFORMATION FOR SEQ ID NO:1324:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: DNA (ix) FEATURE:
        (D) OTHER INFORMATION: oligonucleotide primer (xi) SEQUENCE DESCRIPTION: SEQ ID NO:1324:

CCACCAATCC ACAGTAGGGT CAACCG                                             26

(2) INFORMATION FOR SEQ ID NO:1325:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: DNA (ix) FEATURE:
        (D) OTHER INFORMATION: oligonucleotide primer (xi) SEQUENCE DESCRIPTION: SEQ ID NO:1325:

GAAGCCTGAA GACACAAACA GACGCTC                                            27

(2) INFORMATION FOR SEQ ID NO:1326:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: DNA (ix) FEATURE:
        (D) OTHER INFORMATION: oligonucleotide primer (xi) SEQUENCE DESCRIPTION: SEQ ID NO:1326:

GCAAGGACCT TCCAGTCCTA CTTGTC                                             26

(2) INFORMATION FOR SEQ ID NO:1327:

(i) SEQUENCE CHARACTERISTICS:
        (A) LENGTH: 31 base pairs
        (B) TYPE: nucleic acid
        (C) STRANDEDNESS: single
        (D) TOPOLOGY: linear (ii) MOLECULE TYPE: DNA (ix) FEATURE:
        (D) OTHER INFORMATION: oligonucleotide primer (xi) SEQUENCE DESCRIPTION: SEQ ID NO:1327:

AAACCTAGAA GATGCTTGTG ATGACATCAT G                            31

(2) INFORMATION FOR SEQ ID NO:1328:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: DNA (ix) FEATURE:
        (D) OTHER INFORMATION: oligonucleotide primer (xi) SEQUENCE DESCRIPTION: SEQ ID NO:1328:

AACTGAACTT TCAAATCTGC TAACACTCGC                              30

(2) INFORMATION FOR SEQ ID NO:1329:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: DNA (ix) FEATURE:
        (D) OTHER INFORMATION: oligonucleotide primer (xi) SEQUENCE DESCRIPTION: SEQ ID NO:1329:

CATGGACTTC AGGCTGTTAG TGGCAG                                  26

(2) INFORMATION FOR SEQ ID NO:1330:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: DNA (ix) FEATURE:
        (D) OTHER INFORMATION: oligonucleotide primer (xi) SEQUENCE DESCRIPTION: SEQ ID NO:1330:

CAGTTAAGTG AGAACTGTGC GAACACAG                                28

(2) INFORMATION FOR SEQ ID NO:1331:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: DNA (ix) FEATURE:
        (D) OTHER INFORMATION: oligonucleotide primer (xi) SEQUENCE DESCRIPTION: SEQ ID NO:1331:

GGCTTGCCAG CCACCCGTCC AGT                                     23

(2) INFORMATION FOR SEQ ID NO:1332:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: DNA (ix) FEATURE:
        (D) OTHER INFORMATION: oligonucleotide primer (xi) SEQUENCE DESCRIPTION: SEQ ID NO:1332:

CTTTACGGGC TCCAGGCATT CCCATG                                          26

(2) INFORMATION FOR SEQ ID NO:1333:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: DNA (ix) FEATURE:
        (D) OTHER INFORMATION: oligonucleotide primer (xi) SEQUENCE DESCRIPTION: SEQ ID NO:1333:

CCCAGTGCTG CCTGCATTCG CGG                                             23

(2) INFORMATION FOR SEQ ID NO:1334:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: DNA (ix) FEATURE:
        (D) OTHER INFORMATION: oligonucleotide primer (xi) SEQUENCE DESCRIPTION: SEQ ID NO:1334:

CAGTCATGGC CTCATAGACG GCAGTG                                          26

(2) INFORMATION FOR SEQ ID NO:1335:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: DNA (ix) FEATURE:
        (D) OTHER INFORMATION: oligonucleotide primer (xi) SEQUENCE DESCRIPTION: SEQ ID NO:1335:

GACTGGAGGC CAGCCATCAC AATCAA                                          26

(2) INFORMATION FOR SEQ ID NO:1336:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: DNA

```
        (ix) FEATURE:
             (D) OTHER INFORMATION: oligonucleotide primer (xi) SEQUENCE DESCRIPTION: SEQ ID NO:1336:

CGGGCAATTC AGCGAATCGA GACCG                                              25

(2) INFORMATION FOR SEQ ID NO:1337:

(i) SEQUENCE CHARACTERISTICS:
             (A) LENGTH: 28 base pairs
             (B) TYPE: nucleic acid
             (C) STRANDEDNESS: single
             (D) TOPOLOGY: linear (ii) MOLECULE TYPE: DNA (ix) FEATURE:
             (D) OTHER INFORMATION: oligonucleotide primer (xi) SEQUENCE DESCRIPTION: SEQ ID NO:1337:

CAGAATACCA CCGCCAGGAT GTTACTAG                                           28

(2) INFORMATION FOR SEQ ID NO:1338:

(i) SEQUENCE CHARACTERISTICS:
             (A) LENGTH: 30 base pairs
             (B) TYPE: nucleic acid
             (C) STRANDEDNESS: single
             (D) TOPOLOGY: linear (ii) MOLECULE TYPE: DNA (ix) FEATURE:
             (D) OTHER INFORMATION: oligonucleotide primer (xi) SEQUENCE DESCRIPTION: SEQ ID NO:1338:

CAACAGTTGG TCACAGAGGT CAAGTATTAT                                         30

(2) INFORMATION FOR SEQ ID NO:1339:

(i) SEQUENCE CHARACTERISTICS:
             (A) LENGTH: 23 base pairs
             (B) TYPE: nucleic acid
             (C) STRANDEDNESS: single
             (D) TOPOLOGY: linear (ii) MOLECULE TYPE: DNA (ix) FEATURE:
             (D) OTHER INFORMATION: oligonucleotide primer (xi) SEQUENCE DESCRIPTION: SEQ ID NO:1339:

CCGCTGCACC AAGCCATGCG GGC                                                23

(2) INFORMATION FOR SEQ ID NO:1340:

(i) SEQUENCE CHARACTERISTICS:
             (A) LENGTH: 23 base pairs
             (B) TYPE: nucleic acid
             (C) STRANDEDNESS: single
             (D) TOPOLOGY: linear (ii) MOLECULE TYPE: DNA (ix) FEATURE:
             (D) OTHER INFORMATION: oligonucleotide primer (xi) SEQUENCE DESCRIPTION: SEQ ID NO:1340:

CAGCCGCGTC TCCAGGTAGG CCA                                                23
```

(2) INFORMATION FOR SEQ ID NO:1341:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (ii) MOLECULE TYPE: DNA (ix) FEATURE:
        (D) OTHER INFORMATION: oligonucleotide primer (xi) SEQUENCE DESCRIPTION: SEQ ID NO:1341:

AACTGAAACA CAGTGCTCTG TGCCTATAC                                29

(2) INFORMATION FOR SEQ ID NO:1342:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: DNA (ix) FEATURE:
        (D) OTHER INFORMATION: oligonucleotide primer (xi) SEQUENCE DESCRIPTION: SEQ ID NO:1342:

GAGTCATTGT CCATAGGTGG AAACTTGACA                                30

(2) INFORMATION FOR SEQ ID NO:1343:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: DNA (ix) FEATURE:
        (D) OTHER INFORMATION: oligonucleotide primer (xi) SEQUENCE DESCRIPTION: SEQ ID NO:1343:

CCTGGACACC GGCTATGAGA CCGA                                     24

(2) INFORMATION FOR SEQ ID NO:1344:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: DNA (ix) FEATURE:
        (D) OTHER INFORMATION: oligonucleotide primer (xi) SEQUENCE DESCRIPTION: SEQ ID NO:1344:

CTCCGACTGA CTTCGGAACA CAAGAC                                   26

(2) INFORMATION FOR SEQ ID NO:1345:

(i) SEQUENCE CHARACTERISTICS:
        (A) LENGTH: 28 base pairs
        (B) TYPE: nucleic acid
        (C) STRANDEDNESS: single
        (D) TOPOLOGY: linear -continued (ii) MOLECULE TYPE: DNA (ix) FEATURE:
             (D) OTHER INFORMATION: oligonucleotide primer (xi) SEQUENCE DESCRIPTION: SEQ ID NO:1345:

ATGACTGGGT TATTGAGCCT GTTGTGGG                                              28

(2) INFORMATION FOR SEQ ID NO:1346:

(i) SEQUENCE CHARACTERISTICS:
             (A) LENGTH: 28 base pairs
             (B) TYPE: nucleic acid
             (C) STRANDEDNESS: single
             (D) TOPOLOGY: linear (ii) MOLECULE TYPE: DNA (ix) FEATURE:
             (D) OTHER INFORMATION: oligonucleotide primer (xi) SEQUENCE DESCRIPTION: SEQ ID NO:1346:

TCACTGATTT GCAGGCAGCT CGTTTCTT                                              28

(2) INFORMATION FOR SEQ ID NO:1347:

(i) SEQUENCE CHARACTERISTICS:
             (A) LENGTH: 28 base pairs
             (B) TYPE: nucleic acid
             (C) STRANDEDNESS: single
             (D) TOPOLOGY: linear (ii) MOLECULE TYPE: DNA (ix) FEATURE:
             (D) OTHER INFORMATION: oligonucleotide primer (xi) SEQUENCE DESCRIPTION: SEQ ID NO:1347:

TGGCTTCACC ATCAATCCTG ATTCCTCT                                              28

(2) INFORMATION FOR SEQ ID NO:1348:

(i) SEQUENCE CHARACTERISTICS:
             (A) LENGTH: 28 base pairs
             (B) TYPE: nucleic acid
             (C) STRANDEDNESS: single
             (D) TOPOLOGY: linear (ii) MOLECULE TYPE: DNA (ix) FEATURE:
             (D) OTHER INFORMATION: oligonucleotide primer (xi) SEQUENCE DESCRIPTION: SEQ ID NO:1348:

CCATGTGACT GAATCAAGAC CCGGTATG                                              28

(2) INFORMATION FOR SEQ ID NO:1349:

(i) SEQUENCE CHARACTERISTICS:
             (A) LENGTH: 26 base pairs
             (B) TYPE: nucleic acid
             (C) STRANDEDNESS: single
             (D) TOPOLOGY: linear (ii) MOLECULE TYPE: DNA (ix) FEATURE:
             (D) OTHER INFORMATION: oligonucleotide primer (xi) SEQUENCE DESCRIPTION: SEQ ID NO:1349:

GTGGCTATGC TGGAGAGCTT GGCTTC                                                26

(2) INFORMATION FOR SEQ ID NO:1350:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: DNA (ix) FEATURE:
        (D) OTHER INFORMATION: oligonucleotide primer (xi) SEQUENCE DESCRIPTION: SEQ ID NO:1350:

GCCAACAGTC CTCACTTAGG GCTTTCT                      27

(2) INFORMATION FOR SEQ ID NO:1351:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: DNA (ix) FEATURE:
        (D) OTHER INFORMATION: oligonucleotide primer (xi) SEQUENCE DESCRIPTION: SEQ ID NO:1351:

CCCATAGAGT TGTGACGAGG ATTGAGAT                     28

(2) INFORMATION FOR SEQ ID NO:1352:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: DNA (ix) FEATURE:
        (D) OTHER INFORMATION: oligonucleotide primer (xi) SEQUENCE DESCRIPTION: SEQ ID NO:1352:

TAAAGCATCA CAGTGCTGTA GTAGATGTCT                   30

(2) INFORMATION FOR SEQ ID NO:1353:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (ii) MOLECULE TYPE: DNA (ix) FEATURE:
        (D) OTHER INFORMATION: oligonucleotide primer (xi) SEQUENCE DESCRIPTION: SEQ ID NO:1353:

GGAAAGTGGA ATGAACCGTT TGACGAAAC                    29

(2) INFORMATION FOR SEQ ID NO:1354:

(i) SEQUENCE CHARACTERISTICS:
        (A) LENGTH: 28 base pairs
        (B) TYPE: nucleic acid
        (C) STRANDEDNESS: single (D) TOPOLOGY: linear (ii) MOLECULE TYPE: DNA (ix) FEATURE:
           (D) OTHER INFORMATION: oligonucleotide primer (xi) SEQUENCE DESCRIPTION: SEQ ID NO:1354:

TCAACAATTC CCAAATGCCG AAGCACAG                                        28

(2) INFORMATION FOR SEQ ID NO:1355:

(i) SEQUENCE CHARACTERISTICS:
           (A) LENGTH: 29 base pairs
           (B) TYPE: nucleic acid
           (C) STRANDEDNESS: single
           (D) TOPOLOGY: linear (ii) MOLECULE TYPE: DNA (ix) FEATURE:
           (D) OTHER INFORMATION: oligonucleotide primer (xi) SEQUENCE DESCRIPTION: SEQ ID NO:1355:

AGCTATTAAA GCCTTGGAGC TTCGGTTTC                                       29

(2) INFORMATION FOR SEQ ID NO:1356:

(i) SEQUENCE CHARACTERISTICS:
           (A) LENGTH: 28 base pairs
           (B) TYPE: nucleic acid
           (C) STRANDEDNESS: single
           (D) TOPOLOGY: linear (ii) MOLECULE TYPE: DNA (ix) FEATURE:
           (D) OTHER INFORMATION: oligonucleotide primer (xi) SEQUENCE DESCRIPTION: SEQ ID NO:1356:

ATCATTACCA CCTGCTGCAA TGAGTCTG                                        28

(2) INFORMATION FOR SEQ ID NO:1357:

(i) SEQUENCE CHARACTERISTICS:
           (A) LENGTH: 26 base pairs
           (B) TYPE: nucleic acid
           (C) STRANDEDNESS: single
           (D) TOPOLOGY: linear (ii) MOLECULE TYPE: DNA (ix) FEATURE:
           (D) OTHER INFORMATION: oligonucleotide primer (xi) SEQUENCE DESCRIPTION: SEQ ID NO:1357:

AGCTGACGGG ATCTCCATCC GATTCC                                          26

(2) INFORMATION FOR SEQ ID NO:1358:

(i) SEQUENCE CHARACTERISTICS:
           (A) LENGTH: 26 base pairs
           (B) TYPE: nucleic acid
           (C) STRANDEDNESS: single
           (D) TOPOLOGY: linear (ii) MOLECULE TYPE: DNA (ix) FEATURE:
           (D) OTHER INFORMATION: oligonucleotide primer (xi) SEQUENCE DESCRIPTION: SEQ ID NO:1358:

```
TCATAGCGGA AGGCTTTGCA GTCTGC                                              26
```

(2) INFORMATION FOR SEQ ID NO:1359:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (ii) MOLECULE TYPE: DNA (ix) FEATURE:
        (D) OTHER INFORMATION: oligonucleotide primer (xi) SEQUENCE DESCRIPTION: SEQ ID NO:1359:

```
AAACCCAGAT TGGTGAGATA GGACACTTG                                           29
```

(2) INFORMATION FOR SEQ ID NO:1360:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: DNA (ix) FEATURE:
        (D) OTHER INFORMATION: oligonucleotide primer (xi) SEQUENCE DESCRIPTION: SEQ ID NO:1360:

```
CTTTCCGGGA CACCTGGGTT CACAC                                               25
```

(2) INFORMATION FOR SEQ ID NO:1361:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: DNA (ix) FEATURE:
        (D) OTHER INFORMATION: oligonucleotide primer (xi) SEQUENCE DESCRIPTION: SEQ ID NO:1361:

```
GGGAGACCGC AGCCCATCGG CAT                                                 23
```

(2) INFORMATION FOR SEQ ID NO:1362:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (ii) MOLECULE TYPE: DNA (ix) FEATURE:
        (D) OTHER INFORMATION: oligonucleotide primer (xi) SEQUENCE DESCRIPTION: SEQ ID NO:1362:

```
GACTAGATCA CTGCATCCGC CTATACAAT                                           29
```

(2) INFORMATION FOR SEQ ID NO:1363:

(i) SEQUENCE CHARACTERISTICS:
        (A) LENGTH: 28 base pairs

```
        (B) TYPE: nucleic acid
        (C) STRANDEDNESS: single
        (D) TOPOLOGY: linear (ii) MOLECULE TYPE: DNA (ix) FEATURE:
        (D) OTHER INFORMATION: oligonucleotide primer (xi) SEQUENCE DESCRIPTION: SEQ ID NO:1363:

CTAATGGTGG CTGGTCATCC AAATCCTG                                    28

(2) INFORMATION FOR SEQ ID NO:1364:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (ii) MOLECULE TYPE: DNA (ix) FEATURE:
        (D) OTHER INFORMATION: oligonucleotide primer (xi) SEQUENCE DESCRIPTION: SEQ ID NO:1364:

GGTTCATAAT TTCGTCTGGC AGTGTTGTG                                   29

(2) INFORMATION FOR SEQ ID NO:1365:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: DNA (ix) FEATURE:
        (D) OTHER INFORMATION: oligonucleotide primer (xi) SEQUENCE DESCRIPTION: SEQ ID NO:1365:

AGTGGCCCTG TTAAAGGCTC TTTATGGA                                    28

(2) INFORMATION FOR SEQ ID NO:1366:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: DNA (ix) FEATURE:
        (D) OTHER INFORMATION: oligonucleotide primer (xi) SEQUENCE DESCRIPTION: SEQ ID NO:1366:

GCTGACACAA CTGCTTCAAA GCAATGATTT                                  30

(2) INFORMATION FOR SEQ ID NO:1367:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (ii) MOLECULE TYPE: DNA (ix) FEATURE:
        (D) OTHER INFORMATION: oligonucleotide primer
```

(xi) SEQUENCE DESCRIPTION: SEQ ID NO:1367:

GAAGAGCCTA TTGAAGATGA ACAGACTCC                                    29

(2) INFORMATION FOR SEQ ID NO:1368:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (ii) MOLECULE TYPE: DNA (ix) FEATURE:
        (D) OTHER INFORMATION: oligonucleotide primer (xi) SEQUENCE DESCRIPTION: SEQ ID NO:1368:

CTCCCAAGTC CTCCATAGCA GTGTATTAA                                    29

(2) INFORMATION FOR SEQ ID NO:1369:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: DNA (ix) FEATURE:
        (D) OTHER INFORMATION: oligonucleotide primer (xi) SEQUENCE DESCRIPTION: SEQ ID NO:1369:

TTTCCTGTCC CACCATACGA GCACCT                                       26

(2) INFORMATION FOR SEQ ID NO:1370:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: DNA (ix) FEATURE:
        (D) OTHER INFORMATION: oligonucleotide primer (xi) SEQUENCE DESCRIPTION: SEQ ID NO:1370:

CGCAACAAGA CAGCAGCAAG TTCTGAG                                      27

(2) INFORMATION FOR SEQ ID NO:1371:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: DNA (ix) FEATURE:
        (D) OTHER INFORMATION: oligonucleotide primer (xi) SEQUENCE DESCRIPTION: SEQ ID NO:1371:

AAAGCCCGGA GCTAACGACC GGCC                                         24

(2) INFORMATION FOR SEQ ID NO:1372:

-continued

```
    (i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: DNA (ix) FEATURE:
        (D) OTHER INFORMATION: oligonucleotide primer (xi) SEQUENCE DESCRIPTION: SEQ ID NO:1372:

CCGAAACGGT TGACTCCGTT GGGATC                                   26

(2) INFORMATION FOR SEQ ID NO:1373:

(i) SEQUENCE CHARACTERISTICS:
        (A) LENGTH: 51 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:1373:

TCTAGAATTC AGCGGCCGCT TTTTTTTTTT TTTTTTTTTT TTTTTTTTTV N        51

(2) INFORMATION FOR SEQ ID NO:1374:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: DNA (ix) FEATURE:
        (D) OTHER INFORMATION: oligonucleotide primer (xi) SEQUENCE DESCRIPTION: SEQ ID NO:1374:

CTAATACGAC TCACTATAGG GCGGG                                    25

(2) INFORMATION FOR SEQ ID NO:1375:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: DNA (ix) FEATURE:
        (D) OTHER INFORMATION: oligonucleotide primer (ii) MOLECULE TYPE: cDNA (xi) SEQUENCE DESCRIPTION: SEQ ID NO:1375:

CTAATACGAC TCACTATAGG GC                                       22
```